US008273858B2

(12) United States Patent
Krasnoperov et al.

(10) Patent No.: US 8,273,858 B2
(45) **Date of Patent: *Sep. 25, 2012**

(54) POLYPEPTIDE COMPOUNDS FOR INHIBITING ANGIOGENESIS AND TUMOR GROWTH

(75) Inventors: Valery Krasnoperov, South Pasadena, CA (US); Nathalie Kertesz, Agoura Hills, CA (US); Ramachandra Reddy, Conshohocken, PA (US); Parkash Gill, Agoura Hills, CA (US); Sergey Zozulya, San Diego, CA (US)

(73) Assignee: VasGene Therapeutics, Inc., Agoura Hills, CA (US)

( * ) Notice: Subject to any disclaimer, the term of this patent is extended or adjusted under 35 U.S.C. 154(b) by 298 days.

This patent is subject to a terminal disclaimer.

(21) Appl. No.: 12/156,553

(22) Filed: Jun. 2, 2008

(65) Prior Publication Data

US 2009/0155251 A1 Jun. 18, 2009

Related U.S. Application Data

(63) Continuation of application No. 10/949,720, filed on Sep. 23, 2004, now Pat. No. 7,381,410, which is a continuation-in-part of application No. 10/800,350, filed on Mar. 12, 2004, now Pat. No. 7,862,816.

(60) Provisional application No. 60/454,300, filed on Mar. 12, 2003, provisional application No. 60/454,432, filed on Mar. 12, 2003.

(51) Int. Cl.
*C07K 16/00* (2006.01)

(52) U.S. Cl. .................................................... 530/388.1

(58) Field of Classification Search ........................ None
See application file for complete search history.

(56) References Cited

U.S. PATENT DOCUMENTS

| | | | |
|---|---|---|---|
| 5,264,209 | A | 11/1993 | Mikayama et al. |
| 5,512,591 | A | 4/1996 | Halperin et al. |
| 5,624,899 | A | 4/1997 | Bennett |
| 5,635,177 | A | 6/1997 | Bennett |
| 5,693,762 | A | 12/1997 | Queen et al. |
| 5,770,599 | A | 6/1998 | Gibson |
| 5,795,734 | A | 8/1998 | Flanagan et al. |
| 5,824,303 | A | 10/1998 | Bartley et al. |
| 5,864,020 | A | 1/1999 | Bennett |
| 6,015,711 | A | 1/2000 | Olson et al. |
| 6,303,769 | B1 | 10/2001 | Cerretti |
| 6,413,730 | B1 | 7/2002 | Holland |
| 6,423,685 | B1 | 7/2002 | Drummond et al. |
| 6,440,954 | B1 | 8/2002 | Haber et al. |
| 6,479,459 | B1 | 11/2002 | Cerretti |
| 6,492,140 | B2 | 12/2002 | Cerretti et al. |
| 6,514,497 | B1 | 2/2003 | Briskin et al. |
| 6,579,683 | B2 | 6/2003 | Wang et al. |
| 6,673,343 | B2 | 1/2004 | Bennett et al. |
| 6,864,227 | B1 | 3/2005 | Wang et al. |
| 6,887,674 | B1 | 5/2005 | Wang et al. |
| 6,916,625 | B2 | 7/2005 | Wang et al. |
| 6,926,898 | B2 | 8/2005 | Rosen et al. |
| 7,163,808 | B2 | 1/2007 | Anderson et al. |
| 7,576,052 | B2 | 8/2009 | Kahn et al. |
| 7,585,967 | B2 | 9/2009 | Reddy et al. |
| 7,700,297 | B2 | 4/2010 | Wang et al. |
| 7,741,272 | B2 | 6/2010 | Wang et al. |
| 7,862,816 | B2 | 1/2011 | Krasnoperov et al. |
| 2002/0086819 | A1 | 7/2002 | Drummond et al. |
| 2002/0136726 | A1 | 9/2002 | Anderson et al. |
| 2002/0142444 | A1 | 10/2002 | Caras |
| 2002/0146420 | A1 | 10/2002 | Bennett |
| 2003/0157712 | A1 | 8/2003 | Daniel et al. |
| 2004/0110150 | A1 | 6/2004 | Koller et al. |
| 2004/0234520 | A1 | 11/2004 | Aguet et al. |
| 2004/0247592 | A1 | 12/2004 | Roifman et al. |
| 2005/0049176 | A1 | 3/2005 | Kiener et al. |
| 2005/0084873 | A1 | 4/2005 | Krasnoperov et al. |
| 2005/0164965 | A1 | 7/2005 | Reddy et al. |
| 2005/0187154 | A1 | 8/2005 | Kahn et al. |
| 2005/0204412 | A1 | 9/2005 | Wang et al. |
| 2006/0035328 | A1 | 2/2006 | Wang et al. |
| 2006/0204512 | A1 | 9/2006 | Krasnoperov et al. |
| 2006/0241027 | A1 | 10/2006 | Hauser et al. |
| 2007/0207952 | A1 | 9/2007 | Silva et al. |

FOREIGN PATENT DOCUMENTS

| | | |
|---|---|---|
| EP | 0 442 724 | 8/1991 |
| EP | 0 633 315 A2 | 1/1995 |
| EP | 0999 278 | 5/2000 |
| WO | WO-93/00425 | 1/1993 |
| WO | WO-93/15201 | 8/1993 |
| WO | WO-94/10202 | 5/1994 |
| WO | WO-94/11020 | 5/1994 |
| WO | WO-95/27061 | 10/1995 |
| WO | WO-96/01839 | 1/1996 |
| WO | WO-96/02645 | 2/1996 |
| WO | WO-96/03043 | 2/1996 |
| WO | WO-96/09384 | 3/1996 |
| WO | WO-96/13518 | 5/1996 |
| WO | WO-96/23000 | 8/1996 |

(Continued)

OTHER PUBLICATIONS

Bennett et al (JBC, 1994, 269: 14211-14218).*

(Continued)

*Primary Examiner* — Sean Aeder
(74) *Attorney, Agent, or Firm* — Ropes & Gray LLP

(57) ABSTRACT

In certain embodiments, this present invention provides polypeptide compositions, and methods for inhibiting Ephrin B2 or EphB4 activity. In other embodiments, the present invention provides methods and compositions for treating cancer or for treating angiogenesis-associated diseases.

22 Claims, 109 Drawing Sheets

FOREIGN PATENT DOCUMENTS

| | | | |
|---|---|---|---|
| WO | WO 96/26958 | * | 9/1996 |
| WO | WO-96/26958 | | 9/1996 |
| WO | WO-96/36713 | | 11/1996 |
| WO | WO-97/09427 | | 3/1997 |
| WO | WO-97/23629 | | 7/1997 |
| WO | WO 97/43960 | | 11/1997 |
| WO | WO-97/44453 | | 11/1997 |
| WO | WO-98/01548 | | 1/1998 |
| WO | WO-98/43960 | | 10/1998 |
| WO | WO-98/45331 | | 10/1998 |
| WO | WO-98/45708 | | 10/1998 |
| WO | WO-99/08696 | | 2/1999 |
| WO | WO-99/17796 | | 4/1999 |
| WO | WO 99/45026 | | 9/1999 |
| WO | WO-99/52541 | | 10/1999 |
| WO | WO-00/24413 | | 5/2000 |
| WO | WO-00/30673 | | 6/2000 |
| WO | WO 00/30673 | * | 6/2000 |
| WO | WO 01/49743 | A2 | 7/2001 |
| WO | WO-02/11785 | | 2/2002 |
| WO | WO-02/26827 | | 4/2002 |
| WO | WO-02/058538 | | 8/2002 |
| WO | WO-02/061055 | | 8/2002 |
| WO | WO-02/079382 | | 10/2002 |
| WO | WO-02/102854 | | 12/2002 |
| WO | WO-02/102972 | | 12/2002 |
| WO | WO-02/102973 | | 12/2002 |
| WO | WO 03/000113 | | 1/2003 |
| WO | WO-03/004057 | | 1/2003 |
| WO | WO-03/094859 | | 11/2003 |
| WO | WO-2004/014292 | | 2/2004 |
| WO | WO 2004/020468 | | 3/2004 |
| WO | WO-2004/024773 | | 3/2004 |
| WO | WO-2004/080425 | | 9/2004 |
| WO | WO-2004/091375 | | 10/2004 |
| WO | WO-2005/048917 | | 6/2005 |
| WO | WO-2005/051307 | | 6/2005 |
| WO | WO 2005/090406 | | 9/2005 |

OTHER PUBLICATIONS

Stephenson et al (BMC Molecular Biology, 2001, 2(15): 1-9).*

Adams, R.H., et al., "Eph Receptors and Ephrin Ligands: Essential Mediators of Vascular Development," *Trends. Cardiovasc. Med.*, 10:183-188 (2000).

Adams, R.H., et al., "Roles of ephrinB ligands and EphB receptors in cardiovascular development: demarcation of arterial/venous domains, vascular morphogenesis, and sprouting angiogenesis," Genes Dev., 13:295-306 (1999).

Andres, A. C. et al., "Expression of two novel eph-related receptor protein tyrosine kinases in mammary gland development and carcinogenesis," *Oncogene*, 9:1461-1467 (1994).

Asahara, T. et al., "Isolation of Putative Progenitor Endothelial Cells for Angiogenesis," *Science*, 275:964-967 (1997).

Batlle, E., et al., "EphB receptor activity suppresses colorectal cancer progression," *Nature*, 435(23):1126-1130 (2005).

Bennett, B. D. et al., "Molecular cloning of a ligand for the EPH-related receptor protein-tyrosine kinase Htk," *Proc. Natl. Acad. Sci. USA*, 92:1866-1870 (1995).

Bennett, B.D., et al., "Cloning and Characterization of *HTK*, a Novel Transmembrane Tyrosine Kinase of the EPH Subfamily," *The Journal of Biological Chemistry*, 269(19): 14211-14218 (1994).

Berclaz, G., et al., "Activation of the receptor protein tyrosine kinase EphB4 in endometrial hyperplasia and endometrial carcinoma," Ann. Oncol., 14:220-226 (2003).

Berclaz, G., et al., "Expression of the receptor protein tyrosine kinase myk-1/htk in normal and malignant mammary epithelium," Biochem Biophys Res Commun., 24;226:869-875 (1996).

Berclaz, G., et al., "Loss of EphB4 receptor tyrosine kinase protein expression during carcinogenesis of the human breast," Oncology Reports, 9(5):985-989, (2002).

Bergemann, A. D. et al., "ELF-2, a New Member of the Eph Ligand Family Is Segmentally Expressed in Mouse Embryos in the Region of the Hindbrain and Newly Forming Somites," *Molecular and Cellular Biology*, 15(9):4921-4929 (1995).

Bos et al., "PD153035, a Tyrosine Kinase Inhibitor, Prevents Epidermal Growth Factor Receptor Activation and Inhibitors Growth of Cancer Cells in a Receptor Number-dependent Manner," *Clinical Cancer Research*, 3:2099-2106 (1997).

Boyd, W.A., et al., "Isolation and Characterization of a Novel Receptor-type Protein Tyrosine Kinase (hek) from a Human Pre-B Cell Line," *The Journal of Biological Chemistry*, 267(5):3262-3267 (1992).

Brambilla, R., et al., "Membrane-bound LERK2 ligand can signal through three different Eph-related receptor tyrosine kinases," EMBO J., 14:3116-3126 (1995).

Brehmer et al., "Cellular Targets of Gefitinib," *Cancer Research*, 65(2):379-382 (2005).

Bruckner et al., "Tyrosine Phosphorylaton of Transmembrane Ligands for Eph Receptors," *Science*, 275:1640-1643 (1997).

Bruhl, T., et al., "Homeobox A9 Transcriptionally Regulates the EphB4 Receptor to Modulate Endothelial Cell Migration and Tube Formation," Circ. Res., 743-751 (2004) [Epub ahead of print] DOI 10.1161/01res0000120861.27064.09.

Caplen, N.J., "RNAI as a Gene Therapy Approach," Expert Opin. on Biol. Therapy, 3(4):575-586, (2003).

Carbone, M., et al., "The pathogenesis of mesothelioma," Semin. Oncol., 29(1):2-17 (2002).

Chang, M.W., et al., "Adenovirus-Mediated Over-Expression of the Cyclin/Cyclin-Dependent Kinase Inhibitor, p21 Inhibits Vascular Smooth Muscle Cell Proliferation and Neointima Formation in the Rat Carotid Artery Model of Balloon Angioplasty," *J. Clin. Invest.*, 96:2260-2268 (1995).

Cheng, N., et al., "The ephrins and Eph receptors in angiogenesis," Cytokine & Growth Factor Reviews, 13:75-85 (2002).

Coffman, K.T., et al., "Differential EphA2 Epitope Display on Normal versus Malignant Cells," *Cancer Research*, 63:7907-7912 (2003).

Cowan, C.A., et al., "Ephrins in reverse, park and drive," Trends in Cell Biology, 12(7):339-346 (2002).

Cromer et al., "Identification of genes associated with tumorigenesis and metastatic potential of hypopharyngeal cancer by microarray analysis," Oncogene, Basingstoke, Hants, GB, 23(14):2484-2498, (2004).

Davis, S., et al., "Ligands for EPH-related receptor tyrosine kinases that require membrane attachment or clustering for activity," Science, 266(5186):816-819 1994.

Dermer, G., "Another Anniversary for the War on Cancer," Bio/Technology, 12:320 (1994).

Dodelet, V.C. et al., "Eph Receptors and Ephrin Ligands: Embryogenesis to Tumorigenesis," *Oncogene*, 19(49): 5614-19 (2000).

Durbin, L., et al., "Eph signaling is required for segmentation and differentiation of the somites," *Genes & Development*, 12:3096-3109 (1998).

Easty et al., "Abnormal Protein Tyrosine Kinase Gene Expression During Melanoma Progression and Metastasis," *Int. J. Cancer*, 60:129-136 (1995).

Easty et al., "Cytokine B61 as a growth factor for metastatic melanomas and increasing expression of its receptor ECK during melanoma progression," *Proceedings of the American Association for Cancer Research*, 35(356) (1994) abstract only.

Easty, et al., "Expression of Eck and Lerk-1 During Melanoma Progression," P137 St. George's Hospital Medical School, London, JK and Western Infirmary, Glasgow, UK, Collection of the National Library of Medicine by a third party.

Fabes et al., "Accumulation of the Inhibitory Receptor EphA4 May Prevent Regeneration of Corticospinal Tract Axons Following Lesion," *Eur. J. Neurosci.*, 23(7):1721-1730 (2006).

Feldman, L.J., et al., "Perspectives of Arterial Gene Therapy for the Prevention of Restenosis," *Cardiovasc. Res.*, 32:194-207 (1996).

Folkman et al., "Angiogenic Factors," *Science*, 235:442-447 (1987).

Folkman, "Angiogenesis in cancer, vascular, rheumatoid and other disease," *Nature Medicine*, 1: 27-31, (1995).

Folkman, J. et al., "Blood Vessel Formation: What Is Its Molecular Basis?" *Cell*, 87:1153-1155 (1996).

Folkman, J., "Angiogenic Therapy of the Human Heart," *Circulation*, 97(7): 628-29 (1998).

Folkman, J., "Antiangiogenic Gene Therapy," *Proc. Natl. Acad. Sci. USA*, 95:9064-66 (1998).
Folkman, J., "Fighting Cancer by Attacking Its Blood Supply," *Sci. Am.*, 275(3): 150-54 (1996).
Freshney (Culture of Animal Cells, A Manual of Basic Technique, Alan R. Liss, Inc., 1983, New York, p. 4).
Fuller, T., et al., "Forward EphB4 signaling in endothelial cells controls cellular repulsion and segregation from ephrinB2 positive cells," J. Cell Sci., 116:2461-2470 (2003).
Gale, N.W. et al., "Growth Factors Acting Via Endothelial Cell-Specific Receptor Tyrosine Kinases: VEGFs, Angiopoietins, and Ephrins in Vascular Development," *Genes Dev.*, 13:1055-66 (1999).
Gale, N.W., et al., "Ephrin-B2 Selectively Marks Arterial Vessels and Neovascularization Sites in the Adult, with Expression in Both Endothelial and Smooth-Muscle Cells," *Dev. Biol.*, 230:151-160 (2001).
GenBank Acceisson No. P52803.
Gerety, S.S., et al., "Symmetrical mutant phenotypes of the receptor EphB4 and its specific transmembrane ligand ephrin-B2 in cardiovascular development," Mol. Cell, 4:403-414 (1999).
Glassberg et al., "Cultured endothelial cells derived from the human iliac arteries," *In Vitro*, 18:859-866 (1982).
Goetz et al., "Long-term serial cultivation of arterial and capillary endothelium from adult bovine brain," *In Vitro Cellular and Developmental Biology*, 21:172-180 (1985).
Gura, T., "Systems for Identifying New Drugs Are Often Faulty," *Science*, 278:1041-1042 (1997).
Guzman, R.J., et al., "In Vivo Suppression of Injury-Induced Vascular Smooth Muscle Cell Accumulation Using Adenovirus-Mediated Transfer of the Herpes Simplex Virus Thymidine Kinase Gene," *Proc. Natl. Acad. Sci. USA*, 91:10732-10736 (1994).
Hafner et al., "Differential Gene Expression of Eph Receptors and Ephrins in Benign Human Tissues and Cancers," *Clinical Chemistry*, 50(3):490-499 (2004).
Hafner, et al., "Loss of Eph B6 expression in metastatic melanoma," *International Journal of Oncology*, 23:1553-1559 (2003).
Hamada, K., et al., "Distinct roles of ephrin-B2 forward and EphB4 reverse signaling in endothelial cells," Arterioscler. Thromb. Vasc. Biol., 23:190-197 (2003).
Hausner, C., "Organogenesis Vascular Graft Becomes Physiologically-Responsive Living Tissue After Implantation [online]," *Nature Biotechnol.*, (1999).
Henkemeyer, M., et al., "Nuk Controls Pathfinding of Commissural Axons in the Mammalian Central Nervous System," *Cell*, 86:35-46 (1996).
Himanen, J.P. et al., "Eph signaling: a structural view," Trends in Neurosciences, 26(1):46-51 (2003).
Himanen, J.P., et al., "Eph receptors and ephrins," Intl. J. Biochem. & Cell Bio., 35:130-134 (2003).
Hirai, H., "A novel putative tyrosine kinase receptor encoded by the eph gene," Science, 238:1717-1720 (1987).
Inada et al., "Selective Expression of the Receptor Tyrosine Kinase, HTK, on Human Erythroid Progenitor Cells", Blood, 89(8), pp. 2757-2765 (1997).
Indolfi, C., et al., "Inhibition of Cellular ras Prevents Smooth Muscle Cell Proliferation After Vascular Injury in Vivo," *Nature Med.*, 1(6):541-545 (1995).
Kenyon, B.M., et al., "A Model of Angiogenesis in the Mouse Cornea," *Invest Ophthalmol. Vis. Sci.*, 37:1625-1632 (1996).
Keogh, M-C, et al., "Design of a Muscle Cell-Specific Expression Vector Utilising Human Vascular Smooth Muscle ?—Actin Regulatory elements," *Gene Therapy*, 6:616-628 (1999).
Kitamura et al., "Chemical Engineering of the Monoclonal Antibody A7 by Polyethylene Glycol for Targeting Cancer Chemotherapy," *Cancer Research*, 51:4310-4315 (1991).
Kiyokawa, E., et al., "Overexpression of ERK, an EPH family receptor protein tyrosine kinase, in various human tumors," Cancer Res., 54:3645-3650 (1994).
Kullander, K., et al., "Mechanisms and functions of eph and ephrin signalling," Nature Reviews, Molecular Cell Biology, 3:475-486 (2002).
Lackmann, et al., "Distinct Subdomains of the EphA3 Receptor Mediate Ligand Binding and Receptor Dimerization," *The Journal of Biological Chemistry*, 273 (32):20228-20237 (1998).
Li, J., et al., "Expression of the SM22x Promoter in Transgenic Mice Provides Evidence for Distinct Transcriptional Regulatory Programs in Vascular and Visceral Smooth Muscle Cells," *J. Cell Biol.*, 132:849-59 (1996).
Lin, P., et al., "Antiangiogenic Gene Therapy Targeting the Endothelium-Specific Receptor Tyrosine Kinase Tie2," *Proc. Natl. Acad. Sci., USA*, 95:8829-8834 (1998).
Magal, et al., "B61, a Ligand for the Eck Receptor Protein-Tyrosine Kinase, Exhibits Neurotrophic Activity in Cultures of Rat Spinal Cord Neurons," *Journal of Neuroscience Research*, 43:735-744 (1996).
Maru, et al., "Evolution, Expression, and Chromosomal Location of a Novel Receptor Tyrosine Kinase Gene, eph," *Molecular and Cellular Biology*, 8(9):3770-3776 (1998).
Maru, et al., "Overexpression confers an oncogenic potential upon the eph gene," *Oncogene*, 5:445-447 (1990).
Mellitzer, G., et al., "Control of cell behavior by signalling through Eph receptors and ephrins," Neurobiology, 10:400-408 (2000).
Mellitzer, G., et al., "Eph Receptors and Ephrins Restrict Cell Intermingling and Communication," *Nature*, 400:77-82 (1999).
Munarini, N., et al., "Altered mammary epithelial development, pattern formation and involution in transgenic mice expressing the EphB4 receptor tyrosine kinase," J. Cell Sci., 115(Pt 1):25-37 (2002).
Nakanuma, Y. et al., "Succinylated Wheat Germ Agglutinin Lectin Binding in Intrahepatic Vessels: A New Histochemical Tool," *Arch. Pathol. Lab. Med.*, 117:809-811 (1993).
Niklason, L.E., et al., "Functional Arteries Grown in Vitro," *Science*, 284:489-493 (1999).
Niklason, L.E., et al., "Morphologic and Mechanical Characteristics of Engineered Bovine Arteries," *J. Vasc. Surg.*, 33:628-638 (2001).
Nikolova, et al., "Cell-type specific and estrogen dependent expression of the receptor tyrosine kinase EphB4 and its ligand ephrin-B2 during mammary gland morphogenesis," *Journal of Cell Science*, 111:2741-2751 (1998).
Nomura, A.M., et al., "Prostate cancer: a current perspective," Epidemiol Rev., 13:200-227 (1991).
Ogle et al., "The Role of Vascular Smooth Muscle Cell Integrins in the Compaction and Mechanical Strengthening of a Tissue-Engineered Blood Vessel," *Tissue Engineering*, 5(4):387-402 (1999).
Orioli, D., et al., "Sek4 and Nuk Receptors Cooperate in Guidance of Commissural Axons and in Palate Formation," *Embo J.*, 15(22):6035-6049.
Pandey et al., "Role of B61, the ligand for the eck receptor tyrosine kinase, in TNF-a-induced angiogenisis" *Science*, 268:567-569 (1996).
Parangi et al., "Antiangiogenic therapy of transgenic mice impairs de novo tumor growth," *Proc. Natl. Acad. Sci. USA*, 93:2002-2007 (1996).
Pasquale, E.B., "The Eph family of receptors," Curr. Opin. Cell Biol., 9:608-615 (1997).
Peng et al., "Regulation of Ca2+-activated K+ channels in pulmonary vascular smooth muscle cells: role of nitric oxide," *J. Applied Physiol.*, 81:1264-1272 (1996).
Presta et al., "Humanization of an Anti-Vascular Endothelial Growth Factor Monoclonal Antibody for the Therapy of Solid Tumors and Other Disorders," *Cancer Research*, 57:4593-4599 (1997).
Ramchandran et al., Mettaloprotease-mediated cleavage secretion of pulmonary ACE by vascular endothelial and kidney epithelial cells,: *Am. J. Physiology*, 271:H744-751 (1996).
Risau, W., "Mechanisms of angiogenesis," *Nature*, 386:671-674 (1997).
Sakano, S., et al., "Characterization of a ligand for receptor protein-tyrosine kinase HTK expressed in immature hematopoietic cells," Oncogene., 13:813-822 (1996).
Santa Cruz Biotechnology, Inc., "EphB4 (N-19): sc-7285", retrieved from the Internet: URL:http://www.genetimes.com.cn/support/pdf-ds/7200-7299/sc-7285.pdf (1999).
Santa Cruz, "EphB4 (N-19): sc-7285," Product Catalog of Santa Cruz Biotechnology, Apr. 1999.

Schmucker, D., et al., "Signaling Downstream of Eph Receptors and Ephrin Ligands," Cell, 105:701-704 (2001).
Shepard, et al., "Monoclonal Antibody Therapy of Human Cancer: Taking the HER2 Protooncogene to the Clinic," *Journal of Clinical Immunology*, 11(3):117-127 (1991).
Shin, D., et al., "Expression of ephrinB2 identifies a stable genetic difference between arterial and venous vascular smooth muscle as well as endothelial cells, and marks subsets of microvessels at sites of adult neovascularization," Dev. Biol. 230:139-150 (2001).
Simonet, S., et al., "Venous and Arterial Endothelial Cells Respond Differently to Thrombin and its Endogenous Receptor Agonist," *European Journal of Pharmacology*, 216:135-137 (1992).
Simons, M., et al., "Antisense c-myb Oligonucleotides Inhibit Intimal Arterial Smooth Muscle Cell Accumulation in Vivo," *Nature*, 359(6390):67-70 (1992).
Sinha, et al., "Expression of EphB4 in head and neck squamous cell carcinoma" Ear, Nose and Throat Journal, 82(11), pp. 866-870 & 887 (2003).
Sinha, U.K., et al., "Expression of EphB4 in head and neck squamous cell carcinoma," ENT J 82:721-723 (2003).
Stein, E. et al., "Eph receptors discriminate specific ligand oligomers to determine alternative signaling complexes, attachment, and assembly responses," *Genes & Development*, 12:667-678 (1998).
Stein, E. et al., "Nck Recruitment to Eph Receptor, EphB1/ELK, Couples Ligand Activation to c-Jun Kinase," *The Journal of Biological Chemistry*, 273(3):1303-1308 (1998).
Steinle, J.J., et al., "Eph B4 receptor signaling mediates endothelial cell migration and proliferation via the phosphatidylinositol 3-kinase pathway," J. Biol. Chem., 277(46):43830-5 (Nov. 15, 2002) (Epub Sep. 13, 2002).
Stephenson, S.A., et al., "Receptor protein tyrosine kinase EphB4 is up-regulated in colon cancer," BMC Mol. Biol., 2:15 (2001).
Sturz, et al., "EphB4 signaling is capable of mediating ephrinB2-induced inhibition of cell migration," *Biochemical and Biophysical Research Communications*, 313:80-88 2004.
Sunassee, et al., "Tumour angiogenesis: Hitting cancer where it hurts," *Current Biology*, 7(5):R282-R285 (1997).
Takai, N., et al., "Expression of receptor tyrosine kinase EphB4 and its ligand ephrin-B2 is associated with malignant potential in endometrial cancer," Oncol Rep., 8:567-573 (2001).
Tallquist, M.D., et al., "Growth Factor Signaling Pathways in Vascular Development," *Oncogene*, 18(55):7917-7932 (1999).
Tang, X.X., et al., "Coexpression of transcripts encoding EphB receptor protein tyrosine kinases and their ephrin-B ligands in human small cell lung carcinoma," Clin. Cancer Res., 5:455-460 (1999).
The Eph Nomenclature Committee, "Unified Nomenclature for Eph Family Receptors and Their Ligands, the Ephrins," *Cell*, 90:403-404 (1997).
Thurston et al., "Permeability-related changes revealed at endothelial cell borders in inflamed venules by lectin binding," *American Journal of Physiology*, 271:H2547-H2562 (1996).
Tsui, L.V., et al., "p27-p16 Fusion Gene Inhibits Angioplasty-Induced Neointimal Hyperplasia and Coronary Artery Occlusion," *Circ. Res.*, 89:323-328 (2001).
Twardowski et al., "Clinical trials of antiangiogenic agents," *Current Opinion in Oncology*, 9:584-589 (1997).
van de Wiel et al., "Factors that define the susceptibility of endothelial cells to tumor necrosis factor and lipid A," *Immunopharmacology*, 23:49-56 (1992).
Vasgene Therapeutics, Inc., "Statement of Grounds of Opposition," In the Matter of European Patent No. 1135153 (EP-B-1135153), (2006).
Vector Laboratories, "Wheat Germ Agglutinin (WGA)," [online].
von der Leyen, H.E., et al., "Gene Therapy Inhibiting Neointimal Vascular Lesion: In Vivo Transfer of Endothelial Cell Nitric Oxide Synthase Gene," *Proc. Natl. Acad. Sci.*, 92:1137-1141 (1995).
Wang et al., "Molecular Distinction and Angiogenic Interactions Between Embryonic Arteries and Veins Revealed by EphrinB2 and Its Receptor EphB4," *Circulation: Melvin L. Marcus Young Investigator Award*, Abstract 341.
Wang, H. U. et al., "Eph Family Transmembrane Ligands Can Mediate Repulsive Guidance of Trunk Neural Crest Migration and Motor Axon Outgrowth," *Neuron*, 18:383-396 (1997).
Wang, H., "Transmembrane Ephrin Ligands in Neural and Vascular Development," DAI, 59(11): 5721 (1999).
Wang, H.U., et al., "Molecular distinction and angiogenic interaction between embryonic arteries and veins revealed by ephrin-B2 and its receptor Eph-B4," Cell 93:741-753 (1998).
Waugh, J.M., et al., "Thrombomodulin Overexpression to Limit Neointima Formation," *Circulation*, 102:332-337 (2000).
Winlaw, "Angiogenesis in the Pathobiology and Treatment of Vascular and Malignant Diseases," *Ann. Thorac. Surg.*, 64:1204-1211 (1997).
Xu, et al., "Function of the Eph-related kinase rtk1 in patterning of the zebrafish forebrain," *Nature*, 381:19-322 (1996).
Yamamoto et al., "Differences in Cellular Responses to Mitogens in Arterial Smooth Muscle Cells Derived From Patients With Moyamoya Disease," *Stroke*, 29:1188-1193 (1998).
Yancopoulos, G. D. et al., "Vasculogenesis, Angiogenesis, and Growth Factors: Ephrins Enter the Fray at the Border," Cell, 93:661-664 (1998).
Yang et al, "Gene Targets of Antisense Therapies in Breast Cancer," Expert Opin. on Therapeutic Targets, 6(3):375-385, (2002).
Yuan, et al., "Syndecan-1 up-regulated by ephrinB2/EphB4 plays dual roles in inflammatory angiogenesis," *Blood*, 104(4):1025-1033 (2004).
Zetter, "Angiogenesis and Tumor Metastasis," *Annu. Rev. Med*, 49:407-424, (1998).
Zhang, X-Q, et al., "Stromal Cells Expressing ephrin-B2 Promote the Growth and Sprouting of Ephrin-B2+ Endothelial Cells," *Blood*, 98:1028-37 (2001).
Zhou, "The Eph Family Receptor and Ligands," *Pharmacol. Ther.* ,77(3) 151-181 (1998).
Bowie et al., "Deciphering the message in protein sequences: tolerance to amino acid substitutions," Science, vol. 247(4948), pp. 1306-1310 (1990).
Burgess et al., "Possible dissociation of the heparin-binding and mitogenic activities of heparin-binding (acid fibroblast) growth factor-1 from its receptor-binding activities by site-directed mutagenesis of a single lysine residue," Journal of Cell Biology, vol. 111, pp. 2129-2138 (1990).
Genetech's Response to Final Office Action on U.S. Appl. No. 09/442,898, filed Mar. 29, 2002.
Gill, P.S., et al., "Epidemic (AIDS-related) Kaposi's sarcoma: Epidemiology pathogenesis and treatment," AIDS Updates, (7) 1-11 (1994).
He et al., "The Effect of Soluble EphrinB4 Receptor on Laser-Induced Choroidal Neovascularization," *IOVS*, 45:U804 (2004).
Leger et al., "Identification of CJC-1131-Albumin Bioconjugate as a Stable and Bioactive GLP-1/7-36 Analog," Biorganic & Med. Chem. Ltrs 14:4395-4398 (2004).
Noren et al., The EphB4 receptor suppresses breast cancer cell tumorigenicity through an Abl-Crk pathway, Nature Cell Bio. 8:815-825 (2006).
Noren et al., "Interplay Between EphB4 on Tumor Cells and Vascular Ephrin-B2 Regulates Tumor Growth," *Proceedings of the National Academy of Sciences of USA, National Academy of Science*, 101(15):5583-5588 (2004).
R&D systems. Recombinant Mouse EphB4/Fc chimera. Nov. 14, 2000. p. 1.
Sola et al., "Transgenic Mice Secreting Coronavirus Neutralizing Antibodies into the Milk", Journal of Virology, vol. 72(5), pp. 3762-3772 (1998).
Xia et al., "Up-Regulation of EphB4 in Mesothelioma and Its Biological Significance", Clinical Cancer Research, vol. 11(12), pp. 4305-4315 (2005).
Seffernick et al., "Melamine Deaminase and Atrazine Chlorohydrolase: 98 Percent Identical but Functionally Different", Journal of Bacteriology, vol. 183(8), pp. 2405-2410 (2001).
Santa Cruz Biotechnology Inc datasheet for EphB4 (H-200): sc-5536.
Miki et al., "Association of Ash/Grb-2 with Dynamin through the SrC Homology 3 Domain", The Journal of Biological Chemistry, vol. 269(8); pp. 5489-5492 (1994).

Bennett et al., "Extracellular Domain-IgG Fusion Proteins for Three Human Natriuretic Peptide Receptors," The Journal of Biological Chemistry, vol. 266(34), pp. 23060-23067 (1991).

Kiessig et al., "Application of a green fluorescent fusion protein to study protein-protein interactions by electrophoretic methods," Electrophoresis, vol. 22, pp. 1428-1435 (2001).

Perrin et al., "Expression, Purification, and Characterization of a Soluble Form of the First Extracellular Domain of the Human Type 1 Corticotropin Releasing Factor Receptor," The Journal of Biological Chemistry, vol. 276(34), pp. 31528-31534 (2001).

Benjamini et al., Immunity, A Short Course, 2nd Ed., Wiley-Liss pub. p. 40 (1992).

Breier et al., Angiogenesis in Embryos and Ischemic Diseases, Thrombosis and Haemostosis 78(1):678-683 (1997).

Chrencik et al., Three-dimensional Structure of the EphB2 Receptor in Complex with an Antagonistic Peptide Reveals a Novel Mode of Inhibition, J. Biol. Chem. 282: 36505-36513 Sep. 26, 2007 Epub.

Fox et al., Invasiveness of breast carcinoma cells and transcript profile: Eph receptors and ephrin ligands as molecular markers of potential diagnostic and prognostic application, Biochim. Biophys. Res. Comm. 318(4):882-892 (2004).

Magal et al., Rapid Communication: B61, a Ligand for the Eck Receptor Protein-Tyrosine Kinase, Exhibits Neuroptrophic Activity in Cultures of Rat Spinal Cord Neurons, J. Neuroscience Res. 43:735-744 (1996).

Staton et al., Current Methods for Assaying Angiogenesis in vitro and in vivo, Int. J. Exp. Path. 85:233-248 (2004).

Wang, Eph tumour suppression: the dark side of Gleevec, Nat. Cell Biol. 8(8):785-786 (2006).

Xu et al., Eph-related receptors and their ligands: mediators of contact dependent cell interactions, J. Mol. Med. 75:576-586 (1997).

Himanen et al., Crystal structure of the ligand-binding domain of the receptor tyrosine kinase EphB2, Nature 396:486-491 (1998).

Holder and Klein, Eph Receptors and ephrins: effectors of morphogenesis, Development 126(10):2033-2041 (1999).

Kashiwa-Kawai, A variant transcript encoding a soluble truncated form of the human Eph receptor family tyrosine kinase, EphB4v is generated by alternative splicing, Scientific Reports of Meiji Seika Kaisha, 1998, vol. 37 abstract.

Kertesz et al., "The soluble extracellular domain of EphB4 (sEphB4) antagonized EphB4-EphrinB2 interaction, modulates angiogenesis, and inhibits tumor growth," Blood 107(6):2330-2338 (2006).

* cited by examiner

Amino acid sequence of the B4ECv3 protein

MELRVLLCWASLAAALEETLLNTKLETADLKWVTFPQVDGQWEELSG
LDEEQHSVRTYEVCEVQRAPGQAHWLRTGWVPRRGAVHVYATLRFTM
LECLSLPRAGRSCKETFTVFYYESDADTATALTPAWMENPYIKVDTV
AAEHLTRKRPGAEATGKVNVKTLRLGPLSKAGFYLAFQDQGACMALL
SLHLFYKKCAQLTVNLTRFPETVPRELVVPVAGSCVVDAVPAPGPSP
SLYCREDGQWAEQPVTGCSCAPGFEAAEGNTKCRACAQGTFKPLSGE
GSCQPCPANSHSNTIGSAVCQCRVGYFRARTDPRGAPCTTPPSAPRS
VVSRLNGSSLHLEWSAPLESGGREDLTYALRCRECRPGGSCAPCGGD
LTFDPGPRDLVEPWVVVRGLRPDFTYTFEVTALNGVSSLATGPVPFE
PVNVTTDREVPPAVSDIRVTRSSPSSLSLAWAVPRAPSGAWLDYEVK
YHEKGAEGPSSVRFLKTSENRAELRGLKRGASYLVQVRARSEAGYGP
FGQEHHSQTQLDESEGWREQGSKRAILQIEGKPIPNPLLGLDSTRTG
HHHHHH

Fig. 1

Amino acid sequence of the B4ECv3NT protein

MELRVLLCWASLAAALEETLLNTKLETADLKWVTFPQVDGQWEELSGL
DEEQHSVRTYEVCEVQRAPGQAHWLRTGWVPRRGAVHVYATLRFTMLE
CLSLPRAGRSCKETFTVFYYESDADTATALTPAWMENPYIKVDTVAAE
HLTRKRPGAEATGKVNVKTLRLGPLSKAGFYLAFQDQGACMALLSLHL
FYKKCAQLTVNLTRFPETVPRELVVPVAGSCVVDAVPAPGPSPSLYCR
EDGQWAEQPVTGCSCAPGFEAAEGNTKCRACAQGTFKPLSGEGSCQPC
PANSHSNTIGSAVCQCRVGYFRARTDPRGAPCTTPPSAPRSVVSRLNG
SSLHLEWSAPLESGGREDLTYALRCRECRPGGSCAPCGGDLTFDPGPR
DLVEPWVVVRGLRPDFTYTFEVTALNGVSSLATGPVPFEPVNVTTDRE
VPPAVSDIRVTRSSPSSLSLAWAVPRAPSGAWLDYEVKYHEKGAEGPS
SVRFLKTSENRAELRGLKRGASYLVQVRARSEAGYGPFGQEHHSQTQL
DESEGWREQGSKRAILQISSTVAAARV

Fig. 2

Amino acid sequence of the B2EC protein

MAVRRDSVWKYCWGVLMVLCRTAISKSIVLEPIYWNSSNSKFLPGQGL
VLYPQIGDKLDIICPKVDSKTVGQYEYYKVYMVDKDQADRCTIKKENT
PLLNCAKPDQDIKFTIKFQEFSPNLWGLEFQKNKDYYIISTSNGSLEG
LDNQEGGVCQTRAMKILMKVGQDASSAGSTRNKDPTRRPELEAGTNGR
SSTTSPFVKPNPGSSTDGNSAGHSGNNILGSEVGSHHHHHH

Fig. 3

Amino acid sequence of the B4ECv3-FC protein

MELRVLLCWASLAAALEETLLNTKLETADLKWVTFPQVDGQWEEL
SGLDEEQHSVRTYEVCEVQRAPGQAHWLRTGWVPRRGAVHVYATL
RFTMLECLSLPRAGRSCKETFTVFYYESDADTATALTPAWMENPY
IKVDTVAAEHLTRKRPGAEATGKVNVKTLRLGPLSKAGFYLAFQD
QGACMALLSLHLFYKKCAQLTVNLTRFPETVPRELVVPVAGSCVV
DAVPAPGPSPSLYCREDGQWAEQPVTGCSCAPGFEAAEGNTKCRA
CAQGTFKPLSGEGSCQPCPANSHSNTIGSAVCQCRVGYFRARTDP
RGAPCTTPPSAPRSVVSRLNGSSLHLEWSAPLESGGREDLTYALR
CRECRPGGSCAPCGGDLTFDPGPRDLVEPWVVVRGLRPDFTYTFE
VTALNGVSSLATGPVPFEPVNVTTDREVPPAVSDIRVTRSSPSSL
SLAWAVPRAPSGAWLDYEVKYHEKGAEGPSSVRFLKTSENRAELR
GLKRGASYLVQVRARSEAGYGPFGQEHHSQTQLDESEGWREQDPE
PKSCDKTHTCPPCPAPELLGGPSVFLFPPKPKDTLMISRTPEVTC
VVVDVSHEDPEVKFNWYVDGVEVHNAKTKPREEQYNSTYRVVSVL
TVLHQDWLNGKEYKCKVSNKALPAPIEKTISKAKGQPREPQVYTL
PPSRDELTKNQVSLTCLVKGFYPSDIAVEWESNGQPENNYKTTPP
VLDSDGSFFLYSKLTVDKSRWQQGNVFSCSVMHEALHNHYTQKSL
SLSPGK

Fig. 4

Amino acid sequence of the B2EC-FC protein

MAVRRDSVWKYCWGVLMVLCRTAISKSIVLEPIYWNSSNSKFLPGQ
GLVLYPQIGDKLDIICPKVDSKTVGQYEYYKVYMVDKDQADRCTIK
KENTPLLNCAKPDQDIKFTIKFQEFSPNLWGLEFQKNKDYYIISTS
NGSLEGLDNQEGGVCQTRAMKILMKVGQDASSAGSTRNKDPTRRPE
LEAGTNGRSSTTSPFVKPNPGSSTDGNSAGHSGNNILGSEVDPEPK
SCDKTHTCPPCPAPELLGGPSVFLFPPKPKDTLMISRTPEVTCVVV
DVSHEDPEVKFNWYVDGVEVHNAKTKPREEQYNSTYRVVSVLTVLH
QDWLNGKEYKCKVSNKALPAPIEKTISKAKGQPREPQVYTLPPSRD
ELTKNQVSLTCLVKGFYPSDIAVEWESNGQPENNYKTTPPVLDSDG
SFFLYSKLTVDKSRWQQGNVFSCSVMHEALHNHYTQKSLSLSPGK

Fig. 5

B4EC-FC binding assay (Protein-A-agarose based)

B4EC-FC inhibition assay (inhibition in solution)

B2EC-FC binding assay (Protein-A-agarose based assay)

hEph B4 constructs

| VECTOR | DETAILS | |
|---|---|---|
| pET15b | E.coli | |
| pET15b | E.coli | |
| pGEX | E.coli | |
| pGEX | E.coli | |
| pEF6 | Mammalian, Blasticidin S, EF1a promoter | |
| pEF6 | Mammalian, Blasticidin S, EF1a promoter | |
| pAPtag-2 | Mammalian, CMV promoter | |
| pAPtag-2 | Mammalian, CMV promoter | |
| pAPtag-2 | Mammalian, CMV promoter | |
| pRK5 | Mammalian, CMV promoter | |
| pcDNA3 | Mammalian, G418 CMV promoter | |
| pEF6 | Mammalian, Blasticidin S, EF1a promoter | |
| pEF6 | Mammalian, Blasticidin S, EF1a promoter | |
| pEF6 | Mammalian, Blasticidin S, EF1a promoter | |
| pEF6 | Mammalian, Blasticidin S, EF1a promoter | |
| pEF6 | Mammalian, Blasticidin S, EF1a promoter | |
| pIG-Fc | Mammalian, CMV promoter transient | |
| pIG-Fc | Mammalian, CMV promoter transient | |

Legend: IgG Fc, GST, V5 tag, leader peptide or TM, His tag, AP, hB2, myc tag — 1 kb

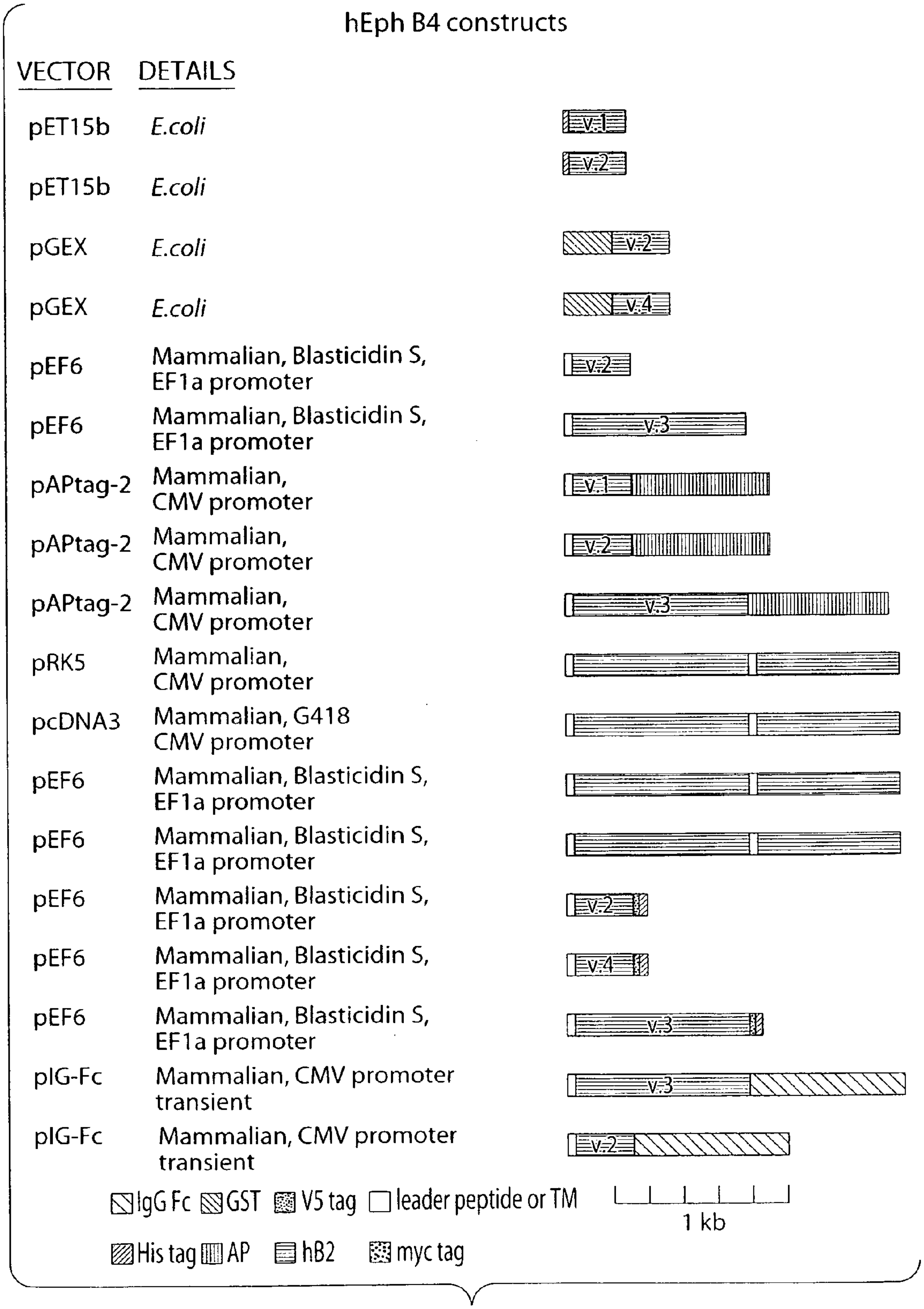

Fig. 15

Purification and ligand binding properties of the EphB4EC proteins

Binding of Ephrin B2-AP fusion to EphB4-derived recombinant proteins immobilized on NTA-agarose beads EPHB4 staining in prostate tissues array

| | negative | positive |
|---|---|---|
| Normal (n = 20) | 17 | 3 |
| Tumor (n = 32) | 8 | 24 |

P = 3.8 x $10^{-5}$ $\chi^2$ analysis

Migration Study of H28 with siRNA472(Boyden Chamber)

Transfection of p53 inhibit the expression of EPHB4 in 5637 cell

Growth inhibition of bladder cancer cell line(5637) upon treatment with EPHB4 siRNA 472

Invasion study of 5637 cell transfected with siRNA 472 or control siRNA

EphB4 gene

```
   1 ggggtttcat catgttggcc aggctggtct tgaactcctg acctcaaatg atccgcctgc
  61 ctctgcctcc caaaatgctg ggactacagg cgtgagccac cgcgcccgcc acacccacct
 121 tttctttacc gttgtttcct cgatttttct ctactcccta gcgcagctta gtgcgcgcct
 181 cctctggaca tttttcaggg cttggttgcg cgcacagtag gtccccaaca ctgaatgttt
 241 atggggtgac tgtgtgaacg ttcgctgcaa ggctatccaa actgggattg ctccttgagg
 301 cccccctgggc ggccgtcaat tctccaaagc ttctactccc ttttccttcc ttttccccca
 361 aaacgcagtc cctgcgccca ctagagggtg gtgggcgcat ccaagagcgg catctagagt
 421 ccgcagcaag gtcagagcgg gctttgtgtg cgcggtgaac atttacgtgc acgcctgggc
 481 ggccctccgt gttgctgctg ggtgtgtgtt ttctctgctc cctggtgcca gccgggttcg
 541 ggcctgtccc gggggtccct gggccccagc cccgacatgc tcggtcctgg acagcgcgca
 601 ccgccacggc gcacatctgg gcggtcccgg ggttcctcac ccgccgcccc tccccccttct
 661 ccaaactttc tctcaacttc ccgacctgct ccactcggtg cccctctccg cttccctcat
 721 gaattattca gtagcgtgag ctccaatcag cgcgcccggg gctcactcgc ggagcccccg
 781 cgttgggaga gctgcccccg cccccgcgc gcccctccct cccgggcccg gcgccgcccg
 841 gcccagttcc agcgcagctc agcccctgcc cggcccggcc cgcccggctc cgcgccgcag
 901 tctccctccc tcccgctccg tccccgctcg ggctcccacc atccccgccc gcgaggagag
 961 cactcggccc ggcggcgcga gcagagccac tccagggagg gggggagacc gcgagcggcc
1021 ggctcagccc ccgccacccg gggcgggacc ccgaggcccc ggagggaccc caactccagc
1081 cacgtcttgc tgcgcgcccg cccggcgcgg ccactgccag cacgctccgg gcccgccgcc
1141 cgcgcgcgcg gcacagacgc ggggccacac ttggcgccgc cgcccggtgc cccgcacgct
1201 cgcatgggcc cgcgctgagg gccccgacga ggagtcccgc gcggagtatc ggcgtccacc
1261 cgcccaggga gagtcagacc tgggggggcg agggcccccc aaactcagtt cggatcctac
1321 ccgagtgagg cggcgccatg gagctccggg tgctgctctg ctgggcttcg ttggccgcag
1381 ctttggaagg tgagtttcct tgcggggggg ggcgcacccc gtcactcctg ggacctcccc
1441 cccaacatct gggcctcgga gtggaggggc cggcctctga ctacccctac ccgggcactg
1501 cagtcccaaa cacttcggac cgatagtgct ggaacgggag gggggcgggg aagaggcgcc
1561 cgacgggtag tggagttttc ttttgtttgg gaaagagatg gagtctggct acgacccggg
1621 acattcccct gcccgggctc cccgaactct cactgctgat tacatacgcc cctggctgcc
1681 tttcctttcc tccctacccc actattcaaa actatctgca aagtttctgt cccagtccca
1741 cctcccgccg tacatgaggg aaggtttctg gagaagcaac agcagacaag gcacaacttt
1801 tcgtgctagg ccctaaaacg acccccagcg ccaattcctt agcgatcaca ccttgatcct
1861 ccagttccac actcctgcaa caggatggcc tcctttgcat tcacacagca aaccccccaaa
1921 ccgctctccc gcccactgct cctgcccctg gtatagggtg gctccttggt ttctacaggc
1981 tgcaccccat ccctttaaat gcggtctaga ccccggcccc aggtgagtcc cgggcttccc
2041 ttgagaccta ggagcgggta gaaactgacc tacacagccc ccaggtagaa actgacctac
2101 acagccccca catcgcccta actaacccag tctatctccc acctcctggt ctctccaagc
2161 atttctttgg ccatggatcg ctgtccctcc tggtccccta aagggggagc caagagccct
2221 agaaactctc ctgtgtccct aatgtccttt cagtgagctg ccaacacccc cctttctctg
2281 tctggtatga aagtggttat ggggcggtag gctatgaggg actcccaaag ggaaggattc
2341 agcggcgtta gaaaaaccct ctccccctgg ctgggcagga ctgccctggg ctggggatca
2401 aaggctaggt gtggggttgg gagtgagggg aggcttgccc agctcagaga acggagaagg
2461 gggaacaaaa accatgaacg aggggaagag gaaggccaaa ggggtggaaa aaccacgagg
2521 acgaggtgtg gtgagaagga aagacgcaaa gaggaaatgg tgattgtgac acctattacc
2581 tgagtgtttc caagcaccag gcctgtgctg agcgccttac aaatattaat ttcacccatc
```

Fig. 61A

```
2641 cagcaacgct aagggtggtg ctattattgc ccccattttt cagatgagga ggctggggct
2701 tagttaaggt taagtagttt atccaaggcc ctgtgccgcg aggaacagcg agaagtggag
2761 gccgaaagcg aaggagagat agtgactgtc agaaagagaa acggaggtgg acagagagtg
2821 gaggagagat aggtgagaga catgcgaact gacagatcaa agcgtggctg cagctgagct
2881 gggacgcaga aagggagcct gcgcttgctc tgggctgcgg acagcccgag gcagagacag
2941 tgtgtaaatt ggagacagga aaacactatc ccggctggaa caatggaggg tggagacggc
3001 agcctctatc cacccccttc ccagaacccg ggcatcctgt ccccagtgag cagggctgtc
3061 tcttgccacc catggggacc ttgcgcctct cacctcaggc tggctggctt cccatctgac
3121 ccctagctgg aggacatcat ttggtcccca ggaagaggct gcctcaccca ccctctttct
3181 cttctctcct gcagctccca tggggtggga gccaggtgtt ctggctcccc tctccaccct
3241 tcccagcgcc caatgccccc cacattgccg gcccccgagg ggattcctgt accctccctc
3301 ctccactctc cactgccagg ggctgtgcag tttttcctaa tcccccccct tcctccagtg
3361 cctgtcccct cccccgatga tccgagccaa gccaggtgtg ttcacccctc ccattcatac
3421 cgccccccag aatctcctcc cctctgcctt cccataacca aatccagatg tgaggcctcg
3481 gcgggagcct gggaacccta gcatcccgac ctccagtgct tcctgatcag ggcactcgtg
3541 gggagggagg tactgggatg gggggccaggg ctatgcccca ggcacggagc gctcccttca
3601 aggagggaag gacggggtgt ttggtctgaa agcagagagg ggtcttggac agggaatgaa
3661 attgtggggt agagaggctg attctgggac ttaggggagg aaacgtggag gctgagacaa
3721 gaggttcccc tcccacacca gcagcctctg ctcgtggggg tcaggaccag ggcgcagctc
3781 tcattttaac cctttctgag ctgccgcccc ttctccccgt acattttgat ctccctccct
3841 cctccaggga ggcctagatc tggggtatcc caagggagcc ccatgcctac cagatgttgg
3901 gggtggggtt ggcacttagc agaagaggcc agaaatcagg cgggtgcaga gggcagggct
3961 tgctcccctc ttggcccccc aactcctcta gctcagagct aagaggatcc acctgcctcg
4021 gttcccaggg atctggtctt cctgacctcc ctcccccacc ccaggcactg actctgtctc
4081 tctgtctgtc tcagagaccc tgctgaacac aaaattggaa actgctgatc tgaagtgggt
4141 gacattccct caggtggacg ggcaggtgag agctgcaccc aggagctgga gctctggagg
4201 gaaactgagg gaggagaggg cgcctgtgcc gcctgctttc tgtgtgccac tcctctcccc
4261 tgtcccccca gatgacagca gccccagcag tgtcgtctga gcccttctca gaggcgccct
4321 cctcgcagta ccagcagccc ccctttctca gtccctctca ctttatagga ttcaccccat
4381 gcagccctct ccctggcggc tccccagccc ccttgctgac ctccttctct gcacagtggg
4441 aggaactgag cggcctggat gaggaacagc acagcgtgcg cacctacgaa gtgtgtgacg
4501 tgcagcgtgc cccgggccag gcccactggc ttcgcacagg ttgggtccca cggcggggcg
4561 ccgtccacgt gtacgccacg ctgcgcttca ccatgctcga gtgcctgtcc ctgcctcggg
4621 ctgggcgctc ctgcaaggag accttcaccg tcttctacta tgagagcgat gcggacacgg
4681 ccacggccct cacgccagcc tggatggaga acccctacat caaggtacct gggtgccccc
4741 agggctcagc cacagccaag gtgggattcc agccagcagg cccgtggcct ggagggcagc
4801 cgatgtagtt gcgaggcctc tggcccgcgc gctgggggct ggaagcagga ggcttaggtc
4861 tggggaggga agggggtgat cttctgggcg gaggagcaga atatacgggg gctgcctggc
4921 ccggccccca gggaggccca agggtcaggc ttctcctcca gtcacctcaa ccaccctacc
4981 ccactgtgct ccagccacac tgagtttctc ccattccctg actgcacctg gctggtttcc
5041 agctcaagac tttgcagcgg tgatgtctcc acctgggggc ctctctgcct ctcacacccc
5101 tacttgtctt cggagttcca gctcccgaga tcttgcctgt gccaccttgg ctgactctct
5161 cctccctaca atcctgcata cctctgtcca cctgcctgtc tcggcactca ttttacttta
5221 tttatttttc ttttatatct atatttttaa agcggggtct tctacgttac ccaggctggt
```

Fig. 61B 5281 ctctaactcc tgggctcaag agatttctcc cacctcggcc tcctaaagtg ctgggattat
5341 aggcatgagg cactacgccc ggcctcatgg tactttataa cttccccagg attcattcat
5401 cgctgtctcc ttgactctga ggtcaaggcc tggcatggcg tcagtgtcag taaatgtttg
5461 tagaacgagt gaataaaaag gggagaggt gcaggccaga ggccgggcat atcgcaggag
5521 ctttgcaagg ctgaatggac agtgtggggg cctgcagaaa gtgtgccctg gggaaggtgg
5581 agggaagatt ctggaacggg aaccaaggag gtccgggagg gtgagctggg aagaacacaa
5641 cagtccgctg ggtcctcagg gagtggggac agcagcggtg tgcctccccc ccgccggcag
5701 gtggacacgg tggccgcgga gcatctcacc cggaagcgcc ctggggccga ggccaccggg
5761 aaggtgaatg tcaagacgct gcgtctggga ccgctcagca aggctggctt ctacctggcc
5821 ttccaggacc agggtgcctg catggccctg ctatccctgc acctcttcta caaaaagtgc
5881 gcccagctga ctgtgaacct gactcgattc ccggagactg tgcctcggga gctggttgtg
5941 cccgtggccg gtagctgcgt ggtggatgcc gtccccgccc ctggccccag ccccagcctc
6001 tactgccgtg aggatggcca gtgggccgaa cagccggtca cgggctgcag ctgtgctccg
6061 gggttcgagg cagctgaggg gaacaccaag tgccgaggtg agagctggag cttcccctgc
6121 gactgctgct catccggggg agagtcctga actccactca ggacccactt cttaagtttc
6181 cattttgtat agttagatgt tgaaatggag gcttgctctg tcacccaggc tggagtgcag
6241 tggcacaatc tctgctcaac tgcaaccttt gcctcccggg tccctgttca agcagttctc
6301 ctgcctcagc ctcgtgagta gctgggacta caggcacacg ccaccacgcc cggctaattt
6361 ttgtatttta gtagagacgg ggtttcgcca tgttggccag gctggtctcg aactcctgac
6421 ctgaagtgat ttgcccgcct cggcctccca aagtgctggg attacaggcg tgcgtcacca
6481 cacccagctg gaaaaaaaaa agactttatt ttcacctgaa attcattaat ttccacttga
6541 aattccacct gcagttgtag caggacctga cacttgggcc ccatggaaat cacaggtatt
6601 gcctgacaca gtggttcatg cccatagtgc cagcactttg agatgccaag gtgggaggat
6661 cacttgagcc caggagttcg agatcagcct gggtgacaga gcaagacccc gtctctaaaa
6721 aaaatttttt tttttttttc aagacagagt cttgctctgt cgcccaggct ggagtgcagt
6781 ggtgcgatct cggctcactg caagctccgc ctcccaagtt aacaccattc tcctgcctca
6841 gcctcccgag tagctgggac tacaggcccc gccaccacgc ccggctaatt tcttgtattt
6901 ttagtagaga tggagtttca ccgtgttagc caggatggtc tcgatctcct gacctcatga
6961 tctgcccgcc ttggcctccc aaagtgctgg gattacaggt gtgagccacc acacccggat
7021 tacaaaaact ttttagataa ttatctgggc gacctgcctg accaacatgg agaaaccctg
7081 tctctactaa aaatacaaaa ttagccggac atggtggcgc atgcctgtaa tcccagctac
7141 ttgggaggct gaggcaggag aatcatttga acccaggaag cagaggttgc ggtaagccga
7201 gatcatgcca ctgcactccg gtctgggagt gcactccaac aagaaggagt ttcgctcttt
7261 ttgcccaggc tggagtgcag tggtgggatc tcagctcacc gcaacctcca cctcccgggt
7321 tcaggcgatt ctcctgcctc agcctcccaa ggagtagctg ggattatagg tatgcatcgt
7381 cacacccggc tacttttgta tttttagtag aggcaggttt ccaccatgtt ggccaggctg
7441 gtcttgaact caagtgatct gccctctttg gcctccttct caggaaaaaa aaaaaatcac
7501 aggtatttac aggccattcc aagtgccaaa agattgtttt tgctcatggt gacttcagta
7561 tcacagatgt taggagactt gctgctatat gttaagaaag aagcacaaat gttgctgtag
7621 cccaaacttt tttcctcatg tttcattgca tttcagctta attggtttcc ctggtattcc
7681 tatgtatttt gtggagtgct tttaaaatca taagttggag tagaggtctt tctgtgggct
7741 tcaccagact gccgagatca gggtcgaaac aggtgaggac cccttctctg gagagagtct
7801 cctttctcct ctaagaggaa aggttttgag atcttttgtc cattttccca ccttagcact
7861 tcatcagcct taaaagaagc tggaattttt tttttttttt ttggagatgg gatctcgata

Fig. 61C

```
7921  tgttgcccag gctggtcttg aacccettgg ctcaagcgat cctccagcct cagcctccca
7981  aagtgctggg attcgaggca tgagccaccg agcccaccgt gcagatggat gtttttgtgc
8041  atgcttttga tgaatgcttt ctctctctca gcctgtgccc agggcacctt caagcccctg
8101  tcaggagaag ggtcctgcca gccatgccca gccaatagcc actctaacac cattggatca
8161  gccgtctgcc agtgccgcgt cgggtacttc cgggcacgca cagacccccg gggtgcaccc
8221  tgcaccagta agtgaccagc acccaggtgc agttcactgg ggaggggtca cagacctctg
8281  aggtggaccc tcacatggcc cccatcctcc ctgggcttct tccctttgtc cctggcatgc
8341  ttgtccctag cccggaggaa catgtggagc ccactgtctc caaggcaaga gtccagcatg
8401  gctgctggtg cctccattgc cctctcccca ccaccgcaga gcaggtcggc ctctgcctga
8461  ctccctggtc tcctgcagcc cctccttcgg ctccgcggag cgtggtttcc cgcctgaacg
8521  gctcctccct gcacctggaa tggagtgccc ccctggagtc tggtggccga gaggacctca
8581  cctacgccct ccgctgccgg gagtgccgac ccggaggctc ctgtgcgccc tgcgggggag
8641  acctgacttt tgaccccggc ccccgggacc tggtggagcc ctgggtggtg gttcgagggc
8701  tacgtcctga cttcacctat acctttgagg tcactgcatt gaacggggta tcctccttag
8761  ccacggggcc cgtcccattt gagcctgtca atgtcaccac tgaccgagag ggtgagactt
8821  gggggctggg gcggctggtg gtctggcggg agagatgtca ctgagggcct gaaggggaga
8881  ggcaggggct gtgaagttgg gtaccccgga agtgtgaggg gctaaggctt tgggggcaag
8941  aggcagaaag agggcaatgg ctgggcgcag tggctcacgc ctgtaatccc agcactttca
9001  gaggctgaga caggcggatc acttgagccc tggagttcaa gaccagcctg ggtaacatag
9061  gaagatctct ctacaaaaaa taaaaatatt agccaggcga ggtggtgcat gcctgtggtc
9121  ccagctactc aagaggctga ggcaggagga ttgcttgagc ccaggagtcg gaggctgcag
9181  tgagctatga tcgcaccgct gcatgccagc ctgggtgaca gagcagtgtg agatcctctc
9241  tcaaaataaa tgaataagaa agagagggtg aggagctcgt aaagctgggc tggagagtta
9301  agtacaggaa ggcccccagt gggactgggg ccagagagaa tcagaaggaa ttctcgaaac
9361  agccaggggg aaattgagac aagtgtagcc agcagaggaa gtgttggaaa agataaggga
9421  catggccagg ctgatcacaa ggtcaggagt tcaagactag cctggccaac gtggtgaaac
9481  cccatgtcta ctaaaaataa aaaaattagc caggcatggt ggtgggcacc tgtaatccac
9541  ttgggaagca accagaagaa ttgcttgaac ccaggaggcg gaggttgcag taagctgaga
9601  ctgcgccact gcactccagc ctgggtgata gagcacgact ccgtctcgaa aaaaaaaatt
9661  ttttttaagt taagggacag agctaccatg cacaagggtt ccctgtgtct ctgcctctca
9721  cagtacctcc tgcagtgtct gacatccggg tgacgcggtc ctcacccagc agcttgagcc
9781  tggcctgggc tgttccccgg gcacccagtg ggctgtgct ggactacgag gtcaaatacc
9841  atgagaaggt aaggccatcc cccagccctg gggtgggtgg gcaatgggtt gtgctctcct
9901  ggctgggaca cctgggttgc aggcacctgg caggcatttg aattccagct ctgccatgga
9961  ttccctgggc agccttgggt aagcccttg gcctgtctga gcctcagact cttcatctat
10021 aaaatagtta ctgtaatagt taccagcagc tggacacagt ggctgaggtt gggtgcggtg
10081 gctcacgcct gtaataccaa gcactttggg aggctgaggc gggcagaatg cttgagccta
10141 ggagtttgag accagcctgg gcaacatggt gaaacttcat ctctataaaa aacttaaaat
10201 gggccgggcg cggtagctta cgcctgtaat cccagcactt tgggaggccg aggtgggcgg
10261 atcacaaggt caggagtatc gagaccatcc tggctaacac ggtgaaaccc catctctact
10321 aaaaatacaa aaaattagcc aggcgcggtg gcaggcgcct gtagtcccag ctactcggga
10381 ggctgaggca ggagaatggc gtgaacccag gaggcggagc ttgcagtgag ccgagatagc
10441 gccactgcag tccggcctgg gcgaaagaac aagactctgt ctccaaaaaa aaaaaaaaaa
10501 aaaaaaaacg caaaaaatac ttaaaatgaa aaaaattaga ctgggcacag tggctcatgc
```

Fig. 61D 10561 ctgtaatccc ggcactttgg gaggccgagg tgggtagaac acctggggtg aagagttcga
10621 gaccagcctg gccaacaagg tgaaatcccc gtctctacta caaatagcaa aatcagctga
10681 gtgtgttggc gggcccctgt aatcccagct actcaggagg ctgagacagg agaatcactg
10741 gaacccaagt gattctcgac ttgaggtcga ggctgcagtg agtcgtgttt gcaccattgc
10801 attccagcct gagaaagtga gaccttgtct taaaaaaaag gaatgatatt atgaatacag
10861 cacatggctt gcatgcgtaa gttctcccaa aggcctcacc agttgcaagg caggctagtg
10921 atgggagtgg agggcgaggg aaggaggcag gaagagcaac aggaacttgg gttccccgggt
10981 gacggccacc ccactacctc tcccggacag ggcgccgagg gtcccagcag cgtgcggttc
11041 ctgaagacgt cagaaaaccg ggcagagctg cgggggctga agcggggagc cagctacctg
11101 gtgcaggtac gggcgcgctc tgaggccggc tacgggccct tcggccagga acatcacagc
11161 cagacccaac tggatggtga gcctggggaa gggggtgagg gtggggggttg gaaagacccc
11221 caaagttcct gggaagaccc caggtctcca aagtcccatc atcttttttt tttttttttt
11281 tttttgagat ggagtcttgc tctgtccctc aggctggagt gcagtggcac catctccgct
11341 cactgcaacc tccgcctccc ggattcaagc cattctcctg cctcagcctc ccgagtagct
11401 gggattacag gcgcctgcca ccgcgcctgg ccgatttttt gtatttttag tagagacggg
11461 gcttcaccgc gttggccagg ctggtctcga actcctgacc ttgtgattcg cccgcctcgg
11521 cctcccgaag tgctgggatt acaggcatga gccactgcac ccggtcaaag tcctatcttc
11581 atgtccttct tcctgtggat cacatggcat gccctagaga ggagagaacg taagatgtcg
11641 aaaccaaaac caacagctga gttttgtgaa gtctggcctg cttcactctg tacccccagg
11701 ctggagcgca gttgctcgat caaagctcac tgcacagcca ggcacagtgg ctcaccctgt
11761 aaccccagca ctttgggagg ctgaagcagg aggatcactt gaggtcagga gttcgagacc
11821 agtctgacca gcatggtgaa accgcgtctc tactaaaaat atagaagtta gctgagcgtg
11881 gtggtgcaca cctgtaatcc cagctactcg ggaggctgag gcaggagaat cgcttgaacc
11941 tgggaggtgg aggttgcagt gagctgagat tgtgccagtg cactccagcc tgggcaacag
12001 agcaagactc tgtctcaaaa aaaaaaaagc tcaccgcagg cttgactttt agcaacaacc
12061 tgacccctga gctccccatt ccccatccaa caaaatggga atatcatgaa gcttcctgca
12121 gggctttgag gattggaggt aacaggttat ttttaatatg ctaggccagt ggctttcttt
12181 tttctttcac attttttttt ttgagacgga gtctcactct gttgcccagg ctggagtgcg
12241 gtggcgcgat ctcagctcac cgcaagctcc acctcctggt ctcgatctgc tgacctcctg
12301 atccacccgc ctcggcttcc cgaaatgctg ggactgctgg cgtgagccac cacgcccggc
12361 ctaacttttt cttttttta agagacacgg tctttttat cacccaggct ggagtgcggt
12421 ggcaccatca tagctcattg cagcctacaa ctcccgagct caaccaatcc ttccacctta
12481 gcctcccaag tagctggggc tataggcatg tgctaccgtg ctcaactaaa ttttttttta
12541 tgttttgttg agacagtttc cctatgttgc ccaggctggt ctcaaattcc tgacctcgag
12601 caatcctccc gcatcggcct cccaaagtgc tgggattaca ggcatgagcc gccacaccca
12661 gcattggacc agtggctttc taaaccttgt aattttctgt aatagcttta ctgaaataca
12721 gttcccctgc catacaattt gcctgttcaa agtgtacaat cgatgacttt tgatacattc
12781 acagaattgt gcagtcacca ccacaagtaa ttttgggaca ttttcagcac cctcaaaaga
12841 gaccctatag cccttagcca tcacccccca cccagatctt tctgttgcct tagtccctgg
12901 caagcactaa cccactttct gtcttgaaat cttccagtgt ggtcttttgt gactgttcac
12961 cgagcagaat gttttcaagg tttatgtatg ttgtagtata tatccgtggg ttttttttggt
13021 tgtggtttgt tttttgtttg ttttggaaac agggtctcgc tctgtcaccc aggctggagt
13081 gcagtggttc aattacagct cactgcagcc tcaacctccc aggctcaagt gatcctccca
13141 cctcagcctc ccaagcagct gggactgtag gcatgagcca ccatgcccag ctaatttttt

Fig. 61E 13201 ttggtatttt ttgtaaagac agggtttcac catgtttccc aggctggtct cgaactcctg
13261 agctcaggca atccacccac ctcagcctcc caaagtgctg tgattacagg catgagccac
13321 tggacctggc ctgtttttg tttttgtttt gaacacacga ttttgctttg tcacccaggc
13381 tggaatgtaa tggtctgatc atagtgcatt gcagcctcaa actcctgggc tcaagcgatc
13441 ctcctacctc agcctcctga gtatctggga ccacacgtgc tcaccaccat gcttggctaa
13501 ttattattat tttttgatag agacggggtc ttgctatgtt tcccaggctg gtcttgaaca
13561 cctggcctca cacaatcctc ccacctcagt atctcagagt gctgggatta caggcatgag
13621 ccactgctcc tggccaatat ttcatttctt tttatggaga cgtaataatc agttgtatgg
13681 aaatagctga ttttgttttt tattgtatct tttggtgaac atttcaattg tatcgacttt
13741 ttggataaaa acctgaaaat gtttcacctt tagaacgttt cattgaatgg agattttttt
13801 gtggactctg gtatttatac tagaaccaaa tcaaaaccac tctggcggct gggcatgcct
13861 aggctggttt gagactagcc tgtccaacct ggtgaaagcc catctctact aaaaatacac
13921 aaattagccg agcatggtgg tacacacctg taatcccagc tactcaggag gctgaggcag
13981 gagaatcgca gaacccggga ggcggagatt gcagtgagct gagattgcgc cactgcactc
14041 cagcctgggc gacagagtga gactgcgtct caaaaaaaca aacaaaaaat tactctggca
14101 gtaagaaaag atttcgaaac ttcctccctt gccctgaggt acttcagagg agcctgctgg
14161 cccctggggg agagtttgaa acccactgtt tgttccctga ccttgcctgc ttgtgtcctc
14221 tccctccacc tgtcccctgt actggggacc tgttctcagg agatcacagt tcattgctca
14281 aagccggggc tggggcctcc tacaggacca tcagtttctc ctgatcagca gcctttcctt
14341 ccgcagagag cgagggctgg cgggagcagc tggccctgat tgcgggcacg gcagtcgtgg
14401 gtgtggtcct ggtcctggtg gtcattgtgg tcgcagttct ctgcctcagg taagggctct
14461 gacacccaga ggcccctgga agccctcagt tgatggccac ctgcctgggt gctacaggac
14521 aagcctttct ggctgtcccc agcctctttt tacttgaaat cttctccaat ccctgctcct
14581 tcctttggtg tgtgtgcctc ataaagatgt gtgactcagt ttaccttttg ttcctttccc
14641 atcggctaca ggaagcagag caatgggaga gaagcagaat attcggacaa acacggacag
14701 tatctcatcg gacatggtgg gttgccctaa tttgatggga atagggcctt ggggccgggt
14761 gtggtggctc ctatctataa tcccagcact ttgggaggca gaggtgggca gatcacttga
14821 ggtcaggagt tcgagaccag cctggccaac atgttgaaac tccatctcta taaaaaatac
14881 atcagtcagc caggcatggt ggtgggcacc tgtaatccca gctactcagg aggctgaggc
14941 agaagaatca ttttaacccg ggaggcggag attgcagtga gccaagatcg cgccactgcg
15001 ctccaggcct gggtgacaga gcgagactcc atctcaggaa aaaaaaaaaa aaaaaaaaaa
15061 accacggaga caggggtttg gggctaaaag ctatgagccg agcctccgag tccagtggga
15121 gttaattccc agctgacggg gccctgcctg atttctcagg tactaaggtc tacatcgacc
15181 ccttcactta tgaagaccct aatgaggctg tgagggaatt tgcaaaagag atcgatgtct
15241 cctacgtcaa gattgaagag gtgattggtg caggtgagag ccgaaggctg cccgggcacc
15301 tgggaacgaa gcgggggtgg gcagggccac actggagcgg gagagctgat gacctctgcg
15361 tccttgtttg aaggtgagtt tggcgaggtg tgccgggggc ggctcaaggc cccagggaag
15421 aaggagagct gtgtggcaat caagaccctg aagggtggct acacggagcg gcagcggcgt
15481 gagtttctga gcgaggcctc catcatgggc cagttcgagc accccaatat catccgcctg
15541 gagggcgtgg tcaccaacag catgcccgtc atgattctca cagagttcat ggagaacggc
15601 gccctggact ccttcctgcg ggtgagcacc ctccctggct tctgcggcca cccggagttc
15661 ccacttacac ccagaggcca cttgggttaa gaagccagga cagacagtgg gtcccaggtc
15721 acctcctcca gccttttcct cttgggctaa gccctggtcc tctgcctttt cttttttta
15781 agacagagcc tcgctctgtc gcccaggctg gagtgcagtg gcgcgatctc ggctcattgc

Fig. 61F 15841 tgtctccacc tccagggttc aagcgattct cctgcctcag tctcccaagt agctggtact
15901 ataggcatgc accaccatgc tgactaattt ttgtattttt agtagacaca gggtttcacc
15961 atgtaggcca ggctggtatc aaactcctga cctcaagtga tctccccacc tcagcctccc
16021 aaagtgctgg tattacaggt gtgaggcacc acgcctggcc agccctctgc ctttaatttt
16081 ccctctggga aaggctgggc tcctgggacc ttcctttccc actgccccat acagctgaag
16141 gttgtcattc cttctttttt tttttaattt tgttttaatt gaattttttt tttttgagat
16201 ggagtttcac tcttgttgcc caggccggag tgcaatggca agatcttggc tcaccgcaac
16261 ctccgcctcc caggttcaag cgattctcct gccttagcct ccccagtagc tgggattata
16321 ggcatgtgcc accacgcttg actaattttg tatttttagt agagacgggg gtttctctgt
16381 gttggtcagg ctggtctcga actcccgacc tcaggtgatc cgcctgcctc ggcctcccaa
16441 agtgctggga ttacagacgt gagccaccgc gcccggccaa tttttttttt tttttttaa
16501 gacagagtct cactctgtcc tctaggctgg agtgcagtgg tgcattcata gctcactgta
16561 gccttgacct cctgggctca agtgatcctc ccgcctcagc ctcctgagta gctggaacta
16621 cactcatgta ccaccatgct cagcaaattt ttaaaatttt ttgtagagac aggatctcga
16681 taggttgccc aggctggtct gaactcctgg cctcaagcga gcctccctcc tcagcctccc
16741 acagcactgg gattgcaggc atgagccact gtgcctggcc tgtcattcct tcttttgaca
16801 aatatttact gagtgctttc tacgcaccgg tcatcctccc agtccccagg aataaagcta
16861 tacacacggc aaactggatt tctcctcttg gggagcagag ggtctaatgg ggcaggggga
16921 ctgaaaatta gcaagtaaat agacaggctt tttaaaaaag taaacaaatc atttcaaatg
16981 tgaaaaaaag caaacggggt ccttcatgca gatgtggcta gagaggaaag agaactgctt
17041 aatttatttg gtcactttac cagattttac tgactttttt tttttttta actttattaa
17101 gcttttcttt tttcttgaga tggagtttcc atctgtcacc caggctggag tgcagtggtg
17161 cgttcttggc tcaccgcaac gtccacctcc tgggttcaag tgattctcct gcctcagcct
17221 cctgagtagc ttggaattgc atggcatgca ccaccatacc cagctgatgt ttgtattttt
17281 agtagagaca gggtttcatc atgttgccca ggctggtctt gaactcctgg gctcaagtga
17341 tccacccatc tcggcccctc aaagtgctgg gattacaggc atgagccacc atgcctggcc
17401 taggcatctt tttaaaaaaa tcaaaacatt tttctatgta gcaaaataac attgcattga
17461 acagagttat agcgattccc tagcgtcatt gaatacccag ttgattttca cgtttctcta
17521 gttgttctaa agatgtcctt cactgctgct ttattccaac caggatccag ttcaagaccg
17581 ggctttgtac ctggttatta tatatatttt atttatttat tttagaaaca aggtcttgcc
17641 ctttcgccca gtttagagtg cagtggtgca atcatagctc actgcagcct ccaaactcct
17701 tggctcaggt gatcctcctg cctcagcctc ctgggtagct ggaactacag gtgcacacca
17761 ccacacctgg ctaattttta aatttttttac ggagatgggg gtctcgctat gttgcccagg
17821 ctggtctcaa actcctggac tcaagcgatc ctccctcctt aacctctcaa agtgctggga
17881 ttacaggcgt gagccaccac gcctgctgat tattatattt tcgagcctct ctaaatcttg
17941 agcagttcct catgatgaca ctgacacact gaagggttag gtcccttgtc cgcctgaatg
18001 tcttgatttc tggatttatg aaattcttct tatgggatca tttagcttgt ctctctgtat
18061 ttcctgtaag agaagctcta tctgatgtgg ggtttttttg gttttgtttg tttgtttttt
18121 gagatggagt cctgctgtcg cccaggctgg agtgcagtgg cacaatctcg gctcactgca
18181 acctccgcct cctgggttca agagattctt ctgcctcagc ctcctgagta gctgggacta
18241 caggcgagtg ccaccatgcc cagctaattt ttgtattttt agtagagaca gggtttcacc
18301 atattggcca ggatggtctc gaacttctga cctcgtgatc tgcccaccac ctcagcctcc
18361 cacagtgctg ggattacagg catgagccac tatgcccggc taatttttgt atttttagta

Fig. 61G 18421 gagacagggc ttcgccatgt tggccaggct gatctgaaac ccctggcctc aagccatcca
18481 ccctccttgg cctcccaaag tgctgggatt aaacgcgtga gccaccgtgc ctggtcgaag
18541 agacagaaag ggtcttaaag gttcagtgac acacacctgt aatcccagca ctttgggaag
18601 ctgaggctgg tggatcactc gaggccagga gttagagatc accctgggca acatggtgaa
18661 accccgtctc tacacaaaat acaaaaatgg gcagagcatg atggtgcata tctgtagtcc
18721 cagctactcg ggaggctgag gcgggaggat cacttaagcc tgggagatcg aggctgtagt
18781 gagccatcat tgcactactg cattccagcc tgggcgatcc catctcttaa aaagagagag
18841 agatgggaag accagcacag gtgaaactgg tgaacagagg agagatggta gatgctgcat
18901 tgggcagtgt gacgggaacc cgctggaggg ctttggcagg agagtagttt aagaggatcc
18961 cagctgggca cagtggctca cacttgtgat cccagcactt ggggaggccg gggcaggtgg
19021 atcacttgag gtcaggagtt cgagaccagc ctggccaaca tggtgaaacc ctgtctgtac
19081 taaaaataca aaaaccagcc aggcatggtg gtgcacccct gtaatcccag ctactcagga
19141 gactaagaca ggagaatcgc ttgaactcag gaggcagagg ttgcagtgag ccaagatcac
19201 gccactttac tccagcctgg gcagtagagc gagactccat ctcaaaaaaa taaataaata
19261 aaaagacctc tttgctgggt gctagggagc aagagcagga gctgggagag gcctgcagca
19321 gaagcctgtt gccagcatcc aggccgtggg gtgaagggaa gggtttggat ttgggacatg
19381 tcttggaagc atcaccagca gaacttgctg atggattgga agtggctggt gagggagaaa
19441 agggggtcaa aggaaactct gaggtctata ccctgaccat ctggcaagtg gtggtgttgc
19501 cacaaactga gcggggagta gggcaggtgc aggtctggag gatggattca aaattcagtt
19561 tttggagtct atgtccctgg ttctgtaggg ctgcagatgg tctgccaaat cttagcggaa
19621 cccagaatac gggatttgtt tactgtctgt gacttgttgg tttccctggt gagagcaaac
19681 tctttaaagg tcaaggttgg gcttcagacc ttggtttttg caccgatcat tggtcatact
19741 gcagttcctc actcttctct tgcaaatcca tacacagcta gtccaagaga gctgaacagc
19801 tttgtggttg gatcagcacc aatgtatctc cacctgtaga cgggttgctc aggtgactca
19861 tgcctgtaat cccagcacct tgggaggcca aggtgggaag attgcttgag gccaggagtt
19921 ggagacaagc ctgggaaaca cagtgagacc ccatatctac caaaaaaacc cctttgtttt
19981 aattagccag gtgcagtggt gtgcacctat agtcccagct actaaggagg ctgaggcaga
20041 aggatcattt gagcccagga gtttaaggct gcggtgaacc atgatcgtgc cactgcactc
20101 caacctgggg gaaagaaaga gaccttgtct ctaaaaaaac taaaaaacag aaaagcattt
20161 gttgagtatt tcctgggtat aaagcagtgt accaggttaa atggaaggaa aagttgaaat
20221 aatttttcaa ctcataatcc gattgggaga gactgaatgc ttaccattga agcaggaacc
20281 attgtaagca atgtgttgtg atactgtagc aagagctgag aaaacttggg aaaagagaaa
20341 ggaggaaggc tcacctgagg gagttggggg gcttgcccta caggtgagtt gtgaggtggg
20401 tctggaagtg acagatgcag tttaggaagt ggacgggagg ctgggtacgg tgactcaaca
20461 tctgtaatcc cagtgctttg ggagacccag gcggaaggat cgcttcaggc caggagttaa
20521 agaccagcct gggcaacata gtgggaacct atctctacta aaaattaaaa aattatccag
20581 gcataatggc acatgcctat tgttccagct actcaggagg cttgcctgag cccaggaggt
20641 tgaggctgca gtgagctatg atggcaccac tgcactccag cctgggcgac agaacaagac
20701 cctgtctcta aaaaaaaaag atgtggatgg gagggggaac ggtgggtggg ctgtcctcac
20761 caagccccca ccctatctgc tctccagcta aacgacggac agttcacagt catccagctc
20821 gtgggcatgc tgcggggcat cgcctcgggc atgcggtacc ttgccgagat gagctacgtc
20881 caccgagacc tggctgctcg caacatccta gtcaacagca acctcgtctg caaagtgtct
20941 gactttggcc tttcccgatt cctggaggag aactcttccg atcccaccta cacgagctcc
21001 ctggtaatgc tgggggtaat actgggtgtg agcttcttag ggccaggtgg gcagggcagg

Fig. 61H 21061 ttggaaaggt gggaggctga gggtttggca gccctgctcc agggagagga tacaggagca
21121 ggctgtgggt gggggacag tcagctccag gaagccgact tccagatgtc taggaaaata
21181 acagttggat aacctgggca acatagcaag accccatctc tacaaaaaa ttaaaagatt
21241 agccaggcgc agtggcatgc acctgtagtc ccagctactt gggaggttga ggcaggagga
21301 ttgcttaagc ccaggagttg gaggctgcag tgagctatga atgtgccact gtactgcaga
21361 ctgggcgaca gagcaagacc ctgtctcaaa agaacagtgg ccaggtgtgg tggctcacgc
21421 ctgtaaatcc agcactttgg gaggctgagg caggaggatc gcctgaggtc aggagttcga
21481 gaccagcctg gccaacatgg gaaaaccctg tcgctactaa aaatacaaaa ttagctgagg
21541 gtggtggtac acgcctgtaa tccgagctac tcaggaggct gaggtaggag aaccagttga
21601 acccgggagg cggagtttca gtgagccaag atcgcaccac tgcactccaa cctgggcaaa
21661 cagagttgga gagtaggagg cttggggcct gagctagggg gaaaaagcag aggcaggtgg
21721 gggactgggg ggcagtgtgc tgggtctggt gagtccctca gtgagtcccc cagctcacct
21781 tttctccttt ttctgcaggg aggaaagatt cccatccgat ggactgcccc ggaggccatt
21841 gccttccgga agttcacttc cgccagtgat gcctggagtt acgggattgt gatgtgggag
21901 gtgatgtcat ttggggagag gccgtactgg gacatgagca atcaggacgt aagtgtcccg
21961 tggtcctacc aagctttcct cgagtgttct ctcacctggg atttggggtg aagggtgggt
22021 tcccagagag tcatcactgc tgggttcttg agaccatgga gatgacaaaa aggagaattg
22081 atctttgtat caaagagttg agatacaggg ccaggcctag tggctcaagc ctgtaatccc
22141 agcactttgg gaggccaagg tgggcagatc acctaaggtt aggagttcaa gaccagcctg
22201 gccaacatgg tgaaaccccg tctctaaaaa aatacaaaaa attagcccag catgatgggc
22261 gggtgcctgt aatcccagct actcaggagg ctgagacagg ataatcgctt gaacccagga
22321 acagaggttg cagtgagctg agatcacgcc attgctttcc agcctgggca actgagcgag
22381 actctgtctt aataaataaa taaaagagtt gggtacagca tatttgggtc gcagaaggat
22441 gcagagatgg agggcagggt tgagaggtaa catgtctgta tcatagccca agagctgctg
22501 gggccttcag ccacagagag cttcaactcc ggctaggagg attcctggat ctgttatttt
22561 ttggggggct gtggctccta tcctaccatc ttccaagtca ccatttcctg ggcctgttag
22621 catctttgct tttcctggac agcctcaccc agagcttctt cccctctttc caggtgatca
22681 atgccattga acaggactac cggctgcccc cgcccccaga ctgtcccacc tccctccacc
22741 agctcatgct ggactgttgg cagaaagacc ggaatgcccg gcccccgcttc ccccaggtgg
22801 tcagcgccct ggacaagatg atccggaacc ccgccagcct caaaatcgtg gcccgggaga
22861 atggcgggtg aggactgcag agaatgggcc ctccttcccg ctctctgccc ccactccttg
22921 cccagaagtg tccgttcatt ggtgttgggt gggagggcct ctgtccgcct ctgcaaggct
22981 gggttccacc tcctccccg gacctgggcc tggtactcag cattcctccc catccttgcc
23041 ccctagggcc tcacaccctc tcctggacca gcggcagcct cactactcag cttttggctc
23101 tgtgggcgag tggcttcggg ccatcaaaat gggaagatac gaagaaagtt tcgcagccgc
23161 tggctttggc tccttcgagc tggtcagcca gatctctgct gagtaagcag tggcaggagc
23221 tggagtgggg ctgggagagc ggggcagctg gagtcaggcc cacggggtct ccaggggctt
23281 ttggggtcag cttcgggtgc caatgctgtc ttcttgcact gcgctcatgc catgcctaga
23341 agggccccag aggagcagtc acagccccat ggagctgagg acccaaggac tctttggggc
23401 cagcctgccc gcctcacctc ctcctgccat cacagccctg ggccatcgcg cttccgcctc
23461 tcacttctag ctatctttgt gcatctatct gcattccagg cccggctctc acggtaacaa
23521 tgtgtcaact cgggttctct ttttccaacc ataaaaggag aagattgggc taggttttgg
23581 agatcctctt cagcttttat gtgaaatggt tttatgattc cttgcctccc aaaggctgcg
23641 tatccccact tggcctttgt ctgctactcc ccctttctgc cttcccgttc ctctcccaag
23701 atctcctctc accccaggtt gaataacaga aatagaagga atagaaatct gaaggccggg
23761 catggtggct catgcctgta atgccagcac tttgggaggc cgaggtgggc agatcacttg

Fig. 61I

```
23821 aggttaggag ttcgagacca ttgtggacaa cttggtgaaa ccttatgtct actaaaaata
23881 caaaaattag ctgggcatgg tggtgcgtgc ctgtaatacc agctactgag gaggctgagg
23941 caggagaatc gcttgaaccc gggaggtgga ggttgcagtg agccgagatc gcaccactgc
24001 actccagcct ggatgacaga gtgaaattcc atctcaaaaa aaaaaaaaaa aaaaaaaaag
24061 aaatgtgaag gccaggtggt ggctcacgcc tgtaatctca gcactttggg aggctcaggt
24121 ggaccgattg cttgagccca ggagtttgag agcagcctgg ccaaaatagc aaaacccccat
24181 ctctacaaaa caaaaacaaa aaaattagct gggcatggtg gtgcgtgcct gtggtcccag
24241 ctactcagga ggctagagcc agagggtctc aggccagtct gcccctgccc cacggggcct
24301 gggcacatcc ctccctaatt cttcccagcc tctctctgac ccaggggggcc tcctctccct
24361 tttttcccct tatctcagcc tccagccatc agcaacctcc tcttcctctc caccccagctc
24421 ttcctctccc acttcggcct tttctttctc acactccatt tccctctacg gcaatctgtg
24481 cagcctcttc ccccagtctc attttgcggg cttttctctc ttttctttcc ttccctggca
24541 cccaagccaa aggccctgcc tctggcctcc agccctaccc ccttctgcgg ttgcacagaa
24601 ggatggctgc ccagctctta aaaaaactgc ccgggaactg ttgacatctg ttctccctcc
24661 cccgctggct tttctgattg gcttacaatc ctgaggctag gaccgtctca ggagccaaga
24721 gaggagagcg gccacaggga acctagggtc tcaccaagct ctcctttcct tctgcaggga
24781 cctgctccga atcggagtca ctctggcggg acaccagaag aaaatcttgg ccagtgtcca
24841 gcacatgaag tcccaggcca agccgggaac cccgggtggg acaggaggac cggcccccgca
24901 gtactgacct gcaggaactc cccaccccag ggacaccgcc tccccatttt ccggggcaga
24961 gtggggactc acagaggccc ccagccctgt gccccgctgg attgcacttt gagcccgtgg
25021 ggtgaggagt tggcaatttg gagagacagg atttgggggt tctgccataa taggagggga
25081 aaatcacccc ccagccacct cggggaactc cagaccaagg gtgagggcgc ctttccctca
25141 ggactgggtg tgaccagagg aaaaggaagt gcccaacatc tcccagcctc cccaggtgcc
25201 cccctcacct tgatgggtgc gttcccgcag accaaagaga gtgtgactcc cttgccagct
25261 ccagagtggg ggggctgtcc cagggggcaa gaaggggtgt cagggcccag tgacaaaatc
25321 attggggttt gtagtcccaa cttgctgctg tcaccaccaa actcaatcat ttttttccct
25381 tgtaaatgcc cctccccccag ctgctgcctt catattgaag gtttttgagt tttgtttttg
25441 gtcttaattt ttctccccgt tcccttttttg tttcttcgtt ttgtttttct accgtccttg
25501 tcataacttt gtgttggagg gaacctgttt cactatggcc tcctttgccc aagttgaaac
25561 aggggcccat catcatgtct gtttccagaa cagtgccttg gtcatcccac atccccggac
25621 cccgcctggg acccccaagc tgtgtcctat gaaggggtgt ggggtgaggt agtgaaaagg
25681 gcggtagttg gtggtggaac ccagaaacgg acgccggtgc ttggaggggt tcttaaatta
25741 tatttaaaaa agtaactttt tgtataaata aaagaaaatg ggacgtgtcc cagctccagg
25801 ggtgatgggg gtgatggact agatttctaa ggagagtggg gctgggtagg gagggctttg
25861 tggctgaccg agaggtgtca gaggtctgga ggctgcaggg ctgtaggggc tggaacttgg
25921 ttatcagccc cagggtatgt ttgaggtggt ggggtggggg ccgagcgaga tgaatcattc
25981 gcagctgctt ctaacgtctc
```

Fig. 61J

EphB4, mRNA

```
   1 ctcggcccgg cggcgcgagc agagccactc cagggagggg gggagaccgc gagcggccgg
  61 ctcagccccc gccacccggg gcgggacccc gaggccccgg agggacccca actccagcca
 121 cgtcttgctg cgcgcccgcc cggcgcggcc actgccagca cgctccgggc ccgccgcccg
 181 cgcgcgcggc acagacgcgg ggccacactt ggcgccgccg cccggtgccc cgcacgctcg
 241 catgggcccg cgctgagggc cccgacgagg agtcccgcgc ggagtatcgg cgtccacccg
 301 cccagggaga gtcagacctg ggggggcgag ggccccccaa actcagttcg gatcctaccc
 361 gagtgaggcg gcgccatgga gctccgggtg ctgctctgct gggcttcgtt ggccgcagct
 421 ttggaagaga ccctgctgaa cacaaaattg gaaactgctg atctgaagtg ggtgacattc
 481 cctcaggtgg acgggcagtg ggaggaactg agcggcctgg atgaggaaca gcacagcgtg
 541 cgcacctacg aagtgtgtga cgtgcagcgt gccccgggcc aggcccactg gcttcgcaca
 601 ggttgggtcc cacggcgggg cgccgtccac gtgtacgcca cgctgcgctt caccatgctc
 661 gagtgcctgt ccctgcctcg ggctgggcgc tcctgcaagg agaccttcac cgtcttctac
 721 tatgagagcg atgcggacac ggccacggcc ctcacgccag cctggatgga gaacccctac
 781 atcaaggtgg acacggtggc cgcggagcat ctcacccgga agcgccctgg ggccgaggcc
 841 accgggaagg tgaatgtcaa gacgctgcgt ctgggaccgc tcagcaaggc tggcttctac
 901 ctggccttcc aggaccaggg tgcctgcatg gccctgctat ccctgcacct cttctacaaa
 961 aagtgcgccc agctgactgt gaacctgact cgattcccgg agactgtgcc tcgggagctg
1021 gttgtgcccg tggccggtag ctgcgtggtg gatgccgtcc ccgcccctgg ccccagcccc
1081 agcctctact gccgtgagga tggccagtgg gccgaacagc cggtcacggg ctgcagctgt
1141 gctccggggt tcgaggcagc tgaggggaac accaagtgcc gagcctgtgc ccagggcacc
1201 ttcaagcccc tgtcaggaga agggtcctgc cagccatgcc cagccaatag ccactctaac
1261 accattggat cagccgtctg ccagtgccgc gtcgggtact tccgggcacg cacagacccc
1321 cggggtgcac cctgcaccac ccctccttcg gctccgcgga gcgtggtttc ccgcctgaac
1381 ggctcctccc tgcacctgga atggagtgcc cccctggagt ctggtggccg agaggacctc
1441 acctacgccc tccgctgccg ggagtgccga cccggaggct cctgtgcgcc ctgcggggga
1501 gacctgactt ttgaccccgg cccccgggac ctggtggagc cctgggtggt ggttcgaggg
1561 ctacgtcctg acttcaccta tacctttgag gtcactgcat tgaacggggt atcctcctta
1621 gccacggggc ccgtcccatt tgagcctgtc aatgtcacca ctgaccgaga ggtacctcct
1681 gcagtgtctg acatccgggt gacgcggtcc tcacccagca gcttgagcct ggcctgggct
1741 gttccccggg cacccagtgg ggctgtgctg gactacgagg tcaaatacca tgagaagggc
1801 gccgagggtc ccagcagcgt gcggttcctg aagacgtcag aaaaccgggc agagctgcgg
1861 gggctgaagc ggggagccag ctacctggtg caggtacggg cgcgctctga ggccggctac
1921 gggcccttcg gccaggaaca tcacagccag acccaactgg atgagagcga gggctggcgg
1981 gagcagctgg ccctgattgc gggcacggca gtcgtgggtg tggtcctggt cctggtggtc
2041 attgtggtcg cagttctctg cctcaggaag cagagcaatg ggagagaagc agaatattcg
2101 gacaaacacg gacagtatct catcggacat ggtactaagg tctacatcga ccccttcact
2161 tatgaagacc ctaatgaggc tgtgagggaa tttgcaaaag agatcgatgt ctcctacgtc
2221 aagattgaag aggtgattgg tgcaggtgag tttggcgagg tgtgccgggg gcggctcaag
2281 gccccaggga agaaggagag ctgtgtggca atcaagaccc tgaagggtgg ctacacggag
2341 cggcagcggc gtgagtttct gagcgaggcc tccatcatgg gccagttcga gcaccccaat
2401 atcatccgcc tggagggcgt ggtcaccaac agcatgcccg tcatgattct cacagagttc
2461 atggagaacg gcgccctgga ctccttcctg cggctaaacg acggacagtt cacagtcatc
2521 cagctcgtgg gcatgctgcg gggcatcgcc tcgggcatgc ggtaccttgc cgagatgagc
2581 tacgtccacc gagacctggc tgctcgcaac atcctagtca acagcaacct cgtctgcaaa
```

Fig. 62A 2641 gtgtctgact ttggcctttc ccgattcctg gaggagaact cttccgatcc cacctacacg
2701 agctccctgg gaggaaagat tcccatccga tggactgccc cggaggccat tgccttccgg
2761 aagttcactt ccgccagtga tgcctggagt tacgggattg tgatgtggga ggtgatgtca
2821 tttggggaga ggccgtactg ggacatgagc aatcaggacg tgatcaatgc cattgaacag
2881 gactaccggc tgcccccgcc cccagactgt cccacctccc tccaccagct catgctggac
2941 tgttggcaga aagaccggaa tgcccggccc cgcttccccc aggtggtcag cgccctggac
3001 aagatgatcc ggaaccccgc cagcctcaaa atcgtggccc gggagaatgg cggggcctca
3061 caccctctcc tggaccagcg gcagcctcac tactcagctt ttggctctgt gggcgagtgg
3121 cttcgggcca tcaaaatggg aagatacgaa gaaagtttcg cagccgctgg ctttggctcc
3181 ttcgagctgg tcagccagat ctctgctgag gacctgctcc gaatcggagt cactctggcg
3241 ggacaccaga agaaaatctt ggccagtgtc cagcacatga agtcccaggc caagccggga
3301 accccgggtg ggacaggagg accggccccg cagtactgac ctgcaggaac tccccacccc
3361 agggacaccg cctccccatt ttccggggca gagtggggac tcacagaggc ccccagccct
3421 gtgccccgct ggattgcact ttgagcccgt ggggtgagga gttggcaatt tggagagaca
3481 ggatttgggg gttctgccat aataggaggg gaaaatcacc ccccagccac ctcggggaac
3541 tccagaccaa gggtgagggc gcctttccct caggactggg tgtgaccaga ggaaaaggaa
3601 gtgcccaaca tctcccagcc tccccaggtg ccccccctcac cttgatgggt gcgttcccgc
3661 agaccaaaga gagtgtgact cccttgccag ctccagagtg ggggggctgt cccagggggc
3721 aagaaggggt gtcagggccc agtgacaaaa tcattggggt ttgtagtccc aacttgctgc
3781 tgtcaccacc aaactcaatc atttttttcc cttgtaaatg cccctccccc agctgctgcc
3841 ttcatattga aggtttttga gttttgtttt tggtcttaat tttctcccc gttccctttt
3901 tgtttcttcg ttttgttttt ctaccgtcct tgtcataact ttgtgttgga gggaacctgt
3961 ttcactatgg cctcctttgc ccaagttgaa acaggggccc atcatcatgt ctgtttccag
4021 aacagtgcct tggtcatccc acatccccgg accccgcctg ggacccccaa gctgtgtcct
4081 atgaaggggt gtggggtgag gtagtgaaaa gggcggtagt tggtggtgga acccagaaac
4141 ggacgccggt gcttggaggg gttcttaaat tatatttaaa aaagtaactt tttgtataaa
4201 taaaagaaaa tgggacgtgt cccagctcca ggggt

Fig. 62B

EphrinB2 Gene

```
   1 gcgcctcgga gctgcctgcg ggcgcacgcc gtcttccccg ccagtctgcc ccggaggatt
  61 gggggtccca gcctgcgtcc cgtcagtccc ttcttggccc ggagtgcgcg gagctgggag
 121 tggcttcgcc atggctgtga gaagggactc cgtgtggaag tactgctggg gtgttttgat
 181 ggttttatgc agaactgcga tttccaaatc gatagtttta gagcctatct attggaattc
 241 ctcgaactcc aagtaagtgg cgtccgcgat ccccctatgt ccccgccccg gggtccgccg
 301 cgccgtccgg gcgggaggag gggtcagtcc gcggggcctc ggagcctgtt tctggaacct
 361 cggttccccg tccccccaccc ccaaccccccg ccccatttca ctaggtggag actcctcgct
 421 cggctttcca acccgagccc cgctggaacg gacggtctct ccgcctttcc tcccccgaac
 481 gctcccaggc gctaaaagct actatcggct cgggtgtcaa gtccgggaag gtgtccgatg
 541 gcgatacctg accctctcct gttttcgagg acgaaggaca tggccacaat ctaggctggc
 601 cggcacgcgg ggactggtgg gctctggaga gaggcggaga tgctgcattc gcggggagcg
 661 cgggcggcgt ggtccggggc ccgcgggcgg gcgaccgggg tggcaggacg ctggcagcga
 721 agcgcgttct ggagagggga gcctggagtc gctacgctgc ccgcagagcc ctggagccgg
 781 ggcgccttgg caccgcgccg ccagcccgag ggtgcgcggg gagctcgcct gcttcgcagg
 841 agaactcggg cgtcgagccc tttcctccgc gccgggggaga cgggccttag gcttctccct
 901 gagggcccgc cgcacctcgg cctccccgctt cgttcataag ccggtagccc cggagtatgc
 961 ggtctcgatg gccgacctga ttgtaatgca cttcctataa aagcttaggg ccctgcccag
1021 tcgacactgc tcctgaagcc ttctccctcg ggaccctggt aggaatggga tccttaggat
1081 cagatttgct cttaccggac tctacagccg ggagcgagcc aggccttgtg gagagtaact
1141 ttcagtttgg gccaccagag tgcattcaga atttagaaaa tcccatccat ccctaaatct
1201 gtgtggtcat aactcgtagt catctgggta ttcagtactg tgtatcccct tatttcgaat
1261 cacagccaaa acatatttta cagaatcttg gaattgtagt ctcgggaaac ttggagaaga
1321 agtatgcaga cattagctgg tttctggaga aaacgtttga gatcagaagc aaaatcaatg
1381 gcctaattga agttgagcaa gttgggcctg gttttaggag aaaagaaatg ggggattgat
1441 ttagaaatca cgtcttaaag gagtgtgtcc attctcttaa aagtgtcaaa tttcaaattc
1501 actaacatgt taaccaagaa tcccttcatg aaaagggcga aaacgtcggt tacaaatcgg
1561 tttaaacaaa tgtttgtatg atgctagaag gcactttcaa caccgctcat acggagaagt
1621 tacttagctc tgcctccttc catgtagtct gctcttgcat ggattatatt tttaatgtaa
1681 attgttgtat ttgctgatga agtactggcg gcggcatctt tgcatcgatg ccggctcggg
1741 aggcgccagg tggtgccgga aggagccggg ctaggacctc gcgcagcagc gggtcccgga
1801 gtccgggaga ggcgggcggg cgggcgaggc ggtcgcgggg agcccgcggc gccgctgccc
1861 gcccggtgcc tccagaggtc actcttccat gcggaatcgc gcagcgccag gcctcgcccc
1921 tcccccaggc cgcctgctcc agccactctg cactttcact gaccggttct ctttgaggct
1981 gttttttttt ttcttatgag gatttaatat ttctgtttaa atctagttga aagcaattcc
2041 gttagcctct tcagcgttta gttcggtgtg tgtatcttta tctttgcgct atattaacta
2101 ttagtttgtg tgtatccggt aggagaatta gaaataccta gttgggagaa aaagaaaagt
2161 agaacaatag ttatttcaac ctaaggttta gacgttaata acttcttttt gtaatgtgtc
2221 gagatggggg gtcctggggg gaggtgacag gtactcacca ctcccccccc ccattctgat
2281 gatgaagatg agtctgtctt tccagctatg tccagacctg cgagggccct gcgtttctgg
2341 aagcctgccg tttgcgcggt tgaggttgct gctgctgtct tgtcctccac agcagcattt
2401 cttttaaaat tctcctgata acggcctgcc tggatgactg gataatgtgt gcctggaaaa
2461 ggtctccctt gcagctgaat gctagctcca gagatcagaa agatttcttc ctgtaggagc
2521 cataggaaag agtcctctct aagtttttga gaatgcatac aaccccctga tgacaggggg
2581 tcgctttcct tggggaagtt ttatatttat ttccagagga aagtttgaat cggtaaatat
```

Fig. 63A

```
2641 gatgtggcag gaaggtaatc aaatgcattg aagtttcaca tcagttccta tgaactgtgg
2701 aacaattcat ttgtaatgaa gccgccatca gtaattagat ttgtttcatt cagaggtcag
2761 ctttttagc aggtggtcga cacagggagc atgcagcagc tgtttggata cagggtccag
2821 aaaacccttt gtaaattcag cgtctccgta actactttaa tcacattgtc ggctctcccg
2881 tccctgactg tatgtaataa tggaaagatg tcctgcgtgc tgaaacagta gctgccctgt
2941 taggttattc acattgcttt gatacgttct ggtagagttg ggtccgttgt agccattttg
3001 gttgtttaaa gttttggttt ttttttgtt tttttttaa ttcagcagag aacagtaatg
3061 cctagcttcc gtttttaact taacacttca gtagaacatt ttcttccaag agggagattt
3121 tggcctaagt aaagtagtgg gctctttttt aaaaaaaaat taattttact ttaatgtgag
3181 caaatctgta ttggtatggt gttctgcaat gcattacact gactttgaaa atttcgagta
3241 ctaatgcctt atgtctgggg ttaccattcc ctgtgcatca catactagtt agttaacata
3301 gcattttgct tttcccatgt aatttttcc ctatataata ctggattcct gatactaatt
3361 gacttgatac aaaagaatgg ctggatgata tccagataac gtataataca tgggcttcac
3421 cacaatcagg ctctgaataa atacagacct gtcagagatt gataaaataa actacaatgg
3481 atagtgctgt ttaaacagtc cattcaataa catatataag ccagcctgcc ttccattgtg
3541 tctgaaattc ttatttttgt aggtaaacaa atgcacattc agcactgatt gaatagcccc
3601 ttgaactatg ctccacagtt tgcgtttggg ttaatcttgt cggttttaat atagagagaa
3661 aaaagctcaa agcaccaggg gtggaattgt tagtgctttc acatccacat tcctcacatt
3721 ttgtcaggat gataaactgt aggtaatgga ctgtcgttgt tctgcaggac aactgagcca
3781 ggcagagcac aaagactaag ctaaagcgat acctcacaac atgcttggta gccttctttt
3841 cagatgagaa tttatttgag aatcatgtgt ctagggactg cacatcttaa cctcaacagt
3901 tacagcttca agccccagaa acaggagctg gaggttaaga tgatttgcta agcacctggt
3961 tctaaatctt ttacaaagca taagctgttg acgctggttc tgccgacgca aagacatgca
4021 gatgactcca acatttccag aggcttctga cttaagctaa agtgtgtgga caggtgaatt
4081 cgccatgggc ctggagacca gcttgctaaa aactatgtgt ttgaatggtt cctccagaca
4141 gagtcagctg aagaacaatt ggtggattta tattaaaacc tcttgtctgt aaacttactg
4201 aggtgcatcc ttcggttggt ggatcagtga gataattgcc ttcagatgga cattgcaact
4261 ggagcaacta aatccttgct gtctttcctt cctctgaaat cttccaggta gctcccgaga
4321 gcttcagtat gacaccaaac ttcgggcgac gttttagagt gcgttcacct aatgggaaac
4381 tattcgagat cccagcgtga ctgcagtaat gcgtcatagg aatgggagtg gcaggggaaa
4441 aggaaataca gattgtagac cctaataaaa aaatttttag gaaagatatt tctttaacgt
4501 tttatgagaa cttcattctt aaaatactta attgcaaatt agacaaatag aagtgctctt
4561 ctaaggaagg tgattaaact ggtcctccta tcagcctaat ctctgcctgc ctttgctgct
4621 gacataaaga acctgttttt caggtcactt aatatacatc tacatagatt tgcttatgag
4681 ctcacccttt gtgtagcgga gtagagcctt aaagaggagt gctcaactgt ttaaaatatt
4741 ttgattaaaa tatgcagaac ccatagaact ataagcttct agtcaggaat tagctctttc
4801 agggaacagc tccccccttc tttttaaggg gggaattaga aggaggctgg gggaggaata
4861 taagaacagc aaagaaggaa ggatagcaaa tgggacatgt tccgaacagc ttggaaaaac
4921 tcctgtggct tcattgtctc tataaagcca aagaatacaa agacataagc aattcagccc
4981 ttctcccatg atggaagatg taaaccgttg acatgcctcc cctgtttaac ttgtttaatt
5041 ctcattttaa attcagcacg atactagccg tgtgaactct gaagatttct ttagtaatcc
5101 attttgtagt tccgaatcaa aaacaaagtg aaagggtctg acacaatttg cttttatttt
5161 taggcaaatc aaccctggtc atagttaata aggggattac aactcagact aggtctttac
5221 agatgtgatg taaatcaagg gcagagtata aagaaactga tccctttga ttgaagtata
```

Fig. 63B 5281 gtaaaaaggc atagagaaac tagcagcagt aatctgattg tatggcaata aaaccaccat
5341 tttctgtctt tcagataaaa ataatgtggt aaatccatgc agttcataag atgtaaaggc
5401 agataaaggg tgaagccatg gcaacatata gattagcttg atgttagaaa tgacacgtct
5461 ctgaaaaggg cgcgggacga aggcccttgc ctccaggctg ttgggcatta tgtgagaacc
5521 acacagactt ggaaactggg attaggaagt atgaaagctc tacttgtggt ctgggatggc
5581 tgaggcagta aagaaaagct gctcagttct tgctcattgg tggtggataa tatggcaaag
5641 gtagatttca ttgactgcct tttttataga ttgagattgg ggctgattaa aacttcagat
5701 cactgcagtt gttagggcct gggagatttt ccttttttaac tcctggccta acagcagcag
5761 ccgttctgta ggattaactg cacttcgcgg tcgttgcctt aatctatttg ggcttcaggc
5821 agggacatgc tgggaaggaa cagagaccag aggggatagg tagggctggg gttatctgaa
5881 aagaaaacag agaccttttg atttcagcca tcttttcaga cccagctccc tctcccgctg
5941 catgggagaa gcaaaggtaa acaggacaca ttgtccctct ccctcagcca cagagctctt
6001 ctgtgagttt tgtctttccc accctggaaa aaaagataaa atacaatttt taaaagggga
6061 gggaggaatt tagttttaat tcaaatgagt agtaatccaa tatgccaaaa gcagtgggct
6121 ctacctagat gtaattttac tcgtaaatgt gagtcttaaa ctttgagttg aatggggcag
6181 gctgttagag gtggtgtaaa ttacaggatt ataaaaatgt tagtgctgcc cagccttaaa
6241 gtcaaaaaca gaaaaatctc tgtgctgttg agtcttcccg ccctctctcc tgaacaacct
6301 tgtaagtaag ctagactttt gtttttgcct tccatacttt ccatttcagc cattaaacaa
6361 aataagccat tgaaaccacg attgggttcc atgcagagtg acatccgcaa tcgggtcaag
6421 ccagaaggaa atacttgctc gattgccccc tatttggcat tacaggaaag tctccacact
6481 ttggaagagt ctgaactctc aagacattga aaatgccaaa ggctgcaaac accctgtgtc
6541 tttcttgatg gagtgcatct tggtgtgttt tacaaagggg aattcagtgc tgttttttttg
6601 ttgttgttgt tgtttttttt ttttaaagag cagcataggg cccttctaga ctcttggatt
6661 ctgtgtctga caaaaatggt cattaaatga gcaatattat aatttagacc catttcactg
6721 attttgttcc aaattctcaa ctgacttgag catctgtttg gggctgtaga tacattgccc
6781 ttgttgactg tttttctcgt ttctatggga attactgtag ccattactat gtagctttca
6841 tagactcaaa acatttttaa agtattgcat ataggctggc catatccagt gcctgttact
6901 ttaccttctt tttctaactt aatgcagcag tctgtattaa cagatccatt tcatttgtct
6961 agcttcatca gagagaggct accccctgat ttacaggctg ctcacatcca agcaccttgc
7021 attctacact tgacagtgat tgctaatggc ccattcaact aaagtatttg cttgttaaca
7081 gggaacagaa catgataaat gtccagcaag cttgctgcct ccttcagctt ttcaaacgca
7141 gactggtgca tatttatggc aggcaaatga caaaagaaaa agctgaattg ccctggcctc
7201 cagctttcta tcagaaacag ggttaaagtg attaaagcaa tcattcaaga aagccctgcc
7261 gtttgtttac taaccttcat ccaacattta gctttgtagt ctacctgtga gaagatattt
7321 cagaagtatt agagataagg aaggaggatc tagcaaacca gtgaaaagag taggtgacca
7381 gttataaaat gctttccatg cacattgaat gccaggcgaa cctatttctg ttattccagc
7441 agacaatcag cagtggctct agattattaa catattttcc tttcatgtat aaattcaaat
7501 atgtaattct agtccaaagc attctgtggc tggtaagcac atacttgctg atttcaaata
7561 agaaaacata gcaagggaaa gctccattaa acaagttgtt tctgccctta gtaattctct
7621 aaacaagata ggaagaaaaa gtggacagta gtggagtatt aatagtgtgc tcttttcatt
7681 ctctaaagca cgagtaagta agcgttcaaa ctactctgtg gtgggcatac atttagagcg
7741 ctgtgaatga accactgctg ttctgccata cttaatttat ttatattatt atttttattt
7801 tattgttgtt tttatgtatt attataatta tttatttata ttactaattt attttctcaa
7861 tttaaatcct gttgcatcca attttaatta cagtttttgt atctgccttc ccatacttgc

Fig. 63C 7921 tacccacgtc cccattgcca ctgcggcctt atccatgttt tctgtgtaca ccactctcgt
7981 atcaccccag aataattatg agtgctaccc agacttttga aaccactaga gtcaacatgt
8041 ttgtctttga ggaaagccaa tgatgcttta gcatttttgg caggggtgga tgtgtgttta
8101 agtggggtgg gtgcagctcc ttattgtctg cctattctac tgttgttccc aatccacatt
8161 ccctgcgggg cacctaacct gtgtgcatag caaagaattt ccgaccttca gagccagaag
8221 tgtttctcaa ttgatctctt ccagcctagg gttatagctg atgaattata atccttgctc
8281 tttccacacc tttacctggg cttaccatgg ccctaaaaca tttgcccaga atcagaattg
8341 tctcatgagt gagtggggca aggcaaatcc tgttccagac cagctgagaa tgtacctagc
8401 tgcagaagaa gttagaaagt gtcatctttt acttatctac cagaactata ttcgaggtac
8461 atttagatt taaaaaaaaa gcaagttctc gtaggccttg aatccccccc ttgctatggg
8521 aaaatggatc attattataa tggactgtcc agtaaagttc atgatttctc ctagacatgt
8581 tctctctctt tatgacctag atcaagagtg atctctttaa gtcttttctt cataatccca
8641 cagcactttg tacttagatg tacttagaaa gaaccatata cacggtacgt catgattgat
8701 atgcaagcct tcaccactct acctgtccta aaagtcaggg acacaccttc ttcatttcat
8761 cagtccctac ttctatccag cattggcatc cagtaagtat tagtggaatg gacagacaac
8821 ccgaatttgt gctgatggca gtttaccctg ttttaactgt catccttctg ctactagaca
8881 tggatgagac ctgagacgat gggactgctc agaggtccct ggctcttgaa ctttagggca
8941 ccagaatccc ctgcagggct tgagaaaaca ggggtttctg ggccccaccc ccagagttcc
9001 tgattcctga ggtctggggt ggggcttgaa gatggacatg tttaacaagc tcccaggtga
9061 cgctggcaac tgctgcctca gggccatgct gagaaccctc gccctacaca aacctttctg
9121 ggaaaacaac tcaacattaa agctgtttgg ggatctctga agaaatctgt agtccttgcc
9181 ttgttggggg agcatcaggg atctaaccat tgatggtgga gtatttgttg ttaattcagc
9241 aagcaactat taagtgttag gcctgttact cggctctaac aatacaaggc agagtgacct
9301 gtaccctcga gatttaaagt ctaagtcctg tagagagaag cccaggtggg agcaagcaca
9361 tttagagtta ggtgcttggt gcaaggtggg gacacagaag aagggaatgg catttgcctc
9421 tggaggggtc cggaaacagc ctagggagga ggagcttgag tcttgaaata ctgtgggcat
9481 ctctaagcaa agtcacagta gacagctgaa ataaagaaaa tagtaagcaa gccaaagaaa
9541 cagtatttca gccaagggca gcgtgtgtct atcacgtcca cctgtgaaca cgtcccagga
9601 ttctctgcat ccggccattg ctcaagacag atccctcaca ggaacagcta agccactgat
9661 ttcagctacc tgttcacgtg agaattatca gtacctactg cttttcaaaa tgagtatgat
9721 catggatagg tgaggcaatt cagtttcgca gagacagtag ggcaagtgcc actgtagttt
9781 agttaagggc acatgcttta gagtttggct atgtgagtcc aatcccagtt tagccattta
9841 ttagctgggt agctttagga gcagtagcct tagtgtctct cagttgtccc atctctataa
9901 tagggacaat aacataatag tgctgaataa aagagtaaca aaattttggt caacatttaa
9961 tgtatttaaa gagctaagct ccgtgattgg cacaatgaac caatcaatca aacaccagtt
10021 gttattaata aaagtcagtt gaatatgtac tgtgtgcctg gccgtggttc aatttgcctt
10081 tgcatacaag gaaaaaatta aaatactctg ttaataaaga ctatagcata atactttcac
10141 cttaaacttc ttgatgttaa tttattttgt ttacctgcca aacttctact cattccttat
10201 gactttctgc tacatgaaac acccttgta attcttttgt cctattaaat taagttctct
10261 ctcctctgct ttcctgcttt tggtgctttc taataacact tttaaccctg gactttctca
10321 ttcagctgtg caactgtgga ctgagaggag gctctttgaa ttcattttgt atattctagt
10381 agagagtact gtgagcagtt gggttgttga atgaatacat taattcaacc tggagggatg
10441 ggcagtattg catttttac attgatatta catgatattt agaaaactgc ttaactggtg
10501 gacgttgttt tattaacagc attttgtgta tagcactcac tatgtgccag ctgctattct

Fig. 63D 10561 aactgcctga caaatactcc tgaaaccttc atggtaacca tatgagggaa gcacttttaa
10621 tatatccata ataccaacgg ggagactgtg gccaaattgg ttaattaact tagccaaagt
10681 catattgaac taataagtgg atttaaaccc agctagtctg gggccagggt ccctctttta
10741 atcttctgcc tcctgcttat gctgttgcat ggagtagtct ttatcatata actaaattaa
10801 gcatgcattt gcttaaagca gtgcatacat gatggatcaa aaagtttgtg gtataattgg
10861 tttaattctg tcattatcca ttttgattta tagtcacttt cttatgatgg tcgtgtagtt
10921 ttaaatggaa cctttgaatc tttgatataa taaggttatg tcaaatcttg ggtataataa
10981 ggttataccc aatggaaaca gaataatgat cagcccattt aaaggatgac tggagagtta
11041 ttacaataca taatagtcat gcatatattg agtagtattc ctttggtaac attttccttt
11101 taaaaattgt aacatttgat tgttccttgt tgggagaaaa ggaggtcaga tttttgaggg
11161 gagatccatt tggtgagatg ctgagtgtgt gtcaagctaa ggagatagta tgacatcttt
11221 tttagagtct agtcacaatt aaatgccatt ttattttgga ttttgggatc cgtgccagct
11281 tccagcttgt cagagctgag aagactcaaa tcaagtccag gcttatttct acagcaaact
11341 gggattctgg cttcttgccg gtggattcat tcagtacagc ccatctggct tttgatgttc
11401 tgcaagtttg gagccatttg ttgaaggaag ccaggcggtg aatattggtg gtcctggggt
11461 tctcttgact ccaagtggtg ccccttggtt tgcattttca ccatgcttag catctgctta
11521 cctggagacc atgcagccgc cggccagagg tctccaacaa ccaaatcttc atgcctttta
11581 gaactcagag tccccagcac atcctccttc ctcctccttg tccaattact ttcatgcagt
11641 tctcagtagc tgcttgtttg aatcacttat agtatttaac ttctagggtg tttttgggtt
11701 ttggtcaagg taattccagg ctgaatgtgg tgactaagca ggaaataaat gggtcgtcct
11761 caaagttaca gtggagcgct gtttctattt tcctaaggta cacagttgtg ggggcgatcc
11821 gtatggaagt caggaaccca gtctgatttt gcttcctttt gatggtagca gtacagacct
11881 ggctgttttg tagcctgctt tgtttttctt ccttttcttc cctaacttca cgggctgtgg
11941 caaagccctg agacgtgcag gaaaatgtct cctgtcatac gcccacagca gacctagccc
12001 tgaccctcct ctgaagccca ggaaggaggt atctgtgaag cagcctgctt gtaaagcaat
12061 tgcacacagc cttgtaaact gtgttactgg gctgattata cttgattggc aaggtgaatc
12121 tcttatagca aaagagaact tggagagttt tatctcatct tatgccttat taatttgttc
12181 attctttaat tacacagcca cctattgagc accctattta tgcaaggtac ctggtcgggg
12241 gtcagaggga gggtcccatg gtaaacgaga cagactcaat cctggaggag caggaatggc
12301 agcccctcgc tgggctgttg gccccaccaa aagggaaagg tttcatttta ataatacatg
12361 ggtgaatcat ttttgtcaat aggcaaaatt ctttgtagtt aaaaaaaaat atgatggtag
12421 gaaggaaagg gatgggcaga gggttaaaac aaaagatatg ctctccctaa ctctagattg
12481 tagtattgtt atgcttgtca ctgtagctga attccatttc tttgagtttt ttcaatgcca
12541 aggcattccc tgtatgactt acgtgagcct ttcatctccg cgatttttcc cattcaggta
12601 aatgagcaaa tggatttgaa cactcatatc taaaacaaga gagaaccagc tggaaatgcc
12661 ctttgaattt ctttctctat gtaaaccatt tttctttctg gtgcctcacc tataaataac
12721 aggagttcca ccttccttta tagactcttg ctgaaagcat ggtttggaac aagaccgtac
12781 aggtgcacac aaattacagt tgggaaagaa gcctgcagtg catcttgtct ctgaaggtta
12841 tgaaatcctc cttttagtaa tggagctggc gtgatcaagc cagcaggatg aaatttggca
12901 tttgtgagat cacccccctt ctcacttgcc cactgtacat agcatcccag ccttactctt
12961 caaatctcca catttttttct tatctagcta caaaattcat aggctgattt ttttggggtg
13021 cgtgtgtggt tttttttttg ttttttttggt aaataaagac ctgcattttt attttgatat
13081 aggtggttga gttttgtctt taatttcatg acagagattt aactagtctc aactttttgaa
13141 aagacaacaa tgatatttgg ggatcacaca cttaaagtta gatttctaga tgattaatac

Fig. 63E 13201 caaagtagat gatttttag cctcagccat ttataggtat gcccttctgt gaatttttta
13261 tgacagtgaa aatcatggca cagataaaaa ttaaataaat acttctgtta ttttcctgaa
13321 gaaaaaaaaa aaaagcttaa actatgagaa tactgtcttt gagcacttta aaataaaatt
13381 gacttcagcc agcaggattt tgagcattac atcacaaata aaaaacaaga ttaacatcaa
13441 aaggagtcag ttttcattca attgtgcagc actgtgggct gtgaaattta atattatttt
13501 gactcatatg ctaattgtag actgacagag gaaaatggat tgtgtttaaa taaaaggata
13561 cacagcatca cacgcagctg tatcaaatac aagttgaggt ctttgggcca ggaactgggg
13621 gccctctagc tctgttattg cagattcaag tttgacaaat aaaactttcc tttagactgt
13681 agtttaatta cttttttca aaggtatgcg tgatgaagag gcacaaatac acctcacctt
13741 gaagagttgc taaactggtt tgtgtgccga tcagttcacc gtgtgtttga atttctgtgc
13801 ttctcatctt tcctttctt gaaaagattt tgcttgtcat tggtgtgaat tgtacccccc
13861 acccccaccc atctagtctt tgctctcaga tttataacac tttaatggtt ccaaattgta
13921 tagcctgctc ttagacccct tttcttttcc ttgaataaat caggttcatg ttgcagacga
13981 tatttgtttt aggaaagtgt gaaagaaggg gcacctgtga aaacacgcaa ttgttccaac
14041 acacatatac atccaaatta aagcagaaaa tgtcaaagcc tccaatcact accttatttc
14101 ttggaggttt aaagccgctg agaagatagt ggtgccctcg ctggaagttt taaggtaatt
14161 actttttact ctaagcagta gtatctggta acctaattcc gtataaacct gacaccctat
14221 cgctacaccc cagtatttct ctgatttcag aataagtctg cgtagaaact tgttctgatg
14281 ttaaagtgca aaaggggca gtaaagtgct atccacaaaa aaggaaaaac attttccaag
14341 tatttcttat tactgcctgt gtctttcgta ggccctgcct ttatttattc attttataac
14401 aaaactctta tgtttggggc attcagagaa taccttatta agctgttgca gcaatctagc
14461 attaaatgga agacatgcaa gactgaagat cctgcc[illegible]t tatgaagtgt gccatcaaat
14521 tcacatgctc atgatgcaga gtccttcttt gggagtattc gtattcccaa gtgcacagag
14581 cacttcggaa aggagccttg gtctttggtg ttaatgctct cctagctccg tatagatgtg
14641 gcaggcccaa agtacatggt ggggtgaagg gtcaagggtt tgggcttatc cagagcagcg
14701 tgcatccttt gtcaggaggt gactggaaac accagccaat tacagcagaa ctgcagactg
14761 ctcatctgca ttcggaattg cagatgaacc agtttgtact cgacttctct tcttcactgt
14821 aggctttgac atttaattaa aaattaaagc cttttatgga aaaagtacat gttttccaaa
14881 atggggtaaa ttcgaagtat acttgataca gaacactggc ttgggaataa acctgtgata
14941 ttacatgact tttggtttgc aactgctagg ctgagcctct ttgtaaagct gggatttaga
15001 atctttgaaa tgtttgtaca gttcaatgat taagcataaa ttgtatatat tcccttttt
15061 tcacttattt gagtaaacaa gtttgttact acagcttctg tggactcaga gatttatgta
15121 ttaaataggc cacaacttca actaggataa ttttatttat ctgcttgtta gggaattgca
15181 tcaaaagttt aagtctgtag gcattaaata ttttaaatgc ttatttttaa agtcaattat
15241 gaaagatagc acaaagtttt tctgaaacta cattaaaaaa ataatgtttt aatcttatca
15301 caaaagcatt gactatttat tgcaaagaaa acacagaaag ctaaaaatca ttctaagtcc
15361 accattcagt agcccaaagt ggtctcaggt aaaggcggtg tgtgtgacca tttgtttatg
15421 gttgtctccg tgcagtcagc aaaataaaca gaacaacatg ccatatatta ttgatgtgta
15481 tattttcaac tgaaattagc catctgctta caatgatcat atacactaat ggtataattt
15541 tgaaatgaaa agaaaaataa aataattctt tgtggagagt aatgcgaatt gacttatgaa
15601 tctcgccctg cttggcagtt tgctctagag gtagaagagc tttatgtgtg ggcctcctcc
15661 ccccccacac atttattctg ctcacacttg caccagcatc catgtcagga ctcaccttgt
15721 cctgttacat gagtaacatg gccctgattc tcaagtgcat gataactgcc ataattacac
15781 ataaatatta aatatttaaa tagatcttta cgtgtgtaat attaggtaga agtggctctg

Fig. 63F 15841 gatcgaatct gatgcttttt aaatagaagc tttcccacaa catttccaag cactgtcatc
15901 gtgtctgtct cgatttgggg tttacctggc ctagttatct gtctgggtgt agaaactggt
15961 agttcctgtt tgtatctttt ttgttctgat ctctttattc tgtgtcagct aaatattctt
16021 gcagtcagtt actaacatat taactcatcc ttgtttggaa actttggcat atccttccat
16081 ggtttccttc cgtggacctg tcgcgtctct caggagagcc accaggtata ttgtcacaca
16141 tttcgcatgt attttcagag actacagcag catcaagtgg ccccccagcg atttgggttt
16201 tcttctcggt taatctacac tctttggcca accgtgagaa aacttgtaag aaggcatcag
16261 atgtttgtgc taaggtgcgt gtagtatggt cagaggaaga aagaagcagg gaaaatggag
16321 tggccgtggg tgggagggga agcagggagt gcaatttcgg gttcactaca cagctctcca
16381 taaacttctc cactgctggc ttcccacgga tcctcctatt acactgggca aagtgcagaa
16441 atagatcagg cgaccactgc ctccgtccat ttcccaggca ccctgtgaga cccgataatg
16501 caatacaggt cagcagaaaa gtccagactt gacatcccaa cgtgccatgg tctggtctgt
16561 gaatgaaaat cacatgaggt gacctctgaa ctctaagtgg ctggtttatg ttttcagtgt
16621 attaggcccg tgttttaaac aagcatgtgc tcgtagtgta ggttaaaact ttctgttgtc
16681 ttcattaatt atgctgtgtt ctagtctatt aatattaaag aatattgtgt tgcataatga
16741 ctaatttttt tatttttttgg agacggagtc ttgctctgtc acccaggctg gagtgcagta
16801 gtgcgatctc ggctcactgc aacctccgcc tctcggattc aagcaattct ctgtctcagc
16861 ctccgagtaa ctaggactac aggcgcccgc caccatgccc agctaagtgt tgtattttta
16921 atagagacgg ggttttacca tcttggccag gctggtcttg aactcctgac ctcgtgatcc
16981 acccgcctca gcctcccaaa gtgctgggat tataggcgtg agccaccacg cctggcaaca
17041 taaggactat tttttaaagt ttttacaatt atgactgtga agttgaaatg tctaaattat
17101 tagagatcca gtttagatta ctaaatattt atgtctaatt gagatgatta gacttagcca
17161 aagtatccat gtagaagtat tagagtctag attggtgaaa aacttgaaaa agcttggctt
17221 aagttcaata ggtaatccaa gagtaaaaac agattccaat atcagatctt ttcaccatag
17281 tcatgttaag tttggaagcc ctacttgagt gtttccagtt ttttccacat tatattgtgt
17341 ctatatttga ttcaaaggca gggcatctat tgtcttgctt aggactgatt cactgggaaa
17401 agccactgga gttgcctatt tccactcagt atgcctcact cttagagtag cttcccatgg
17461 ttcccaggca ggccctccag tgagaatgca ccaagccaca cgccatggcc tgggaagcag
17521 tcctgaacct ggagattgtc ttgatggaaa ggaagaggca gccttcccct cccaggaaga
17581 tagtagagag cctgctctga cttcgctcag ggatggaact ggtctggctc agttctctct
17641 cctgtgtggg acatgaatca ctcttggtgg tctttgcttt ttatttgggc ttaaaatcag
17701 cagactttat taaatgacac ctctctctaa ccactctctg tctgggcgaa gtttaacaag
17761 aacagcctcc ccccatgtgg tatgggttgt aactgtggcg gtttccctct gctgtttttg
17821 gttacaagat gaacattatc tgaacacaca gaaagaaatc tgtatttggc atccataatg
17881 gaaagtcagt ttagtaattt aaacttagcc agttatcatc atcataattc tttttaacac
17941 tttcaaagtc agcataggag aagtgtattg ttgaatatta caaaatattt agggcataga
18001 tagatgtgct gtgtagtttg atttgttaat gtgtctaagc aatcaaagca acagaattca
18061 aatataaacc ccatcacttc caaaatagga actctgttta ctgacttgat tataacatat
18121 ggaactcaat tgttttccat taaaaaatga tactattagg aaactcaccc cattttcttt
18181 tcatatatat tctgctattt gcataattgt ctggagtcca tatgtaatat taaatgtaaa
18241 acacaaatgc catgtagctg gtctgtttct tcctcacctt ttggttcctg gcctcctggg
18301 gaagggttgc acatctgagc cgtggtctca gatgactgcc tcggaagaag cctcttccct
18361 tcaggcacca ctgatgtgtg cttggtgtgg agctagactt tccctggctc tccatgtgac
18421 gctcacatgt gcgtgtcttg atttccctta acttcatggc ttatctatga acagcttgat

Fig. 63G 18481 ttgggggaaa aaaatgtgtt tcccaatgct ggagttataa ttgaatgtgc tgcagtcaaa
18541 actgaaatgt gtgcagagaa agggggcttt tcctgtcatg ctcattgggc accagtgtgt
18601 cttcacctgt tttgtgtgtt aggtccatgc gtcatgctga aatgaagaac atgggatgta
18661 tggggctttg gacagtgctg agccaaaagc aagtgctcaa aagcagctgt gtttgtatta
18721 ttagtggttc tggaggtggc tgattgcctt gcattttaag tagagaggga ttgtagaaga
18781 ctgccaatac ttagaacttt ttccagagag gaagggtcag aaactgcatc tgcagggctc
18841 cttgctctcc agaaatgcca gtgtgcctgg gagggcatct tcagaaatcc agtctctcct
18901 cctcagtgtg tcctgtaccg actcagtggt tctgtcttca gaattcctat catgtctgtg
18961 atctgcaaat agtggtattt aatttgactt caatttgtat aaatgttagc ttctatttgt
19021 tcattcctat tttttgttca attaatacat tatttattga gcatctactc tgtgtcagcc
19081 ccttgggtgt ttaatactga attagtcaca tgtgggactt gcctgccctc agggagctag
19141 actataaatt cctaatgatc agtggtctcc acttttctgt cactcataat gtctggcaca
19201 acataggtta cttgagttgt tacactcaca gtactgttgt ttgctgccat ggtgctttag
19261 gaagtgtgag agttcccggg aggcagagtc aataatgcag actacacgta gtgaaaacat
19321 ggccaggaga gctgtagttc aggctctcag ctcaactgca ctctgtccac tgagaagcca
19381 taatttcttc acttaaagtg actgtgcgct atggctgttt atatatacgc ttaaaaagta
19441 aaagctgcta aaccactcaa ggattggggc cttttgtatt gatttaatta aaggaacaat
19501 cattgtttta atgagctcta gaaacaatta cttttgaaga gccgaggatc aaattcttgc
19561 ctcacgtttt gccacagtgt gttctgaaag gtgaattaat gcttttggaa tcatcaggaa
19621 tagtgagctt tgtcacgatt tactttttac aagcgtatct aatatgcata ttgaaatgtg
19681 agcctcccca ccacacttcc gctttgataa gcatcccccg gattgccgtc actgaccatt
19741 atagattttt aacaaagttg gacagtacac actgaatgaa aactttacat caaggaaggc
19801 ctggcgtgtt tgtaaaatga attaaaaggc tcattaaatg atttatatga cttacgcctt
19861 ctgaaaatat ggcctcaaac acagagatcc ccaaagccac accgacccct gcgtcccatg
19921 ttctcgacct caccgcatca gcaccagcaa gacctgtcgc tgagacggtg agtgatgaga
19981 gtcaagagga gtgacttgca tggcctggga ggaaacctcc tgtgaatctt tagttaagca
20041 ggaaaaaaaa aatcctcatg aaggaaacag gatcttggga gcattttgaa tgaagaagga
20101 gcttagtgag ccaaacttga gacatagggt gtaatgtggg agagttttaa gatttgcaga
20161 gatgtacagc ttgggagggg gtgtaatgca ttttcttaaa agagctgaat gaatggttga
20221 ggaaatgggt acatctggtt tggttaagga tcctaatctc tgaagcctgg gatgccccca
20281 gggcttgtaa tttaggaata cttcccctaa tagtagctaa cccttatata gtgctgtctg
20341 tgcaggctac aaaaggagca gattaaggat agaaaaggtt tggagtgtat gagaaacccct
20401 aggcaggaat tgactcctgg tgtttgtaaa ccttaaagat gtcctaaaaa ggtcaaggaa
20461 taagacagga gaaaaaggaa atgtcaggaa gatgatcaat ttaatgttta tggaatttag
20521 tttgtactta ctgcccggca tcttgcctga ggtttttaac ctcagcagca catcagaatt
20581 actgtgtgtg tgttggaggg gctgggggag ataaagaaat tagcctcatc ccaaacattc
20641 tgattcagtc tgttacttga gaaactgaat tgtgttttgt ccataaagaa gatgaaattg
20701 tctacagaga acacattgcc attcacaagg ttgaggggat accacagaga ggctccccact
20761 gtgatttgca tttgtcaaaa gttctagaga attcttcaac agtacacaca tggttgtttt
20821 aaatatatca ttgttataaa aattcgtttt gagttctgtt tcacagaaag tttttttgaa
20881 tgaatgaatg tcatatatcc ttgctaaagg agctcagtta aaaaaaaagg gaccatcctt
20941 ctcttttggg ggttgtacag taacacattc ccaagaaaga ggtaacagcc acatacattt
21001 ttcttcccaa taaagagtgt gggtttttaa tatgaatcca tagtatgatt tctgttatgt
21061 tttgtgctgc ttcataacca cactcatgca cttttcagaa aattaatacc attcattagc

Fig. 63H

```
21121 ataaatcata aactattccc ttggtatggg tttgaaattg ggggtgccct atcatccttg
21181 ctttatctct tagtgaatta tgaccctgta gtcatcatgg ctggtgggcg tctctggtta
21241 aagaaagggt tggattggaa ggattcagag gcgattcttt gttcttaggc tttaatattt
21301 taatgagcct gcaggcttgg ctgcttacga acgagctgag atttctaagt gtgttgttag
21361 tgttagcact tgtagaagga tgttcattag gaagttcttg tttcagtttt tcagagaaac
21421 tccccattaa gaaagatcat tcaggaacat ggctaccaag aaagaggaaa gggaggaggg
21481 aggctttcag ctataagcat taaggggata ttgtatcagt agtcttagtt ctaaagattt
21541 gcttctgaga attaattgga gcaaatacat ctcaagggaa gaaaaaaaaa gatttatagg
21601 gcagggacag tagttgtcct tgcaagtaga ggacacttca ttttgcagct gaatcaatac
21661 cacaactaat tatttctggt tatcttttac gcatttgtaa gacattgctt ttgttcagtg
21721 taataaaaaa cccattgttt gatcagtgac tgactaatta tgataagtaa tttgaaacat
21781 tcttgatgaa acttgtctgt taattaacat caacagcaca gggaaactaa caggacaaca
21841 aagtattagt ggatccactg ttccctccaa ttgacgagct ttctctgtgg catgccccaat
21901 aaactaaagc tgccaatggt taaaaaataa caaacatgtg ggagatctga ctcaccacgg
21961 aggaagagtt atggtaaagt tacacaaagg agtactgaaa tattacaagc gagggggtgg
22021 taaagaaatg tcagcaggta gcctgatcct acagcttaga gtaaggaaag tggtttcttt
22081 ctgtctttcc tttttctttt aaagcttaat tccaaaatac attcatccca tattgatctg
22141 aagtaagaga cttttgataa attaaagtgt gaatctgaaa atgtgtagtt tgggattatg
22201 ggcattgcct ggctatcttg taactgtcat taatactgtt aatttttatc aactcaatgg
22261 cttttttttc ttatgctttt agatttctac ctggacaagg actggtacta taccccacaga
22321 taggagacaa attggatatt atttgcccca aagtggactc taaaactgtt ggccagtatg
22381 aatattataa agtttatatg gttgataaag accaagcaga cagatgcact attaagaagg
22441 aaaatacccc tctcctcaac tgtgccaaac cagaccaaga tatcaaattc accatcaagt
22501 ttcaagaatt cagccctaac ctctggggtc tagaatttca gaagaacaaa gattattaca
22561 ttatatgtaa gtataatttt attcatttat tttatagaaa ttaagataag ctatataggt
22621 ttgtatcaat tttttgtttc cttaaaatta ttgtgacaaa taatttgatg aaaatctatg
22681 tggaaaaatt gtcccccccc ccttttttttt tttcaaagaa aacttcattg aatttgggac
22741 cctgtgctac cagtattcat taagtataca tacccaaaga gaaaaaaaaa cactagaatt
22801 cttaatagta ttgaaataaa tgtattatat gaatatattc agcatctcta ctgacaaaac
22861 catttttaag gaccattggt ggattttgat aggtaaatct tgtgcattgc cttttctctt
22921 cacccatcca tccattcatt cactcattca tttcgtattt attctgtgcc agagactgtg
22981 cttaagggct agggattcag cagtgaaagg tggtaaaata gcatgttttc ctcaagaagt
23041 taacagtcta gagaagatgg agctcataaa ttcgaaagat ggggatgaca ggtcacatta
23101 aaaccagatt cagaagaaaa agacgaaact tggtttgctt agtacattac tctttttgc
23161 atacatatat ataatttgac acgctgtttc aagaagagat ggtacgtatc ccttgggtca
23221 tatctgaggc tgacttgtga ggatgtgaag tcagctgatg agcacatttg gagcccacgc
23281 ctactatgtg cagatctctc gtcagcgtca ttcccagggc cccaggtggt gttaaagtct
23341 aggtgactca gacagctgtt cgcgtcattc aagcaatgaa gtcttttttc ttaatttctt
23401 tggtttaaaa ttatactcat aattaattgg gttgaatttt ccagtggctt ggttaccata
23461 gacttcagtt tattagggaa ctgctatctg ccactggttt attatttgcc ccaaggtgga
23521 ctctaaaact ttaggtagga gactcttggt gatcaaactg aaactcttgc atctcaacct
23581 atgagccgca ctttattgtt attttatttt tttagagaca gggtctagct ttgttgccga
23641 ggctggcgtg cagtggcatg atcacagctc actgtagcct tgaactccag ggctcaagtg
23701 atcctcccac ctcagcctcc aagtagctcg gactacaggc atgtgccact gcacccagct
23761 caagagctac acttcaaagc acagaatgaa aacctatttt taaagccaac ttgatacata
```

Fig. 63I 23821 gagtagctta ccaagaatta gtaacaacaa caacaagaaa aaaaagagag aatgtggtag
23881 agtatatact tagtaaggag taattattat aaaataaaag cattctgaaa tgaaacaggt
23941 agatggggtg gccaagtatg cagcatagta gggaaatctt tgaaaatgta aaatagttac
24001 caggtaaaat aaatggaaac tttaagcttt tggaagccta acaatgtatt tatattagta
24061 aagactttat tttttttattt tattttattt tatttttgag acggagtctc tctctttcgt
24121 caggctggag tgcagtggcg tgatctcggc tcactgcaac ctccacctcc tgggttcaag
24181 tgattctcct gcctcagcct cccaagtagc tgggactaca ggtgtgcgct aatttttgta
24241 tttttagtca agacggggtt tcaccatgtt ggccaggatc atctggatct cttgaccttg
24301 tgatccttcc gccttggcct cccaaagtac tgggattcca ggcgtgagcc accgcgcctg
24361 gccttagtaa agacttttaa agtaagactt tttcagtgaa agctactgtt aggcatgaca
24421 tttacaggca actgaaactg atcagatgca tttattaaga aggttaatgc ccctaggtgg
24481 ggtgggagaa agaaggtcgt ggtacgggaa gaggggacac actagagatg agatgcccta
24541 gggcagtgaa cgcatgtccc taatgcgtgg atgcagccca cgtccaccga taatgccgac
24601 acacccagag tctctcttct tactttagct tatgacttca cgaagaatgc tttgcaaatt
24661 ctaagttcgc actgggcgca agtggaattt tagtaaacat taagagttta acctttagtg
24721 tgaaataata tgcaagatat gcaaataatt gtttaccaac atctctttgc ttaatgtggt
24781 gagcatttaa taattgcttt ttattaatac atgagagatt tgtatttaga agcagtttaa
24841 tttataatta taatattaat ctacacaata acgacatcta ttattttctt tttttggaaa
24901 ctcttcatac cacactaaca ggttcattgc agttactgaa ctactctggc catcagagct
24961 ctccttagag ttacgattta ccatgcaaaa gcatatggta gcctgggata aatgaatctt
25021 tcttaataca gaattgaggg tctcaagttt gaaactacga gaggctattt gaatgttgct
25081 ttgggggact gtcataaggg ctgggtggag gactcagggc taagaagttt gccaggaagt
25141 ccagttgaga ctttcagcag agttgaaaga cttccacgat ggcgtaggca gaggaaggcg
25201 tttcagatac ttgggaaaat atagaagcca atttctcacc caccctacag caaagctcat
25261 tgatctacaa gtttccctag aaaggaaatg ggaaatgcag agaacaaatg ttaaaatagt
25321 tttagaaatt aatattgact ttgtattgct tctgcataag ttccaagaca ccaaaacaat
25381 gaatggattt taaaaagtca ctactttgca tatcagacaa atgcacacac acacacacac
25441 acacacacac acacacacac acacacagtc aagctctgta ctggcttttt tgagaaggaa
25501 agtgtttgaa gttagtaatt tttatatcag tacatttata aatagtgcta ggtagcatga
25561 cggaaagtat taaaatttac atgtatattt ttaacacttc aaatcgttgg ttcactttga
25621 gacagtaaat aatattagca tttgagttca gctttaataa attctacatg ggtttaaccc
25681 caaatctgag tgtctagttg gtaagcgcct tcagaacgag cagtgttata ataaatatgt
25741 tattgtgtgc tggtttcttt ccatggagag gaaaaagaga cctgatgctt tggaggagtg
25801 cttgactttt ccccagtgag gagtagtcca gagggactga cttgcattgg ggagtaccct
25861 acatgaacag catttcagaa gaattaaacc aggaacctag agtcctactt gctagtcctg
25921 cttcctaagc ttaatgagaa agtcaatttt atttctttga actttaattt atttccctaa
25981 aaaacgcttt tagtattgtc attgttctgg ctaatgatgg cggtctcctc cagtttcaag
26041 ccaccttagg gctgggcata caaatgcaat ataggatcac ttgttagtgt ggtttcaaat
26101 ggacatgatc ctctgtaaat tctttaaaaa catttaattt gatttgtggt gttacctgct
26161 ttaaaatata gtcatcacac ttgtgagttt cagacgtgaa tatgaatttt taatttgaac
26221 tgtattttta aacacactaa gtattaacta agtcccctta ggagatatgt ggcaaactga
26281 tatgcatcct cattcattct tctcatagat ggttatttgt tttttaactt gtggcaaaat
26341 tatatatgaa tggtcaccga cttaaaatag ttccacttaa atttttcaac tttctgatgg

Fig. 63J 26401 gtttattgga gtattaaatg tattttcaat ttaatgatat tttcagctta ccttgtgctt
26461 atcaagtatc aagacatagc cccacctaag tcatggagca tctgtatatg ggtttttatt
26521 cttgtttaga attgactttt tcaagtgacc tatttcagta attagccctg ggcctgattt
26581 gcataatgag atctcctaat cttcaagtaa tgcaaagatg gagatattat ggccatgtgg
26641 tctgaagaga ccttttcttt attatgttca gatctttaat tgccttaaaa atagagtagc
26701 taatttacct aacctctagt tattttatta ttgtctttaa agttttttt aatgttcatg
26761 aaataactgt tctgaaattg cctattttca agggaagctg tgtcttagac ttactaaatg
26821 ctccagttga tactgggaaa gccttcttgt gttcgtagcc tttatccgta gagttttctt
26881 tgcagcattt tctgtgcctg gtttagtttc ttttcagagg cgacacccag agctgaatga
26941 gtcagcaggt ttggtgtgtc gacccttttgc aacagctgtc cttacgaagg ttctgtgggc
27001 tggttattct accttcgcat aaaaccttgc aaaataaccc acaaagaggt tttcgtcaca
27061 ctaccaaaat catgtgagtc agagatggat gaaaaatgaa tgccattgtg ttcatacttt
27121 tccagtgaac agtagctaca gcagagctgt tagacaaaga aaaccgtatt aatgaagcgc
27181 ctcccaattt agcttcatat ggcttttgca ttattttgct gcaaatccat agctaagaca
27241 catcttgtgg catagtccgt aagtcatctt tccgaaggac tgtttgatta aaggttgttc
27301 tgtgagatcc accctgtgtt gttcatggca tcctcttgga ggcctccctc actctccatg
27361 ccttggcaaa gtcttcctta aggaacactg aacaagtctg gagaagctgc catttcttag
27421 ggccctcatt ggttcagttg tctatagctt tttattttt attttttttt taataaagag
27481 tatgtaaaat tggaaagctt cacaaacagc tttgctattt tttagacatg tactccactt
27541 ctaagcaaaa tcacaaaata aagtaaaatg cttccacaaa tataatgaaa caatattctt
27601 aaagaatcaa agcagaagaa cttcagagtc tgttgcttat gttaagcata tatttgtttt
27661 cttctctgct tttgatttac ttatttctgg ggtgtaggtt tggcaagtag tactgaaacg
27721 tactgaatgc actgttcttt agcaagatag ttacaggagc tttcaaatgt cctcttaaca
27781 tatagatttc ttttagaata tagaataatg tgtgggctgt ataaagcgat tatgtgcttt
27841 atttgatgaa ttatttatgt acgataaatg tagcaaaagc cacatttcca tcattaaatg
27901 taatcccatt tggtgataca gcaacatcag cctgtcattt gggtcctctg attgaggggt
27961 gaggatttct gtttgatacc ttgtgcataa tggctgcgtt caagcattta aactcatttt
28021 tatttctaac ctacagctgt catctttgta ataggatatt catcagaatc ttgccagaga
28081 ctgtgcattt gggatcttgg gggatacagc accaccacca ccctccccct gtccaagaga
28141 aacagatcaa catcttaggt tgagagtctg gggtctggaa gacccgagtt cctgagtgcc
28201 ctttgacaag taacttaacc cctgtctgcc tcagtctctt catctgtaaa gtggggataa
28261 tgacagcacc tgcttcacag ggttgatggg aatccagatg tggtgggata tagaaaatgc
28321 ttattacttc cacctttgac accaaataca tataactaag agttaacttt ggagcagggg
28381 aggaagtgtg aggctccagg ctggaggcag acctgtgttc ggctgcaagc tggagaggat
28441 ggaccccaaa agcttggctg atttgaagtc catccataaa atggaactcc agagagttta
28501 cacgtttcag taatgctgca taacttaatt ataagatctt ctctctttgt cttctttcag
28561 tgttataaaa gctcttttgt ccttgagctt cctttaccaa gaaacatgca tttatgtatc
28621 tttttgttca tggaattgcc caagcttgtt agcagatcct ttgtaagacc caaaagagac
28681 agacagggga ggagtcttca gatacatata atcattttc ccaatttcca tgttaccagc
28741 cttgccagga ctttttctca gttccctgtt acacaatgaa aatagtgtct ctttattgat
28801 aattttagta gcatcctaat gtggtataaa tcgtcttcca gagaagaaaa tgtgtcaggg
28861 ttgcgttatc actgaggcta gctgggaaag tagatcagcc cattagtctg ataattcgaa
28921 gcgttgtttc tgttatttct gaacatcatg tgaactcctt ttctgggtgt attaaaggtt
28981 ttcccagtgt gtgtcagtga gactcctgat tgaatttaat atgaataaag ataaattctt
29041 tacatttaag gattaaagtc tcagcttctg cttaacttga gattgcactg agaaactcct

Fig. 63K 29101 ggctctcggg tatagcggag tcacgacctg gggatgtctg tcccatatgg ctctgtgtgt
29161 aagaagaaaa agctgctgtg gacggagact ctgttcacat taaatgacat cacctaagcc
29221 atcatgacag caagaattat ttaggaattg ctcagaataa aactgccttc attatttcat
29281 aaaatgtatc ttggtatctt tagcacctta tttatggctt tttaaaggtt cactgggatt
29341 tataaataat tggacaatgc tagagaccta gtacaagaat gaaagaggac aggcttcttt
29401 cttaataacc tttaaacatt catcaggaag ataaaacttt aaagcaaaat aaaacacatg
29461 aaaatagcca agatgcacag accagacaag caaatactac tttaacttat ttgtatagtt
29521 cttaagagtc acatttgttc ctgaagtttc aaaatctcgg gctgagtgtt tgatcactta
29581 gggaagtgtt gtggccttca catactcttg tctcactttg aagtctagaa acacaggtct
29641 tagagcaatt tttatcactg tgagaaagct gaaacttagt gtgagtagct tagtacaatt
29701 cagttggcca tcaaatgtca gaaacaaaac tcagtccagg gccgctggac ccttaggccg
29761 gcgttgttag tttacaacag tgcctcctgg gtccaaacat ctaagtgcac atgtagcaat
29821 agtaaagata gtatgtatgc atacataaca catatgtaga gacagcagag tatacgtaca
29881 cacatgttgc atacatagca acagcagaga agctcatgaa ctataaagga tggactgtat
29941 gcttgtatca gacattttgg tactgacgct ttgtcatata ttgtgtaaca tataaccagc
30001 ttgcaatcat ctgcccccaa agttgaacta agaaaatcct acagggtact aggaaaggaa
30061 ggccattggg aaaaggtggt tatagtggca atttgttagc tcttatgaat tttctttttc
30121 tttttagaca tactcttaat tccatttttt caataaatct atactatttt gtgtttttat
30181 gttagcaagt actttaagcc cctcaataga aagttgctac atcatatagt gattaaaaat
30241 aaaaatctct caaacataca agtagaggtg gtatgagact tcaaattccc ttagccaagt
30301 acaagtgcag cagttttgtt ggctggctgg ctgcatagaa ggactgatgg attggcagac
30361 cctcaagctg gagtgtaatt gatctcatta cagaggagcc aggctgggtg acagttgtgc
30421 tttgcaagtg gtttttttgca ttggtgaagt agcccatttt gttgttcctg atgttaaaca
30481 ggggatgaag gtattctttt attggcacaa acgcgggaaa ttgctctgga ttcttagagg
30541 atagaacatg tcccctggac ggaataaggt tcatgtgtag ggcaaattta gataggggca
30601 ccttattggg gttactactg gtctctagat ggtcaaagca aacaacatgt ccatctaagc
30661 tgtgatgtcc atctaagctg tgtgtgtcca tgagagtgac gcattttctc ctctgcagtg
30721 ttgttatatt ctaaactgtc agcagacatt aattcggtcg ctggtgaagt cccaccgcct
30781 agagatgaac tctgcctccg atggatgttt tccacttcag tgccactcgt ctcgcaatta
30841 ctgggtcatt aatatcattg catgcaatta gtgacagtag aaagagctag agggttgtgg
30901 gatgtgcacc ctcccccacca tgaacttttt actctgaccc tttcccagct agaccttttc
30961 gtatcttggc aaggatattt taatgattga gactgtcaga atcttcagag caggcactgg
31021 attatgtgct ggaaataatt cactcaaaca cctgcttctc catggttcag aatattttca
31081 ttagatatta tcactatccc ttccctggga agtttcattt ttaaaaatct gatgcttaag
31141 tacagctaat atagacaata gggaattatg ttttatcttt agaactctta cattattctt
31201 ttctttaaaa atgtgagctg agtcattgct attgcagtgg tcatctggcc gcctattttt
31261 aaaacacaat tcctctatct tagtagattt tggcccatat taagcatatc aagaatgact
31321 tttttttttt caagacatgg ggttttattg gggcttata tacaaggaaa gagagagtcc
31381 agtggcagtg ggctggacaa gatatccaca tggccctgtg gcagtgagct gggcaggaaa
31441 actgcaactg cttgcaaaca gcatgtagtt catctatagc attttcactt aacaccaccc
31501 agctaatgac ttccacctgg caaccttcat ttaatccaga acttaggacc tcgagtccct
31561 gtacggccca tgttccacag gatgggccga gggctcagct gttcctcata gacaaggaat
31621 gactctccac attggccact cccggattcc ctagctcagg acacatattc aggtgtgtct
31681 aaggctggct cttctatgtg aagttactta ttcttttacc attgactctc atgttcccac
31741 tatattaagt tttctgaat tactgtggca ataagaaacg gtcccttaaa ttatactaga

Fig. 63L 31801 agaaaagctt tttttttgtt ttgtttttta ttttgaaatt atgttaaatt tttttctta
31861 actgagagat tccacctgca taaatcgtca taacttttaa cagtaagatc ttagacttag
31921 aaagtgatgt ttttcctcaa cagaatttat taaaaatcaa gacaccaagc tgttccaaac
31981 aatagtttga ggggaaataa aataaacaac tccataaata atcttatgtt gttaaacatg
32041 tctctagcaa aacaaacaaa caaaaaagtc gggggttggg ggaggtgcag tttattgcca
32101 gtactgtctg gtctttctca gaaaagcgtc agtgtacatc actgagcctg gacggtatgt
32161 tttcttgatc tataccccct atgtgtacat gtgcttgcac gcacacacat gtagacacgc
32221 acacatgtgc acctgccatc actttctgct cttccgtctt ttcactcttg agtgtctgta
32281 gccagtagct ttccaggtct gtatagtcaa agatacctat ggccctgaat gtcttcactg
32341 attgctattt gacattcata cggtttttaa tggttaaaag gctttatgcg aaagctgtga
32401 tagaatttct cctgttctag atgtggtgtt tattgcttta ttttgtgact tttctctcag
32461 tagattgacc ttctccctca gtgtccaagc ctcgcatagc atgatggcac ctgtaaactc
32521 agttctgtat cctggtatcc tttctcttcc caagtagaag caattaagta atatatgtca
32581 tcaaaacctt ttaagtgcac atacaaacaa aatcaactta ccaaactgct tcaaagttgt
32641 tccatgttta acactcttct ttctgagctc tgggtagaat gtcctattat tgttcatcat
32701 gaatatttga aattaaagaa ataaaactgt accatttctt ttaagagcat ccatttgtac
32761 ttgataacat cttcagtcat atttcaatgc tggcaaagag gaggggagtt ctaaactgtg
32821 actcaatttt agaatctact ttttccaaat tattctgttt agtgcagaaa actaattaat
32881 agtgttgcat agaaaagtca ctgaagctaa gccagttatt acttcttaat gcatgattta
32941 ctgctttaag ttttcaaaac acaaccatag caatgtggta ttaattcaag tgattcttcc
33001 tatcatattg aacgatattt tcacgggtga aaaactcaca catcctacat cactgatagt
33061 ttatacagtg ttttagctgt ggctccctgc atgcaaaata agagttaatc aaatgtcagt
33121 gagaaccatc tcatcaagta gagggcttgt tttgtttaaa ttaactttgc taagtataaa
33181 tttcttcttg aaaataaatt ctgggccggg cgcggtggct cacgcctgta atcctagcac
33241 tttgggaggc cgaggcgggc ggatcacgag gtcaggagat cgagaccaaa ctggctaaca
33301 ctgtgaaacc ccgtctctac taaaaataca aaaaatgagc cgggtgtggt ggcgggctcc
33361 tgtagtccca gctactcggg aggctgaggc aggagaatgg cgtgaacctg ggaggcagag
33421 cttgtggtga gccaagatca caccactgca ctccagcctg ggtgacagag cgagactccg
33481 tctcaaaaaa aaaaaaaagg aaaataaatt cttctgtatt tttctttctt caagtgaggc
33541 catttagggg aaagtatacc ataaaacttg ctctaagata aggcaaattt ggtattatag
33601 gatgaagtgc tatgtgattt gaagtaatgc tgaatttttt aaatatatta aactaaacaa
33661 gaataatgag gccctcggaa agtcatgatt atatttctca tttttctcat tttaaagcca
33721 cagtgaaaaa cacataaaag gaagaagtta gaaaaaaaaa tgaatgaaat tcttttttc
33781 cttttggcaa attaaataga tgtttctgtt tcagaagatt ttattaatta actttaaaga
33841 aacagtcatt tatttttggc attcagtgaa cactatcatt tccatgttta gaacttttct
33901 tctaagttag catcttaaaa gataactgtg aaactcaagg cattcaacta cattaatttg
33961 agtttcagaa attgaattct tgtttctaga gtacatagtt tgaattgatg tcagggtgtt
34021 aaatagataa atcttagctt cctaggttgt atattcacac taattatttt tttatcagcc
34081 ttcttatttt tcaacttacc ttattctttt tgtttttttg acactcagat ttgatagccc
34141 tgtggtagaa gaaaacagta atacagtttg gtttgttgtt gtgtttgtgt ttattttaaa
34201 gtcacggctt tgctttccat gttgttactg gattatgctt tttttaattc ttcagtttgc
34261 caagataaca gtcttccgat cttcagaagt ctgtatcaag cttaaggaaa ctgatgtgta
34321 ggaagactcg cctaagaagt ccaaattagc aaggctagca tgtgaggaca tgctggaaaa
34381 gaatagttcc catagatatt gacagagaat gttcataaaa tgctacttgt tttgtggtta
34441 catgagagta acttgtgtcc agtgcagctg tatgtaaggg caacgttttt attctgacga

Fig. 63M 34501 ctctgtggtt ttcatgaccc tggatgctta tcatgtctct ctgttggact tcttcaacgg
34561 agttgataca aatacttgct tccaagtgtc catctgccct ctcctccatc ctggccccat
34621 acaaatacgc tacattttta aataatttga aataccctca atagtattta tatttcctgg
34681 tgcttcattc tttccataag aactgtgata ccattattct gtaggatttt tttgtgcttc
34741 cccgtttcac atctctgtgc cagtgagacc catatatcgg tgcaaatcca gaagtttgat
34801 tgtccatctg attagcacac tgttagcaat gtggtggact aaacacagcc aagatgtggg
34861 gctggagctt agcctcctgg gagcagagcg gtgaacatca gatgaagaca tgtgaaaatg
34921 gagtactact tcctcttcct ggggatgggc taaaaagcac agccagaaat attcttgccc
34981 ttccagtctg ctttacagtt actcactggt tctctttttt ttcctactca gataaccagt
35041 atactcttcc cagtgactaa gaactgcaga taagtatagg tgcaaataga tggcaaaccg
35101 cagatggcag ctgtgtggtt tcagatgtgc tgcagaactt ttagacgatg tgaacgcaag
35161 gaactttttt gctgagcagt aatctctacc cactggaaat taggccctgg ggggaacaat
35221 gtagtgactt ctatatactt actacatgca gttagacccc tgaagcaaaa gcttttaaaa
35281 acaggctgta aaatgcccat gtatctttat taagcctatt ttccaactgg atagagaaat
35341 tttctggtaa tttttaaatt tgtaaagtct atttttttcc tgagccaagg gaaaaaaaat
35401 atctgggccc taaaagctta gttataacaa tgttattttt tctatctctg aatgattaaa
35461 tgtgatttca tttatgtagc aatactatga ttgtggctgc attagatcac gctgatagaa
35521 agatacaaag aaaaactaag tataatgaac taacaattta ttttcactct ttctctaagt
35581 taaaaattcc cagtacattc aaatgaacaa tgaaaataat tgcagaattg tctcctgaaa
35641 tggaaataga tttttttcc caagcattag caatttcttg ttatttttca aaatcagcca
35701 ctaagccttt cagagcttct tggtgactat tgcaggagaa atcagaatat taatcttgtg
35761 gttttatttc agagttcgct gccaggaagg aggtataatt gggataggag actttttttt
35821 tttagctgtg tcactgttca aggagggggg tttggaacct cagcataaga attacactct
35881 gtgatgagga tgtagcaggg gagaagaaag gtgattttca ctatgggaag ctatacttac
35941 atcaagtata aaatagactg aagtcatttt gaattacgtt atacttgtaa agtttacctc
36001 ctggagtttc agttagtacc agtgtactaa ctgggttaaa acagttcatg gcaccttaga
36061 tcatttctaa ctcatggcaa aaatctttcc tggtggaacg tgtaactgta ttttaaatgc
36121 ccctttataa gcaaccaagt atttgggatg ttattttgat attagtagtg aatttttcag
36181 tatcttccag taccctttgc aagtcacagg ttgacttaaa aggaaaagaa gcaaaatgct
36241 gaatatagca gaaaaactgt ctgcattcag actgttcagc ccacttttgc tccccacgtg
36301 gcaagcacac tcccccaaac aagcaatagc ctgtggcttc agaggaacct acaaaggcag
36361 catctgtaga tttttccttc ttcaactcta agacttgaat gtttccctct tccccacaca
36421 cttttttttt aaaccaagaa ataaaaaagt tttcactctt aaaggtgcaa agcagtttca
36481 ttcttatgca acacagcctt cctcctactg tcttatagtc tgtggatgtt aaattataga
36541 ttccaattga attttaatac tctagagatt ttacatttgt ggttgtcaag accccgtttt
36601 ggtaaaccta gggagctccg cacaaaagca ttgatattca gaaaaggcac tgacctacaa
36661 attaaaagaa aaaaaaatca aataatgtgc acctcttgtg cttccagttt gacaaagcag
36721 aagtcatcag cagtttctcc ctctgcagac gcagttctca attctattta caagtaactg
36781 ctctactgtg cctgtttttc tcttgctgat actcatttaa ttgtttttct tttggatctg
36841 aatctttgac tgtcttttcc ccctcaagat taaaataaat acatctgtat tcctcccctt
36901 tctttctgtg cactgccctt cagatctcat tttgtcattt ttcagcttag tgttgaaact
36961 tttagcaaca aaaagtcagt tacttacttt gagtaagtaa ctcaaagtaa gttaactttg
37021 agtttgagtg cacttttgcg tgtaggttca tttatgtgct tgtgaattta aaaacattgg
37081 gattccacct gaatgaagta aaccaaacat tttaaactat cagccagata gagacatcag
37141 cctttcactt ctttctatat gcagacatat cctaattttt tagaaaaatc aaataggaaa

Fig. 63N 37201 attctcaaca attaattgaa gattatagct ctgctctgaa atggtccaga aataggatct
37261 gctcatagaa actcatagtt tgaagcctct gggaggaaag gatactttaa aatttagtca
37321 catatttgga ggagggaaaa gggaaagagc agaatgaaga actgaaaaaa atcacacacc
37381 ggggcctgtc gtgaggtggg ggactggggg agggatagca ttaggagata tacctaatgt
37441 aaatgacgag ttaacaggcg cagcccacca acatggcaca cgtatacata tgtaacaaac
37501 ctgcacgttg tgcacatgta ccctagaact taaagtataa taaaaaaaaa ttttaatagc
37561 cccattaaat aattaaaaag attttttttta gattcacaga agtgtacaaa atttttaggt
37621 tttttttttt ttaagctgtc tgctgaatag tttcttaatg gtctacaatg tttgtatcta
37681 caaacagata ctgtctgctt cttactaccc ttccaagaca agtattatta tggcaattat
37741 tgcccagttt cccgggaaaa atttatccac agttacagaa gaatgagatg caattgtgag
37801 actgtaaagt ttaagcaagc actcagagaa gcacagtgat atgtatgcac agaagaggca
37861 gtctttgttt tgaggaaaac agtgaaagta aagttaattc aagaccacaa agacaagtaa
37921 ataagtgcct tatttttgta gttaatataa tttcagtgga atgcatattt ctaccataaa
37981 tgcatataga acttgtttgc tgacctactg tttggaaaac aaacaatccc attagaagaa
38041 tgtctttggg atttattttt accagaaaat caatcctttt ttcagtccct tgcaaagtac
38101 agtgttacaa gccaagactt tgataatcag gtagaaaatg gatttaaatt gcagaaatgt
38161 atatgaaaca cttttgttcc ttgccccttg aactttaggg gaatgaaaat gtctagcact
38221 ctccaccttc ttttctctcc tggaacttga actgtaattc aaagcctgtt tctcattaaa
38281 gtacctggca gcctatctct ttacagcttg agttacaaag ctattcagag acctcgctgg
38341 tctaaagaga cagaacaagg atgtgtttaa atagagcata ggctgttgaa aaaaaaaatg
38401 ctgaaaatgg taaaatgatt ctgtccttcc ttccactcct cactgctgag gtggagaggg
38461 aattcagttg gtgaacacca gcaagtggct ggtaaaagtc cccactttct ctccagggct
38521 gccacaggac ccagaatgag tggtgggcat gtgtgtgaac cctctattca gccagagttt
38581 tcccgcaaca ggtagtttgg ttgaagaggt tgactaaggt tgacattggc agtaataaca
38641 cgtatgttct tctgatttac aaaacgatgg aggaaaaagg ggagattttg aagacctgat
38701 ttctggtata cttcttaagc atgcataagg ctgaaaaaag aagacaaggg ttgtgggagg
38761 ctcctggtct agtgtttaca gaacttggat gcttgacaaa cagagcgtca agctaattgt
38821 tcttgaagca ggaaatctgc agtggaggaa gcaggtgtgg ggggatgatt accacgtttg
38881 gaaatggctg cattaactat tttgctcttc tgagtttggc cccaaaagag tccatagact
38941 ttttgaagga tgccatccct tttatttata gactaacatt aaatcagtca tttgtgaagg
39001 aaggagaaag tgcctaaata aatttggagt cagatagcat acgtgcggca gtgtttccga
39061 tatccatttc tctttatttc tttttctttt tctttttggc tttcagcatc cccatacttt
39121 cagaaaactt gtgactaaga gtgaattctt atttttcaaa ttgttttcag acatttcatg
39181 ttcatgtaaa cttggcttat tgatttcctg atttttcttt atttttttgt tttgtccatt
39241 ttatttttaa tcagctacat caaatgggtc tttggagggc ctggataacc aggagggagg
39301 ggtgtgccag acaagagcca tgaagatcct catgaaagtt ggacaaggta aagaccatct
39361 gctgcttcat gacgccactg tgacctggtg tagcccccag ctagtatggt gctaatgttg
39421 ccgatgccca ccttcattcg ctcttctttt tagttttcaa agcaaaccct tctgcacttt
39481 gagccactga cagatttcct caagtcaatg tactaagctt ttattggaga tctaagagtt
39541 aagatcagca aggtagaatg tctattgcca tagatagata gatagataga tagataatag
39601 atagatagat agatagatag atatttcttt ttaaaaagca aaacactttg gttcaaaatc
39661 aaaatatcca gaatgaaaac taaaagcttg tgcagttttg ctcatttctg aatcttgact
39721 acagaagagt tttgttcatt gtgacttttc caatatagat aacctattgt gcagaaagaa
39781 ataattattc ttctaattaa aaattggtat agtagtcaat caacttgctc agttaaattg
39841 aaatgtcatc tgcaatgctt tgcctgccaa atgcaagaat ccctatagtt tccacagatg

Fig. 63O

```
39901 gcctcacgtt ctaaacctct gaaataacta gtataaccat tttgttttaa aagaaaaatt
39961 atattcttgt atttcacagt actttgcata aagactctta tgttcattgc tattcatgcc
40021 tgttgaaata tatatgcagc tcctaaagct agatattgtc agatgtctgt gccgtaatta
40081 atcatttgtt tttcatatag atgcaagttc tgctggatca accaggaata aagatccaac
40141 aagacgtcca gaactagaag ctggtacaaa tggaagaagt tcgacaacaa gtccctttgt
40201 aaaaccaaat ccaggtataa cagcatgatc tgtgtgtatg gaggtctgtg ggtaccacat
40261 tcttagtagt atcttaaaag gtagggcaga gtctaaagac ttctaaccag ttaggattag
40321 ctggaagtta cagtgatcag gaatctttgc tgtcagtgag tcattattaa ttacactcaa
40381 taagaacaaa ataactcatt ccaatgaaag tcatatattc aaaggagtag agttcatgag
40441 ctgtaagtgc cagttattag aactactctg tcaggccaaa ggtttcattg gctgacattt
40501 tatcaagctg gttgtcaact ccagcttaaa gctgatgtta atgtatatgt aattaatgtg
40561 ctaatccctc atctaattat atctaagcca cagagggttt aattgatcct cttctaaatt
40621 ttaaatggta acatttttaa atattgcata atagtatttt ttcaggtggt tatcgttatt
40681 ttgtttcaca ttttccatgt aaaagaaaat attaaacagg tccctgacaa aagtgtagaa
40741 taccagataa aattgtccgt cgttgacctt cgttttctta acagtcttgg aacaaatagt
40801 tctgtatttg ttaccatgct aatgaaggtt ttatagagta gctgttgagc agacatcagc
40861 agttttgtat taggattgtt gtgtgcttgc ttggtcgttg tgcaaattta tcgtctgcag
40921 caatattcca tccctttcca agagtcaagg agggaagttg ttatttctaa ctttcaatga
40981 caagatgtgt caaattcttg tgacaaactg ataaatggat aatataatga tgccaggcag
41041 ttttttagtg cttaacattt gggctggcag tctgttcggt gtgagagttt ctgctgcctt
41101 ccaaatatat tttaagtgta aatcaaataa tacagacgag ttacgagctg aacatttcc
41161 caggcccccct cactccttcc gcgttcccga gctgttctgt tctgccagga ggcagggctc
41221 ttctttagaa ggcaggccct ttgaaggttt gcatgaaact ccctttctca aaggaggcgg
41281 aagagcaata ccacataaac gctcaccgct gacctggaga attggccact tcccttttc
41341 ttccctgccg ctgccccagg ctggctgaca cgggttagaa gatgaagcaa gatcaagggc
41401 tggctgtcac cgacagtctg tgctcttgct ggataatgat acaaaggaaa ccctgtggct
41461 tgggagggta gggaagtccc tcctagagat acctctcatt tcctttgcg ttgagctctt
41521 agacgaggta ttggcgaggc aaagtccagc ttctagttag taataagcct ggcttatttt
41581 tcacattttt aagggtcata aaagcagtcc gtctgcactg ggacagcagt aactatctct
41641 gacctttttct gtctccgcgt ctgcaggttc tagcacagac ggcaacagcg ccggacattc
41701 ggggaacaac atcctcggtt ccgaagtggc cttatttgca gggattgctt caggatgcat
41761 catcttcatc gtcatcatca tcacgctggt ggtcctcttg ctgaagtacc ggaggagaca
41821 caggaagcac tcgccgcagc acacgaccac gctgtcgctc agcacactgg ccacacccaa
41881 gcgcagcggc aacaacaacg gctcagagcc cagtgacatt atcatcccgc taaggactgc
41941 ggacagcgtc ttctgccctc actacgagaa ggtcagcggc gactacgggc acccggtgta
42001 catcgtccag gagatgcccc cgcagagccc ggcgaacatt tactacaagg tctgagaggg
42061 accctggtgg tacctgtgct ttcccagagg acacctaatg tcccgatgcc tcccttgagg
42121 gtttgagagc ccgcgtgctg gagaattgac tgaagcacag caccgggga gagggacact
42181 cctcctcgga agagcccgtc gcgctggaca gcttacctag tcttgtagca ttcggccttg
42241 gtgaacacac acgctccctg gaagctggaa gactgtgcag aagacgccca ttcggactgc
42301 tgtgccgcgt cccacgtctc ctcctcgaag ccatgtgctg cggtcactca ggcctctgca
42361 gaagccaagg gaagacagtg gtttgtggac gagagggctg tgagcatcct ggcaggtgcc
42421 ccaggatgcc acgcctggaa gggccggctt ctgcctgggg tgcatttccc ccgcagtgca
42481 taccggactt gtcacacgga cctcgggcta gttaaggtgt gcaaagatct ctagagttta
42541 gtccttactg tctcactcgt tctgttaccc agggctctgc agcacctcac ctgagacctc
```

Fig. 63P

```
42601 cactccacat ctgcatcact catggaacac tcatgtctgg agtcccctcc tccagccgct
42661 ggcaacaaca gcttcagtcc atgggtaatc cgttcataga aattgtgttt gctaacaagg
42721 tgccctttag ccagatgcta ggctgtctgc gaagaaggct aggagttcat agaagggagt
42781 ggggctgggg aaagggctgg ctgcaattgc agctcactgc tgctgcctct gaaacagaaa
42841 gttggaaagg aaaaaagaaa aaagcaatta ggtagcacag cactttggtt ttgctgagat
42901 cgaagaggcc agtaggagac acgacagcac acacagtgga ttccagtgca tggggaggca
42961 ctcgctgtta tcaaatagcg atgtgcagga agaaaagccc ctcttcattc cggggaacaa
43021 agacgggtat tgttgggaaa ggaacaggct tggagggaag ggagaaagta ggccgctgat
43081 gatatattcg ggcaggactg ttgtggtact ggcaataaga tacacagctc cgagctgtag
43141 gagagtcggt ctgctttgga tgatttttta agcagactca gctgctatac ttatcacatt
43201 ttattaaaca cagggaaagc atttaggaga atagcagaga gccaaatctg acctaaaagt
43261 tgaaaagcca aaggtcaaac aggctgtaat tccatcatca tcgttgttat taaagaatcc
43321 ttatctataa aaggtaggtc agatccccct ccccccaggt tcctccttcc cctcccgatt
43381 gagccttacg acactttggt ttatgcggtg ctgtccgggt gccagggctg cagggtcggt
43441 actgatggag gctgcagcgc ccggtgctct gtgtcaaggt gaagcacata cggcagacct
43501 cttagagtcc ttaagacgga agtaaattat gatgtccagg gggagaagga agataggacg
43561 tatttataat aggtatatag aacacaaggg atataaaatg aaagattttt actaatatat
43621 attttaaggt tgcacacagt acacaccaga agatgtgaaa ttcatttgtg gcaattaagt
43681 ggtcccaatg ctcagcgctt aaaaaaacaa attggacagc tacttctggg aaaaacaaca
43741 tcattccaaa aagaacaata atgagagcaa atgcaaaaat aaccaagtcc tccgaaggca
43801 tctcacggaa ccgtagacta ggaagtacga gccccacaga gcaggaagcc gatgtgactg
43861 catcatatat ttaacaatga caagatgttc cggcgtttat ttctgcgttg ggttttccct
43921 tgccttatgg gctgaagtgt tctctaga
```

Fig. 63Q

EphrinB2, mRNA

```
   1 gcgcggagct gggagtggct tcgccatggc tgtgagaagg gactccgtgt ggaagtactg
  61 ctggggtgtt ttgatggttt tatgcagaac tgcgatttcc aaatcgatag ttttagagcc
 121 tatctattgg aattcctcga actccaaatt tctacctgga caaggactgg tactataccc
 181 acagatagga gacaaattgg atattatttg ccccaaagtg gactctaaaa ctgttggcca
 241 gtatgaatat tataaagttt atatggttga taaagaccaa gcagacagat gcactattaa
 301 gaaggaaaat acccctctcc tcaactgtgc caaaccagac caagatatca aattcaccat
 361 caagtttcaa gaattcagcc ctaacctctg gggtctagaa tttcagaaga acaaagatta
 421 ttacattata tctacatcaa atgggtcttt ggagggcctg gataaccagg agggaggggt
 481 gtgccagaca agagccatga agatcctcat gaaagttgga caagatgcaa gttctgctgg
 541 atcaaccagg aataaagatc caacaagacg tccagaacta gaagctggta caaatggaag
 601 aagttcgaca acaagtccct ttgtaaaacc aaatccaggt tctagcacag acggcaacag
 661 cgccggacat tcggggaaca acatcctcgg ttccgaagtg gccttatttg cagggattgc
 721 ttcaggatgc atcatcttca tcgtcatcat catcacgctg gtggtcctct tgctgaagta
 781 ccggaggaga cacaggaagc actcgccgca gcacacgacc acgctgtcgc tcagcacact
 841 ggccacaccc aagcgcagcg gcaacaacaa cggctcagag cccagtgaca ttatcatccc
 901 gctaaggact gcggacagcg tcttctgccc tcactacgag aaggtcagcg gggactacgg
 961 gcacccggtg tacatcgtcc aggagatgcc cccgcagagc ccggcgaaca tttactacaa
1021 ggtctgagag ggaccctggt ggtacctgtg ctttcccaga ggacacctaa tgtcccgatg
1081 cctcccttga gggtttgaga gcccgcgtgc tggagaattg actgaagcac agcaccgggg
1141 gagagggaca ctcctcctcg gaagagcccg tcgcgctgga cagcttacct agtcttgtag
1201 cattcggcct tggtgaacac acacgctccc tggaagctgg aagactgtgc agaagacgcc
1261 cattcggact gctgtgccgc gtcccacgtc tcctcctcga agccatgtgc tgcggtcact
1321 caggcctctg cagaagccaa gggaagacag tggtttgtgg acgagagggc tgtgagcatc
1381 ctggcaggtg ccccaggatg ccacgcctgg aagggccggc ttctgcctgg ggtgcatttc
1441 ccccgcagtg cataccggac ttgtcacacg gacctcgggc tagttaaggt gtgcaaagat
1501 ctctagagtt tagtccttac tgtctcactc gttctgttac ccagggctct gcagcacctc
1561 acctgagacc tccactccac atctgcatca ctcatggaac actcatgtct ggagtcccct
1621 cctccagccg ctggcaacaa cagcttcagt ccatgggtaa tccgttcata gaaattgtgt
1681 ttgctaacaa ggtgcccttt agccagatgc taggctgtct gcgaagaagg ctaggagttc
1741 atagaaggga gtggggctgg ggaaagggct ggctgcaatt gcagctcact gctgctgcct
1801 ctgaaacaga aagttggaaa ggaaaaaaga aaaaagcaat taggtagcac agcactttgg
1861 ttttgctgag atcgaagagg ccagtaggag acacgacagc acacacagtg gattccagtg
1921 catggggagg cactcgctgt tatcaaatag cgatgtgcag gaagaaaagc ccctcttcat
1981 tccggggaac aaagacgggt attgttggga aaggaacagg cttggaggga agggagaaag
2041 taggccgctg atgatatatt cgggcaggac tgttgtggta ctggcaataa gatacacagc
2101 tccgagctgt aggagagtcg gtctgctttg gatgattttt taagcagact cagctgctat
2161 acttatcaca ttttattaaa cacagggaaa gcatttagga gaatagcaga gagccaaatc
2221 tgacctaaaa gttgaaaagc caaaggtcaa acaggctgta attccatcat catcgttgtt
2281 attaaagaat ccttatctat aaaaggtagg tcagatcccc ctccccccag gttcctcctt
2341 cccctcccga ttgagcctta cgacactttg gtttatgcgg tgctgtccgg gtgccagggc
2401 tgcagggtcg gtactgatgg aggctgcagc gcccggtgct ctgtgtcaag gtgaagcaca
2461 tacggcagac ctcttagagt ccttaagacg gaagtaaatt atgatgtcca gggggagaag
2521 gaagatagga cgtatttata ataggtatat agaacacaag ggatataaaa tgaaagattt
2581 ttactaatat atattttaag gttgcacaca gtacacacca gaagatgtga aattcatttg
```

Fig. 64A 2641 tggcaattaa gtggtcccaa tgctcagcgc ttaaaaaaac aaattggaca gctacttctg
2701 ggaaaaacaa catcattcca aaaagaacaa taatgagagc aaatgcaaaa ataaccaagt
2761 cctccgaagg catctcacgg aaccgtagac taggaagtac gagccccaca gagcaggaag
2821 ccgatgtgac tgcatcatat atttaacaat gacaagatgt tccggcgttt atttctgcgt
2881 tgggttttcc cttgccttat gggctgaagt gttctctaga atccagcagg tcacactggg
2941 ggcttcaggt gacgatttag ctgtggctcc ctcctcctgt cctcccccgc accccctccc
3001 ttctgggaaa caagaagagt aaacaggaaa cctacttttt atgtgctatg caaaatagac
3061 atctttaaca tagtcctgtt actatggtaa cactttgctt tctgaattgg aagggaaaaa
3121 aaatgtagcg acagcatttt aaggttctca gacctccagt gagtacctgc aaaaatgagt
3181 tgtcacagaa attatgatcc tctatttcct gaacctggaa atgatgttgg tccaaagtgc
3241 gtgtgtgtat gtgtgagtgg gtgcgtggta tacatgtgta catatatgta taatatatat
3301 ctacaatata tattatatat atctatatca tatttctgtg gagggttgcc atggtaacca
3361 gccacagtac atatgtaatt ctttccatca ccccaacctc tcctttctgt gcattcatgc
3421 aagagtttct tgtaagccat cagaagttac ttttaggatg ggggagaggg gcgagaaggg
3481 gaaaaatggg aaatagtctg attttaatga aatcaaatgt atgtatcatc agttggctac
3541 gttttggttc tatgctaaac tgtgaaaaat cagatgaatt gataaaagag ttccctgcaa
3601 ccaattgaaa agtgttctgt gcgtctgttt tgtgtctggt gcagaatatg acaatctacc
3661 aactgtccct ttgtttgaag ttggtttagc tttggaaagt tactgtaaat gccttgcttg
3721 tatgatcgtc cctggtcacc cgactttgga atttgcacca tcatgtttca gtgaagatgc
3781 tgtaaatagg ttcagatttt actgtctatg gatttggggt gttacagtag ccttattcac
3841 ctttttaata aaaatacaca tgaaaacaag aaagaaatgg cttttcttac ccagattgtg
3901 tacatagagc aatgttggtt ttttataaag tctaagcaag atgttttgta taaaatctga
3961 attttgcaat gtatttagct acagcttgtt taacggcagt gtcattcccc tttgcactgt
4021 aatgaggaaa aaatggtata aaaggttgcc aaattgctgc atatttgtgc cgtaattatg
4081 taccatgaat atttatttaa aatttcgttg tccaatttgt aagtaacaca gtattatgcc
4141 tgagttataa atattttttt ctttctttgt tttattttaa tagcctgtca taggttttaa
4201 atctgcttta gtttcacatt gcagttagcc ccagaaaatg aaatccgtga agtcacattc
4261 cacatctgtt tcaaactgaa tttgttctta aaaaaataaa atattttttt cctatggaaa
4321 aaaaaaaaaa aaaaa

Fig. 64B

EphB4 Precursor Protein

```
  1 melrvllcwa slaaaleetl lntkletadl kwvtfpqvdg qweelsglde eqhsvrtyev
 61 cdvqrapgqa hwlrtgwvpr rgavhvyatl rftmleclsl pragrscket ftvfyyesda
121 dtataltpaw menpyikvdt vaaehltrkr pgaeatgkvn vktlrlgpls kagfylafqd
181 qgacmallsl hlfykkcaql tvnltrfpet vprelvvpva gscvvdavpa pgpspslycr
241 edgqwaeqpv tgcscapgfe aaegntkcra caqgtfkpls gegscqpcpa nshsntigsa
301 vcqcrvgyfr artdprgapc ttppsaprsv vsrlngsslh lewsaplesg gredltyalr
361 crecrpggsc apcggdltfd pgprdlvepw vvvrglrpdf tytfevtaln gvsslatgpv
421 pfepvnvttd revppavsdi rvtrsspssl slawavprap sgavldyevk yhekgaegps
481 svrflktsen raelrglkrg asylvqvrar seagygpfgq ehhsqtqlde segwreqlal
541 iagtavvgvv lvlvvivvav lclrkqsngr eaeysdkhgq ylighgtkvy idpftyedpn
601 eavrefakei dvsyvkieev igagefgevc rgrlkapgkk escvaiktlk ggyterqrre
661 flseasimgq fehpniirle gvvtnsmpvm iltefmenga ldsflrlndg qftviqlvgm
721 lrgiasgmry laemsyvhrd laarnilvns nlvckvsdfg lsrfleenss dptytsslgg
781 kipirwtape aiafrkftsa sdawsygivm wevmsfgerp ywdmsnqdvi naieqdyrlp
841 pppdcptslh qlmldcwqkd rnarprfpqv vsaldkmirn paslkivare nggashplld
901 qrqphysafg svgewlraik mgryeesfaa agfgsfelvs qisaedllri gvtlaghqkk
961 ilasvqhmks qakpgtpggt ggpapqy
```

Fig. 65

EphrinB2

```
  1 mavrrdsvwk ycwgvlmvlc rtaisksivl epiywnssns kflpgqglvl ypqigdkldi
 61 icpkvdsktv gqyeyykvym vdkdqadrct ikkentplln cakpdqdikf tikfqefspn
121 lwglefqknk dyyiistsng slegldnqeg gvcqtramki lmkvgqdass agstrnkdpt
181 rrpeleagtn grssttspfv kpnpgsstdg nsaghsgnni lgsevalfag iasgciifiv
241 iiitlvvlll kyrrrhrkhs pqhtttlsls tlatpkrsgn nngsepsdii iplrtadsvf
301 cphyekvsgd yghpvyivqe mppqspaniy ykv
```

Fig. 66

SEQUENCE LISTING

```
<160> NUMBER OF SEQ ID NOS: 425

<210> SEQ ID NO 1
<211> LENGTH: 29
<212> TYPE: DNA
<213> ORGANISM: Unknown
<220> FEATURE:
<223> OTHER INFORMATION: Oligonucleotide

<400> SEQUENCE: 1
```

-continued ggatccgcca tggagctccg ggtgctgct 29

<210> SEQ ID NO 2
<211> LENGTH: 36
<212> TYPE: DNA
<213> ORGANISM: Unknown
<220> FEATURE:
<223> OTHER INFORMATION: Oligonucleotide

<400> SEQUENCE: 2
tggatccctg ctcccgccag ccctcgctct catcca 36

<210> SEQ ID NO 3
<211> LENGTH: 28
<212> TYPE: DNA
<213> ORGANISM: Unknown
<220> FEATURE:
<223> OTHER INFORMATION: Oligonucleotide

<400> SEQUENCE: 3
tggatccacc atggctgtga gaagggac 28

<210> SEQ ID NO 4
<211> LENGTH: 53
<212> TYPE: DNA
<213> ORGANISM: Unknown
<220> FEATURE:
<223> OTHER INFORMATION: Oligonucleotide

<400> SEQUENCE: 4
attaatggtg atggtgatga tgactaccca cttcggaacc gaggatgttg ttc 53

<210> SEQ ID NO 5
<211> LENGTH: 31
<212> TYPE: DNA
<213> ORGANISM: Unknown
<220> FEATURE:
<223> OTHER INFORMATION: Oligonucleotide

<400> SEQUENCE: 5
taaagcttcc gccatggctg tgagaaggga c 31

<210> SEQ ID NO 6
<211> LENGTH: 34
<212> TYPE: DNA
<213> ORGANISM: Unknown
<220> FEATURE:
<223> OTHER INFORMATION: Oligonucleotide

<400> SEQUENCE: 6
taggatccac ttcggaaccg aggatgttgt tccc 34

<210> SEQ ID NO 7
<211> LENGTH: 31
<212> TYPE: DNA
<213> ORGANISM: Unknown
<220> FEATURE:
<223> OTHER INFORMATION: Oligonucleotide

<400> SEQUENCE: 7
ataagcttcc gccatggagc tccgggtgct g 31

<210> SEQ ID NO 8
<211> LENGTH: 34
<212> TYPE: DNA
<213> ORGANISM: Unknown

<220> FEATURE:
<223> OTHER INFORMATION: Oligonucleotide

<400> SEQUENCE: 8
ttggatcctg ctcccgccag ccctcgctct catc 34

<210> SEQ ID NO 9
<211> LENGTH: 32
<212> TYPE: DNA
<213> ORGANISM: Unknown
<220> FEATURE:
<223> OTHER INFORMATION: Oligonucleotide

<400> SEQUENCE: 9
tactagtccg ccatggagct ccgggtgctg ct 32

<210> SEQ ID NO 10
<211> LENGTH: 50
<212> TYPE: DNA
<213> ORGANISM: Unknown
<220> FEATURE:
<223> OTHER INFORMATION: Oligonucleotide

<400> SEQUENCE: 10
gcggccgctt aatggtgatg gtgatgatga gccgaaggag gggtggtgca 50

<210> SEQ ID NO 11
<211> LENGTH: 53
<212> TYPE: DNA
<213> ORGANISM: Unknown
<220> FEATURE:
<223> OTHER INFORMATION: Oligonucleotide

<400> SEQUENCE: 11
agcggccgct taatggtgat ggtgatgatg gacattgaca ggctcaaatg gga 53

<210> SEQ ID NO 12
<211> LENGTH: 56
<212> TYPE: DNA
<213> ORGANISM: Unknown
<220> FEATURE:
<223> OTHER INFORMATION: Oligonucleotide

<400> SEQUENCE: 12
tgcggccgct taatggtgat ggtgatgatg ctgctcccgc cagccctcgc tctcat 56

<210> SEQ ID NO 13
<211> LENGTH: 32
<212> TYPE: DNA
<213> ORGANISM: Unknown
<220> FEATURE:
<223> OTHER INFORMATION: Oligonucleotide

<400> SEQUENCE: 13
tactagtccg ccatggagct ccgggtgctg ct 32

<210> SEQ ID NO 14
<211> LENGTH: 25
<212> TYPE: DNA
<213> ORGANISM: Unknown
<220> FEATURE:
<223> OTHER INFORMATION: Oligonucleotide

<400> SEQUENCE: 14
cagctgagtt tccaattttg tgttc 25

-continued

<210> SEQ ID NO 15
<211> LENGTH: 39
<212> TYPE: DNA
<213> ORGANISM: Unknown
<220> FEATURE:
<223> OTHER INFORMATION: Oligonucleotide

<400> SEQUENCE: 15
gaacacaaaa ttggaaactc agctgactgt gaacctgac 39

<210> SEQ ID NO 16
<211> LENGTH: 30
<212> TYPE: DNA
<213> ORGANISM: Unknown
<220> FEATURE:
<223> OTHER INFORMATION: Oligonucleotide

<400> SEQUENCE: 16
gcggccgccc tgctcccgcc agccctcgct 30

<210> SEQ ID NO 17
<211> LENGTH: 31
<212> TYPE: DNA
<213> ORGANISM: Unknown
<220> FEATURE:
<223> OTHER INFORMATION: Oligonucleotide

<400> SEQUENCE: 17
taaagcttcc gccatggctg tgagaaggga c 31

<210> SEQ ID NO 18
<211> LENGTH: 32
<212> TYPE: DNA
<213> ORGANISM: Unknown
<220> FEATURE:
<223> OTHER INFORMATION: Oligonucleotide

<400> SEQUENCE: 18
taggatcctt cggaaccgag gatgttgttc cc 32

<210> SEQ ID NO 19
<211> LENGTH: 20
<212> TYPE: DNA
<213> ORGANISM: Unknown
<220> FEATURE:
<223> OTHER INFORMATION: Oligonucleotide

<400> SEQUENCE: 19
tcctgcaagg agaccttcac 20

<210> SEQ ID NO 20
<211> LENGTH: 21
<212> TYPE: DNA
<213> ORGANISM: Unknown
<220> FEATURE:
<223> OTHER INFORMATION: Oligonucleotide

<400> SEQUENCE: 20
gtgcagggat agcagggcca t 21

<210> SEQ ID NO 21
<211> LENGTH: 20
<212> TYPE: DNA
<213> ORGANISM: Unknown
<220> FEATURE:
<223> OTHER INFORMATION: Oligonucleotide

<400> SEQUENCE: 21
atggaggcct cgctcagaaa 20

<210> SEQ ID NO 22
<211> LENGTH: 21
<212> TYPE: RNA
<213> ORGANISM: Unknown
<220> FEATURE:
<223> OTHER INFORMATION: Oligonucleotide

<400> SEQUENCE: 22
ggugaauguc aagacgcugu u 21

<210> SEQ ID NO 23
<211> LENGTH: 21
<212> TYPE: RNA
<213> ORGANISM: Unknown
<220> FEATURE:
<223> OTHER INFORMATION: Oligonucleotide

<400> SEQUENCE: 23
cucuuccgau cccaccuacu u 21

<210> SEQ ID NO 24
<211> LENGTH: 19
<212> TYPE: DNA
<213> ORGANISM: Unknown
<220> FEATURE:
<223> OTHER INFORMATION: Oligonucleotide

<400> SEQUENCE: 24
ggacctgact gactaccta 19

<210> SEQ ID NO 25
<211> LENGTH: 20
<212> TYPE: DNA
<213> ORGANISM: Unknown
<220> FEATURE:
<223> OTHER INFORMATION: Oligonucleotide

<400> SEQUENCE: 25
aaggagacct tcaccgtctt 20

<210> SEQ ID NO 26
<211> LENGTH: 20
<212> TYPE: DNA
<213> ORGANISM: Unknown
<220> FEATURE:
<223> OTHER INFORMATION: Oligonucleotide

<400> SEQUENCE: 26
ttgaaggtag tttcgtggat 20

<210> SEQ ID NO 27
<211> LENGTH: 20
<212> TYPE: DNA
<213> ORGANISM: Unknown
<220> FEATURE:
<223> OTHER INFORMATION: Oligonucleotide

<400> SEQUENCE: 27
tcgagtcagg ttcacagtca 20

<210> SEQ ID NO 28
<211> LENGTH: 20
<212> TYPE: DNA
<213> ORGANISM: Unknown

<220> FEATURE:
<223> OTHER INFORMATION: Oligonucleotide

<400> SEQUENCE: 28
ggagccaaaa gggtcatcat 20

<210> SEQ ID NO 29
<211> LENGTH: 21
<212> TYPE: DNA
<213> ORGANISM: Unknown
<220> FEATURE:
<223> OTHER INFORMATION: Oligonucleotide

<400> SEQUENCE: 29
ggcattgctg caaagaaaga g 21

<210> SEQ ID NO 30
<211> LENGTH: 20
<212> TYPE: DNA
<213> ORGANISM: Unknown
<220> FEATURE:
<223> OTHER INFORMATION: Oligonucleotide

<400> SEQUENCE: 30
tccgtgtgga agtactgctg 20

<210> SEQ ID NO 31
<211> LENGTH: 20
<212> TYPE: DNA
<213> ORGANISM: Unknown
<220> FEATURE:
<223> OTHER INFORMATION: Oligonucleotide

<400> SEQUENCE: 31
tctggtttgg cacagttgag 20

<210> SEQ ID NO 32
<211> LENGTH: 20
<212> TYPE: DNA
<213> ORGANISM: Unknown
<220> FEATURE:
<223> OTHER INFORMATION: Oligonucleotide

<400> SEQUENCE: 32
ctttggaaga gaccctgctg 20

<210> SEQ ID NO 33
<211> LENGTH: 20
<212> TYPE: DNA
<213> ORGANISM: Unknown
<220> FEATURE:
<223> OTHER INFORMATION: Oligonucleotide

<400> SEQUENCE: 33
agacggtgaa ggtctccttg 20

<210> SEQ ID NO 34
<211> LENGTH: 21
<212> TYPE: RNA
<213> ORGANISM: Unknown
<220> FEATURE:
<223> OTHER INFORMATION: Oligonucleotide

<400> SEQUENCE: 34
gagacccugc ugaacacaau u 21

<210> SEQ ID NO 35
<211> LENGTH: 21
<212> TYPE: RNA
<213> ORGANISM: Unknown
<220> FEATURE:
<223> OTHER INFORMATION: Oligonucleotide

<400> SEQUENCE: 35
uuguguucag cagggucucu u 21

<210> SEQ ID NO 36
<211> LENGTH: 21
<212> TYPE: RNA
<213> ORGANISM: Unknown
<220> FEATURE:
<223> OTHER INFORMATION: Oligonucleotide

<400> SEQUENCE: 36
ggugaauguc aagacgcugu u 21

<210> SEQ ID NO 37
<211> LENGTH: 21
<212> TYPE: RNA
<213> ORGANISM: Unknown
<220> FEATURE:
<223> OTHER INFORMATION: Oligonucleotide

<400> SEQUENCE: 37
cagcgucuug acauucaccu u 21

<210> SEQ ID NO 38
<211> LENGTH: 21
<212> TYPE: RNA
<213> ORGANISM: Unknown
<220> FEATURE:
<223> OTHER INFORMATION: Oligonucleotide

<400> SEQUENCE: 38
caucacagcc agacccaacu u 21

<210> SEQ ID NO 39
<211> LENGTH: 21
<212> TYPE: RNA
<213> ORGANISM: Unknown
<220> FEATURE:
<223> OTHER INFORMATION: Oligonucleotide

<400> SEQUENCE: 39
guugggucug gcugugaugu u 21

<210> SEQ ID NO 40
<211> LENGTH: 21
<212> TYPE: RNA
<213> ORGANISM: Unknown
<220> FEATURE:
<223> OTHER INFORMATION: Oligonucleotide

<400> SEQUENCE: 40
cucuuccgau cccaccuacu u 21

<210> SEQ ID NO 41
<211> LENGTH: 21
<212> TYPE: RNA
<213> ORGANISM: Unknown
<220> FEATURE:
<223> OTHER INFORMATION: Oligonucleotide

<400> SEQUENCE: 41
guagguggga ucggaagagu u 21

<210> SEQ ID NO 42
<211> LENGTH: 21
<212> TYPE: DNA
<213> ORGANISM: Unknown
<220> FEATURE:
<223> OTHER INFORMATION: Oligonucleotide

<400> SEQUENCE: 42
gtgcagggat agcagggcca t 21

<210> SEQ ID NO 43
<211> LENGTH: 21
<212> TYPE: DNA
<213> ORGANISM: Unknown
<220> FEATURE:
<223> OTHER INFORMATION: Oligonucleotide

<400> SEQUENCE: 43
aaggaggggt ggtgcacggt g 21

<210> SEQ ID NO 44
<211> LENGTH: 21
<212> TYPE: DNA
<213> ORGANISM: Unknown
<220> FEATURE:
<223> OTHER INFORMATION: Oligonucleotide

<400> SEQUENCE: 44
ttccaggtgc agggaggagc c 21

<210> SEQ ID NO 45
<211> LENGTH: 21
<212> TYPE: DNA
<213> ORGANISM: Unknown
<220> FEATURE:
<223> OTHER INFORMATION: Oligonucleotide

<400> SEQUENCE: 45
gtggtgacat tgacaggctc a 21

<210> SEQ ID NO 46
<211> LENGTH: 21
<212> TYPE: DNA
<213> ORGANISM: Unknown
<220> FEATURE:
<223> OTHER INFORMATION: Oligonucleotide

<400> SEQUENCE: 46
tctggctgtg atgttcctgg c 21

<210> SEQ ID NO 47
<211> LENGTH: 18
<212> TYPE: DNA
<213> ORGANISM: Unknown
<220> FEATURE:
<223> OTHER INFORMATION: Oligonucleotide

<400> SEQUENCE: 47
gccgctcagt tcctccca 18

<210> SEQ ID NO 48
<211> LENGTH: 18
<212> TYPE: DNA
<213> ORGANISM: Unknown

<220> FEATURE:
<223> OTHER INFORMATION: Oligonucleotide

<400> SEQUENCE: 48
tgaaggtctc cttgcagg 18

<210> SEQ ID NO 49
<211> LENGTH: 21
<212> TYPE: DNA
<213> ORGANISM: Unknown
<220> FEATURE:
<223> OTHER INFORMATION: Oligonucleotide

<400> SEQUENCE: 49
cgcggccacc gtgtccacct t 21

<210> SEQ ID NO 50
<211> LENGTH: 21
<212> TYPE: DNA
<213> ORGANISM: Unknown
<220> FEATURE:
<223> OTHER INFORMATION: Oligonucleotide

<400> SEQUENCE: 50
cttcagggtc ttgattgcca c 21

<210> SEQ ID NO 51
<211> LENGTH: 20
<212> TYPE: DNA
<213> ORGANISM: Unknown
<220> FEATURE:
<223> OTHER INFORMATION: Oligonucleotide

<400> SEQUENCE: 51
atggaggcct cgctcagaaa 20

<210> SEQ ID NO 52
<211> LENGTH: 21
<212> TYPE: DNA
<213> ORGANISM: Unknown
<220> FEATURE:
<223> OTHER INFORMATION: Oligonucleotide

<400> SEQUENCE: 52
catgcccacg agctggatga c 21

<210> SEQ ID NO 53
<211> LENGTH: 19
<212> TYPE: DNA
<213> ORGANISM: Unknown
<220> FEATURE:
<223> OTHER INFORMATION: Oligonucleotide

<400> SEQUENCE: 53
tccgtgtgga gtactgctg 19

<210> SEQ ID NO 54
<211> LENGTH: 20
<212> TYPE: DNA
<213> ORGANISM: Unknown
<220> FEATURE:
<223> OTHER INFORMATION: Oligonucleotide

<400> SEQUENCE: 54
tctggtttgg cacagttgag 20

<210> SEQ ID NO 55
<211> LENGTH: 20
<212> TYPE: DNA
<213> ORGANISM: Unknown
<220> FEATURE:
<223> OTHER INFORMATION: Oligonucleotide

<400> SEQUENCE: 55
ctttggaaga gaccctgctg 20

<210> SEQ ID NO 56
<211> LENGTH: 20
<212> TYPE: DNA
<213> ORGANISM: Unknown
<220> FEATURE:
<223> OTHER INFORMATION: Oligonucleotide

<400> SEQUENCE: 56
agacggtgaa ggtctccttg 20

<210> SEQ ID NO 57
<211> LENGTH: 20
<212> TYPE: DNA
<213> ORGANISM: Unknown
<220> FEATURE:
<223> OTHER INFORMATION: Oligonucleotide

<400> SEQUENCE: 57
agacaagagc catgaagatc 20

<210> SEQ ID NO 58
<211> LENGTH: 21
<212> TYPE: DNA
<213> ORGANISM: Unknown
<220> FEATURE:
<223> OTHER INFORMATION: Oligonucleotide

<400> SEQUENCE: 58
ggatcccact tcggacccga g 21

<210> SEQ ID NO 59
<211> LENGTH: 22
<212> TYPE: DNA
<213> ORGANISM: Unknown
<220> FEATURE:
<223> OTHER INFORMATION: Oligonucleotide

<400> SEQUENCE: 59
tcaggtcact gcattgaacg gg 22

<210> SEQ ID NO 60
<211> LENGTH: 19
<212> TYPE: DNA
<213> ORGANISM: Unknown
<220> FEATURE:
<223> OTHER INFORMATION: Oligonucleotide

<400> SEQUENCE: 60
aactcgctct catccagtt 19

<210> SEQ ID NO 61
<211> LENGTH: 20
<212> TYPE: DNA
<213> ORGANISM: Unknown
<220> FEATURE:
<223> OTHER INFORMATION: Oligonucleotide

<400> SEQUENCE: 61
gtggggcgcc ccaggcacca 20

<210> SEQ ID NO 62
<211> LENGTH: 24
<212> TYPE: DNA
<213> ORGANISM: Unknown
<220> FEATURE:
<223> OTHER INFORMATION: Oligonucleotide

<400> SEQUENCE: 62
ctccttaatg tcacgcacga tttc 24

<210> SEQ ID NO 63
<211> LENGTH: 21
<212> TYPE: RNA
<213> ORGANISM: Unknown
<220> FEATURE:
<223> OTHER INFORMATION: Oligonucleotide

<400> SEQUENCE: 63
gcagacagau gcacuauuau u 21

<210> SEQ ID NO 64
<211> LENGTH: 21
<212> TYPE: RNA
<213> ORGANISM: Unknown
<220> FEATURE:
<223> OTHER INFORMATION: Oligonucleotide

<400> SEQUENCE: 64
uaauagugca ucugucugcu u 21

<210> SEQ ID NO 65
<211> LENGTH: 21
<212> TYPE: RNA
<213> ORGANISM: Unknown
<220> FEATURE:
<223> OTHER INFORMATION: Oligonucleotide

<400> SEQUENCE: 65
cugcgauuuc caaaucgauu u 21

<210> SEQ ID NO 66
<211> LENGTH: 21
<212> TYPE: RNA
<213> ORGANISM: Unknown
<220> FEATURE:
<223> OTHER INFORMATION: Oligonucleotide

<400> SEQUENCE: 66
aucgauuugg aaaucgcagu u 21

<210> SEQ ID NO 67
<211> LENGTH: 21
<212> TYPE: RNA
<213> ORGANISM: Unknown
<220> FEATURE:
<223> OTHER INFORMATION: Oligonucleotide

<400> SEQUENCE: 67
ggacugguac uauacccacu u 21

<210> SEQ ID NO 68
<211> LENGTH: 21
<212> TYPE: RNA
<213> ORGANISM: Unknown

```
<220> FEATURE:
<223> OTHER INFORMATION: Oligonucleotide

<400> SEQUENCE: 68

guggguauag uaccaguccu u                                              21

<210> SEQ ID NO 69
<211> LENGTH: 21
<212> TYPE: RNA
<213> ORGANISM: Unknown
<220> FEATURE:
<223> OTHER INFORMATION: Oligonucleotide

<400> SEQUENCE: 69

gagacccugc ugaacacaau u                                              21

<210> SEQ ID NO 70
<211> LENGTH: 21
<212> TYPE: RNA
<213> ORGANISM: Unknown
<220> FEATURE:
<223> OTHER INFORMATION: Oligonucleotide

<400> SEQUENCE: 70

uuguguucag cagggucucu u                                              21

<210> SEQ ID NO 71
<211> LENGTH: 21
<212> TYPE: RNA
<213> ORGANISM: Unknown
<220> FEATURE:
<223> OTHER INFORMATION: Oligonucleotide

<400> SEQUENCE: 71

cgcugacccu gaaguucauu u                                              21

<210> SEQ ID NO 72
<211> LENGTH: 21
<212> TYPE: RNA
<213> ORGANISM: Unknown
<220> FEATURE:
<223> OTHER INFORMATION: Oligonucleotide

<400> SEQUENCE: 72

augaacuuca gggucagcgu u                                              21

<210> SEQ ID NO 73
<211> LENGTH: 21
<212> TYPE: DNA
<213> ORGANISM: Unknown
<220> FEATURE:
<223> OTHER INFORMATION: Oligonucleotide

<400> SEQUENCE: 73

tcagtactgc ggggccggtc c                                              21

<210> SEQ ID NO 74
<211> LENGTH: 20
<212> TYPE: DNA
<213> ORGANISM: Unknown
<220> FEATURE:
<223> OTHER INFORMATION: Oligonucleotide

<400> SEQUENCE: 74

tcctgtccca cccggggttc                                                20
```

<210> SEQ ID NO 75
<211> LENGTH: 20
<212> TYPE: DNA
<213> ORGANISM: Unknown
<220> FEATURE:
<223> OTHER INFORMATION: Oligonucleotide

<400> SEQUENCE: 75
ccggcttggc ctgggacttc 20

<210> SEQ ID NO 76
<211> LENGTH: 20
<212> TYPE: DNA
<213> ORGANISM: Unknown
<220> FEATURE:
<223> OTHER INFORMATION: Oligonucleotide

<400> SEQUENCE: 76
atgtgctgga cactggccaa 20

<210> SEQ ID NO 77
<211> LENGTH: 20
<212> TYPE: DNA
<213> ORGANISM: Unknown
<220> FEATURE:
<223> OTHER INFORMATION: Oligonucleotide

<400> SEQUENCE: 77
gattttcttc tggtgtcccg 20

<210> SEQ ID NO 78
<211> LENGTH: 20
<212> TYPE: DNA
<213> ORGANISM: Unknown
<220> FEATURE:
<223> OTHER INFORMATION: Oligonucleotide

<400> SEQUENCE: 78
ccagagtgac tccgattcgg 20

<210> SEQ ID NO 79
<211> LENGTH: 20
<212> TYPE: DNA
<213> ORGANISM: Unknown
<220> FEATURE:
<223> OTHER INFORMATION: Oligonucleotide

<400> SEQUENCE: 79
agcaggtcct cagcagagat 20

<210> SEQ ID NO 80
<211> LENGTH: 20
<212> TYPE: DNA
<213> ORGANISM: Unknown
<220> FEATURE:
<223> OTHER INFORMATION: Oligonucleotide

<400> SEQUENCE: 80
ctggctgacc agctcgaagg 20

<210> SEQ ID NO 81
<211> LENGTH: 20
<212> TYPE: DNA
<213> ORGANISM: Unknown
<220> FEATURE:
<223> OTHER INFORMATION: Oligonucleotide

<400> SEQUENCE: 81
agccaaagcc agcggctgcg 20

<210> SEQ ID NO 82
<211> LENGTH: 20
<212> TYPE: DNA
<213> ORGANISM: Unknown
<220> FEATURE:
<223> OTHER INFORMATION: Oligonucleotide

<400> SEQUENCE: 82
aaactttctt cgtatcttcc 20

<210> SEQ ID NO 83
<211> LENGTH: 20
<212> TYPE: DNA
<213> ORGANISM: Unknown
<220> FEATURE:
<223> OTHER INFORMATION: Oligonucleotide

<400> SEQUENCE: 83
cattttgatg gcccgaagcc 20

<210> SEQ ID NO 84
<211> LENGTH: 20
<212> TYPE: DNA
<213> ORGANISM: Unknown
<220> FEATURE:
<223> OTHER INFORMATION: Oligonucleotide

<400> SEQUENCE: 84
actcgcccac agagccaaaa 20

<210> SEQ ID NO 85
<211> LENGTH: 20
<212> TYPE: DNA
<213> ORGANISM: Unknown
<220> FEATURE:
<223> OTHER INFORMATION: Oligonucleotide

<400> SEQUENCE: 85
gctgagtagt gaggctgccg 20

<210> SEQ ID NO 86
<211> LENGTH: 20
<212> TYPE: DNA
<213> ORGANISM: Unknown
<220> FEATURE:
<223> OTHER INFORMATION: Oligonucleotide

<400> SEQUENCE: 86
ctggtccagg agagggtgtg 20

<210> SEQ ID NO 87
<211> LENGTH: 20
<212> TYPE: DNA
<213> ORGANISM: Unknown
<220> FEATURE:
<223> OTHER INFORMATION: Oligonucleotide

<400> SEQUENCE: 87
aggccccgcc attctcccgg 20

<210> SEQ ID NO 88
<211> LENGTH: 20
<212> TYPE: DNA
<213> ORGANISM: Unknown

<220> FEATURE:
<223> OTHER INFORMATION: Oligonucleotide

<400> SEQUENCE: 88
gccacgattt tgaggctggc 20

<210> SEQ ID NO 89
<211> LENGTH: 20
<212> TYPE: DNA
<213> ORGANISM: Unknown
<220> FEATURE:
<223> OTHER INFORMATION: Oligonucleotide

<400> SEQUENCE: 89
ggggttccgg atcatcttgt 20

<210> SEQ ID NO 90
<211> LENGTH: 20
<212> TYPE: DNA
<213> ORGANISM: Unknown
<220> FEATURE:
<223> OTHER INFORMATION: Oligonucleotide

<400> SEQUENCE: 90
ccagggcgct gaccacctgg 20

<210> SEQ ID NO 91
<211> LENGTH: 20
<212> TYPE: DNA
<213> ORGANISM: Unknown
<220> FEATURE:
<223> OTHER INFORMATION: Oligonucleotide

<400> SEQUENCE: 91
gggaagcggg gccgggcatt 20

<210> SEQ ID NO 92
<211> LENGTH: 20
<212> TYPE: DNA
<213> ORGANISM: Unknown
<220> FEATURE:
<223> OTHER INFORMATION: Oligonucleotide

<400> SEQUENCE: 92
ccggtctttc tgccaacagt 20

<210> SEQ ID NO 93
<211> LENGTH: 20
<212> TYPE: DNA
<213> ORGANISM: Unknown
<220> FEATURE:
<223> OTHER INFORMATION: Oligonucleotide

<400> SEQUENCE: 93
ccagcatgag ctggtggagg 20

<210> SEQ ID NO 94
<211> LENGTH: 20
<212> TYPE: DNA
<213> ORGANISM: Unknown
<220> FEATURE:
<223> OTHER INFORMATION: Oligonucleotide

<400> SEQUENCE: 94
gaggtgggac agtctggggg 20

-continued

<210> SEQ ID NO 95
<211> LENGTH: 20
<212> TYPE: DNA
<213> ORGANISM: Unknown
<220> FEATURE:
<223> OTHER INFORMATION: Oligonucleotide

<400> SEQUENCE: 95
cgggggcagc cggtagtcct 20

<210> SEQ ID NO 96
<211> LENGTH: 20
<212> TYPE: DNA
<213> ORGANISM: Unknown
<220> FEATURE:
<223> OTHER INFORMATION: Oligonucleotide

<400> SEQUENCE: 96
gttcaatggc attgatcacg 20

<210> SEQ ID NO 97
<211> LENGTH: 20
<212> TYPE: DNA
<213> ORGANISM: Unknown
<220> FEATURE:
<223> OTHER INFORMATION: Oligonucleotide

<400> SEQUENCE: 97
tcctgattgc tcatgtccca 20

<210> SEQ ID NO 98
<211> LENGTH: 20
<212> TYPE: DNA
<213> ORGANISM: Unknown
<220> FEATURE:
<223> OTHER INFORMATION: Oligonucleotide

<400> SEQUENCE: 98
gtacggcctc tccccaaatg 20

<210> SEQ ID NO 99
<211> LENGTH: 20
<212> TYPE: DNA
<213> ORGANISM: Unknown
<220> FEATURE:
<223> OTHER INFORMATION: Oligonucleotide

<400> SEQUENCE: 99
acatcacctc ccacatcaca 20

<210> SEQ ID NO 100
<211> LENGTH: 20
<212> TYPE: DNA
<213> ORGANISM: Unknown
<220> FEATURE:
<223> OTHER INFORMATION: Oligonucleotide

<400> SEQUENCE: 100
atcccgtaac tccaggcatc 20

<210> SEQ ID NO 101
<211> LENGTH: 20
<212> TYPE: DNA
<213> ORGANISM: Unknown
<220> FEATURE:
<223> OTHER INFORMATION: Oligonucleotide

<400> SEQUENCE: 101
actggcggaa gtgaacttcc 20

<210> SEQ ID NO 102
<211> LENGTH: 20
<212> TYPE: DNA
<213> ORGANISM: Unknown
<220> FEATURE:
<223> OTHER INFORMATION: Oligonucleotide

<400> SEQUENCE: 102
ggaaggcaat ggcctccggg 20

<210> SEQ ID NO 103
<211> LENGTH: 20
<212> TYPE: DNA
<213> ORGANISM: Unknown
<220> FEATURE:
<223> OTHER INFORMATION: Oligonucleotide

<400> SEQUENCE: 103
gcagtccatc ggatgggaat 20

<210> SEQ ID NO 104
<211> LENGTH: 20
<212> TYPE: DNA
<213> ORGANISM: Unknown
<220> FEATURE:
<223> OTHER INFORMATION: Oligonucleotide

<400> SEQUENCE: 104
ctttcctccc agggagctcg 20

<210> SEQ ID NO 105
<211> LENGTH: 20
<212> TYPE: DNA
<213> ORGANISM: Unknown
<220> FEATURE:
<223> OTHER INFORMATION: Oligonucleotide

<400> SEQUENCE: 105
tgtaggtggg atcggaagag 20

<210> SEQ ID NO 106
<211> LENGTH: 20
<212> TYPE: DNA
<213> ORGANISM: Unknown
<220> FEATURE:
<223> OTHER INFORMATION: Oligonucleotide

<400> SEQUENCE: 106
ttctcctcca ggaatcggga 20

<210> SEQ ID NO 107
<211> LENGTH: 20
<212> TYPE: DNA
<213> ORGANISM: Unknown
<220> FEATURE:
<223> OTHER INFORMATION: Oligonucleotide

<400> SEQUENCE: 107
aaggccaaag tcagacactt 20

<210> SEQ ID NO 108
<211> LENGTH: 20
<212> TYPE: DNA
<213> ORGANISM: Unknown

<220> FEATURE:
<223> OTHER INFORMATION: Oligonucleotide

<400> SEQUENCE: 108
gcagacgagg ttgctgttga 20

<210> SEQ ID NO 109
<211> LENGTH: 20
<212> TYPE: DNA
<213> ORGANISM: Unknown
<220> FEATURE:
<223> OTHER INFORMATION: Oligonucleotide

<400> SEQUENCE: 109
ctaggatgtt gcgagcagcc 20

<210> SEQ ID NO 110
<211> LENGTH: 20
<212> TYPE: DNA
<213> ORGANISM: Unknown
<220> FEATURE:
<223> OTHER INFORMATION: Oligonucleotide

<400> SEQUENCE: 110
aggtctcggt ggacgtagct 20

<210> SEQ ID NO 111
<211> LENGTH: 20
<212> TYPE: DNA
<213> ORGANISM: Unknown
<220> FEATURE:
<223> OTHER INFORMATION: Oligonucleotide

<400> SEQUENCE: 111
catctcggca aggtaccgca 20

<210> SEQ ID NO 112
<211> LENGTH: 20
<212> TYPE: DNA
<213> ORGANISM: Unknown
<220> FEATURE:
<223> OTHER INFORMATION: Oligonucleotide

<400> SEQUENCE: 112
tgcccgaggc gatgccccgc 20

<210> SEQ ID NO 113
<211> LENGTH: 20
<212> TYPE: DNA
<213> ORGANISM: Unknown
<220> FEATURE:
<223> OTHER INFORMATION: Oligonucleotide

<400> SEQUENCE: 113
agcatgccca cgagctggat 20

<210> SEQ ID NO 114
<211> LENGTH: 20
<212> TYPE: DNA
<213> ORGANISM: Unknown
<220> FEATURE:
<223> OTHER INFORMATION: Oligonucleotide

<400> SEQUENCE: 114
gactgtgaac tgtccgtcgt 20

<210> SEQ ID NO 115
<211> LENGTH: 20
<212> TYPE: DNA
<213> ORGANISM: Unknown
<220> FEATURE:
<223> OTHER INFORMATION: Oligonucleotide

<400> SEQUENCE: 115
ttagccgcag gaaggagtcc 20

<210> SEQ ID NO 116
<211> LENGTH: 20
<212> TYPE: DNA
<213> ORGANISM: Unknown
<220> FEATURE:
<223> OTHER INFORMATION: Oligonucleotide

<400> SEQUENCE: 116
agggcgccgt tctccatgaa 20

<210> SEQ ID NO 117
<211> LENGTH: 20
<212> TYPE: DNA
<213> ORGANISM: Unknown
<220> FEATURE:
<223> OTHER INFORMATION: Oligonucleotide

<400> SEQUENCE: 117
ctctgtgaga atcatgacgg 20

<210> SEQ ID NO 118
<211> LENGTH: 20
<212> TYPE: DNA
<213> ORGANISM: Unknown
<220> FEATURE:
<223> OTHER INFORMATION: Oligonucleotide

<400> SEQUENCE: 118
gcatgctgtt ggtgaccacg 20

<210> SEQ ID NO 119
<211> LENGTH: 20
<212> TYPE: DNA
<213> ORGANISM: Unknown
<220> FEATURE:
<223> OTHER INFORMATION: Oligonucleotide

<400> SEQUENCE: 119
ccctccaggc ggatgatatt 20

<210> SEQ ID NO 120
<211> LENGTH: 20
<212> TYPE: DNA
<213> ORGANISM: Unknown
<220> FEATURE:
<223> OTHER INFORMATION: Oligonucleotide

<400> SEQUENCE: 120
ggggtgctcg aactggccca 20

<210> SEQ ID NO 121
<211> LENGTH: 20
<212> TYPE: DNA
<213> ORGANISM: Unknown
<220> FEATURE:
<223> OTHER INFORMATION: Oligonucleotide

<400> SEQUENCE: 121
tgatggaggc ctcgctcaga 20

<210> SEQ ID NO 122
<211> LENGTH: 20
<212> TYPE: DNA
<213> ORGANISM: Unknown
<220> FEATURE:
<223> OTHER INFORMATION: Oligonucleotide

<400> SEQUENCE: 122
aactcacgcc gctgccgctc 20

<210> SEQ ID NO 123
<211> LENGTH: 20
<212> TYPE: DNA
<213> ORGANISM: Unknown
<220> FEATURE:
<223> OTHER INFORMATION: Oligonucleotide

<400> SEQUENCE: 123
cgtgtagcca cccttcaggg 20

<210> SEQ ID NO 124
<211> LENGTH: 20
<212> TYPE: DNA
<213> ORGANISM: Unknown
<220> FEATURE:
<223> OTHER INFORMATION: Oligonucleotide

<400> SEQUENCE: 124
tcttgattgc cacacagctc 20

<210> SEQ ID NO 125
<211> LENGTH: 20
<212> TYPE: DNA
<213> ORGANISM: Unknown
<220> FEATURE:
<223> OTHER INFORMATION: Oligonucleotide

<400> SEQUENCE: 125
tccttcttcc ctggggcctt 20

<210> SEQ ID NO 126
<211> LENGTH: 20
<212> TYPE: DNA
<213> ORGANISM: Unknown
<220> FEATURE:
<223> OTHER INFORMATION: Oligonucleotide

<400> SEQUENCE: 126
gagccgcccc cggcacacct 20

<210> SEQ ID NO 127
<211> LENGTH: 20
<212> TYPE: DNA
<213> ORGANISM: Unknown
<220> FEATURE:
<223> OTHER INFORMATION: Oligonucleotide

<400> SEQUENCE: 127
cgccaaactc acctgcacca 20

<210> SEQ ID NO 128
<211> LENGTH: 20
<212> TYPE: DNA
<213> ORGANISM: Unknown

<220> FEATURE:
<223> OTHER INFORMATION: Oligonucleotide

<400> SEQUENCE: 128
atcacctctt caatcttgac 20

<210> SEQ ID NO 129
<211> LENGTH: 20
<212> TYPE: DNA
<213> ORGANISM: Unknown
<220> FEATURE:
<223> OTHER INFORMATION: Oligonucleotide

<400> SEQUENCE: 129
gtaggagaca tcgatctctt 20

<210> SEQ ID NO 130
<211> LENGTH: 20
<212> TYPE: DNA
<213> ORGANISM: Unknown
<220> FEATURE:
<223> OTHER INFORMATION: Oligonucleotide

<400> SEQUENCE: 130
ttgcaaattc cctcacagcc 20

<210> SEQ ID NO 131
<211> LENGTH: 20
<212> TYPE: DNA
<213> ORGANISM: Unknown
<220> FEATURE:
<223> OTHER INFORMATION: Oligonucleotide

<400> SEQUENCE: 131
tcattagggt cttcataagt 20

<210> SEQ ID NO 132
<211> LENGTH: 20
<212> TYPE: DNA
<213> ORGANISM: Unknown
<220> FEATURE:
<223> OTHER INFORMATION: Oligonucleotide

<400> SEQUENCE: 132
gaaggggtcg atgtagacct 20

<210> SEQ ID NO 133
<211> LENGTH: 20
<212> TYPE: DNA
<213> ORGANISM: Unknown
<220> FEATURE:
<223> OTHER INFORMATION: Oligonucleotide

<400> SEQUENCE: 133
tagtaccatg tccgatgaga 20

<210> SEQ ID NO 134
<211> LENGTH: 20
<212> TYPE: DNA
<213> ORGANISM: Unknown
<220> FEATURE:
<223> OTHER INFORMATION: Oligonucleotide

<400> SEQUENCE: 134
tactgtccgt gtttgtccga 20

<210> SEQ ID NO 135
<211> LENGTH: 20
<212> TYPE: DNA
<213> ORGANISM: Unknown
<220> FEATURE:
<223> OTHER INFORMATION: Oligonucleotide

<400> SEQUENCE: 135
atattctgct tctctcccat 20

<210> SEQ ID NO 136
<211> LENGTH: 20
<212> TYPE: DNA
<213> ORGANISM: Unknown
<220> FEATURE:
<223> OTHER INFORMATION: Oligonucleotide

<400> SEQUENCE: 136
tgctctgctt cctgaggcag 20

<210> SEQ ID NO 137
<211> LENGTH: 20
<212> TYPE: DNA
<213> ORGANISM: Unknown
<220> FEATURE:
<223> OTHER INFORMATION: Oligonucleotide

<400> SEQUENCE: 137
agaactgcga ccacaatgac 20

<210> SEQ ID NO 138
<211> LENGTH: 20
<212> TYPE: DNA
<213> ORGANISM: Unknown
<220> FEATURE:
<223> OTHER INFORMATION: Oligonucleotide

<400> SEQUENCE: 138
caccaggacc aggaccacac 20

<210> SEQ ID NO 139
<211> LENGTH: 20
<212> TYPE: DNA
<213> ORGANISM: Unknown
<220> FEATURE:
<223> OTHER INFORMATION: Oligonucleotide

<400> SEQUENCE: 139
ccacgactgc cgtgcccgca 20

<210> SEQ ID NO 140
<211> LENGTH: 20
<212> TYPE: DNA
<213> ORGANISM: Unknown
<220> FEATURE:
<223> OTHER INFORMATION: Oligonucleotide

<400> SEQUENCE: 140
atcagggcca gctgctcccg 20

<210> SEQ ID NO 141
<211> LENGTH: 20
<212> TYPE: DNA
<213> ORGANISM: Unknown
<220> FEATURE:
<223> OTHER INFORMATION: Oligonucleotide

<400> SEQUENCE: 141

-continued ccagccctcg ctctcatcca 20

<210> SEQ ID NO 142
<211> LENGTH: 20
<212> TYPE: DNA
<213> ORGANISM: Unknown
<220> FEATURE:
<223> OTHER INFORMATION: Oligonucleotide

<400> SEQUENCE: 142
gttgggtctg gctgtgatgt 20

<210> SEQ ID NO 143
<211> LENGTH: 20
<212> TYPE: DNA
<213> ORGANISM: Unknown
<220> FEATURE:
<223> OTHER INFORMATION: Oligonucleotide

<400> SEQUENCE: 143
tcctggccga agggcccgta 20

<210> SEQ ID NO 144
<211> LENGTH: 20
<212> TYPE: DNA
<213> ORGANISM: Unknown
<220> FEATURE:
<223> OTHER INFORMATION: Oligonucleotide

<400> SEQUENCE: 144
gccggcctca gagcgcgccc 20

<210> SEQ ID NO 145
<211> LENGTH: 20
<212> TYPE: DNA
<213> ORGANISM: Unknown
<220> FEATURE:
<223> OTHER INFORMATION: Oligonucleotide

<400> SEQUENCE: 145
gtacctgcac caggtagctg 20

<210> SEQ ID NO 146
<211> LENGTH: 20
<212> TYPE: DNA
<213> ORGANISM: Unknown
<220> FEATURE:
<223> OTHER INFORMATION: Oligonucleotide

<400> SEQUENCE: 146
gctccccgct tcagcccccg 20

<210> SEQ ID NO 147
<211> LENGTH: 20
<212> TYPE: DNA
<213> ORGANISM: Unknown
<220> FEATURE:
<223> OTHER INFORMATION: Oligonucleotide

<400> SEQUENCE: 147
cagctctgcc cggttttctg 20

<210> SEQ ID NO 148
<211> LENGTH: 20
<212> TYPE: DNA
<213> ORGANISM: Unknown

<220> FEATURE:
<223> OTHER INFORMATION: Oligonucleotide

<400> SEQUENCE: 148
acgtcttcag gaaccgcacg 20

<210> SEQ ID NO 149
<211> LENGTH: 20
<212> TYPE: DNA
<213> ORGANISM: Unknown
<220> FEATURE:
<223> OTHER INFORMATION: Oligonucleotide

<400> SEQUENCE: 149
ctgctgggac cctcggcgcc 20

<210> SEQ ID NO 150
<211> LENGTH: 20
<212> TYPE: DNA
<213> ORGANISM: Unknown
<220> FEATURE:
<223> OTHER INFORMATION: Oligonucleotide

<400> SEQUENCE: 150
cttctcatgg tatttgacct 20

<210> SEQ ID NO 151
<211> LENGTH: 20
<212> TYPE: DNA
<213> ORGANISM: Unknown
<220> FEATURE:
<223> OTHER INFORMATION: Oligonucleotide

<400> SEQUENCE: 151
cgtagtccag cacagcccca 20

<210> SEQ ID NO 152
<211> LENGTH: 20
<212> TYPE: DNA
<213> ORGANISM: Unknown
<220> FEATURE:
<223> OTHER INFORMATION: Oligonucleotide

<400> SEQUENCE: 152
ctgggtgccc ggggaacagc 20

<210> SEQ ID NO 153
<211> LENGTH: 20
<212> TYPE: DNA
<213> ORGANISM: Unknown
<220> FEATURE:
<223> OTHER INFORMATION: Oligonucleotide

<400> SEQUENCE: 153
ccaggccagg ctcaagctgc 20

<210> SEQ ID NO 154
<211> LENGTH: 20
<212> TYPE: DNA
<213> ORGANISM: Unknown
<220> FEATURE:
<223> OTHER INFORMATION: Oligonucleotide

<400> SEQUENCE: 154
tgggtgagga ccgcgtcacc 20

<210> SEQ ID NO 155
<211> LENGTH: 20
<212> TYPE: DNA
<213> ORGANISM: Unknown
<220> FEATURE:
<223> OTHER INFORMATION: Oligonucleotide

<400> SEQUENCE: 155
cggatgtcag acactgcagg 20

<210> SEQ ID NO 156
<211> LENGTH: 20
<212> TYPE: DNA
<213> ORGANISM: Unknown
<220> FEATURE:
<223> OTHER INFORMATION: Oligonucleotide

<400> SEQUENCE: 156
aggtacctct cggtcagtgg 20

<210> SEQ ID NO 157
<211> LENGTH: 20
<212> TYPE: DNA
<213> ORGANISM: Unknown
<220> FEATURE:
<223> OTHER INFORMATION: Oligonucleotide

<400> SEQUENCE: 157
tgacattgac aggctcaaat 20

<210> SEQ ID NO 158
<211> LENGTH: 20
<212> TYPE: DNA
<213> ORGANISM: Unknown
<220> FEATURE:
<223> OTHER INFORMATION: Oligonucleotide

<400> SEQUENCE: 158
gggacgggcc ccgtggctaa 20

<210> SEQ ID NO 159
<211> LENGTH: 20
<212> TYPE: DNA
<213> ORGANISM: Unknown
<220> FEATURE:
<223> OTHER INFORMATION: Oligonucleotide

<400> SEQUENCE: 159
ggaggatacc ccgttcaatg 20

<210> SEQ ID NO 160
<211> LENGTH: 20
<212> TYPE: DNA
<213> ORGANISM: Unknown
<220> FEATURE:
<223> OTHER INFORMATION: Oligonucleotide

<400> SEQUENCE: 160
cagtgacctc aaaggtatag 20

<210> SEQ ID NO 161
<211> LENGTH: 20
<212> TYPE: DNA
<213> ORGANISM: Unknown
<220> FEATURE:
<223> OTHER INFORMATION: Oligonucleotide

<400> SEQUENCE: 161
gtgaagtcag gacgtagccc 20

<210> SEQ ID NO 162
<211> LENGTH: 20
<212> TYPE: DNA
<213> ORGANISM: Unknown
<220> FEATURE:
<223> OTHER INFORMATION: Oligonucleotide

<400> SEQUENCE: 162
tcgaaccacc acccagggct 20

<210> SEQ ID NO 163
<211> LENGTH: 20
<212> TYPE: DNA
<213> ORGANISM: Unknown
<220> FEATURE:
<223> OTHER INFORMATION: Oligonucleotide

<400> SEQUENCE: 163
ccaccaggtc ccgggggccg 20

<210> SEQ ID NO 164
<211> LENGTH: 20
<212> TYPE: DNA
<213> ORGANISM: Unknown
<220> FEATURE:
<223> OTHER INFORMATION: Oligonucleotide

<400> SEQUENCE: 164
gggtcaaaag tcaggtctcc 20

<210> SEQ ID NO 165
<211> LENGTH: 20
<212> TYPE: DNA
<213> ORGANISM: Unknown
<220> FEATURE:
<223> OTHER INFORMATION: Oligonucleotide

<400> SEQUENCE: 165
cccgcagggc gcacaggagc 20

<210> SEQ ID NO 166
<211> LENGTH: 20
<212> TYPE: DNA
<213> ORGANISM: Unknown
<220> FEATURE:
<223> OTHER INFORMATION: Oligonucleotide

<400> SEQUENCE: 166
ctccgggtcg gcactcccgg 20

<210> SEQ ID NO 167
<211> LENGTH: 20
<212> TYPE: DNA
<213> ORGANISM: Unknown
<220> FEATURE:
<223> OTHER INFORMATION: Oligonucleotide

<400> SEQUENCE: 167
cagcggaggg cgtaggtgag 20

<210> SEQ ID NO 168
<211> LENGTH: 20
<212> TYPE: DNA
<213> ORGANISM: Unknown

<220> FEATURE:
<223> OTHER INFORMATION: Oligonucleotide

<400> SEQUENCE: 168
gtcctctcgg ccaccagact 20

<210> SEQ ID NO 169
<211> LENGTH: 20
<212> TYPE: DNA
<213> ORGANISM: Unknown
<220> FEATURE:
<223> OTHER INFORMATION: Oligonucleotide

<400> SEQUENCE: 169 ccagggggc actccattcc 20

<210> SEQ ID NO 170
<211> LENGTH: 20
<212> TYPE: DNA
<213> ORGANISM: Unknown
<220> FEATURE:
<223> OTHER INFORMATION: Oligonucleotide

<400> SEQUENCE: 170
aggtgcaggg aggagccgtt 20

<210> SEQ ID NO 171
<211> LENGTH: 20
<212> TYPE: DNA
<213> ORGANISM: Unknown
<220> FEATURE:
<223> OTHER INFORMATION: Oligonucleotide

<400> SEQUENCE: 171
caggcgggaa accacgctcc 20

<210> SEQ ID NO 172
<211> LENGTH: 20
<212> TYPE: DNA
<213> ORGANISM: Unknown
<220> FEATURE:
<223> OTHER INFORMATION: Oligonucleotide

<400> SEQUENCE: 172
gcggagccga aggaggggtg 20

<210> SEQ ID NO 173
<211> LENGTH: 20
<212> TYPE: DNA
<213> ORGANISM: Unknown
<220> FEATURE:
<223> OTHER INFORMATION: Oligonucleotide

<400> SEQUENCE: 173
gtgcagggtg caccccgggg 20

<210> SEQ ID NO 174
<211> LENGTH: 20
<212> TYPE: DNA
<213> ORGANISM: Unknown
<220> FEATURE:
<223> OTHER INFORMATION: Oligonucleotide

<400> SEQUENCE: 174
gtctgtgcgt gcccggaagt 20

<210> SEQ ID NO 175
<211> LENGTH: 20
<212> TYPE: DNA
<213> ORGANISM: Unknown
<220> FEATURE:
<223> OTHER INFORMATION: Oligonucleotide

<400> SEQUENCE: 175
acccgacgcg gcactggcag 20

<210> SEQ ID NO 176
<211> LENGTH: 20
<212> TYPE: DNA
<213> ORGANISM: Unknown
<220> FEATURE:
<223> OTHER INFORMATION: Oligonucleotide

<400> SEQUENCE: 176
acggctgatc caatggtgtt 20

<210> SEQ ID NO 177
<211> LENGTH: 20
<212> TYPE: DNA
<213> ORGANISM: Unknown
<220> FEATURE:
<223> OTHER INFORMATION: Oligonucleotide

<400> SEQUENCE: 177
agagtggcta ttggctgggc 20

<210> SEQ ID NO 178
<211> LENGTH: 20
<212> TYPE: DNA
<213> ORGANISM: Unknown
<220> FEATURE:
<223> OTHER INFORMATION: Oligonucleotide

<400> SEQUENCE: 178
atggctggca ggacccttct 20

<210> SEQ ID NO 179
<211> LENGTH: 20
<212> TYPE: DNA
<213> ORGANISM: Unknown
<220> FEATURE:
<223> OTHER INFORMATION: Oligonucleotide

<400> SEQUENCE: 179
cctgacaggg gcttgaaggt 20

<210> SEQ ID NO 180
<211> LENGTH: 20
<212> TYPE: DNA
<213> ORGANISM: Unknown
<220> FEATURE:
<223> OTHER INFORMATION: Oligonucleotide

<400> SEQUENCE: 180
gccctgggca caggctcggc 20

<210> SEQ ID NO 181
<211> LENGTH: 20
<212> TYPE: DNA
<213> ORGANISM: Unknown
<220> FEATURE:
<223> OTHER INFORMATION: Oligonucleotide

<400> SEQUENCE: 181
acttggtgtt cccctcagct 20

<210> SEQ ID NO 182
<211> LENGTH: 20
<212> TYPE: DNA
<213> ORGANISM: Unknown
<220> FEATURE:
<223> OTHER INFORMATION: Oligonucleotide

<400> SEQUENCE: 182
gcctcgaacc ccggagcaca 20

<210> SEQ ID NO 183
<211> LENGTH: 20
<212> TYPE: DNA
<213> ORGANISM: Unknown
<220> FEATURE:
<223> OTHER INFORMATION: Oligonucleotide

<400> SEQUENCE: 183
gctgcagccc gtgaccggct 20

<210> SEQ ID NO 184
<211> LENGTH: 20
<212> TYPE: DNA
<213> ORGANISM: Unknown
<220> FEATURE:
<223> OTHER INFORMATION: Oligonucleotide

<400> SEQUENCE: 184
gttcggccca ctggccatcc 20

<210> SEQ ID NO 185
<211> LENGTH: 20
<212> TYPE: DNA
<213> ORGANISM: Unknown
<220> FEATURE:
<223> OTHER INFORMATION: Oligonucleotide

<400> SEQUENCE: 185
tcacggcagt agaggctggg 20

<210> SEQ ID NO 186
<211> LENGTH: 20
<212> TYPE: DNA
<213> ORGANISM: Unknown
<220> FEATURE:
<223> OTHER INFORMATION: Oligonucleotide

<400> SEQUENCE: 186
gctggggcca ggggcgggga 20

<210> SEQ ID NO 187
<211> LENGTH: 20
<212> TYPE: DNA
<213> ORGANISM: Unknown
<220> FEATURE:
<223> OTHER INFORMATION: Oligonucleotide

<400> SEQUENCE: 187
cggcatccac cacgcagcta 20

<210> SEQ ID NO 188
<211> LENGTH: 20
<212> TYPE: DNA
<213> ORGANISM: Unknown

<220> FEATURE:
<223> OTHER INFORMATION: Oligonucleotide

<400> SEQUENCE: 188
ccggccacgg gcacaaccag 20

<210> SEQ ID NO 189
<211> LENGTH: 20
<212> TYPE: DNA
<213> ORGANISM: Unknown
<220> FEATURE:
<223> OTHER INFORMATION: Oligonucleotide

<400> SEQUENCE: 189
ctcccgaggc acagtctccg 20

<210> SEQ ID NO 190
<211> LENGTH: 20
<212> TYPE: DNA
<213> ORGANISM: Unknown
<220> FEATURE:
<223> OTHER INFORMATION: Oligonucleotide

<400> SEQUENCE: 190
ggaatcgagt caggttcaca 20

<210> SEQ ID NO 191
<211> LENGTH: 20
<212> TYPE: DNA
<213> ORGANISM: Unknown
<220> FEATURE:
<223> OTHER INFORMATION: Oligonucleotide

<400> SEQUENCE: 191
gtcagctggg cgcacttttt 20

<210> SEQ ID NO 192
<211> LENGTH: 20
<212> TYPE: DNA
<213> ORGANISM: Unknown
<220> FEATURE:
<223> OTHER INFORMATION: Oligonucleotide

<400> SEQUENCE: 192
gtagaagagg tgcagggata 20

<210> SEQ ID NO 193
<211> LENGTH: 20
<212> TYPE: DNA
<213> ORGANISM: Unknown
<220> FEATURE:
<223> OTHER INFORMATION: Oligonucleotide

<400> SEQUENCE: 193
gcagggccat gcaggcaccc 20

<210> SEQ ID NO 194
<211> LENGTH: 20
<212> TYPE: DNA
<213> ORGANISM: Unknown
<220> FEATURE:
<223> OTHER INFORMATION: Oligonucleotide

<400> SEQUENCE: 194
tggtcctgga aggccaggta 20

<210> SEQ ID NO 195
<211> LENGTH: 20
<212> TYPE: DNA
<213> ORGANISM: Unknown
<220> FEATURE:
<223> OTHER INFORMATION: Oligonucleotide

<400> SEQUENCE: 195
gaagccagcc ttgctgagcg 20

<210> SEQ ID NO 196
<211> LENGTH: 20
<212> TYPE: DNA
<213> ORGANISM: Unknown
<220> FEATURE:
<223> OTHER INFORMATION: Oligonucleotide

<400> SEQUENCE: 196
gtcccagacg cagcgtcttg 20

<210> SEQ ID NO 197
<211> LENGTH: 20
<212> TYPE: DNA
<213> ORGANISM: Unknown
<220> FEATURE:
<223> OTHER INFORMATION: Oligonucleotide

<400> SEQUENCE: 197
acattcacct tcccggtggc 20

<210> SEQ ID NO 198
<211> LENGTH: 20
<212> TYPE: DNA
<213> ORGANISM: Unknown
<220> FEATURE:
<223> OTHER INFORMATION: Oligonucleotide

<400> SEQUENCE: 198
ctcggcccca gggcgcttcc 20

<210> SEQ ID NO 199
<211> LENGTH: 20
<212> TYPE: DNA
<213> ORGANISM: Unknown
<220> FEATURE:
<223> OTHER INFORMATION: Oligonucleotide

<400> SEQUENCE: 199
gggtgagatg ctccgcggcc 20

<210> SEQ ID NO 200
<211> LENGTH: 20
<212> TYPE: DNA
<213> ORGANISM: Unknown
<220> FEATURE:
<223> OTHER INFORMATION: Oligonucleotide

<400> SEQUENCE: 200
accgtgtcca ccttgatgta 20

<210> SEQ ID NO 201
<211> LENGTH: 20
<212> TYPE: DNA
<213> ORGANISM: Unknown
<220> FEATURE:
<223> OTHER INFORMATION: Oligonucleotide

<400> SEQUENCE: 201
ggggttctcc atccaggctg 20

<210> SEQ ID NO 202
<211> LENGTH: 20
<212> TYPE: DNA
<213> ORGANISM: Unknown
<220> FEATURE:
<223> OTHER INFORMATION: Oligonucleotide

<400> SEQUENCE: 202
gcgtgagggc cgtggccgtg 20

<210> SEQ ID NO 203
<211> LENGTH: 20
<212> TYPE: DNA
<213> ORGANISM: Unknown
<220> FEATURE:
<223> OTHER INFORMATION: Oligonucleotide

<400> SEQUENCE: 203
tccgcatcgc tctcatagta 20

<210> SEQ ID NO 204
<211> LENGTH: 20
<212> TYPE: DNA
<213> ORGANISM: Unknown
<220> FEATURE:
<223> OTHER INFORMATION: Oligonucleotide

<400> SEQUENCE: 204
gaagacggtg aaggtctcct 20

<210> SEQ ID NO 205
<211> LENGTH: 20
<212> TYPE: DNA
<213> ORGANISM: Unknown
<220> FEATURE:
<223> OTHER INFORMATION: Oligonucleotide

<400> SEQUENCE: 205
tgcaggagcg cccagcccga 20

<210> SEQ ID NO 206
<211> LENGTH: 20
<212> TYPE: DNA
<213> ORGANISM: Unknown
<220> FEATURE:
<223> OTHER INFORMATION: Oligonucleotide

<400> SEQUENCE: 206
ggcagggaca ggcactcgag 20

<210> SEQ ID NO 207
<211> LENGTH: 20
<212> TYPE: DNA
<213> ORGANISM: Unknown
<220> FEATURE:
<223> OTHER INFORMATION: Oligonucleotide

<400> SEQUENCE: 207
catggtgaag cgcagcgtgg 20

<210> SEQ ID NO 208
<211> LENGTH: 20
<212> TYPE: DNA
<213> ORGANISM: Unknown

<220> FEATURE:
<223> OTHER INFORMATION: Oligonucleotide

<400> SEQUENCE: 208
cgtacacgtg gacggcgccc 20

<210> SEQ ID NO 209
<211> LENGTH: 20
<212> TYPE: DNA
<213> ORGANISM: Unknown
<220> FEATURE:
<223> OTHER INFORMATION: Oligonucleotide

<400> SEQUENCE: 209
cgccgtggga cccaacctgt 20

<210> SEQ ID NO 210
<211> LENGTH: 20
<212> TYPE: DNA
<213> ORGANISM: Unknown
<220> FEATURE:
<223> OTHER INFORMATION: Oligonucleotide

<400> SEQUENCE: 210
gcgaagccag tgggcctggc 20

<210> SEQ ID NO 211
<211> LENGTH: 20
<212> TYPE: DNA
<213> ORGANISM: Unknown
<220> FEATURE:
<223> OTHER INFORMATION: Oligonucleotide

<400> SEQUENCE: 211
ccggggcacg ctgcacgtca 20

<210> SEQ ID NO 212
<211> LENGTH: 20
<212> TYPE: DNA
<213> ORGANISM: Unknown
<220> FEATURE:
<223> OTHER INFORMATION: Oligonucleotide

<400> SEQUENCE: 212
cacacttcgt aggtgcgcac 20

<210> SEQ ID NO 213
<211> LENGTH: 20
<212> TYPE: DNA
<213> ORGANISM: Unknown
<220> FEATURE:
<223> OTHER INFORMATION: Oligonucleotide

<400> SEQUENCE: 213
gctgtgctgt tcctcatcca 20

<210> SEQ ID NO 214
<211> LENGTH: 20
<212> TYPE: DNA
<213> ORGANISM: Unknown
<220> FEATURE:
<223> OTHER INFORMATION: Oligonucleotide

<400> SEQUENCE: 214
ggccgctcag ttcctcccac 20

-continued

<210> SEQ ID NO 215
<211> LENGTH: 20
<212> TYPE: DNA
<213> ORGANISM: Unknown
<220> FEATURE:
<223> OTHER INFORMATION: Oligonucleotide

<400> SEQUENCE: 215
tgcccgtcca cctgagggaa 20

<210> SEQ ID NO 216
<211> LENGTH: 20
<212> TYPE: DNA
<213> ORGANISM: Unknown
<220> FEATURE:
<223> OTHER INFORMATION: Oligonucleotide

<400> SEQUENCE: 216
tgtcacccac ttcagatcag 20

<210> SEQ ID NO 217
<211> LENGTH: 20
<212> TYPE: DNA
<213> ORGANISM: Unknown
<220> FEATURE:
<223> OTHER INFORMATION: Oligonucleotide

<400> SEQUENCE: 217
cagtttccaa ttttgtgttc 20

<210> SEQ ID NO 218
<211> LENGTH: 20
<212> TYPE: DNA
<213> ORGANISM: Unknown
<220> FEATURE:
<223> OTHER INFORMATION: Oligonucleotide

<400> SEQUENCE: 218
agcagggtct cttccaaagc 20

<210> SEQ ID NO 219
<211> LENGTH: 20
<212> TYPE: DNA
<213> ORGANISM: Unknown
<220> FEATURE:
<223> OTHER INFORMATION: Oligonucleotide

<400> SEQUENCE: 219
tgcggccaac gaagcccagc 20

<210> SEQ ID NO 220
<211> LENGTH: 20
<212> TYPE: DNA
<213> ORGANISM: Unknown
<220> FEATURE:
<223> OTHER INFORMATION: Oligonucleotide

<400> SEQUENCE: 220
agagcagcac ccggagctcc 20

<210> SEQ ID NO 221
<211> LENGTH: 20
<212> TYPE: DNA
<213> ORGANISM: Unknown
<220> FEATURE:
<223> OTHER INFORMATION: Oligonucleotide

<400> SEQUENCE: 221
agcagcaccc ggagctccat 20

<210> SEQ ID NO 222
<211> LENGTH: 21
<212> TYPE: DNA
<213> ORGANISM: Unknown
<220> FEATURE:
<223> OTHER INFORMATION: Oligonucleotide

<400> SEQUENCE: 222
gtgcagggat agcagggcca t 21

<210> SEQ ID NO 223
<211> LENGTH: 21
<212> TYPE: DNA
<213> ORGANISM: Unknown
<220> FEATURE:
<223> OTHER INFORMATION: Oligonucleotide

<400> SEQUENCE: 223
aaggaggggt ggtgcacggt g 21

<210> SEQ ID NO 224
<211> LENGTH: 21
<212> TYPE: DNA
<213> ORGANISM: Unknown
<220> FEATURE:
<223> OTHER INFORMATION: Oligonucleotide

<400> SEQUENCE: 224
ttccaggtgc agggaggagc c 21

<210> SEQ ID NO 225
<211> LENGTH: 21
<212> TYPE: DNA
<213> ORGANISM: Unknown
<220> FEATURE:
<223> OTHER INFORMATION: Oligonucleotide

<400> SEQUENCE: 225
gtggtgacat tgacaggctc a 21

<210> SEQ ID NO 226
<211> LENGTH: 21
<212> TYPE: DNA
<213> ORGANISM: Unknown
<220> FEATURE:
<223> OTHER INFORMATION: Oligonucleotide

<400> SEQUENCE: 226
tctggctgtg atgttcctgg c 21

<210> SEQ ID NO 227
<211> LENGTH: 18
<212> TYPE: DNA
<213> ORGANISM: Unknown
<220> FEATURE:
<223> OTHER INFORMATION: Oligonucleotide

<400> SEQUENCE: 227
gccgctcagt tcctccca 18

<210> SEQ ID NO 228
<211> LENGTH: 18
<212> TYPE: DNA
<213> ORGANISM: Unknown

<220> FEATURE:
<223> OTHER INFORMATION: Oligonucleotide

<400> SEQUENCE: 228
tgaaggtctc cttgcagg 18

<210> SEQ ID NO 229
<211> LENGTH: 21
<212> TYPE: DNA
<213> ORGANISM: Unknown
<220> FEATURE:
<223> OTHER INFORMATION: Oligonucleotide

<400> SEQUENCE: 229
cgcggccacc gtgtccacct t 21

<210> SEQ ID NO 230
<211> LENGTH: 21
<212> TYPE: DNA
<213> ORGANISM: Unknown
<220> FEATURE:
<223> OTHER INFORMATION: Oligonucleotide

<400> SEQUENCE: 230
cttcagggtc ttgattgcca c 21

<210> SEQ ID NO 231
<211> LENGTH: 20
<212> TYPE: DNA
<213> ORGANISM: Unknown
<220> FEATURE:
<223> OTHER INFORMATION: Oligonucleotide

<400> SEQUENCE: 231
atggaggcct cgctcagaaa 20

<210> SEQ ID NO 232
<211> LENGTH: 21
<212> TYPE: DNA
<213> ORGANISM: Unknown
<220> FEATURE:
<223> OTHER INFORMATION: Oligonucleotide

<400> SEQUENCE: 232
catgcccacg agctggatga c 21

<210> SEQ ID NO 233
<211> LENGTH: 21
<212> TYPE: DNA
<213> ORGANISM: Unknown
<220> FEATURE:
<223> OTHER INFORMATION: Oligonucleotide

<400> SEQUENCE: 233
aaattggaaa ctgctgatct g 21

<210> SEQ ID NO 234
<211> LENGTH: 21
<212> TYPE: DNA
<213> ORGANISM: Unknown
<220> FEATURE:
<223> OTHER INFORMATION: Oligonucleotide

<400> SEQUENCE: 234
aattggaaac tgctgatctg a 21

<210> SEQ ID NO 235
<211> LENGTH: 21
<212> TYPE: DNA
<213> ORGANISM: Unknown
<220> FEATURE:
<223> OTHER INFORMATION: Oligonucleotide

<400> SEQUENCE: 235
aaactgctga tctgaagtgg g 21

<210> SEQ ID NO 236
<211> LENGTH: 21
<212> TYPE: DNA
<213> ORGANISM: Unknown
<220> FEATURE:
<223> OTHER INFORMATION: Oligonucleotide

<400> SEQUENCE: 236
aactgctgat ctgaagtggg t 21

<210> SEQ ID NO 237
<211> LENGTH: 21
<212> TYPE: DNA
<213> ORGANISM: Unknown
<220> FEATURE:
<223> OTHER INFORMATION: Oligonucleotide

<400> SEQUENCE: 237
aatgtcaaga cgctgcgtct g 21

<210> SEQ ID NO 238
<211> LENGTH: 21
<212> TYPE: DNA
<213> ORGANISM: Unknown
<220> FEATURE:
<223> OTHER INFORMATION: Oligonucleotide

<400> SEQUENCE: 238
aagtgggtga cattccctca g 21

<210> SEQ ID NO 239
<211> LENGTH: 21
<212> TYPE: DNA
<213> ORGANISM: Unknown
<220> FEATURE:
<223> OTHER INFORMATION: Oligonucleotide

<400> SEQUENCE: 239
aaggtgaatg tcaagacgct g 21

<210> SEQ ID NO 240
<211> LENGTH: 21
<212> TYPE: DNA
<213> ORGANISM: Unknown
<220> FEATURE:
<223> OTHER INFORMATION: Oligonucleotide

<400> SEQUENCE: 240
aaggagacct tcaccgtctt c 21

<210> SEQ ID NO 241
<211> LENGTH: 21
<212> TYPE: DNA
<213> ORGANISM: Unknown
<220> FEATURE:
<223> OTHER INFORMATION: Oligonucleotide

<400> SEQUENCE: 241
aaaaagtgcg cccagctgac t 21

<210> SEQ ID NO 242
<211> LENGTH: 21
<212> TYPE: DNA
<213> ORGANISM: Unknown
<220> FEATURE:
<223> OTHER INFORMATION: Oligonucleotide

<400> SEQUENCE: 242
aatagccact ctaacaccat t 21

<210> SEQ ID NO 243
<211> LENGTH: 21
<212> TYPE: DNA
<213> ORGANISM: Unknown
<220> FEATURE:
<223> OTHER INFORMATION: Oligonucleotide

<400> SEQUENCE: 243
aacaccattg gatcagccgt c 21

<210> SEQ ID NO 244
<211> LENGTH: 21
<212> TYPE: DNA
<213> ORGANISM: Unknown
<220> FEATURE:
<223> OTHER INFORMATION: Oligonucleotide

<400> SEQUENCE: 244
aatgtcacca ctgaccgaga g 21

<210> SEQ ID NO 245
<211> LENGTH: 21
<212> TYPE: DNA
<213> ORGANISM: Unknown
<220> FEATURE:
<223> OTHER INFORMATION: Oligonucleotide

<400> SEQUENCE: 245
aaataccatg agaagggcgc c 21

<210> SEQ ID NO 246
<211> LENGTH: 21
<212> TYPE: DNA
<213> ORGANISM: Unknown
<220> FEATURE:
<223> OTHER INFORMATION: Oligonucleotide

<400> SEQUENCE: 246
aagacgtcag aaaaccgggc a 21

<210> SEQ ID NO 247
<211> LENGTH: 21
<212> TYPE: DNA
<213> ORGANISM: Unknown
<220> FEATURE:
<223> OTHER INFORMATION: Oligonucleotide

<400> SEQUENCE: 247
aacatcacag ccagacccaa c 21

<210> SEQ ID NO 248
<211> LENGTH: 21
<212> TYPE: DNA
<213> ORGANISM: Unknown

<220> FEATURE:
<223> OTHER INFORMATION: Oligonucleotide

<400> SEQUENCE: 248
aagcagagca atgggagaga a 21

<210> SEQ ID NO 249
<211> LENGTH: 21
<212> TYPE: DNA
<213> ORGANISM: Unknown
<220> FEATURE:
<223> OTHER INFORMATION: Oligonucleotide

<400> SEQUENCE: 249
aatgggagag aagcagaata t 21

<210> SEQ ID NO 250
<211> LENGTH: 21
<212> TYPE: DNA
<213> ORGANISM: Unknown
<220> FEATURE:
<223> OTHER INFORMATION: Oligonucleotide

<400> SEQUENCE: 250
aagcagaata ttcggacaaa c 21

<210> SEQ ID NO 251
<211> LENGTH: 21
<212> TYPE: DNA
<213> ORGANISM: Unknown
<220> FEATURE:
<223> OTHER INFORMATION: Oligonucleotide

<400> SEQUENCE: 251
aatattcgga caaacacgga c 21

<210> SEQ ID NO 252
<211> LENGTH: 21
<212> TYPE: DNA
<213> ORGANISM: Unknown
<220> FEATURE:
<223> OTHER INFORMATION: Oligonucleotide

<400> SEQUENCE: 252
aaacacggac agtatctcat c 21

<210> SEQ ID NO 253
<211> LENGTH: 21
<212> TYPE: DNA
<213> ORGANISM: Unknown
<220> FEATURE:
<223> OTHER INFORMATION: Oligonucleotide

<400> SEQUENCE: 253
aacacggaca gtatctcatc g 21

<210> SEQ ID NO 254
<211> LENGTH: 21
<212> TYPE: DNA
<213> ORGANISM: Unknown
<220> FEATURE:
<223> OTHER INFORMATION: Oligonucleotide

<400> SEQUENCE: 254
aaaagagatc gatgtctcct a 21

-continued

<210> SEQ ID NO 255
<211> LENGTH: 21
<212> TYPE: DNA
<213> ORGANISM: Unknown
<220> FEATURE:
<223> OTHER INFORMATION: Oligonucleotide

<400> SEQUENCE: 255
aatgaggctg tgagggaatt t 21

<210> SEQ ID NO 256
<211> LENGTH: 21
<212> TYPE: DNA
<213> ORGANISM: Unknown
<220> FEATURE:
<223> OTHER INFORMATION: Oligonucleotide

<400> SEQUENCE: 256
aagaccctaa tgaggctgtg a 21

<210> SEQ ID NO 257
<211> LENGTH: 21
<212> TYPE: DNA
<213> ORGANISM: Unknown
<220> FEATURE:
<223> OTHER INFORMATION: Oligonucleotide

<400> SEQUENCE: 257
aaagagatcg atgtctccta c 21

<210> SEQ ID NO 258
<211> LENGTH: 21
<212> TYPE: DNA
<213> ORGANISM: Unknown
<220> FEATURE:
<223> OTHER INFORMATION: Oligonucleotide

<400> SEQUENCE: 258
aagagatcga tgtctcctac g 21

<210> SEQ ID NO 259
<211> LENGTH: 21
<212> TYPE: DNA
<213> ORGANISM: Unknown
<220> FEATURE:
<223> OTHER INFORMATION: Oligonucleotide

<400> SEQUENCE: 259
aagaggtgat tggtgcaggt g 21

<210> SEQ ID NO 260
<211> LENGTH: 21
<212> TYPE: DNA
<213> ORGANISM: Unknown
<220> FEATURE:
<223> OTHER INFORMATION: Oligonucleotide

<400> SEQUENCE: 260
aagattgaag aggtgattgg t 21

<210> SEQ ID NO 261
<211> LENGTH: 21
<212> TYPE: DNA
<213> ORGANISM: Unknown
<220> FEATURE:
<223> OTHER INFORMATION: Oligonucleotide

<400> SEQUENCE: 261
aacagcatgc ccgtcatgat t 21

<210> SEQ ID NO 262
<211> LENGTH: 21
<212> TYPE: DNA
<213> ORGANISM: Unknown
<220> FEATURE:
<223> OTHER INFORMATION: Oligonucleotide

<400> SEQUENCE: 262
aagaaggaga gctgtgtggc a 21

<210> SEQ ID NO 263
<211> LENGTH: 21
<212> TYPE: DNA
<213> ORGANISM: Unknown
<220> FEATURE:
<223> OTHER INFORMATION: Oligonucleotide

<400> SEQUENCE: 263
aaggagagct gtgtggcaat c 21

<210> SEQ ID NO 264
<211> LENGTH: 21
<212> TYPE: DNA
<213> ORGANISM: Unknown
<220> FEATURE:
<223> OTHER INFORMATION: Oligonucleotide

<400> SEQUENCE: 264
aatcaagacc ctgaagggtg g 21

<210> SEQ ID NO 265
<211> LENGTH: 21
<212> TYPE: DNA
<213> ORGANISM: Unknown
<220> FEATURE:
<223> OTHER INFORMATION: Oligonucleotide

<400> SEQUENCE: 265
aaacgacgga cagttcacag t 21

<210> SEQ ID NO 266
<211> LENGTH: 21
<212> TYPE: DNA
<213> ORGANISM: Unknown
<220> FEATURE:
<223> OTHER INFORMATION: Oligonucleotide

<400> SEQUENCE: 266
aacgacggac agttcacagt c 21

<210> SEQ ID NO 267
<211> LENGTH: 21
<212> TYPE: DNA
<213> ORGANISM: Unknown
<220> FEATURE:
<223> OTHER INFORMATION: Oligonucleotide

<400> SEQUENCE: 267
aacatcctag tcaacagcaa c 21

<210> SEQ ID NO 268
<211> LENGTH: 21
<212> TYPE: DNA
<213> ORGANISM: Unknown

<220> FEATURE:
<223> OTHER INFORMATION: Oligonucleotide

<400> SEQUENCE: 268
aacagcaacc tcgtctgcaa a 21

<210> SEQ ID NO 269
<211> LENGTH: 21
<212> TYPE: DNA
<213> ORGANISM: Unknown
<220> FEATURE:
<223> OTHER INFORMATION: Oligonucleotide

<400> SEQUENCE: 269
aactcttccg atcccaccta c 21

<210> SEQ ID NO 270
<211> LENGTH: 21
<212> TYPE: DNA
<213> ORGANISM: Unknown
<220> FEATURE:
<223> OTHER INFORMATION: Oligonucleotide

<400> SEQUENCE: 270
aagtgtctga ctttggcctt t 21

<210> SEQ ID NO 271
<211> LENGTH: 21
<212> TYPE: DNA
<213> ORGANISM: Unknown
<220> FEATURE:
<223> OTHER INFORMATION: Oligonucleotide

<400> SEQUENCE: 271
aacctcgtct gcaaagtgtc t 21

<210> SEQ ID NO 272
<211> LENGTH: 21
<212> TYPE: DNA
<213> ORGANISM: Unknown
<220> FEATURE:
<223> OTHER INFORMATION: Oligonucleotide

<400> SEQUENCE: 272
aaagtgtctg actttggcct t 21

<210> SEQ ID NO 273
<211> LENGTH: 21
<212> TYPE: DNA
<213> ORGANISM: Unknown
<220> FEATURE:
<223> OTHER INFORMATION: Oligonucleotide

<400> SEQUENCE: 273
aatcaggacg tgatcaatgc c 21

<210> SEQ ID NO 274
<211> LENGTH: 21
<212> TYPE: DNA
<213> ORGANISM: Unknown
<220> FEATURE:
<223> OTHER INFORMATION: Oligonucleotide

<400> SEQUENCE: 274
aaagattccc atccgatgga c 21

<210> SEQ ID NO 275
<211> LENGTH: 21
<212> TYPE: DNA
<213> ORGANISM: Unknown
<220> FEATURE:
<223> OTHER INFORMATION: Oligonucleotide

<400> SEQUENCE: 275
aagattccca tccgatggac t 21

<210> SEQ ID NO 276
<211> LENGTH: 21
<212> TYPE: DNA
<213> ORGANISM: Unknown
<220> FEATURE:
<223> OTHER INFORMATION: Oligonucleotide

<400> SEQUENCE: 276
aagttcactt ccgccagtga t 21

<210> SEQ ID NO 277
<211> LENGTH: 21
<212> TYPE: DNA
<213> ORGANISM: Unknown
<220> FEATURE:
<223> OTHER INFORMATION: Oligonucleotide

<400> SEQUENCE: 277
aagatacgaa gaaagtttcg c 21

<210> SEQ ID NO 278
<211> LENGTH: 21
<212> TYPE: DNA
<213> ORGANISM: Unknown
<220> FEATURE:
<223> OTHER INFORMATION: Oligonucleotide

<400> SEQUENCE: 278
aatgggaaga tacgaagaaa g 21

<210> SEQ ID NO 279
<211> LENGTH: 21
<212> TYPE: DNA
<213> ORGANISM: Unknown
<220> FEATURE:
<223> OTHER INFORMATION: Oligonucleotide

<400> SEQUENCE: 279
aatgccattg aacaggacta c 21

<210> SEQ ID NO 280
<211> LENGTH: 21
<212> TYPE: DNA
<213> ORGANISM: Unknown
<220> FEATURE:
<223> OTHER INFORMATION: Oligonucleotide

<400> SEQUENCE: 280
aaaatcgtgg cccgggagaa t 21

<210> SEQ ID NO 281
<211> LENGTH: 21
<212> TYPE: DNA
<213> ORGANISM: Unknown
<220> FEATURE:
<223> OTHER INFORMATION: Oligonucleotide

<400> SEQUENCE: 281
aaaatcttgg ccagtgtcca g 21

<210> SEQ ID NO 282
<211> LENGTH: 21
<212> TYPE: DNA
<213> ORGANISM: Unknown
<220> FEATURE:
<223> OTHER INFORMATION: Oligonucleotide

<400> SEQUENCE: 282
aaatcttggc cagtgtccag c 21

<210> SEQ ID NO 283
<211> LENGTH: 21
<212> TYPE: DNA
<213> ORGANISM: Unknown
<220> FEATURE:
<223> OTHER INFORMATION: Oligonucleotide

<400> SEQUENCE: 283
aagaaagttt cgcagccgct g 21

<210> SEQ ID NO 284
<211> LENGTH: 21
<212> TYPE: DNA
<213> ORGANISM: Unknown
<220> FEATURE:
<223> OTHER INFORMATION: Oligonucleotide

<400> SEQUENCE: 284
aagaaaatct tggccagtgt c 21

<210> SEQ ID NO 285
<211> LENGTH: 21
<212> TYPE: DNA
<213> ORGANISM: Unknown
<220> FEATURE:
<223> OTHER INFORMATION: Oligonucleotide

<400> SEQUENCE: 285
aatcttggcc agtgtccagc a 21

<210> SEQ ID NO 286
<211> LENGTH: 21
<212> TYPE: RNA
<213> ORGANISM: Unknown
<220> FEATURE:
<223> OTHER INFORMATION: Oligonucleotide

<400> SEQUENCE: 286
gagacccugc ugaacacaau u 21

<210> SEQ ID NO 287
<211> LENGTH: 21
<212> TYPE: RNA
<213> ORGANISM: Unknown
<220> FEATURE:
<223> OTHER INFORMATION: Oligonucleotide

<400> SEQUENCE: 287
ggugaauguc aagacgcugu u 21

<210> SEQ ID NO 288
<211> LENGTH: 21
<212> TYPE: RNA
<213> ORGANISM: Unknown

<220> FEATURE:
<223> OTHER INFORMATION: Oligonucleotide

<400> SEQUENCE: 288
caucacagcc agacccaacu u 21

<210> SEQ ID NO 289
<211> LENGTH: 21
<212> TYPE: RNA
<213> ORGANISM: Unknown
<220> FEATURE:
<223> OTHER INFORMATION: Oligonucleotide

<400> SEQUENCE: 289
cucuuccgau cccaccuacu u 21

<210> SEQ ID NO 290
<211> LENGTH: 21
<212> TYPE: RNA
<213> ORGANISM: Unknown
<220> FEATURE:
<223> OTHER INFORMATION: Oligonucleotide

<400> SEQUENCE: 290
cucuuccgau cccaccuacu u 21

<210> SEQ ID NO 291
<211> LENGTH: 20
<212> TYPE: DNA
<213> ORGANISM: Unknown
<220> FEATURE:
<223> OTHER INFORMATION: Oligonucleotide

<400> SEQUENCE: 291
tcagaccttg tagtaaatgt 20

<210> SEQ ID NO 292
<211> LENGTH: 20
<212> TYPE: DNA
<213> ORGANISM: Unknown
<220> FEATURE:
<223> OTHER INFORMATION: Oligonucleotide

<400> SEQUENCE: 292
tcgccgggct ctgcgggggc 20

<210> SEQ ID NO 293
<211> LENGTH: 20
<212> TYPE: DNA
<213> ORGANISM: Unknown
<220> FEATURE:
<223> OTHER INFORMATION: Oligonucleotide

<400> SEQUENCE: 293
atctcctgga cgatgtacac 20

<210> SEQ ID NO 294
<211> LENGTH: 20
<212> TYPE: DNA
<213> ORGANISM: Unknown
<220> FEATURE:
<223> OTHER INFORMATION: Oligonucleotide

<400> SEQUENCE: 294
cgggtgcccg tagtccccgc 20

<210> SEQ ID NO 295
<211> LENGTH: 20
<212> TYPE: DNA
<213> ORGANISM: Unknown
<220> FEATURE:
<223> OTHER INFORMATION: Oligonucleotide

<400> SEQUENCE: 295
tgaccttctc gtagtgaggg 20

<210> SEQ ID NO 296
<211> LENGTH: 20
<212> TYPE: DNA
<213> ORGANISM: Unknown
<220> FEATURE:
<223> OTHER INFORMATION: Oligonucleotide

<400> SEQUENCE: 296
cagaagacgc tgtccgcagt 20

<210> SEQ ID NO 297
<211> LENGTH: 20
<212> TYPE: DNA
<213> ORGANISM: Unknown
<220> FEATURE:
<223> OTHER INFORMATION: Oligonucleotide

<400> SEQUENCE: 297
ccttagcggg atgataatgt 20

<210> SEQ ID NO 298
<211> LENGTH: 20
<212> TYPE: DNA
<213> ORGANISM: Unknown
<220> FEATURE:
<223> OTHER INFORMATION: Oligonucleotide

<400> SEQUENCE: 298
cactgggctc tgagccgttg 20

<210> SEQ ID NO 299
<211> LENGTH: 20
<212> TYPE: DNA
<213> ORGANISM: Unknown
<220> FEATURE:
<223> OTHER INFORMATION: Oligonucleotide

<400> SEQUENCE: 299
ttgttgccgc tgcgcttggg 20

<210> SEQ ID NO 300
<211> LENGTH: 20
<212> TYPE: DNA
<213> ORGANISM: Unknown
<220> FEATURE:
<223> OTHER INFORMATION: Oligonucleotide

<400> SEQUENCE: 300
tgtggccagt gtgctgagcg 20

<210> SEQ ID NO 301
<211> LENGTH: 20
<212> TYPE: DNA
<213> ORGANISM: Unknown
<220> FEATURE:
<223> OTHER INFORMATION: Oligonucleotide

<400> SEQUENCE: 301
acagcgtggt cgtgtgctgc 20

<210> SEQ ID NO 302
<211> LENGTH: 20
<212> TYPE: DNA
<213> ORGANISM: Unknown
<220> FEATURE:
<223> OTHER INFORMATION: Oligonucleotide

<400> SEQUENCE: 302
ggcgagtgct tcctgtgtct 20

<210> SEQ ID NO 303
<211> LENGTH: 20
<212> TYPE: DNA
<213> ORGANISM: Unknown
<220> FEATURE:
<223> OTHER INFORMATION: Oligonucleotide

<400> SEQUENCE: 303
cctccggtac ttcagcaaga 20

<210> SEQ ID NO 304
<211> LENGTH: 20
<212> TYPE: DNA
<213> ORGANISM: Unknown
<220> FEATURE:
<223> OTHER INFORMATION: Oligonucleotide

<400> SEQUENCE: 304
ggaccaccag cgtgatgatg 20

<210> SEQ ID NO 305
<211> LENGTH: 20
<212> TYPE: DNA
<213> ORGANISM: Unknown
<220> FEATURE:
<223> OTHER INFORMATION: Oligonucleotide

<400> SEQUENCE: 305
atgacgatga agatgatgca 20

<210> SEQ ID NO 306
<211> LENGTH: 20
<212> TYPE: DNA
<213> ORGANISM: Unknown
<220> FEATURE:
<223> OTHER INFORMATION: Oligonucleotide

<400> SEQUENCE: 306
tcctgaagca atccctgcaa 20

<210> SEQ ID NO 307
<211> LENGTH: 20
<212> TYPE: DNA
<213> ORGANISM: Unknown
<220> FEATURE:
<223> OTHER INFORMATION: Oligonucleotide

<400> SEQUENCE: 307
ataaggccac ttcggaaccg 20

<210> SEQ ID NO 308
<211> LENGTH: 20
<212> TYPE: DNA
<213> ORGANISM: Unknown

<220> FEATURE:
<223> OTHER INFORMATION: Oligonucleotide

<400> SEQUENCE: 308
aggatgttgt tccccgaatg 20

<210> SEQ ID NO 309
<211> LENGTH: 20
<212> TYPE: DNA
<213> ORGANISM: Unknown
<220> FEATURE:
<223> OTHER INFORMATION: Oligonucleotide

<400> SEQUENCE: 309
tccggcgctg ttgccgtctg 20

<210> SEQ ID NO 310
<211> LENGTH: 20
<212> TYPE: DNA
<213> ORGANISM: Unknown
<220> FEATURE:
<223> OTHER INFORMATION: Oligonucleotide

<400> SEQUENCE: 310
tgctagaacc tggatttggt 20

<210> SEQ ID NO 311
<211> LENGTH: 20
<212> TYPE: DNA
<213> ORGANISM: Unknown
<220> FEATURE:
<223> OTHER INFORMATION: Oligonucleotide

<400> SEQUENCE: 311
tttacaaagg gacttgttgt 20

<210> SEQ ID NO 312
<211> LENGTH: 20
<212> TYPE: DNA
<213> ORGANISM: Unknown
<220> FEATURE:
<223> OTHER INFORMATION: Oligonucleotide

<400> SEQUENCE: 312
cgaacttctt ccatttgtac 20

<210> SEQ ID NO 313
<211> LENGTH: 20
<212> TYPE: DNA
<213> ORGANISM: Unknown
<220> FEATURE:
<223> OTHER INFORMATION: Oligonucleotide

<400> SEQUENCE: 313
cagcttctag ttctggacgt 20

<210> SEQ ID NO 314
<211> LENGTH: 20
<212> TYPE: DNA
<213> ORGANISM: Unknown
<220> FEATURE:
<223> OTHER INFORMATION: Oligonucleotide

<400> SEQUENCE: 314
cttgttggat ctttattcct 20

<210> SEQ ID NO 315
<211> LENGTH: 20
<212> TYPE: DNA
<213> ORGANISM: Unknown
<220> FEATURE:
<223> OTHER INFORMATION: Oligonucleotide

<400> SEQUENCE: 315
ggttgatcca gcagaacttg 20

<210> SEQ ID NO 316
<211> LENGTH: 20
<212> TYPE: DNA
<213> ORGANISM: Unknown
<220> FEATURE:
<223> OTHER INFORMATION: Oligonucleotide

<400> SEQUENCE: 316
catcttgtcc aactttcatg 20

<210> SEQ ID NO 317
<211> LENGTH: 20
<212> TYPE: DNA
<213> ORGANISM: Unknown
<220> FEATURE:
<223> OTHER INFORMATION: Oligonucleotide

<400> SEQUENCE: 317
aggatcttca tggctcttgt 20

<210> SEQ ID NO 318
<211> LENGTH: 20
<212> TYPE: DNA
<213> ORGANISM: Unknown
<220> FEATURE:
<223> OTHER INFORMATION: Oligonucleotide

<400> SEQUENCE: 318
ctggcacacc cctccctcct 20

<210> SEQ ID NO 319
<211> LENGTH: 20
<212> TYPE: DNA
<213> ORGANISM: Unknown
<220> FEATURE:
<223> OTHER INFORMATION: Oligonucleotide

<400> SEQUENCE: 319
ggttatccag gccctccaaa 20

<210> SEQ ID NO 320
<211> LENGTH: 20
<212> TYPE: DNA
<213> ORGANISM: Unknown
<220> FEATURE:
<223> OTHER INFORMATION: Oligonucleotide

<400> SEQUENCE: 320
gacccatttg atgtagatat 20

<210> SEQ ID NO 321
<211> LENGTH: 20
<212> TYPE: DNA
<213> ORGANISM: Unknown
<220> FEATURE:
<223> OTHER INFORMATION: Oligonucleotide

<400> SEQUENCE: 321
aatgtaataa tctttgttct 20

<210> SEQ ID NO 322
<211> LENGTH: 20
<212> TYPE: DNA
<213> ORGANISM: Unknown
<220> FEATURE:
<223> OTHER INFORMATION: Oligonucleotide

<400> SEQUENCE: 322
tctgaaattc tagaccccag 20

<210> SEQ ID NO 323
<211> LENGTH: 20
<212> TYPE: DNA
<213> ORGANISM: Unknown
<220> FEATURE:
<223> OTHER INFORMATION: Oligonucleotide

<400> SEQUENCE: 323
aggttagggc tgaattcttg 20

<210> SEQ ID NO 324
<211> LENGTH: 20
<212> TYPE: DNA
<213> ORGANISM: Unknown
<220> FEATURE:
<223> OTHER INFORMATION: Oligonucleotide

<400> SEQUENCE: 324
aaacttgatg gtgaatttga 20

<210> SEQ ID NO 325
<211> LENGTH: 20
<212> TYPE: DNA
<213> ORGANISM: Unknown
<220> FEATURE:
<223> OTHER INFORMATION: Oligonucleotide

<400> SEQUENCE: 325
tatcttggtc tggtttggca 20

<210> SEQ ID NO 326
<211> LENGTH: 20
<212> TYPE: DNA
<213> ORGANISM: Unknown
<220> FEATURE:
<223> OTHER INFORMATION: Oligonucleotide

<400> SEQUENCE: 326
cagttgagga gaggggtatt 20

<210> SEQ ID NO 327
<211> LENGTH: 20
<212> TYPE: DNA
<213> ORGANISM: Unknown
<220> FEATURE:
<223> OTHER INFORMATION: Oligonucleotide

<400> SEQUENCE: 327
ttccttctta atagtgcatc 20

<210> SEQ ID NO 328
<211> LENGTH: 20
<212> TYPE: DNA
<213> ORGANISM: Unknown

```
<220> FEATURE:
<223> OTHER INFORMATION: Oligonucleotide

<400> SEQUENCE: 328

tgtctgcttg gtctttatca                                               20

<210> SEQ ID NO 329
<211> LENGTH: 20
<212> TYPE: DNA
<213> ORGANISM: Unknown
<220> FEATURE:
<223> OTHER INFORMATION: Oligonucleotide

<400> SEQUENCE: 329

accatataaa ctttataata                                               20

<210> SEQ ID NO 330
<211> LENGTH: 20
<212> TYPE: DNA
<213> ORGANISM: Unknown
<220> FEATURE:
<223> OTHER INFORMATION: Oligonucleotide

<400> SEQUENCE: 330

ttcatactgg ccaacagttt                                               20

<210> SEQ ID NO 331
<211> LENGTH: 20
<212> TYPE: DNA
<213> ORGANISM: Unknown
<220> FEATURE:
<223> OTHER INFORMATION: Oligonucleotide

<400> SEQUENCE: 331

tagagtccac tttggggcaa                                               20

<210> SEQ ID NO 332
<211> LENGTH: 20
<212> TYPE: DNA
<213> ORGANISM: Unknown
<220> FEATURE:
<223> OTHER INFORMATION: Oligonucleotide

<400> SEQUENCE: 332

ataatatcca atttgtctcc                                               20

<210> SEQ ID NO 333
<211> LENGTH: 20
<212> TYPE: DNA
<213> ORGANISM: Unknown
<220> FEATURE:
<223> OTHER INFORMATION: Oligonucleotide

<400> SEQUENCE: 333

tatctgtggg tatagtacca                                               20

<210> SEQ ID NO 334
<211> LENGTH: 20
<212> TYPE: DNA
<213> ORGANISM: Unknown
<220> FEATURE:
<223> OTHER INFORMATION: Oligonucleotide

<400> SEQUENCE: 334

gtccttgtcc aggtagaaat                                               20
```

-continued

<210> SEQ ID NO 335
<211> LENGTH: 20
<212> TYPE: DNA
<213> ORGANISM: Unknown
<220> FEATURE:
<223> OTHER INFORMATION: Oligonucleotide

<400> SEQUENCE: 335
ttggagttcg aggaattcca 20

<210> SEQ ID NO 336
<211> LENGTH: 20
<212> TYPE: DNA
<213> ORGANISM: Unknown
<220> FEATURE:
<223> OTHER INFORMATION: Oligonucleotide

<400> SEQUENCE: 336
atagataggc tctaaaacta 20

<210> SEQ ID NO 337
<211> LENGTH: 20
<212> TYPE: DNA
<213> ORGANISM: Unknown
<220> FEATURE:
<223> OTHER INFORMATION: Oligonucleotide

<400> SEQUENCE: 337
tcgatttgga aatcgcagtt 20

<210> SEQ ID NO 338
<211> LENGTH: 20
<212> TYPE: DNA
<213> ORGANISM: Unknown
<220> FEATURE:
<223> OTHER INFORMATION: Oligonucleotide

<400> SEQUENCE: 338
ctgcataaaa ccatcaaaac 20

<210> SEQ ID NO 339
<211> LENGTH: 20
<212> TYPE: DNA
<213> ORGANISM: Unknown
<220> FEATURE:
<223> OTHER INFORMATION: Oligonucleotide

<400> SEQUENCE: 339
accccagcag tacttccaca 20

<210> SEQ ID NO 340
<211> LENGTH: 20
<212> TYPE: DNA
<213> ORGANISM: Unknown
<220> FEATURE:
<223> OTHER INFORMATION: Oligonucleotide

<400> SEQUENCE: 340
cggagtccct tctcacagcc 20

<210> SEQ ID NO 341
<211> LENGTH: 20
<212> TYPE: DNA
<213> ORGANISM: Unknown
<220> FEATURE:
<223> OTHER INFORMATION: Oligonucleotide

<400> SEQUENCE: 341
gagtcccttc tcacagccat 20

<210> SEQ ID NO 342
<211> LENGTH: 21
<212> TYPE: DNA
<213> ORGANISM: Unknown
<220> FEATURE:
<223> OTHER INFORMATION: Oligonucleotide

<400> SEQUENCE: 342
aactgcgatt tccaaatcga t 21

<210> SEQ ID NO 343
<211> LENGTH: 21
<212> TYPE: DNA
<213> ORGANISM: Unknown
<220> FEATURE:
<223> OTHER INFORMATION: Oligonucleotide

<400> SEQUENCE: 343
aactccaaat ttctacctgg a 21

<210> SEQ ID NO 344
<211> LENGTH: 21
<212> TYPE: DNA
<213> ORGANISM: Unknown
<220> FEATURE:
<223> OTHER INFORMATION: Oligonucleotide

<400> SEQUENCE: 344
aatttctacc tggacaagga c 21

<210> SEQ ID NO 345
<211> LENGTH: 21
<212> TYPE: DNA
<213> ORGANISM: Unknown
<220> FEATURE:
<223> OTHER INFORMATION: Oligonucleotide

<400> SEQUENCE: 345
aaatttctac ctggacaagg a 21

<210> SEQ ID NO 346
<211> LENGTH: 21
<212> TYPE: DNA
<213> ORGANISM: Unknown
<220> FEATURE:
<223> OTHER INFORMATION: Oligonucleotide

<400> SEQUENCE: 346
aaggactggt actataccca c 21

<210> SEQ ID NO 347
<211> LENGTH: 21
<212> TYPE: DNA
<213> ORGANISM: Unknown
<220> FEATURE:
<223> OTHER INFORMATION: Oligonucleotide

<400> SEQUENCE: 347
aagtggactc taaaactgtt g 21

<210> SEQ ID NO 348
<211> LENGTH: 21
<212> TYPE: DNA
<213> ORGANISM: Unknown

<220> FEATURE:
<223> OTHER INFORMATION: Oligonucleotide

<400> SEQUENCE: 348
aaactgttgg ccagtatgaa t 21

<210> SEQ ID NO 349
<211> LENGTH: 21
<212> TYPE: DNA
<213> ORGANISM: Unknown
<220> FEATURE:
<223> OTHER INFORMATION: Oligonucleotide

<400> SEQUENCE: 349
aaaactgttg gccagtatga a 21

<210> SEQ ID NO 350
<211> LENGTH: 21
<212> TYPE: DNA
<213> ORGANISM: Unknown
<220> FEATURE:
<223> OTHER INFORMATION: Oligonucleotide

<400> SEQUENCE: 350
aagaccaagc agacagatgc a 21

<210> SEQ ID NO 351
<211> LENGTH: 21
<212> TYPE: DNA
<213> ORGANISM: Unknown
<220> FEATURE:
<223> OTHER INFORMATION: Oligonucleotide

<400> SEQUENCE: 351
aaagaccaag cagacagatg c 21

<210> SEQ ID NO 352
<211> LENGTH: 21
<212> TYPE: DNA
<213> ORGANISM: Unknown
<220> FEATURE:
<223> OTHER INFORMATION: Oligonucleotide

<400> SEQUENCE: 352
aagtttcaag aattcagccc t 21

<210> SEQ ID NO 353
<211> LENGTH: 21
<212> TYPE: DNA
<213> ORGANISM: Unknown
<220> FEATURE:
<223> OTHER INFORMATION: Oligonucleotide

<400> SEQUENCE: 353
aagaattcag ccctaacctc t 21

<210> SEQ ID NO 354
<211> LENGTH: 21
<212> TYPE: DNA
<213> ORGANISM: Unknown
<220> FEATURE:
<223> OTHER INFORMATION: Oligonucleotide

<400> SEQUENCE: 354
aattcagccc taacctctgg g 21

<210> SEQ ID NO 355
<211> LENGTH: 21
<212> TYPE: DNA
<213> ORGANISM: Unknown
<220> FEATURE:
<223> OTHER INFORMATION: Oligonucleotide

<400> SEQUENCE: 355
aactgtgcca aaccagacca a 21

<210> SEQ ID NO 356
<211> LENGTH: 21
<212> TYPE: DNA
<213> ORGANISM: Unknown
<220> FEATURE:
<223> OTHER INFORMATION: Oligonucleotide

<400> SEQUENCE: 356
aaatgggtct ttggagggcc t 21

<210> SEQ ID NO 357
<211> LENGTH: 21
<212> TYPE: DNA
<213> ORGANISM: Unknown
<220> FEATURE:
<223> OTHER INFORMATION: Oligonucleotide

<400> SEQUENCE: 357
aagatcctca tgaaagttgg a 21

<210> SEQ ID NO 358
<211> LENGTH: 21
<212> TYPE: DNA
<213> ORGANISM: Unknown
<220> FEATURE:
<223> OTHER INFORMATION: Oligonucleotide

<400> SEQUENCE: 358
aaagttggac aagatgcaag t 21

<210> SEQ ID NO 359
<211> LENGTH: 21
<212> TYPE: DNA
<213> ORGANISM: Unknown
<220> FEATURE:
<223> OTHER INFORMATION: Oligonucleotide

<400> SEQUENCE: 359
aagagccatg aagatcctca t 21

<210> SEQ ID NO 360
<211> LENGTH: 21
<212> TYPE: DNA
<213> ORGANISM: Unknown
<220> FEATURE:
<223> OTHER INFORMATION: Oligonucleotide

<400> SEQUENCE: 360
aagttggaca agatgcaagt t 21

<210> SEQ ID NO 361
<211> LENGTH: 21
<212> TYPE: DNA
<213> ORGANISM: Unknown
<220> FEATURE:
<223> OTHER INFORMATION: Oligonucleotide

<400> SEQUENCE: 361

-continued aagatgcaag ttctgctgga t 21

<210> SEQ ID NO 362
<211> LENGTH: 21
<212> TYPE: DNA
<213> ORGANISM: Unknown
<220> FEATURE:
<223> OTHER INFORMATION: Oligonucleotide

<400> SEQUENCE: 362
aagttctgct ggatcaacca g 21

<210> SEQ ID NO 363
<211> LENGTH: 21
<212> TYPE: DNA
<213> ORGANISM: Unknown
<220> FEATURE:
<223> OTHER INFORMATION: Oligonucleotide

<400> SEQUENCE: 363
aaccaggaat aaagatccaa c 21

<210> SEQ ID NO 364
<211> LENGTH: 21
<212> TYPE: DNA
<213> ORGANISM: Unknown
<220> FEATURE:
<223> OTHER INFORMATION: Oligonucleotide

<400> SEQUENCE: 364
aaagatccaa caagacgtcc a 21

<210> SEQ ID NO 365
<211> LENGTH: 21
<212> TYPE: DNA
<213> ORGANISM: Unknown
<220> FEATURE:
<223> OTHER INFORMATION: Oligonucleotide

<400> SEQUENCE: 365
aagatccaac aagacgtcca g 21

<210> SEQ ID NO 366
<211> LENGTH: 21
<212> TYPE: DNA
<213> ORGANISM: Unknown
<220> FEATURE:
<223> OTHER INFORMATION: Oligonucleotide

<400> SEQUENCE: 366
aacaagacgt ccagaactag a 21

<210> SEQ ID NO 367
<211> LENGTH: 21
<212> TYPE: DNA
<213> ORGANISM: Unknown
<220> FEATURE:
<223> OTHER INFORMATION: Oligonucleotide

<400> SEQUENCE: 367
aagacgtcca gaactagaag c 21

<210> SEQ ID NO 368
<211> LENGTH: 21
<212> TYPE: DNA
<213> ORGANISM: Unknown

<220> FEATURE:
<223> OTHER INFORMATION: Oligonucleotide

<400> SEQUENCE: 368
aaatggaaga agttcgacaa c 21

<210> SEQ ID NO 369
<211> LENGTH: 21
<212> TYPE: DNA
<213> ORGANISM: Unknown
<220> FEATURE:
<223> OTHER INFORMATION: Oligonucleotide

<400> SEQUENCE: 369
aactagaagc tggtacaaat g 21

<210> SEQ ID NO 370
<211> LENGTH: 21
<212> TYPE: DNA
<213> ORGANISM: Unknown
<220> FEATURE:
<223> OTHER INFORMATION: Oligonucleotide

<400> SEQUENCE: 370
aatggaagaa gttcgacaac a 21

<210> SEQ ID NO 371
<211> LENGTH: 21
<212> TYPE: DNA
<213> ORGANISM: Unknown
<220> FEATURE:
<223> OTHER INFORMATION: Oligonucleotide

<400> SEQUENCE: 371
aagctggtac aaatggaaga a 21

<210> SEQ ID NO 372
<211> LENGTH: 21
<212> TYPE: DNA
<213> ORGANISM: Unknown
<220> FEATURE:
<223> OTHER INFORMATION: Oligonucleotide

<400> SEQUENCE: 372
aacaagtccc tttgtaaaac c 21

<210> SEQ ID NO 373
<211> LENGTH: 21
<212> TYPE: DNA
<213> ORGANISM: Unknown
<220> FEATURE:
<223> OTHER INFORMATION: Oligonucleotide

<400> SEQUENCE: 373
aagaagttcg acaacaagtc c 21

<210> SEQ ID NO 374
<211> LENGTH: 21
<212> TYPE: DNA
<213> ORGANISM: Unknown
<220> FEATURE:
<223> OTHER INFORMATION: Oligonucleotide

<400> SEQUENCE: 374
aagttcgaca acaagtccct t 21

<210> SEQ ID NO 375
<211> LENGTH: 21
<212> TYPE: DNA
<213> ORGANISM: Unknown
<220> FEATURE:
<223> OTHER INFORMATION: Oligonucleotide

<400> SEQUENCE: 375
aaaaccaaat ccaggttcta g 21

<210> SEQ ID NO 376
<211> LENGTH: 21
<212> TYPE: DNA
<213> ORGANISM: Unknown
<220> FEATURE:
<223> OTHER INFORMATION: Oligonucleotide

<400> SEQUENCE: 376
aaaccaaatc caggttctag c 21

<210> SEQ ID NO 377
<211> LENGTH: 21
<212> TYPE: DNA
<213> ORGANISM: Unknown
<220> FEATURE:
<223> OTHER INFORMATION: Oligonucleotide

<400> SEQUENCE: 377
aaccaaatcc aggttctagc a 21

<210> SEQ ID NO 378
<211> LENGTH: 21
<212> TYPE: DNA
<213> ORGANISM: Unknown
<220> FEATURE:
<223> OTHER INFORMATION: Oligonucleotide

<400> SEQUENCE: 378
aaatccaggt tctagcacag a 21

<210> SEQ ID NO 379
<211> LENGTH: 21
<212> TYPE: DNA
<213> ORGANISM: Unknown
<220> FEATURE:
<223> OTHER INFORMATION: Oligonucleotide

<400> SEQUENCE: 379
aatccaggtt ctagcacaga c 21

<210> SEQ ID NO 380
<211> LENGTH: 21
<212> TYPE: DNA
<213> ORGANISM: Unknown
<220> FEATURE:
<223> OTHER INFORMATION: Oligonucleotide

<400> SEQUENCE: 380
aacaacatcc tcggttccga a 21

<210> SEQ ID NO 381
<211> LENGTH: 21
<212> TYPE: DNA
<213> ORGANISM: Unknown
<220> FEATURE:
<223> OTHER INFORMATION: Oligonucleotide

<400> SEQUENCE: 381
aacatcctcg gttccgaagt g 21

<210> SEQ ID NO 382
<211> LENGTH: 21
<212> TYPE: DNA
<213> ORGANISM: Unknown
<220> FEATURE:
<223> OTHER INFORMATION: Oligonucleotide

<400> SEQUENCE: 382
aagtggcctt atttgcaggg a 21

<210> SEQ ID NO 383
<211> LENGTH: 21
<212> TYPE: RNA
<213> ORGANISM: Unknown
<220> FEATURE:
<223> OTHER INFORMATION: Oligonucleotide

<400> SEQUENCE: 383
gcagacagau gcacuauuau u 21

<210> SEQ ID NO 384
<211> LENGTH: 21
<212> TYPE: RNA
<213> ORGANISM: Unknown
<220> FEATURE:
<223> OTHER INFORMATION: Oligonucleotide

<400> SEQUENCE: 384
cugcgauuuc caaaucgauu u 21

<210> SEQ ID NO 385
<211> LENGTH: 21
<212> TYPE: RNA
<213> ORGANISM: Unknown
<220> FEATURE:
<223> OTHER INFORMATION: Oligonucleotide

<400> SEQUENCE: 385
ggacugguac uauacccacu u 21

<210> SEQ ID NO 386
<211> LENGTH: 570
<212> TYPE: PRT
<213> ORGANISM: Unknown
<220> FEATURE:
<223> OTHER INFORMATION: Recombinant B4ECv3 protein

<400> SEQUENCE: 386

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
```

```
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525
```

```
Asp Glu Ser Glu Gly Trp Arg Glu Gln Gly Ser Lys Arg Ala Ile Leu
    530                 535                 540

Gln Ile Glu Gly Lys Pro Ile Pro Asn Pro Leu Leu Gly Leu Asp Ser
545                 550                 555                 560

Thr Arg Thr Gly His His His His His His
                565                 570
```

<210> SEQ ID NO 387
<211> LENGTH: 555
<212> TYPE: PRT
<213> ORGANISM: Unknown
<220> FEATURE:
<223> OTHER INFORMATION: Recombinant B4ECv3NT protein

<400> SEQUENCE: 387

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
```

```
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
    530                 535                 540

Gln Ile Ser Ser Thr Val Ala Ala Ala Arg Val
545                 550                 555


<210> SEQ ID NO 388
<211> LENGTH: 233
<212> TYPE: PRT
<213> ORGANISM: Unknown
<220> FEATURE:
<223> OTHER INFORMATION: Recombinant B2EC protein

<400> SEQUENCE: 388

Met Ala Val Arg Arg Asp Ser Val Trp Lys Tyr Cys Trp Gly Val Leu
 1               5                  10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140
```

```
Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Gly Ser His His His His His His
225                 230


<210> SEQ ID NO 389
<211> LENGTH: 771
<212> TYPE: PRT
<213> ORGANISM: Unknown
<220> FEATURE:
<223> OTHER INFORMATION: Recombinant B4ECv3-FC protein

<400> SEQUENCE: 389

Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270
```

-continued

```
Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Asp Pro Glu Pro Lys Ser Cys
    530                 535                 540

Asp Lys Thr His Thr Cys Pro Pro Cys Pro Ala Pro Glu Leu Leu Gly
545                 550                 555                 560

Gly Pro Ser Val Phe Leu Phe Pro Pro Lys Pro Lys Asp Thr Leu Met
                565                 570                 575

Ile Ser Arg Thr Pro Glu Val Thr Cys Val Val Val Asp Val Ser His
            580                 585                 590

Glu Asp Pro Glu Val Lys Phe Asn Trp Tyr Val Asp Gly Val Glu Val
        595                 600                 605

His Asn Ala Lys Thr Lys Pro Arg Glu Glu Gln Tyr Asn Ser Thr Tyr
    610                 615                 620

Arg Val Val Ser Val Leu Thr Val Leu His Gln Asp Trp Leu Asn Gly
625                 630                 635                 640

Lys Glu Tyr Lys Cys Lys Val Ser Asn Lys Ala Leu Pro Ala Pro Ile
                645                 650                 655

Glu Lys Thr Ile Ser Lys Ala Lys Gly Gln Pro Arg Glu Pro Gln Val
            660                 665                 670

Tyr Thr Leu Pro Pro Ser Arg Asp Glu Leu Thr Lys Asn Gln Val Ser
        675                 680                 685

Leu Thr Cys Leu Val Lys Gly Phe Tyr Pro Ser Asp Ile Ala Val Glu
    690                 695                 700
```

```
Trp Glu Ser Asn Gly Gln Pro Glu Asn Asn Tyr Lys Thr Thr Pro Pro
705                 710                 715                 720

Val Leu Asp Ser Asp Gly Ser Phe Phe Leu Tyr Ser Lys Leu Thr Val
                725                 730                 735

Asp Lys Ser Arg Trp Gln Gln Gly Asn Val Phe Ser Cys Ser Val Met
            740                 745                 750

His Glu Ala Leu His Asn His Tyr Thr Gln Lys Ser Leu Ser Leu Ser
        755                 760                 765

Pro Gly Lys
    770


<210> SEQ ID NO 390
<211> LENGTH: 459
<212> TYPE: PRT
<213> ORGANISM: Unknown
<220> FEATURE:
<223> OTHER INFORMATION: Recombinant B2EC-FC protein

<400> SEQUENCE: 390

Met Ala Val Arg Arg Asp Ser Val Trp Lys Tyr Cys Trp Gly Val Leu
 1               5                  10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Asp Pro Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285
```

-continued

```
Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455
```

```
<210> SEQ ID NO 391
<211> LENGTH: 26000
<212> TYPE: DNA
<213> ORGANISM: Homo sapiens

<400> SEQUENCE: 391

ggggtttcat catgttggcc aggctggtct tgaactcctg acctcaaatg atccgcctgc     60

ctctgcctcc caaaatgctg ggactacagg cgtgagccac cgcgcccgcc acacccacct    120

tttctttacc gttgtttcct cgatttttct ctactcccta gcgcagctta gtgcgcgcct    180

cctctggaca tttttcaggg cttggttgcg cgcacagtag gtccccaaca ctgaatgttt    240

atggggtgac tgtgtgaacg ttcgctgcaa ggctatccaa actgggattg ctccttgagg    300

ccccctgggc ggccgtcaat tctccaaagc ttctactccc ttttccttcc ttttccccca    360

aaacgcagtc cctgcgccca ctagagggtg gtgggcgcat ccaagagcgg catctagagt    420

ccgcagcaag gtcagagcgg gctttgtgtg cgcggtgaac atttacgtgc acgcctgggc    480

ggccctccgt gttgctgctg ggtgtgtgtt ttctctgctc cctggtgcca gccgggttcg    540

ggcctgtccc gggggtccct gggccccagc cccgacatgc tcggtcctgg acagcgcgca    600

ccgccacggc gcacatctgg gcggtcccgg ggttcctcac ccgccgcccc tccccccttct    660

ccaaactttc tctcaacttc ccgacctgct ccactcggtg cccctctccg cttccctcat    720

gaattattca gtagcgtgag ctccaatcag cgcgcccggg gctcactcgc ggagcccccg    780

cgttgggaga gctgccccccg ccccccgcgc gcccctccct cccgggcccg gcgccgcccg    840

gcccagttcc agcgcagctc agcccctgcc cggcccggcc cgcccggctc cgcgccgcag    900

tctccctccc tcccgctccg tccccgctcg ggctcccacc atccccgccc gcgaggagag    960

cactcggccc ggcggcgcga gcagagccac tccagggagg gggggagacc gcgagcggcc   1020

ggctcagccc ccgccacccg gggcgggacc ccgaggcccc ggagggaccc caactccagc   1080

cacgtcttgc tgcgcgcccg cccggcgcgg ccactgccag cacgctccgg gcccgccgcc   1140

cgcgcgcgcg gcacagacgc ggggccacac ttggcgccgc cgcccggtgc cccgcacgct   1200
```

cgcatgggcc cgcgctgagg gccccgacga ggagtcccgc gcggagtatc ggcgtccacc 1260
cgcccaggga gagtcagacc tgggggggcg agggcccccc aaactcagtt cggatcctac 1320
ccgagtgagg cggcgccatg gagctccggg tgctgctctg ctgggcttcg ttggccgcag 1380
ctttggaagg tgagtttcct tgcggggggg ggcgcacccc gtcactcctg ggacctcccc 1440
cccaacatct gggcctcgga gtggaggggc cggcctctga ctacccctac ccgggcactg 1500
cagtcccaaa cacttcggac cgatagtgct ggaacgggag gggggcgggg aagaggcgcc 1560
cgacgggtag tggagttttc ttttgtttgg gaaagagatg gagtctggct acgacccggg 1620
acattcccct gcccgggctc cccgaactct cactgctgat tacatacgcc cctggctgcc 1680
tttcctttcc tccctacccc actattcaaa actatctgca aagtttctgt cccagtccca 1740
cctcccgccg tacatgaggg aaggtttctg gagaagcaac agcagacaag gcacaacttt 1800
tcgtgctagg ccctaaaacg acccccagcg ccaattcctt agcgatcaca ccttgatcct 1860
ccagttccac actcctgcaa caggatggcc tcctttgcat tcacacagca aacccccaaa 1920
ccgctctccc gcccactgct cctgcccctg gtatagggtg gctccttggt ttctacaggc 1980
tgcaccccat ccctttaaat gcggtctaga ccccggcccc aggtgagtcc cgggcttccc 2040
ttgagaccta ggagcgggta gaaactgacc tacacagccc ccaggtagaa actgacctac 2100
acagccccca catcgcccta actaacccag tctatctccc acctcctggt ctctccaagc 2160
atttctttgg ccatggatcg ctgtccctcc tggtccccta aagggggagc caagagccct 2220
agaaactctc ctgtgtccct aatgtccttt cagtgagctg ccaacacccc cctttctctg 2280
tctggtatga aagtggttat ggggcggtag gctatgaggg actcccaaag ggaaggattc 2340
agcggcgtta gaaaaaccct ctccccctgg ctgggcagga ctgccctggg ctggggatca 2400
aaggctaggt gtggggttgg gagtgagggg aggcttgccc agctcagaga acggagaagg 2460
gggaacaaaa accatgaacg aggggaagag gaaggccaaa ggggtggaaa aaccacgagg 2520
acgaggtgtg gtgagaagga aagacgcaaa gaggaaatgg tgattgtgac acctattacc 2580
tgagtgtttc caagcaccag gcctgtgctg agcgccttac aaatattaat ttcacccatc 2640
cagcaacgct aagggtggtg ctattattgc cccccatttt cagatgagga ggctggggct 2700
tagttaaggt taagtagttt atccaaggcc ctgtgccgcg aggaacagcg agaagtggag 2760
gccgaaagcg aaggagagat agtgactgtc agaaagagaa acggaggtgg acagagagtg 2820
gaggagagat aggtgagaga catgcgaact gacagatcaa agcgtggctg cagctgagct 2880
gggacgcaga aagggagcct gcgcttgctc tgggctgcgg acagcccgag gcagagacag 2940
tgtgtaaatt ggagacagga aaacactatc ccggctggaa caatggaggg tggagacggc 3000
agcctctatc cacccccttc ccagaacccg ggcatcctgt ccccagtgag cagggctgtc 3060
tcttgccacc catggggacc ttgcgcctct cacctcaggc tggctggctt cccatctgac 3120
ccctagctgg aggacatcat ttggtcccca ggaagaggct gcctcaccca ccctctttct 3180
cttctctcct gcagctccca tggggtggga gccaggtgtt ctggctcccc tctccaccct 3240
tcccagcgcc caatgccccc cacattgccg gcccccgagg ggattcctgt accctccctc 3300
ctccactctc cactgccagg ggctgtgcag tttttcctaa tccccccccct tcctccagtg 3360
cctgtcccct cccccgatga tccgagccaa gccaggtgtg ttcacccctc ccattcatac 3420
cgccccccag aatctcctcc cctctgcctt cccataacca aatccagatg tgaggcctcg 3480
gcgggagcct gggaacccta gcatcccgac ctccagtgct tcctgatcag ggcactcgtg 3540
gggagggagg tactgggatg ggggccaggg ctatgcccca ggcacggagc gctcccttca 3600
aggagggaag gacggggtgt ttggtctgaa agcagagagg ggtcttggac agggaatgaa 3660
attgtggggt agagaggctg attctgggac ttaggggagg aaacgtggag gctgagacaa 3720
gaggttcccc tcccacacca gcagcctctg ctcgtggggg tcaggaccag ggcgcagctc 3780
tcattttaac cctttctgag ctgccgcccc ttctccccgt acattttgat ctccctccct 3840
cctccaggga ggcctagatc tggggtatcc caagggagcc ccatgcctac cagatgttgg 3900
gggtggggtt ggcacttagc agaagaggcc agaaatcagg cgggtgcaga gggcagggct 3960
tgctcccctc ttggcccccc aactcctcta gctcagagct aagaggatcc acctgcctcg 4020
gttcccaggg atctggtctt cctgacctcc ctcccccacc ccaggcactg actctgtctc 4080
tctgtctgtc tcagagaccc tgctgaacac aaaattggaa actgctgatc tgaagtgggt 4140
gacattccct caggtggacg ggcaggtgag agctgcaccc aggagctgga gctctggagg 4200
gaaactgagg gaggagaggg cgcctgtgcc gcctgctttc tgtgtgccac tcctctcccc 4260
tgtcccccca gatgacagca gccccagcag tgtcgtctga gcccttctca gaggcgccct 4320
cctcgcagta ccagcagccc ccctttctca gtccctctca ctttatagga ttcaccccat 4380
gcagccctct ccctggcggc tccccagccc ccttgctgac ctccttctct gcacagtggg 4440
aggaactgag cggcctggat gaggaacagc acagcgtgcg cacctacgaa gtgtgtgacg 4500
tgcagcgtgc cccgggccag gcccactggc ttcgcacagg ttgggtccca cggcggggcg 4560
ccgtccacgt gtacgccacg ctgcgcttca ccatgctcga gtgcctgtcc ctgcctcggg 4620
ctgggcgctc ctgcaaggag accttcaccg tcttctacta tgagagcgat gcggacacgg 4680
ccacggccct cacgccagcc tggatggaga accccctacat caaggtacct gggtgccccc 4740
agggctcagc cacagccaag gtgggattcc agccagcagg cccgtggcct ggagggcagc 4800
cgatgtagtt gcgaggcctc tggcccgcgc gctgggggct ggaagcagga ggcttaggtc 4860
tggggaggga agggggtgat cttctgggcg gaggagcaga atatacgggg gctgcctggc 4920
ccggccccca gggaggccca agggtcaggc ttctcctcca gtcacctcaa ccaccctacc 4980
ccactgtgct ccagccacac tgagtttctc ccattccctg actgcacctg gctggtttcc 5040
agctcaagac tttgcagcgg tgatgtctcc acctgggggc ctctctgcct ctcacacccc 5100
tacttgtctt cggagttcca gctcccgaga tcttgcctgt gccaccttgg ctgactctct 5160
cctccctaca atcctgcata cctctgtcca cctgcctgtc tcggcactca ttttacttta 5220
tttatttttc ttttatatct atatttttaa agcggggtct tctacgttac ccaggctggt 5280
ctctaactcc tgggctcaag agatttctcc cacctcggcc tcctaaagtg ctgggattat 5340
aggcatgagg cactacgccc ggcctcatgg tactttataa cttccccagg attcattcat 5400
cgctgtctcc ttgactctga ggtcaaggcc tggcatggcg tcagtgtcag taaatgtttg 5460
tagaacgagt gaataaaaag gggagaggt gcaggccaga ggccgggcat atcgcaggag 5520
ctttgcaagg ctgaatggac agtgtggggg cctgcagaaa gtgtgccctg ggaaggtgg 5580 agggaagatt ctggaacggg aaccaaggag gtccgggagg gtgagctggg aagaacacaa 5640
cagtccgctg ggtcctcagg gagtggggac agcagcggtg tgcctccccc ccgccggcag 5700
gtggacacgg tggccgcgga gcatctcacc cggaagcgcc ctggggccga ggccaccggg 5760
aaggtgaatg tcaagacgct gcgtctggga ccgctcagca aggctggctt ctacctggcc 5820
ttccaggacc agggtgcctg catggccctg ctatccctgc acctcttcta caaaaagtgc 5880
gcccagctga ctgtgaacct gactcgattc ccggagactg tgcctcggga gctggttgtg 5940
cccgtggccg gtagctgcgt ggtggatgcc gtccccgccc ctggccccag ccccagcctc 6000

```
tactgccgtg aggatggcca gtgggccgaa cagccggtca cgggctgcag ctgtgctccg   6060
gggttcgagg cagctgaggg gaacaccaag tgccgaggtg agagctggag cttcccctgc   6120
gactgctgct catccggggg agagtcctga actccactca ggacccactt cttaagtttc   6180
cattttgtat agttagatgt tgaaatggag gcttgctctg tcacccaggc tggagtgcag   6240
tggcacaatc tctgctcaac tgcaaccttt gcctcccggg tccctgttca agcagttctc   6300
ctgcctcagc ctcgtgagta gctgggacta caggcacacg ccaccacgcc cggctaattt   6360
ttgtatttta gtagagacgg ggtttcgcca tgttggccag gctggtctcg aactcctgac   6420
ctgaagtgat ttgcccgcct cggcctccca aagtgctggg attacaggcg tgcgtcacca   6480
cacccagctg gaaaaaaaaa agactttatt ttcacctgaa attcattaat ttccacttga   6540
aattccacct gcagttgtag caggacctga cacttgggcc ccatggaaat cacaggtatt   6600
gcctgacaca gtggttcatg cccatagtgc cagcactttg agatgccaag gtgggaggat   6660
cacttgagcc caggagttcg agatcagcct gggtgacaga gcaagacccc gtctctaaaa   6720
aaaatttttt tttttttttc aagacagagt cttgctctgt cgcccaggct ggagtgcagt   6780
ggtgcgatct cggctcactg caagctccgc ctcccaagtt aacaccattc tcctgcctca   6840
gcctcccgag tagctgggac tacaggcccc gccaccacgc ccggctaatt tcttgtattt   6900
ttagtagaga tggagtttca ccgtgttagc caggatggtc tcgatctcct gacctcatga   6960
tctgcccgcc ttggcctccc aaagtgctgg gattacaggt gtgagccacc acacccggat   7020
tacaaaaact ttttagataa ttatctgggc gacctgcctg accaacatgg agaaaccctg   7080
tctctactaa aaatacaaaa ttagccggac atggtggcgc atgcctgtaa tcccagctac   7140
ttgggaggct gaggcaggag aatcatttga acccaggaag cagaggttgc ggtaagccga   7200
gatcatgcca ctgcactccg gtctgggagt gcactccaac aagaaggagt ttcgctcttt   7260
ttgcccaggc tggagtgcag tggtgggatc tcagctcacc gcaacctcca cctcccgggt   7320
tcaggcgatt ctcctgcctc agcctcccaa ggagtagctg ggattatagg tatgcatcgt   7380
cacacccggc tacttttgta tttttagtag aggcaggttt ccaccatgtt ggccaggctg   7440
gtcttgaact caagtgatct gccctctttg gcctccttct caggaaaaaa aaaaaatcac   7500
aggtatttac aggccattcc aagtgccaaa agattgtttt tgctcatggt gacttcagta   7560
tcacagatgt taggagactt gctgctatat gttaagaaag aagcacaaat gttgctgtag   7620
cccaaacttt tttcctcatg tttcattgca tttcagctta attggtttcc ctggtattcc   7680
tatgtatttt gtggagtgct tttaaaatca taagttggag tagaggtctt tctgtgggct   7740
tcaccagact gccgagatca gggtcgaaac aggtgaggac cccttctctg gagagagtct   7800
cctttctcct ctaagaggaa aggttttgag atcttttgtc cattttccca ccttagcact   7860
tcatcagcct taaaagaagc tggaattttt tttttttttt ttggagatgg gatctcgata   7920
tgttgcccag gctggtcttg aaccccttgg ctcaagcgat cctccagcct cagcctccca   7980
aagtgctggg attcgaggca tgagccaccg agcccaccgt gcagatggat gtttttgtgc   8040
atgcttttga tgaatgcttt ctctctctca gcctgtgccc agggcacctt caagcccctg   8100
tcaggagaag ggtcctgcca gccatgccca gccaatagcc actctaacac cattggatca   8160
gccgtctgcc agtgccgcgt cgggtacttc cgggcacgca cagacccccg gggtgcaccc   8220
tgcaccagta agtgaccagc acccaggtgc agttcactgg ggaggggtca cagacctctg   8280
aggtggaccc tcacatggcc cccatcctcc ctgggcttct tccctttgtc cctggcatgc   8340
ttgtccctag cccggaggaa catgtggagc ccactgtctc caaggcaaga gtccagcatg   8400
```

gctgctggtg cctccattgc cctctcccca ccaccgcaga gcaggtcggc ctctgcctga 8460
ctccctggtc tcctgcagcc cctccttcgg ctccgcggag cgtggtttcc cgcctgaacg 8520
gctcctccct gcacctggaa tggagtgccc ccctggagtc tggtggccga gaggacctca 8580
cctacgccct ccgctgccgg gagtgccgac ccggaggctc ctgtgcgccc tgcgggggag 8640
acctgacttt tgaccccggc ccccgggacc tggtggagcc ctgggtggtg gttcgagggc 8700
tacgtcctga cttcacctat acctttgagg tcactgcatt gaacggggta tcctccttag 8760
ccacggggcc cgtcccattt gagcctgtca atgtcaccac tgaccgagag ggtgagactt 8820
gggggctggg gcggctggtg gtctggcggg agagatgtca ctgagggcct gaaggggaga 8880
ggcaggggct gtgaagttgg gtaccccgga agtgtgaggg gctaaggctt tgggggcaag 8940
aggcagaaag agggcaatgg ctgggcgcag tggctcacgc ctgtaatccc agcactttca 9000
gaggctgaga caggcggatc acttgagccc tggagttcaa gaccagcctg ggtaacatag 9060
gaagatctct ctacaaaaaa taaaaatatt agccaggcga ggtggtgcat gcctgtggtc 9120
ccagctactc aagaggctga ggcaggagga ttgcttgagc ccaggagtcg gaggctgcag 9180
tgagctatga tcgcaccgct gcatgccagc ctgggtgaca gagcagtgtg agatcctctc 9240
tcaaaataaa tgaataagaa agagagggtg aggagctcgt aaagctgggc tggagagtta 9300
agtacaggaa ggcccccagt gggactgggg ccagagagaa tcagaaggaa ttctcgaaac 9360
agccaggggg aaattgagac aagtgtagcc agcagaggaa gtgttggaaa agataaggga 9420
catggccagg ctgatcacaa ggtcaggagt tcaagactag cctggccaac gtggtgaaac 9480
cccatgtcta ctaaaaataa aaaaattagc caggcatggt ggtgggcacc tgtaatccac 9540
ttgggaagca accagaagaa ttgcttgaac ccaggaggcg gaggttgcag taagctgaga 9600
ctgcgccact gcactccagc ctgggtgata gagcacgact ccgtctcgaa aaaaaaaatt 9660
tttttaagt taagggacag agctaccatg cacaagggtt ccctgtgtct ctgcctctca 9720
cagtacctcc tgcagtgtct gacatccggg tgacgcggtc ctcacccagc agcttgagcc 9780
tggcctgggc tgttccccgg gcacccagtg gggctgtgct ggactacgag gtcaaatacc 9840
atgagaaggt aaggccatcc cccagccctg gggtgggtgg gcaatgggtt gtgctctcct 9900
ggctgggaca cctgggttgc aggcacctgg caggcatttg aattccagct ctgccatgga 9960
ttccctgggc agccttgggt aagccccttg gcctgtctga gcctcagact cttcatctat 10020
aaaatagtta ctgtaatagt taccagcagc tggacacagt ggctgaggtt gggtgcggtg 10080
gctcacgcct gtaataccaa gcactttggg aggctgaggc gggcagaatg cttgagccta 10140
ggagtttgag accagcctgg gcaacatggt gaaacttcat ctctataaaa aacttaaaat 10200
gggccgggcg cggtagctta cgcctgtaat cccagcactt tgggaggccg aggtgggcgg 10260
atcacaaggt caggagtatc gagaccatcc tggctaacac ggtgaaaccc catctctact 10320
aaaaatacaa aaaattagcc aggcgcggtg gcaggcgcct gtagtcccag ctactcggga 10380
ggctgaggca ggagaatggc gtgaacccag gaggcggagc ttgcagtgag ccgagatagc 10440
gccactgcag tccggcctgg gcgaaagaac aagactctgt ctccaaaaaa aaaaaaaaaa 10500
aaaaaaaacg caaaaaatac ttaaaatgaa aaaaattaga ctgggcacag tggctcatgc 10560
ctgtaatccc ggcactttgg gaggccgagg tgggtagaac acctggggtg aagagttcga 10620
gaccagcctg gccaacaagg tgaaatcccc gtctctacta caaatagcaa aatcagctga 10680
gtgtgttggc gggcccctgt aatcccagct actcaggagg ctgagacagg agaatcactg 10740
gaacccaagt gattctcgac ttgaggtcga ggctgcagtg agtcgtgttt gcaccattgc 10800
attccagcct gagaaagtga gaccttgtct taaaaaaaag gaatgatatt atgaatacag 10860
cacatggctt gcatgcgtaa gttctcccaa aggcctcacc agttgcaagg caggctagtg 10920
atgggagtgg agggcgaggg aaggaggcag gaagagcaac aggaacttgg gttcccgggt 10980
gacggccacc ccactacctc tcccggacag ggcgccgagg gtcccagcag cgtgcggttc 11040
ctgaagacgt cagaaaaccg ggcagagctg cgggggctga agcggggagc cagctacctg 11100
gtgcaggtac gggcgcgctc tgaggccggc tacgggccct tcggccagga acatcacagc 11160
cagacccaac tggatggtga gcctggggaa gggggtgagg gtgggggttg gaaagacccc 11220
caaagttcct gggaagaccc caggtctcca aagtcccatc atcttttttt tttttttttt 11280
tttttgagat ggagtcttgc tctgtccctc aggctggagt gcagtggcac catctccgct 11340
cactgcaacc tccgcctccc ggattcaagc cattctcctg cctcagcctc ccgagtagct 11400
gggattacag gcgcctgcca ccgcgcctgg ccgatttttt gtatttttag tagagacggg 11460
gcttcaccgc gttggccagg ctggtctcga actcctgacc ttgtgattcg cccgcctcgg 11520
cctcccgaag tgctgggatt acaggcatga gccactgcac ccggtcaaag tcctatcttc 11580
atgtccttct tcctgtggat cacatggcat gccctagaga ggagagaacg taagatgtcg 11640
aaaccaaaac caacagctga gttttgtgaa gtctggcctg cttcactctg tacccccagg 11700
ctggagcgca gttgctcgat caaagctcac tgcacagcca ggcacagtgg ctcaccctgt 11760
aaccccagca ctttgggagg ctgaagcagg aggatcactt gaggtcagga gttcgagacc 11820
agtctgacca gcatggtgaa accgcgtctc tactaaaaat atagaagtta gctgagcgtg 11880
gtggtgcaca cctgtaatcc cagctactcg ggaggctgag gcaggagaat cgcttgaacc 11940
tgggaggtgg aggttgcagt gagctgagat tgtgccagtg cactccagcc tgggcaacag 12000
agcaagactc tgtctcaaaa aaaaaaaagc tcaccgcagg cttgactttt agcaacaacc 12060
tgacccctga gctccccatt ccccatccaa caaaatggga atatcatgaa gcttcctgca 12120
gggctttgag gattggaggt aacaggttat ttttaatatg ctaggccagt ggctttcttt 12180
tttctttcac attttttttt ttgagacgga gtctcactct gttgcccagg ctggagtgcg 12240
gtggcgcgat ctcagctcac cgcaagctcc acctcctggt ctcgatctgc tgacctcctg 12300
atccacccgc ctcggcttcc cgaaatgctg ggactgctgg cgtgagccac cacgcccggc 12360
ctaacttttt cttttttta agagacacgg tcttttttat cacccaggct ggagtgcggt 12420
ggcaccatca tagctcattg cagcctacaa ctcccgagct caaccaatcc ttccacctta 12480
gcctcccaag tagctggggc tataggcatg tgctaccgtg ctcaactaaa ttttttttta 12540
tgttttgttg agacagtttc cctatgttgc ccaggctggt ctcaaattcc tgacctcgag 12600
caatcctccc gcatcggcct cccaaagtgc tgggattaca ggcatgagcc gccacaccca 12660
gcattggacc agtggctttc taaaccttgt aattttctgt aatagcttta ctgaaataca 12720
gttcccctgc catacaattt gcctgttcaa agtgtacaat cgatgacttt tgatacattc 12780
acagaattgt gcagtcacca ccacaagtaa ttttgggaca ttttcagcac cctcaaaaga 12840
gaccctatag cccttagcca tcacccccca cccagatctt tctgttgcct tagtccctgg 12900
caagcactaa cccactttct gtcttgaaat cttccagtgt ggtcttttgt gactgttcac 12960
cgagcagaat gttttcaagg tttatgtatg ttgtagtata tatccgtggg ttttttttggt 13020
tgtggtttgt tttttgtttg ttttggaaac agggtctcgc tctgtcaccc aggctggagt 13080
gcagtggttc aattacagct cactgcagcc tcaacctccc aggctcaagt gatcctccca 13140
cctcagcctc ccaagcagct gggactgtag gcatgagcca ccatgcccag ctaatttttt 13200
ttggtatttt ttgtaaagac agggtttcac catgtttccc aggctggtct cgaactcctg 13260
agctcaggca atccacccac ctcagcctcc caaagtgctg tgattacagg catgagccac 13320
tggacctggc ctgttttttg tttttgtttt gaacacacga ttttgctttg tcacccaggc 13380
tggaatgtaa tggtctgatc atagtgcatt gcagcctcaa actcctgggc tcaagcgatc 13440
ctcctacctc agcctcctga gtatctggga ccacacgtgc tcaccaccat gcttggctaa 13500
ttattattat tttttgatag agacggggtc ttgctatgtt tcccaggctg gtcttgaaca 13560
cctggcctca cacaatcctc ccacctcagt atctcagagt gctgggatta caggcatgag 13620
ccactgctcc tggccaatat ttcatttctt tttatggaga cgtaataatc agttgtatgg 13680
aaatagctga ttttgttttt tattgtatct tttggtgaac atttcaattg tatcgacttt 13740
ttggataaaa acctgaaaat gtttcacctt tagaacgttt cattgaatgg agattttttt 13800
gtggactctg gtatttatac tagaaccaaa tcaaaaccac tctggcggct gggcatgcct 13860
aggctggttt gagactagcc tgtccaacct ggtgaaagcc catctctact aaaaatacac 13920
aaattagccg agcatggtgg tacacacctg taatcccagc tactcaggag gctgaggcag 13980
gagaatcgca gaacccggga ggcggagatt gcagtgagct gagattgcgc cactgcactc 14040
cagcctgggc gacagagtga gactgcgtct caaaaaaaca aacaaaaaat tactctggca 14100
gtaagaaaag atttcgaaac ttcctccctt gccctgaggt acttcagagg agcctgctgg 14160
cccctggggg agagtttgaa acccactgtt tgttccctga ccttgcctgc ttgtgtcctc 14220
tccctccacc tgtcccctgt actggggacc tgttctcagg agatcacagt tcattgctca 14280
aagccggggc tggggcctcc tacaggacca tcagtttctc ctgatcagca gcctttcctt 14340
ccgcagagag cgagggctgg cgggagcagc tggccctgat tgcgggcacg gcagtcgtgg 14400
gtgtggtcct ggtcctggtg gtcattgtgg tcgcagttct ctgcctcagg taagggctct 14460
gacacccaga ggcccctgga agccctcagt tgatggccac ctgcctgggt gctacaggac 14520
aagcctttct ggctgtcccc agcctctttt tacttgaaat cttctccaat ccctgctcct 14580
tcctttggtg tgtgtgcctc ataaagatgt gtgactcagt ttaccttttg ttcctttccc 14640
atcggctaca ggaagcagag caatgggaga gaagcagaat attcggacaa acacggacag 14700
tatctcatcg gacatggtgg gttgccctaa tttgatggga ataggggctt ggggccgggt 14760
gtggtggctc ctatctataa tcccagcact ttgggaggca gaggtgggca gatcacttga 14820
ggtcaggagt tcgagaccag cctggccaac atgttgaaac tccatctcta taaaaaatac 14880
atcagtcagc caggcatggt ggtgggcacc tgtaatccca gctactcagg aggctgaggc 14940
agaagaatca ttttaacccg ggaggcggag attgcagtga gccaagatcg cgccactgcg 15000
ctccaggcct gggtgacaga gcgagactcc atctcaggaa aaaaaaaaaa aaaaaaaaaa 15060
accacggaga caggggtttg gggctaaaag ctatgagccg agcctccgag tccagtggga 15120
gttaattccc agctgacggg gccctgcctg atttctcagg tactaaggtc tacatcgacc 15180
ccttcactta tgaagaccct aatgaggctg tgagggaatt tgcaaaagag atcgatgtct 15240
cctacgtcaa gattgaagag gtgattggtg caggtgagag ccgaaggctg cccgggcacc 15300
tgggaacgaa gcgggggtgg gcagggccac actggagcgg gagagctgat gacctctgcg 15360
tccttgtttg aaggtgagtt tggcgaggtg tgccgggggc ggctcaaggc cccagggaag 15420
aaggagagct gtgtggcaat caagaccctg aagggtggct acacggagcg gcagcggcgt 15480
gagtttctga gcgaggcctc catcatgggc cagttcgagc accccaatat catccgcctg 15540
gagggcgtgg tcaccaacag catgcccgtc atgattctca cagagttcat ggagaacggc 15600
gccctggact ccttcctgcg ggtgagcacc ctccctggct tctgcggcca cccggagttc 15660
ccacttacac ccagaggcca cttgggttaa gaagccagga cagacagtgg gtcccaggtc 15720
acctcctcca gccttttcct cttgggctaa gccctggtcc tctgcctttt ctttttttta 15780
agacagagcc tcgctctgtc gcccaggctg gagtgcagtg gcgcgatctc ggctcattgc 15840
tgtctccacc tccagggttc aagcgattct cctgcctcag tctcccaagt agctggtact 15900
ataggcatgc accaccatgc tgactaattt ttgtattttt agtagacaca gggtttcacc 15960
atgtaggcca ggctggtatc aaactcctga cctcaagtga tctccccacc tcagcctccc 16020
aaagtgctgg tattacaggt gtgaggcacc acgcctggcc agccctctgc ctttaatttt 16080
ccctctggga aaggctgggc tcctgggacc ttcctttccc actgccccat acagctgaag 16140
gttgtcattc cttctttttt tttttaattt tgttttaatt gaattttttt tttttgagat 16200
ggagtttcac tcttgttgcc caggccggag tgcaatggca agatcttggc tcaccgcaac 16260
ctccgcctcc caggttcaag cgattctcct gccttagcct ccccagtagc tgggattata 16320
ggcatgtgcc accacgcttg actaattttg tatttttagt agagacgggg gtttctctgt 16380
gttggtcagg ctggtctcga actcccgacc tcaggtgatc cgcctgcctc ggcctcccaa 16440
agtgctggga ttacagacgt gagccaccgc gcccggccaa tttttttttt ttttttttaa 16500
gacagagtct cactctgtcc tctaggctgg agtgcagtgg tgcattcata gctcactgta 16560
gccttgacct cctgggctca agtgatcctc ccgcctcagc ctcctgagta gctggaacta 16620
cactcatgta ccaccatgct cagcaaattt ttaaaatttt ttgtagagac aggatctcga 16680
taggttgccc aggctggtct gaactcctgg cctcaagcga gcctccctcc tcagcctccc 16740
acagcactgg gattgcaggc atgagccact gtgcctggcc tgtcattcct tcttttgaca 16800
aatatttact gagtgctttc tacgcaccgg tcatcctccc agtccccagg aataaagcta 16860
tacacacggc aaactggatt tctcctcttg gggagcagag ggtctaatgg ggcaggggga 16920
ctgaaaatta gcaagtaaat agacaggctt tttaaaaaag taaacaaatc atttcaaatg 16980
tgaaaaaaag caaacggggt ccttcatgca gatgtggcta gagaggaaag agaactgctt 17040
aatttatttg gtcactttac cagattttac tgactttttt ttttttttta actttattaa 17100
gcttttcttt tttcttgaga tggagtttcc atctgtcacc caggctggag tgcagtggtg 17160
cgttcttggc tcaccgcaac gtccacctcc tgggttcaag tgattctcct gcctcagcct 17220
cctgagtagc ttggaattgc atggcatgca ccaccatacc cagctgatgt ttgtattttt 17280
agtagagaca gggtttcatc atgttgccca ggctggtctt gaactcctgg gctcaagtga 17340
tccacccatc tcggcccctc aaagtgctgg gattacaggc atgagccacc atgcctggcc 17400
taggcatctt tttaaaaaaa tcaaaacatt tttctatgta gcaaaataac attgcattga 17460
acagagttat agcgattccc tagcgtcatt gaatacccag ttgattttca cgtttctcta 17520
gttgttctaa agatgtcctt cactgctgct ttattccaac caggatccag ttcaagaccg 17580
ggctttgtac ctggttatta tatatatttt atttatttat tttagaaaca aggtcttgcc 17640
ctttcgccca gtttagagtg cagtggtgca atcatagctc actgcagcct ccaaactcct 17700
tggctcaggt gatcctcctg cctcagcctc ctgggtagct ggaactacag gtgcacacca 17760
ccacacctgg ctaattttta aattttttac ggagatgggg gtctcgctat gttgcccagg 17820
ctggtctcaa actcctggac tcaagcgatc ctccctcctt aacctctcaa agtgctggga 17880
ttacaggcgt gagccaccac gcctgctgat tattatattt tcgagcctct ctaaatcttg 17940
agcagttcct catgatgaca ctgacacact gaagggttag gtcccttgtc cgcctgaatg 18000
tcttgatttc tggatttatg aaattcttct tatgggatca tttagcttgt ctctctgtat 18060
ttcctgtaag agaagctcta tctgatgtgg ggtttttttg gttttgtttg tttgtttttt 18120
gagatggagt cctgctgtcg cccaggctgg agtgcagtgg cacaatctcg gctcactgca 18180
acctccgcct cctgggttca agagattctt ctgcctcagc ctcctgagta gctgggacta 18240
caggcgagtg ccaccatgcc cagctaattt ttgtattttt agtagagaca gggtttcacc 18300
atattggcca ggatggtctc gaacttctga cctcgtgatc tgcccaccac ctcagcctcc 18360
cacagtgctg ggattacagg catgagccac tatgcccggc taatttttgt atttttagta 18420
gagacagggc ttcgccatgt tggccaggct gatctgaaac ccctggcctc aagccatcca 18480
ccctccttgg cctcccaaag tgctgggatt aaacgcgtga gccaccgtgc ctggtcgaag 18540
agacagaaag ggtcttaaag gttcagtgac acacacctgt aatcccagca ctttgggaag 18600
ctgaggctgg tggatcactc gaggccagga gttagagatc accctgggca acatggtgaa 18660
accccgtctc tacacaaaat acaaaaatgg gcagagcatg atggtgcata tctgtagtcc 18720
cagctactcg ggaggctgag gcgggaggat cacttaagcc tgggagatcg aggctgtagt 18780
gagccatcat tgcactactg cattccagcc tgggcgatcc catctcttaa aaagagagag 18840
agatgggaag accagcacag gtgaaactgg tgaacagagg agagatggta gatgctgcat 18900
tgggcagtgt gacgggaacc cgctggaggg ctttggcagg agagtagttt aagaggatcc 18960
cagctgggca cagtggctca cacttgtgat cccagcactt ggggaggccg gggcaggtgg 19020
atcacttgag gtcaggagtt cgagaccagc ctggccaaca tggtgaaacc ctgtctgtac 19080
taaaaataca aaaaccagcc aggcatggtg gtgcacccct gtaatcccag ctactcagga 19140
gactaagaca ggagaatcgc ttgaactcag gaggcagagg ttgcagtgag ccaagatcac 19200
gccactttac tccagcctgg gcagtagagc gagactccat ctcaaaaaaa taaataaata 19260
aaaagacctc tttgctgggt gctagggagc aagagcagga gctgggagag gcctgcagca 19320
gaagcctgtt gccagcatcc aggccgtggg gtgaagggaa gggtttggat ttgggacatg 19380
tcttggaagc atcaccagca gaacttgctg atggattgga agtggctggt gagggagaaa 19440
agggggtcaa aggaaactct gaggtctata ccctgaccat ctggcaagtg gtggtgttgc 19500
cacaaactga gcggggagta gggcaggtgc aggtctggag gatggattca aaattcagtt 19560
tttggagtct atgtccctgg ttctgtaggg ctgcagatgg tctgccaaat cttagcggaa 19620
cccagaatac gggatttgtt tactgtctgt gacttgttgg tttccctggt gagagcaaac 19680
tctttaaagg tcaaggttgg gcttcagacc ttggtttttg caccgatcat tggtcatact 19740
gcagttcctc actcttctct tgcaaatcca tacacagcta gtccaagaga gctgaacagc 19800
tttgtggttg gatcagcacc aatgtatctc cacctgtaga cgggttgctc aggtgactca 19860
tgcctgtaat cccagcacct tgggaggcca aggtgggaag attgcttgag gccaggagtt 19920
ggagacaagc ctgggaaaca cagtgagacc ccatatctac caaaaaaacc cctttgtttt 19980
aattagccag gtgcagtggt gtgcacctat agtcccagct actaaggagg ctgaggcaga 20040
aggatcattt gagcccagga gtttaaggct gcggtgaacc atgatcgtgc cactgcactc 20100
caacctgggg gaaagaaaga gaccttgtct ctaaaaaaac taaaaaacag aaaagcattt 20160
gttgagtatt tcctgggtat aaagcagtgt accaggttaa atggaaggaa aagttgaaat 20220
aatttttcaa ctcataatcc gattgggaga gactgaatgc ttaccattga agcaggaacc 20280
attgtaagca atgtgttgtg atactgtagc aagagctgag aaaacttggg aaaagagaaa 20340
ggaggaaggc tcacctgagg gagttggggg gcttgcccta caggtgagtt gtgaggtggg 20400

```
tctggaagtg acagatgcag tttaggaagt ggacgggagg ctgggtacgg tgactcaaca  20460
tctgtaatcc cagtgctttg ggagacccag gcggaaggat cgcttcaggc caggagttaa  20520
agaccagcct gggcaacata gtgggaacct atctctacta aaaattaaaa aattatccag  20580
gcataatggc acatgcctat tgttccagct actcaggagg cttgcctgag cccaggaggt  20640
tgaggctgca gtgagctatg atggcaccac tgcactccag cctgggcgac agaacaagac  20700
cctgtctcta aaaaaaaaag atgtggatgg gagggggaac ggtgggtggg ctgtcctcac  20760
caagccccca ccctatctgc tctccagcta aacgacggac agttcacagt catccagctc  20820
gtgggcatgc tgcggggcat cgcctcgggc atgcggtacc ttgccgagat gagctacgtc  20880
caccgagacc tggctgctcg caacatccta gtcaacagca acctcgtctg caaagtgtct  20940
gactttggcc tttcccgatt cctggaggag aactcttccg atcccaccta cacgagctcc  21000
ctggtaatgc tgggggtaat actgggtgtg agcttcttag ggccaggtgg gcagggcagg  21060
ttggaaaggt gggaggctga gggtttggca gccctgctcc agggagagga tacaggagca  21120
ggctgtgggt ggggggacag tcagctccag gaagccgact tccagatgtc taggaaaata  21180
acagttggat aacctgggca acatagcaag accccatctc tacaaaaaaa ttaaaagatt  21240
agccaggcgc agtggcatgc acctgtagtc ccagctactt gggaggttga ggcaggagga  21300
ttgcttaagc ccaggagttg gaggctgcag tgagctatga atgtgccact gtactgcaga  21360
ctgggcgaca gagcaagacc ctgtctcaaa agaacagtgg ccaggtgtgg tggctcacgc  21420
ctgtaaatcc agcactttgg gaggctgagg caggaggatc gcctgaggtc aggagttcga  21480
gaccagcctg gccaacatgg gaaaaccctg tcgctactaa aaatacaaaa ttagctgagg  21540
gtggtggtac acgcctgtaa tccgagctac tcaggaggct gaggtaggag aaccagttga  21600
acccgggagg cggagtttca gtgagccaag atcgcaccac tgcactccaa cctgggcaaa  21660
cagagttgga gagtaggagg cttggggcct gagctagggg gaaaaagcag aggcaggtgg  21720
gggactgggg ggcagtgtgc tgggtctggt gagtccctca gtgagtcccc cagctcacct  21780
tttctccttt ttctgcaggg aggaaagatt cccatccgat ggactgcccc ggaggccatt  21840
gccttccgga agttcacttc cgccagtgat gcctggagtt acgggattgt gatgtgggag  21900
gtgatgtcat ttggggagag gccgtactgg gacatgagca atcaggacgt aagtgtcccg  21960
tggtcctacc aagctttcct cgagtgttct ctcacctggg atttggggtg aagggtgggt  22020
tcccagagag tcatcactgc tgggttcttg agaccatgga gatgacaaaa aggagaattg  22080
atctttgtat caaagagttg agatacaggg ccaggcctag tggctcaagc ctgtaatccc  22140
agcactttgg gaggccaagg tgggcagatc acctaaggtt aggagttcaa gaccagcctg  22200
gccaacatgg tgaaaccccg tctctaaaaa aatacaaaaa attagcccag catgatgggc  22260
gggtgcctgt aatcccagct actcaggagg ctgagacagg ataatcgctt gaacccagga  22320
acagaggttg cagtgagctg agatcacgcc attgctttcc agcctgggca actgagcgag  22380
actctgtctt aataaataaa taaaagagtt gggtacagca tatttgggtc gcagaaggat  22440
gcagagatgg agggcagggt tgagaggtaa catgtctgta tcatagccca agagctgctg  22500
gggccttcag ccacagagag cttcaactcc ggctaggagg attcctggat ctgttatttt  22560
ttggggggct gtggctccta tcctaccatc ttccaagtca ccatttcctg ggcctgttag  22620
catctttgct tttcctggac agcctcaccc agagcttctt cccctctttc caggtgatca  22680
atgccattga acaggactac cggctgcccc cgcccccaga ctgtcccacc tccctccacc  22740
agctcatgct ggactgttgg cagaaagacc ggaatgcccg gccccgcttc ccccaggtgg  22800
```

```
tcagcgccct ggacaagatg atccggaacc ccgccagcct caaaatcgtg gcccgggaga  22860
atggcgggtg aggactgcag agaatgggcc ctccttcccg ctctctgccc ccactccttg  22920
cccagaagtg tccgttcatt ggtgttgggt gggagggcct ctgtccgcct ctgcaaggct  22980
gggttccacc tcctcccccg gacctgggcc tggtactcag cattcctccc catccttgcc  23040
ccctagggcc tcacaccctc tcctggacca gcggcagcct cactactcag cttttggctc  23100
tgtgggcgag tggcttcggg ccatcaaaat gggaagatac gaagaaagtt tcgcagccgc  23160
tggctttggc tccttcgagc tggtcagcca gatctctgct gagtaagcag tggcaggagc  23220
tggagtgggg ctgggagagc ggggcagctg gagtcaggcc cacggggtct ccaggggctt  23280
ttggggtcag cttcgggtgc caatgctgtc ttcttgcact gcgctcatgc catgcctaga  23340
agggccccag aggagcagtc acagccccat ggagctgagg acccaaggac tctttggggc  23400
cagcctgccc gcctcacctc ctcctgccat cacagccctg ggccatcgcg cttccgcctc  23460
tcacttctag ctatctttgt gcatctatct gcattccagg cccggctctc acggtaacaa  23520
tgtgtcaact cgggttctct tttccaacc ataaaaggag aagattgggc taggttttgg  23580
agatcctctt cagcttttat gtgaaatggt tttatgattc cttgcctccc aaaggctgcg  23640
tatccccact tggcctttgt ctgctactcc ccctttctgc cttcccgttc ctctcccaag  23700
atctcctctc accccaggtt gaataacaga aatagaagga atagaaatct gaaggccggg  23760
catggtggct catgcctgta atgccagcac tttgggaggc cgaggtgggc agatcacttg  23820
aggttaggag ttcgagacca ttgtggacaa cttggtgaaa ccttatgtct actaaaaata  23880
caaaaattag ctgggcatgg tggtgcgtgc ctgtaatacc agctactgag gaggctgagg  23940
caggagaatc gcttgaaccc gggaggtgga ggttgcagtg agccgagatc gcaccactgc  24000
actccagcct ggatgacaga gtgaaattcc atctcaaaaa aaaaaaaaaa aaaaaaaaag  24060
aaatgtgaag gccaggtggt ggctcacgcc tgtaatctca gcactttggg aggctcaggt  24120
ggaccgattg cttgagccca ggagtttgag agcagcctgg ccaaaatagc aaaaccccat  24180
ctctacaaaa caaaaacaaa aaaattagct gggcatggtg gtgcgtgcct gtggtcccag  24240
ctactcagga ggctagagcc agagggtctc aggccagtct gcccctgccc cacggggcct  24300
gggcacatcc ctccctaatt cttcccagcc tctctctgac ccagggggcc tcctctccct  24360
tttttcccct tatctcagcc tccagccatc agcaacctcc tcttcctctc cacccagctc  24420
ttcctctccc acttcggcct tttctttctc acactccatt tccctctacg gcaatctgtg  24480
cagcctcttc ccccagtctc attttgcggg cttttctctc ttttctttcc ttccctggca  24540
cccaagccaa aggccctgcc tctggcctcc agccctaccc ccttctgcgg ttgcacagaa  24600
ggatggctgc ccagctctta aaaaaactgc ccgggaactg ttgacatctg ttctccctcc  24660
cccgctggct tttctgattg gcttacaatc ctgaggctag gaccgtctca ggagccaaga  24720
gaggagagcg gccacaggga acctagggtc tcaccaagct ctcctttcct tctgcaggga  24780
cctgctccga atcggagtca ctctggcggg acaccagaag aaaatcttgg ccagtgtcca  24840
gcacatgaag tcccaggcca agccgggaac cccgggtggg acaggaggac cggcccccgca  24900
gtactgacct gcaggaactc cccaccccag ggacaccgcc tccccatttt ccggggcaga  24960
gtggggactc acagaggccc ccagccctgt gccccgctgg attgcacttt gagcccgtgg  25020
ggtgaggagt tggcaatttg gagagacagg atttgggggt tctgccataa taggagggga  25080
aaatcacccc ccagccacct cggggaactc cagaccaagg gtgagggcgc ctttccctca  25140
ggactgggtg tgaccagagg aaaaggaagt gcccaacatc tcccagcctc cccaggtgcc  25200
```

```
ccccctcacct tgatgggtgc gttcccgcag accaaagaga gtgtgactcc cttgccagct  25260
ccagagtggg ggggctgtcc cagggggcaa gaaggggtgt cagggcccag tgacaaaatc  25320
attggggttt gtagtcccaa cttgctgctg tcaccaccaa actcaatcat ttttttccct  25380
tgtaaatgcc cctcccccag ctgctgcctt catattgaag gtttttgagt tttgtttttg  25440
gtcttaattt ttctccccgt tccctttttg tttcttcgtt ttgtttttct accgtccttg  25500
tcataacttt gtgttggagg gaacctgttt cactatggcc tcctttgccc aagttgaaac  25560
aggggcccat catcatgtct gtttccagaa cagtgccttg gtcatcccac atccccggac  25620
cccgcctggg acccccaagc tgtgtcctat gaaggggtgt ggggtgaggt agtgaaaagg  25680
gcggtagttg gtggtggaac ccagaaacgg acgccggtgc ttggaggggt tcttaaatta  25740
tatttaaaaa agtaactttt tgtataaata aaagaaaatg ggacgtgtcc cagctccagg  25800
ggtgatgggg gtgatggact agatttctaa ggagagtggg gctgggtagg gagggctttg  25860
tggctgaccg agaggtgtca gaggtctgga ggctgcaggg ctgtaggggc tggaacttgg  25920
ttatcagccc cagggtatgt ttgaggtggt ggggtggggg ccgagcgaga tgaatcattc  25980
gcagctgctt ctaacgtctc                                              26000
```

<210> SEQ ID NO 392
<211> LENGTH: 4235
<212> TYPE: DNA
<213> ORGANISM: Homo sapiens

<400> SEQUENCE: 392

```
ctcggcccgg cggcgcgagc agagccactc cagggagggg gggagaccgc gagcggccgg     60
ctcagccccc gccacccggg gcgggacccc gaggccccgg agggacccca actccagcca    120
cgtcttgctg cgcgcccgcc cggcgcggcc actgccagca cgctccgggc ccgccgcccg    180
cgcgcgcggc acagacgcgg ggccacactt ggcgccgccg cccggtgccc cgcacgctcg    240
catgggcccg cgctgagggc cccgacgagg agtcccgcgc ggagtatcgg cgtccacccg    300
cccagggaga gtcagacctg ggggggcgag ggccccccaa actcagttcg gatcctaccc    360
gagtgaggcg gcgccatgga gctccgggtg ctgctctgct gggcttcgtt ggccgcagct    420
ttggaagaga ccctgctgaa cacaaaattg gaaactgctg atctgaagtg ggtgacattc    480
cctcaggtgg acgggcagtg ggaggaactg agcggcctgg atgaggaaca gcacagcgtg    540
cgcacctacg aagtgtgtga cgtgcagcgt gccccgggcc aggcccactg gcttcgcaca    600
ggttgggtcc cacggcgggg cgccgtccac gtgtacgcca cgctgcgctt caccatgctc    660
gagtgcctgt ccctgcctcg ggctgggcgc tcctgcaagg agaccttcac cgtcttctac    720
tatgagagcg atgcggacac ggccacggcc ctcacgccag cctggatgga gaacccctac    780
atcaaggtgg acacggtggc cgcggagcat ctcacccgga agcgccctgg ggccgaggcc    840
accgggaagg tgaatgtcaa gacgctgcgt ctgggaccgc tcagcaaggc tggcttctac    900
ctggccttcc aggaccaggg tgcctgcatg gccctgctat ccctgcacct cttctacaaa    960
aagtgcgccc agctgactgt gaacctgact cgattcccgg agactgtgcc tcgggagctg   1020
gttgtgcccg tggccggtag ctgcgtggtg gatgccgtcc ccgcccctgg ccccagcccc   1080
agcctctact gccgtgagga tggccagtgg gccgaacagc cggtcacggg ctgcagctgt   1140
gctccggggt tcgaggcagc tgaggggaac accaagtgcc gagcctgtgc ccagggcacc   1200
ttcaagcccc tgtcaggaga agggtcctgc cagccatgcc cagccaatag ccactctaac   1260
accattggat cagccgtctg ccagtgccgc gtcgggtact tccgggcacg cacagacccc   1320
```

-continued

```
cggggtgcac cctgcaccac ccctccttcg gctccgcgga gcgtggtttc ccgcctgaac   1380
ggctcctccc tgcacctgga atggagtgcc cccctggagt ctggtggccg agaggacctc   1440
acctacgccc tccgctgccg ggagtgccga cccggaggct cctgtgcgcc ctgcgggggga   1500
gacctgactt ttgaccccgg cccccgggac ctggtggagc cctgggtggt ggttcgaggg   1560
ctacgtcctg acttcaccta tacctttgag gtcactgcat tgaacggggt atcctcctta   1620
gccacggggc ccgtcccatt tgagcctgtc aatgtcacca ctgaccgaga ggtacctcct   1680
gcagtgtctg acatccgggt gacgcggtcc tcacccagca gcttgagcct ggcctgggct   1740
gttccccggg cacccagtgg ggctgtgctg gactacgagg tcaaatacca tgagaagggc   1800
gccgagggtc ccagcagcgt gcggttcctg aagacgtcag aaaaccgggc agagctgcgg   1860
gggctgaagc ggggagccag ctacctggtg caggtacggg cgcgctctga ggccggctac   1920
gggcccttcg gccaggaaca tcacagccag acccaactgg atgagagcga gggctggcgg   1980
gagcagctgg ccctgattgc gggcacggca gtcgtgggtg tggtcctggt cctggtggtc   2040
attgtggtcg cagttctctg cctcaggaag cagagcaatg ggagagaagc agaatattcg   2100
gacaaacacg gacagtatct catcggacat ggtactaagg tctacatcga ccccttcact   2160
tatgaagacc ctaatgaggc tgtgagggaa tttgcaaaag agatcgatgt ctcctacgtc   2220
aagattgaag aggtgattgg tgcaggtgag tttggcgagg tgtgccgggg gcggctcaag   2280
gccccaggga agaaggagag ctgtgtggca atcaagaccc tgaagggtgg ctacacggag   2340
cggcagcggc gtgagtttct gagcgaggcc tccatcatgg gccagttcga gcaccccaat   2400
atcatccgcc tggagggcgt ggtcaccaac agcatgcccg tcatgattct cacagagttc   2460
atggagaacg gcgccctgga ctccttcctg cggctaaacg acggacagtt cacagtcatc   2520
cagctcgtgg gcatgctgcg gggcatcgcc tcgggcatgc ggtaccttgc cgagatgagc   2580
tacgtccacc gagacctggc tgctcgcaac atcctagtca acagcaacct cgtctgcaaa   2640
gtgtctgact ttggcctttc ccgattcctg gaggagaact cttccgatcc cacctacacg   2700
agctccctgg gaggaaagat tcccatccga tggactgccc cggaggccat tgccttccgg   2760
aagttcactt ccgccagtga tgcctggagt tacgggattg tgatgtggga ggtgatgtca   2820
tttggggaga ggccgtactg ggacatgagc aatcaggacg tgatcaatgc cattgaacag   2880
gactaccggc tgcccccgcc cccagactgt cccacctccc tccaccagct catgctggac   2940
tgttggcaga aagaccggaa tgcccggccc cgcttccccc aggtggtcag cgccctggac   3000
aagatgatcc ggaaccccgc cagcctcaaa atcgtggccc gggagaatgg cggggcctca   3060
caccctctcc tggaccagcg gcagcctcac tactcagctt ttggctctgt gggcgagtgg   3120
cttcgggcca tcaaaatggg aagatacgaa gaaagtttcg cagccgctgg ctttggctcc   3180
ttcgagctgg tcagccagat ctctgctgag gacctgctcc gaatcggagt cactctggcg   3240
ggacaccaga agaaaatctt ggccagtgtc cagcacatga agtcccaggc caagccggga   3300
accccgggtg ggacaggagg accggccccg cagtactgac ctgcaggaac tccccacccc   3360
agggacaccg cctccccatt ttccggggca gagtggggac tcacagaggc ccccagccct   3420
gtgccccgct ggattgcact ttgagcccgt ggggtgagga gttggcaatt tggagagaca   3480
ggatttgggg gttctgccat aataggaggg gaaaatcacc ccccagccac ctcggggaac   3540
tccagaccaa gggtgagggc gcctttccct caggactggg tgtgaccaga ggaaaaggaa   3600
gtgcccaaca tctcccagcc tccccaggtg ccccccctcac cttgatgggt gcgttcccgc   3660
agaccaaaga gagtgtgact cccttgccag ctccagagtg ggggggctgt cccagggggc   3720
```

```
aagaaggggt gtcagggccc agtgacaaaa tcattggggt ttgtagtccc aacttgctgc   3780
tgtcaccacc aaactcaatc atttttttcc cttgtaaatg cccctccccc agctgctgcc   3840
ttcatattga aggtttttga gttttgtttt tggtcttaat tttctcccc gttccctttt   3900
tgtttcttcg ttttgttttt ctaccgtcct tgtcataact ttgtgttgga gggaacctgt   3960
ttcactatgg cctcctttgc ccaagttgaa acaggggccc atcatcatgt ctgtttccag   4020
aacagtgcct tggtcatccc acatccccgg accccgcctg ggacccccaa gctgtgtcct   4080
atgaaggggt gtggggtgag gtagtgaaaa gggcggtagt tggtggtgga acccagaaac   4140
ggacgccggt gcttggaggg gttcttaaat tatatttaaa aaagtaactt tttgtataaa   4200
taaaagaaaa tgggacgtgt cccagctcca ggggt                               4235
```

<210> SEQ ID NO 393
<211> LENGTH: 43948
<212> TYPE: DNA
<213> ORGANISM: Homo sapiens

<400> SEQUENCE: 393

```
gcgcctcgga gctgcctgcg ggcgcacgcc gtcttccccg ccagtctgcc ccggaggatt     60
gggggtccca gcctgcgtcc cgtcagtccc ttcttggccc ggagtgcgcg gagctgggag    120
tggcttcgcc atggctgtga gaagggactc cgtgtggaag tactgctggg gtgttttgat    180
ggttttatgc agaactgcga tttccaaatc gatagtttta gagcctatct attggaattc    240
ctcgaactcc aagtaagtgg cgtccgcgat cccccctatgt ccccgccccg gggtccgccg    300
cgccgtccgg gcgggaggag gggtcagtcc gcggggcctc ggagcctgtt tctggaacct    360
cggttccccg tcccccaccc ccaacccccg ccccatttca ctaggtggag actcctcgct    420
cggctttcca acccgagccc cgctggaacg gacggtctct ccgcctttcc tcccccgaac    480
gctcccaggc gctaaaagct actatcggct cgggtgtcaa gtccgggaag gtgtccgatg    540
gcgatacctg accctctcct gttttcgagg acgaaggaca tggccacaat ctaggctggc    600
cggcacgcgg ggactggtgg gctctggaga gaggcggaga tgctgcattc gcggggagcg    660
cgggcggcgt ggtccggggc ccgcgggcgg gcgaccgggg tggcaggacg ctggcagcga    720
agcgcgttct ggagagggga gcctggagtc gctacgctgc ccgcagagcc ctggagccgg    780
ggcgccttgg caccgcgccg ccagcccgag ggtgcgcggg gagctcgcct gcttcgcagg    840
agaactcggg cgtcgagccc tttcctccgc gccggggaga cgggccttag gcttctccct    900
gagggcccgc cgcacctcgg cctcccgctt cgttcataag ccggtagccc cggagtatgc    960
ggtctcgatg gccgacctga ttgtaatgca cttcctataa aagcttaggg ccctgcccag   1020
tcgacactgc tcctgaagcc ttctccctcg ggaccctggt aggaatggga tccttaggat   1080
cagatttgct cttaccggac tctacagccg ggagcgagcc aggccttgtg gagagtaact   1140
ttcagtttgg gccaccagag tgcattcaga atttagaaaa tcccatccat ccctaaatct   1200
gtgtggtcat aactcgtagt catctgggta ttcagtactg tgtatcccct tatttcgaat   1260
cacagccaaa acatatttta cagaatcttg gaattgtagt ctcgggaaac ttggagaaga   1320
agtatgcaga cattagctgg tttctggaga aaacgtttga gatcagaagc aaaatcaatg   1380
gcctaattga agttgagcaa gttgggcctg gttttaggag aaaagaaatg gggattgat    1440
ttagaaatca cgtcttaaag gagtgtgtcc attctcttaa aagtgtcaaa tttcaaattc   1500
actaacatgt taaccaagaa tcccttcatg aaaagggcga aaacgtcggt tacaaatcgg   1560
tttaaacaaa tgtttgtatg atgctagaag gcactttcaa caccgctcat acggagaagt   1620
```

-continued

```
tacttagctc tgcctccttc catgtagtct gctcttgcat ggattatatt tttaatgtaa   1680
attgttgtat ttgctgatga agtactggcg gcggcatctt tgcatcgatg ccggctcggg   1740
aggcgccagg tggtgccgga aggagccggg ctaggacctc gcgcagcagc gggtcccgga   1800
gtccgggaga ggcgggcggg cgggcgaggc ggtcgcgggg agcccgcggc gccgctgccc   1860
gcccggtgcc tccagaggtc actcttccat gcggaatcgc gcagcgccag gcctcgcccc   1920
tcccccaggc cgcctgctcc agccactctg cactttcact gaccggttct ctttgaggct   1980
gttttttttt ttcttatgag gatttaatat ttctgtttaa atctagttga aagcaattcc   2040
gttagcctct tcagcgttta gttcggtgtg tgtatcttta tctttgcgct atattaacta   2100
ttagtttgtg tgtatccggt aggagaatta gaaataccta gttgggagaa aaagaaaagt   2160
agaacaatag ttatttcaac ctaaggttta gacgttaata acttcttttt gtaatgtgtc   2220
gagatggggg gtcctggggg gaggtgacag gtactcacca ctcccccccc ccattctgat   2280
gatgaagatg agtctgtctt tccagctatg tccagacctg cgagggccct gcgtttctgg   2340
aagcctgccg tttgcgcggt tgaggttgct gctgctgtct tgtcctccac agcagcattt   2400
cttttaaaat tctcctgata acggcctgcc tggatgactg gataatgtgt gcctggaaaa   2460
ggtctccctt gcagctgaat gctagctcca gagatcagaa agatttcttc ctgtaggagc   2520
cataggaaag agtcctctct aagtttttga gaatgcatac aacccccctga tgacaggggg   2580
tcgctttcct tggggaagtt ttatatttat ttccagagga aagtttgaat cggtaaatat   2640
gatgtggcag gaaggtaatc aaatgcattg aagtttcaca tcagttccta tgaactgtgg   2700
aacaattcat ttgtaatgaa gccgccatca gtaattagat ttgtttcatt cagaggtcag   2760
ctttttttagc aggtggtcga cacagggagc atgcagcagc tgtttggata cagggtccag   2820
aaaacccttt gtaaattcag cgtctccgta actactttaa tcacattgtc ggctctcccg   2880
tccctgactg tatgtaataa tggaaagatg tcctgcgtgc tgaaacagta gctgccctgt   2940
taggttattc acattgcttt gatacgttct ggtagagttg ggtccgttgt agccattttg   3000
gttgtttaaa gttttggttt tttttttgtt tttttttttaa ttcagcagag aacagtaatg   3060
cctagcttcc gtttttaact taacacttca gtagaacatt ttcttccaag agggagattt   3120
tggcctaagt aaagtagtgg gctctttttt aaaaaaaaaat taattttact ttaatgtgag   3180
caaatctgta ttggtatggt gttctgcaat gcattacact gactttgaaa atttcgagta   3240
ctaatgcctt atgtctgggg ttaccattcc ctgtgcatca catactagtt agttaacata   3300
gcattttgct tttcccatgt aattttttcc ctatataata ctggattcct gatactaatt   3360
gacttgatac aaaagaatgg ctggatgata tccagataac gtataataca tgggcttcac   3420
cacaatcagg ctctgaataa atacagacct gtcagagatt gataaaataa actacaatgg   3480
atagtgctgt ttaaacagtc cattcaataa catatataag ccagcctgcc ttccattgtg   3540
tctgaaattc ttatttttgt aggtaaacaa atgcacattc agcactgatt gaatagcccc   3600
ttgaactatg ctccacagtt tgcgtttggg ttaatcttgt cggttttaat atagagagaa   3660
aaaagctcaa agcaccaggg gtggaattgt tagtgctttc acatccacat tcctcacatt   3720
ttgtcaggat gataaactgt aggtaatgga ctgtcgttgt tctgcaggac aactgagcca   3780
ggcagagcac aaagactaag ctaaagcgat acctcacaac atgcttggta gccttctttt   3840
cagatgagaa tttatttgag aatcatgtgt ctagggactg cacatcttaa cctcaacagt   3900
tacagcttca agccccagaa acaggagctg gaggttaaga tgatttgcta agcacctggt   3960
tctaaatctt ttacaaagca taagctgttg acgctggttc tgccgacgca aagacatgca   4020
```

gatgactcca acatttccag aggcttctga cttaagctaa agtgtgtgga caggtgaatt 4080
cgccatgggc ctggagacca gcttgctaaa aactatgtgt ttgaatggtt cctccagaca 4140
gagtcagctg aagaacaatt ggtggattta tattaaaacc tcttgtctgt aaacttactg 4200
aggtgcatcc ttcggttggt ggatcagtga gataattgcc ttcagatgga cattgcaact 4260
ggagcaacta aatccttgct gtctttcctt cctctgaaat cttccaggta gctcccgaga 4320
gcttcagtat gacaccaaac ttcgggcgac gttttagagt gcgttcacct aatgggaaac 4380
tattcgagat cccagcgtga ctgcagtaat gcgtcatagg aatgggagtg gcaggggaaa 4440
aggaaataca gattgtagac cctaataaaa aaatttttag gaaagatatt tctttaacgt 4500
tttatgagaa cttcattctt aaaatactta attgcaaatt agacaaatag aagtgctctt 4560
ctaaggaagg tgattaaact ggtcctccta tcagcctaat ctctgcctgc ctttgctgct 4620
gacataaaga acctgttttt caggtcactt aatatacatc tacatagatt tgcttatgag 4680
ctcacccttt gtgtagcgga gtagagcctt aaagaggagt gctcaactgt ttaaaatatt 4740
ttgattaaaa tatgcagaac ccatagaact ataagcttct agtcaggaat tagctctttc 4800
agggaacagc tccccccttc tttttaaggg gggaattaga aggaggctgg gggaggaata 4860
taagaacagc aaagaaggaa ggatagcaaa tgggacatgt tccgaacagc ttggaaaaac 4920
tcctgtggct tcattgtctc tataaagcca aagaatacaa agacataagc aattcagccc 4980
ttctcccatg atggaagatg taaaccgttg acatgcctcc cctgtttaac ttgtttaatt 5040
ctcattttaa attcagcacg atactagccg tgtgaactct gaagatttct ttagtaatcc 5100
attttgtagt tccgaatcaa aaacaaagtg aaagggtctg acacaatttg cttttatttt 5160
taggcaaatc aaccctggtc atagttaata aggggattac aactcagact aggtctttac 5220
agatgtgatg taaatcaagg gcagagtata aagaaactga tccctttga ttgaagtata 5280
gtaaaaaggc atagagaaac tagcagcagt aatctgattg tatggcaata aaaccaccat 5340
tttctgtctt tcagataaaa ataatgtggt aaatccatgc agttcataag atgtaaaggc 5400
agataaaggg tgaagccatg gcaacatata gattagcttg atgttagaaa tgacacgtct 5460
ctgaaaaggg cgcgggacga aggcccttgc ctccaggctg ttgggcatta tgtgagaacc 5520
acacagactt ggaaactggg attaggaagt atgaaagctc tacttgtggt ctgggatggc 5580
tgaggcagta aagaaaagct gctcagttct tgctcattgg tggtggataa tatggcaaag 5640
gtagatttca ttgactgcct tttttataga ttgagattgg ggctgattaa aacttcagat 5700
cactgcagtt gttagggcct gggagatttt cctttttaac tcctggccta acagcagcag 5760
ccgttctgta ggattaactg cacttcgcgg tcgttgcctt aatctatttg ggcttcaggc 5820
agggacatgc tgggaaggaa cagagaccag aggggatagg tagggctggg gttatctgaa 5880
aagaaaacag agaccttttg atttcagcca tcttttcaga cccagctccc tctcccgctg 5940
catgggagaa gcaaaggtaa acaggacaca ttgtccctct ccctcagcca cagagctctt 6000
ctgtgagttt tgtctttccc accctggaaa aaaagataaa atacaatttt taaaagggga 6060
gggaggaatt tagttttaat tcaaatgagt agtaatccaa tatgccaaaa gcagtgggct 6120
ctacctagat gtaattttac tcgtaaatgt gagtcttaaa ctttgagttg aatggggcag 6180
gctgttagag gtggtgtaaa ttacaggatt ataaaaatgt tagtgctgcc cagccttaaa 6240
gtcaaaaaca gaaaaatctc tgtgctgttg agtcttcccg ccctctctcc tgaacaacct 6300
tgtaagtaag ctagactttt gtttttgcct tccatacttt ccatttcagc cattaaacaa 6360
aataagccat tgaaaccacg attgggttcc atgcagagtg acatccgcaa tcgggtcaag 6420
ccagaaggaa atacttgctc gattgccccc tatttggcat tacaggaaag tctccacact 6480
ttggaagagt ctgaactctc aagacattga aaatgccaaa ggctgcaaac accctgtgtc 6540
tttcttgatg gagtgcatct tggtgtgttt tacaaagggg aattcagtgc tgtttttttg 6600
ttgttgttgt tgtttttttt ttttaaagag cagcataggg cccttctaga ctcttggatt 6660
ctgtgtctga caaaaatggt cattaaatga gcaatattat aatttagacc catttcactg 6720
attttgttcc aaattctcaa ctgacttgag catctgtttg gggctgtaga tacattgccc 6780
ttgttgactg tttttctcgt ttctatggga attactgtag ccattactat gtagctttca 6840
tagactcaaa acatttttaa agtattgcat ataggctggc catatccagt gcctgttact 6900
ttaccttctt tttctaactt aatgcagcag tctgtattaa cagatccatt tcatttgtct 6960
agcttcatca gagagaggct accccctgat ttacaggctg ctcacatcca agcaccttgc 7020
attctacact tgacagtgat tgctaatggc ccattcaact aaagtatttg cttgttaaca 7080
gggaacagaa catgataaat gtccagcaag cttgctgcct ccttcagctt ttcaaacgca 7140
gactggtgca tatttatggc aggcaaatga caaaagaaaa agctgaattg ccctggcctc 7200
cagctttcta tcagaaacag ggttaaagtg attaaagcaa tcattcaaga aagccctgcc 7260
gtttgtttac taaccttcat ccaacattta gctttgtagt ctacctgtga gaagatattt 7320
cagaagtatt agagataagg aaggaggatc tagcaaacca gtgaaaagag taggtgacca 7380
gttataaaat gctttccatg cacattgaat gccaggcgaa cctatttctg ttattccagc 7440
agacaatcag cagtggctct agattattaa catattttcc tttcatgtat aaattcaaat 7500
atgtaattct agtccaaagc attctgtggc tggtaagcac atacttgctg atttcaaata 7560
agaaaacata gcaagggaaa gctccattaa acaagttgtt tctgccctta gtaattctct 7620
aaacaagata ggaagaaaaa gtggacagta gtggagtatt aatagtgtgc tcttttcatt 7680
ctctaaagca cgagtaagta agcgttcaaa ctactctgtg gtgggcatac atttagagcg 7740
ctgtgaatga accactgctg ttctgccata cttaatttat ttatattatt atttttattt 7800
tattgttgtt tttatgtatt attataatta tttatttata ttactaattt attttctcaa 7860
tttaaatcct gttgcatcca attttaatta cagtttttgt atctgccttc ccatacttgc 7920
tacccacgtc cccattgcca ctgcggcctt atccatgttt tctgtgtaca ccactctcgt 7980
atcaccccag aataattatg agtgctaccc agacttttga aaccactaga gtcaacatgt 8040
ttgtctttga ggaaagccaa tgatgcttta gcatttttgg caggggtgga tgtgtgttta 8100
agtggggtgg gtgcagctcc ttattgtctg cctattctac tgttgttccc aatccacatt 8160
ccctgcgggg cacctaacct gtgtgcatag caaagaattt ccgaccttca gagccagaag 8220
tgtttctcaa ttgatctctt ccagcctagg gttatagctg atgaattata atccttgctc 8280
tttccacacc tttacctggg cttaccatgg ccctaaaaca tttgcccaga atcagaattg 8340
tctcatgagt gagtggggca aggcaaatcc tgttccagac cagctgagaa tgtacctagc 8400
tgcagaagaa gttagaaagt gtcatctttt acttatctac cagaactata ttcgaggtac 8460
attttagatt taaaaaaaaa gcaagttctc gtaggccttg aatccccccc ttgctatggg 8520
aaaatggatc attattataa tggactgtcc agtaaagttc atgatttctc ctagacatgt 8580
tctctctctt tatgacctag atcaagagtg atctctttaa gtcttttctt cataatccca 8640
cagcactttg tacttagatg tacttagaaa gaaccatata cacggtacgt catgattgat 8700
atgcaagcct tcaccactct acctgtccta aaagtcaggg acacaccttc ttcatttcat 8760
cagtccctac ttctatccag cattggcatc cagtaagtat tagtggaatg gacagacaac 8820

-continued

```
ccgaatttgt gctgatggca gtttaccctg ttttaactgt catccttctg ctactagaca   8880
tggatgagac ctgagacgat gggactgctc agaggtccct ggctcttgaa ctttagggca   8940
ccagaatccc ctgcagggct tgagaaaaca ggggtttctg ggccccaccc ccagagttcc   9000
tgattcctga ggtctggggt ggggcttgaa gatggacatg tttaacaagc tcccaggtga   9060
cgctggcaac tgctgcctca gggccatgct gagaaccctc gccctacaca aacctttctg   9120
ggaaaacaac tcaacattaa agctgtttgg ggatctctga agaaatctgt agtccttgcc   9180
ttgttggggg agcatcaggg atctaaccat tgatggtgga gtatttgttg ttaattcagc   9240
aagcaactat taagtgttag gcctgttact cggctctaac aatacaaggc agagtgacct   9300
gtaccctcga gatttaaagt ctaagtcctg tagagagaag cccaggtggg agcaagcaca   9360
tttagagtta ggtgcttggt gcaaggtggg gacacagaag aagggaatgg catttgcctc   9420
tggaggggtc cggaaacagc ctagggagga ggagcttgag tcttgaaata ctgtgggcat   9480
ctctaagcaa agtcacagta gacagctgaa ataaagaaaa tagtaagcaa gccaaagaaa   9540
cagtatttca gccaagggca gcgtgtgtct atcacgtcca cctgtgaaca cgtcccagga   9600
ttctctgcat ccggccattg ctcaagacag atccctcaca ggaacagcta agccactgat   9660
ttcagctacc tgttcacgtg agaattatca gtacctactg cttttcaaaa tgagtatgat   9720
catggatagg tgaggcaatt cagtttcgca gagacagtag ggcaagtgcc actgtagttt   9780
agttaagggc acatgcttta gagtttggct atgtgagtcc aatcccagtt tagccattta   9840
ttagctgggt agctttagga gcagtagcct tagtgtctct cagttgtccc atctctataa   9900
tagggacaat aacataatag tgctgaataa aagagtaaca aaattttggt caacatttaa   9960
tgtatttaaa gagctaagct ccgtgattgg cacaatgaac caatcaatca aacaccagtt  10020
gttattaata aaagtcagtt gaatatgtac tgtgtgcctg gccgtggttc aatttgcctt  10080
tgcatacaag gaaaaaatta aaatactctg ttaataaaga ctatagcata atactttcac  10140
cttaaacttc ttgatgttaa tttattttgt ttacctgcca aacttctact cattccttat  10200
gactttctgc tacatgaaac accctttgta attcttttgt cctattaaat taagttctct  10260
ctcctctgct ttcctgcttt tggtgctttc taataacact tttaaccctg gactttctca  10320
ttcagctgtg caactgtgga ctgagaggag gctctttgaa ttcattttgt atattctagt  10380
agagagtact gtgagcagtt gggttgttga atgaatacat taattcaacc tggagggatg  10440
ggcagtattg catttttttac attgatatta catgatattt agaaaactgc ttaactggtg  10500
gacgttgttt tattaacagc attttgtgta tagcactcac tatgtgccag ctgctattct  10560
aactgcctga caaatactcc tgaaaccttc atggtaacca tatgagggaa gcacttttaa  10620
tatatccata ataccaacgg ggagactgtg gccaaattgg ttaattaact tagccaaagt  10680
catattgaac taataagtgg atttaaaccc agctagtctg gggccagggt ccctctttta  10740
atcttctgcc tcctgcttat gctgttgcat ggagtagtct ttatcatata actaaattaa  10800
gcatgcattt gcttaaagca gtgcatacat gatggatcaa aaagtttgtg gtataattgg  10860
tttaattctg tcattatcca ttttgattta tagtcacttt cttatgatgg tcgtgtagtt  10920
ttaaatggaa cctttgaatc tttgatataa taaggttatg tcaaatcttg ggtataataa  10980
ggttataccc aatggaaaca gaataatgat cagcccattt aaaggatgac tggagagtta  11040
ttacaataca taatagtcat gcatatattg agtagtattc ctttggtaac attttccttt  11100
taaaaattgt aacatttgat tgttccttgt tgggagaaaa ggaggtcaga tttttgaggg  11160
gagatccatt tggtgagatg ctgagtgtgt gtcaagctaa ggagatagta tgacatcttt  11220
```

```
tttagagtct agtcacaatt aaatgccatt ttattttgga ttttgggatc cgtgccagct  11280
tccagcttgt cagagctgag aagactcaaa tcaagtccag gcttatttct acagcaaact  11340
gggattctgg cttcttgccg gtggattcat tcagtacagc ccatctggct tttgatgttc  11400
tgcaagtttg gagccatttg ttgaaggaag ccaggcggtg aatattggtg gtcctggggt  11460
tctcttgact ccaagtggtg ccccttggtt tgcattttca ccatgcttag catctgctta  11520
cctggagacc atgcagccgc cggccagagg tctccaacaa ccaaatcttc atgcctttta  11580
gaactcagag tccccagcac atcctccttc ctcctccttg tccaattact ttcatgcagt  11640
tctcagtagc tgcttgtttg aatcacttat agtatttaac ttctagggtg tttttgggtt  11700
ttggtcaagg taattccagg ctgaatgtgg tgactaagca ggaaataaat gggtcgtcct  11760
caaagttaca gtggagcgct gtttctattt tcctaaggta cacagttgtg ggggcgatcc  11820
gtatggaagt caggaaccca gtctgatttt gcttcctttt gatggtagca gtacagacct  11880
ggctgttttg tagcctgctt tgtttttctt cctttttcttc cctaacttca cgggctgtgg  11940
caaagccctg agacgtgcag gaaaatgtct cctgtcatac gcccacagca gacctagccc  12000
tgaccctcct ctgaagccca ggaaggaggt atctgtgaag cagcctgctt gtaaagcaat  12060
tgcacacagc cttgtaaact gtgttactgg gctgattata cttgattggc aaggtgaatc  12120
tcttatagca aaagagaact tggagagttt tatctcatct tatgccttat taatttgttc  12180
attctttaat tacacagcca cctattgagc accctattta tgcaaggtac ctggtcgggg  12240
gtcagaggga gggtcccatg gtaaacgaga cagactcaat cctggaggag caggaatggc  12300
agcccctcgc tgggctgttg gccccaccaa aagggaaagg tttcatttta ataatacatg  12360
ggtgaatcat ttttgtcaat aggcaaaatt ctttgtagtt aaaaaaaaat atgatggtag  12420
gaaggaaagg gatgggcaga gggttaaaac aaaagatatg ctctccctaa ctctagattg  12480
tagtattgtt atgcttgtca ctgtagctga attccatttc tttgagtttt ttcaatgcca  12540
aggcattccc tgtatgactt acgtgagcct ttcatctccg cgatttttcc cattcaggta  12600
aatgagcaaa tggatttgaa cactcatatc taaaacaaga gagaaccagc tggaaatgcc  12660
ctttgaattt ctttctctat gtaaaccatt tttctttctg gtgcctcacc tataaataac  12720
aggagttcca ccttccttta tagactcttg ctgaaagcat ggtttggaac aagaccgtac  12780
aggtgcacac aaattacagt tgggaaagaa gcctgcagtg catcttgtct ctgaaggtta  12840
tgaaatcctc cttttagtaa tggagctggc gtgatcaagc cagcaggatg aaatttggca  12900
tttgtgagat caccccccctt ctcacttgcc cactgtacat agcatcccag ccttactctt  12960
caaatctcca catttttttct tatctagcta caaaattcat aggctgattt ttttggggtg  13020
cgtgtgtggt tttttttttg tttttttggt aaataaagac ctgcattttt attttgatat  13080
aggtggttga gttttgtctt taatttcatg acagagattt aactagtctc aacttttgaa  13140
aagacaacaa tgatatttgg ggatcacaca cttaaagtta gatttctaga tgattaatac  13200
caaagtagat gattttttag cctcagccat ttataggtat gcccttctgt gaattttttta  13260
tgacagtgaa aatcatggca cagataaaaa ttaaataaat acttctgtta ttttcctgaa  13320
gaaaaaaaaa aaaagcttaa actatgagaa tactgtcttt gagcacttta aaataaaatt  13380
gacttcagcc agcaggattt tgagcattac atcacaaata aaaaacaaga ttaacatcaa  13440
aaggagtcag ttttcattca attgtgcagc actgtgggct gtgaaattta atattatttt  13500
gactcatatg ctaattgtag actgacagag gaaaatggat tgtgtttaaa taaaaggata  13560
cacagcatca cacgcagctg tatcaaatac aagttgaggt ctttgggcca ggaactgggg  13620
```

gccctctagc tctgttattg cagattcaag tttgacaaat aaaactttcc tttagactgt 13680
agtttaatta cttttttttca aaggtatgcg tgatgaagag gcacaaatac acctcacctt 13740
gaagagttgc taaactggtt tgtgtgccga tcagttcacc gtgtgtttga atttctgtgc 13800
ttctcatctt tccttttctt gaaaagattt tgcttgtcat tggtgtgaat tgtacccccc 13860
acccccaccc atctagtctt tgctctcaga tttataacac tttaatggtt ccaaattgta 13920
tagcctgctc ttagacccct tttcttttcc ttgaataaat caggttcatg ttgcagacga 13980
tatttgtttt aggaaagtgt gaaagaaggg gcacctgtga aaacacgcaa ttgttccaac 14040
acacatatac atccaaatta aagcagaaaa tgtcaaagcc tccaatcact accttatttc 14100
ttggaggttt aaagccgctg agaagatagt ggtgccctcg ctggaagttt taaggtaatt 14160
actttttact ctaagcagta gtatctggta acctaattcc gtataaacct gacaccctat 14220
cgctacaccc cagtatttct ctgatttcag aataagtctg cgtagaaact tgttctgatg 14280
ttaaagtgca aaagggggca gtaaagtgct atccacaaaa aaggaaaaac attttccaag 14340
tatttcttat tactgcctgt gtctttcgta ggccctgcct ttatttattc attttataac 14400
aaaactctta tgtttggggc attcagagaa taccttatta agctgttgca gcaatctagc 14460
attaaatgga agacatgcaa gactgaagat cctgcctgtt tatgaagtgt gccatcaaat 14520
tcacatgctc atgatgcaga gtccttcttt gggagtattc gtattcccaa gtgcacagag 14580
cacttcggaa aggagccttg gtctttggtg ttaatgctct cctagctccg tatagatgtg 14640
gcaggcccaa agtacatggt ggggtgaagg gtcaagggtt tgggcttatc cagagcagcg 14700
tgcatccttt gtcaggaggt gactggaaac accagccaat tacagcagaa ctgcagactg 14760
ctcatctgca ttcggaattg cagatgaacc agtttgtact cgacttctct tcttcactgt 14820
aggctttgac atttaattaa aaattaaagc cttttatgga aaaagtacat gttttccaaa 14880
atggggtaaa ttcgaagtat acttgataca gaacactggc ttgggaataa acctgtgata 14940
ttacatgact tttggtttgc aactgctagg ctgagcctct ttgtaaagct gggatttaga 15000
atctttgaaa tgtttgtaca gttcaatgat taagcataaa ttgtatatat tcccttttt 15060
tcacttattt gagtaaacaa gtttgttact acagcttctg tggactcaga gatttatgta 15120
ttaaataggc cacaacttca actaggataa ttttatttat ctgcttgtta gggaattgca 15180
tcaaaagttt aagtctgtag gcattaaata ttttaaatgc ttatttttaa agtcaattat 15240
gaaagatagc acaaagtttt tctgaaacta cattaaaaaa ataatgtttt aatcttatca 15300
caaaagcatt gactatttat tgcaaagaaa acacagaaag ctaaaaatca ttctaagtcc 15360
accattcagt agcccaaagt ggtctcaggt aaaggcggtg tgtgtgacca tttgtttatg 15420
gttgtctccg tgcagtcagc aaaataaaca gaacaacatg ccatatatta ttgatgtgta 15480
tattttcaac tgaaattagc catctgctta caatgatcat atacactaat ggtataattt 15540
tgaaatgaaa agaaaaataa aataattctt tgtggagagt aatgcgaatt gacttatgaa 15600
tctcgccctg cttggcagtt tgctctagag gtagaagagc tttatgtgtg ggcctcctcc 15660
ccccccacac atttattctg ctcacacttg caccagcatc catgtcagga ctcaccttgt 15720
cctgttacat gagtaacatg gccctgattc tcaagtgcat gataactgcc ataattacac 15780
ataaatatta aatatttaaa tagatcttta cgtgtgtaat attaggtaga agtggctctg 15840
gatcgaatct gatgcttttt aaatagaagc tttcccacaa catttccaag cactgtcatc 15900
gtgtctgtct cgatttgggg tttacctggc ctagttatct gtctgggtgt agaaactggt 15960
agttcctgtt tgtatctttt ttgttctgat ctctttattc tgtgtcagct aaatattctt 16020
gcagtcagtt actaacatat taactcatcc ttgtttggaa actttggcat atccttccat 16080
ggtttccttc cgtggacctg tcgcgtctct caggagagcc accaggtata ttgtcacaca 16140
tttcgcatgt attttcagag actacagcag catcaagtgg ccccccagcg atttgggttt 16200
tcttctcggt taatctacac tctttggcca accgtgagaa aacttgtaag aaggcatcag 16260
atgtttgtgc taaggtgcgt gtagtatggt cagaggaaga aagaagcagg gaaaatggag 16320
tggccgtggg tgggagggga agcagggagt gcaatttcgg gttcactaca cagctctcca 16380
taaacttctc cactgctggc ttcccacgga tcctcctatt acactgggca aagtgcagaa 16440
atagatcagg cgaccactgc ctccgtccat ttcccaggca ccctgtgaga cccgataatg 16500
caatacaggt cagcagaaaa gtccagactt gacatcccaa cgtgccatgg tctggtctgt 16560
gaatgaaaat cacatgaggt gacctctgaa ctctaagtgg ctggtttatg ttttcagtgt 16620
attaggcccg tgttttaaac aagcatgtgc tcgtagtgta ggttaaaact ttctgttgtc 16680
ttcattaatt atgctgtgtt ctagtctatt aatattaaag aatattgtgt tgcataatga 16740
ctaatttttt tattttttgg agacggagtc ttgctctgtc acccaggctg gagtgcagta 16800
gtgcgatctc ggctcactgc aacctccgcc tctcggattc aagcaattct ctgtctcagc 16860
ctccgagtaa ctaggactac aggcgcccgc caccatgccc agctaagtgt tgtattttta 16920
atagagacgg ggttttacca tcttggccag gctggtcttg aactcctgac ctcgtgatcc 16980
acccgcctca gcctcccaaa gtgctgggat tataggcgtg agccaccacg cctggcaaca 17040
taaggactat tttttaaagt ttttacaatt atgactgtga agttgaaatg tctaaattat 17100
tagagatcca gtttagatta ctaaatattt atgtctaatt gagatgatta gacttagcca 17160
aagtatccat gtagaagtat tagagtctag attggtgaaa aacttgaaaa agcttggctt 17220
aagttcaata ggtaatccaa gagtaaaaac agattccaat atcagatctt ttcaccatag 17280
tcatgttaag tttggaagcc ctacttgagt gtttccagtt ttttccacat tatattgtgt 17340
ctatatttga ttcaaaggca gggcatctat tgtcttgctt aggactgatt cactgggaaa 17400
agccactgga gttgcctatt tccactcagt atgcctcact cttagagtag cttcccatgg 17460
ttcccaggca ggccctccag tgagaatgca ccaagccaca cgccatggcc tgggaagcag 17520
tcctgaacct ggagattgtc ttgatggaaa ggaagaggca gccttcccct cccaggaaga 17580
tagtagagag cctgctctga cttcgctcag ggatggaact ggtctggctc agttctctct 17640
cctgtgtggg acatgaatca ctcttggtgg tctttgcttt ttatttgggc ttaaaatcag 17700
cagactttat taaatgacac ctctctctaa ccactctctg tctgggcgaa gtttaacaag 17760
aacagcctcc ccccatgtgg tatgggttgt aactgtggcg gtttccctct gctgtttttg 17820
gttacaagat gaacattatc tgaacacaca gaaagaaatc tgtatttggc atccataatg 17880
gaaagtcagt ttagtaattt aaacttagcc agttatcatc atcataattc tttttaacac 17940
tttcaaagtc agcataggag aagtgtattg ttgaatatta caaaatattt agggcataga 18000
tagatgtgct gtgtagtttg atttgttaat gtgtctaagc aatcaaagca acagaattca 18060
aatataaacc ccatcacttc caaaatagga actctgttta ctgacttgat tataacatat 18120
ggaactcaat tgttttccat taaaaaatga tactattagg aaactcaccc cattttcttt 18180
tcatatatat tctgctattt gcataattgt ctggagtcca tatgtaatat taaatgtaaa 18240
acacaaatgc catgtagctg gtctgtttct tcctcacctt ttggttcctg gcctcctggg 18300
gaagggttgc acatctgagc cgtggtctca gatgactgcc tcggaagaag cctcttccct 18360
tcaggcacca ctgatgtgtg cttggtgtgg agctagactt tccctggctc tccatgtgac 18420
gctcacatgt gcgtgtcttg atttccctta acttcatggc ttatctatga acagcttgat 18480
ttgggggaaa aaaatgtgtt tcccaatgct ggagttataa ttgaatgtgc tgcagtcaaa 18540
actgaaatgt gtgcagagaa agggggcttt tcctgtcatg ctcattgggc accagtgtgt 18600
cttcacctgt tttgtgtgtt aggtccatgc gtcatgctga aatgaagaac atgggatgta 18660
tggggctttg gacagtgctg agccaaaagc aagtgctcaa aagcagctgt gtttgtatta 18720
ttagtggttc tggaggtggc tgattgcctt gcattttaag tagagaggga ttgtagaaga 18780
ctgccaatac ttagaacttt ttccagagag gaagggtcag aaactgcatc tgcagggctc 18840
cttgctctcc agaaatgcca gtgtgcctgg gagggcatct tcagaaatcc agtctctcct 18900
cctcagtgtg tcctgtaccg actcagtggt tctgtcttca gaattcctat catgtctgtg 18960
atctgcaaat agtggtattt aatttgactt caatttgtat aaatgttagc ttctatttgt 19020
tcattcctat tttttgttca attaatacat tatttattga gcatctactc tgtgtcagcc 19080
ccttgggtgt ttaatactga attagtcaca tgtgggactt gcctgccctc agggagctag 19140
actataaatt cctaatgatc agtggtctcc acttttctgt cactcataat gtctggcaca 19200
acataggtta cttgagttgt tacactcaca gtactgttgt ttgctgccat ggtgctttag 19260
gaagtgtgag agttcccggg aggcagagtc aataatgcag actacacgta gtgaaaacat 19320
ggccaggaga gctgtagttc aggctctcag ctcaactgca ctctgtccac tgagaagcca 19380
taatttcttc acttaaagtg actgtgcgct atggctgttt atatatacgc ttaaaaagta 19440
aaagctgcta aaccactcaa ggattggggc cttttgtatt gatttaatta aaggaacaat 19500
cattgtttta atgagctcta gaaacaatta cttttgaaga gccgaggatc aaattcttgc 19560
ctcacgtttt gccacagtgt gttctgaaag gtgaattaat gcttttggaa tcatcaggaa 19620
tagtgagctt tgtcacgatt tactttttac aagcgtatct aatatgcata ttgaaatgtg 19680
agcctcccca ccacacttcc gctttgataa gcatcccccg gattgccgtc actgaccatt 19740
atagattttt aacaaagttg gacagtacac actgaatgaa aactttacat caaggaaggc 19800
ctggcgtgtt tgtaaaatga attaaaaggc tcattaaatg atttatatga cttacgcctt 19860
ctgaaaatat ggcctcaaac acagagatcc ccaaagccac accgacccct gcgtcccatg 19920
ttctcgacct caccgcatca gcaccagcaa gacctgtcgc tgagacggtg agtgatgaga 19980
gtcaagagga gtgacttgca tggcctggga ggaaacctcc tgtgaatctt tagttaagca 20040
ggaaaaaaaa aatcctcatg aaggaaacag gatcttggga gcattttgaa tgaagaagga 20100
gcttagtgag ccaaacttga gacatagggt gtaatgtggg agagttttaa gatttgcaga 20160
gatgtacagc ttgggagggg gtgtaatgca ttttcttaaa agagctgaat gaatggttga 20220
ggaaatgggt acatctggtt tggttaagga tcctaatctc tgaagcctgg gatgccccca 20280
gggcttgtaa tttaggaata cttcccctaa tagtagctaa cccttatata gtgctgtctg 20340
tgcaggctac aaaaggagca gattaaggat agaaaaggtt tggagtgtat gagaaaccct 20400
aggcaggaat tgactcctgg tgtttgtaaa ccttaaagat gtcctaaaaa ggtcaaggaa 20460
taagacagga gaaaaaggaa atgtcaggaa gatgatcaat ttaatgttta tggaatttag 20520
tttgtactta ctgcccggca tcttgcctga ggtttttaac ctcagcagca catcagaatt 20580
actgtgtgtg tgttggaggg gctgggggag ataaagaaat tagcctcatc ccaaacattc 20640
tgattcagtc tgttacttga gaaactgaat tgtgttttgt ccataaagaa gatgaaattg 20700
tctacagaga acacattgcc attcacaagg ttgaggggat accacagaga ggctccccact 20760
gtgatttgca tttgtcaaaa gttctagaga attcttcaac agtacacaca tggttgtttt 20820

```
aaatatatca ttgttataaa aattcgtttt gagttctgtt tcacagaaag tttttttgaa  20880
tgaatgaatg tcatatatcc ttgctaaagg agctcagtta aaaaaaaagg gaccatcctt  20940
ctcttttggg ggttgtacag taacacattc ccaagaaaga ggtaacagcc acatacattt  21000
ttcttcccaa taaagagtgt gggtttttaa tatgaatcca tagtatgatt tctgttatgt  21060
tttgtgctgc ttcataacca cactcatgca cttttcagaa aattaatacc attcattagc  21120
ataaatcata aactattccc ttggtatggg tttgaaattg ggggtgccct atcatccttg  21180
ctttatctct tagtgaatta tgaccctgta gtcatcatgg ctggtgggcg tctctggtta  21240
aagaaagggt tggattggaa ggattcagag gcgattcttt gttcttaggc tttaatattt  21300
taatgagcct gcaggcttgg ctgcttacga acgagctgag atttctaagt gtgttgttag  21360
tgttagcact tgtagaagga tgttcattag gaagttcttg tttcagtttt tcagagaaac  21420
tccccattaa gaaagatcat tcaggaacat ggctaccaag aaagaggaaa gggaggaggg  21480
aggctttcag ctataagcat taaggggata ttgtatcagt agtcttagtt ctaaagattt  21540
gcttctgaga attaattgga gcaaatacat ctcaagggaa gaaaaaaaaa gatttatagg  21600
gcagggacag tagttgtcct tgcaagtaga ggacacttca ttttgcagct gaatcaatac  21660
cacaactaat tatttctggt tatcttttac gcatttgtaa gacattgctt ttgttcagtg  21720
taataaaaaa cccattgttt gatcagtgac tgactaatta tgataagtaa tttgaaacat  21780
tcttgatgaa acttgtctgt taattaacat caacagcaca gggaaactaa caggacaaca  21840
aagtattagt ggatccactg ttccctccaa ttgacgagct ttctctgtgg catgcccaat  21900
aaactaaagc tgccaatggt taaaaaataa caaacatgtg ggagatctga ctcaccacgg  21960
aggaagagtt atggtaaagt tacacaaagg agtactgaaa tattacaagc gagggggtgg  22020
taaagaaatg tcagcaggta gcctgatcct acagcttaga gtaaggaaag tggtttcttt  22080
ctgtctttcc tttttctttt aaagcttaat tccaaaatac attcatccca tattgatctg  22140
aagtaagaga cttttgataa attaaagtgt gaatctgaaa atgtgtagtt tgggattatg  22200
ggcattgcct ggctatcttg taactgtcat taatactgtt aatttttatc aactcaatgg  22260
cttttttttc ttatgctttt agatttctac ctggacaagg actggtacta tacccacaga  22320
taggagacaa attggatatt atttgcccca aagtggactc taaaactgtt ggccagtatg  22380
aatattataa agtttatatg gttgataaag accaagcaga cagatgcact attaagaagg  22440
aaaatacccc tctcctcaac tgtgccaaac cagaccaaga tatcaaattc accatcaagt  22500
ttcaagaatt cagccctaac ctctggggtc tagaatttca gaagaacaaa gattattaca  22560
ttatatgtaa gtataatttt attcatttat tttatagaaa ttaagataag ctatataggt  22620
ttgtatcaat tttttgtttc cttaaaatta ttgtgacaaa taatttgatg aaaatctatg  22680
tggaaaaatt gtcccccccc cctttttttt tttcaaagaa aacttcattg aatttgggac  22740
cctgtgctac cagtattcat taagtataca tacccaaaga gaaaaaaaaa cactagaatt  22800
cttaatagta ttgaaataaa tgtattatat gaatatattc agcatctcta ctgacaaaac  22860
catttttaag gaccattggt ggattttgat aggtaaatct tgtgcattgc cttttctctt  22920
cacccatcca tccattcatt cactcattca tttcgtattt attctgtgcc agagactgtg  22980
cttaagggct agggattcag cagtgaaagg tggtaaaata gcatgttttc ctcaagaagt  23040
taacagtcta gagaagatgg agctcataaa ttcgaaagat ggggatgaca ggtcacatta  23100
aaaccagatt cagaagaaaa agacgaaact tggtttgctt agtacattac tctttttttgc  23160
atacatatat ataatttgac acgctgtttc aagaagagat ggtacgtatc ccttgggtca  23220
```

```
tatctgaggc tgacttgtga ggatgtgaag tcagctgatg agcacatttg gagcccacgc  23280
ctactatgtg cagatctctc gtcagcgtca ttcccagggc cccaggtggt gttaaagtct  23340
aggtgactca gacagctgtt cgcgtcattc aagcaatgaa gtcttttttc ttaatttctt  23400
tggtttaaaa ttatactcat aattaattgg gttgaatttt ccagtggctt ggttaccata  23460
gacttcagtt tattagggaa ctgctatctg ccactggttt attatttgcc ccaaggtgga  23520
ctctaaaact ttaggtagga gactcttggt gatcaaactg aaactcttgc atctcaacct  23580
atgagccgca ctttattgtt attttatttt tttagagaca gggtctagct ttgttgccga  23640
ggctggcgtg cagtggcatg atcacagctc actgtagcct tgaactccag ggctcaagtg  23700
atcctcccac ctcagcctcc aagtagctcg gactacaggc atgtgccact gcacccagct  23760
caagagctac acttcaaagc acagaatgaa aacctatttt taaagccaac ttgatacata  23820
gagtagctta ccaagaatta gtaacaacaa caacaagaaa aaaaagagag aatgtggtag  23880
agtatatact tagtaaggag taattattat aaaataaaag cattctgaaa tgaaacaggt  23940
agatggggtg gccaagtatg cagcatagta gggaaatctt tgaaaatgta aaatagttac  24000
caggtaaaat aaatggaaac tttaagcttt tggaagccta acaatgtatt tatattagta  24060
aagactttat ttttttattt tattttattt tatttttgag acggagtctc tctctttcgt  24120
caggctggag tgcagtggcg tgatctcggc tcactgcaac ctccacctcc tgggttcaag  24180
tgattctcct gcctcagcct cccaagtagc tgggactaca ggtgtgcgct aatttttgta  24240
tttttagtca agacggggtt tcaccatgtt ggccaggatc atctggatct cttgaccttg  24300
tgatccttcc gccttggcct cccaaagtac tgggattcca ggcgtgagcc accgcgcctg  24360
gccttagtaa agacttttaa agtaagactt tttcagtgaa agctactgtt aggcatgaca  24420
tttacaggca actgaaactg atcagatgca tttattaaga aggttaatgc ccctaggtgg  24480
ggtgggagaa agaaggtcgt ggtacgggaa gaggggacac actagagatg agatgcccta  24540
gggcagtgaa cgcatgtccc taatgcgtgg atgcagccca cgtccaccga taatgccgac  24600
acacccagag tctctcttct tactttagct tatgacttca cgaagaatgc tttgcaaatt  24660
ctaagttcgc actgggcgca agtggaattt tagtaaacat taagagttta acctttagtg  24720
tgaaataata tgcaagatat gcaaataatt gtttaccaac atctctttgc ttaatgtggt  24780
gagcatttaa taattgcttt ttattaatac atgagagatt tgtatttaga agcagtttaa  24840
tttataatta taatattaat ctacacaata acgacatcta ttattttctt tttttggaaa  24900
ctcttcatac cacactaaca ggttcattgc agttactgaa ctactctggc catcagagct  24960
ctccttagag ttacgattta ccatgcaaaa gcatatggta gcctgggata aatgaatctt  25020
tcttaataca gaattgaggg tctcaagttt gaaactacga gaggctattt gaatgttgct  25080
ttgggggact gtcataaggg ctgggtggag gactcagggc taagaagttt gccaggaagt  25140
ccagttgaga ctttcagcag agttgaaaga cttccacgat ggcgtaggca gaggaaggcg  25200
tttcagatac ttgggaaaat atagaagcca atttctcacc caccctacag caaagctcat  25260
tgatctacaa gtttccctag aaaggaaatg ggaaatgcag agaacaaatg ttaaaatagt  25320
tttagaaatt aatattgact ttgtattgct tctgcataag ttccaagaca ccaaaacaat  25380
gaatggattt taaaaagtca ctactttgca tatcagacaa atgcacacac acacacacac  25440
acacacacac acacacacac acacacagtc aagctctgta ctggcttttt tgagaaggaa  25500
agtgtttgaa gttagtaatt tttatatcag tacatttata aatagtgcta ggtagcatga  25560
cggaaagtat taaaatttac atgtatattt ttaacacttc aaatcgttgg ttcactttga  25620
```

```
gacagtaaat aatattagca tttgagttca gctttaataa attctacatg ggtttaaccc  25680
caaatctgag tgtctagttg gtaagcgcct tcagaacgag cagtgttata ataaatatgt  25740
tattgtgtgc tggtttcttt ccatggagag gaaaaagaga cctgatgctt tggaggagtg  25800
cttgactttt ccccagtgag gagtagtcca gagggactga cttgcattgg ggagtaccct  25860
acatgaacag catttcagaa gaattaaacc aggaacctag agtcctactt gctagtcctg  25920
cttcctaagc ttaatgagaa agtcaatttt atttctttga actttaattt atttccctaa  25980
aaaacgcttt tagtattgtc attgttctgg ctaatgatgg cggtctcctc cagtttcaag  26040
ccaccttagg gctgggcata caaatgcaat ataggatcac ttgttagtgt ggtttcaaat  26100
ggacatgatc ctctgtaaat tctttaaaaa catttaattt gatttgtggt gttacctgct  26160
ttaaaatata gtcatcacac ttgtgagttt cagacgtgaa tatgaatttt taatttgaac  26220
tgtattttta aacacactaa gtattaacta agtcccctta ggagatatgt ggcaaactga  26280
tatgcatcct cattcattct tctcatagat ggttatttgt tttttaactt gtggcaaaat  26340
tatatatgaa tggtcaccga cttaaaatag ttccacttaa atttttcaac tttctgatgg  26400
gtttattgga gtattaaatg tattttcaat ttaatgatat tttcagctta ccttgtgctt  26460
atcaagtatc aagacatagc ccccacctaag tcatggagca tctgtatatg ggtttttatt  26520
cttgtttaga attgactttt tcaagtgacc tatttcagta attagccctg ggcctgattt  26580
gcataatgag atctcctaat cttcaagtaa tgcaaagatg gagatattat ggccatgtgg  26640
tctgaagaga ccttttcttt attatgttca gatctttaat tgccttaaaa atagagtagc  26700
taatttacct aacctctagt tattttatta ttgtctttaa agtttttttt aatgttcatg  26760
aaataactgt tctgaaattg cctattttca agggaagctg tgtcttagac ttactaaatg  26820
ctccagttga tactgggaaa gccttcttgt gttcgtagcc tttatccgta gagttttctt  26880
tgcagcattt tctgtgcctg gtttagtttc ttttcagagg cgacacccag agctgaatga  26940
gtcagcaggt ttggtgtgtc gaccctttgc aacagctgtc cttacgaagg ttctgtgggc  27000
tggttattct accttcgcat aaaaccttgc aaaataaccc acaaagaggt tttcgtcaca  27060
ctaccaaaat catgtgagtc agagatggat gaaaaatgaa tgccattgtg ttcatacttt  27120
tccagtgaac agtagctaca gcagagctgt tagacaaaga aaaccgtatt aatgaagcgc  27180
ctcccaattt agcttcatat ggcttttgca ttattttgct gcaaatccat agctaagaca  27240
catcttgtgg catagtccgt aagtcatctt tccgaaggac tgtttgatta aaggttgttc  27300
tgtgagatcc accctgtgtt gttcatggca tcctcttgga ggcctccctc actctccatg  27360
ccttggcaaa gtcttcctta aggaacactg aacaagtctg gagaagctgc catttcttag  27420
ggccctcatt ggttcagttg tctatagctt tttatttttt attttttttt taataaagag  27480
tatgtaaaat tggaaagctt cacaaacagc tttgctattt tttagacatg tactccactt  27540
ctaagcaaaa tcacaaaata aagtaaaatg cttccacaaa tataatgaaa caatattctt  27600
aaagaatcaa agcagaagaa cttcagagtc tgttgcttat gttaagcata tatttgtttt  27660
cttctctgct tttgatttac ttatttctgg ggtgtaggtt tggcaagtag tactgaaacg  27720
tactgaatgc actgttcttt agcaagatag ttacaggagc tttcaaatgt cctcttaaca  27780
tatagatttc ttttagaata tagaataatg tgtgggctgt ataaagcgat tatgtgcttt  27840
atttgatgaa ttatttatgt acgataaatg tagcaaaagc cacatttcca tcattaaatg  27900
taatcccatt tggtgataca gcaacatcag cctgtcattt gggtcctctg attgaggggt  27960
gaggatttct gtttgatacc ttgtgcataa tggctgcgtt caagcattta aactcatttt  28020
```

tatttctaac ctacagctgt catctttgta ataggatatt catcagaatc ttgccagaga 28080
ctgtgcattt gggatcttgg gggatacagc accaccacca ccctccccct gtccaagaga 28140
aacagatcaa catcttaggt tgagagtctg gggtctggaa gacccgagtt cctgagtgcc 28200
ctttgacaag taacttaacc cctgtctgcc tcagtctctt catctgtaaa gtggggataa 28260
tgacagcacc tgcttcacag ggttgatggg aatccagatg tggtgggata tagaaaatgc 28320
ttattacttc cacctttgac accaaataca tataactaag agttaacttt ggagcagggg 28380
aggaagtgtg aggctccagg ctggaggcag acctgtgttc ggctgcaagc tggagaggat 28440
ggaccccaaa agcttggctg atttgaagtc catccataaa atggaactcc agagagttta 28500
cacgtttcag taatgctgca taacttaatt ataagatctt ctctctttgt cttctttcag 28560
tgttataaaa gctcttttgt ccttgagctt cctttaccaa gaaacatgca tttatgtatc 28620
tttttgttca tggaattgcc caagcttgtt agcagatcct ttgtaagacc caaaagagac 28680
agacagggga ggagtcttca gatacatata atcatttttc ccaatttcca tgttaccagc 28740
cttgccagga ctttttctca gttccctgtt acacaatgaa aatagtgtct ctttattgat 28800
aattttagta gcatcctaat gtggtataaa tcgtcttcca gagaagaaaa tgtgtcaggg 28860
ttgcgttatc actgaggcta gctgggaaag tagatcagcc cattagtctg ataattcgaa 28920
gcgttgtttc tgttatttct gaacatcatg tgaactcctt ttctgggtgt attaaaggtt 28980
ttcccagtgt gtgtcagtga gactcctgat tgaatttaat atgaataaag ataaattctt 29040
tacatttaag gattaaagtc tcagcttctg cttaacttga gattgcactg agaaactcct 29100
ggctctcggg tatagcggag tcacgacctg ggatgtctg tcccatatgg ctctgtgtgt 29160
aagaagaaaa agctgctgtg gacggagact ctgttcacat taaatgacat cacctaagcc 29220
atcatgacag caagaattat ttaggaattg ctcagaataa aactgccttc attatttcat 29280
aaaatgtatc ttggtatctt tagcacctta tttatggctt tttaaaggtt cactgggatt 29340
tataaataat tggacaatgc tagagaccta gtacaagaat gaaagaggac aggcttcttt 29400
cttaataacc tttaaacatt catcaggaag ataaaacttt aaagcaaaat aaaacacatg 29460
aaaatagcca agatgcacag accagacaag caaatactac tttaacttat ttgtatagtt 29520
cttaagagtc acatttgttc ctgaagtttc aaaatctcgg gctgagtgtt tgatcactta 29580
gggaagtgtt gtggccttca catactcttg tctcactttg aagtctagaa acacaggtct 29640
tagagcaatt tttatcactg tgagaaagct gaaacttagt gtgagtagct tagtacaatt 29700
cagttggcca tcaaatgtca gaaacaaaac tcagtccagg gccgctggac ccttaggccg 29760
gcgttgttag tttacaacag tgcctcctgg gtccaaacat ctaagtgcac atgtagcaat 29820
agtaaagata gtatgtatgc atacataaca catatgtaga gacagcagag tatacgtaca 29880
cacatgttgc atacatagca acagcagaga agctcatgaa ctataaagga tggactgtat 29940
gcttgtatca gacattttgg tactgacgct ttgtcatata ttgtgtaaca tataaccagc 30000
ttgcaatcat ctgcccccaa agttgaacta agaaaatcct acagggtact aggaaaggaa 30060
ggccattggg aaaaggtggt tatagtggca atttgttagc tcttatgaat tttctttttc 30120
tttttagaca tactcttaat tccatttttt caataaatct atactatttt gtgtttttat 30180
gttagcaagt actttaagcc cctcaataga aagttgctac atcatatagt gattaaaaat 30240
aaaaatctct caaacataca agtagaggtg gtatgagact tcaaattccc ttagccaagt 30300
acaagtgcag cagttttgtt ggctggctgg ctgcatagaa ggactgatgg attggcagac 30360
cctcaagctg gagtgtaatt gatctcatta cagaggagcc aggctgggtg acagttgtgc 30420

-continued

```
tttgcaagtg gttttttgca ttggtgaagt agcccatttt gttgttcctg atgttaaaca  30480
ggggatgaag gtattctttt attggcacaa acgcgggaaa ttgctctgga ttcttagagg  30540
atagaacatg tcccctggac ggaataaggt tcatgtgtag ggcaaattta gataggggca  30600
ccttattggg gttactactg gtctctagat ggtcaaagca aacaacatgt ccatctaagc  30660
tgtgatgtcc atctaagctg tgtgtgtcca tgagagtgac gcattttctc ctctgcagtg  30720
ttgttatatt ctaaactgtc agcagacatt aattcggtcg ctggtgaagt cccaccgcct  30780
agagatgaac tctgcctccg atggatgttt tccacttcag tgccactcgt ctcgcaatta  30840
ctgggtcatt aatatcattg catgcaatta gtgacagtag aaagagctag agggttgtgg  30900
gatgtgcacc ctccccacca tgaacttttt actctgaccc tttcccagct agaccttttc  30960
gtatcttggc aaggatattt taatgattga gactgtcaga atcttcagag caggcactgg  31020
attatgtgct ggaaataatt cactcaaaca cctgcttctc catggttcag aatattttca  31080
ttagatatta tcactatccc ttccctggga agtttcattt ttaaaaatct gatgcttaag  31140
tacagctaat atagacaata gggaattatg ttttatcttt agaactctta cattattctt  31200
ttctttaaaa atgtgagctg agtcattgct attgcagtgg tcatctggcc gcctattttt  31260
aaaacacaat tcctctatct tagtagattt tggcccatat taagcatatc aagaatgact  31320
tttttttttt caagacatgg ggttttattg ggggcttata tacaaggaaa gagagagtcc  31380
agtggcagtg ggctggacaa gatatccaca tggccctgtg gcagtgagct gggcaggaaa  31440
actgcaactg cttgcaaaca gcatgtagtt catctatagc attttcactt aacaccaccc  31500
agctaatgac ttccacctgg caaccttcat ttaatccaga acttaggacc tcgagtccct  31560
gtacggccca tgttccacag gatgggccga gggctcagct gttcctcata gacaaggaat  31620
gactctccac attggccact cccggattcc ctagctcagg acacatattc aggtgtgtct  31680
aaggctggct cttctatgtg aagttactta ttcttttacc attgactctc atgttcccac  31740
tatattaagt ttttctgaat tactgtggca ataagaaacg gtcccttaaa ttatactaga  31800
agaaaagctt ttttttgtt ttgtttttta ttttgaaatt atgttaaatt tttttcttta  31860
actgagagat tccacctgca taaatcgtca taacttttaa cagtaagatc ttagacttag  31920
aaagtgatgt ttttcctcaa cagaatttat taaaaatcaa gacaccaagc tgttccaaac  31980
aatagtttga ggggaaataa aataaacaac tccataaata atcttatgtt gttaaacatg  32040
tctctagcaa aacaaacaaa caaaaaagtc gggggttggg ggaggtgcag tttattgcca  32100
gtactgtctg gtctttctca gaaaagcgtc agtgtacatc actgagcctg gacggtatgt  32160
tttcttgatc tatacccccct atgtgtacat gtgcttgcac gcacacacat gtagacacgc  32220
acacatgtgc acctgccatc actttctgct cttccgtctt ttcactcttg agtgtctgta  32280
gccagtagct ttccaggtct gtatagtcaa agatacctat ggccctgaat gtcttcactg  32340
attgctattt gacattcata cggtttttaa tggttaaaag gctttatgcg aaagctgtga  32400
tagaatttct cctgttctag atgtggtgtt tattgcttta ttttgtgact tttctctcag  32460
tagattgacc ttctccctca gtgtccaagc ctcgcatagc atgatggcac ctgtaaactc  32520
agttctgtat cctggtatcc tttctcttcc caagtagaag caattaagta atatatgtca  32580
tcaaaacctt ttaagtgcac atacaaacaa aatcaactta ccaaactgct tcaaagttgt  32640
tccatgttta acactcttct ttctgagctc tgggtagaat gtcctattat tgttcatcat  32700
gaatatttga aattaaagaa ataaaactgt accattttct ttaagagcat ccatttgtac  32760
ttgataacat cttcagtcat atttcaatgc tggcaaagag gaggggagtt ctaaactgtg  32820
```

```
actcaatttt agaatctact ttttccaaat tattctgttt agtgcagaaa actaattaat  32880
agtgttgcat agaaaagtca ctgaagctaa gccagttatt acttcttaat gcatgattta  32940
ctgctttaag ttttcaaaac acaaccatag caatgtggta ttaattcaag tgattcttcc  33000
tatcatattg aacgatattt tcacgggtga aaaactcaca catcctacat cactgatagt  33060
ttatacagtg ttttagctgt ggctccctgc atgcaaaata agagttaatc aaatgtcagt  33120
gagaaccatc tcatcaagta gagggcttgt tttgtttaaa ttaactttgc taagtataaa  33180
tttcttcttg aaaataaatt ctgggccggg cgcggtggct cacgcctgta atcctagcac  33240
tttgggaggc cgaggcgggc ggatcacgag gtcaggagat cgagaccaaa ctggctaaca  33300
ctgtgaaacc ccgtctctac taaaaataca aaaaatgagc cgggtgtggt ggcgggctcc  33360
tgtagtccca gctactcggg aggctgaggc aggagaatgg cgtgaacctg ggaggcagag  33420
cttgtggtga gccaagatca caccactgca ctccagcctg ggtgacagag cgagactccg  33480
tctcaaaaaa aaaaaaaagg aaaataaatt cttctgtatt tttctttctt caagtgaggc  33540
catttagggg aaagtatacc ataaaacttg ctctaagata aggcaaattt ggtattatag  33600
gatgaagtgc tatgtgattt gaagtaatgc tgaatttttt aaatatatta aactaaacaa  33660
gaataatgag gccctcggaa agtcatgatt atatttctca tttttctcat tttaaagcca  33720
cagtgaaaaa cacataaaag gaagaagtta gaaaaaaaaa tgaatgaaat tcttttttttc  33780
cttttggcaa attaaataga tgtttctgtt tcagaagatt ttattaatta actttaaaga  33840
aacagtcatt tatttttggc attcagtgaa cactatcatt tccatgttta gaacttttct  33900
tctaagttag catcttaaaa gataactgtg aaactcaagg cattcaacta cattaatttg  33960
agtttcagaa attgaattct tgtttctaga gtacatagtt tgaattgatg tcagggtgtt  34020
aaatagataa atcttagctt cctaggttgt atattcacac taattatttt tttatcagcc  34080
ttcttatttt tcaacttacc ttattctttt tgttttttttg acactcagat ttgatagccc  34140
tgtggtagaa gaaaacagta atacagtttg gtttgttgtt gtgtttgtgt ttattttaaa  34200
gtcacggctt tgctttccat gttgttactg gattatgctt tttttaattc ttcagtttgc  34260
caagataaca gtcttccgat cttcagaagt ctgtatcaag cttaaggaaa ctgatgtgta  34320
ggaagactcg cctaagaagt ccaaattagc aaggctagca tgtgaggaca tgctggaaaa  34380
gaatagttcc catagatatt gacagagaat gttcataaaa tgctacttgt tttgtggtta  34440
catgagagta acttgtgtcc agtgcagctg tatgtaaggg caacgttttt attctgacga  34500
ctctgtggtt ttcatgaccc tggatgctta tcatgtctct ctgttggact tcttcaacgg  34560
agttgataca aatacttgct tccaagtgtc catctgccct ctcctccatc ctggccccat  34620
acaaatacgc tacattttta aataatttga aataccctca atagtattta tatttcctgg  34680
tgcttcattc tttccataag aactgtgata ccattattct gtaggatttt tttgtgcttc  34740
cccgtttcac atctctgtgc cagtgagacc catatatcgg tgcaaatcca gaagtttgat  34800
tgtccatctg attagcacac tgttagcaat gtggtggact aaacacagcc aagatgtggg  34860
gctggagctt agcctcctgg gagcagagcg gtgaacatca gatgaagaca tgtgaaaatg  34920
gagtactact tcctcttcct ggggatgggc taaaaagcac agccagaaat attcttgccc  34980
ttccagtctg ctttacagtt actcactggt tctctttttt ttcctactca gataaccagt  35040
atactcttcc cagtgactaa gaactgcaga taagtatagg tgcaaataga tggcaaaccg  35100
cagatggcag ctgtgtggtt tcagatgtgc tgcagaactt ttagacgatg tgaacgcaag  35160
gaactttttt gctgagcagt aatctctacc cactggaaat taggccctgg ggggaacaat  35220
```

```
gtagtgactt ctatatactt actacatgca gttagacccc tgaagcaaaa gcttttaaaa  35280
acaggctgta aaatgcccat gtatctttat taagcctatt ttccaactgg atagagaaat  35340
tttctggtaa tttttaaatt tgtaaagtct attttttttcc tgagccaagg gaaaaaaaat  35400
atctgggccc taaaagctta gttataacaa tgttattttt tctatctctg aatgattaaa  35460
tgtgatttca tttatgtagc aatactatga ttgtggctgc attagatcac gctgatagaa  35520
agatacaaag aaaaactaag tataatgaac taacaattta ttttcactct ttctctaagt  35580
taaaaattcc cagtacattc aaatgaacaa tgaaaataat tgcagaattg tctcctgaaa  35640
tggaaataga tttttttttcc caagcattag caatttcttg ttatttttca aaatcagcca  35700
ctaagccttt cagagcttct tggtgactat tgcaggagaa atcagaatat taatcttgtg  35760
gttttatttc agagttcgct gccaggaagg aggtataatt gggataggag actttttttt  35820
tttagctgtg tcactgttca aggagggggg tttggaacct cagcataaga attacactct  35880
gtgatgagga tgtagcaggg gagaagaaag gtgattttca ctatgggaag ctatacttac  35940
atcaagtata aaatagactg aagtcatttt gaattacgtt atacttgtaa agtttacctc  36000
ctggagtttc agttagtacc agtgtactaa ctgggttaaa acagttcatg gcaccttaga  36060
tcatttctaa ctcatggcaa aaatctttcc tggtggaacg tgtaactgta ttttaaatgc  36120
ccctttataa gcaaccaagt atttgggatg ttattttgat attagtagtg aatttttcag  36180
tatcttccag taccctttgc aagtcacagg ttgacttaaa aggaaaagaa gcaaaatgct  36240
gaatatagca gaaaaactgt ctgcattcag actgttcagc ccacttttgc tccccacgtg  36300
gcaagcacac tcccccaaac aagcaatagc ctgtggcttc agaggaacct acaaaggcag  36360
catctgtaga tttttccttc ttcaactcta agacttgaat gtttccctct tccccacaca  36420
cttttttttt aaaccaagaa ataaaaaagt tttcactctt aaaggtgcaa agcagtttca  36480
ttcttatgca acacagcctt cctcctactg tcttatagtc tgtggatgtt aaattataga  36540
ttccaattga attttaatac tctagagatt ttacatttgt ggttgtcaag accccgtttt  36600
ggtaaaccta gggagctccg cacaaaagca ttgatattca gaaaaggcac tgacctacaa  36660
attaaaagaa aaaaaaatca aataatgtgc acctcttgtg cttccagttt gacaaagcag  36720
aagtcatcag cagtttctcc ctctgcagac gcagttctca attctattta caagtaactg  36780
ctctactgtg cctgttttc tcttgctgat actcatttaa ttgtttttct tttggatctg  36840
aatctttgac tgtcttttcc ccctcaagat taaaataaat acatctgtat tcctcccctt  36900
tctttctgtg cactgccctt cagatctcat tttgtcattt ttcagcttag tgttgaaact  36960
tttagcaaca aaaagtcagt tacttacttt gagtaagtaa ctcaaagtaa gttaactttg  37020
agtttgagtg cacttttgcg tgtaggttca tttatgtgct tgtgaattta aaaacattgg  37080
gattccacct gaatgaagta aaccaaacat tttaaactat cagccagata gagacatcag  37140
cctttcactt ctttctatat gcagacatat cctaattttt tagaaaaatc aaataggaaa  37200
attctcaaca attaattgaa gattatagct ctgctctgaa atggtccaga aataggatct  37260
gctcatagaa actcatagtt tgaagcctct gggaggaaag gatactttaa aatttagtca  37320
catatttgga ggagggaaaa gggaaagagc agaatgaaga actgaaaaaa atcacacacc  37380
ggggcctgtc gtgaggtggg ggactggggg agggatagca ttaggagata tacctaatgt  37440
aaatgacgag ttaacaggcg cagcccacca acatggcaca cgtatacata tgtaacaaac  37500
ctgcacgttg tgcacatgta ccctagaact taaagtataa taaaaaaaaa ttttaatagc  37560
cccattaaat aattaaaaag atttttttta gattcacaga agtgtacaaa atttttaggt  37620
```

-continued

```
ttttttttt ttaagctgtc tgctgaatag tttcttaatg gtctacaatg tttgtatcta  37680
caaacagata ctgtctgctt cttactaccc ttccaagaca agtattatta tggcaattat  37740
tgcccagttt cccgggaaaa atttatccac agttacagaa gaatgagatg caattgtgag  37800
actgtaaagt ttaagcaagc actcagagaa gcacagtgat atgtatgcac agaagaggca  37860
gtctttgttt tgaggaaaac agtgaaagta aagttaattc aagaccacaa agacaagtaa  37920
ataagtgcct tatttttgta gttaatataa tttcagtgga atgcatattt ctaccataaa  37980
tgcatataga acttgtttgc tgacctactg tttggaaaac aaacaatccc attagaagaa  38040
tgtctttggg atttattttt accagaaaat caatcctttt ttcagtccct tgcaaagtac  38100
agtgttacaa gccaagactt tgataatcag gtagaaaatg gatttaaatt gcagaaatgt  38160
atatgaaaca cttttgttcc ttgccccttg aactttaggg gaatgaaaat gtctagcact  38220
ctccaccttc ttttctctcc tggaacttga actgtaattc aaagcctgtt tctcattaaa  38280
gtacctggca gcctatctct ttacagcttg agttacaaag ctattcagag acctcgctgg  38340
tctaaagaga cagaacaagg atgtgtttaa atagagcata ggctgttgaa aaaaaaaatg  38400
ctgaaaatgg taaaatgatt ctgtccttcc ttccactcct cactgctgag gtggagaggg  38460
aattcagttg gtgaacacca gcaagtggct ggtaaaagtc ccccactttct ctccagggct  38520
gccacaggac ccagaatgag tggtgggcat gtgtgtgaac cctctattca gccagagttt  38580
tcccgcaaca ggtagtttgg ttgaagaggt tgactaaggt tgacattggc agtaataaca  38640
cgtatgttct tctgatttac aaaacgatgg aggaaaaagg ggagattttg aagacctgat  38700
ttctggtata cttcttaagc atgcataagg ctgaaaaaag aagacaaggg ttgtgggagg  38760
ctcctggtct agtgtttaca gaacttggat gcttgacaaa cagagcgtca agctaattgt  38820
tcttgaagca ggaaatctgc agtggaggaa gcaggtgtgg ggggatgatt accacgtttg  38880
gaaatggctg cattaactat tttgctcttc tgagtttggc ccccaaaagag tccatagact  38940
ttttgaagga tgccatccct tttatttata gactaacatt aaatcagtca tttgtgaagg  39000
aaggagaaag tgcctaaata aatttggagt cagatagcat acgtgcggca gtgtttccga  39060
tatccatttc tctttatttc tttttctttt tctttttggc tttcagcatc cccatacttt  39120
cagaaaactt gtgactaaga gtgaattctt atttttcaaa ttgttttcag acatttcatg  39180
ttcatgtaaa cttggcttat tgatttcctg atttttcttt attttttgt tttgtccatt  39240
ttatttttaa tcagctacat caaatgggtc tttggagggc ctggataacc aggagggagg  39300
ggtgtgccag acaagagcca tgaagatcct catgaaagtt ggacaaggta aagaccatct  39360
gctgcttcat gacgccactg tgacctggtg tagcccccag ctagtatggt gctaatgttg  39420
ccgatgccca ccttcattcg ctcttctttt tagttttcaa agcaaaccct tctgcacttt  39480
gagccactga cagatttcct caagtcaatg tactaagctt ttattggaga tctaagagtt  39540
aagatcagca aggtagaatg tctattgcca tagatagata gatagataga tagataatag  39600
atagatagat agatagatag atatttcttt ttaaaaagca aaacactttg gttcaaaatc  39660
aaaatatcca gaatgaaaac taaaagcttg tgcagttttg ctcatttctg aatcttgact  39720
acagaagagt tttgttcatt gtgacttttc caatatagat aacctattgt gcagaaagaa  39780
ataattattc ttctaattaa aaattggtat agtagtcaat caacttgctc agttaaattg  39840
aaatgtcatc tgcaatgctt tgcctgccaa atgcaagaat ccctatagtt tccacagatg  39900
gcctcacgtt ctaaacctct gaaataacta gtataaccat tttgttttaa aagaaaaatt  39960
atattcttgt atttcacagt actttgcata aagactctta tgttcattgc tattcatgcc  40020
```

tgttgaaata tatatgcagc tcctaaagct agatattgtc agatgtctgt gccgtaatta 40080
atcatttgtt tttcatatag atgcaagttc tgctggatca accaggaata aagatccaac 40140
aagacgtcca gaactagaag ctggtacaaa tggaagaagt tcgacaacaa gtccctttgt 40200
aaaaccaaat ccaggtataa cagcatgatc tgtgtgtatg gaggtctgtg ggtaccacat 40260
tcttagtagt atcttaaaag gtagggcaga gtctaaagac ttctaaccag ttaggattag 40320
ctggaagtta cagtgatcag gaatctttgc tgtcagtgag tcattattaa ttacactcaa 40380
taagaacaaa ataactcatt ccaatgaaag tcatatattc aaaggagtag agttcatgag 40440
ctgtaagtgc cagttattag aactactctg tcaggccaaa ggtttcattg gctgacattt 40500
tatcaagctg gttgtcaact ccagcttaaa gctgatgtta atgtatatgt aattaatgtg 40560
ctaatccctc atctaattat atctaagcca cagagggttt aattgatcct cttctaaatt 40620
ttaaatggta acatttttaa atattgcata atagtatttt ttcaggtggt tatcgttatt 40680
ttgtttcaca ttttccatgt aaaagaaaat attaaacagg tccctgacaa aagtgtagaa 40740
taccagataa aattgtccgt cgttgacctt cgttttctta acagtcttgg aacaaatagt 40800
tctgtatttg ttaccatgct aatgaaggtt ttatagagta gctgttgagc agacatcagc 40860
agttttgtat taggattgtt gtgtgcttgc ttggtcgttg tgcaaattta tcgtctgcag 40920
caatattcca tccctttcca agagtcaagg agggaagttg ttatttctaa ctttcaatga 40980
caagatgtgt caaattcttg tgacaaactg ataaatggat aatataatga tgccaggcag 41040
ttttttagtg cttaacattt gggctggcag tctgttcggt gtgagagttt ctgctgcctt 41100
ccaaatatat tttaagtgta aatcaaataa tacagacgag ttacgagctg aacattttcc 41160
caggccccct cactccttcc gcgttcccga gctgttctgt tctgccagga ggcagggctc 41220
ttctttagaa ggcaggccct ttgaaggttt gcatgaaact ccctttctca aaggaggcgg 41280
aagagcaata ccacataaac gctcaccgct gacctggaga attggccact tcccttttc 41340
ttccctgccg ctgccccagg ctggctgaca cgggttagaa gatgaagcaa gatcaagggc 41400
tggctgtcac cgacagtctg tgctcttgct ggataatgat acaaaggaaa ccctgtggct 41460
tgggagggta gggaagtccc tcctagagat acctctcatt tccttttgcg ttgagctctt 41520
agacgaggta ttggcgaggc aaagtccagc ttctagttag taataagcct ggcttatttt 41580
tcacattttt aagggtcata aaagcagtcc gtctgcactg ggacagcagt aactatctct 41640
gaccttttct gtctccgcgt ctgcaggttc tagcacagac ggcaacagcg ccggacattc 41700
ggggaacaac atcctcggtt ccgaagtggc cttatttgca gggattgctt caggatgcat 41760
catcttcatc gtcatcatca tcacgctggt ggtcctcttg ctgaagtacc ggaggagaca 41820
caggaagcac tcgccgcagc acacgaccac gctgtcgctc agcacactgg ccacacccaa 41880
gcgcagcggc aacaacaacg gctcagagcc cagtgacatt atcatcccgc taaggactgc 41940
ggacagcgtc ttctgccctc actacgagaa ggtcagcggc gactacgggc acccggtgta 42000
catcgtccag gagatgcccc cgcagagccc ggcgaacatt tactacaagg tctgagaggg 42060
accctggtgg tacctgtgct ttcccagagg acacctaatg tcccgatgcc tcccttgagg 42120
gtttgagagc ccgcgtgctg gagaattgac tgaagcacag caccgggga gagggacact 42180
cctcctcgga agagcccgtc gcgctggaca gcttacctag tcttgtagca ttcggccttg 42240
gtgaacacac acgctccctg gaagctggaa gactgtgcag aagacgccca ttcggactgc 42300
tgtgccgcgt cccacgtctc ctcctcgaag ccatgtgctg cggtcactca ggcctctgca 42360
gaagccaagg gaagacagtg gtttgtggac gagagggctg tgagcatcct ggcaggtgcc 42420

```
ccaggatgcc acgcctggaa gggccggctt ctgcctgggg tgcatttccc ccgcagtgca  42480
taccggactt gtcacacgga cctcgggcta gttaaggtgt gcaaagatct ctagagttta  42540
gtccttactg tctcactcgt tctgttaccc agggctctgc agcacctcac ctgagacctc  42600
cactccacat ctgcatcact catggaacac tcatgtctgg agtcccctcc tccagccgct  42660
ggcaacaaca gcttcagtcc atgggtaatc cgttcataga aattgtgttt gctaacaagg  42720
tgccctttag ccagatgcta ggctgtctgc gaagaaggct aggagttcat agaagggagt  42780
ggggctgggg aaagggctgg ctgcaattgc agctcactgc tgctgcctct gaaacagaaa  42840
gttggaaagg aaaaaagaaa aaagcaatta ggtagcacag cactttggtt ttgctgagat  42900
cgaagaggcc agtaggagac acgacagcac acacagtgga ttccagtgca tggggaggca  42960
ctcgctgtta tcaaatagcg atgtgcagga agaaaagccc ctcttcattc cggggaacaa  43020
agacgggtat tgttgggaaa ggaacaggct tggagggaag ggagaaagta ggccgctgat  43080
gatatattcg ggcaggactg ttgtggtact ggcaataaga tacacagctc cgagctgtag  43140
gagagtcggt ctgctttgga tgatttttta agcagactca gctgctatac ttatcacatt  43200
ttattaaaca cagggaaagc atttaggaga atagcagaga gccaaatctg acctaaaagt  43260
tgaaaagcca aaggtcaaac aggctgtaat tccatcatca tcgttgttat taaagaatcc  43320
ttatctataa aaggtaggtc agatcccccct cccccaggt tcctccttcc cctcccgatt  43380
gagccttacg acactttggt ttatgcggtg ctgtccgggt gccagggctg cagggtcggt  43440
actgatggag gctgcagcgc ccggtgctct gtgtcaaggt gaagcacata cggcagacct  43500
cttagagtcc ttaagacgga agtaaattat gatgtccagg gggagaagga agataggacg  43560
tatttataat aggtatatag aacacaaggg atataaaatg aaagattttt actaatatat  43620
attttaaggt tgcacacagt acacaccaga agatgtgaaa ttcatttgtg gcaattaagt  43680
ggtcccaatg ctcagcgctt aaaaaaacaa attggacagc tacttctggg aaaaacaaca  43740
tcattccaaa aagaacaata atgagagcaa atgcaaaaat aaccaagtcc tccgaaggca  43800
tctcacggaa ccgtagacta ggaagtacga gccccacaga gcaggaagcc gatgtgactg  43860
catcatatat ttaacaatga caagatgttc cggcgtttat ttctgcgttg ggttttccct  43920
tgccttatgg gctgaagtgt tctctaga                                     43948
```

<210> SEQ ID NO 394
<211> LENGTH: 4335
<212> TYPE: DNA
<213> ORGANISM: Homo sapiens

<400> SEQUENCE: 394

```
gcgcggagct gggagtggct tcgccatggc tgtgagaagg gactccgtgt ggaagtactg     60
ctggggtgtt ttgatggttt tatgcagaac tgcgatttcc aaatcgatag ttttagagcc    120
tatctattgg aattcctcga actccaaatt tctacctgga caaggactgg tactataccc    180
acagatagga gacaaattgg atattatttg ccccaaagtg gactctaaaa ctgttggcca    240
gtatgaatat tataaagttt atatggttga taaagaccaa gcagacagat gcactattaa    300
gaaggaaaat acccctctcc tcaactgtgc caaaccagac caagatatca aattcaccat    360
caagtttcaa gaattcagcc ctaacctctg ggtctagaa tttcagaaga acaaagatta    420
ttacattata tctacatcaa atgggtcttt ggagggcctg gataaccagg agggaggggt    480
gtgccagaca agagccatga agatcctcat gaaagttgga caagatgcaa gttctgctgg    540
atcaaccagg aataaagatc caacaagacg tccagaacta gaagctggta caaatggaag    600
```

```
aagttcgaca acaagtccct ttgtaaaacc aaatccaggt tctagcacag acggcaacag    660
cgccggacat tcggggaaca acatcctcgg ttccgaagtg gccttatttg cagggattgc    720
ttcaggatgc atcatcttca tcgtcatcat catcacgctg gtggtcctct tgctgaagta    780
ccggaggaga cacaggaagc actcgccgca gcacacgacc acgctgtcgc tcagcacact    840
ggccacaccc aagcgcagcg gcaacaacaa cggctcagag cccagtgaca ttatcatccc    900
gctaaggact gcggacagcg tcttctgccc tcactacgag aaggtcagcg gggactacgg    960
gcacccggtg tacatcgtcc aggagatgcc cccgcagagc ccggcgaaca tttactacaa   1020
ggtctgagag ggaccctggt ggtacctgtg ctttcccaga ggacacctaa tgtcccgatg   1080
cctcccttga gggtttgaga gcccgcgtgc tggagaattg actgaagcac agcaccgggg   1140
gagagggaca ctcctcctcg gaagagcccg tcgcgctgga cagcttacct agtcttgtag   1200
cattcggcct tggtgaacac acacgctccc tggaagctgg aagactgtgc agaagacgcc   1260
cattcggact gctgtgccgc gtcccacgtc tcctcctcga agccatgtgc tgcggtcact   1320
caggcctctg cagaagccaa gggaagacag tggtttgtgg acgagagggc tgtgagcatc   1380
ctggcaggtg ccccaggatg ccacgcctgg aagggccggc ttctgcctgg ggtgcatttc   1440
ccccgcagtg cataccggac ttgtcacacg gacctcgggc tagttaaggt gtgcaaagat   1500
ctctagagtt tagtccttac tgtctcactc gttctgttac ccagggctct gcagcacctc   1560
acctgagacc tccactccac atctgcatca ctcatggaac actcatgtct ggagtcccct   1620
cctccagccg ctggcaacaa cagcttcagt ccatgggtaa tccgttcata gaaattgtgt   1680
ttgctaacaa ggtgcccttt agccagatgc taggctgtct gcgaagaagg ctaggagttc   1740
atagaaggga gtggggctgg ggaaagggct ggctgcaatt gcagctcact gctgctgcct   1800
ctgaaacaga aagttggaaa ggaaaaaaga aaaaagcaat taggtagcac agcactttgg   1860
ttttgctgag atcgaagagg ccagtaggag acacgacagc acacacagtg gattccagtg   1920
catggggagg cactcgctgt tatcaaatag cgatgtgcag gaagaaaagc ccctcttcat   1980
tccggggaac aaagacgggt attgttggga aaggaacagg cttggaggga agggagaaag   2040
taggccgctg atgatatatt cgggcaggac tgttgtggta ctggcaataa gatacacagc   2100
tccgagctgt aggagagtcg gtctgctttg gatgattttt taagcagact cagctgctat   2160
acttatcaca ttttattaaa cacagggaaa gcatttagga gaatagcaga gagccaaatc   2220
tgacctaaaa gttgaaaagc caaaggtcaa acaggctgta attccatcat catcgttgtt   2280
attaaagaat ccttatctat aaaaggtagg tcagatcccc ctccccccag gttcctcctt   2340
cccctcccga ttgagcctta cgacactttg gtttatgcgg tgctgtccgg gtgccagggc   2400
tgcagggtcg gtactgatgg aggctgcagc gcccggtgct ctgtgtcaag gtgaagcaca   2460
tacggcagac ctcttagagt ccttaagacg gaagtaaatt atgatgtcca gggggagaag   2520
gaagatagga cgtatttata ataggtatat agaacacaag ggatataaaa tgaaagattt   2580
ttactaatat atattttaag gttgcacaca gtacacacca gaagatgtga aattcatttg   2640
tggcaattaa gtggtcccaa tgctcagcgc ttaaaaaaac aaattggaca gctacttctg   2700
ggaaaaacaa catcattcca aaaagaacaa taatgagagc aaatgcaaaa ataaccaagt   2760
cctccgaagg catctcacgg aaccgtagac taggaagtac gagccccaca gagcaggaag   2820
ccgatgtgac tgcatcatat atttaacaat gacaagatgt tccggcgttt atttctgcgt   2880
tgggttttcc cttgccttat gggctgaagt gttctctaga atccagcagg tcacactggg   2940
ggcttcaggt gacgatttag ctgtggctcc ctcctcctgt cctcccccgc accccctccc   3000
```

ttctgggaaa caagaagagt aaacaggaaa cctacttttt atgtgctatg caaaatagac 3060
atctttaaca tagtcctgtt actatggtaa cactttgctt tctgaattgg aagggaaaaa 3120
aaatgtagcg acagcatttt aaggttctca gacctccagt gagtacctgc aaaaatgagt 3180
tgtcacagaa attatgatcc tctatttcct gaacctggaa atgatgttgg tccaaagtgc 3240
gtgtgtgtat gtgtgagtgg gtgcgtggta tacatgtgta catatatgta taatatatat 3300
ctacaatata tattatatat atctatatca tatttctgtg gagggttgcc atggtaacca 3360
gccacagtac atatgtaatt ctttccatca ccccaacctc tcctttctgt gcattcatgc 3420
aagagtttct tgtaagccat cagaagttac ttttaggatg ggggagaggg gcgagaaggg 3480
gaaaaatggg aaatagtctg attttaatga aatcaaatgt atgtatcatc agttggctac 3540
gttttggttc tatgctaaac tgtgaaaaat cagatgaatt gataaaagag ttccctgcaa 3600
ccaattgaaa agtgttctgt gcgtctgttt tgtgtctggt gcagaatatg acaatctacc 3660
aactgtccct ttgtttgaag ttggtttagc tttggaaagt tactgtaaat gccttgcttg 3720
tatgatcgtc cctggtcacc cgactttgga atttgcacca tcatgtttca gtgaagatgc 3780
tgtaaatagg ttcagatttt actgtctatg gatttggggt gttacagtag ccttattcac 3840
ctttttaata aaaatacaca tgaaaacaag aaagaaatgg cttttcttac ccagattgtg 3900
tacatagagc aatgttggtt ttttataaag tctaagcaag atgttttgta taaaatctga 3960
attttgcaat gtatttagct acagcttgtt taacggcagt gtcattcccc tttgcactgt 4020
aatgaggaaa aaatggtata aaaggttgcc aaattgctgc atatttgtgc cgtaattatg 4080
taccatgaat atttatttaa aatttcgttg tccaatttgt aagtaacaca gtattatgcc 4140
tgagttataa atattttttt ctttctttgt tttattttaa tagcctgtca taggttttaa 4200
atctgcttta gtttcacatt gcagttagcc ccagaaaatg aaatccgtga agtcacattc 4260
cacatctgtt tcaaactgaa tttgttctta aaaaaataaa atattttttt cctatggaaa 4320
aaaaaaaaaa aaaaa 4335

<210> SEQ ID NO 395
<211> LENGTH: 987
<212> TYPE: PRT
<213> ORGANISM: Homo sapiens

<400> SEQUENCE: 395

Met Glu Leu Arg Val Leu Leu Cys Trp Ala Ser Leu Ala Ala Ala Leu
1 5 10 15

Glu Glu Thr Leu Leu Asn Thr Lys Leu Glu Thr Ala Asp Leu Lys Trp
20 25 30

Val Thr Phe Pro Gln Val Asp Gly Gln Trp Glu Glu Leu Ser Gly Leu
35 40 45

Asp Glu Glu Gln His Ser Val Arg Thr Tyr Glu Val Cys Asp Val Gln
50 55 60

Arg Ala Pro Gly Gln Ala His Trp Leu Arg Thr Gly Trp Val Pro Arg
65 70 75 80

Arg Gly Ala Val His Val Tyr Ala Thr Leu Arg Phe Thr Met Leu Glu
85 90 95

Cys Leu Ser Leu Pro Arg Ala Gly Arg Ser Cys Lys Glu Thr Phe Thr
100 105 110

Val Phe Tyr Tyr Glu Ser Asp Ala Asp Thr Ala Thr Ala Leu Thr Pro
115 120 125

Ala Trp Met Glu Asn Pro Tyr Ile Lys Val Asp Thr Val Ala Ala Glu

```
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Leu Ala Leu Ile Ala Gly Thr
    530                 535                 540

Ala Val Val Gly Val Val Leu Val Leu Val Val Ile Val Val Ala Val
545                 550                 555                 560
```

-continued

```
Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
        595                 600                 605

Glu Ile Asp Val Ser Tyr Val Lys Ile Glu Glu Val Ile Gly Ala Gly
    610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Met Pro
        675                 680                 685

Val Met Ile Leu Thr Glu Phe Met Glu Asn Gly Ala Leu Asp Ser Phe
    690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
        755                 760                 765

Ser Ser Asp Pro Thr Tyr Thr Ser Ser Leu Gly Gly Lys Ile Pro Ile
    770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Pro Asp Cys Pro Thr Ser
        835                 840                 845

Leu His Gln Leu Met Leu Asp Cys Trp Gln Lys Asp Arg Asn Ala Arg
    850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
        915                 920                 925

Ala Ala Ala Gly Phe Gly Ser Phe Glu Leu Val Ser Gln Ile Ser Ala
    930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
                965                 970                 975

Pro Gly Gly Thr Gly Gly Pro Ala Pro Gln Tyr
            980                 985
```

-continued

<210> SEQ ID NO 396
<211> LENGTH: 333
<212> TYPE: PRT
<213> ORGANISM: Homo sapiens

<400> SEQUENCE: 396

```
Met Ala Val Arg Arg Asp Ser Val Trp Lys Tyr Cys Trp Gly Val Leu
 1               5                  10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Ala Leu Phe Ala Gly Ile Ala Ser Gly Cys Ile Ile Phe Ile Val
225                 230                 235                 240

Ile Ile Ile Thr Leu Val Val Leu Leu Leu Lys Tyr Arg Arg Arg His
                245                 250                 255

Arg Lys His Ser Pro Gln His Thr Thr Thr Leu Ser Leu Ser Thr Leu
            260                 265                 270

Ala Thr Pro Lys Arg Ser Gly Asn Asn Asn Gly Ser Glu Pro Ser Asp
        275                 280                 285

Ile Ile Ile Pro Leu Arg Thr Ala Asp Ser Val Phe Cys Pro His Tyr
    290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
                325                 330
```

<210> SEQ ID NO 397
<211> LENGTH: 29
<212> TYPE: DNA
<213> ORGANISM: Unknown
<220> FEATURE:
<223> OTHER INFORMATION: oligonucleotide primer

<400> SEQUENCE: 397
ggatccgcca tggagctccg ggtgctgct 29

<210> SEQ ID NO 398
<211> LENGTH: 27
<212> TYPE: DNA
<213> ORGANISM: Unknown
<220> FEATURE:
<223> OTHER INFORMATION: oligonucleotide primer

<400> SEQUENCE: 398
gcggccgctc agtactgcgg ggccggt 27

<210> SEQ ID NO 399
<211> LENGTH: 2981
<212> TYPE: DNA
<213> ORGANISM: Homo sapiens

<400> SEQUENCE: 399
ggatccgcca tggagctccg ggtgctgctc tgctgggctt cgttggccgc agctttggaa 60
gagaccctgc tgaacacaaa attggaaact gctgatctga agtgggtgac attccctcag 120
gtggacgggc agtgggagga actgagcggc ctggatgagg aacagcacag cgtgcgcacc 180
tacgaagtgt gtgaagtgca gcgtgccccg ggccaggccc actggcttcg cacaggttgg 240
gtcccacggc ggggcgccgt ccacgtgtac gccacgctgc gcttcaccat gctcgagtgc 300
ctgtccctgc ctcgggctgg gcgctcctgc aaggagacct tcaccgtctt ctactatgag 360
agcgatgcgg acacggccac ggccctcacg ccagcctgga tggagaaccc ctacatcaag 420
gtggacacgg tggccgcgga gcatctcacc cggaagcgcc ctggggccga ggccaccggg 480
aaggtgaatg tcaagacgct gcgtctggga ccgctcagca aggctggctt ctacctggcc 540
ttccaggacc agggtgcctg catggccctg ctatccctgc acctcttcta caaaaagtgc 600
gcccagctga ctgtgaacct gactcgattc ccggagactg tgcctcggga gctggttgtg 660
cccgtggccg gtagctgcgt ggtggatgcc gtccccgccc ctggccccag ccccagcctc 720
tactgccgtg aggatggcca gtgggccgaa cagccggtca cgggctgcag ctgtgctccg 780
gggttcgagg cagctgaggg gaacaccaag tgccgagcct gtgcccaggg caccttcaag 840
cccctgtcag gagaagggtc ctgccagcca tgcccagcca atagccactc taacaccatt 900
ggatcagccg tctgccagtg ccgcgtcggg tacttccggg cacgcacaga cccccggggt 960
gcaccctgca ccacccctcc ttcggctccg cggagcgtgg tttcccgcct gaacggctcc 1020
tccctgcacc tggaatggag tgcccccctg gagtctggtg gccgagagga cctcacctac 1080
gccctccgct gccgggagtg ccgacccgga ggctcctgtg cgccctgcgg gggagacctg 1140
acttttgacc ccggcccccg ggacctggtg gagccctggg tggtggttcg agggctacgt 1200
ccggacttca cctatacctt tgaggtcact gcattgaacg ggtatcctc cttagccacg 1260 gggcccgtcc catttgagcc tgtcaatgtc accactgacc gagaggtacc tcctgcagtg 1320
tctgacatcc gggtgacgcg gtcctcaccc agcagcttga gcctggcctg ggctgttccc 1380
cgggcaccca gtggggcgtg gctggactac gaggtcaaat accatgagaa gggcgccgag 1440
ggtcccagca gcgtgcggtt cctgaagacg tcagaaaacc gggcagagct gcgggggctg 1500
aagcggggag ccagctacct ggtgcaggta cgggcgcgct ctgaggccgg ctacgggccc 1560
ttcggccagg aacatcacag ccagacccaa ctggatgaga gcgagggctg gcgggagcag 1620
ctggccctga ttgcgggcac ggcagtcgtg ggtgtggtcc tggtcctggt ggtcattgtg 1680

-continued

```
gtcgcagttc tctgcctcag gaagcagagc aatgggagag aagcagaata ttcggacaaa   1740

cacggacagt atctcatcgg acatggtact aaggtctaca tcgacccctt cacttatgaa   1800

gaccctaatg aggctgtgag ggaatttgca aaagagatcg atgtctccta cgtcaagatt   1860

gaagaggtga ttggtgcagg tgagtttggc gaggtgtgcc gggggcggct caaggcccca   1920

gggaagaagg agagctgtgt ggcaatcaag accctgaagg gtggctacac ggagcggcag   1980

cggcgtgagt ttctgagcga ggcctccatc atgggccagt tcgagcaccc caatatcatc   2040

cgcctggagg gcgtggtcac caacagcatg cccgtcatga ttctcacaga gttcatggag   2100

aacggcgccc tggactcctt cctgcggcta aacgacggac agttcacagt catccagctc   2160

gtgggcatgc tgcggggcat cgcctcgggc atgcggtacc ttgccgagat gagctacgtc   2220

caccgagacc tggctgctcg caacatccta gtcaacagca acctcgtctg caaagtgtct   2280

gactttggcc tttcccgatt cctggaggag aactcttccg atcccaccta cacgagctcc   2340

ctgggaggaa agattcccat ccgatggact gccccggagg ccattgcctt ccggaagttc   2400

acttccgcca gtgatgcctg gagttacggg attgtgatgt gggaggtgat gtcatttggg   2460

gagaggccgt actgggacat gagcaatcag gacgtgatca atgccattga acaggactac   2520

cggctgcccc cgcccccaga ctgtcccacc tccctccacc agctcatgct ggactgttgg   2580

cagaaagacc ggaatgcccg gccccgcttc ccccaggtgg tcagcgccct ggacaagatg   2640

atccggaacc ccgccagcct caaaatcgtg gcccgggaga atggcggggc ctcacaccct   2700

ctcctggacc agcggcagcc tcactactca gcttttggct ctgtgggcga gtggcttcgg   2760

gccatcaaaa tgggaagata cgaagaaagt ttcgcagccg ctggctttgg ctccttcgag   2820

ctggtcagcc agatctctgc tgaggacctg ctccgaatcg gagtcactct ggcgggacac   2880

cagaagaaaa tcttggccag tgtccagcac atgaagtccc aggccaagcc gggaaccccg   2940

ggtgggacag gaggaccggc cccgcagtac tgagcggccg c                       2981
```

```
<210> SEQ ID NO 400
<211> LENGTH: 27
<212> TYPE: DNA
<213> ORGANISM: Unknown
<220> FEATURE:
<223> OTHER INFORMATION: oligonucleotide primer

<400> SEQUENCE: 400

gcggccgctc agtactgcgg ggccggt                                         27


<210> SEQ ID NO 401
<211> LENGTH: 29
<212> TYPE: DNA
<213> ORGANISM: Unknown
<220> FEATURE:
<223> OTHER INFORMATION: oligonucleotide primer

<400> SEQUENCE: 401

gcggccgcag ttcctgcagg tcaagtact                                       29


<210> SEQ ID NO 402
<211> LENGTH: 32
<212> TYPE: DNA
<213> ORGANISM: Unknown
<220> FEATURE:
<223> OTHER INFORMATION: oligonucleotide primer

<400> SEQUENCE: 402

tactagtccg ccatggagct ccgggtgctg ct                                   32
```

<210> SEQ ID NO 403
<211> LENGTH: 50
<212> TYPE: DNA
<213> ORGANISM: Unknown
<220> FEATURE:
<223> OTHER INFORMATION: oligonucleotide primer

<400> SEQUENCE: 403
gcggccgctt aatggtgatg gtgatgatga gccgaaggag gggtggtgca 50

<210> SEQ ID NO 404
<211> LENGTH: 1018
<212> TYPE: DNA
<213> ORGANISM: Homo sapiens

<400> SEQUENCE: 404
actagtccgc catggagctc cgggtgctgc tctgctgggc ttcgttggcc gcagctttgg 60
aagagaccct gctgaacaca aaattggaaa ctgctgatct gaagtgggtg acattccctc 120
aggtggacgg gcagtgggag gaactgagcg gcctggatga ggaacagcac agcgtgcgca 180
cctacgaagt gtgtgaagtg cagcgtgccc cgggccaggc ccactggctt cgcacaggtt 240
gggtcccacg gcggggcgcc gtccacgtgt acgccacgct gcgcttcacc atgctcgagt 300
gcctgtccct gcctcgggct gggcgctcct gcaaggagac cttcaccgtc ttctactatg 360
agagcgatgc ggacacggcc acggccctca cgccagcctg gatggagaac ccctacatca 420
aggtggacac ggtggccgcg gagcatctca cccggaagcg ccctggggcc gaggccaccg 480
ggaaggtgaa tgtcaagacg ctgcgtctgg gaccgctcag caaggctggc ttctacctgg 540
ccttccagga ccagggtgcc tgcatggccc tgctatccct gcacctcttc tacaaaaagt 600
gcgcccagct gactgtgaac ctgactcgat tcccggagac tgtgcctcgg gagctggttg 660
tgcccgtggc cggtagctgc gtggtggatg ccgtccccgc ccctggcccc agccccagcc 720
tctactgccg tgaggatggc cagtgggccg aacagccggt cacgggctgc agctgtgctc 780
cggggttcga ggcagctgag gggaacacca agtgccgagc ctgtgcccag ggcaccttca 840
agcccctgtc aggagaaggg tcctgccagc catgcccagc caatagccac tctaacacca 900
ttggatcagc cgtctgccag tgccgcgtcg ggtacttccg ggcacgcaca gacccccggg 960
gtgcaccctg caccacccct ccttcggctc atcatcacca tcaccattaa gcggccgc 1018

<210> SEQ ID NO 405
<211> LENGTH: 332
<212> TYPE: PRT
<213> ORGANISM: Homo sapiens

<400> SEQUENCE: 405

Met Glu Leu Arg Val Leu Leu Cys Trp Ala Ser Leu Ala Ala Ala Leu
1 5 10 15

Glu Glu Thr Leu Leu Asn Thr Lys Leu Glu Thr Ala Asp Leu Lys Trp
20 25 30

Val Thr Phe Pro Gln Val Asp Gly Gln Trp Glu Glu Leu Ser Gly Leu
35 40 45

Asp Glu Glu Gln His Ser Val Arg Thr Tyr Glu Val Cys Glu Val Gln
50 55 60

Arg Ala Pro Gly Gln Ala His Trp Leu Arg Thr Gly Trp Val Pro Arg
65 70 75 80

Arg Gly Ala Val His Val Tyr Ala Thr Leu Arg Phe Thr Met Leu Glu
85 90 95

```
Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala His His His His His His
                325                 330
```

<210> SEQ ID NO 406
<211> LENGTH: 6860
<212> TYPE: DNA
<213> ORGANISM: Unknown
<220> FEATURE:
<223> OTHER INFORMATION: plasmid vector sequence

<400> SEQUENCE: 406

```
aatattattg aagcatttat cagggttatt gtctcatgag cggatacata tttgaatgta      60

tttagaaaaa taaacaaata ggggttccgc gcacatttcc ccgaaaagtg ccacctgacg     120

tcgacggatc gggagatctc ccgatcccct atggtcgact ctcagtacaa tctgctctga     180

tgccgcatag ttaagccagt atctgctccc tgcttgtgtg ttggaggtcg ctgagtagtg     240

cgcgagcaaa atttaagcta caacaaggca aggcttgacc gacaattgca tgaagaatct     300

gcttagggtt aggcgttttg cgctgcttcg cgatgtacgg gccagatata cgcgttgaca     360

ttgattattg actaggcttt tgcaaaaagc tttgcaaaga tggataaagt tttaaacaga     420

gaggaatctt tgcagctaat ggaccttcta ggtcttgaaa ggagtgcctc gtgaggctcc     480

ggtgcccgtc agtgggcaga gcgcacatcg cccacagtcc ccgagaagtt ggggggaggg     540

gtcggcaatt gaaccggtgc ctagagaagg tggcgcgggg taaactggga aagtgatgtc     600

gtgtactggc tccgcctttt tcccgagggt gggggagaac cgtatataag tgcagtagtc     660

gccgtgaacg ttctttttcg caacgggttt gccgccagaa cacaggtaag tgccgtgtgt     720

ggttcccgcg ggcctggcct ctttacgggt tatggccctt gcgtgccttg aattacttcc     780
```

-continued

```
acctggctgc agtacgtgat tcttgatccc gagcttcggg ttggaagtgg gtgggagagt    840
tcgaggcctt gcgcttaagg agccccttcg cctcgtgctt gagttgaggc ctggcctggg    900
cgctggggcc gccgcgtgcg aatctggtgg caccttcgcg cctgtctcgc tgctttcgat    960
aagtctctag ccatttaaaa tttttgatga cctgctgcga cgcttttttt ctggcaagat   1020
agtcttgtaa atgcgggcca agatctgcac actggtattt cggtttttgg ggccgcgggc   1080
ggcgacgggg cccgtgcgtc ccagcgcaca tgttcggcga ggcggggcct gcgagcgcgg   1140
ccaccgagaa tcggacgggg gtagtctcaa gctggccggc ctgctctggt gcctggcctc   1200
gcgccgccgt gtatcgcccc gccctgggcg gcaaggctgg cccggtcggc accagttgcg   1260
tgagcggaaa gatggccgct tcccggccct gctgcaggga gctcaaaatg gaggacgcgg   1320
cgctcgggag agcgggcggg tgagtcaccc acacaaagga aaagggcctt tccgtcctca   1380
gccgtcgctt catgtgactc cacggagtac cgggcgccgt ccaggcacct cgattagttc   1440
tcgagctttt ggagtacgtc gtctttaggt tggggggagg ggttttatgc gatggagttt   1500
ccccacactg agtgggtgga gactgaagtt aggccagctt ggcacttgat gtaattctcc   1560
ttggaatttg cccttttga gtttggatct tggttcattc tcaagcctca gacagtggtt   1620
caaagttttt ttcttccatt tcaggtgtcg tgaggaatta gcttggtact aatacgactc   1680
actataggga gacccaagct ggctaggtaa gcttggtacc gagctcggat ccactagtcc   1740
agtgtggtgg aattgccctt tactagtccg ccatggagct ccgggtgctg ctctgctggg   1800
cttcgttggc cgcagctttg gaagagaccc tgctgaacac aaaattggaa actgctgatc   1860
tgaagtgggt gacattccct caggtggacg ggcagtggga ggaactgagc ggcctggatg   1920
aggaacagca cagcgtgcgc acctacgaag tgtgtgacgt gcagcgtgcc ccgggccagg   1980
cccactggct tcgcacaggt tgggtcccac ggcggggcgc cgtccacgtg tacgccacgc   2040
tgcgcttcac catgctcgag tgcctgtccc tgcctcgggc tgggcgctcc tgcaaggaga   2100
ccttcaccgt cttctactat gagagcgatg cggacacggc cacggccctc acgccagcct   2160
ggatggagaa cccctacatc aaggtggaca cggtggccgc ggagcatctc acccggaagc   2220
gccctggggc cgaggccacc gggaaggtga atgtcaagac gctgcgtctg ggaccgctca   2280
gcaaggctgg cttctacctg gccttccagg accagggtgc ctgcatggcc ctgctatccc   2340
tgcacctctt ctacaaaaag tgcgcccagc tgactgtgaa cctgactcga ttcccggaga   2400
ctgtgcctcg ggagctggtt gtgcccgtgg ccggtagctg cgtggtggat gccgtccccg   2460
cccctggccc cagccccagc ctctactgcc gtgaggatgg ccagtgggcc gaacagccgg   2520
tcacgggctg cagctgtgct ccggggttcg aggcagctga ggggaacacc aagtgccgag   2580
cctgtgccca gggcaccttc aagcccctgt caggagaagg gtcctgccag ccatgcccag   2640
ccaatagcca ctctaacacc attggatcag ccgtctgcca gtgccgcgtc gggtacttcc   2700
gggcacgcac agacccccgg ggtgcaccct gcaccacccc tccttcggct catcatcacc   2760
atcaccatta agcggccgca agggcaattc tgcagatatc cagcacagtg gcggccgctc   2820
gagtctagag ggcccgcggt tcgaaggtaa gcctatccct aaccctctcc tcggtctcga   2880
ttctacgcgt accggtcatc atcaccatca ccattgagtt taaacccgct gatcagcctc   2940
gactgtgcct tctagttgcc agccatctgt tgtttgcccc tcccccgtgc cttccttgac   3000
cctggaaggt gccactccca ctgtcctttc ctaataaaat gaggaaattg catcgcattg   3060
tctgagtagg tgtcattcta ttctgggggg tggggtgggg caggacagca agggggagga   3120
ttgggaagac aatagcaggc atgctgggga tgcggtgggc tctatggctt ctgaggcgga   3180
```

-continued

```
aagaaccagc tggggctcta gggggtatcc ccacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggc atccctttag ggttccgatt tagtgcttta cggcacctcg accccaaaaa   3420
acttgattag ggtgatggtt cacgtagtgg gccatcgccc tgatagacgg tttttcgccc   3480
tttgacgttg gagtccacgt tctttaatag tggactcttg ttccaaactg gaacaacact   3540
caaccctatc tcggtctatt cttttgattt ataagggatt ttggggattt cggcctattg   3600
gttaaaaaat gagctgattt aacaaaaatt taacgcgaat taattctgtg gaatgtgtgt   3660
cagttagggt gtggaaagtc cccaggctcc ccaggcaggc agaagtatgc aaagcatgca   3720
tctcaattag tcagcaacca ggtgtggaaa gtccccaggc tccccagcag gcagaagtat   3780
gcaaagcatg catctcaatt agtcagcaac catagtcccg cccctaactc cgcccatccc   3840
gcccctaact ccgcccagtt ccgcccattc tccgccccat ggctgactaa ttttttttat   3900
ttatgcagag gccgaggccg cctctgcctc tgagctattc cagaagtagt gaggaggctt   3960
ttttggaggc ctaggctttt gcaaaaagct cccgggagct tgtatatcca ttttcggatc   4020
tgatcagcac gtgttgacaa ttaatcatcg gcatagtata tcggcatagt ataatacgac   4080
aaggtgagga actaaaccat ggccaagcct ttgtctcaag aagaatccac cctcattgaa   4140
agagcaacgg ctacaatcaa cagcatcccc atctctgaag actacagcgt cgccagcgca   4200
gctctctcta gcgacggccg catcttcact ggtgtcaatg tatatcattt tactgggga   4260
ccttgtgcag aactcgtggt gctgggcact gctgctgctg cggcagctgg caacctgact   4320
tgtatcgtcg cgatcggaaa tgagaacagg ggcatcttga gcccctgcgg acggtgtcga   4380
caggtgcttc tcgatctgca tcctgggatc aaagcgatag tgaaggacag tgatggacag   4440
ccgacggcag ttgggattcg tgaattgctg ccctctggtt atgtgtggga gggctaagca   4500
cttcgtggcc gaggagcagg actgacacgt gctacgagat ttcgattcca ccgccgcctt   4560
ctatgaaagg ttgggcttcg gaatcgtttt ccgggacgcc ggctggatga tcctccagcg   4620
cggggatctc atgctggagt tcttcgccca ccccaacttg tttattgcag cttataatgg   4680
ttacaaataa agcaatagca tcacaaattt cacaaataaa gcattttttt cactgcattc   4740
tagttgtggt ttgtccaaac tcatcaatgt atcttatcat gtctgtatac cgtcgacctc   4800
tagctagagc ttggcgtaat catggtcata gctgtttcct gtgtgaaatt gttatccgct   4860
cacaattcca cacaacatac gagccggaag cataaagtgt aaagcctggg gtgcctaatg   4920
agtgagctaa ctcacattaa ttgcgttgcg ctcactgccc gctttccagt cgggaaacct   4980
gtcgtgccag ctgcattaat gaatcggcca acgcgcgggg agaggcggtt tgcgtattgg   5040
gcgctcttcc gcttcctcgc tcactgactc gctgcgctcg gtcgttcggc tgcggcgagc   5100
ggtatcagct cactcaaagg cggtaatacg gttatccaca gaatcagggg ataacgcagg   5160
aaagaacatg tgagcaaaag gccagcaaaa ggccaggaac cgtaaaaagg ccgcgttgct   5220
ggcgtttttc cataggctcc gcccccctga cgagcatcac aaaaatcgac gctcaagtca   5280
gaggtggcga aacccgacag gactataaag ataccaggcg tttccccctg gaagctccct   5340
cgtgcgctct cctgttccga ccctgccgct taccggatac ctgtccgcct ttctcccttc   5400
gggaagcgtg gcgctttctc aatgctcacg ctgtaggtat ctcagttcgg tgtaggtcgt   5460
tcgctccaag ctgggctgtg tgcacgaacc ccccgttcag cccgaccgct gcgccttatc   5520
cggtaactat cgtcttgagt ccaacccggt aagacacgac ttatcgccac tggcagcagc   5580
```

cactggtaac aggattagca gagcgaggta tgtaggcggt gctacagagt tcttgaagtg 5640
gtggcctaac tacggctaca ctagaaggac agtatttggt atctgcgctc tgctgaagcc 5700
agttaccttc ggaaaaagag ttggtagctc ttgatccggc aaacaaacca ccgctggtag 5760
cggtggtttt tttgtttgca agcagcagat tacgcgcaga aaaaaaggat ctcaagaaga 5820
tcctttgatc ttttctacgg ggtctgacgc tcagtggaac gaaaactcac gttaagggat 5880
tttggtcatg agattatcaa aaaggatctt cacctagatc cttttaaatt aaaaatgaag 5940
ttttaaatca atctaaagta tatatgagta aacttggtct gacagttacc aatgcttaat 6000
cagtgaggca cctatctcag cgatctgtct atttcgttca tccatagttg cctgactccc 6060
cgtcgtgtag ataactacga tacgggaggg cttaccatct ggccccagtg ctgcaatgat 6120
accgcgagac ccacgctcac cggctccaga tttatcagca ataaaccagc cagccggaag 6180
ggccgagcgc agaagtggtc ctgcaacttt atccgcctcc atccagtcta ttaattgttg 6240
ccgggaagct agagtaagta gttcgccagt taatagtttg cgcaacgttg ttgccattgc 6300
tacaggcatc gtggtgtcac gctcgtcgtt tggtatggct tcattcagct ccggttccca 6360
acgatcaagg cgagttacat gatcccccat gttgtgcaaa aaagcggtta gctccttcgg 6420
tcctccgatc gttgtcagaa gtaagttggc cgcagtgtta tcactcatgg ttatggcagc 6480
actgcataat tctcttactg tcatgccatc cgtaagatgc ttttctgtga ctggtgagta 6540
ctcaaccaag tcattctgag aatagtgtat gcggcgaccg agttgctctt gcccggcgtc 6600
aatacgggat aataccgcgc cacatagcag aactttaaaa gtgctcatca ttggaaaacg 6660
ttcttcgggg cgaaaactct caaggatctt accgctgttg agatccagtt cgatgtaacc 6720
cactcgtgca cccaactgat cttcagcatc ttttactttc accagcgttt ctgggtgagc 6780
aaaaacagga aggcaaaatg ccgcaaaaaa gggaataagg gcgacacgga aatgttgaat 6840
actcatactc ttcctttttc 6860

<210> SEQ ID NO 407
<211> LENGTH: 32
<212> TYPE: DNA
<213> ORGANISM: Unknown
<220> FEATURE:
<223> OTHER INFORMATION: oligonucleotide primer

<400> SEQUENCE: 407
tactagtccg ccatggagct ccgggtgctg ct 32

<210> SEQ ID NO 408
<211> LENGTH: 53
<212> TYPE: DNA
<213> ORGANISM: Unknown
<220> FEATURE:
<223> OTHER INFORMATION: oligonucleotide primer

<400> SEQUENCE: 408
agcggccgct taatggtgat ggtgatgatg gacattgaca ggctcaaatg gga 53

<210> SEQ ID NO 409
<211> LENGTH: 1323
<212> TYPE: DNA
<213> ORGANISM: Homo sapiens

<400> SEQUENCE: 409
tactagtccg ccatggagct ccgggtgctg ctctgctggg cttcgttggc cgcagctttg 60
gaagagaccc tgctgaacac aaaattggaa actgctgatc tgaagtgggt gacattccct 120

-continued

```
caggtggacg ggcagtggga ggaactgagc ggcctggatg aggaacagca cagcgtgcgc    180

acctacgaag tgtgtgaagt gcagcgtgcc ccgggccagg cccactggct tcgcacaggt    240

tgggtcccac ggcggggcgc cgtccacgtg tacgccacgc tgcgcttcac catgctcgag    300

tgcctgtccc tgcctcgggc tgggcgctcc tgcaaggaga ccttcaccgt cttctactat    360

gagagcgatg cggacacggc cacggccctc acgccagcct ggatggagaa cccctacatc    420

aaggtggaca cggtggccgc ggagcatctc acccggaagc gccctggggc cgaggccacc    480

gggaaggtga atgtcaagac gctgcgtctg ggaccgctca gcaaggctgg cttctacctg    540

gccttccagg accagggtgc ctgcatggcc ctgctatccc tgcacctctt ctacaaaaag    600

tgcgcccagc tgactgtgaa cctgactcga ttcccggaga ctgtgcctcg ggagctggtt    660

gtgcccgtgg ccggtagctg cgtggtggat gccgtccccg cccctggccc cagccccagc    720

ctctactgcc gtgaggatgg ccagtgggcc gaacagccgg tcacgggctg cagctgtgct    780

ccggggttcg aggcagctga ggggaacacc aagtgccgag cctgtgccca gggcaccttc    840

aagcccctgt caggagaagg gtcctgccag ccatgcccag ccaatagcca ctctaacacc    900

attggatcag ccgtctgcca gtgccgcgtc gggtacttcc gggcacgcac agacccccgg    960

ggtgcaccct gcaccacccc tccttcggct ccgcggagcg tggtttcccg cctgaacggc   1020

tcctccctgc acctggaatg gagtgccccc ctggagtctg gtggccgaga ggacctcacc   1080

tacgccctcc gctgccggga gtgccgaccc ggaggctcct gtgcgccctg cgggggagac   1140

ctgacttttg accccggccc ccgggacctg gtggagccct gggtggtggt tcgagggcta   1200

cgtccggact tcacctatac ctttgaggtc actgcattga acggggtatc ctccttagcc   1260

acggggcccg tcccatttga gcctgtcaat gtccatcatc accatcacca ttaagcggcc   1320

gct                                                                 1323
```

<210> SEQ ID NO 410
<211> LENGTH: 431
<212> TYPE: PRT
<213> ORGANISM: Homo sapiens

<400> SEQUENCE: 410

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160
```

```
Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Ala Glu Gly Asn Thr Lys Cys Arg Ala Cys Ala Gln Gly
            260                 265                 270

Thr Phe Lys Pro Leu Ser Gly Glu Gly Ser Cys Gln Pro Cys Pro Ala
        275                 280                 285

Asn Ser His Ser Asn Thr Ile Gly Ser Ala Val Cys Gln Cys Arg Val
    290                 295                 300

Gly Tyr Phe Arg Ala Arg Thr Asp Pro Arg Gly Ala Pro Cys Thr Thr
305                 310                 315                 320

Pro Pro Ser Ala Pro Arg Ser Val Val Ser Arg Leu Asn Gly Ser Ser
                325                 330                 335

Leu His Leu Glu Trp Ser Ala Pro Leu Glu Ser Gly Gly Arg Glu Asp
            340                 345                 350

Leu Thr Tyr Ala Leu Arg Cys Arg Glu Cys Arg Pro Gly Gly Ser Cys
        355                 360                 365

Ala Pro Cys Gly Gly Asp Leu Thr Phe Asp Pro Gly Pro Arg Asp Leu
    370                 375                 380

Val Glu Pro Trp Val Val Val Arg Gly Leu Arg Pro Asp Phe Thr Tyr
385                 390                 395                 400

Thr Phe Glu Val Thr Ala Leu Asn Gly Val Ser Ser Leu Ala Thr Gly
                405                 410                 415

Pro Val Pro Phe Glu Pro Val Asn Val His His His His His His
            420                 425                 430
```

<210> SEQ ID NO 411
<211> LENGTH: 7164
<212> TYPE: DNA
<213> ORGANISM: Unknown
<220> FEATURE:
<223> OTHER INFORMATION: plasmid vector sequence

<400> SEQUENCE: 411

```
aatattattg aagcatttat cagggttatt gtctcatgag cggatacata tttgaatgta      60

tttagaaaaa taaacaaata ggggttccgc gcacatttcc ccgaaaagtg ccacctgacg     120

tcgacggatc gggagatctc ccgatcccct atggtcgact ctcagtacaa tctgctctga     180

tgccgcatag ttaagccagt atctgctccc tgcttgtgtg ttggaggtcg ctgagtagtg     240

cgcgagcaaa atttaagcta caacaaggca aggcttgacc gacaattgca tgaagaatct     300

gcttagggtt aggcgttttg cgctgcttcg cgatgtacgg gccagatata cgcgttgaca     360

ttgattattg actaggcttt tgcaaaaagc tttgcaaaga tggataaagt tttaaacaga     420

gaggaatctt tgcagctaat ggaccttcta ggtcttgaaa ggagtgcctc gtgaggctcc     480

ggtgcccgtc agtgggcaga gcgcacatcg cccacagtcc ccgagaagtt ggggggaggg     540
```

-continued

```
gtcggcaatt gaaccggtgc ctagagaagg tggcgcgggg taaactggga aagtgatgtc    600
gtgtactggc tccgcctttt tcccgagggt gggggagaac cgtatataag tgcagtagtc    660
gccgtgaacg ttcttttcg caacgggttt gccgccagaa cacaggtaag tgccgtgtgt    720
ggttcccgcg ggcctggcct ctttacgggt tatggccctt gcgtgccttg aattacttcc    780
acctggctgc agtacgtgat tcttgatccc gagcttcggg ttggaagtgg gtgggagagt    840
tcgaggcctt gcgcttaagg agccccttcg cctcgtgctt gagttgaggc ctggcctggg    900
cgctggggcc gccgcgtgcg aatctggtgg caccttcgcg cctgtctcgc tgctttcgat    960
aagtctctag ccatttaaaa tttttgatga cctgctgcga cgcttttttt ctggcaagat   1020
agtcttgtaa atgcgggcca agatctgcac actggtattt cggtttttgg ggccgcgggc   1080
ggcgacgggg cccgtgcgtc ccagcgcaca tgttcggcga ggcggggcct gcgagcgcgg   1140
ccaccgagaa tcggacgggg gtagtctcaa gctggccggc ctgctctggt gcctggcctc   1200
gcgccgccgt gtatcgcccc gccctgggcg gcaaggctgg cccggtcggc accagttgcg   1260
tgagcggaaa gatggccgct tcccggccct gctgcaggga gctcaaaatg gaggacgcgg   1320
cgctcgggag agcgggcggg tgagtcaccc acacaaagga aaagggcctt tccgtcctca   1380
gccgtcgctt catgtgactc cacggagtac cgggcgccgt ccaggcacct cgattagttc   1440
tcgagctttt ggagtacgtc gtctttaggt tggggggagg ggttttatgc gatggagttt   1500
ccccacactg agtgggtgga gactgaagtt aggccagctt ggcacttgat gtaattctcc   1560
ttggaatttg cccttttga gtttggatct tggttcattc tcaagcctca gacagtggtt   1620
caaagttttt ttcttccatt tcaggtgtcg tgaggaatta gcttggtact aatacgactc   1680
actataggga gacccaagct ggctaggtaa gcttggtacc gagctcggat ccactagtcc   1740
agtgtggtgg aattgccctt tactagtccg ccatggagct ccgggtgctg ctctgctggg   1800
cttcgttggc cgcagctttg gaagagaccc tgctgaacac aaaattggaa actgctgatc   1860
tgaagtgggt gacattccct caggtggacg ggcagtggga ggaactgagc ggcctggatg   1920
aggaacagca cagcgtgcgc acctacgaag tgtgtgacgt gcagcgtgcc ccgggccagg   1980
cccactggct tcgcacaggt tgggtcccac ggcggggcgc cgtccacgtg tacgccacgc   2040
tgcgcttcac catgctcgag tgcctgtccc tgcctcgggc tgggcgctcc tgcaaggaga   2100
ccttcaccgt cttctactat gagagcgatg cggacacggc cacggccctc acgccagcct   2160
ggatggagaa cccctacatc aaggtggaca cggtggccgc ggagcatctc acccggaagc   2220
gccctggggc cgaggccacc gggaaggtga atgtcaagac gctgcgcctg ggaccgctca   2280
gcaaggctgg cttctacctg gccttccagg accagggtgc ctgcatggcc ctgctatccc   2340
tgcacctctt ctacaaaaag tgcgcccagc tgactgtgaa cctgactcga ttcccggaga   2400
ctgtgcctcg ggagctggtt gtgcccgtgg ccggtagctg cgtggtggat gccgtccccg   2460
cccctggccc cagccccagc ctctactgcc gtgaggatgg ccagtgggcc gaacagccgg   2520
tcacgggctg cagctgtgct ccggggttcg aggcagctga ggggaacacc aagtgccgag   2580
cctgtgccca gggcaccttc aagcccctgt caggagaagg gtcctgccag ccatgcccag   2640
ccaatagcca ctctaacacc attggatcag ccgtctgcca gtgccgcgtc gggtacttcc   2700
gggcacgcac agacccccgg ggtgcaccct gcaccacccc tccttcggct ccgcggagcg   2760
tggtttcccg cctgaacggc tcctccctgc acctggaatg gagtgccccc ctggagtctg   2820
gtggccgaga ggacctcacc tacgccctcc gctgccggga gtgtcgaccc ggaggctcct   2880
gtgcgccctg cgggggagac ctgactttg accccggccc ccgggacctg gtggagccct   2940
```

-continued

```
gggtggtggt tcgagggcta cgtcctgact tcacctatac ctttgaggtc actgcattga   3000
acggggtatc ctccttagcc acggggcccg tcccatttga gcctgtcaat gtccatcatc   3060
accatcacca ttaagcggcc gctaagggca attctgcaga tatccagcac agtggcggcc   3120
gctcgagtct agagggcccg cggttcgaag gtaagcctat ccctaaccct ctcctcggtc   3180
tcgattctac gcgtaccggt catcatcacc atcaccattg agtttaaacc cgctgatcag   3240
cctcgactgt gccttctagt tgccagccat ctgttgtttg cccctccccc gtgccttcct   3300
tgaccctgga aggtgccact cccactgtcc tttcctaata aaatgaggaa attgcatcgc   3360
attgtctgag taggtgtcat tctattctgg ggggtggggt ggggcaggac agcaaggggg   3420
aggattggga agacaatagc aggcatgctg gggatgcggt gggctctatg gcttctgagg   3480
cggaaagaac cagctggggc tctagggggt atccccacgc gccctgtagc ggcgcattaa   3540
gcgcggcggg tgtggtggtt acgcgcagcg tgaccgctac acttgccagc gccctagcgc   3600
ccgctccttt cgctttcttc ccttcctttc tcgccacgtt cgccggcttt ccccgtcaag   3660
ctctaaatcg ggcatccct ttagggttcc gatttagtgc tttacggcac ctcgacccca   3720
aaaaacttga ttagggtgat ggttcacgta gtgggccatc gccctgatag acggtttttc   3780
gccctttgac gttggagtcc acgttcttta atagtggact cttgttccaa actggaacaa   3840
cactcaaccc tatctcggtc tattcttttg atttataagg gattttgggg atttcggcct   3900
attggttaaa aaatgagctg atttaacaaa aatttaacgc gaattaattc tgtggaatgt   3960
gtgtcagtta gggtgtggaa agtccccagg ctccccaggc aggcagaagt atgcaaagca   4020
tgcatctcaa ttagtcagca accaggtgtg gaaagtcccc aggctcccca gcaggcagaa   4080
gtatgcaaag catgcatctc aattagtcag caaccatagt cccgccccta actccgccca   4140
tcccgcccct aactccgccc agttccgccc attctccgcc ccatggctga ctaatttttt   4200
ttatttatgc agaggccgag gccgcctctg cctctgagct attccagaag tagtgaggag   4260
gcttttttgg aggcctaggc ttttgcaaaa agctcccggg agcttgtata tccattttcg   4320
gatctgatca gcacgtgttg acaattaatc atcggcatag tatatcggca tagtataata   4380
cgacaaggtg aggaactaaa ccatggccaa gcctttgtct caagaagaat ccaccctcat   4440
tgaaagagca acggctacaa tcaacagcat ccccatctct gaagactaca gcgtcgccag   4500
cgcagctctc tctagcgacg gccgcatctt cactggtgtc aatgtatatc attttactgg   4560
gggaccttgt gcagaactcg tggtgctggg cactgctgct gctgcggcag ctggcaacct   4620
gacttgtatc gtcgcgatcg gaaatgagaa caggggcatc ttgagcccct gcggacggtg   4680
tcgacaggtg cttctcgatc tgcatcctgg gatcaaagcg atagtgaagg acagtgatgg   4740
acagccgacg gcagttggga ttcgtgaatt gctgccctct ggttatgtgt gggagggcta   4800
agcacttcgt ggccgaggag caggactgac acgtgctacg agatttcgat tccaccgccg   4860
ccttctatga aaggttgggc ttcggaatcg ttttccggga cgccggctgg atgatcctcc   4920
agcgcgggga tctcatgctg gagttcttcg cccaccccaa cttgtttatt gcagcttata   4980
atggttacaa ataaagcaat agcatcacaa atttcacaaa taaagcattt ttttcactgc   5040
attctagttg tggtttgtcc aaactcatca atgtatctta tcatgtctgt ataccgtcga   5100
cctctagcta gagcttggcg taatcatggt catagctgtt tcctgtgtga aattgttatc   5160
cgctcacaat tccacacaac atacgagccg gaagcataaa gtgtaaagcc tggggtgcct   5220
aatgagtgag ctaactcaca ttaattgcgt tgcgctcact gcccgctttc cagtcgggaa   5280
acctgtcgtg ccagctgcat taatgaatcg gccaacgcgc ggggagaggc ggtttgcgta   5340
```

```
ttgggcgctc ttccgcttcc tcgctcactg actcgctgcg ctcggtcgtt cggctgcggc   5400

gagcggtatc agctcactca aaggcggtaa tacggttatc cacagaatca ggggataacg   5460

caggaaagaa catgtgagca aaaggccagc aaaaggccag gaaccgtaaa aaggccgcgt   5520

tgctggcgtt tttccatagg ctccgccccc ctgacgagca tcacaaaaat cgacgctcaa   5580

gtcagaggtg gcgaaacccg acaggactat aaagatacca ggcgtttccc cctggaagct   5640

ccctcgtgcg ctctcctgtt ccgaccctgc cgcttaccgg atacctgtcc gcctttctcc   5700

cttcgggaag cgtggcgctt tctcaatgct cacgctgtag gtatctcagt tcggtgtagg   5760

tcgttcgctc caagctgggc tgtgtgcacg aaccccccgt tcagcccgac cgctgcgcct   5820

tatccggtaa ctatcgtctt gagtccaacc cggtaagaca cgacttatcg ccactggcag   5880

cagccactgg taacaggatt agcagagcga ggtatgtagg cggtgctaca gagttcttga   5940

agtggtggcc taactacggc tacactagaa ggacagtatt tggtatctgc gctctgctga   6000

agccagttac cttcggaaaa agagttggta gctcttgatc cggcaaacaa accaccgctg   6060

gtagcggtgg tttttttgtt tgcaagcagc agattacgcg cagaaaaaaa ggatctcaag   6120

aagatccttt gatcttttct acggggtctg acgctcagtg gaacgaaaac tcacgttaag   6180

ggattttggt catgagatta tcaaaaagga tcttcaccta gatcctttta aattaaaaat   6240

gaagttttaa atcaatctaa agtatatatg agtaaacttg gtctgacagt taccaatgct   6300

taatcagtga ggcacctatc tcagcgatct gtctatttcg ttcatccata gttgcctgac   6360

tccccgtcgt gtagataact acgatacggg agggcttacc atctggcccc agtgctgcaa   6420

tgataccgcg agacccacgc tcaccggctc cagatttatc agcaataaac cagccagccg   6480

gaagggccga gcgcagaagt ggtcctgcaa ctttatccgc ctccatccag tctattaatt   6540

gttgccggga agctagagta agtagttcgc cagttaatag tttgcgcaac gttgttgcca   6600

ttgctacagg catcgtggtg tcacgctcgt cgtttggtat ggcttcattc agctccggtt   6660

cccaacgatc aaggcgagtt acatgatccc ccatgttgtg caaaaaagcg gttagctcct   6720

tcggtcctcc gatcgttgtc agaagtaagt tggccgcagt gttatcactc atggttatgg   6780

cagcactgca taattctctt actgtcatgc catccgtaag atgcttttct gtgactggtg   6840

agtactcaac caagtcattc tgagaatagt gtatgcggcg accgagttgc tcttgcccgg   6900

cgtcaatacg ggataatacc gcgccacata gcagaacttt aaaagtgctc atcattggaa   6960

aacgttcttc ggggcgaaaa ctctcaagga tcttaccgct gttgagatcc agttcgatgt   7020

aacccactcg tgcacccaac tgatcttcag catcttttac tttcaccagc gtttctgggt   7080

gagcaaaaac aggaaggcaa aatgccgcaa aaaagggaat aagggcgaca cggaaatgtt   7140

gaatactcat actcttcctt tttc                                          7164
```

<210> SEQ ID NO 412
<211> LENGTH: 570
<212> TYPE: PRT
<213> ORGANISM: Homo sapiens

<400> SEQUENCE: 412

```
Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
```

```
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480
```

```
Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
    530                 535                 540

Gln Ile Glu Gly Lys Pro Ile Pro Asn Pro Leu Leu Gly Leu Asp Ser
545                 550                 555                 560

Thr Arg Thr Gly His His His His His His
                565                 570


<210> SEQ ID NO 413
<211> LENGTH: 7429
<212> TYPE: DNA
<213> ORGANISM: Unknown
<220> FEATURE:
<223> OTHER INFORMATION: plasmid vector sequence

<400> SEQUENCE: 413

aatattattg aagcatttat cagggttatt gtctcatgag cggatacata tttgaatgta     60

tttagaaaaa taaacaaata ggggttccgc gcacatttcc ccgaaaagtg ccacctgacg    120

tcgacggatc gggagatctc ccgatcccct atggtcgact ctcagtacaa tctgctctga    180

tgccgcatag ttaagccagt atctgctccc tgcttgtgtg ttggaggtcg ctgagtagtg    240

cgcgagcaaa atttaagcta caacaaggca aggcttgacc gacaattgca tgaagaatct    300

gcttagggtt aggcgttttg cgctgcttcg cgatgtacgg gccagatata cgcgttgaca    360

ttgattattg actaggcttt tgcaaaaagc tttgcaaaga tggataaagt tttaaacaga    420

gaggaatctt tgcagctaat ggaccttcta ggtcttgaaa ggagtgcctc gtgaggctcc    480

ggtgcccgtc agtgggcaga gcgcacatcg cccacagtcc ccgagaagtt ggggggaggg    540

gtcggcaatt gaaccggtgc ctagagaagg tggcgcgggg taaactggga aagtgatgtc    600

gtgtactggc tccgcctttt tcccgagggt gggggagaac cgtatataag tgcagtagtc    660

gccgtgaacg ttcttttttcg caacgggttt gccgccagaa cacaggtaag tgccgtgtgt    720

ggttcccgcg ggcctggcct ctttacgggt tatggccctt gcgtgccttg aattacttcc    780

acctggctgc agtacgtgat tcttgatccc gagcttcggg ttggaagtgg gtgggagagt    840

tcgaggcctt gcgcttaagg agccccttcg cctcgtgctt gagttgaggc ctggcctggg    900

cgctggggcc gccgcgtgcg aatctggtgg caccttcgcg cctgtctcgc tgctttcgat    960

aagtctctag ccatttaaaa tttttgatga cctgctgcga cgcttttttt ctggcaagat   1020

agtcttgtaa atgcgggcca agatctgcac actggtattt cggtttttgg ggccgcgggc   1080

ggcgacgggg cccgtgcgtc ccagcgcaca tgttcggcga ggcggggcct gcgagcgcgg   1140

ccaccgagaa tcggacgggg gtagtctcaa gctggccggc ctgctctggt gcctggcctc   1200

gcgccgccgt gtatcgcccc gccctgggcg gcaaggctgg cccggtcggc accagttgcg   1260

tgagcggaaa gatggccgct tcccggccct gctgcaggga gctcaaaatg gaggacgcgg   1320

cgctcgggag agcgggcggg tgagtcaccc acacaaagga aaagggcctt tccgtcctca   1380

gccgtcgctt catgtgactc cacggagtac cgggcgccgt ccaggcacct cgattagttc   1440

tcgagctttt ggagtacgtc gtctttaggt tggggggagg ggttttatgc gatggagttt   1500

ccccacactg agtgggtgga gactgaagtt aggccagctt ggcacttgat gtaattctcc   1560
```

```
ttggaatttg cccttttga gtttggatct tggttcattc tcaagcctca gacagtggtt   1620
caaagttttt ttcttccatt tcaggtgtcg tgaggaatta gcttggtact aatacgactc   1680
actataggga gacccaagct ggctaggtaa gcttggtacc gagctcggat ccactagtcc   1740
agtgtggtgg aattgccctt ataagcttcc gccatggagc tccgggtgct gctctgctgg   1800
gcttcgttgg ccgcagcttt ggaagagacc ctgctgaaca caaaattgga aactgctgat   1860
ctgaagtggg tgacattccc tcaggtggac gggcagtggg aggaactgag cggcctggat   1920
gaggaacagc acagcgtgcg cacctacgaa gtgtgtgaag tgcagcgtgc cccgggccag   1980
gcccactggc ttcgcacagg ttgggtccca cggcggggcg ccgtccacgt gtacgccacg   2040
ctgcgcttca ccatgctcga gtgcctgtcc ctgcctcggg ctgggcgctc ctgcaaggag   2100
accttcaccg tcttctacta tgagagcgat gcggacacgg ccacggccct cacgccagcc   2160
tggatggaga acccctacat caaggtggac acggtggccg cggagcatct cacccggaag   2220
cgccctgggg ccgaggccac cgggaaggtg aatgtcaaga cgctgcgtct gggaccgctc   2280
agcaaggctg gcttctacct ggccttccag gaccagggtg cctgcatggc cctgctatcc   2340
ctgcacctct tctacaaaaa gtgcgcccag ctgactgtga acctgactcg attcccggag   2400
actgtgcctc gggagctggt tgtgcccgtg gccggtagct gcgtggtgga tgccgtcccc   2460
gcccctggcc ccagccccag cctctactgc cgtgaggatg gccagtgggc cgaacagccg   2520
gtcacgggct gcagctgtgc tccggggttc gaggcagctg aggggaacac caagtgccga   2580
gcctgtgccc agggcacctt caagcccctg tcaggagaag ggtcctgcca gccatgccca   2640
gccaatagcc actctaacac cattggatca gccgtctgcc agtgccgcgt cgggtacttc   2700
cgggcacgca cagacccccg gggtgcaccc tgcaccaccc ctccttcggc tccgcggagc   2760
gtggtttccc gcctgaacgg ctcctccctg cacctggaat ggagtgcccc cctggagtct   2820
ggtggccgag aggacctcac ctacgccctc cgctgccggg agtgccgacc cggaggctcc   2880
tgtgcgccct gcgggggaga cctgactttt gaccccggcc cccgggacct ggtggagccc   2940
tgggtggtgg ttcgagggct acgtccggac ttcacctata cctttgaggt cactgcattg   3000
aacggggtat cctccttagc cacggggccc gtcccatttg agcctgtcaa tgtcaccact   3060
gaccgagagg tacctcctgc agtgtctgac atccgggtga cgcggtcctc acccagcagc   3120
ttgagcctgg cctgggctgt tccccgggca cccagtgggg cgtggctgga ctacgaggtc   3180
aaataccatg agaagggcgc cgagggtccc agcagcgtgc ggttcctgaa gacgtcagaa   3240
aaccgggcag agctgcgggg gctgaagcgg ggagccagct acctggtgca ggtacgggcg   3300
cgctctgagg ccggctacgg gcccttcggc caggaacatc acagccagac ccaactggat   3360
gagagcgagg gctggcggga gcagggatcc aaaagggcaa ttctgcagat cgaaggtaag   3420
cctatcccta accctctcct cggtctcgat tctacgcgta ccggtcatca tcaccatcac   3480
cattgagttt aaacccgctg atcagcctcg actgtgcctt ctagttgcca gccatctgtt   3540
gtttgcccct cccccgtgcc ttccttgacc ctggaaggtg ccactcccac tgtcctttcc   3600
taataaaatg aggaaattgc atcgcattgt ctgagtaggt gtcattctat tctggggggt   3660
ggggtggggc aggacagcaa gggggaggat tgggaagaca atagcaggca tgctggggat   3720
gcggtgggct ctatggcttc tgaggcggaa agaaccagct ggggctctag ggggtatccc   3780
cacgcgccct gtagcggcgc attaagcgcg gcgggtgtgg tggttacgcg cagcgtgacc   3840
gctacacttg ccagcgccct agcgcccgct cctttcgctt tcttcccttc ctttctcgcc   3900
acgttcgccg gctttccccg tcaagctcta aatcggggca tccctttagg gttccgattt   3960
```

-continued

```
agtgctttac ggcacctcga ccccaaaaaa cttgattagg gtgatggttc acgtagtggg   4020
ccatcgccct gatagacggt ttttcgccct ttgacgttgg agtccacgtt ctttaatagt   4080
ggactcttgt tccaaactgg aacaacactc aaccctatct cggtctattc ttttgattta   4140
taagggattt tggggatttc ggcctattgg ttaaaaaatg agctgattta acaaaaattt   4200
aacgcgaatt aattctgtgg aatgtgtgtc agttagggtg tggaaagtcc ccaggctccc   4260
caggcaggca gaagtatgca aagcatgcat ctcaattagt cagcaaccag gtgtggaaag   4320
tccccaggct ccccagcagg cagaagtatg caaagcatgc atctcaatta gtcagcaacc   4380
atagtcccgc ccctaactcc gcccatcccg cccctaactc cgcccagttc cgcccattct   4440
ccgccccatg gctgactaat tttttttatt tatgcagagg ccgaggccgc ctctgcctct   4500
gagctattcc agaagtagtg aggaggcttt tttggaggcc taggcttttg caaaaagctc   4560
ccgggagctt gtatatccat tttcggatct gatcagcacg tgttgacaat taatcatcgg   4620
catagtatat cggcatagta taatacgaca aggtgaggaa ctaaaccatg gccaagcctt   4680
tgtctcaaga agaatccacc ctcattgaaa gagcaacggc tacaatcaac agcatcccca   4740
tctctgaaga ctacagcgtc gccagcgcag ctctctctag cgacggccgc atcttcactg   4800
gtgtcaatgt atatcatttt actgggggac cttgtgcaga actcgtggtg ctgggcactg   4860
ctgctgctgc ggcagctggc aacctgactt gtatcgtcgc gatcggaaat gagaacaggg   4920
gcatcttgag cccctgcgga cggtgtcgac aggtgcttct cgatctgcat cctgggatca   4980
aagcgatagt gaaggacagt gatggacagc cgacggcagt tgggattcgt gaattgctgc   5040
cctctggtta tgtgtgggag ggctaagcac ttcgtggccg aggagcagga ctgacacgtg   5100
ctacgagatt tcgattccac cgccgccttc tatgaaaggt tgggcttcgg aatcgttttc   5160
cgggacgccg gctggatgat cctccagcgc ggggatctca tgctggagtt cttcgcccac   5220
cccaacttgt ttattgcagc ttataatggt tacaaataaa gcaatagcat cacaaatttc   5280
acaaataaag catttttttc actgcattct agttgtggtt tgtccaaact catcaatgta   5340
tcttatcatg tctgtatacc gtcgacctct agctagagct tggcgtaatc atggtcatag   5400
ctgtttcctg tgtgaaattg ttatccgctc acaattccac acaacatacg agccggaagc   5460
ataaagtgta aagcctgggg tgcctaatga gtgagctaac tcacattaat tgcgttgcgc   5520
tcactgcccg ctttccagtc gggaaacctg tcgtgccagc tgcattaatg aatcggccaa   5580
cgcgcgggga gaggcggttt gcgtattggg cgctcttccg cttcctcgct cactgactcg   5640
ctgcgctcgg tcgttcggct gcggcgagcg gtatcagctc actcaaaggc ggtaatacgg   5700
ttatccacag aatcagggga taacgcagga aagaacatgt gagcaaaagg ccagcaaaag   5760
gccaggaacc gtaaaaaggc cgcgttgctg gcgtttttcc ataggctccg cccccctgac   5820
gagcatcaca aaaatcgacg ctcaagtcag aggtggcgaa acccgacagg actataaaga   5880
taccaggcgt ttccccctgg aagctccctc gtgcgctctc ctgttccgac cctgccgctt   5940
accggatacc tgtccgcctt tctcccttcg ggaagcgtgg cgctttctca atgctcacgc   6000
tgtaggtatc tcagttcggt gtaggtcgtt cgctccaagc tgggctgtgt gcacgaaccc   6060
cccgttcagc ccgaccgctg cgccttatcc ggtaactatc gtcttgagtc caacccggta   6120
agacacgact tatcgccact ggcagcagcc actggtaaca ggattagcag agcgaggtat   6180
gtaggcggtg ctacagagtt cttgaagtgg tggcctaact acggctacac tagaaggaca   6240
gtatttggta tctgcgctct gctgaagcca gttaccttcg gaaaaagagt tggtagctct   6300
tgatccggca aacaaaccac cgctggtagc ggtggttttt ttgtttgcaa gcagcagatt   6360
```

acgcgcagaa aaaaaggatc tcaagaagat cctttgatct tttctacggg gtctgacgct 6420
cagtggaacg aaaactcacg ttaagggatt ttggtcatga gattatcaaa aaggatcttc 6480
acctagatcc ttttaaatta aaaatgaagt tttaaatcaa tctaaagtat atatgagtaa 6540
acttggtctg acagttacca atgcttaatc agtgaggcac ctatctcagc gatctgtcta 6600
tttcgttcat ccatagttgc ctgactcccc gtcgtgtaga taactacgat acgggagggc 6660
ttaccatctg gccccagtgc tgcaatgata ccgcgagacc cacgctcacc ggctccagat 6720
ttatcagcaa taaaccagcc agccggaagg gccgagcgca gaagtggtcc tgcaacttta 6780
tccgcctcca tccagtctat taattgttgc cgggaagcta gagtaagtag ttcgccagtt 6840
aatagtttgc gcaacgttgt tgccattgct acaggcatcg tggtgtcacg ctcgtcgttt 6900
ggtatggctt cattcagctc cggttcccaa cgatcaaggc gagttacatg atcccccatg 6960
ttgtgcaaaa aagcggttag ctccttcggt cctccgatcg ttgtcagaag taagttggcc 7020
gcagtgttat cactcatggt tatggcagca ctgcataatt ctcttactgt catgccatcc 7080
gtaagatgct tttctgtgac tggtgagtac tcaaccaagt cattctgaga atagtgtatg 7140
cggcgaccga gttgctcttg cccggcgtca atacgggata ataccgcgcc acatagcaga 7200
actttaaaag tgctcatcat tggaaaacgt tcttcggggc gaaaactctc aaggatctta 7260
ccgctgttga gatccagttc gatgtaaccc actcgtgcac ccaactgatc ttcagcatct 7320
tttactttca ccagcgtttc tgggtgagca aaaacaggaa ggcaaaatgc cgcaaaaaag 7380
ggaataaggg cgacacggaa atgttgaata ctcatactct tcctttttc 7429

<210> SEQ ID NO 414
<211> LENGTH: 32
<212> TYPE: DNA
<213> ORGANISM: Unknown
<220> FEATURE:
<223> OTHER INFORMATION: oligonucleotide primer

<400> SEQUENCE: 414
tactagtccg ccatggagct ccgggtgctg ct 32

<210> SEQ ID NO 415
<211> LENGTH: 25
<212> TYPE: DNA
<213> ORGANISM: Unknown
<220> FEATURE:
<223> OTHER INFORMATION: oligonucleotide primer

<400> SEQUENCE: 415
cagctgagtt tccaattttg tgttc 25

<210> SEQ ID NO 416
<211> LENGTH: 39
<212> TYPE: DNA
<213> ORGANISM: Unknown
<220> FEATURE:
<223> OTHER INFORMATION: oligonucleotide primer

<400> SEQUENCE: 416
gaacacaaaa ttggaaactc agctgactgt gaacctgac 39

<210> SEQ ID NO 417
<211> LENGTH: 30
<212> TYPE: DNA
<213> ORGANISM: Unknown
<220> FEATURE:
<223> OTHER INFORMATION: oligonucleotide primer

<400> SEQUENCE: 417
gcggccgccc tgctcccgcc agccctcgct 30

<210> SEQ ID NO 418
<211> LENGTH: 1119
<212> TYPE: DNA
<213> ORGANISM: Homo sapiens

<400> SEQUENCE: 418
tactagtccg ccatggagct ccgggtgctg ctctgctggg cttcgttggc cgcagctttg 60
gaagagaccc tgctgaacac aaaattggaa actcagctga ctgtgaacct gactcgattc 120
ccggagactg tgcctcggga gctggttgtg cccgtggccg gtagctgcgt ggtggatgcc 180
gtccccgccc ctggccccag ccccagcctc tactgccgtg aggatggcca gtgggccgaa 240
cagccggtca cgggctgcag ctgtgctccg gggttcgagg cagctgaggg gaacaccaag 300
tgccgagcct gtgcccaggg caccttcaag cccctgtcag gagaagggtc ctgccagcca 360
tgcccagcca atagccactc taacaccatt ggatcagccg tctgccagtg ccgcgtcggg 420
tacttccggg cacgcacaga cccccggggt gcaccctgca ccacccctcc ttcggctccg 480
cggagcgtgg tttcccgcct gaacggctcc tccctgcacc tggaatggag tgccccccctg 540 gagtctggtg gccgagagga cctcacctac gccctccgct gccgggagtg ccgacccgga 600
ggctcctgtg cgccctgcgg gggagacctg acttttgacc ccggcccccg ggacctggtg 660
gagccctggg tggtggttcg agggctacgt ccggacttca cctatacctt tgaggtcact 720
gcattgaacg gggtatcctc cttagccacg gggcccgtcc catttgagcc tgtcaatgtc 780
accactgacc gagaggtacc tcctgcagtg tctgacatcc gggtgacgcg gtcctcaccc 840
agcagcttga gcctggcctg ggctgttccc cgggcaccca gtggggcgtg gctggactac 900
gaggtcaaat accatgagaa gggcgccgag ggtcccagca gcgtgcggtt cctgaagacg 960
tcagaaaacc gggcagagct gcgggggctg aagcggggag ccagctacct ggtgcaggta 1020
cgggcgcgct ctgaggccgg ctacgggccc ttcggccagg aacatcacag ccagacccaa 1080
ctggatgaga gcgagggctg gcgggagcag ggcggccgc 1119

<210> SEQ ID NO 419
<211> LENGTH: 401
<212> TYPE: PRT
<213> ORGANISM: Homo sapiens

<400> SEQUENCE: 419

Met Glu Leu Arg Val Leu Leu Cys Trp Ala Ser Leu Ala Ala Ala Leu
1 5 10 15

Glu Glu Thr Leu Leu Asn Thr Lys Leu Glu Thr Gln Leu Thr Val Asn
20 25 30

Leu Thr Arg Phe Pro Glu Thr Val Pro Arg Glu Leu Val Val Pro Val
35 40 45

Ala Gly Ser Cys Val Val Asp Ala Val Pro Ala Pro Gly Pro Ser Pro
50 55 60

Ser Leu Tyr Cys Arg Glu Asp Gly Gln Trp Ala Glu Gln Pro Val Thr
65 70 75 80

Gly Cys Ser Cys Ala Pro Gly Phe Glu Ala Ala Glu Gly Asn Thr Lys
85 90 95

Cys Arg Ala Cys Ala Gln Gly Thr Phe Lys Pro Leu Ser Gly Glu Gly
100 105 110

Ser Cys Gln Pro Cys Pro Ala Asn Ser His Ser Asn Thr Ile Gly Ser

-continued

```
        115                 120                 125

Ala Val Cys Gln Cys Arg Val Gly Tyr Phe Arg Ala Arg Thr Asp Pro
    130                 135                 140

Arg Gly Ala Pro Cys Thr Thr Pro Pro Ser Ala Pro Arg Ser Val Val
145                 150                 155                 160

Ser Arg Leu Asn Gly Ser Ser Leu His Leu Glu Trp Ser Ala Pro Leu
                165                 170                 175

Glu Ser Gly Gly Arg Glu Asp Leu Thr Tyr Ala Leu Arg Cys Arg Glu
            180                 185                 190

Cys Arg Pro Gly Gly Ser Cys Ala Pro Cys Gly Gly Asp Leu Thr Phe
        195                 200                 205

Asp Pro Gly Pro Arg Asp Leu Val Glu Pro Trp Val Val Val Arg Gly
    210                 215                 220

Leu Arg Pro Asp Phe Thr Tyr Thr Phe Glu Val Thr Ala Leu Asn Gly
225                 230                 235                 240

Val Ser Ser Leu Ala Thr Gly Pro Val Pro Phe Glu Pro Val Asn Val
                245                 250                 255

Thr Thr Asp Arg Glu Val Pro Pro Ala Val Ser Asp Ile Arg Val Thr
            260                 265                 270

Arg Ser Ser Pro Ser Ser Leu Ser Leu Ala Trp Ala Val Pro Arg Ala
        275                 280                 285

Pro Ser Gly Ala Trp Leu Asp Tyr Glu Val Lys Tyr His Glu Lys Gly
    290                 295                 300

Ala Glu Gly Pro Ser Ser Val Arg Phe Leu Lys Thr Ser Glu Asn Arg
305                 310                 315                 320

Ala Glu Leu Arg Gly Leu Lys Arg Gly Ala Ser Tyr Leu Val Gln Val
                325                 330                 335

Arg Ala Arg Ser Glu Ala Gly Tyr Gly Pro Phe Gly Gln Glu His His
            340                 345                 350

Ser Gln Thr Gln Leu Asp Glu Ser Glu Gly Trp Arg Glu Gln Gly Gly
        355                 360                 365

Arg Ser Ser Leu Glu Gly Pro Arg Phe Glu Gly Lys Pro Ile Pro Asn
    370                 375                 380

Pro Leu Leu Gly Leu Asp Ser Thr Arg Thr Gly His His His His His
385                 390                 395                 400

His


<210> SEQ ID NO 420
<211> LENGTH: 6921
<212> TYPE: DNA
<213> ORGANISM: Unknown
<220> FEATURE:
<223> OTHER INFORMATION: plasmid vector sequence

<400> SEQUENCE: 420

aatattattg aagcatttat cagggttatt gtctcatgag cggatacata tttgaatgta     60

tttagaaaaa taaacaaata ggggttccgc gcacatttcc ccgaaaagtg ccacctgacg    120

tcgacggatc gggagatctc ccgatcccct atggtcgact ctcagtacaa tctgctctga    180

tgccgcatag ttaagccagt atctgctccc tgcttgtgtg ttggaggtcg ctgagtagtg    240

cgcgagcaaa atttaagcta caacaaggca aggcttgacc gacaattgca tgaagaatct    300

gcttagggtt aggcgttttg cgctgcttcg cgatgtacgg gccagatata cgcgttgaca    360

ttgattattg actaggcttt tgcaaaaagc tttgcaaaga tggataaagt tttaaacaga    420

gaggaatctt tgcagctaat ggaccttcta ggtcttgaaa ggagtgcctc gtgaggctcc    480
```

-continued

```
ggtgcccgtc agtgggcaga gcgcacatcg cccacagtcc ccgagaagtt ggggggaggg    540
gtcggcaatt gaaccggtgc ctagagaagg tggcgcgggg taaactggga aagtgatgtc    600
gtgtactggc tccgcctttt tcccgagggt gggggagaac cgtatataag tgcagtagtc    660
gccgtgaacg ttctttttcg caacgggttt gccgccagaa cacaggtaag tgccgtgtgt    720
ggttcccgcg ggcctggcct ctttacgggt tatggccctt gcgtgccttg aattacttcc    780
acctggctgc agtacgtgat tcttgatccc gagcttcggg ttggaagtgg gtgggagagt    840
tcgaggcctt gcgcttaagg agccccttcg cctcgtgctt gagttgaggc ctggcctggg    900
cgctggggcc gccgcgtgcg aatctggtgg caccttcgcg cctgtctcgc tgctttcgat    960
aagtctctag ccatttaaaa tttttgatga cctgctgcga cgcttttttt ctggcaagat   1020
agtcttgtaa atgcgggcca agatctgcac actggtattt cggtttttgg ggccgcgggc   1080
ggcgacgggg cccgtgcgtc ccagcgcaca tgttcggcga ggcggggcct gcgagcgcgg   1140
ccaccgagaa tcggacgggg gtagtctcaa gctggccggc ctgctctggt gcctggcctc   1200
gcgccgccgt gtatcgcccc gccctgggcg gcaaggctgg cccggtcggc accagttgcg   1260
tgagcggaaa gatggccgct tcccggccct gctgcaggga gctcaaaatg gaggacgcgg   1320
cgctcgggag agcgggcggg tgagtcaccc acacaaagga aaagggcctt tccgtcctca   1380
gccgtcgctt catgtgactc cacggagtac cgggcgccgt ccaggcacct cgattagttc   1440
tcgagctttt ggagtacgtc gtctttaggt tggggggagg ggttttatgc gatggagttt   1500
ccccacactg agtgggtgga gactgaagtt aggccagctt ggcacttgat gtaattctcc   1560
ttggaatttg cccttttttga gtttggatct tggttcattc tcaagcctca gacagtggtt   1620
caaagttttt ttcttccatt tcaggtgtcg tgaggaatta gcttggtact aatacgactc   1680
actataggga gacccaagct ggctaggtaa gcttggtacc gagctcggat ccactagtcc   1740
agtgtggtgg aattgccctt tactagtccg ccatggagct ccgggtgctg ctctgctggg   1800
cttcgttggc cgcagctttg gaagagaccc tgctgaacac aaaattggaa actcagctga   1860
ctgtgaacct gactcgattc ccggagactg tgcctcggga gctggttgtg cccgtggccg   1920
gtagctgcgt ggtggatgcc gtccccgccc ctggccccag ccccagcctc tactgccgtg   1980
aggatggcca gtgggccgaa cagccggtca cgggctgcag ctgtgctccg gggttcgagg   2040
cagctgaggg gaacaccaag tgccgagcct gtgcccaggg caccttcaag cccctgtcag   2100
gagaagggtc ctgccagcca tgcccagcca atagccactc taacaccatt ggatcagccg   2160
tctgccagtg ccgcgtcggg tacttccggg cacgcacaga cccccggggt gcaccctgca   2220
ccacccctcc ttcggctccg cggagcgtgg tttcccgcct gaacggctcc tccctgcacc   2280
tggaatggag tgccccccctg gagtctggtg gccgagagga cctcacctac gccctccgct   2340
gccgggagtg tcgacccgga ggctcctgtg cgccctgcgg gggagacctg acttttgacc   2400
ccggcccccg ggacctggtg gagccctggg tggtggttcg agggctacgt cctgacttca   2460
cctatacctt tgaggtcact gcattgaacg gggtatcctc cttagccacg gggcccgtcc   2520
catttgagcc tgtcaatgtc accactgacc gagaggtacc tcctgcagtg tctgacatcc   2580
gggtgacgcg gtcctcaccc agcagcttga gcctggcctg ggctgttccc cgggcaccca   2640
gtggggctgt gctggactac gaggtcaaat accatgagaa gggcgccgag ggtcccagca   2700
gcgtgcggtt cctgaagacg tcagaaaacc gggcagagct gcgggggctg aagcggggag   2760
ccagctacct ggtgcaggta cgggcgcgct ctgaggccgg ctacgggccc ttcggccagg   2820
aacatcacag ccagacccaa ctggatgaga gcgagggctg gcgggagcag ggcggccgct   2880
```

-continued

```
cgagtctaga gggcccgcgg ttcgaaggta agcctatccc taaccctctc ctcggtctcg   2940
attctacgcg taccggtcat catcaccatc accattgagt ttaaacccgc tgatcagcct   3000
cgactgtgcc ttctagttgc cagccatctg ttgtttgccc ctcccccgtg ccttccttga   3060
ccctggaagg tgccactccc actgtccttt cctaataaaa tgaggaaatt gcatcgcatt   3120
gtctgagtag gtgtcattct attctggggg gtggggtggg gcaggacagc aagggggagg   3180
attgggaaga caatagcagg catgctgggg atgcggtggg ctctatggct tctgaggcgg   3240
aaagaaccag ctggggctct agggggtatc cccacgcgcc ctgtagcggc gcattaagcg   3300
cggcgggtgt ggtggttacg cgcagcgtga ccgctacact tgccagcgcc ctagcgcccg   3360
ctcctttcgc tttcttccct tcctttctcg ccacgttcgc cggctttccc cgtcaagctc   3420
taaatcgggg catcccttta gggttccgat ttagtgcttt acggcacctc gaccccaaaa   3480
aacttgatta gggtgatggt tcacgtagtg ggccatcgcc ctgatagacg gtttttcgcc   3540
ctttgacgtt ggagtccacg ttctttaata gtggactctt gttccaaact ggaacaacac   3600
tcaaccctat ctcggtctat tcttttgatt tataagggat tttggggatt tcggcctatt   3660
ggttaaaaaa tgagctgatt taacaaaaat ttaacgcgaa ttaattctgt ggaatgtgtg   3720
tcagttaggg tgtggaaagt ccccaggctc cccaggcagg cagaagtatg caaagcatgc   3780
atctcaatta gtcagcaacc aggtgtggaa agtccccagg ctccccagca ggcagaagta   3840
tgcaaagcat gcatctcaat tagtcagcaa ccatagtccc gcccctaact ccgcccatcc   3900
cgcccctaac tccgcccagt tccgcccatt ctccgcccca tggctgacta atttttttta   3960
tttatgcaga ggccgaggcc gcctctgcct ctgagctatt ccagaagtag tgaggaggct   4020
tttttggagg cctaggcttt tgcaaaaagc tcccgggagc ttgtatatcc attttcggat   4080
ctgatcagca cgtgttgaca attaatcatc ggcatagtat atcggcatag tataatacga   4140
caaggtgagg aactaaacca tggccaagcc tttgtctcaa gaagaatcca ccctcattga   4200
aagagcaacg gctacaatca acagcatccc catctctgaa gactacagcg tcgccagcgc   4260
agctctctct agcgacggcc gcatcttcac tggtgtcaat gtatatcatt ttactggggg   4320
accttgtgca gaactcgtgg tgctgggcac tgctgctgct gcggcagctg gcaacctgac   4380
ttgtatcgtc gcgatcggaa atgagaacag gggcatcttg agcccctgcg gacggtgtcg   4440
acaggtgctt ctcgatctgc atcctgggat caaagcgata gtgaaggaca gtgatggaca   4500
gccgacggca gttgggattc gtgaattgct gccctctggt tatgtgtggg agggctaagc   4560
acttcgtggc cgaggagcag gactgacacg tgctacgaga tttcgattcc accgccgcct   4620
tctatgaaag gttgggcttc ggaatcgttt tccgggacgc cggctggatg atcctccagc   4680
gcggggatct catgctggag ttcttcgccc accccaactt gtttattgca gcttataatg   4740
gttacaaata aagcaatagc atcacaaatt tcacaaataa agcatttttt tcactgcatt   4800
ctagttgtgg tttgtccaaa ctcatcaatg tatcttatca tgtctgtata ccgtcgacct   4860
ctagctagag cttggcgtaa tcatggtcat agctgtttcc tgtgtgaaat tgttatccgc   4920
tcacaattcc acacaacata cgagccggaa gcataaagtg taaagcctgg ggtgcctaat   4980
gagtgagcta actcacatta attgcgttgc gctcactgcc cgctttccag tcgggaaacc   5040
tgtcgtgcca gctgcattaa tgaatcggcc aacgcgcggg gagaggcggt ttgcgtattg   5100
ggcgctcttc cgcttcctcg ctcactgact cgctgcgctc ggtcgttcgg ctgcggcgag   5160
cggtatcagc tcactcaaag gcggtaatac ggttatccac agaatcaggg gataacgcag   5220
gaaagaacat gtgagcaaaa ggccagcaaa aggccaggaa ccgtaaaaag gccgcgttgc   5280
```

tggcgttttt ccataggctc cgcccccctg acgagcatca caaaaatcga cgctcaagtc 5340
agaggtggcg aaacccgaca ggactataaa gataccaggc gtttccccct ggaagctccc 5400
tcgtgcgctc tcctgttccg accctgccgc ttaccggata cctgtccgcc tttctccctt 5460
cgggaagcgt ggcgctttct caatgctcac gctgtaggta tctcagttcg gtgtaggtcg 5520
ttcgctccaa gctgggctgt gtgcacgaac cccccgttca gcccgaccgc tgcgccttat 5580
ccggtaacta tcgtcttgag tccaacccgg taagacacga cttatcgcca ctggcagcag 5640
ccactggtaa caggattagc agagcgaggt atgtaggcgg tgctacagag ttcttgaagt 5700
ggtggcctaa ctacggctac actagaagga cagtatttgg tatctgcgct ctgctgaagc 5760
cagttacctt cggaaaaaga gttggtagct cttgatccgg caaacaaacc accgctggta 5820
gcggtggttt ttttgtttgc aagcagcaga ttacgcgcag aaaaaaagga tctcaagaag 5880
atcctttgat cttttctacg gggtctgacg ctcagtggaa cgaaaactca cgttaaggga 5940
ttttggtcat gagattatca aaaaggatct tcacctagat ccttttaaat taaaaatgaa 6000
gttttaaatc aatctaaagt atatatgagt aaacttggtc tgacagttac caatgcttaa 6060
tcagtgaggc acctatctca gcgatctgtc tatttcgttc atccatagtt gcctgactcc 6120
ccgtcgtgta gataactacg atacgggagg gcttaccatc tggccccagt gctgcaatga 6180
taccgcgaga cccacgctca ccggctccag atttatcagc aataaaccag ccagccggaa 6240
gggccgagcg cagaagtggt cctgcaactt tatccgcctc catccagtct attaattgtt 6300
gccgggaagc tagagtaagt agttcgccag ttaatagttt gcgcaacgtt gttgccattg 6360
ctacaggcat cgtggtgtca cgctcgtcgt ttggtatggc ttcattcagc tccggttccc 6420
aacgatcaag gcgagttaca tgatccccca tgttgtgcaa aaaagcggtt agctccttcg 6480
gtcctccgat cgttgtcaga agtaagttgg ccgcagtgtt atcactcatg gttatggcag 6540
cactgcataa ttctcttact gtcatgccat ccgtaagatg cttttctgtg actggtgagt 6600
actcaaccaa gtcattctga gaatagtgta tgcggcgacc gagttgctct tgcccggcgt 6660
caatacggga taataccgcg ccacatagca gaactttaaa agtgctcatc attggaaaac 6720
gttcttcggg gcgaaaactc tcaaggatct taccgctgtt gagatccagt tcgatgtaac 6780
ccactcgtgc acccaactga tcttcagcat cttttacttt caccagcgtt tctgggtgag 6840
caaaaacagg aaggcaaaat gccgcaaaaa agggaataag ggcgacacgg aaatgttgaa 6900
tactcatact cttccttttt c 6921

<210> SEQ ID NO 421
<211> LENGTH: 20
<212> TYPE: DNA
<213> ORGANISM: Unknown
<220> FEATURE:
<223> OTHER INFORMATION: oligonucleotide primer

<400> SEQUENCE: 421
cattggatca gccgtctgcc 20

<210> SEQ ID NO 422
<211> LENGTH: 44
<212> TYPE: DNA
<213> ORGANISM: Homo sapiens

<400> SEQUENCE: 422
tgtttaaact tactgctccc gccagccctc gctctcatcc agtt 44

<210> SEQ ID NO 423
<211> LENGTH: 1633
<212> TYPE: DNA
<213> ORGANISM: Homo sapiens

<400> SEQUENCE: 423
aagcttccgc catggagctc cgggtgctgc tctgctgggc ttcgttggcc gcagctttgg 60
aagagaccct gctgaacaca aaattggaaa ctgctgatct gaagtgggtg acattccctc 120
aggtggacgg gcagtgggag gaactgagcg gcctggatga ggaacagcac agcgtgcgca 180
cctacgaagt gtgtgaagtg cagcgtgccc cgggccaggc ccactggctt cgcacaggtt 240
gggtcccacg gcggggcgcc gtccacgtgt acgccacgct gcgcttcacc atgctcgagt 300
gcctgtccct gcctcgggct gggcgctcct gcaaggagac cttcaccgtc ttctactatg 360
agagcgatgc ggacacggcc acggccctca cgccagcctg gatggagaac ccctacatca 420
aggtggacac ggtggccgcg gagcatctca cccggaagcg ccctggggcc gaggccaccg 480
ggaaggtgaa tgtcaagacg ctgcgtctgg gaccgctcag caaggctggc ttctacctgg 540
ccttccagga ccagggtgcc tgcatggccc tgctatccct gcacctcttc tacaaaaagt 600
gcgcccagct gactgtgaac ctgactcgat tcccggagac tgtgcctcgg gagctggttg 660
tgcccgtggc cggtagctgc gtggtggatg ccgtccccgc ccctggcccc agccccagcc 720
tctactgccg tgaggatggc cagtgggccg aacagccggt cacgggctgc agctgtgctc 780
cggggttcga ggcagctgag gggaacacca agtgccgagc ctgtgcccag ggcaccttca 840
agcccctgtc aggagaaggg tcctgccagc catgcccagc caatagccac tctaacacca 900
ttggatcagc cgtctgccag tgccgcgtcg ggtacttccg ggcacgcaca gacccccggg 960
gtgcaccctg caccacccct ccttcggctc cgcggagcgt ggtttcccgc ctgaacggct 1020
cctccctgca cctggaatgg agtgcccccc tggagtctgg tggccgagag gacctcacct 1080
acgccctccg ctgccgggag tgccgacccg gaggctcctg tgcgccctgc gggggagacc 1140
tgacttttga ccccggcccc cgggacctgg tggagccctg ggtggtggtt cgagggctac 1200
gtccggactt cacctatacc tttgaggtca ctgcattgaa cggggtatcc tccttagcca 1260
cggggcccgt cccatttgag cctgtcaatg tcaccactga ccgagaggta cctcctgcag 1320
tgtctgacat ccgggtgacg cggtcctcac ccagcagctt gagcctggcc tgggctgttc 1380
cccgggcacc cagtggggcg tggctggact acgaggtcaa ataccatgag aagggcgccg 1440
agggtcccag cagcgtgcgg ttcctgaaga cgtcagaaaa ccgggcagag ctgcgggggc 1500
tgaagcgggg agccagctac ctggtgcagg tacgggcgcg ctctgaggcc ggctacgggc 1560
ccttcggcca ggaacatcac agccagaccc aactggatga gagcgagggc tggcgggagc 1620
agtaagttta aac 1633

<210> SEQ ID NO 424
<211> LENGTH: 537
<212> TYPE: PRT
<213> ORGANISM: Homo sapiens

<400> SEQUENCE: 424

Met Glu Leu Arg Val Leu Leu Cys Trp Ala Ser Leu Ala Ala Ala Leu
1 5 10 15

Glu Glu Thr Leu Leu Asn Thr Lys Leu Glu Thr Ala Asp Leu Lys Trp
20 25 30

Val Thr Phe Pro Gln Val Asp Gly Gln Trp Glu Glu Leu Ser Gly Leu
35 40 45

-continued

```
Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480
```

```
Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln
    530                 535


<210> SEQ ID NO 425
<211> LENGTH: 522
<212> TYPE: PRT
<213> ORGANISM: Homo sapiens

<400> SEQUENCE: 425

Leu Glu Glu Thr Leu Leu Asn Thr Lys Leu Glu Thr Ala Asp Leu Lys
 1               5                  10                  15

Trp Val Thr Phe Pro Gln Val Asp Gly Gln Trp Glu Glu Leu Ser Gly
            20                  25                  30

Leu Asp Glu Glu Gln His Ser Val Arg Thr Tyr Glu Val Cys Glu Val
        35                  40                  45

Gln Arg Ala Pro Gly Gln Ala His Trp Leu Arg Thr Gly Trp Val Pro
    50                  55                  60

Arg Arg Gly Ala Val His Val Tyr Ala Thr Leu Arg Phe Thr Met Leu
65                  70                  75                  80

Glu Cys Leu Ser Leu Pro Arg Ala Gly Arg Ser Cys Lys Glu Thr Phe
                85                  90                  95

Thr Val Phe Tyr Tyr Glu Ser Asp Ala Asp Thr Ala Thr Ala Leu Thr
            100                 105                 110

Pro Ala Trp Met Glu Asn Pro Tyr Ile Lys Val Asp Thr Val Ala Ala
        115                 120                 125

Glu His Leu Thr Arg Lys Arg Pro Gly Ala Glu Ala Thr Gly Lys Val
    130                 135                 140

Asn Val Lys Thr Leu Arg Leu Gly Pro Leu Ser Lys Ala Gly Phe Tyr
145                 150                 155                 160

Leu Ala Phe Gln Asp Gln Gly Ala Cys Met Ala Leu Leu Ser Leu His
                165                 170                 175

Leu Phe Tyr Lys Lys Cys Ala Gln Leu Thr Val Asn Leu Thr Arg Phe
            180                 185                 190

Pro Glu Thr Val Pro Arg Glu Leu Val Val Pro Val Ala Gly Ser Cys
        195                 200                 205

Val Val Asp Ala Val Pro Ala Pro Gly Pro Ser Pro Ser Leu Tyr Cys
    210                 215                 220

Arg Glu Asp Gly Gln Trp Ala Glu Gln Pro Val Thr Gly Cys Ser Cys
225                 230                 235                 240

Ala Pro Gly Phe Glu Ala Ala Glu Gly Asn Thr Lys Cys Arg Ala Cys
                245                 250                 255

Ala Gln Gly Thr Phe Lys Pro Leu Ser Gly Glu Gly Ser Cys Gln Pro
            260                 265                 270

Cys Pro Ala Asn Ser His Ser Asn Thr Ile Gly Ser Ala Val Cys Gln
        275                 280                 285

Cys Arg Val Gly Tyr Phe Arg Ala Arg Thr Asp Pro Arg Gly Ala Pro
    290                 295                 300

Cys Thr Thr Pro Pro Ser Ala Pro Arg Ser Val Val Ser Arg Leu Asn
305                 310                 315                 320
```

-continued

```
Gly Ser Ser Leu His Leu Glu Trp Ser Ala Pro Leu Glu Ser Gly Gly
                325                 330                 335

Arg Glu Asp Leu Thr Tyr Ala Leu Arg Cys Arg Glu Cys Arg Pro Gly
            340                 345                 350

Gly Ser Cys Ala Pro Cys Gly Gly Asp Leu Thr Phe Asp Pro Gly Pro
        355                 360                 365

Arg Asp Leu Val Glu Pro Trp Val Val Val Arg Gly Leu Arg Pro Asp
    370                 375                 380

Phe Thr Tyr Thr Phe Glu Val Thr Ala Leu Asn Gly Val Ser Ser Leu
385                 390                 395                 400

Ala Thr Gly Pro Val Pro Phe Glu Pro Val Asn Val Thr Thr Asp Arg
                405                 410                 415

Glu Val Pro Pro Ala Val Ser Asp Ile Arg Val Thr Arg Ser Ser Pro
            420                 425                 430

Ser Ser Leu Ser Leu Ala Trp Ala Val Pro Arg Ala Pro Ser Gly Ala
        435                 440                 445

Trp Leu Asp Tyr Glu Val Lys Tyr His Glu Lys Gly Ala Glu Gly Pro
    450                 455                 460

Ser Ser Val Arg Phe Leu Lys Thr Ser Glu Asn Arg Ala Glu Leu Arg
465                 470                 475                 480

Gly Leu Lys Arg Gly Ala Ser Tyr Leu Val Gln Val Arg Ala Arg Ser
                485                 490                 495

Glu Ala Gly Tyr Gly Pro Phe Gly Gln Glu His His Ser Gln Thr Gln
            500                 505                 510

Leu Asp Glu Ser Glu Gly Trp Arg Glu Gln
        515                 520
```

POLYPEPTIDE COMPOUNDS FOR INHIBITING ANGIOGENESIS AND TUMOR GROWTH

RELATED APPLICATIONS

This application is a continuation of U.S. patent application Ser. No. 10/949,720 filed Sep. 23, 2004 (issued Jun. 3, 2008 as U.S. Pat. No. 7,381,410), which is a continuation-in-part of U.S. patent application Ser. No. 10/800,350 filed Mar. 12, 2004 (issued Jan. 4, 2011 as U.S. Pat. No, 7,862,816), which claims the benefit of priority of U.S. Provisional Application No. 60/454,300 filed Mar. 12, 2003 and U.S. Provisional Application No. 60/454,432 filed Mar. 12, 2003. The entire teachings of the referenced Applications are incorporated herein by reference in their entirety.

BACKGROUND OF THE INVENTION

Angiogenesis, the development of new blood vessels from the endothelium of a preexisting vasculature, is a critical process in the growth, progression, and metastasis of solid tumors within the host. During physiologically normal angiogenesis, the autocrine, paracrine, and amphicrine interactions of the vascular endothelium with its surrounding stromal components are tightly regulated both spatially and temporally. Additionally, the levels and activities of proangiogenic and angiostatic cytokines and growth factors are maintained in balance. In contrast, the pathological angiogenesis necessary for active tumor growth is sustained and persistent, representing a dysregulation of the normal angiogenic system. Solid and hematopoietic tumor types are particularly associated with a high level of abnormal angiogenesis.

It is generally thought that the development of tumor consists of sequential, and interrelated steps that lead to the generation of an autonomous clone with aggressive growth potential. These steps include sustained growth and unlimited self-renewal. Cell populations in a tumor are generally characterized by growth signal self-sufficiency, decreased sensitivity to growth suppressive signals, and resistance to apoptosis. Genetic or cytogenetic events that initiate aberrant growth sustain cells in a prolonged "ready" state by preventing apoptosis.

It is a goal of the present disclosure to provide agents and therapeutic treatments for inhibiting angiogenesis and tumor growth.

SUMMARY OF THE INVENTION

In certain aspects, the disclosure provides polypeptide agents that inhibit EphB4 or EphrinB2 mediated functions, including monomeric ligand binding portions of the EphB4 and EphrinB2 proteins and antibodies that bind to and affect EphB4 or EphrinB2 in particular ways. As demonstrated herein, EphB4 and EphrinB2 participate in various disease states, including cancers and diseases related to unwanted or excessive angiogenesis. Accordingly, certain polypeptide agents disclosed herein may be used to treat such diseases. In further aspects, the disclosure relates to the discovery that EphB4 and/or EphrinB2 are expressed, often at high levels, in a variety of tumors. Therefore, polypeptide agents that down-regulate EphB4 or EphrinB2 function may affect tumors by a direct effect on the tumor cells as well as an indirect effect on the angiogenic processes recruited by the tumor. In certain embodiments, the disclosure provides the identity of tumor types particularly suited to treatment with an agent that down-regulates EphB4 or EphrinB2 function.

In certain aspects, the disclosure provides soluble EphB4 polypeptides comprising an amino acid sequence of an extracellular domain of an EphB4 protein. The soluble EphB4 polypeptides bind specifically to an EphrinB2 polypeptide. The term "soluble" is used merely to indicate that these polypeptides do not contain a transmembrane domain or a portion of a transmembrane domain sufficient to compromise the solubility of the polypeptide in a physiological salt solution. Soluble polypeptides are preferably prepared as monomers that compete with EphB4 for binding to ligand such as EphrinB2 and inhibit the signaling that results from EphB4 activation. Optionally, a soluble polypeptide may be prepared in a multimeric form, by, for example, expressing as an Fc fusion protein or fusion with another multimerization domain. Such multimeric forms may have complex activities, having agonistic or antagonistic effects depending on the context. In certain embodiments the soluble EphB4 polypeptide comprises a globular domain of an EphB4 protein. A soluble EphB4 polypeptide may comprise a sequence at least 90% identical to residues 1-522 of the amino acid sequence defined by FIG. 65. A soluble EphB4 polypeptide may comprise a sequence at least 90% identical to residues 1-412 of the amino acid sequence defined by FIG. 65. A soluble EphB4 polypeptide may comprise a sequence at least 90% identical to residues 1-312 of the amino acid sequence defined by FIG. 65. A soluble EphB4 polypeptide may comprise a sequence encompassing the globular (G) domain (amino acids 29-197 of FIG. 65), and optionally additional domains, such as the cysteine-rich domain (amino acids 239-321 of FIG. 65), the first fibronectin type 3 domain (amino acids 324-429 of FIG. 65) and the second fibronectin type 3 domain (amino acids 434-526 of FIG. 65). Preferred polypeptides described herein and demonstrated as having ligand binding activity include polypeptides corresponding to 1-537, 1-427 and 1-326, respectively, of the amino acid sequence shown in FIG. 65. A soluble EphB4 polypeptide may comprise a sequence as set forth in FIG. 1 or 2. As is well known in the art, expression of such EphB4 polypeptides in a suitable cell, such as HEK293T cell line, will result in cleavage of a leader peptide. Although such cleavage is not always complete or perfectly consistent at a single site, it is known that EphB4 tends to be cleaved so as to remove the first 15 amino acids of the sequence shown in FIG. 65. Accordingly, as specific examples, the disclosure provides unprocessed soluble EphB4 polypeptides that bind to EphrinB2 and comprise an amino acid sequence selected from the following group (numbering is with respect to the sequence of FIG. 65): 1-197, 29-197, 1-312, 29-132, 1-321, 29-321, 1-326, 29-326, 1-412, 29-412, 1-427, 29-427, 1-429, 29-429, 1-526, 29-526, 1-537 and 29-537. Such polypeptides may be used in a processed form, such forms having a predicted amino acid sequence selected from the following group (numbering is with respect to the sequence of FIG. 65): 16-197, 16-312, 16-321, 16-326, 16-412, 16-427, 16-429, 16-526 and 16-537. Additionally, a soluble EphB4 polypeptide may be one that comprises an amino acid sequence at least 90%, and optionally 95% or 99% identical to any of the preceding amino acid sequences while retaining EphrinB2 binding activity. Preferably, any variations in the amino acid sequence from the sequence shown in FIG. 65 are conservative changes or deletions of no more than 1, 2, 3, 4 or 5 amino acids, particularly in a surface loop region. In certain embodiments, the soluble EphB4 polypeptide may inhibit the interaction between Ephrin B2 and EphB4. The soluble EphB4 polypeptide may inhibit clustering of or phosphorylation of Ephrin B2 or EphB4. Phosphorylation of EphrinB2 or EphB4 is generally considered to be one of the initial events in triggering intracellular signaling pathways regulated by these proteins. As noted above, the soluble EphB4 polypeptide may be prepared as a monomeric or multimeric fusion protein. The soluble polypeptide may include one or more modified amino acids. Such amino acids may contribute to desirable properties, such as increased resistance to protease digestion.

In certain aspects, the disclosure provides soluble EphrinB2 polypeptides comprising an amino acid sequence of an extracellular domain of an EphrinB2 protein. The soluble EphrinB2 polypeptides bind specifically to an EphB4 polypeptide. The term "soluble" is used merely to indicate that these polypeptides do not contain a transmembrane domain or a portion of a transmembrane domain sufficient to compromise the solubility of the polypeptide in a physiological salt solution. Soluble polypeptides are preferably prepared as monomers that compete with EphrinB2 for binding to ligand such as EphB4 and inhibit the signaling that results from EphrinB2 activation. Optionally, a soluble polypeptide may be prepared in a multimeric form, by, for example, expressing as an Fc fusion protein or fusion with another multimerization domain. Such multimeric forms may have complex activities, having agonistic or antagonistic effects depending on the context. A soluble EphrinB2 polypeptide may comprise residues 1-225 of the amino acid sequence defined by FIG. 66. A soluble EphrinB2 polypeptide may comprise a sequence defined by FIG. 3. As is well known in the art, expression of such EphrinB2 polypeptides in a suitable cell, such as HEK293T cell line, will result in cleavage of a leader peptide. Although such cleavage is not always complete or perfectly consistent at a single site, it is known that EphrinB2 tends to be cleaved so as to remove the first 26 amino acids of the sequence shown in FIG. 66. Accordingly, as specific examples, the disclosure provides unprocessed soluble EphrinB2 polypeptides that bind to EphB4 and comprise an amino acid sequence corresponding to amino acids 1-225 of FIG. 66. Such polypeptides may be used in a processed form, such forms having a predicted amino acid sequence selected from the following group (numbering is with respect to the sequence of FIG. 66): 26-225. In certain embodiments, the soluble EphrinB2 polypeptide may inhibit the interaction between Ephrin B2 and EphB4. The soluble EphrinB2 polypeptide may inhibit clustering of or phosphorylation of EphrinB2 or EphB4. As noted above, the soluble EphrinB2 polypeptide may be prepared as a monomeric or multimeric fusion protein. The soluble polypeptide may include one or more modified amino acids. Such amino acids may contribute to desirable properties, such as increased resistance to protease digestion.

In certain aspects, the disclosure provides antagonist antibodies for EphB4 and EphrinB2. An antibody may be designed to bind to an extracellular domain of an EphB4 protein and inhibit an activity of the EphB4. An antibody may be designed to bind to an extracellular domain of an Ephrin B2 protein and inhibit an activity of the Ephrin B2. An antibody may be designed to inhibit the interaction between Ephrin B2 and EphB4. An antagonist antibody will generally affect Eph and/or Ephrin signaling. For example, an antibody may inhibit clustering or phosphorylation of Ephrin B2 or EphB4. An antagonist antibody may be essentially any polypeptide comprising a variable portion of an antibody, including, for example, monoclonal and polyclonal antibodies, single chain antibodies, diabodies, minibodies, etc.

In certain aspects, the disclosure provides pharmaceutical formulations comprising a polypeptide reagent and a pharmaceutically acceptable carrier. The polypeptide reagent may be any disclosed herein, including, for example, soluble EphB4 or EphrinB2 polypeptides and antagonist antibodies. Additional formulations include cosmetic compositions and diagnostic kits.

In certain aspects the disclosure provides methods of inhibiting signaling through Ephrin B2/EphB4 pathway in a cell. A method may comprise contacting the cell with an effective amount of a polypeptide agent, such as (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; or (d) an antibody which binds to an extracellular domain of an Ephrin B2 protein and inhibits an activity of the Ephrin B2.

In certain aspects the disclosure provides methods for reducing the growth rate of a tumor, comprising administering an amount of a polypeptide agent sufficient to reduce the growth rate of the tumor, wherein the polypeptide agent is selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2. Optionally, the tumor comprises cells expressing a higher level of EphB4 and/or EphrinB2 than noncancerous cells of a comparable tissue.

In certain aspects, the disclosure provides methods for treating a patient suffering from a cancer. A method may comprise administering to the patient a polypeptide agent selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2. Optionally, the cancer comprises cancer cells expressing EphrinB2 and/or EphB4 at a higher level than noncancerous cells of a comparable tissue. The cancer may be a metastatic cancer. The cancer may be selected from the group consisting of colon carcinoma, breast tumor, mesothelioma, prostate tumor, squamous cell carcinoma, Kaposi sarcoma, and leukemia. Optionally, the cancer is an angiogenesis-dependent cancer or an angiogenesis independent cancer. The polypeptide agent employed may inhibit clustering or phosphorylation of Ephrin B2 or EphB4. A polypeptide agent may be co-administered with one or more additional anti-cancer chemotherapeutic agents that inhibit cancer cells in an additive or synergistic manner with the polypeptide agent.

In certain aspects, the disclosure provides methods of inhibiting angiogenesis. A method may comprise contacting a cell with an amount of a polypeptide agent sufficient to inhibit angiogenesis, wherein the polypeptide agent is selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2.

In certain aspects, the disclosure provides methods for treating a patient suffering from an angiogenesis-associated disease, comprising administering to the patient a polypeptide agent selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2. The soluble polypeptide may be formulated with a pharmaceutically acceptable carrier. An angiogenesis related disease or unwanted angiogenesis related process may be selected from the group consisting of angiogenesis-dependent cancer, benign tumors, inflammatory disorders, chronic articular rheumatism and psoriasis, ocular angiogenic diseases, Osler-Webber Syndrome, myocardial angiogenesis, plaque neovascularization, telangiectasia, hemophiliac joints, angiofibroma, wound granulation, wound healing, telangiectasia psoriasis scleroderma, pyogenic granuloma, cororany collaterals, ischemic limb angiogenesis, rubeosis, arthritis, diabetic neovascularization, fractures, vasculogenesis, and hematopoiesis. An polypeptide agent may be co-administered with at least one additional anti-angiogenesis agent that inhibits angiogenesis in an additive or synergistic manner with the soluble polypeptide.

In certain aspects, the disclosure provides for the use of a polypeptide agent in the manufacture of medicament for the treatment of cancer or an angiogenesis related disorder, wherein the polypeptide agent is selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide; (c) an antibody which binds to an extracellular domain of an EphB4 protein and inhibits an activity of the EphB4; and (d) an antibody which binds to an extracellular domain of an Ephrin B2 protein and inhibits an activity of the Ephrin B2.

In certain aspects, the disclosure provides methods for treating a patient suffering from a cancer, comprising: (a) identifying in the patient a tumor having a plurality of cancer cells that express EphB4 and/or EphrinB2; and (b) administering to the patient a polypeptide agent selected from the group consisting of: (i) a soluble polypeptide comprising an amino acid sequence of an extracellular domain of an EphB4 protein, wherein the EphB4 polypeptide is a monomer and binds specifically to an Ephrin B2 polypeptide; (ii) a soluble polypeptide comprising an amino acid sequence of an extracellular domain of an Ephrin B2 protein, wherein the soluble EphrinB2 polypeptide is a monomer and binds with high affinity to an EphB4 polypeptide; (iii) an antibody which binds to an extracellular domain of an EphB4 protein and inhibits an activity of the EphB4; and (iv) an antibody which binds to an extracellular domain of an Ephrin B2 protein and inhibits an activity of the Ephrin B2. Optionally, a method may comprise identifying in the patient a tumor having a plurality of cancer cells having a gene amplification of the EphB4 and/or EphrinB2 gene.

In certain aspects, the disclosure provides methods for identifying a tumor that is suitable for treatment with an EphrinB2 or EphB4 antagonist. A method may comprise detecting in the tumor cell one or more of the following characteristics: (a) expression of EphB4 protein and/or mRNA; (b) expression of EphrinB2 protein and/or mRNA; (c) gene amplification of the EphB4 gene; or (d) gene amplification of the EphrinB2 gene. A tumor cell having one or more of characteristics (a)-(d) may be suitable for treatment with an EphrinB2 or EphB4 antagonist, such as a polypeptide agent described herein.

In certain aspects, the disclosure provides polypeptide agents that inhibit EphB4 mediated functions, including antibodies and antigen binding portions thereof that bind to and affect EphB4 in particular ways. As demonstrated herein, EphB4 and EphrinB2 participate in various disease states, including cancers and diseases related to unwanted or excessive angiogenesis. Accordingly, certain polypeptide agents disclosed herein may be used to treat such diseases. In further aspects, the disclosure relates to the discovery that EphB4 and/or EphrinB2 are expressed, often at high levels, in a variety of tumors. Therefore, polypeptide agents that downregulate EphB4 or EphrinB2 function may affect tumors by a direct effect on the tumor cells as well as an indirect effect on the angiogenic processes recruited by the tumor. In certain embodiments, the disclosure provides the identity of tumor types particularly suited to treatment with an agent that downregulates EphB4 or EphrinB2 function.

In certain aspects, the disclosure provides an isolated antibody or antigen binding portion thereof that binds to an epitope situated in the extracellular portion of EphB4 and inhibits an EphB4 activity. The isolated antibody or antigen binding portion thereof may binds to an epitope situated within amino acids 16-198 of the EphB4 sequence of FIG. 1. For example, the epitope may be situated within the Globular Domain (GD) of EphB4 that binds to EphrinB2. The isolated antibody or antigen binding portion thereof may inhibit the binding of EphB4 to the extracellular portion of EphrinB2. The isolated antibody or antigen binding portion thereof may bind to an epitope situated within amino acids 327-427 or 428-537 of the EphB4 sequence of FIG. 1. For example, the isolated antibody or antigen binding portion thereof may bind to the first fibronectin-like domain (FND1) or the second fibronectin-like domain (FND2) of EphB4. The isolated antibody or antigen binding portion thereof may inhibit EphB4 dimerization or multimerization and may optionally inhibit the EphrinB2-stimulated autophosphorylation of EphB4. The isolated antibody or antigen binding portion thereof may inhibit the formation of tubes by cultured endothelial cells, the vascularization of a tissue in vivo, the vascularization of tissue implanted in the cornea of an animal, the vascularization of a Matrigel tissue plug implanted in an animal, and/or the growth of a human tumor xenograft in a mouse. Preferred antibodies that bind to an epitope situated within amino acids 16-198 of the EphB4 sequence of FIG. 1 include antibodies denoted herein as No. 001, No. 023, No. 035, and No. 079. Preferred antibodies that bind to an epitope situated within amino acids 428-537 of the EphB4 sequence of FIG. 1 include antibodies denoted herein as No. 047, No. 057, No. 85H, No. 098, and No. 138.

In certain aspects, the disclosure provides an isolated antibody or antigen binding portion thereof that binds to an epitope situated in the extracellular portion of EphB4 and stimulates EphB4 kinase activity. For example, described herein are isolated antibodies or antigen binding portion thereof that bind to an epitope situated within amino acids 327-427 of the EphB4 sequence of FIG. 1 and stimulate EphB4 kinase activity. The isolated antibody or antigen binding portion thereof may bind to the first fibronectin-like domain (FND1) of EphB4. The antibody may be selected from the group consisting of antibodies denoted herein as No. 85L, No. 091, No. 121, and No. 131.

The disclosure provides humanized versions of any of the antibodies disclosed herein, as well as antibodies and antigen binding portions thereof that comprise at least one CDR portion derived from an antibody disclosed herein, particularly the CDR3. In preferred embodiments, the antibody is a monoclonal antibody that is immunocompatible with the subject to which it is to be administered, and preferably is clinically acceptable for administration to a human.

In certain aspects, the disclosure provides a hybridoma that produces an antibody disclosed herein, and particularly a hybridoma that produces an antibody selected from the group consisting of antibodies denoted herein as No. 001, No. 023, No. 035, No. 079, No. 047, No. 057, No. 85H, No. 098, No. 138, No. 085L, N0. 091 and No. 131. Hybridomas producing antibody No. 098 (epitope within amino acids 428-537), antibody No, 091 (kinase activating antibody; epitope within amino acids 327-427), antibody No. 023 (epitope within amino acids 16-198), antibody No. 131 (epitope within amino acids 327-427), and antibody No. 138 (epitope within amino acids 428-537) were deposited in the American Type Culture Collection (ATCC), 10801 University Boulevard, Manassas, Va. 20110-2209 on Sep. 14 and 16, 2004, The ATCC Deposit Designation Nos. for antibody No, 023, No. 091, No. 098, No. 131, No. 47 and No. 138 are PTA-6208, PTA-6209, PTA.-6210, PTA-6214, PTA-11338 and PTA-6211, respectively.

Surprisingly, antibodies that inhibit ligand binding, antibodies that inhibit EphB4 kinase activation and antibodies that activate EphB4 kinase activity all inhibit EphB4 mediated events in bioassays. Accordingly, the disclosure provides a method of treating cancer, the method comprising administering to a patient in need thereof an effective amount of an isolated antibody or antigen binding portion thereof that binds to an epitope situated in the extracellular portion of EphB4 and either inhibits an EphB4 activity or activates EphB4 kinase activity. Optionally the patient has been diagnosed with a cancer selected from the group consisting of colon carcinoma, breast tumor, mesothelioma, prostate tumor, squamous cell carcinoma, Kaposi sarcoma, and leukemia. The isolated antibody or antigen binding portion thereof may be administered systemically or locally. Additionally, the disclosure provides methods of inhibiting angiogenesis in a patient, the method comprising administering to a patient in need thereof an effective amount of an isolated antibody or antigen binding portion thereof that binds to an epitope situated in the extracellular portion of EphB4 and inhibits an EphB4 activity or activates an EphB4 kinase activity. Optionally, the patient is diagnosed macular degeneration.

In certain aspects, the disclosure provides a pharmaceutical preparation comprising any of the isolated antibodies or antigen binding portions thereof disclosed herein, as well as the use of such antibodies or antigen binding portions thereof to make a pharmaceutical preparation for treating cancer. Optionally, the cancer is selected from the group consisting of colon carcinoma, breast tumor, mesothelioma, prostate tumor, squamous cell carcinoma, Kaposi sarcoma, and leukemia.

In certain aspects, the antibodies disclosed herein may be covalently linked (or otherwise stably associated with) an additional functional moiety, such as a label or a moiety that confers desirable pharmacokinetic properties. Exemplary labels include those that are suitable for detection by a method selected from the group consisting of: fluorescence detection methods, positron emission tomography detection methods and nuclear magnetic resonance detection methods. Labels may, for example, be selected from the group consisting of: a fluorescent label, a radioactive label, and a label having a distinctive nuclear magnetic resonance signature. Moieties such as a polyethylene glycol (PEG) moiety may be affixed to an antibody or antigen binding portion thereof to increase serum half-life.

BRIEF DESCRIPTION OF THE DRAWINGS

FIG. 1 shows amino acid sequence of the B4ECv3 protein (predicted sequence of the precursor including uncleaved Eph B4 leader peptide is shown), SEQ ID NO: 386.

FIG. 2 shows amino acid sequence of the B4ECv3NT protein (predicted sequence of the precursor including uncleaved Eph B4 leader peptide is shown), SEQ ID NO: 387.

FIG. 3 shows amino acid sequence of the B2EC protein (predicted sequence of the precursor including uncleaved Ephrin B2 leader peptide is shown), SEQ ID NO: 388.

FIG. 4 shows amino acid sequence of the B4ECv3-FC protein (predicted sequence of the precursor including uncleaved Eph B4 leader peptide is shown), SEQ ID NO: 389.

FIG. 5 shows amino acid sequence of the B2EC-FC protein (predicted sequence of the precursor including uncleaved Ephrin B2 leader peptide is shown), SEQ ID NO: 390.

FIG. 15 is a schematic representation of human EphB4 constructs.

FIG. 61 shows a genomic nucleotide sequence of human EphB4, SEQ ID NO: 391.

FIG. 62 shows a cDNA nucleotide sequence of human EphB4, SEQ ID NO: 392.

FIG. 63 shows a genomic nucleotide sequence of human Ephrin B2, SEQ ID NO: 393.

FIG. 64 shows a cDNA nucleotide sequence of human Ephrin B2, SEQ ID NO: 394.

FIG. 65 shows an amino acid sequence of human EphB4, SEQ ID NO: 395.

FIG. 66 shows an amino acid sequence of human Ephrin B2, SEQ ID NO: 396.

DETAILED DESCRIPTION OF THE INVENTION

1. Overview

The current invention is based in part on the discovery that signaling through the ephrin/ephrin receptor (ephrin/eph) pathway contributes to tumorigenesis. Applicants detected expression of ephrin B2 and EphB4 in tumor tissues and developed anti-tumor therapeutic agents for blocking signaling through the ephrin/eph. In addition, the disclosure provides polypeptide therapeutic agents and methods for polypeptide-based inhibition of the function of EphB4 and/or Ephrin B2. Accordingly, in certain aspects, the disclosure provides numerous polypeptide compounds (agents) that may be used to treat cancer as well as angiogenesis related disorders and unwanted angiogenesis related processes.

As used herein, the terms Ephrin and Eph are used to refer, respectively, to ligands and receptors. They can be from any of a variety of animals (e.g., mammals/non-mammals, vertebrates/non-vertebrates, including humans). The nomenclature in this area has changed rapidly and the terminology used herein is that proposed as a result of work by the Eph Nomenclature Committee.

The work described herein, particularly in the examples, refers to Ephrin B2 and EphB4. However, the present invention contemplates any ephrin ligand and/or Eph receptor within their respective family, which is expressed in a tumor. The ephrins (ligands) are of two structural types, which can be further subdivided on the basis of sequence relationships and, functionally, on the basis of the preferential binding they exhibit for two corresponding receptor subgroups. Structurally, there are two types of ephrins: those which are membrane-anchored by a glycerophosphatidylinositol (GPI) linkage and those anchored through a transmembrane domain. Conventionally, the ligands are divided into the Ephrin-A subclass, which are GPI-linked proteins which bind preferentially to EphA receptors, and the Ephrin-B subclass, which are transmembrane proteins which generally bind preferentially to EphB receptors.

The Eph family receptors are a family of receptor protein-tyrosine kinases which are related to Eph, a receptor named for its expression in an erythropoietin-producing human hepatocellular carcinoma cell line. They are divided into two subgroups on the basis of the relatedness of their extracellular domain sequences and their ability to bind preferentially to Ephrin-A proteins or Ephrin-B proteins. Receptors which interact preferentially with Ephrin-A proteins are EphA receptors and those which interact preferentially with Ephrin-B proteins are EphB receptors.

Figure 16:
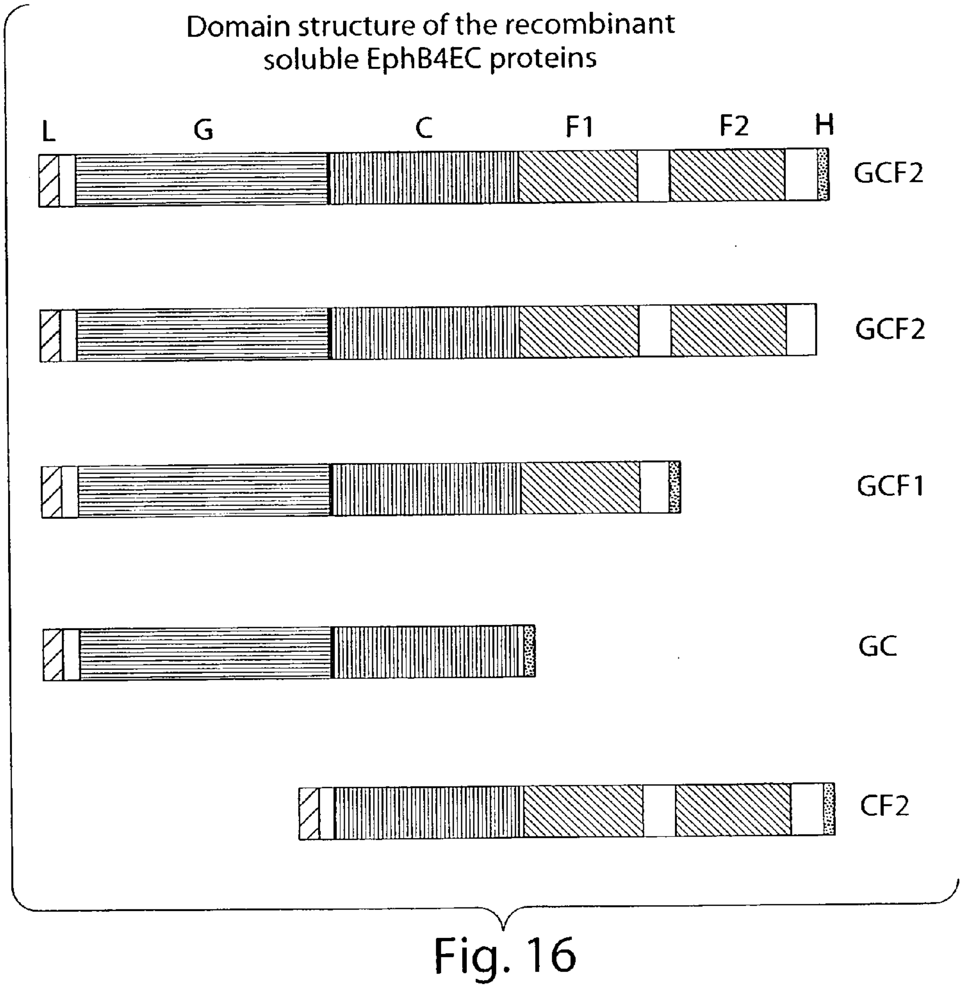
FIG. 16 shows the domain structure of the recombinant soluble EphB4EC proteins. Designation of the domains are as follows: L—leader peptide, G—globular (ligand-binding domain), C—Cys-rich domain, F1, F2—fibronectin type III repeats, H—6×His-tag.

Eph receptors have an extracellular domain composed of the ligand-binding globular domain, a cysteine rich region followed by a pair of fibronectin type III repeats (e.g., see FIG. 16). The cytoplasmic domain consists of a juxtamembrane region containing two conserved tyrosine residues; a protein tyrosine kinase domain; a sterile α-motif (SAM) and a PDZ-domain binding motif. EphB4 is specific for the membrane-bound ligand Ephrin B2 (Sakano, S. et al 1996; Brambilla R. et al 1995). Ephrin B2 belongs to the class of Eph ligands that have a transmembrane domain and cytoplasmic region with five conserved tyrosine residues and PDZ domain. Eph receptors are activated by binding of clustered, membrane attached ephrins (Davis S et al, 1994), indicating that contact between cells expressing the receptors and cells expressing the ligands is required for Eph activation.

Upon ligand binding, an Eph receptor dimerizes and autophosphorylate the juxtamembrane tyrosine residues to acquire full activation (Kalo M S et al, 1999, Binns K S, 2000). In addition to forward signaling through the Eph receptor, reverse signaling can occur through the ephrin Bs. Eph engagement of ephrins results in rapid phosphorylation of the conserved intracellular tyrosines (Bruckner K, 1997) and somewhat slower recruitment of PDZ binding proteins (Palmer A 2002). Recently, several studies have shown that high expression of Eph/ephrins may be associated with increased potentials for tumor growth, tumorigenicity, and metastasis (Easty D J, 1999; Kiyokawa E, 1994; Tang X X, 1999; Vogt T, 1998; Liu W, 2002; Stephenson S A, 2001; Steube K G 1999; Berclaz G, 1996).

In certain embodiments, the present invention provides polypeptide therapeutic agents that inhibit activity of Ephrin B2, EphB4, or both. As used herein, the term "polypeptide therapeutic agent" or "polypeptide agent" is a generic term which includes any polypeptide that blocks signaling through the Ephrin B2/EphB4 pathway. A preferred polypeptide therapeutic agent of the invention is a soluble polypeptide of Ephrin B2 or EphB4. Another preferred polypeptide therapeutic agent of the invention is an antagonist antibody that binds to Ephrin B2 or EphB4. For example, such polypeptide therapeutic agent can inhibit function of Ephrin B2 or EphB4, inhibit the interaction between Ephrin B2 and EphB4, inhibit the phosphorylation of Ephrin B2 or EphB4, or inhibit any of the downstream signaling events upon binding of Ephrin B2 to EphB4.

II. Soluble Polypeptides

Figure 14:
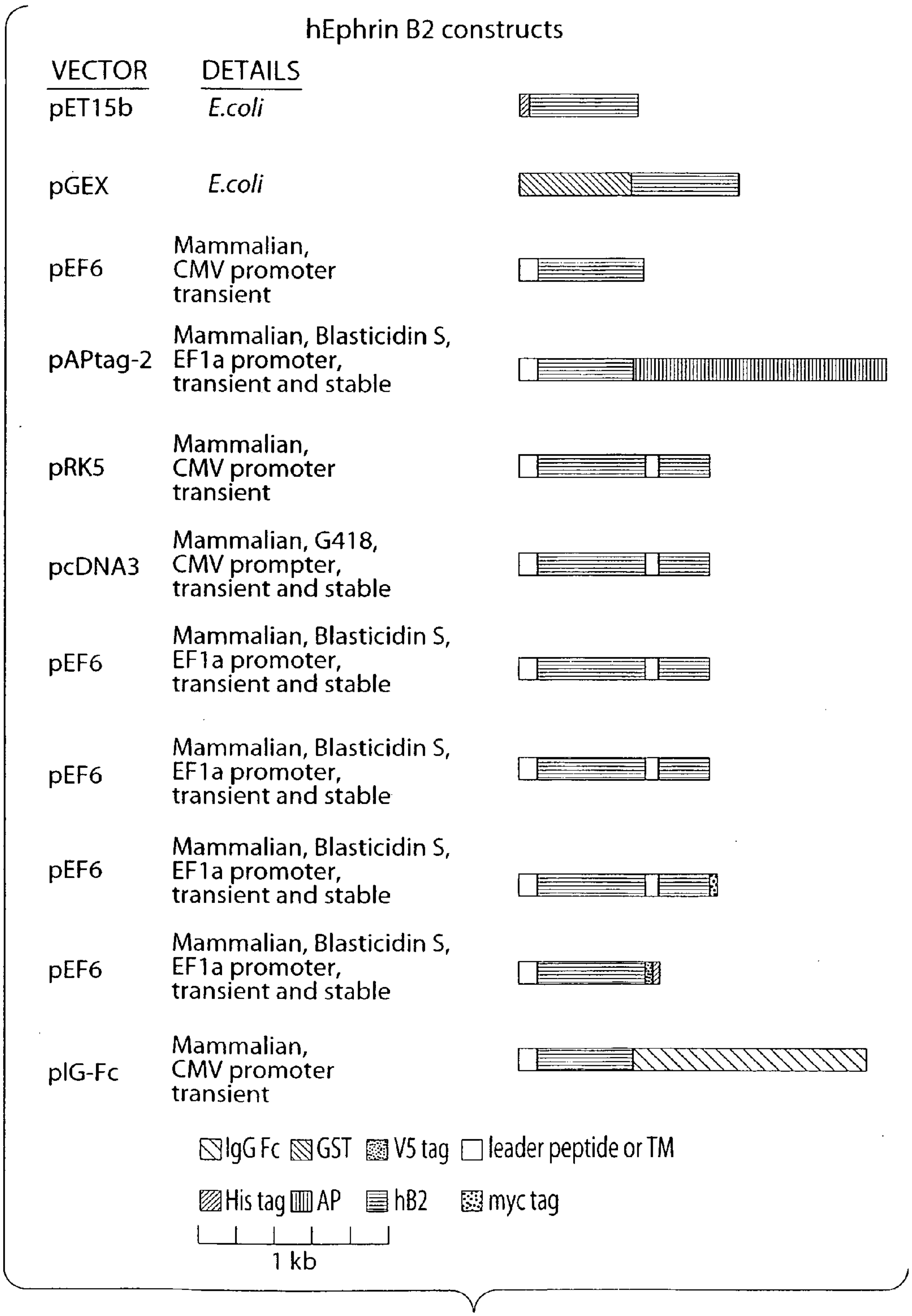
FIG. 14 is a schematic representation of human Ephrin B2 constructs.

In certain aspects, the invention relates to a soluble polypeptide comprising an extracellular domain of an Ephrin B2 protein (referred to herein as an Ephrin B2 soluble polypeptide) or comprising an extracellular domain of an EphB4 protein (referred to herein as an EphB4 soluble polypeptide). Preferably, the subject soluble polypeptide is a monomer and is capable of binding with high affinity to Ephrin B2 or EphB4. In a specific embodiment, the EphB4 soluble polypeptide of the invention comprises a globular domain of an EphB4 protein. Specific examples EphB4 soluble polypeptides are provided in FIGS. 1, 2, and 15. Specific examples of Ephrin B2 soluble polypeptides are provided in FIGS. 3 and 14.

As used herein, the subject soluble polypeptides include fragments, functional variants, and modified forms of EphB4 soluble polypeptide or an Ephrin B2 soluble polypeptide. These fragments, functional variants, and modified forms of the subject soluble polypeptides antagonize function of EphB4, Ephrin B2 or both.

In certain embodiments, isolated fragments of the subject soluble polypeptides can be obtained by screening polypeptides recombinantly produced from the corresponding fragment of the nucleic acid encoding an EphB4 or Ephrin B2 soluble polypeptides. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function to inhibit function of EphB4 or Ephrin B2, for example, by testing the ability of the fragments to inhibit angiogenesis or tumor growth.

In certain embodiments, a functional variant of an EphB4 soluble polypeptide comprises an amino acid sequence that is at least 90%, 95%, 97%, 99% or 100% identical to residues 1-197, 29-197, 1-312, 29-132, 1-321, 29-321, 1-326, 29-326, 1-412, 29-412, 1-427, 29-427, 1-429, 29-429, 1-526, 29-526, 1-537 and 29-537 of the amino acid sequence defined by FIG. 65. Such polypeptides may be used in a processed form, and accordingly, in certain embodiments, an EphB4 soluble polypeptide comprises an amino acid sequence that is at least 90%, 95%, 97%, 99% or 100% identical to residues 16-197, 16-312, 16-321, 16-326, 16-412, 16-427, 16-429, 16-526 and 16-537 of the amino acid sequence defined by FIG. 65.

In other embodiments, a functional variant of an Ephrin B2 soluble polypeptide comprises a sequence at least 90%, 95%, 97%, 99% or 100% identical to residues 1-225 of the amino acid sequence defined by FIG. 66 or a processed form, such as one comprising a sequence at least 90%, 95%, 97%, 99% or 100% identical to residues 26-225 of the amino acid sequence defined by FIG. 66.

In certain embodiments, the present invention contemplates making functional variants by modifying the structure of the subject soluble polypeptide for such purposes as enhancing therapeutic or prophylactic efficacy, or stability (e.g., ex vivo shelf life and resistance to proteolytic degradation in vivo). Such modified soluble polypeptide are considered functional equivalents of the naturally-occurring EphB4 or Ephrin B2 soluble polypeptide. Modified soluble polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

This invention further contemplates a method of generating sets of combinatorial mutants of the EphB4 or Ephrin B2 soluble polypeptides, as well as truncation mutants, and is especially useful for identifying functional variant sequences. The purpose of screening such combinatorial libraries may be to generate, for example, soluble polypeptide variants which can act as antagonists of EphB4, EphB2, or both. Combinatorially-derived variants can be generated which have a selective potency relative to a naturally occurring soluble polypeptide. Such variant proteins, when expressed from recombinant DNA constructs, can be used in gene therapy protocols. Likewise, mutagenesis can give rise to variants which have intracellular half-lives dramatically different than the corresponding wild-type soluble polypeptide. For example, the altered protein can be rendered either more stable or less stable to proteolytic degradation or other cellular process which result in destruction of, or otherwise inactivation of the protein of interest (e.g., a soluble polypeptide). Such variants, and the genes which encode them, can be utilized to alter the subject soluble polypeptide levels by modulating their half-life. For instance, a short half-life can give rise to more transient biological effects and, when part of an inducible expression system, can allow tighter control of recombinant soluble polypeptide levels within the cell. As above, such proteins, and particularly their recombinant nucleic acid constructs, can be used in gene therapy protocols.

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential soluble polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, soluble polypeptide variants (e.g., the antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137: 109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193: 653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, NY; and Greener et al., (1994) Strategies in Mol Biol 7:32-34). Linker scanning mutagenesis, particularly in a combinatorial setting, is an attractive method for identifying truncated (bioactive) forms of the subject soluble polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the subject soluble polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the subject soluble polypeptides of the invention include a small molecule such as a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the EphB4 or Ephrin B2 soluble polypeptides.

To illustrate, by employing scanning mutagenesis to map the amino acid residues of a soluble polypeptide which are involved in binding to another protein, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the soluble polypeptides of the invention may further comprise post-translational modifications. Such modifications include, but are not limited to, acetylation, carboxylation, glycosylation, phosphorylation, lipidation, and acylation. As a result, the modified soluble polypeptides may contain non-amino acid elements, such as polyethylene glycols, lipids, poly- or mono-saccharide, and phosphates. Effects of such non-amino acid elements on the functionality of a soluble polypeptide may be tested for its antagozing role in EphB4 or Ephrin B2 function, e.g., it inhibitory effect on angiogenesis or on tumor growth.

In certain aspects, functional variants or modified forms of the subject soluble polypeptides include fusion proteins having at least a portion of the soluble polypeptide and one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Another fusion domain well known in the art is green fluorescent protein (GFP). Fusion domains also include "epitope tags", which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the soluble polypeptides of the present invention contain one or more modifications that are capable of stabilizing the soluble polypeptides. For example, such modifications enhance the in vitro half life of the soluble polypeptides, enhance circulatory half life of the soluble polypeptides or reducing proteolytic degradation of the soluble polypeptides.

In certain embodiments, soluble polypeptides (unmodified or modified) of the invention can be produced by a variety of art-known techniques. For example, such soluble polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the soluble polypeptides, fragments or variants thereof may be recombinantly produced using various expression systems as is well known in the art (also see below).

III. Nucleic Acids Encoding Soluble Polypeptides

In certain aspects, the invention relates to isolated and/or recombinant nucleic acids encoding an EphB4 or Ephrin B2 soluble polypeptide. The subject nucleic acids may be single-stranded or double-stranded, DNA or RNA molecules. These nucleic acids are useful as therapeutic agents. For example, these nucleic acids are useful in making recombinant soluble polypeptides which are administered to a cell or an individual as therapeutics. Alternative, these nucleic acids can be directly administered to a cell or an individual as therapeutics such as in gene therapy.

In certain embodiments, the invention provides isolated or recombinant nucleic acid sequences that are at least 80%, 85%, 90%, 95%, 97%, 98%, 99% or 100% identical to a region of the nucleotide sequence depicted in FIG. 62 or 63. One of ordinary skill in the art will appreciate that nucleic acid sequences complementary to the subject nucleic acids, and variants of the subject nucleic acids are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence depicted in FIG. 62 or 63, or complement sequences thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the subject nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspect of the invention, the subject nucleic acid is provided in an expression vector comprising a nucleotide sequence encoding an EphB4 or Ephrin B2 soluble polypeptide and operably linked to at least one regulatory sequence. Regulatory sequences are art-recognized and are selected to direct expression of the soluble polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a soluble polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This invention also pertains to a host cell transfected with a recombinant gene including a coding sequence for one or more of the subject soluble polypeptide. The host cell may be any prokaryotic or eukaryotic cell. For example, a soluble polypeptide of the invention may be expressed in bacterial cells such as *E. coli*, insect cells (e.g., using a baculovirus expression system), yeast, or mammalian cells. Other suitable host cells are known to those skilled in the alt.

Accordingly, the present invention further pertains to methods of producing the subject soluble polypeptides. For example, a host cell transfected with an expression vector encoding an EphB4 soluble polypeptide can be cultured under appropriate conditions to allow expression of the EphB4 soluble polypeptide to occur. The EphB4 soluble polypeptide may be secreted and isolated from a mixture of cells and medium containing the soluble polypeptides. Alternatively, the soluble polypeptides may be retained cytoplasmically or in a membrane fraction and the cells harvested, lysed and the protein isolated. A cell culture includes host cells, media and other byproducts. Suitable media for cell culture are well known in the art. The soluble polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the soluble polypeptides. In a preferred embodiment, the soluble polypeptide is a fusion protein containing a domain which facilitates its purification.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant soluble polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

The preferred mammalian expression vectors contain both prokaryotic sequences to facilitate the propagation of the vector in bacteria, and one or more eukaryotic transcription units that are expressed in eukaryotic cells. The pcDNA1/amp, pcDNA1/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant SLC5A8 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

IV. Antibodies

The disclosure provides, in part, defined portions of the EphB4 molecule that can be effectively targeted by polypeptide binding agents, such as antibodies, antigen binding portions of antibodies, and non-immunoglobulin antigen binding scaffolds. The EphB4 polypeptide binding agents described herein may be used to treat a variety of disorders, particularly cancers and disorders related to unwanted angiogenesis. The disclosure provides antibodies and antigen binding portions thereof that inhibit one or more EphB4 mediated functions, such as EphrinB2 binding or EphB4 kinase activity. Such binding agents may be used to inhibit EphB4 function in vitro and in vivo, and preferably for treating cancer or disorders associated with unwanted angiogenesis. The disclosure also provides antibodies and antigen binding portions thereof that activate EphB4 kinase activity (typically assessed by evaluating EphB4 phosphorylation state). Surprisingly, such antibodies also inhibit EphB4 functions in cell based and in vivo assays. Accordingly, such binding agents may be used to inhibit EphB4 function in vitro and in vivo, and preferably for treating cancer or disorders associated with unwanted angiogenesis. While not wishing to be limited to any particular mechanism, it is expected that these antibodies stimulate not only EphB4 kinase activity, but also EphB4 removal from the membrane, thus decreasing overall EphB4 levels.

EphB4 belongs to a family of transmembrane receptor protein tyrosine kinases. The extracellular portion of EphB4 is composed of the ligand-binding domain (also referred to as globular domain), a cysteine-rich domain, and a pair of fibronectin type III repeats (e.g., see FIG. 1). The ligand binding domain corresponds to The cytoplasmic domain consists of a juxtamembrane region containing two conserved tyrosine residues; a protein tyrosine kinase domain; a sterile α-motif (SAM) and a PDZ-domain binding motif. EphB4 is specific for the membrane-bound ligand Ephrin B2 (Sakano, S. et al 1996; Brambilla R. et al 1995). EphB4 is activated by binding of clustered, membrane-attached ephrin ligands (Davis S et al, 1994), indicating that contact between cells expressing the receptor and cells expressing the ligand is required for the Eph receptor activation. Upon ligand binding, an EphB4 receptor dimerizes and autophosphorylates the juxtamembrane tyrosine residues to acquire full activation.

As used herein, the term EphB4 refers to an EphB4 polypeptide from a mammal including humans. In one embodiment, the antibodies (immunoglobulins) are raised against an isolated and/or recombinant mammalian EphB4 or portion thereof (e.g., peptide) or against a host cell which expresses recombinant mammalian EphB4. In certain aspects, antibodies of the invention specifically bind to an extracellular domain of an EphB4 protein (referred to herein as an EphB4 soluble polypeptide). For example, an EphB4 soluble polypeptide comprises a globular domain and is capable of binding to Ephrin B2. An example of EphB4 soluble polypeptides is provided in FIG. 2. As used herein, the EphB4 soluble polypeptides include fragments, functional variants, and modified forms of EphB4 soluble polypeptide.

The term "antibody" as used herein is intended to include monoclonal and polyclonal antibodies as well as any full length immunoglobulin chains, including chimeric and humanized forms. An "isolated antibody" is simply an antibody that is substantially purified or produced so as to be free of other species of antibodies that bind to the same target. Monoclonal antibodies and most recombinant antibody forms are isolated, while an antibody species present in a polyclonal antibody mixture is not isolated. Antigen binding portions of an antibody include, e.g., F(ab')2, Fab, Fv; scFv and single domain antibodies.

As shown in the Examples below, Applicants have generated a number of monoclonal antibodies against EphB4 as well as hybridoma cell lines producing EphB4 monoclonal antibodies. These antibodies were further characterized in many ways, such as, their ability to inhibit interaction between EphB4 and its ligand (e.g., Ephrin B2), their ability to inhibit dimerization or multimerization of EphB4 receptor, their ability to induce tyrosine phosphorylation of EphB4, their cross-reactivity with other Eph family members, their ability to inhibit angiogenesis, and their ability to inhibit tumor growth. Further, epitope mapping studies reveals that these EphB4 antibodies may specifically bind to one or more regions of EphB4 (e.g., a globular domain, a cystein-rich domain, or a fibronectin type III domain). For example, an EphB4 antibody may bind to both fibronectin type 3 domains.

In certain aspects, antibodies of the invention specifically bind to an extracellular domain (ECD) of an EphB4 protein (also referred to herein as a soluble EphB4 polypeptide). A soluble EphB4 polypeptide may comprise a sequence encompassing the globular (G) domain (amino acids 29-197 of SEQ ID NO: 386), and optionally additional domains, such as the cysteine-rich domain (amino acids 239-321 of SEQ ID NO: 386), the first fibronectin type 3 domain (amino acids 324-429 of SEQ ID NO: 386) and the second fibronectin type 3 domain (amino acids 434-526 of SEQ ID NO: 386). Exemplary EphB4 soluble polypeptides are provided in FIGS. 3-4. As used herein, the EphB4 soluble polypeptides include fragments, functional variants, and modified forms of EphB4 soluble polypeptide.

In certain aspects, the present invention provides antibodies (anti-EphB4) having binding specificity for an EphB4 or a portion of EphB4. Examples of these antibodies include, but are not limited to, EphB4 antibody Nos. 1, 23, 35, 47, 57, 79, 85L, 85H, 91, 98, 121, 131, and 138 as shown in FIG. 5. Optionally, the immunoglobulins can bind to EphB4 with an affinity of at least about $1\times10^{-6}$, $1\times10^{-7}$, $1\times10^{-8}$, $1\times10^{-9}$ M or less. Optionally, antibodies and portions thereof bind to EphrinB2 with an affinity that is roughly equivalent to that of a soluble extracellular EphB4 polypeptide comprising the globular ligand binding domain. Antibodies disclosed herein will preferably be specific for EphB4, with minimal binding to other members of the Eph or Ephrin families.

In certain embodiments, antibodies of the present invention bind to one or more specific domain of EphB4. For example, an antibody binds to one or more extracellular domains of EphB4 (such as the globular domain, the cysteinrich domain, and the first fibronectin type 3 domain, and the second fibronectin type 3 domain). For example, EphB4 antibody Nos. 1, 23, 35, and 79 bind to an epitope in the region spanning amino acids 16-198 of the sequence in FIG. 1, spanning the globular domain. EphB4 antibody Nos. 85L, 85H, 91, and 131 bind to an epitope in the region spanning amino acids 327-427, including the first fibronectin type 3 domain. EphB4 antibody Nos. 47, 57, 85H, 98, 121, and 138 bind to an epitope in the region spanning amino acids 428-537, including the second fibronectin type 3 domain. Optionally, the subject antibody (e.g., EphB4 antibody No. 85H) can bind to at least two domains of an EphB4 (FIG. 5).

In certain embodiments, single chain antibodies, and chimeric, humanized or primatized (CDR-grafted) antibodies, as well as chimeric or CDR-grafted single chain antibodies, comprising portions derived from different species, are also encompassed by the present invention as antigen binding portions of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody. See, e.g., Ladner et al., U.S. Pat. No. 4,946,778; and Bird, R. E. et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived. Preferred functional fragments retain an antigen binding function of a corresponding full-length antibody (e.g., specificity for an EphB4). Certain preferred functional fragments retain the ability to inhibit one or more functions characteristic of an EphB4, such as a binding activity, a signaling activity, and/or stimulation of a cellular response. For example, in one embodiment, a functional fragment of an EphB4 antibody can inhibit the interaction of EphB4 with one or more of its ligands (e.g., Ephrin B2) and/or can inhibit one or more receptor-mediated functions, such as cell migration, cell proliferation, angiogenesis, and/or tumor growth.

For example, antibody fragments capable of binding to an EphB4 receptor or portion thereof, including, but not limited to, Fv, Fab, Fab' and $F(ab')_2$ fragments are encompassed by the invention. Such fragments can be produced by enzymatic cleavage or by recombinant techniques. For instance, papain or pepsin cleavage can generate Fab or $F(ab')_2$ fragments, respectively. Antibodies can also be produced in a variety of truncated forms using antibody genes in which one or more stop codons has been introduced upstream of the natural stop site. For example, a chimeric gene encoding a $F(ab')_2$ heavy chain portion can be designed to include DNA sequences encoding the $CH_1$ domain and hinge region of the heavy chain.

The term “humanized immunoglobulin” as used herein refers to an immunoglobulin comprising portions of immunoglobulins of different origin, wherein at least one portion is of human origin. Accordingly, the present invention relates to a humanized immunoglobulin having binding specificity for an EphB4 (e.g., human EphB4), said immunoglobulin comprising an antigen binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain).

Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with murine monoclonal antibody for binding to an EphB4 polypeptide. Chimeric or CDR-grafted single chain antibodies are also encompassed by the term humanized immunoglobulin.

In certain embodiments, the present invention provides EphB4 antagonist antibodies. As described herein, the term “antagonist antibody” refers to an antibody that can inhibit one or more functions of an EphB4, such as a binding activity (e.g., ligand binding) and a signaling activity (e.g., clustering or phosphorylation of EphB4, stimulation of a cellular response, such as stimulation of cell migration or cell proliferation). For example, an antagonist antibody can inhibit (reduce or prevent) the interaction of an EphB4 receptor with a natural ligand (e.g., Ephrin B2 or fragments thereof). Preferably, antagonist antibodies directed against EphB4 can inhibit functions mediated by EphB4, including endothelial cell migration, cell proliferation, angiogenesis, and/or tumor growth. Optionally, the antagonist antibody binds to an extracellular domain of EphB4.

In other embodiments, the present invention provides EphB4 kinase activating antibodies. Such antibodies enhance EphB4 kinase activity, even independent of EphrinB2. In some instances, such antibodies may be used to stimulate EphB4. However, applicants note that in most cell-based and in vivo assays, such antibodies surprisingly behaved like antagonist antibodies. Such antibodies appear to bind to the fibronectin type III domains, particularly the region of amino acids 327-427 of FIG. 1.

In certain embodiments, anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See e.g., U.S. Pat. No. 4,699,880. In one embodiment, antibodies are raised against receptor or a portion thereof, and these antibodies are used in turn to produce an anti-idiotypic antibody. The anti-idiotypic antibodies produced thereby can bind compounds which bind receptor, such as ligands of receptor function, and can be used in an immunoassay to detect or identify or quantitate such compounds. Such an anti-idotypic antibody can also be an inhibitor of an EphB4 receptor function, although it does not bind receptor itself. Such an anti-idotypic antibody can also be called an antagonist antibody.

In certain aspects, the present invention provides the hybridoma cell lines, as well as to the monoclonal antibodies produced by these hybridoma cell lines. The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-EphB4 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-EphB4 light or heavy chain can be isolated (e.g., by PCR) or cDNA libraries can be prepared from mRNA isolated from the cell lines, and cDNA clones encoding an anti-EphB4 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells or medium). It will be appreciated that the method of production encompasses expression in a host cell of a transgenic animal (see e.g., WO 92/03918, GenPharm International, published Mar. 19, 1992).

Preparation of Immunizing Antigen, and Polyclonal and Monoclonal Antibody Production can be performed as described herein, or using other suitable techniques. A variety of methods have been described. See e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer ’94), Ausubel, F. M. et al., Eds., (John Wiley & Sons: New York, N.Y.), Chapter 11, (1991). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545,807.

To illustrate, immunogens derived from an EphB4 polypeptide (e.g., an EphB4 polypeptide or an antigenic fragment thereof which is capable of eliciting an antibody response, or an EphB4 fusion protein) can be used to immunize a mammal, such as a mouse, a hamster or rabbit. See, for example, Antibodies: A Laboratory Manual ed. by Harlow and Lane (Cold Spring Harbor Press: 1988). Techniques for conferring immunogenicity on a protein or peptide include conjugation to carriers or other techniques well known in the art. An immunogenic portion of an EphB4 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In one embodiment, antibodies of the invention are specific for the extracellular portion of the EphB4 protein (e.g., SEQ ID NO: 2) or fragments thereof. In another embodiment, antibodies of the invention are specific for the intracellular portion or the transmembrane portion of the EphB4 protein.

Following immunization of an animal with an antigenic preparation of an EphB4 polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an EphB4 polypeptide and monoclonal antibodies isolated from a culture comprising such hybridoma cells.

In certain embodiments, antibodies of the present invention can be fragmented using conventional techniques and the fragments screened for utility in the same manner as described above for whole antibodies. For example, F(ab)2 fragments can be generated by treating antibody with pepsin. The resulting $F(ab)_2$ fragment can be treated to reduce disulfide bridges to produce Fab fragments.

In certain embodiments, antibodies of the present invention are further intended to include bispecific, single-chain, and chimeric and humanized molecules having affinity for an EphB4 polypeptide conferred by at least one CDR region of the antibody. Techniques for the production of single chain antibodies (U.S. Pat. No. 4,946,778) can also be adapted to produce single chain antibodies. Also, transgenic mice or other organisms including other mammals, may be used to express humanized antibodies. Methods of generating these antibodies are known in the art. See, e.g., Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 E1; Neuberger, M. S. et al., WO 86/01533; Neuberger, M. S. et al., European Patent No. 0,194,276 B1; Winter, U.S. Pat. No. 5,225,539; winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)).

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

In certain embodiments, the antibodies are further attached to a label that is able to be detected (e.g., the label can be a radioisotope, fluorescent compound, enzyme or enzyme cofactor). The active moiety may be a radioactive agent, such as: radioactive heavy metals such as iron chelates, radioactive chelates of gadolinium or manganese, positron emitters of oxygen, nitrogen, iron, carbon, or gallium, $^{43}K$, $^{52}Fe$, $^{57}Co$, $^{67}Cu$, $^{67}Ga$, $^{68}Ga$, $^{123}I$, $^{125}I$, $^{131}I$, $^{132}I$, or $^{99}Tc$. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using antibodies or other binding polypeptides directed at EphB4 may be used to detect and/or diagnose cancers and vasculature. For example, monoclonal antibodies against the EphB4 marker labeled with $^{99}$Technetium, $^{111}$Indium, $^{125}$Iodine-may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

In certain preferred embodiments, an antibody of the invention is a monoclonal antibody, and in certain embodiments the invention makes available methods for generating novel antibodies. For example, a method for generating a monoclonal antibody that binds specifically to an EphB4 polypeptide may comprise administering to a mouse an amount of an immunogenic composition comprising the EphB4 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the EphB4 polypeptide. Once obtained, a hybridoma can be propagated in a cell culture, optionally in culture conditions where the hybridoma-derived cells produce the monoclonal antibody that binds specifically to EphB4 polypeptide. The monoclonal antibody may be purified from the cell culture.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays and immunohistochemistry.

The antibodies of the present invention are useful in a variety of applications, including research, diagnostic and therapeutic applications. For instance, they can be used to isolate and/or purify receptor or portions thereof, and to study receptor structure (e.g., conformation) and function.

In certain aspects, the various antibodies of the present invention can be used to detect or measure the expression of EphB4 receptor, for example, on endothelial cells (e.g., venous endothelial cells), or on cells transfected with an EphB4 receptor gene. Thus, they also have utility in applications such as cell sorting and imaging (e.g., flow cytometry, and fluorescence activated cell sorting), for diagnostic or research purposes.

In certain embodiments, the antibodies or antigen binding fragments of the antibodies can be labeled or unlabeled for diagnostic purposes. Typically, diagnostic assays entail detecting the formation of a complex resulting from the binding of an antibody to EphB4. The antibodies can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the antibodies can be used in assays, such as agglutination assays. Unlabeled antibodies can also be used in combination with another (one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies of the present invention can be utilized in enzyme immunoassays, wherein the subject antibodies, or second antibodies, are conjugated to an enzyme. When a biological sample comprising an EphB4 protein is combined with the subject antibodies, binding occurs between the antibodies and EphB4 protein. In one embodiment, a sample containing cells expressing an EphB4 protein (e.g., endothelial cells) is combined with the subject antibodies, and binding occurs between the antibodies and cells bearing an EphB4 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

In certain aspects, kits for use in detecting the presence of an EphB4 protein in a biological sample can also be prepared. Such kits will include an antibody which binds to an EphB4 protein or portion of said receptor, as well as one or more ancillary reagents suitable for detecting the presence of a complex between the antibody and EphB4 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of an EphB4 or portion of the receptor by a cell, wherein a composition comprising a cell or fraction thereof (e.g., membrane fraction) is contacted with an antibody which binds to an EphB4 or portion of the receptor under conditions appropriate for binding of the antibody thereto, and antibody binding is monitored. Detection of the antibody, indicative of the formation of a complex between antibody and EphB4 or a portion thereof, indicates the presence of the receptor. Binding of antibody to the cell can be determined by standard methods, such as those described in the working examples. The method can be used to detect expression of EphB4 on cells from an individual. Optionally, a quantitative expression of EphB4 on the surface of endothelial cells can be evaluated, for instance, by flow cytometry, and the staining intensity can be correlated with disease susceptibility, progression or risk.

The present invention also relates to a method of detecting the susceptibility of a mammal to certain diseases. To illustrate, the method can be used to detect the susceptibility of a mammal to diseases which progress based on the amount of EphB4 present on cells and/or the number of EphB4-positive cells in a mammal. In one embodiment, the invention relates to a method of detecting susceptibility of a mammal to a tumor. In this embodiment, a sample to be tested is contacted with an antibody which binds to an EphB4 or portion thereof under conditions appropriate for binding of said antibody thereto, wherein the sample comprises cells which express EphB4 in normal individuals. The binding of antibody and/or amount of binding is detected, which indicates the susceptibility of the individual to a tumor, wherein higher levels of receptor correlate with increased susceptibility of the individual to a tumor. Applicants and other groups have found that expression of EphB4 has a correlation with tumor growth and progression. The antibodies of the present invention can also be used to further elucidate the correlation of EphB4 expression with progression of angiogenesis-associated diseases in an individual.

V. Drug Screening Assays

There are numerous approaches to screening for polypeptide therapeutic agents as antagonists of EphB4, Ephrin B2 or both. For example, high-throughput screening of compounds or molecules can be carried out to identify agents or drugs which inhibit angiogenesis or inhibit tumor growth. Test agents can be any chemical (element, molecule, compound, drug), made synthetically, made by recombinant techniques or isolated from a natural source. For example, test agents can be peptides, polypeptides, peptoids, sugars, hormones, or nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps.

For example, an assay can be carried out to screen for compounds that specifically inhibit binding of Ephrin B2 (ligand) to EphB4 (receptor), or vice-versa, e.g., by inhibition of binding of labeled ligand- or receptor-Fc fusion proteins to immortalized cells. Compounds identified through this screening can then be tested in animals to assess their anti-angiogenesis or anti-tumor activity in vivo.

In one embodiment of an assay to identify a substance that interferes with interaction of two cell surface molecules (e.g., Ephrin B2 and EphB4), samples of cells expressing one type of cell surface molecule (e.g., EphB4) are contacted with either labeled ligand (e.g., Ephrin B2, or a soluble portion thereof, or a fusion protein such as a fusion of the extracellular domain and the Fc domain of IgG) or labeled ligand plus a test compound (or group of test compounds). The amount of labeled ligand which has bound to the cells is determined. A lesser amount of label (where the label can be, for example, a radioactive isotope, a fluorescent or colormetric label) in the sample contacted with the test compound(s) is an indication that the test compound(s) interferes with binding. The reciprocal assay using cells expressing a ligand (e.g., an Ephrin B2 ligand or a soluble form thereof) can be used to test for a substance that interferes with the binding of an Eph receptor or soluble portion thereof.

An assay to identify a substance which interferes with interaction between an Eph receptor and an ephrin can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

In one embodiment, an isolated or purified protein (e.g., an Eph receptor or an ephrin) can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all, or a portion of, a protein (e.g., an Eph receptor or an ephrin) linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by inserting the protein (e.g., an Eph receptor or an ephrin) or a portion thereof into a suitable expression vector which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In one aspect of this embodiment, a fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the receptor or ligand protein portion of the bound fusion protein. Next, the affinity matrix with bound fusion protein can be washed with a suitable wash buffer to remove unbound compounds and non-specifically bound compounds without significantly disrupting binding of specifically bound compounds. Compounds which remain bound can be released by contacting the affinity matrix having fusion protein bound thereto with a suitable elution buffer (a compound elution buffer). In this aspect, compound elution buffer can be formulated to permit retention of the fusion protein by the affinity matrix, but can be formulated to interfere with binding of the compound(s) tested to the receptor or ligand protein portion of the fusion protein. For example, a change in the ionic strength or pH of the elution buffer can lead to release of compounds, or the elution buffer can comprise a release component or components designed to disrupt binding of compounds to the receptor or ligand protein portion of the fusion protein (e.g., one or more ligands or receptors or analogs thereof which can disrupt binding of compounds to the receptor or ligand protein portion of the fusion protein). Immobilization can be performed prior to, simultaneous with, or after contacting the fusion protein with compound, as appropriate. Various permutations of the method are possible, depending upon factors such as the compounds tested, the affinity matrix selected, and elution buffer formulation. For example, after the wash step, fusion protein with compound bound thereto can be eluted from the affinity matrix with a suitable elution buffer (a matrix elution buffer). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

VI. Methods of Treatment

In certain embodiments, the present invention provides methods of inhibiting angiogenesis and methods of treating angiogenesis-associated diseases. In other embodiments, the present invention provides methods of inhibiting or reducing tumor growth and methods of treating an individual suffering from cancer. These methods involve administering to the individual a therapeutically effective amount of one or more polypeptide therapeutic agents as described above. These methods are particularly aimed at therapeutic and prophylactic treatments of animals, and more particularly, humans.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

It is understood that methods and compositions of the invention are also useful for treating any angiogenesis-independent cancers (tumors). As used herein, the term "angiogenesis-independent cancer" refers to a cancer (tumor) where there is no or little neovascularization in the tumor tissue.

In particular, polypeptide therapeutic agents of the present invention are useful for treating or preventing a cancer (tumor), including, but not limited to, colon carcinoma, breast cancer, mesothelioma, prostate cancer, bladder cancer, squamous cell carcinoma of the head and neck (HNSCC), Kaposi sarcoma, and leukemia.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject methods of the invention can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present invention recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent is shown to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules", such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the polypeptide therapeutic agents of the invention may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

VII. Methods of Administration and Pharmaceutical Compositions

In certain embodiments, the subject polypeptide therapeutic agents (e.g., soluble polypeptides or antibodies) of the present invention are formulated with a pharmaceutically acceptable carrier. Such therapeutic agents can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject polypeptide therapeutic agents include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-tumor or anti-angiogenesis therapeutic agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia)

and/or as mouth washes and the like, each containing a predetermined amount of a subject polypeptide therapeutic agent as an active ingredient.

In solid dosage forms for oral administration (capsules, tablets, pills, dragees, powders, granules, and the like), one or more polypeptide therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, methods of the invention can be administered topically, either to skin or to mucosal membranes such as those on the cervix and vagina. This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject polypeptide therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more polypeptide therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations for intravaginal or rectally administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In other embodiments, the polypeptide therapeutic agents of the instant invention can be expressed within cells from eukaryotic promoters. For example, a soluble polypeptide of EphB4 or Ephrin B2 can be expressed in eukaryotic cells from an appropriate vector. The vectors are preferably DNA plasmids or viral vectors. Viral vectors can be constructed based on, but not limited to, adeno-associated virus, retrovirus, adenovirus, or alphavirus. Preferably, the vectors stably introduced in and persist in target cells. Alternatively, viral vectors can be used that provide for transient expression. Such vectors can be repeatedly administered as necessary. Delivery of vectors encoding the subject polypeptide therapeutic agent can be systemic, such as by intravenous or intramuscular administration, by administration to target cells ex-planted from the patient followed by reintroduction into the patient, or by any other means that would allow for introduction into the desired target cell (for a review see Couture et al., 1996, TIG., 12, 510).

EXEMPLIFICATION

The invention now being generally described, it will be more readily understood by reference to the following examples, which are included merely for purposes of illustration of certain aspects and embodiments of the present invention, and are not intended to limit the invention.

Example 1

Soluble Derivatives of the Extracellular Domains of Human Ephrin B2 and EphB4 Proteins Soluble derivatives of the extracellular domains of human Ephrin B2 and EphB4 proteins represent either truncated full-length predicted extracellular domains of Ephrin B2 (B4ECv3, B2EC) or translational fusions of the domains with constant region of human immunoglobulins (IgG1 Fc fragment), such as B2EC-FC, B4ECv2-FC and B4ECv3-FC. Representative human Ephrin B2 constructs and human EphB4 constructs are shown FIGS. 14 and 15.

Figure 7:
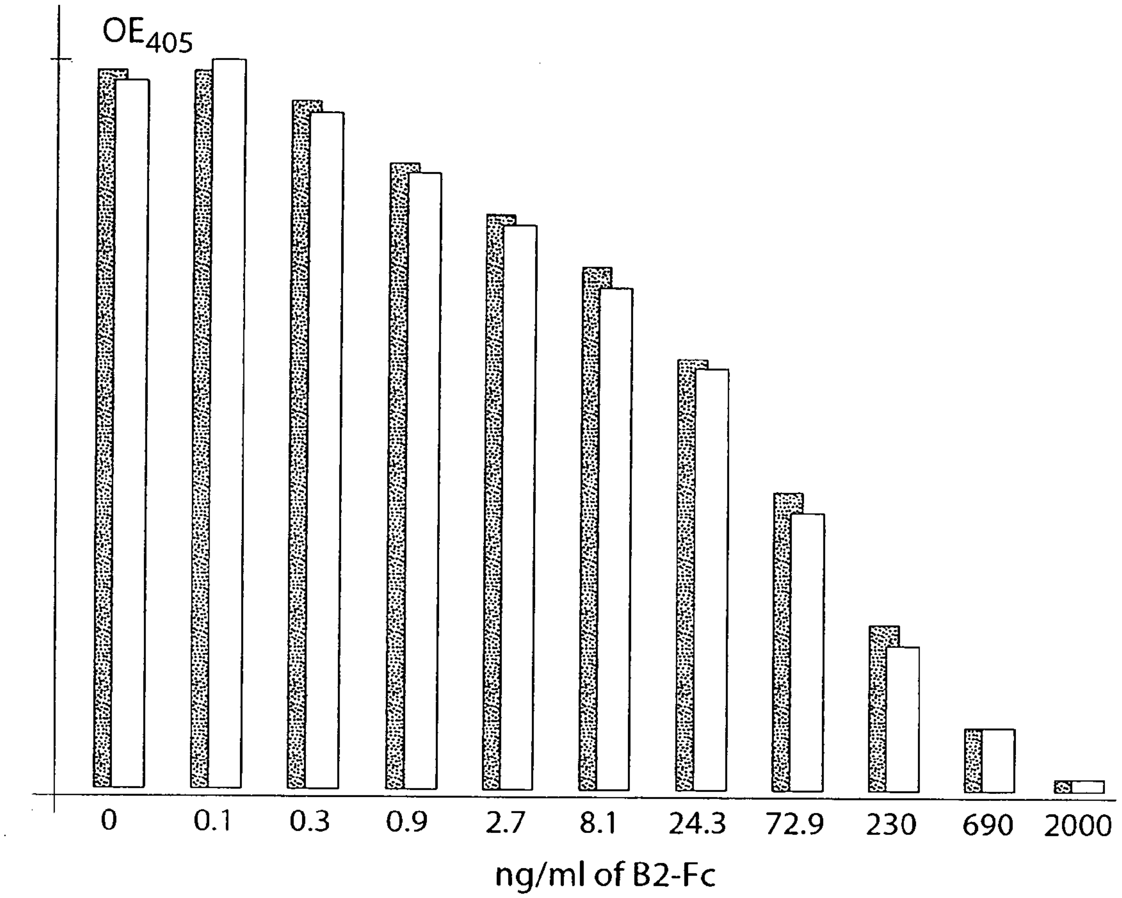
FIG. 7 shows B4EC-FC inhibition assay (Inhibition in solution).
Figure 8:
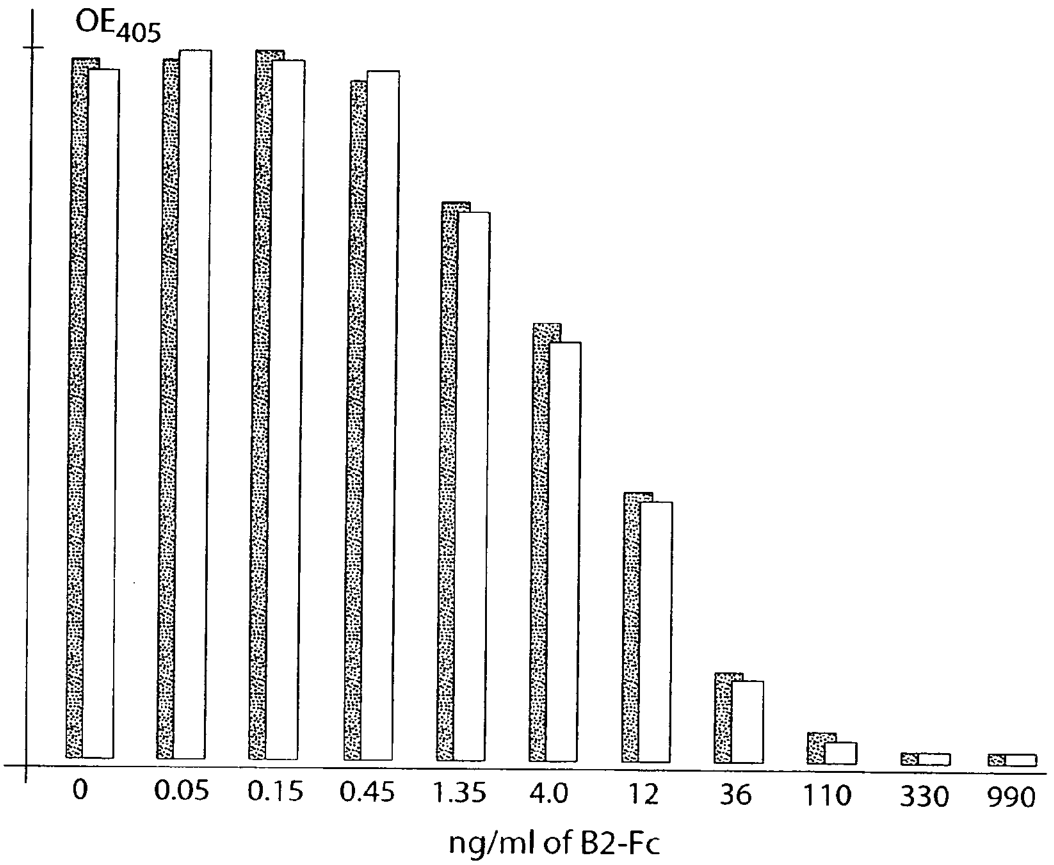
FIG. 8 shows B2EC-FC binding assay (Protein-A-agarose based assay).

The cDNA fragments encoding these recombinant proteins were subcloned into mammalian expression vectors, expressed in transiently or stably transfected mammalian cell lines and purified to homogeneity as described in detail in Materials and Methods section (see below). Predicted amino acid sequences of the proteins are shown in FIGS. 1-5. High purity of the isolated proteins and their recognition by the corresponding anti-Ephrin B2 and anti-EphB4 monoclonal or polyclonal antibodies were confirmed. The recombinant proteins exhibit the expected high-affinity binding, binding competition and specificity properties with their corresponding binding partners as corroborated by the biochemical assays (see e.g., FIGS. 6-8).

Figure 9:
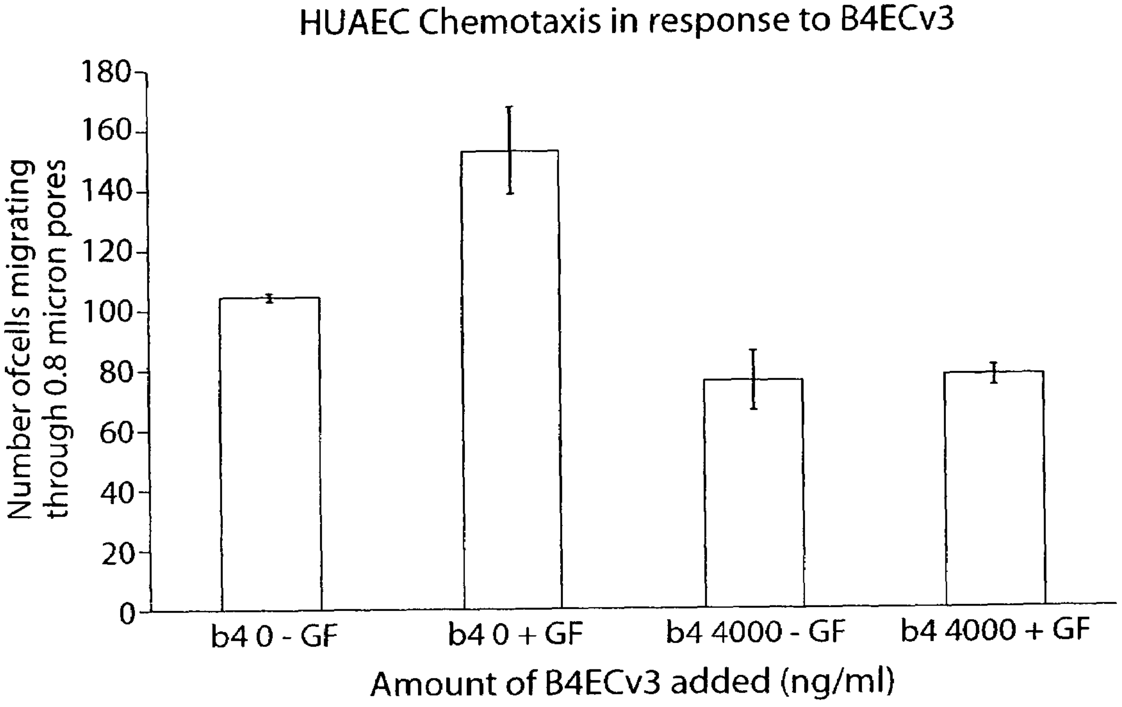
FIG. 9 shows chemotaxis of HUAEC in response to B4Ecv3.
Figure 10:
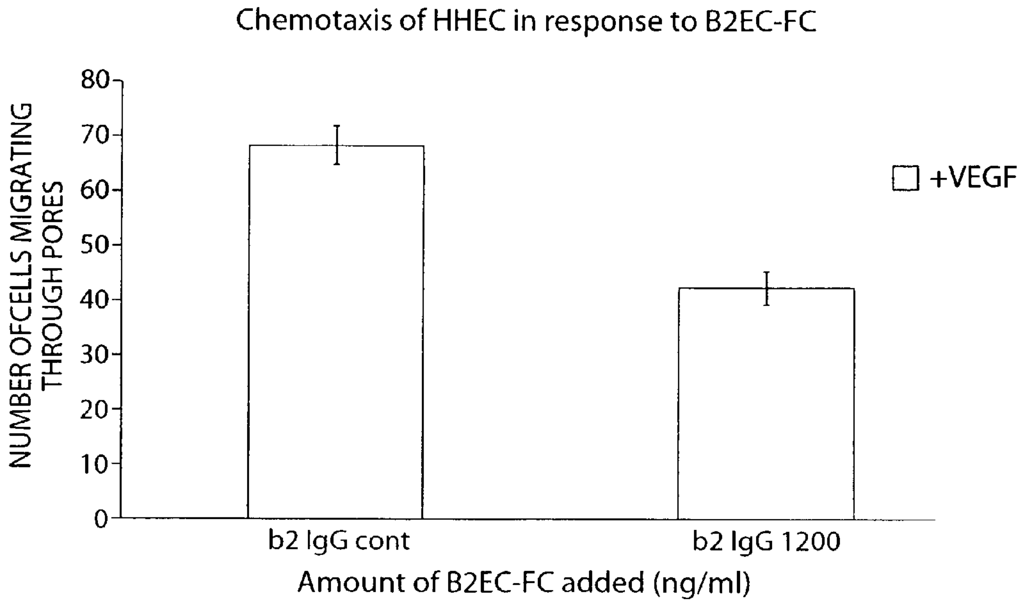
FIG. 10 shows chemotaxis of HHEC in response to B2EC-FC.
Figure 11:
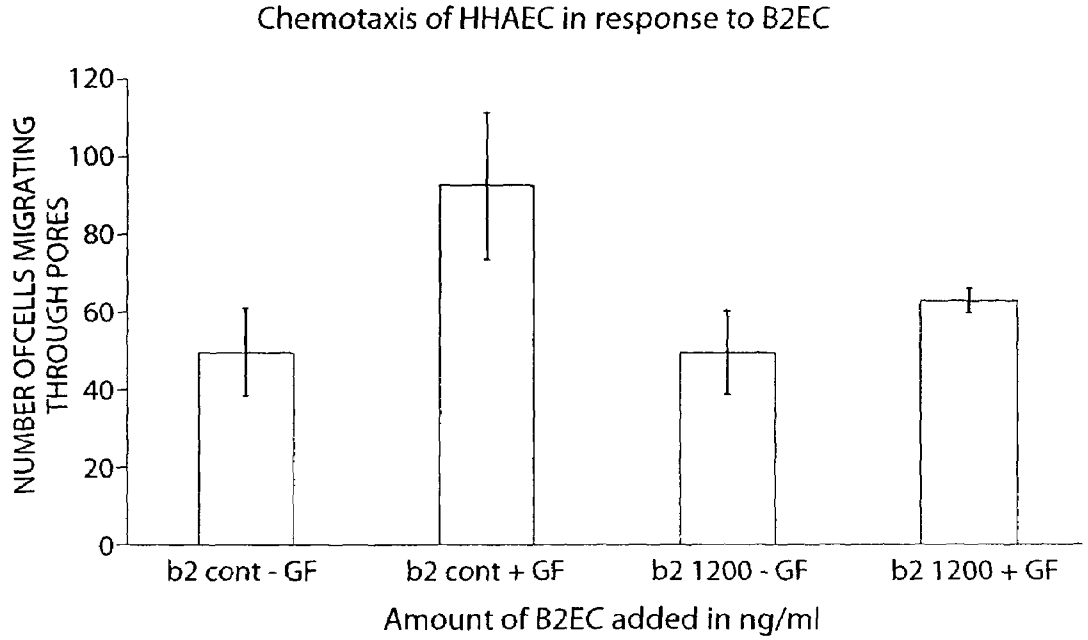
FIG. 11 shows chemotaxis of HHAEC in response to B2EC.
Figure 12:
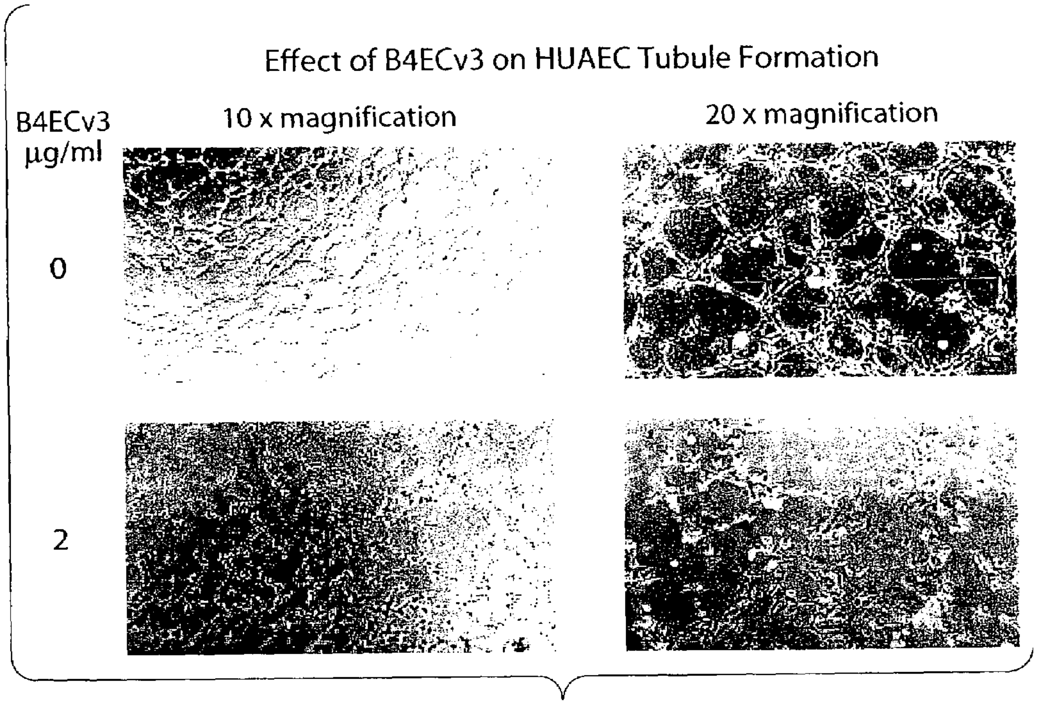
FIG. 12 shows effect of B4Ecv3 on HUAEC tubule formation.
Figure 13:
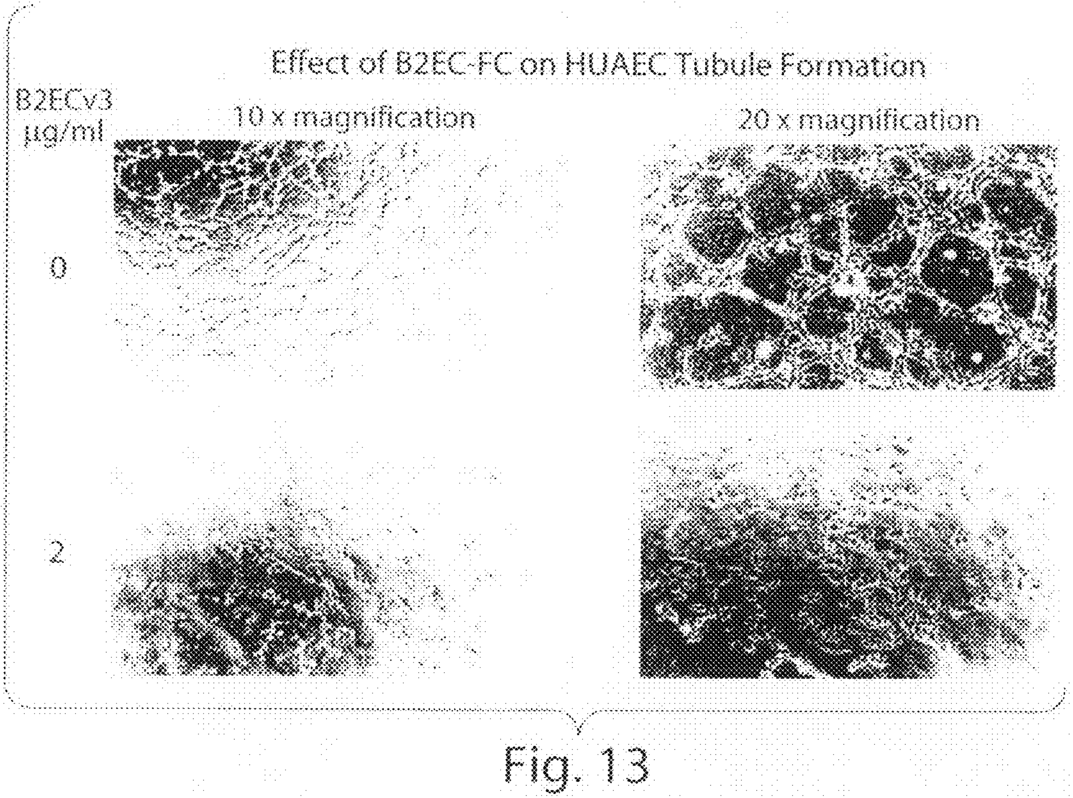
FIG. 13 shows effect of B2EC-FC on HUAEC tubule formation.

Such soluble derivative proteins human Ephrin B2 and EphB4 exhibit potent biological activity in several cell-based assays and in vivo assays which measure angiogenesis or anti-cancer activities, and are therefore perspective drug candidates for anti-angiogenic and anti-cancer therapy. B4ECv3 as well as B2EC and B2EC-FC proteins blocked chemotaxis of human endothelial cells (as tested with umbilical cord and hepatic AECs or VECs), with a decrease in degradation of the extracellular matrix, Matrigel, and a decrease in migration in response to growth factor stimuli (FIGS. 9-11). B4ECv3 and B2EC-FC proteins have potent anti-angiogenic effect as demonstrated by their inhibition of endothelial cell tube formation (FIGS. 12-13).

Materials and Methods

1) Mammalian expression vectors for producing recombinant soluble derivatives of Ephrin B2 and Eph B4.

A vector comprising a human EphB4 (hB4) cDNA comprising the full length ORF was amplified by PCR out with primers

```
                                     (SEQ ID NO: 397)
GGATCCgccATGGAGCTCCGGGTGCTGCT - 5Bam-hB4

                                     (SEQ ID NO: 398)
GCGGCCGCTCAGTACTGCGGGGCCGGT - 3Notl-B4
```

and cloned in BamHI-NotI cut pRK5 vector.

Sequence of BamHI-NotI-1 fragment with full length hB4 ORF is shown below (SEQ ID NO: 399):

```
ggatccgccatggagctccgggtgctgctctgctgggcttcgttggccgc
agctttggaagagaccctgctgaacacaaaattggaaactgctgatctga
agtgggtgacattccctcaggtggacgggcagtgggaggaactgagcggc
ctggatgaggaacagcacagcgtgcgcacctacgaagtgtgtgaagtgca
gcgtgccccgggccaggcccactggcttcgcacaggttgggtcccacggc
ggggcgccgtccacgtgtacgccacgctgcgcttcaccatgctcgagtgc
ctgtccctgcctcgggctgggcgctcctgcaaggagaccttcaccgtctt
ctactatgagagcgatgcggacacggccacggccctcacgccagcctgga
tggagaaccccctacatcaaggtggacacggtggccgcggagcatctcacc
cggaagcgccctggggccgaggccaccgggaaggtgaatgtcaagacgct
gcgtctgggaccgctcagcaaggctggcttctacctggccttccaggacc
agggtgcctgcatggccctgctatccctgcacctcttctacaaaaagtgc
gcccagctgactgtgaacctgactcgattcccggagactgtgcctcggga
gctggttgtgcccgtggccggtagctgcgtggtggatgccgtccccgccc
ctggccccagccccagcctctactgccgtgaggatggccagtgggccgaa
cagccggtcacgggctgcagctgtgctccggggttcgaggcagctgaggg
gaacaccaagtgccgagcctgtgcccagggcaccttcaagcccctgtcag
gagaagggtcctgccagccatgcccagccaatagccactctaacaccatt
ggatcagccgtctgccagtgccgcgtcgggtacttccgggcacgcacaga
cccccggggtgcaccctgcaccacccctccttcggctccgcggagcgtgg
tttcccgcctgaacggctcctccctgcacctggaatggagtgccccctg
gagtctggtggccgagaggacctcacctacgccctccgctgccgggagtg
ccgacccggaggctcctgtgcgccctgcggggggagacctgacttttgacc
ccggcccccgggacctggtggagccctgggtggtggttcgagggctacgt
ccggacttcacctatacctttgaggtcactgcattgaacggggtatcctc
cttagccacggggcccgtcccatttgagcctgtcaatgtcaccactgacc
gagaggtacctcctgcagtgtctgacatccgggtgacgcggtcctcaccc
agcagcttgagcctggcctgggctgttccccgggcacccagtggggcgtg
gctggactacgaggtcaaataccatgagaagggcgccgagggtcccagca
gcgtgcggttcctgaagacgtcagaaaaccgggcagagctgcgggggctg
aagcggggagccagctacctggtgcaggtacgggcgcgctctgaggccgg
ctacgggcccttcggccaggaacatcacagccagacccaactggatgaga
```

-continued

```
gcgagggctggcgggagcagctggccctgattgcgggcacggcagtcgtg

ggtgtggtcctggtcctggtggtcattgtggtcgcagttctctgcctcag

gaagcagagcaatgggagagaagcagaatattcggacaaacacggacagt

atctcatcggacatggtactaaggtctacatcgaccccttcacttatgaa

gaccctaatgaggctgtgagggaatttgcaaaagagatcgatgtctccta

cgtcaagattgaagaggtgattggtgcaggtgagtttggcgaggtgtgcc

gggggcggctcaaggccccagggaagaaggagagctgtgtggcaatcaag

accctgaagggtggctacacggagcggcagcggcgtgagttctgagcga

ggcctccatcatgggccagttcgagcaccccaatatcatccgcctggagg

gcgtggtcaccaacagcatgcccgtcatgattctcacagagttcatggag

aacggcgccctggactccttcctgcggctaaacgacggacagttcacagt

catccagctcgtgggcatgctgcggggcatcgcctcgggcatgcggtacc

ttgccgagatgagctacgtccaccgagacctggctgctcgcaacatccta

gtcaacagcaacctcgtctgcaaagtgtctgactttggcctttcccgatt

cctggaggagaactcttccgatcccacctacacgagctccctgggaggaa

agattcccatccgatggactgccccggaggccattgccttccggaagttc

acttccgccagtgatgcctggagttacgggattgtgatgtgggaggtgat

gtcatttggggagaggccgtactgggacatgagcaatcaggacgtgatca

atgccattgaacaggactaccggctgcccccgcccccagactgtcccacc

tccctccaccagctcatgctggactgttggcagaaagaccggaatgcccg

gccccgcttcccccaggtggtcagcgccctggacaagatgatccggaacc

ccgccagcctcaaaatcgtggcccgggagaatggcggggcctcacaccct

ctcctggaccagcggcagcctcactactcagcttttggctctgtgggcga

gtggcttcgggccatcaaaatgggaagatacgaagaaagtttcgcagccg

ctggctttggctccttcgagctggtcagccagatctctgctgaggacctg

ctccgaatcggagtcactctggcgggacaccagaagaaaatcttggccag

tgtccagcacatgaagtcccaggccaagccgggaaccccgggtgggacag

gaggaccggccccgcagtactgagcggccgc
```

Another version of BamHI-NotI full length (FL) human EphB4 was also cloned. The difference is the 3'-terminal PCR oligo primer used for cloning:

```
                                   (SEQ ID NO: 400)
3Not1-B4 GCGGCCGCTCAGTACTGCGGGGCCGGT

                                   (SEQ ID NO: 401)
3Not2-B4 GCGGCCGCAGTTCCTGCAGGTCAAGTACT
```

Plasmids vectors for expressing recombinant soluble derivatives of Ephrin B2 and EphB4 were based on pEF6/V5-His-TOPO vector (Invitrogen), pIG (Novagen) or pRK5. pEF6/V5-His-TOPO contains human elongation factor 1α enhancer/promoter and blasticidin resistance marker. pIG vector is designed for high-level expression of protein fusions with Fc portion of human IgG1 under CMV promoter control and pRK5 is a general purpose CMV promoter-containing mammalian expression vector. To generate plasmid construct pEF6-B4EC-NT, cDNA fragment of human EphB4 was amplified by PCR using oligo primers 5'-GGATCCGCC ATGGAGCTC CGGGTGCTGCT-3' (SEQ ID NO: 1) and 5'-TGGATCCCT GCTCCCGC CAGCCCTCG CTCT-CATCCA-3'(SEQ ID NO: 2), and TOPO-cloned into pEF6/V5-His-TOPO vector. pEF6-hB4ECv3 was derived from pEF6-B4ECNT by digesting the plasmid DNA with EcoRV and BstBI, filling-in the ends with Klenow enzyme and religating the vector. Recombinant EphB4 derivative encoded by pEF6-B4EC-NT does not contain epitope- or purification tags, while the similar B4ECv3 protein encoded by pEF6-hB4ECv3 contains V5 epitope tag and 6×His tag on its C-terminus to facilitate purification from conditioned media. Plasmid construct pEF6-hB2EC was created by PCR amplification of Ephrin B2 cDNA using oligo primers 5'-TG-GATCCAC CATGGCTGT GAGAAGGGAC-3' (SEQ ID NO: 3) plus 5'-ATTAATGGTGATGGT GAT GATGACTAC CCACTTCGG AACCGAGGATGTTGTTC-3' (SEQ ID NO: 4) and TOPO-cloning into pEF6/V5-His-TOPO vector. Plasmid construct pIG-hB2EC-FC was created by PCR amplification of Ephrin B2 cDNA with oligo primers 5'-TAAAGCT-TCCGCCATGG CTGTGAGAAGGGAC-3' (SEQ ID NO: 5) and 5'-TAGGATCCACTTCGGA ACCGAGGATGTTGTT CCC-3'(SEQ ID NO: 6), followed by TOPO-cloning and sequencing the resulting PCR fragment with consecutive subcloning in pIG hIgG1 Fc fusion expression vector cut with Bam HI and Hind III. Similarly, pIG-hB2EC and pIG-hB4ECv3 were generated by PCR amplifying portions of EphB4 ECD cDNA using oligo primers 5'-ATAAGCTTCC GCCATGGAGC TCCGGGTGCTG-3' (SEQ ID NO: 7) plus 5'-TTGGATCCTGCTCCCG CCAGCCCTCGC TCT-CATC-3' (SEQ ID NO: 8) with consecutive subcloning into pIG hIgG1 Fc fusion expression vector cut with Bam HI and Hind III. Predicted sequences of the proteins encoded by the vectors described above are shown in FIGS. 1-5.

A construct encoding a truncated human EphB4 polypeptide comprising the globular (G) and cysteine-rich domains (C), the "GC" polypeptide, was prepared by PCR amplification using oligonucleotides:

```
                                   (SEQ ID NO: 402)
5SpeB4
TACTAGTCCGCCATGGAGCTCCGGGTGCTGCT

                                   (SEQ ID NO: 403)
3NotB4GC
gcggccgcttaatggtgatggtgatgatgAGCCGAAGGAGGGGTGGTGCA
```

The amplified portion was cloned by TA cloning into pEF6.

Sequence of the cloned fragment (SpeI-NotI fragment) is shown below (SEQ ID NO: 404):

```
actagtccgccATGGAGCTCCGGGTGCTGCTCTGCTGGGCTTCGTTGGCC

GCAGCTTTGGAAGAGACCCTGCTGAACACAAAATTGGAAACTGCTGATCT

GAAGTGGGTGACATTCCCTCAGGTGGACGGGCAGTGGGAGGAACTGAGCG

GCCTGGATGAGGAACAGCACAGCGTGCGCACCTACGAAGTGTGTGAAGTG

CAGCGTGCCCCGGGCCAGGCCCACTGGCTTCGCACAGGTTGGGTCCCACG

GCGGGGCGCCGTCCACGTGTACGCCACGCTGCGCTTCACCATGCTCGAGT

GCCTGTCCCTGCCTCGGGCTGGGCGCTCCTGCAAGGAGACCTTCACCGTC

TTCTACTATGAGAGCGATGCGGACACGGCCACGGCCCTCACGCCAGCCTG

GATGGAGAACCCCTACATCAAGGTGGACACGGTGGCCGCGGAGCATCTCA

CCCGGAAGCGCCCTGGGGCCGAGGCCACCGGGAAGGTGAATGTCAAGACG
```

-continued

```
CTGCGTCTGGGACCGCTCAGCAAGGCTGGCTTCTACCTGGCCTTCCAGGA
CCAGGGTGCCTGCATGGCCCTGCTATCCCTGCACCTCTTCTACAAAAAGT
GCGCCCAGCTGACTGTGAACCTGACTCGATTCCCGGAGACTGTGCCTCGG
GAGCTGGTTGTGCCCGTGGCCGGTAGCTGCGTGGTGGATGCCGTCCCCGC
CCCTGGCCCCAGCCCCAGCCTCTACTGCCGTGAGGATGGCCAGTGGGCCG
AACAGCCGGTCACGGGCTGCAGCTGTGCTCCGGGGTTCGAGGCAGCTGAG
GGGAACACCAAGTGCCGAGCCTGTGCCCAGGGCACCTTCAAGCCCCTGTC
AGGAGAAGGGTCCTGCCAGCCATGCCCAGCCAATAGCCACTCTAACACCA
TTGGATCAGCCGTCTGCCAGTGCCGCGTCGGGTACTTCCGGGCACGCACA
GACCCCCGGGGTGCACCCTGCACCACCCCTCCTTCGGCTcatcatcacca
tcaccattaagcggccgc
```

The sequence of the Globular domain+Cys-rich domain (B4EC-GC), precursor protein is shown below (SEQ ID NO: 405):

```
MELRVLLCWASLAAALEETLLNTKLETADLKWVTFPQVDGQWEELSGLDE
EQHSVRTYEVCEVQRAPGQAHWLRTGWVPRRGAVHVYATLRFTMLECLSL
PRAGRSCKETFTVFYYESDADTATALTPAWMENPYIKVDTVAAEHLTRKR
PGAEATGKVNVKTLRLGPLSKAGFYLAFQDQGACMALLSLHLFYKKCAQL
TVNLTRFPETVPRELVVPVAGSCVVDAVPAPGPSPSLYCREDGQWAEQPV
TGCSCAPGFEAAEGNTKCRACAQGTFKPLSGEGSCQPCPANSHSNTIGSA
VCQCRVGYFRARTDPRGAPCTTPPSAHHHHHH
```

For many uses, including therapeutic use, the leader sequence (first 15 amino acids, so that the processed form begins Leu-Glu-Glu . . . ) and the c-terminal hexahistidine tag may be removed or omitted.

The plasmid for the GC protein has the sequence:

```
AATATTATTGAAGCATTTATCAGGGTTATTGTCTCATGAGCGGATACATA
TTTGAATGTATTTAGAAAAATAAACAAATAGGGGTTCCGCGCACATTTCC
CCGAAAAGTGCCACCTGACGTCGACGGATCGGGAGATCTCCCGATCCCCT
ATGGTCGACTCTCAGTACAATCTGCTCTGATGCCGCATAGTTAAGCCAGT
ATCTGCTCCCTGCTTGTGTGTTGGAGGTCGCTGAGTAGTGCGCGAGCAAA
ATTTAAGCTACAACAAGGCAAGGCTTGACCGACAATTGCATGAAGAATCT
GCTTAGGGTTAGGCGTTTTGCGCTGCTTCGCGATGTACGGGCCAGATATA
CGCGTTGACATTGATTATTGACTAGGCTTTTGCAAAAAGCTTTGCAAAGA
TGGATAAAGTTTTAAACAGAGAGGAATCTTTGCAGCTAATGGACCTTCTA
GGTCTTGAAAGGAGTGCCTCGTGAGGCTCCGGTGCCCGTCAGTGGGCAGA
GCGCACATCGCCCACAGTCCCCGAGAAGTTGGGGGGAGGGGTCGGCAATT
GAACCGGTGCCTAGAGAAGGTGGCGCGGGGTAAACTGGGAAAGTGATGTC
GTGTACTGGCTCCGCCTTTTTCCCGAGGGTGGGGGAGAACCGTATATAAG
TGCAGTAGTCGCCGTGAACGTTCTTTTTCGCAACGGGTTTGCCGCCAGAA
CACAGGTAAGTGCCGTGTGTGGTTCCCGCGGGCCTGGCCTCTTTACGGGT
```

-continued

```
TATGGCCCTTGCGTGCCTTGAATTACTTCCACCTGGCTGCAGTACGTGAT
TCTTGATCCCGAGCTTCGGGTTGGAAGTGGGTGGGAGAGTTCGAGGCCTT
GCGCTTAAGGAGCCCCTTCGCCTCGTGCTTGAGTTGAGGCCTGGCCTGGG
CGCTGGGGCCGCCGCGTGCGAATCTGGTGGCACCTTCGCGCCTGTCTCGC
TGCTTTCGATAAGTCTCTAGCCATTTAAAATTTTTGATGACCTGCTGCGA
CGCTTTTTTTCTGGCAAGATAGTCTTGTAAATGCGGGCCAAGATCTGCAC
ACTGGTATTTCGGTTTTTGGGGCCGCGGGCGGCGACGGGGCCCGTGCGTC
CCAGCGCACATGTTCGGCGAGGCGGGGCCTGCGAGCGCGGCCACCGAGAA
TCGGACGGGGGTAGTCTCAAGCTGGCCGGCCTGCTCTGGTGCCTGGCCTC
GCGCCGCCGTGTATCGCCCCGCCCTGGGCGGCAAGGCTGGCCCGGTCGGC
ACCAGTTGCGTGAGCGGAAAGATGGCCGCTTCCCGGCCCTGCTGCAGGGA
GCTCAAAATGGAGGACGCGGCGCTCGGGAGAGCGGGCGGGTGAGTCACCC
ACACAAAGGAAAAGGGCCTTTCCGTCCTCAGCCGTCGCTTCATGTGACTC
CACGGAGTACCGGGCGCCGTCCAGGCACCTCGATTAGTTCTCGAGCTTTT
GGAGTACGTCGTCTTTAGGTTGGGGGGAGGGGTTTTATGCGATGGAGTTT
CCCCACACTGAGTGGGTGGAGACTGAAGTTAGGCCAGCTTGGCACTTGAT
GTAATTCTCCTTGGAATTTGCCCTTTTTGAGTTTGGATCTTGGTTCATTC
TCAAGCCTCAGACAGTGGTTCAAAGTTTTTTTCTTCCATTTCAGGTGTCG
TGAGGAATTAGCTTGGTACTAATACGACTCACTATAGGGAGACCCAAGCT
GGCTAGGTAAGCTTGGTACCGAGCTCGGATCCACTAGTCCAGTGTGGTGG
AATTGCCCTTIactagtccgccATGGAGCTCCGGGTGCTGCTCTGCTGGG
CTTCGTTGGCCGCAGCTTTGGAAGAGACCCTGCTGAACACAAAATTGGAA
ACTGCTGATCTGAAGTGGGTGACATTCCCTCAGGTGGACGGGCAGTGGGA
GGAACTGAGCGGCCTGGATGAGGAACAGCACAGCGTGCGCACCTACGAAG
TGTGTGACGTGCAGCGTGCCCCGGGCCAGGCCCACTGGCTTCGCACAGGT
TGGGTCCCACGGCGGGGCGCCGTCCACGTGTACGCCACGCTGCGCTTCAC
CATGCTCGAGTGCCTGTCCCTGCCTCGGGCTGGGCGCTCCTGCAAGGAGA
CCTTCACCGTCTTCTACTATGAGAGCGATGCGGACACGGCCACGGCCCTC
ACGCCAGCCTGGATGGAGAACCCCTACATCAAGGTGGACACGGTGGCCGC
GGAGCATCTCACCCGGAAGCGCCCTGGGGCCGAGGCCACCGGGAAGGTGA
ATGTCAAGACGCTGCGTCTGGGACCGCTCAGCAAGGCTGGCTTCTACCTG
GCCTTCCAGGACCAGGGTGCCTGCATGGCCCTGCTATCCCTGCACCTCTT
CTACAAAAAGTGCGCCCAGCTGACTGTGAACCTGACTCGATTCCCGGAGA
CTGTGCCTCGGGAGCTGGTTGTGCCCGTGGCCGGTAGCTGCGTGGTGGAT
GCCGTCCCCGCCCCTGGCCCCAGCCCCAGCCTCTACTGCCGTGAGGATGG
CCAGTGGGCCGAACAGCCGGTCACGGGCTGCAGCTGTGCTCCGGGGTTCG
AGGCAGCTGAGGGGAACACCAAGTGCCGAGCCTGTGCCCAGGGCACCTTC
AAGCCCCTGTCAGGAGAAGGGTCCTGCCAGCCATGCCCAGCCAATAGCCA
CTCTAACACCATTGGATCAGCCGTCTGCCAGTGCCGCGTCGGGTACTTCC
GGGCACGCACAGACCCCCGGGGTGCACCCTGCACCACCCCTCCTTCGGCT
```

-continued catcatcaccatcaccattaagcggccgcAAGGGCAATTCTGCAGATATC

CAGCACAGTGGCGGCCGCTCGAGTCTAGAGGGCCCGCGGTTCGAAGGTAA

GCCTATCCCTAACCCTCTCCTCGGTCTCGATTCTACGCGTACCGGTCATC

ATCACCATCACCATTGAGTTTAAACCCGCTGATCAGCCTCGACTGTGCCT

TCTAGTTGCCAGCCATCTGTTGTTTGCCCCTCCCCCGTGCCTTCCTTGAC

CCTGGAAGGTGCCACTCCCACTGTCCTTTCCTAATAAAATGAGGAAATTG

CATCGCATTGTCTGAGTAGGTGTCATTCTATTCTGGGGGGTGGGGTGGGG

CAGGACAGCAAGGGGGAGGATTGGGAAGACAATAGCAGGCATGCTGGGGA

TGCGGTGGGCTCTATGGCTTCTGAGGCGGAAAGAACCAGCTGGGGCTCTA

GGGGGTATCCCCACGCGCCCTGTAGCGGCGCATTAAGCGCGGCGGGTGTG

GTGGTTACGCGCAGCGTGACCGCTACACTTGCCAGCGCCCTAGCGCCCGC

TCCTTTCGCTTTCTTCCCTTCCTTTCTCGCCACGTTCGCCGGCTTTCCCC

GTCAAGCTCTAAATCGGGGCATCCCTTTAGGGTTCCCATTTAGTGCTTTA

CGGCACCTCGACCCCAAAAAACTTGATTAGGGTGATGGTTCACGTAGTGG

GCCATCGCCCTGATAGACGGTTTTTCGCCCTTTGACGTTGGAGTCCACGT

TCTTTAATAGTGGACTCTTGTTCCAAACTGGAACAACACTCAACCCTATC

TCGGTCTATTCTTTTGATTTATAAGGGATTTTGGGGATTTCGGCCTATTG

GTTAAAAAATGAGCTGATTTAACAAAAATTTAACGCGAATTAATTCTGTG

GAATGTGTGTCAGTTAGGGTGTGGAAAGTCCCCAGGCTCCCCAGGCAGGC

AGAAGTATGCAAAGCATGCATCTCAATTAGTCAGCAACCAGGTGTGGAAA

GTCCCCAGGCTCCCCAGCAGGCAGAAGTATGCAAAGCATGCATCTCAATT

AGTCAGCAACCATAGTCCCGCCCCTAACTCCGCCCATCCCGCCCCTAACT

CCGCCCAGTTCCGCCCATTCTCCGCCCCATGGCTGACTAATTTTTTTTAT

TTATGCAGAGGCCGAGGCCGCCTCTGCCTCTGAGCTATTCCAGAAGTAGT

GAGGAGGCTTTTTTGGAGGCCTAGGCTTTTGCAAAAAGCTCCCGGGAGCT

TGTATATCCATTTTCGGATCTGATCAGCACGTGTTGACAATTAATCATCG

GCATAGTATATCGGCATAGTATAATACGACAAGGTGAGGAACTAAACCAT

GGCCAAGCCTTTGTCTCAAGAAGAATCCACCCTCATTGAAAGAGCAACGG

CTACAATCAACAGCATCCCCATCTCTGAAGACTACAGCGTCGCCAGCGCA

GCTCTCTCTAGCGACGGCCGCATCTTCACTGGTGTCAATGTATATCATTT

TACTGGGGGACCTTGTGCAGAACTCGTGGTGCTGGGCACTGCTGCTGCTG

CGGCAGCTGGCAACCTGACTTGTATCGTCGCGATCGGAAATGAGAACAGG

GGCATCTTGAGCCCCTGCGGACGGTGTCGACAGGTGCTTCTCGATCTGCA

TCCTGGGATCAAAGCGATAGTGAAGGACAGTGATGGACAGCCGACGGCAG

TTGGGATTCGTGAATTGCTGCCCTCTGGTTATGTGTGGGAGGGCTAAGCA

CTTCGTGGCCGAGGAGCAGGACTGACACGTGCTACGAGATTTCGATTCCA

CCGCCGCCTTCTATGAAAGGTTGGGCTTCGGAATCGTTTTCCGGGACGCC

GGCTGGATGATCCTCCAGCGCGGGGATCTCATGCTGGAGTTCTTCGCCCA

CCCCAACTTGTTTATTGCAGCTTATAATGGTTACAAATAAAGCAATAGCA

TCACAAATTTCACAAATAAAGCATTTTTTTCACTGCATTCTAGTTGTGGT

TTGTCCAAACTCATCAATGTATCTTATCATGTCTGTATACCGTCGACCTC

-continued

TAGCTAGAGCTTGGCGTAATCATGGTCATAGCTGTTTCCTTGTTATCCGC

TCACAATTCCACACAACATACGAGCCGGAAGCATAAAGTGTAAAGCCTGG

GGTGCCTAATGAGTGAGCTAACTCACATTAATTGCGTTGCGCTCACTGCC

CGCTTTCCAGTCGGGAAACCTGTCGTGCCAGCTGCATTAATGAATCGGCC

AACGCGCGGGGAGAGGCGGTTTGCGTATTGGGCGCTCTTCCGCTTCCTCG

CTCACTGACTCGCTGCGCTCGGTCGTTCGGCTGCGGCGAGCGGTATCAGC

TCACTCAAAGGCGGTAATACGGTTATCCACAGAATCAGGGGATAACGCAG

GAAAGAACATGTGAGCAAAAGGCCAGCAAAAGGCCAGGAACCGTAAAAAG

GCCGCGTTGCTGGCGTTTTTCCATAGGCTCCGCCCCCCTGACGAGCATCA

CAAAAATCGACGCTCAAGTCAGAGGTGGCGAAACCCGACAGGACTATAAA

GATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGT

GGCGCTTTCTCAATGCTCACGCTGTAGGTATCTCAGTTCGGTGTAGGTCG

TTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGA

CTTATCGCCACTGGCAGCAGCCACTGGTAACAGGATTAGCAGAGCGAGGT

ATGTAGGCGGTGCTACAGAGTTCTTGAAGTGGTGGCCTAACTACGGCTAC

ACTAGAAGGACAGTATTTGGTATCTGCGCTCTGCTGAAGCCAGTTACCTT

CGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGA

TCTCAAGAAGATCCTTTGATCTTTTCTACGGGGTCTGACGCTCAGTGGAA

CGAAAACTCACGTTAAGGGATTTTGGTCATGAGATTATCAAAAAGGATCT

TCACCTAGATCCTTTTAAATTAAAAATGAAGTTTTAAATCAATCTAAAGT

ATATATGAGTAAACTTGGTCTGACAGTTACCAATGCTTAATCAGTGAGGC

ACCTATCTCAGCGATCTGTCTATTTCGTTCATCCATAGTTGCCTGACTCC

CCGTCGTGTAGATAACTACGATACGGGAGGGCTTACCATCTGGCCCCAGT

GCTCCAATGATACCGCGAGACCCACGCTCACCGGCTCCAGATTTATCAGC

AATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCAT

CGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTT

AGCTCCTTCGGTCCTCCGATCGTTGTCAGAAGTAAGTTGGCCGCAGTGTT

ATCACTCATGGTTATGGCAGCACTGCATAATTCTCTTACTGTCATGCCAT

CCGTAAGATGCTTTTCTGTGACTGGTGAGTACTCAACCAAGTCATTCTGA

GAATAGTGTATGCGGCGACCGAGTTGCTCTTGCCCGGCGTCAATACGGGA

TAATACCGCGCCACATAGCAGAACTTTAAAAGTGCTCATCATTGGAAAAC

GTTCTTCGGGGCGAAAACTCTCAAGGATCTTACCGCTGTTGAGATCCAGT

TCGATGTAACCCACTCGTGCACCCAACTGATCTTCAGCATCTTTTACTTT

CACCAGCGTTTCTGGGTGAGCAAAAACAGGAAGGCAAAATGCCGCAAAAA

-continued

AGGGAATAAGGGCGACACGGAAATGTTGAATACTCATACTCTTCCTTTTT

C

A nucleic acid encoding truncated human EphB4 protein comprising the globular domain, Cys-rich domain and the first FNIII domain (GCF) was prepared by PCR with oligonucleotides:

(SEQ ID NO: 407)
5SpeB4 TACTAGTCCGCCATGGAGCTCCGGGTGCTGCT (SEQ ID NO: 408)
3NotB4GCF1 AGCGGCCGCTTAATGGTGATGGTGATGATGGACATTGAC

AGGCTCAAATGGGA

TA cloned into pEF6. Sequence of the cloned fragment (SpeI-NotI fragment) is shown below (SEQ ID NO: 409):

tactagtccgccATGGAGCTCCGGGTGCTGCTCTGCTGGGCTTCGTTGGC

CGCAGCTTTGGAAGAGACCCTGCTGAACACAAAATTGGAAACTGCTGATC

TGAAGTGGGTGACATTCCCTCAGGTGGACGGGCAGTGGGAGGAACTGAGC

GGCCTGGATGAGGAACAGCACAGCGTGCGCACCTACGAAGTGTGTGAAGT

GCAGCGTGCCCCGGGCCAGGCCCACTGGCTTCGCACAGGTTGGGTCCCAC

GGCGGGGCGCCGTCCACGTGTACGCCACGCTGCGCTTCACCATGCTCGAG

TGCCTGTCCCTGCCTCGGGCTGGGCGCTCCTGCAAGGAGACCTTCACCGT

CTTCTACTATGAGAGCGATGCGGACACGGCCACGGCCCTCACGCCAGCCT

GGATGGAGAACCCCTACATCAAGGTGGACACGGTGGCCGCGGAGCATCTC

ACCCGGAAGCGCCCTGGGGCCGAGGCCACCGGGAAGGTGAATGTCAAGAC

CGCTGCGTCTGGGACCGCTCAGCAAGGCTGGCTTCTACCTGGCCTTCCAG

ACCAGGGTGCCTGCATGGCCCTGCTATCCCTGCACCTCTTCTACAAAAAG

TGCGCCCAGCTGACTGTGAACCTGACTCGATTCCCGGAGACTGTGCCTCG

GGAGCTGGTTGTGCCCGTGGCCGGTAGCTGCGTGGTGGATGCCGTCCCCG

CCCCTGGCCCCAGCCCCAGCCTCTACTGCCGTGAGGATGGCCAGTGGGCC

GAACAGCCGGTCACGGGCTGCAGCTGTGCTCCGGGGTTCGAGGCAGCTGA

GGGGAACACCAAGTGCCGAGCCTGTGCCCAGGGCACCTTCAAGCCCCTGT

CAGGAGAAGGGTCCTGCCAGCCATGCCCAGCCAATAGCCACTCTAACACC

ATTGGATCAGCCGTCTGCCAGTGCCGCGTCGGGTACTTCCGGGCACGCAC

AGACCCCCGGGGTGCACCCTGCACCACCCCTCCTTCGGCTCCGCGGAGCG

TGGTTTCCCGCCTGAACGGCTCCTCCCTGCACCTGGAATGGAGTGCCCCC

CTGGAGTCTGGTGGCCGAGAGGACCTCACCTACGCCCTCCGCTGCCGGGA

GTGCCGACCCGGAGGCTCCTGTGCGCCCTGCGGGGGAGACCTGACTTTTG

ACCCCGGCCCCCGGGACCTGGTGGAGCCCTGGGTGGTGGTTCGAGGGCTA

CGTCCGGACTTCACCTATACCTTTGAGGTCACTGCATTGAACGGGGTATC

CTCCTTAGCCACGGGGCCCGTCCCATTTGAGCCTGTCAATGTCCATCATC

ACCATCACCATTAAgcggccgct

Sequence of the GCF precursor protein is shown below (SEQ ID NO: 410):

MELRVLLCWASLAAALEETLLNTKLETADLKWVTFPQVDGQWEELSGLDE

EQHSVRTYEVCEVQRAPGQAHWLRTGWVPRRGAVHVYATLRFTMLECLSL

PRAGRSCKETFTVFYYESDADTATALTPAWMENPYIKVDTVAAEHLTRKR

PGAEATGKVNVKTLRLGPLSKAGFYLAFQDQGACMALLSLHLFYKKCAQL

TVNLTRFPETVPRELVVPVAGSCVVDAVPAPGPSPSLYCREDGQWAEQPV

TGCSCAPGFAEGNTKCRACAQGTFKPLSGEGSCQPCPANSHSNTIGSAVC

QCRVGYFRARTDPRGAPCTTPPSAPRSVVSRLNGSSLHLEWSAPLESGGR

EDLTYALRCRECRPGGSCAPCGGDLTFDPGPRDLVEPWVVVRGLRPDFTY

TFEVTALNGVSSLATGPVPFEPVNVHHHHHH

For many uses, including therapeutic use, the leader sequence (first 15 amino acids, so that the processed form begins Leu-Glu-Glu . . . ) and the c-terminal hexahistidine tag may be removed or omitted.

Plasmid DNA sequence is shown below (SEQ ID NO: 411):

AATATTATTGAAGCATTTATCAGGGTTATTGTCTCATGAGCGGATACATA

TTTGAATGTATTTAGAAAAATAAACAAATAGGGGTTCCGCGCACATTTCC

CCGAAAAGTGCCACCTGACGTCGACGGATCGGGAGATCTCCCGATCCCCT

ATGGTCGACTCTCAGTACAATCTGCTCTGATGCCGCATAGTTAAGCCAGT

ATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCT

GCTTAGGGTTAGGCGTTTTGCGCTGCTTCGCGATGTACGGGCCAGATATA

CGCGTTGACATTGATTATTGACTAGGCTTTTGCAAAAAGCTTTGCAAAGA

TGGATAAAGTTTTAAACAGAGAGGAATCTTTGCAGCTAATGGACCTTCTA

GGTCTTGAAAGGAGTGCCTCGTGAGGCTCCGGTGCCCGTCAGTGGGCAGA

GCGCACATCGCCCACAGTCCCCGAGAAGTTGGGGGGAGGGGTCGGCAATT

GAACCGGTGCCTAGAGAAGGTGGCGCGGGGTAAACTGGGAAAGTGATGTC

GTGTACTGGCTCCGCCTTTTTCCCGAGGGTGGGGGAGAACCGTATATAAG

TGCAGTAGTCGCCGTGAACGTTCTTTTTCGCAACGGGTTTGCCGCCAGAA

CACAGGTAAGTGCCGTGTGTGGTTCCCGCGGGCCTGGCCTCTTTACGGGT

TATGGCCCTTGCGTGCCTTGAATTACTTCCACCTGGCTGCAGTACGTGAT

TCTTGATCCCGAGCTTCGGGTTGGAAGTGGGTGGGAGAGTTCGAGGCCTT

GCGCTTAAGGAGCCCCTTCGCCTCGTGCTTGAGTTGAGGCCTGGCCTGGG

CGCTGGGGCCGCCGCGTGCGAATCTGGTGGCACCTTCGCGCCTGTCTCGC

TGCTTTCGATAAGTCTCTAGCCATTTAAAATTTTTGATGACCTGCTGCGA

CGCTTTTTTTCTGGCAAGATAGTCTTGTAAATGCGGGCCAAGATCTGCAC

ACTGGTATTTCGGTTTTTGGGGCCGCGGGCGGCGACGGGGCCCGTGCGTC

CCAGCGCACATGTTCGGCGAGGCGGGGCCTGCGAGCGCGGCCACCGAGAA

TCGGACGGGGGTAGTCTCAAGCTGGCCGGCCTGCTCTGGTGCCTGGCCTC

GCGCCGCCGTGTATCGCCCCGCCCTGGGCGGCAAGGCTGGCCCGGTCGGC

ACCAGTTGCGTGAGCGGAAAGATGGCCGCTTCCCGGCCCTGCTGCAGGGA

GCTCAAAATGGAGGACGCGGCGCTCGGGAGAGCGGGCGGGTGAGTCACCC

-continued

ACACAAAGGAAAAGGGCCTTTCCGTCCTCAGCCGTCGCTTCATGTGACTC
CACGGAGTACCGGGCGCCGTCCAGGCACCTCGATTAGTTCTCGAGCTTTT
GGAGTACGTCGTCTTTAGGTTGGGGGGAGGGGTTTTATGCGATGGAGTTT
CCCCACACTGAGTGGGTGGAGACTGAAGTTAGGCCAGCTTGGCACTTGAT
GTAATTCTCCTTGGAATTTGCCCTTTTTGAGTTTGGATCTTGGTTCATTC
TCAAGCCTCAGACAGTGGTTCAAAGTTTTTTTCTTCCATTTCAGGTGTCG
TGAGGAATTAGCTTGGTACTAATACGACTCACTATAGGGAGACCCAAGCT
GGCTAGGTAAGCTTGGTACCGAGCTCGGATCCACTAGTCCAGTGTGGTGG
AATTGCCCTTtactagtccgccATGGAGCTCCGGGTGCTGCTCTGCTGGG
CTTCGTTGGCCGCAGCTTTGGAAGAGACCCTGCTGAACACAAAATTGGAA
ACTGCTGATCTGAAGTGGGTGACATTCCCTCAGGTGGACGGGCAGTGGGA
GGAACTGAGCGGCCTGGATGAGGAACAGCACAGCGTGCGCACCTACGAAG
TGTGTGACGTGCAGCGTGCCCCGGGCCAGGCCCACTGGCTTCGCACAGGT
TGGGTCCCACGGCGGGGCGCCGTCCACGTGTACGCCACGCTGCGCTTCAC
CATGCTCGAGTGCCTGTCCCTGCCTCGGGCTGGGCGCTCCTGCAAGGAGA
CCTTCACCGTCTTCTACTATGAGAGCGATGCGGACACGGCCACGGCCCTC
ACGCCAGCCTGGATGGAGAACCCCTACATCAAGGTGGACACGGTGGCCGC
GGAGCATCTCACCCGGAAGCGCCCTGGGGCCGAGGCCACCGGGAAGGTGA
ATGTCAAGACGCTGCGCCTGGGACCGCTCAGCAAGGCTGGCTTCTACCTG
GCCTTCCAGGACCAGGGTGCCTGCATGGCCCTGCTATCCCTGCACCTCTT
CTACAAAAAGTGCGCCCAGCTGACTGTGAACCTGACTCGATTCCCGGAGA
CTGTGCCTCGGGAGCTGGTTGTGCCCGTGGCCGGTAGCTGCGTGGTGGAT
GCCGTCCCCGCCCCTGGCCCCAGCCCCAGCCTCTACTGCCGTGAGGATGG
CCAGTGGGCCGAACAGCCGGTCACGGGCTGCAGCTGTGCTCCGGGGTTCG
AGGCAGCTGAGGGGAACACCAAGTGCCGAGCCTGTGCCCAGGGCACCTTC
AAGCCCCTGTCAGGAGAAGGGTCCTGCCAGCCATGCCCAGCCAATAGCCA
CTCTAACACCATTGGATCAGCCGTCTGCCAGTGCCGCGTCGGGTACTTCC
GGGCACGCACAGACCCCCGGGGTGCACCCTGCACCACCCCTCCTTCGGCT
CCGCGGAGCGTGGTTTCCCGCCTGAACGGCTCCTCCCTGCACCTGGAATG
GAGTGCCCCCCTGGAGTCTGGTGGCCGAGAGGACCTCACCTACGCCCTCC
GCTGCCGGGAGTGTCGACCCGGAGGCTCCTGTGCGCCCTGCGGGGGAGAC
CTGACTTTTGACCCCGGCCCCCGGGACCTGGTGGAGCCCTGGGTGGTGGT
TCGAGGGCTACGTCCTGACTTCACCTATACCTTTGAGGTCACTGCATTGA
ACGGGGTATCCTCCTTAGCCACGGGGCCCGTCCCATTTGAGCCTGTCAAT
GTCCATCATCACCATCACCATTAAgcggccgctAAGGGCAATTCTGCAGA
TATCCAGCACAGTGGCGGCCGCTCGAGTCTAGAGGGCCCGCGGTTCGAAG
GTAAGCCTATCCCTAACCCTCTCCTCGGTCTCGATTCTACGCGTACCGGT
CATCATCACCATCACCATTGAGTTTAAACCCGCTGATCAGCCTCGACTGT
GCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAA -continued ATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTG
GGGATGCGGTGGGCTCTATGGCTTCTGAGGCGGAAAGAACCAGCTGGGGC
TCTAGGGGGTATCCCCACGCGCCCTGTAGCGGCGCATTAAGCGCGGCGGG
TGTGGTGGTTACGCGCAGCGTGACCGCTACACTTGCCAGCGCCCTAGCGC
CCGCTCCTTTCGCTTTCTTCCCTTCCTTTCTCGCCACGTTCGCCGGCTTT
CCCCGTCAAGCTCTAAATCGGGGCATCCCTTTAGGGTTCCGATTTAGTGC
TTTACGGCACCTCGACCCCAAAAAACTTGATTAGGGTGATGGTTCACGTA
GTGGGCCATCGCCCTGATAGACGGTTTTTCGCCCTTTGACGTTGGAGTCC
ACGTTCTTTAATAGTGGACTCTTGTTCCAAACTGGAACAACACTCAACCC
TATCTCGGTCTATTCTTTTGATTTATAAGGGATTTTGGGGATTTCGGCCT
ATTGGTTAAAAAATGAGCTGATTTAACAAAAATTTAACGCGAATTAATTC
TGTGGAATGTGTGTCAGTTAGGGTGTGGAAAGTCCCCAGGCTCCCCAGGC
AGGCAGAAGTATGCAAAGCATGCATCTCAATTAGTCAGCAACCAGGTGTG
GAAAGTCCCCAGGCTCCCCAGCAGGCAGAAGTATGCAAAGCATGCATCTC
AATTAGTCAGCAACCATAGTCCCGCCCCTAACTCCGCCCATCCCGCCCCT
AACTCCGCCCAGTTCCGCCCATTCTCCGCCCCATGGCTGACTAATTTTTT
TTATTTATGCAGAGGCCGAGGCCGCCTCTGCCTCTGAGCTATTCCAGAAG
TAGTGAGGAGGCTTTTTTGGAGGCCTAGGCTTTTGCAAAAAGCTCCCGGG
AGCTTGTATATCCATTTTCGGATCTGATCAGCACGTGTTGACAATTAATC
ATCGGCATAGTATATCGGCATAGTATAATACGACAAGGTGAGGAACTAAA
CCATGGCCAAGCCTTTGTCTCAAGAAGAATCCACCCTCATTGAAAGAGCA
ACGGCTACAATCAACAGCATCCCCATCTCTGAAGACTACAGCGTCGCCAG
CGCAGCTCTCTCTAGCGACGGCCGCATCTTCACTGGTGTCAATGTATATC
ATTTTACTGGGGGACCTTGTGCAGAACTCGTGGTGCTGGGCACTGCTGCT
GCTGCGGCAGCTGGCAACCTGACTTGTATCGTCGCGATCGGAAATGAGAA
CAGGGGCATCTTGAGCCCCTGCGGACGGTGTCGACAGGTGCTTCTCGATC
TGCATCCTGGGATCAAAGCGATAGTGAAGGACAGTGATGGACAGCCGACG
GCAGTTGGGATTCGTGAATTGCTGCCCTCTGGTTATGTGTGGGAGGGCTA
AGCACTTCGTGGCCGAGGAGCAGGACTGACACGTGCTACGAGATTTCGAT
TCCACCGCCGCCTTCTATGAAAGGTTGGGCTTCGGAATCGTTTTCCGGGA
CGCCGGCTGGATGATCCTCCAGCGCGGGGATCTCATGCTGGAGTTCTTCG
CCCACCCCAACTTGTTTATTGCAGCTTATAATGGTTACAAATAAAGCAAT
AGCATCACAAATTTCACAAATAAAGCATTTTTTTCACTGCATTCTAGTTG
TGGTTTGTCCAAACTCATCAATGTATCTTATCATGTCTGTATACCGTCGA
CCTCTAGCTAGAGCTTGGCGTAATCATGGTCATAGCTGTTTCCTGTGTGA
AATTGTTATCCGCTCACAATTCCACACAACATACGAGCCGGAAGCATAAA
GTGTAAAGCCTGGGGTGCCTAATGAGTGAGCTAACTCACATTAATTGCGT
TGCGCTCACTGCCCGCTTTCCAGTCGGGAAACCTGTCGTGCCAGCTGCAT
TAATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGGC -continued

```
GAGCGGTATCAGCTCACTCAAAGGCGGTAATACGGTTATCCACAGAATCA
GGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCG
ACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCC
CTTCGGGAAGCGTGGCGCTTTCTCAATGCTCACGCTGTAGGTATCTCAGT
TCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACC
CGGTAAGACACGACTTATCGCCACTGGCAGCAGCCACTGGTAACAGGATT
AGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGA
AGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTG
ACGCTCAGTGGAACGAAAACTCACGTTAAGGGATTTTGGTCATGAGATTA
TCAAAAAGGATCTTCACCTAGATCCTTTTAAATTAAAAATGAAGTTTTAA
ATCAATCTAAAGTATATATGAGTAAACTTGGTCTGACAGTTACCAATGCT
TAATCAGTGAGGCACCTATCTCAGCGATCTGTCTATTTCGTTCATCCATA
GTTGCCTGACTCCCCGTCGTGTAGATAACTACGATACGGGAGGGCTTACC
ATCTGGCCCCAGTGCTGCAATGATACCGCGAGACCCACGCTCACCGGCTC
CAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTC
AGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTT
ACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGG
CGTCAATACGGGATAATACCGCGCCACATAGCAGAACTTTAAAAGTGCTC
ATCATTGGAAAACGTTCTTCGGGGCGAAAACTCTCAAGGATCTTACCGCT
GTTGAGATCCAGTTCGATGTAACCCACTCGTGCACCCAACTGATCTTCAG
CATCTTTTACTTTCACCAGCGTTTCTGGGTGAGCAAAAACAGGAAGGCAA
AATGCCGCAAAAAAGGGAATAAGGGCGACACGGAAATGTTGAATACTCAT
ACTCTTCCTTTTTC
```

A vector encoding truncated human EphB4 protein having the Globular, Cys-rich and two FNIII domains with a c-terminal tag, GCF2 (v.3) was derived from pEF6-FL-hB4EC by digesting with EcoRV and BstBI, treating with Klenow and religating.

Amino acid sequence of encoded FL-hB4EC precursor (His-tagged) is shown below (SEQ ID NO: 412):

```
MELRVLLCWASLAAALEETLLNTKLETADLKWVTFPQVDGQWEELSGLDE
EQHSVRTYEVCEVQRAPGQAHWLRTGWVPRRGAVHVYATLRFTMLECLSL
PRAGRSCKETFTVFYYESDADTATALTPAWMENPYIKVDTVAAEHLTRKR
PGAEATGKVNVKTLRLGPLSKAGFYLAFQDQGACMALLSLHLFYKKCAQL
TVNLTRFPETVPRELVVPVAGSCVVDAVPAPGPSPSLYCREDGQWAEQPV
TGCSCAPGFEAAEGNTKCRACAQGTFKPLSGEGSCQPCPANSHSNTIGSA
VCQCRVGYFRARTDPRGAPCTTPPSAPRSVVSRLNGSSLHLEWSAPLESG
GREDLTYALRCRECRPGGSCAPCGGDLTFDPGPRDLVEPWVVVRGLRPDF
TYTFEVTALNGVSSLATGPVPFEPVNVTTDREVPPAVSDIRVTRSSPSSL
SLAWAVPRAPSGAWLDYEVKYHEKGAEGPSSVRFLKTSENRAELRGLKRG
ASYLVQVRARSEAGYGPFGQEHHSQTQLDESEGWREQGSKRAILQIEGKP
IPNPLLGLDSTRTGHHHHHH
```

For many uses, including therapeutic use, the leader sequence (first 15 amino acids, so that the processed form begins Leu-Glu-Glu . . . ) and the c-terminal hexahistidine tag may be removed or omitted.

Plasmid DNA sequence is shown below (SEQ ID NO: 413):

```
aatattattgaagcatttatcagggttattgtctcatgagcggatacata
tttgaatgtatttagaaaaataaacaaataggggttccgcgcacatttcc
ccgaaaagtgccacctgacgtcgacggatcgggagatctcccgatcccct
atggtcgactctcagtacaatctgctctgatgccgcatagttaagccagt
atctgctccctgcttgtgtgttggaggtcgctgagtagtgcgcgagcaaa
atttaagctacaacaaggcaaggcttgaccgacaattgcatgaagaatct
gcttagggttaggcgttttgcgctgcttcgcgatgtacgggccagatata
cgcgttgacattgattattgactaggcttttgcaaaaagctttgcaaaga
tggataaagttttaaacagagaggaatctttgcagctaatggaccttcta
ggtcttgaaaggagtgcctcgtgaggctccggtgcccgtcagtgggcaga
gcgcacategcccacagtccccgagaagttggggggaggggtcggcaatt
gaaccggtgcctagagaaggtggcgcggggtaaactgggaaagtgatgtc
gtgtactggctccgcctttttcccgagggtgggggagaaccgtatataag
tgcagtagtcgccgtgaacgttctttttcgcaacgggtttgccgccagaa
cacaggtaagtgccgtgtgtggttcccgcgggcctggcctctttacgggt
tatggcccttgcgtgccttgaattacttccacctggctgcagtacgtgat
tcttgatcccgagcttcgggttggaagtgggtgggagagttcgaggcctt
gcgcttaaggagccccttcgcctcgtgcttgagttgaggcctggcctggg
cgctggggccgccgcgtgcgaatctggtggcaccttcgcgcctgtctcgc
tgctttcgataagtctctagccatttaaaatttttgatgacctgctgcga
cgctttttttctggcaagatagtcttgtaaatgcgggccaagatctgcac
actggtatttcggtttttggggccgcgggcggcgacggggcccgtgcgtc
ccagcgcacatgttcggcgaggcggggcctgcgagcgcggccaccgagaa
tcggacgggggtagtctcaagctggccggcctgctctggtgcctggcctc
```

-continued gcgccgccgtgtatcgccccgccctgggcggcaaggctggcccggtcggc accagttgcgtgagcggaaagatggccgcttcccggccctgctgcaggga gctcaaaatggaggacgCggCgCtcgggagagcgggcgggtgagtcaccc acaCaaaggaaaagggcctttCCgtcctcagccgtcgcttcatgtgactc cacggagtaccgggcgccgtccaggcacctcgattagttctcgagctttt ggagtacgtcgtctttaggttggggggaggggttttatgcgatggagttt ccccacactgagtgggtggagactgaagttaggccagcttggcacttgat gtaattctccgcttggtactaatacgactcactatagggagacccaagct ggctaggtaagcttggtaccgagCtCggatCCaCtagtCcagtgtggtgg aattgcccttATAAGCTTCCGCCATGGAGCTCCGGGTGCTGCTCTGCTGG

GCTTCGTTGGCCGCAGCTTTGGAAGAGACCCTGCTGAACACAAAATTGGA

AACTGCTGATCTGAAGTGGGTGACATTCCCTCAGGTGGACGGGCAGTGGG

AGGAACTGAGCGGCCTGGATGAGGAACAGCACAGCGTGCGCACCTACGAA

GTGTGTGAAGTGCAGCGTGCCCCGGGCCAGGCCCACTGGCTTCGCACAGG

TTGGGTCCCACGGCGGGGCGCCGTCCACGTGTACGCCACGCTGCGCTTCA

CCATGCTCGAGTGCCTGTCCCTGCCTCGGGCTGGGCGCTCCTGCAAGGAG

ACCTTCACCGTCTTCTACTATGAGAGCGATGCGGACACGGCCACGGCCCT

CACGCCAGCCTGGATGGAGAACCCCTACATCAAGGTGGACACGGTGGCCG

CGGAGCATCTCACCCGGAAGCGCCCTGGGGCCGAGGCCACCGGGAAGGTG

AATGTCAAGACGCTGCGTCTGGGACCGCTCAGCAAGGCTGGCTTCTACCT

GGCCTTCCAGGACCAGGGTGCCTGCATGGCCCTGCTATCCCTGCACCTCT

TCTACAAAAAGTGCGCCCAGCTGACTGTGAACCTGACTCGATTCCCGGAG

ACTGTGCCTCGGGAGCTGGTTGTGCCCGTGGCCGGTAGCTGCGTGGTGGA

TGCCGTCCCCGCCCCTGGCCCCAGCCCCAGCCTCTACTGCCGTGAGGATG

GCCAGTGGGCCGAACAGCCGGTCACGGGCTGCAGCTGTGCTCCGGGGTTC

GAGGCAGCTGAGGGGAACACCAAGTGCCGAGCCTGTGCCCAGGGCACCTT

CAAGCCCCTGTCAGGAGAAGGGTCCTGCCAGCCATGCCCAGCCAATAGCC

ACTCTAACACCATTGGATCAGCCGTCTGCCAGTGCCGCGTCGGGTACTTC

CGGGCACGCACAGACCCCCGGGGTGCACCCTGCACCACCCCTCCTTCGGC

TCCGCGGAGCGTGGTTTCCCGCCTGAACGGCTCCTCCCTGCACCTGGAAT

GGAGTGCCCCCCTGGAGTCTGGTGGCCGAGAGGACCTCACCTACGCCCTC

CGCTGCCGGGAGTGCCGACCCGGAGGCTCCTGTGCGCCCTGCGGGGGAGA

CCTGACTTTTGACCCCGGCCCCCGGGACCTGGTGGAGCCCTGGGTGGTGG

TTCGAGGGCTACGTCCGGACTTCACCTATACCTTTGAGGTCACTGCATTG

AACGGGGTATCCTCCTTAGCCACGGGGCCCGTCCCATTTGAGCCTGTCAA

TGTCACCACTGACCGAGAGGTACCTCCTGCAGTGTCTGACATCCGGGTGA

CGCGGTCCTCACCCAGCAGCTTGAGCCTGGCCTGGGCTGTTCCCCGGGCA

CCCAGTGGGGCGTGGCTGGACTACGAGGTCAAATACCATGAGAAGGGCGC

CGAGGGTCCCAGCAGCGTGCGGTTCCTGAAGACGTCAGAAAACCGGGCAG

AGCTGCGGGGGCTGAAGCGGGGAGCCAGCTACCTGGTGCAGGTACGGGCG

-continued

CGCTCTGAGGCCGGCTACGGGCCCTTCGGCCAGGAACATCACAGCCAGAC

CCAACTGGATGAGAGCGAGGGCTGGCGGGAGCAGGGATCCAAaagggcaa ttctgcagatcgaaggtaagcctatccctaaccctctcctcggtctcgat tctacgcgtaccggtcatcatcaccatcaccattgagtttaaacccgctg atcagcctcgactgtgccttctagttgccagccatctgttgtttgcccct cccccgtgccttccttgaccctggaaggtgccactcccactgtcctttcc taataaaatgaggaaattgcatcgcattgtctgagtaggtgtcattctat tctggggggtggggtggggcaggacagcaagggggaggattgggaagaca atagcaggcatgctggggatgcggtgggctctatggcttctgaggcggaa agaaccagctggggctctagggggtatccccacgcgccctgtagcggcgc attaagcgcggcgggtgtggtggttacgcgcagcgtgaccgctacacttg ccagcgccctagcgcccgctcctttcgctttcttcccttcctttctcgcc acgttcgccggctttccccgtcaagctctaaatcgggggcatccctttagg gttccgatttagtgctttacggcacctcgaccccaaaaaacttgattagg gtgatggttcacgtagtgggccatcgccctgatagacggtttttcgccct ttgacgttggagtccacgttctttaatagtggactcttgttccaaactgg aacaacactcaaccctatctcggtctattcttttgatttataagggattt tggggatttcggcctattggttaaaaaatgagctgatttaacaaaaattt aacgcgaattaattctgtggaatgtgtgtcagttagggtgtggaaagtcc ccaggctccccaggcaggcagaagtatgcaaagcatgcatctcaattagt cagcaaccaggtgtggaaagtccccaggctccccagcaggcagaagtatg caaagcatgcatctcaattagtcagcaaccatagtcccgcccctaactcc gcccatcccgcccctaactccgcccagttccgcccattctccgccccatg gctgactaattttttttatttatgcagaggccgaggccgcctctgcctct gagctattccagaagtagtgaggaggcttttttggaggcctaggcttttg caaaaagctcccgggagcttgtatatccattttcggatctgatcagcacg tgttgacaattaatcatcggcatagtatatcggcatagtataatacgaca aggtgaggaactaaaccatggccaagcctttgtctcaagaagaatccacc ctcattgaaagagcaacggctacaatcaacagcatccccatctctgaaga ctacagcgtcgccagcgcagctctctctagcgacggccgcatcttcactg gtgtcaatgtatatcattttactgggggaccttgtgcagaactcgtggtg ctgggcactgctgctgctgcggcagctggcaacctgacttgtatcgtcgc gatcggaaatgagaacaggggcatcttgagcccctgcggacggtgtcgac aggtgcttctcgatctgcatcctgggatcaaagcgatagtgaaggacagt gatggacagccgacggcagttgggattcgtgaattgctgccctctggtta tgtgtgggagggctaagcacttcgtggccgaggagcaggactgacacgtg ctacgagatttcgattccaccgccgccttctatgaaaggttgggcttcgg aatcgttttccgggacgccggctggatgatcctccagcgcggggatctca tgctggagttcttcgcccaccccaacttgtttattgcagcttataatggt tacaaataccgtcgacctctagctagagcttggcgtaatcatggtcatag ctgtttcctgtgtgaaattgttatccgctcacaattccacacaacatacg -continued agccggaagcataaagtgtaaagcctggggtgcctaatgagtgagctaac tcacattaattgcgttgcgctcactgcccgctttccagtcgggaaacctg tcgtgccagctgcattaatgaatcggccaacgcgcggggagaggcggttt gcgtattgggcgctcttccgcttcctcgctcactgactcgctgcgctcgg tcgttcggctgcggcgagcggtatcagctcactcaaaggcggtaatacgg ttatccacagaatcaggggataacgcaggaaagaacatgtgagcaaaagg ccagcaaaaggccaggaaccgtaaaaaggccgcgttgctggcgtttttcc ataggctccgcccccctgacgagcatcacaaaaatcgacgctcaagtcag aggtggcgaaacccgacaggactataaagataccaggcgtttccccctgg aagctccctcgtgcgctctcctgttccgaccctgccgcttaccggatacc tgtccgcctttctcccttcgggaagcgtggcgctttctcaatgctcacgc -continued gttgctcttgcccggcgtcaatacgggataataccgcgccacatagcaga actttaaaagtgctcatcattggaaaacgttcttcggggcgaaaactctc aaggatcttaccgctgttgagatccagttcgatgtaacccactcgtgcac ccaactgatcttcagcatcttttactttcaccagcgtttctgggtgagca aaaacaggaaggcaaaatgccgcaaaaaagggaataagggcgaeacggaa atgttgaatactcatactcttcctttttc A vector encoding a truncated human EphB4 protein having the normal leader sequence followed by the Cys-rich and two FNIII domains (CF2) was prepared by deleting the globular domain. Overlap PCR was performed with oligonucleotides designed to delete G:

```
Fragment 1: 5'-primer - 5SpeB4 TACTAGTCCGCCATGGAGCTCCGGGTGCTGCT   (SEQ ID NO: 414)
            3'-primer - 3RevB4 CAGCTGagtttccaattttgtgttc          (SEQ ID NO: 415)

Fragment 2: 5overB4 - gaacacaaaattggaaactCAGCTGACTGTGAACCTGAC     (SEQ ID NO: 416)
            3NotB4GCF2 - GCGGCCGCCCTGCTCCCGCCAGCCCTCGCT           (SEQ ID NO: 417)
```

-continued tgtaggtatctcagttcggtgtaggtcgttcgctccaagctgggctgtgt gcacgaaccccccgttcagcccgaccgctgcgccttatccggtaactatc gtcttgagtccaacccggtaagacacgacttatcgccactggcagcagcc actggtaacaggattagcagagcgaggtatgtaggcggtgctacagagtt cttgaagtggtggcctaactacggctacactagaaggacagtatttggta tctgcgctctgctgaagccagttaccttcggaaaaagagttggtagctct tgatccggcaaacaaaccaccgctggtagcggtggtttttttgtttgcaa gcagcagattacgcgcagaaaaaaaggatctcaagaagatcctttgatct tttctacggggtctgacgctcagtggaacgaaaactcacgttaagggatt ttggtcatgagattatcaaaaaggatcttcacctagatccttttaaatta aaaatgaagttttaaatcaatctaaagtatatatgagtaaacttggtctg acagttaccaatgcttaatcagtgaggcacctatctcagcgatctgtcta tttcgttcatccatagttgcctgactccccgtcgtgtagataactacgat acgggagggcttaccatctggccccagtgctgcaatgataccgcgagacc cacgctcaccggctccagatttatcagcaataaaccagccagccggaagg gccgagcgcagaagtggtcctgcaactttatccgcctccatccagtctat taattgttgccgggaagctagagtaagtagttcgccagttaatagtttgc gcaacgttgttgccattgctacaggcatcgtggtgtcacgctcgtcgttt ggtatggcttcattcagctccggttcccaacgatcaaggcgagttacatg atcccccatgttgtgcaaaaaagcggttagctccttcggtcctccgatcg ttgtcagaagtaagttggccgcagtgttatcactcatggttatggcagca ctgcataattctcttactgtcatgccatccgtaagatgcttttctgtgac tggtgagtactcaaccaagtcattctgagaatagtgtatgcggcgaccga (adds NotI site after the C-terminal B4EC FL sequence after 2nd fibronectin repeat to allow in-frame fusion to V5 and His-tag in pEF6). TA clone into pEF6, then cut with NotI, gel-purify and self ligate.

Sequence of the cloned fragment (SpeI-NotI fragment is shown below (SEQ ID NO: 418):

tactagtccgccATGGAGCTCCGGGTGCTGCTCTGCTGGGCTTCGTTGGC

CGCAGCTTTGGAAGAGACCCTGCTGAACACAAAATTGGAAACTCAGCTGA

CTGTGAACCTGACTCGATTCCCGGAGACTGTGCCTCGGGAGCTGGTTGTG

CCCGTGGCCGGTAGCTGCGTGGTGGATGCCGTCCCCGCCCCTGGCCCCAG

CCCCAGCCTCTACTGCCGTGAGGATGGCCAGTGGGCCGAACAGCCGGTCA

CGGGCTGCAGCTGTGCTCCGGGGTTCGAGGCAGCTGAGGGGAACACCAAG

TGCCGAGCCTGTGCCCAGGGCACCTTCAAGCCCCTGTCAGGAGAAGGGTC

CTGCCAGCCATGCCCAGCCAATAGCCACTCTAACACCATTGGATCAGCCG

TCTGCCAGTGCCGCGTCGGGTACTTCCGGGCACGCACAGACCCCCGGGGT

GCACCCTGCACCACCCCTCCTTCGGCTCCGCGGAGCGTGGTTTCCCGCCT

GAACGGCTCCTCCCTGCACCTGGAATGGAGTGCCCCCCTGGAGTCTGGTG

GCCGAGAGGACCTCACCTACGCCCTCCGCTGCCGGGAGTGCCGACCCGGA

GGCTCCTGTGCGCCCTGCGGGGGAGACCTGACTTTTGACCCCGGCCCCCG

GGACCTGGTGGAGCCCTGGGTGGTGGTTCGAGGGCTACGTCCGGACTTCA

CCTATACCTTTGAGGTCACTGCATTGAACGGGGTATCCTCCTTAGCCACG

GGGCCCGTCCCATTTGAGCCTGTCAATGTCACCACTGACCGAGAGGTACC

TCCTGCAGTGTCTGACATCCGGGTGACGCGGTCCTCACCCAGCAGCTTGA

GCCTGGCCTGGGCTGTTCCCCGGGCACCCAGTGGGGCGTGGCTGGACTAC

GAGGTCAAATACCATGAGAAGGGCGCCGAGGGTCCCAGCAGCGTGCGGTT

-continued

CCTGAAGACGTCAGAAAACCGGGCAGAGCTGCGGGGGCTGAAGCGGGGAG

CCAGCTACCTGGTGCAGGTACGGGCGCGCTCTGAGGCCGGCTACGGGCCC

TTCGGCCAGGAACATCACAGCCAGACCCAACTGGATGAGAGCGAGGGCTG

GCGGGAGCAGGgcggccgc

CF2, precursor is shown below (SEQ ID NO: 419):

MELRVLLCWASLAAALEETLLNTKLETQLT1WNLTRFPETVPRELVVPVA

GSCVVDAVPAPGPSPSLYCREDGQWAEQPVTGCSCAPGFEAAEGNTKCRA

CAQGTFKPLSGEGSCQPCPANSHSNTIGSAVCQCRVGYFRARTDPRGAPC

TTPPSAPRSVVSRLNGSSLHLEWSAPLESGGREDLTYALRCRECRPGGSC

APCGGDLTFDPGPRDLVEPWVVVRGLRPDFTYTFEVTALNGVSSLATGPV

PFEPVNVTTDREVPPAVSDIRVTRSSPSSLSLAWAVPRAPSGAWLDYEVK

YHEKGAEGPSSVRFLKTSENRAELRGLKRGASYLVQVRARSEAGYGPFGQ

EHHSQTQLDESEGWREQGGRSSLEGPRFEGKPIPNPLLGLDSTRTGHHHH

HH

Plasmid DNA sequence is shown below (SEQ ID NO: 420):

AATATTATTGAAGCATTTATCAGGGTTATTGTCTCATGAGCGGATACATA

TTTGAATGTATTTAGAAAAATAAACAAATAGGGGTTCCGCGCACATTTCC

CCGAAAAGTGCCACCTGACGTCGACGGATCGGGAGATCTCCCGATCCCCT

ATGGTCGACTCTCAGTACAATCTGCTCTGATGCCGCATAGTTAAGCCAGT

ATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCT

GCTTAGGGTTAGGCGTTTTGCGCTGCTTCGCGATGTACGGGCCAGATATA

CGCGTTGACATTGATTATTGACTAGGCTTTTGCAAAAAGCTTTGCAAAGA

TGGATAAAGTTTTAAACAGAGAGGAATCTTTGCAGCTAATGGACCTTCTA

GGTCTTGAAAGGAGTGCCTCGTGAGGCTCCGGTGCCCGTCAGTGGGCAGA

GCGCACATCGCCCACAGTCCCCGAGAAGTTGGGGGGAGGGGTCGGCAATT

GAACCGGTGCCTAGAGAAGGTGGCGCGGGGTAAACTGGGAAAGTGATGTC

GTGTACTGGCTCCGCCTTTTTCCCGAGGGTGGGGGAGAACCGTATATAAG

TGCAGTAGTCGCCGTGAACGTTCTTTTTCGCAACGGGTTTGCCGCCAGAA

CACAGGTAAGTGCCGTGTGTGGTTCCCGCGGGCCTGGCCTCTTTACGGGT

TATGGCCCTTGCGTGCCTTGAATTACTTCCACCTGGCTGCAGTACGTGAT

TCTTGATCCCGAGCTTCGGGTTGGAAGTGGGTGGGAGAGTTCGAGGCCTT

GCGCTTAAGGAGCCCCTTCGCCTCGTGCTTGAGTTGAGGCCTGGCCTGGG

CGCTGGGGCCGCCGCGTGCGAATCTGGTGGCACCTTCGCGCCTGTCTCGC

TGCTTTCGATAAGTCTCTAGCCATTTAAAATTTTTGATGACCTGCTGCGA

CGCTTTTTTTCTGGCAAGATAGTCTTGTAAATGCGGGCCAAGATCTGCAC

ACTGGTATTTCGGTTTTTGGGGCCGCGGGCGGCGACGGGGCCCGTGCGTC

CCAGCGCACATGTTCGGCGAGGCGGGGCCTGCGAGCGCGGCCACCGAGAA

-continued

TCGGACGGGGGTAGTCTCAAGCTGGCCGGCCTGCTCTGGTGCCTGGCCTC

GCGCCGCCGTGTATCGCCCCGCCCTGGGCGGCAAGGCTGGCCCGGTCGGC

ACCAGTTGCGTGAGCGGAAAGATGGCCGCTTCCCGGCCCTGCTGCAGGGA

GCTCAAAATGGAGGACGCGGCGCTCGGGAGAGCGGGCGGGTGAGTCACCC

ACACAAAGGAAAAGGGCCTTTCCGTCCTCAGCCGTCGCTTCATGTGACTC

CACGGAGTACCGGGCGCCGTCCAGGCACCTCGATTAGTTCTCGAGCTTTT

GGAGTACGTCGTCTTTAGGTTGGGGGGAGGGGTTTTATGCGATGGAGTTT

CCCCACACTGAGTGGGTGGAGACTGAAGTTAGGCCAGCTTGGCACTTGAT

GTAATTCTCCTTGGAATTTGCCCTTTTTGAGTTTGGATCTTGGTTCATTC

TCAAGCCTCAGACAGTGGTTCAAAGTTTTTTTCTTCCATTTCAGGTGTCG

TGAGGAATTAGCTTGGTACTAATACGACTCACTATAGGGAGACCCAAGCT

GGCTAGGTAAGCTTGGTACCGAGCTCGGATCCACTAGTCCAGTGTGGTGG

AATTGCCCTTtactagtccgccATGGAGCTCCGGGTGCTGCTCTGCTGGG

CTTCGTTGGCCGCAGCTTTGGAAGAGACCCTGCTGAACACAAAATTGGAA

ACTCAGCTGACTGTGAACCTGACTCGATTCCCGGAGACTGTGCCTCGGGA

GCTGGTTGTGCCCGTGGCCGGTAGCTGCGTGGTGGATGCCGTCCCCGCCC

CTGGCCCCAGCCCCAGCCTCTACTGCCGTGAGGATGGCCAGTGGGCCGAA

CAGCCGGTCACGGGCTGCAGCTGTGCTCCGGGGTTCGAGGCAGCTGAGGG

GAACACCAAGTGCCGAGCCTGTGCCCAGGGCACCTTCAAGCCCCTGTCAG

GAGAAGGGTCCTGCCAGCCATGCCCAGCCAATAGCCACTCTAACACCATT

GGATCAGCCGTCTGCCAGTGCCGCGTCGGGTACTTCCGGGCACGCACAGA

CCCCCGGGGTGCACCCTGCACCACCCCTCCTTCGGCTCCGCGGAGCGTGG

TTTCCCGCCTGAACGGCTCCTCCCTGCACCTGGAATGGAGTGCCCCCCTG

GAGTCTGGTGGCCGAGAGGACCTCACCTACGCCCTCCGCTGCCGGGAGTG

TCGACCCGGAGGCTCCTGTGCGCCCTGCGGGGGAGACCTGACTTTTGACC

CCGGCCCCCGGGACCTGGTGGAGCCCTGGGTGGTGGTTCGAGGGCTACGT

CCTGACTTCACCTATACCTTTGAGGTCACTGCATTGAACGGGGTATCCTC

CTTAGCCACGGGGCCCGTCCCATTTGAGCCTGTCAATGTCACCACTGACC

GAGAGGTACCTCCTGCAGTGTCTGACATCCGGGTGACGCGGTCCTCACCC

AGCAGCTTGAGCCTGGCCTGGGCTGTTCCCCGGGCACCCAGTGGGGCTGT

GCTGGACTACGAGGTCAAATACCATGAGAAGGGCGCCGAGGGTCCCAGCA

GCGTGCGGTTCCTGAAGACGTCAGAAAACCGGGCAGAGCTGCGGGGGCTG

AAGCGGGGAGCCAGCTACCTGGTGCAGGTACGGGCGCGCTCTGAGGCCGG

CTACGGGCCCTTCGGCCAGGAACATCACAGCCAGACCCAACTGGATGAGA

GCGAGGGCTGGCGGGAGCAGGgcggccgcTCGAGTCTAGAGGGCCCGCGG

TTCGAAGGTAAGCCTATCCCTAACCCTCTCCTCGGTCTCGATTCTACGCG

TACCGGTCATCATCACCATCACCATTGAGTTTAAACCCGCTGATCAGCCT

CGACTGTGCCTTCTAGTTGCCAGCCATCTGTTGTTTGCCCCTCCCCCGTG

CCTTCCTTGACCCTGGAAGGTGCCACTCCCACTGTCCTTTCCTAATAAAA

TGAGGAAATTGCATCGCATTGTCTGAGTAGGTGTCATTCTATTCTGGGGG

GTGGGGTGGGGCAGGACAGCAAGGGGGAGGATTGGGAAGACAATAGCAGG

-continued

CATGCTGGGGATGCGGTGGGCTCTATGGCTTCTGAGGCGGAAAGAACCAG
CTGGGGCTCTAGGGGGTATCCCCACGCGCCCTGTAGCGGCGCATTAAGCG
CGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGC
CGGCTTFITCCCCGTCAAGCTCTAAATCGGGGCATCCCTTTAGGGTTCCG
ATTTAGTGCTTTACGGCACCTCGACCCCAAAAAACTTGATTAGGGTGATG
GTTCACGTAGTGGGCCATCGCCCTGATAGACGGTTTTTCGCCCTTTGACG
TTGGAGTCCACGTTCTTTAATAGTGGACTCTTGTTCCAAACTGGAACAAC
ACTCAACCCTATCTCGGTCTATTCTTTTGATTTATAAGGGATTTTGGGGA
TTTCGGCCTATTGGTTAAAAAATGAGCTGATTTAACAAAAATTTAACGCG
AATTAATTCTGTGGAATGTGTGTCAGTTAGGGTGTGGAAAGTCCCCAGGC
TCCCCAGGCAGGCAGAAGTATGCAAAGCATGCATCTCAATTAGTCAGCAA
CCAGGTGTGGAAAGTCCCCAGGCTCCCCAGCAGGCAGAAGTATGCAAAGC
ATGCATCTCAATTAGTCAGCAACCATAGTCCCGCCCCTAACTCCGCCCAT
CCCGCCCCTAACTCCGCCCAGTTCCGCCCATTCTCCGCCCCATGGCTGAC
TAATTTTTTTTATTTATGCAGAGGCCGAGGCCGCCTCTGCCTCTGAGCTA
TTCCAGAAGTAGTGAGGAGGCTTTTTTGGAGGCCTAGGCTTTTGCAAAAA
GCTCCCGGGAGCTTGTATATCCATTTTCGGATCTGATCAGCACGTGTTGA
CAATTAATCATCGGCATAGTATATCGGCATAGTATAATACGACAAGGTGA
GGAACTAAACCATGGCCAAGCCTTTGTCTCAAGAAGAATCCACCCTCATT
GAAAGAGCAACGGCTACAATCAACAGCATCCCCATCTCTGAAGACTACAG
CGTCGCCAGCGCAGCTCTCTCTAGCGACGGCCGCATCTTCACTGGTGTCA
ATGTATATCATTTTACTGGGGGACCTTGTGCAGAACTCGTGGTGCTGGGC
ACTGCTGCTGCTGCGGCAGCTGGCAACCTGACTTGTATCGTCGCGATCGG
AAATGAGAACAGGGGCATCTTGAGCCCCTGCGGACGGTGTCGACAGGTGC
TTCTCGATCTGCATCCTGGGATCAAAGCGATAGTGAAGGACAGTGATGGA
CAGCCGACGGCAGTTGGGATTCGTGAATTGCTGCCCTCTGGTTATGTGTG
GGAGGGCTAAGCACTTCGTGGCCGAGGAGCAGGACTGACACGTGCTACGA
GATTTCGATTCCACCGCCGCCTTCTATGAAAGGTTGGGCTTCGGAATCGT
TTTCCGGGACGCCGGCTGGATGATCCTCCAGCGCGGGGATCTCATGCTGG
AGTTCTTCGCCCACCCCAACTTGTTTATTGCAGCTTATAATGGTTACAAA
TAAAGCAATAGCATCACAAATTTCACAAATAAAGCATTTTTTTCACTGCA
TTCTAGTTGTGGTTTGTCCAAACTCATCAATGTATCTTATCATGTCTGTA
TACCGTCGACCTCTAGCTAGAGCTTGGCGTAATCATGGTCATAGCTGTTT
CCTGTGTGAAATTGTTATCCGCTCACAATTCCACACAACATACGAGCCGG
AAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGC
CAGCTGCATTAATGAATCGGCCAACGCGCGGGGAGAGGCGGTTTGCGTAT
TGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCC

-continued

ACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGC
TCCGCCCCCCTGACGAGCATCACAAAAATCGACGCTCAAGTCAGAGGTGG
CGAAACCCGACAGGACTATAAAGATACCAGGCGTTTCCCCCTGGAAGCTC
CCTCGTGCGCTCTCCTGTTCCGACCCTGCCGCTTACCGGATACCTGTCCG
CCTTTCTCCCTTCGGGAAGCGTGGCGCTTTCTCAATGCTCACGCTGTAGG
TATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTG
AGTCCAACCCGGTAAGACACGACTTATCGCCACTGGCAGCAGCCACTGGT
AACAGGATTAGCAGAGCGAGGTATGTAGGCGGTGCTACAGAGTTCTTGAA
GTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCA
GATTACGCGCAGAAAAAAAGGATCTCAAGAAGATCCTTTGATCTTTTCTA
CGGGGTCTGACGCTCAGTGGAACGAAAACTCACGTTAAGGGATTTTGGTC
ATGAGATTATCAAAAAGGATCTTCACCTAGATCCTTTTAAATTAAAAATG
AAGTTTTAAATCAATCTAAAGTATATATGAGTAAACTTGGTCTGACAGTT
ACCAATGCTTAATCAGTGAGGCACCTATCTCAGCGATCTGTCTATTTCGT
TCATCCATAGTTGCCTGACTCCCCGTCGTGTAGATAACTACGATACGGGA
GGGCTTACCATCTGGCCCCAGTGCTGCAATGATACCGCGAGACCCACGCT
CACCGGCTCCAGATTTATCAGCAATAAACCAGCCAGCCGGAAGGGCCGAG
CGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATG
GCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCAT
AATTCTCTTACTGTCATGCCATCCGTAAGATGCTTTTCTGTGACTGGTGA
GTACTCAACCAAGTCATTCTGAGAATAGTGTATGCGGCGACCGAGTTGCT
CTTGCCCGGCGTCAATACGGGATAATACCGCGCCACATAGCAGAACTTTA
AAAGTGCTCATCATTGGAAAACGTTCTTCGGGGCGAAAACTCTCAAGGAT
CTTACCGCTGTTGAGATCCAGTTCGATGTAACCCACTCGTGCACCCAACT
GATCTTCAGCATCTTTTACTTTCACCAGCGTTTCTGGGTGAGCAAAAACA
GGAAGGCAAAATGCCGCAAAAAAGGGAATAAGGGCGACACGGAAATGTTG
AATACTCATACTCTTCCTTTTTC

A vector encoding a preferred GCF2 truncated protein, lacking any c-terminal tags, such as a hexahistidine tag was derived from pEF6-B4ECv3-V5-His by re-amplifying the 3' (C-terminal) part of B4ECv3 to eliminate V5 and His tags ands subcloning back into pEF6-B4ECv3-V5-His.

PCR primers used:

(SEQ ID NO: 421)
IntB4-3:
CATTGGATCAGCCGTCTGCC
and (SEQ ID NO: 422)
B4ECv3FIN
(tgtttaaacTTACTGCTCCCGCCAGCCCTCGCTCTCATCCAGTT).

The fragment with the correct N-terminal part of B4ECv3 was cut out from pEF6-B4ECv3-V5-His and subcloned into Kpn I-cut pEF6-Int3-B4ECv3FIN intermediate construct.

Sequence of the whole HindIII-PmeI fragment is shown below (SEQ ID NO: 423):

AAGCTTCCGCCATGGAGCTCCGGGTGCTGCTCTGCTGGGCTTCGTTGGCC
GCAGCTTTGGAAGAGACCCTGCTGAACACAAAATTGGAAACTGCTGATCT
GAAGTGGGTGACATTCCCTCAGGTGGACGGGCAGTGGGAGGAACTGAGCG
GCCTGGATGAGGAACAGCACAGCGTGCGCACCTACGAAGTGTGTGAAGTG
CAGCGTGCCCCGGGCCAGGCCCACTGGCTTCGCACAGGTTGGGTCCCACG
GCGGGGCGCCGTCCACGTGTACGCCACGCTGCGCTTCACCATGCTCGAGT
GCCTGTCCCTGCCTCGGGCTGGGCGCTCCTGCAAGGAGACCTTCACCGTC
TTCTACTATGAGAGCGATGCGGACACGGCCACGGCCCTCACGCCAGCCTG
GATGGAGAACCCCTACATCAAGGTGGACACGGTGGCCGCGGAGCATCTCA
CCCGGAAGCGCCCTGGGGCCGAGGCCACCGGGAAGGTGAATGTCAAGACG
CTGCGTCTGGGACCGCTCAGCAAGGCTGGCTTCTACCTGGCCTTCCAGGA
CCAGGGTGCCTGCATGGCCCTGCTATCCCTGCACCTCTTCTACAAAAAGT
GCGCCCAGCTGACTGTGAACCTGACTCGATTCCCGGAGACTGTGCCTCGG
GAGCTGGTTGTGCCCGTGGCCGGTAGCTGCGTGGTGGATGCCGTCCCCGC
CCCTGGCCCCAGCCCCAGCCTCTACTGCCGTGAGGATGGCCAGTGGGCCG
AACAGCCGGTCACGGGCTGCAGCTGTGCTCCGGGGTTCGAGGCAGCTGAG
GGGAACACCAAGTGCCGAGCCTGTGCCCAGGGCACCTTCAAGCCCCTGTC
AGGAGAAGGGTCCTGCCAGCCATGCCCAGCCAATAGCCACTCTAACACCA
TTGGATCAGCCGTCTGCCAGTGCCGCGTCGGGTACTTCCGGGCACGCACA
GACCCCCGGGGTGCACCCTGCACCACCCCTCCTTCGGCTCCGCGGAGCGT
GGTTTCCCGCCTGAACGGCTCCTCCCTGCACCTGGAATGGAGTGCCCCCC
TGGAGTCTGGTGGCCGAGAGGACCTCACCTACGCCCTCCGCTGCCGGGAG
TGCCGACCCGGAGGCTCCTGTGCGCCCTGCGGGGGAGACCTGACTTTTGA
CCCCGGCCCCCGGGACCTGGTGGAGCCCTGGGTGGTGGTTCGAGGGCTAC
GTCCGGACTTCACCTATACCTTTGAGGTCACTGCATTGAACGGGGTATCC
TCCTTAGCCACGGGGCCCGTCCCATTTGAGCCTGTCAATGTCACCACTGA
CCGAGAGGTACCTCCTGCAGTGTCTGACATCCGGGTGACGCGGTCCTCAC
CCAGCAGCTTGAGCCTGGCCTGGGCTGTTCCCCGGGCACCCAGTGGGGCG
TGGCTGGACTACGAGGTCAAATACCATGAGAAGGGCGCCGAGGGTCCCAG
CAGCGTGCGGTTCCTGAAGACGTCAGAAAACCGGGCAGAGCTGCGGGGGC
TGAAGCGGGGAGCCAGCTACCTGGTGCAGGTACGGGCGCGCTCTGAGGCC

-continued

GGCTACGGGCCCTTCGGCCAGGAACATCACAGCCAGACCCAACTGGATGA
GAGCGAGGGCTGGCGGGAGCAGTAAgtttaaac The precursor sequence of the preferred GCF2 protein (also referred to herein as GCF2F) is shown below (SEQ ID NO: 424):

MELRVLLCWASLAAALEETLLNTKLETADLKWVTFPQVDGQWEELSGLDE
EQHSVRTYEVCEVQRAPGQAHWLRTGWVPRRGAVHVYATLRFTMLECLSL
PRAGRSCKETFTVFYYESDADTATALTPAWMENPYIKVDTVAAEHLTRKR
PGAEATGKVNVKTLRLGPLSKAGFYLAFQDQGACMALLSLHLFYKKCAQL
TVNLTRFPETVPRELVVPVAGSCVVDAVPAPGPSPSLYCREDGQWAEQPV
TGCSCAPGFEAAEGNTKCRACAQGTFKPLSGEGSCQPCPANSHSNTIGSA
VCQCRVGYFRARTDPRGAPCTTPPSAPRSVVSRLNGSSLHLEWSAPLESG
GREDLTYALRCRECRPGGSCAPCGGDLTFDPGPRDLVEPWVVVRGLRPDF
TYTFEVTALNGVSSLATGPVPFEPVNVTTDREVPPAVSDIRVTRSSPSSL
SLAWAVPRAPSGAWLDYEVKYHEKGAEGPSSVRFLKTSENRAELRGLKRG
ASYLVQVRARSEAGYGPFGQEHHSQTQLDESEGWREQ

The processed sequence is shown below (SEQ ID NO: 425):

LEETLLNTKLETADLKWVTFPQVDGQWEELSGLDEEQHSVRTYEVCEVQR
APGQAHWLRTGWVPRRGAVHVYATLRFTMLECLSLPRAGRSCKETFTVFY
YESDADTATALTPAWMENPYIKVDTVAAEHLTRKRPGAEATGKVNVKTLR
LGPLSKAGFYLAFQDQGACMALLSLHLFYKKCAQLTVNLTRFPETVPREL
VVPVAGSCVVDAVPAPGPSPSLYCREDGQWAEQPVTGCSCAPGFEAAEGN
TKCRACAQGTFKPLSGEGSCQPCPANSHSNTIGSAVCQCRVGYFRARTDP
RGAPCTTPPSAPRSVVSRLNGSSLHLEWSAPLESGGREDLTYALRCRECR
PGGSCAPCGGDLTFDPGPRDLVEPWVVVRGLRPDFTYTFEVTALNGVSSL
ATGPVPFEPVNVTTDREVPPAVSDIRVTRSSPSSLSLAWAVPRAPSGAWL
DYEVKYHEKGAEGPSSVRFLKTSENRAELRGLKRGASYLVQVRARSEAGY
GPFGQEHHSQTQLDESEGWREQ

2) Mammalian Cell Culture and Transfections

HEK293T (human embryonic kidney line) cells were maintained in DMEM with 10% dialyzed fetal calf serum and 1% penicillin/streptomycin/neomycin antibiotics. Cells were maintained at 37° C. in a humidified atmosphere of 5% $CO_2$/95% air. Transfections were performed using Lipofectamine 2000 reagent (Invitrogen) according to the manufacturer's protocol. One day before transfections, 293T cells were seeded at a high density to reach 80% confluence at the time of transfection. Plasmid DNA and Lipofectamine reagent at 1:3 ratio were diluted in Opti-MEM I reduced serum medium (Invitrogen) for 5 min and mixed together to form DNA: Lipofectamine complex. For each 10 cm culture dish, 10 μg of plasmid DNA was used. After 20 min, above complex was added directly to cells in culture medium. After 16 hours of transfection, medium was aspirated, washed once with serum free DMEM and replaced with serum free DMEM. Secreted proteins were harvested after 48 hours by collecting conditional medium. Conditional medium was clarified by centrifugation at 10,000 g for 20 min, filtered through 0.2 μm filter and used for purification.

3) Generating Stable Cell Lines

To create stable cell lines producing EphB4ECv3 and EphB4ECnt HEK293 or HEK293T cells were transfected with either pEF6-B4ECv3 or pEF6-B4EC-NT plasmid constructs as described above and selected using antibiotic Blasticidin. After 24 hours of transfection, cells were seeded at low density. Next day, cells were treated with 10 μg/ml of Blasticidin. After two weeks of drug selection, surviving cells were pooled and selected further for single cell clone expansion. After establishing stable cells, they were maintained at 4 μg/ml Blasticidin. Conditioned media were tested to confirm expression and secretion of the respective recombinant proteins. Specificity of expression was confirmed by Western blot with anti-B4 mono- or polyclonal ABs and B2EC-AP reagent binding and competition assays.

4) Protein Purification

HEK293 cells were transiently transfected with a plasmid encoding secreted form of EphB4ectodomain (B4ECv3). Conditional media was harvested and supplemented with 10 mM imidazole, 0.3 M NaCl and centrifuged at 20,000 g for 30 min to remove cell debris and insoluble particles. 80 ml of obtained supernatant were applied onto the pre-equilibrated column with 1 ml of Ni-NTA-agarose (Qiagen) at the flow rate of 10 ml/h. After washing the column with 10 ml of 50 mM Tris-HCl, 0.3 M NaCl and 10 mM imidazole, pH 8, remaining proteins were eluted with 3 ml of 0.25 M imidazole. Eluted proteins were dialyzed against 20 mM Tris-HCl, 0.15 M NaCl, pH 8 overnight. Purity and identity of B4ECv3 was verified by PAGE/Coomassie G-250 and Western blot with anti-Eph.B4 antibody. Finally, the concentration of B4ECv3 was measured, and the protein was aliquoted and stored at −70° C.

B4EC-FC protein and B2EC-FC protein were similarly purified.

5) Biochemical Assays

A. Binding Assay

10 μl of Ni-NTA-Agarose were incubated in microcentrifuge tubes with 50 μl of indicated amount of B4ECv3 diluted in binding buffer BB (20 mM Tris-HCl, 0.15 M NaCl, 0.1% bovine serum albumin pH 8) After incubation for 30 min on shaking platform, Ni-NTA beads were washed twice with 1.4 ml of BB, followed by application of 50 μl of B2-AP in the final concentration of 50 nM. Binding was performed for 30 min on shaking platform, and then tubes were centrifuged and washed one time with 1.4 ml of BB. Amount of precipitated AP was measured colorimetrically after application of PNPP.

B. Inhibition Assay

Inhibition in solution. Different amounts of B4ECv3 diluted in 50 μl of BB were pre-incubated with 50 μl of 5 nM B2EC-AP reagent (protein fusion of Ephrin B2 ectodomain with placental alkaline phosphatase). After incubation for 1 h, unbound B2EC-AP was precipitated with 5,000 HEK293 cells expressing membrane-associated full-length EphB4 for 20 min. Binding reaction was stopped by dilution with 1.2 ml of BB, followed by centrifugation for 10 min. Supernatants were discarded and alkaline phosphatase activities associated with collected cells were measured by adding para-nitrophenyl phosphate (PNPP) substrate.

Cell based inhibition. B4ECv3 was serially diluted in 20 mM Tris-HCl, 0.15 M NaCl, 0.1% BSA, pH 8 and mixed with 5,000 HEK293 cells expressing membrane-associated full-length Ephrin B2. After incubation for 1 h, 50 μl of 5 nM B4EC-AP reagent (protein fusion of EphB4 ectodomain with placental alkaline phosphatase were added into each tube for 30 min to detect unoccupied Ephrin B2 binding sites. Binding reactions were stopped by dilution with 1.2 ml of BB and centrifugation. Colorimetric reaction of cell-precipitated AP was developed with PNPP substrate.

C. B4EC-FC Binding Assay

Figure 6:
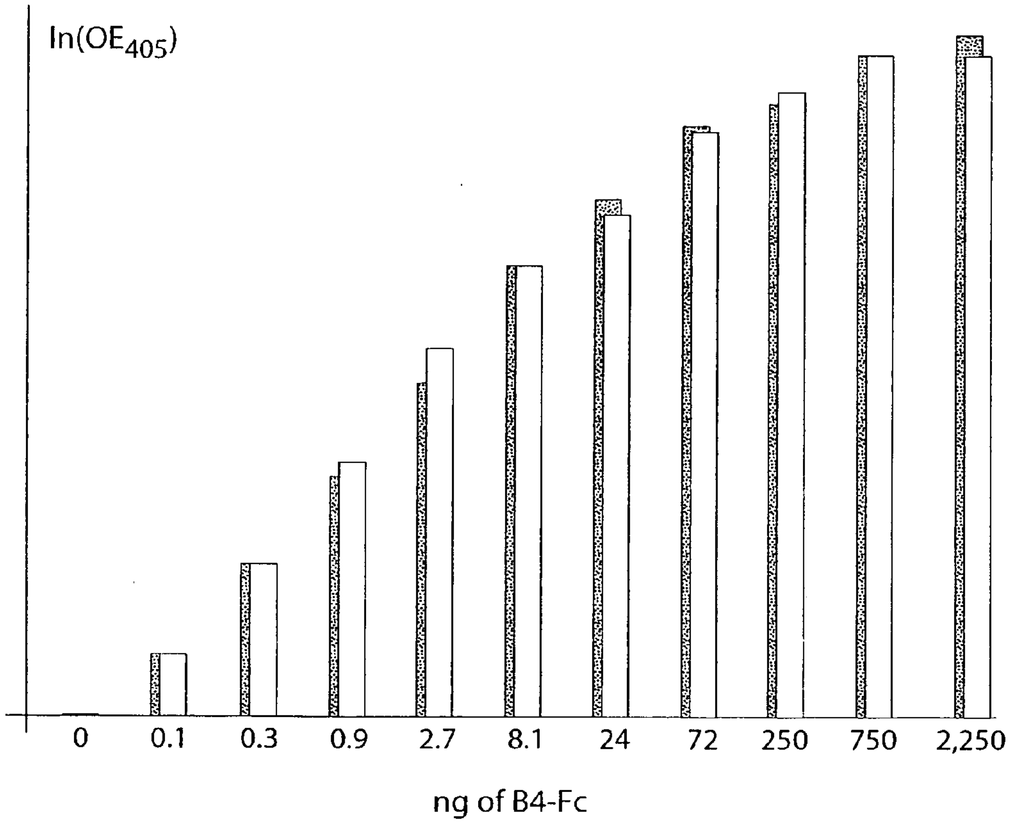
FIG. 6 shows B4EC-FC binding assay (Protein A-agarose based).

Protein A-agarose based assay. 10 μl of Protein A-agarose were incubated in Eppendorf tubes with 50 μl of indicated amount of B4EC-FC diluted in binding buffer BB (20 mM Tris-HCl, 0.15 M NaCl, 0.1% BSA pH 8). After incubation for 30 min on shaking platform, Protein AAagarose beads were washed twice with 1.4 ml of BB, followed by application of 50 μl of B2ECAP reagent at the final concentration of 50 nM. Binding was performed for 30 min on shaking platform, and then tubes were centrifuged and washed once with 1.4 ml of BB. Colorimetric reaction of precipitated AP was measured after application of PNPP (FIG. 6).

Nitrocellulose based assay. B4EC-FC was serially diluted in 20 mM Tris-HCl, 0.15 M NaCl, 50 μg/ml BSA, pH 8. 2 μl of each fraction were applied onto nitrocellulose strip and spots were dried out for 3 min. Nitrocellulose strip was blocked with 5% non-fat milk for 30 min, followed by incubation with 5 nM B2EC-AP reagent. After 45 min incubation for binding, nitrocellulose was washed twice with 20 mM Tris-HCl, 0.15 M NaCl, 50 μg/ml BSA, pH 8 and color was developed by application of alkaline phosphatase substrate Sigma Fast (Sigma).

D. B4EC-FC Inhibition Assay

Inhibition in solution. See above, for B4ECv3. The results were shown in FIG. 7.

Cell based inhibition. See above, for B4ECv3.

E. B2EC-FC Binding Assay

Protein-A-agarose based assay. See above, for B4EC-FC. The results were shown in FIG. 8.

Nitrocellulose based assay. See above, for B4EC-FC.

6) Cell-Based Assays

A. Growth Inhibition Assay

Human umbilical cord vein endothelial cells (HUVEC) ($1.5\times10^3$) are plated in a 96-well plate in 100 μl of EBM-2 (Clonetic # CC3162). After 24 hours (day 0), the test recombinant protein (100 μl) is added to each well at 2× the desired concentration (5-7 concentration levels) in EBM-2 medium. On day 0, one plate is stained with 0.5% crystal violet in 20% methanol for 10 minutes, rinsed with water, and air-dried. The remaining plates are incubated for 72 h at 37° C. After 72 h, plates are stained with 0.5% crystal violet in 20% methanol, rinsed with water and airdried. The stain is eluted with 1:1 solution of ethanol: 0.1 M sodium citrate (including day 0 plate), and absorbance is measured at 540 nm with an ELISA reader (Dynatech Laboratories). Day 0 absorbance is subtracted from the 72 h plates and data is plotted as percentage of control proliferation (vehicle treated cells). IC50 (drug concentration causing 50% inhibition) is calculated from the plotted data.

B. Cord Formation Assay (Endothelial Cell Tube Formation Assay)

Matrigel (60 μl of 10 mg/ml; Collaborative Lab # 35423) is placed in each well of an ice-cold 96-well plate. The plate is allowed to sit at room temperature for 15 minutes then incubated at 37° C. for 30 minutes to permit the matrigel to polymerize. In the mean time, HUVECs are prepared in EGM-2 (Clonetic # CC3162) at a concentration of $2\times10^5$ cells/ml. The test compound is prepared at 2× the desired concentration (5 concentration levels) in the same medium. Cells (500 μl) and 2× drug (500 μl) is mixed and 200 μl of this suspension are placed in duplicate on the polymerized matrigel. After 24 h incubation, triplicate pictures are taken for each concentration using a Bioquant Image Analysis system.

Drug effect (IC50) is assessed compared to untreated controls by measuring the length of cords formed and number of junctions.

C. Cell Migration Assay

Migration is assessed using the 48-well Boyden chamber and 8 μm pore size collagen-coated (10 μg/ml rat tail collagen; Collaborative Laboratories) polycarbonate filters (Osmonics, Inc.). The bottom chamber wells receive 27-29 μl of DMEM medium alone (baseline) or medium containing chemo-attractant (bFGF, VEGF or Swiss 3T3 cell conditioned medium). The top chambers receive 45 μl of HUVEC cell suspension ($1\times10^6$ cells/ml) prepared in DMEM+1% BSA with or without test compound. After 5 h incubation at 37° C., the membrane is rinsed in PBS, fixed and stained in Diff-Quick solutions. The filter is placed on a glass slide with the migrated cells facing down and cells on top are removed using a Kimwipe. The testing is performed in 4-6 replicates and five fields are counted from each well. Negative unstimulated control values are subtracted from stimulated control and drug treated values and data is plotted as mean migrated cell ±S.D. IC50 is calculated from the plotted data.

Example 2

Extracellular Domain Fragments of EphB4 Receptor Inhibit Angiogenesis and Tumor Growth A. Globular Domain of EphB4 is Required for EphrinB2 Binding and for the Activity of EphB4-Derived Soluble Proteins in Endothelial Tube Formation Assay.

To identify subdomain(s) of the ectopic part of EphB4 necessary and sufficient for the anti-angiogenic activity of the soluble recombinant derivatives of the receptor, four recombinant deletion variants of EphB4EC were produced and tested (FIG. 16). Extracellular part of EphB4, similarly to the other members of EphB and EphA receptor family, contains N-terminal ligand-binding globular domain followed by cysteine-rich domain and two fibronectin type III repeats (FNIII). In addition to the recombinant B4-GCF2 protein containing the complete ectopic part of EphB4, we constructed three deletion variants of EphB4EC containing globular domain and Cys-rich domain (B4-GC); globular, Cys-rich and the first FNIII domain (GCF1) as well as the ECD version with deleted globular domain (CF2). Our attempts to produce several versions of truncated EphB4EC protein containing the globular domain alone were not successful due to the lack of secretion of proteins expressed from all these constructs and absence of ligand binding by the intracellularly expressed recombinant proteins. In addition, a non-tagged version of B4-GCF2, called GCF2-F, containing complete extracellular domain of EphB4 with no additional fused amino acids was expressed, purified and used in some of the experiments described here.

Figure 17A:
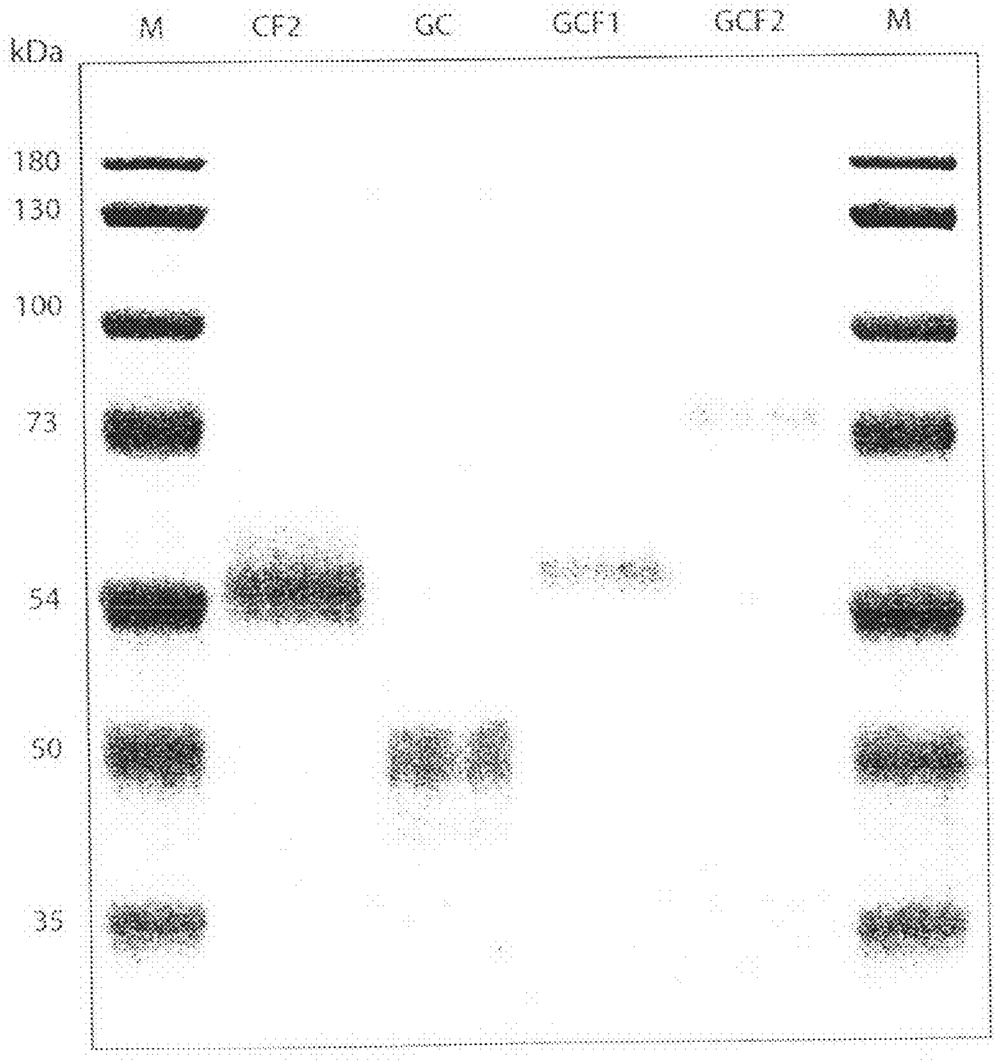
FIG. 17 shows purification and ligand binding properties of the EphB4EC proteins. A. SDS-PAAG gel electrophoresis of purified EphB4-derived recombinant soluble proteins (Coomassie-stained). B. Binding of Ephrin B2-AP fusion to EphB4-derived recombinant proteins immobilized on Ni-NTA-agarose beads. Results of three independent experiments are shown for each protein. Vertical axis—optical density at 420 nm.
Figure 17B:
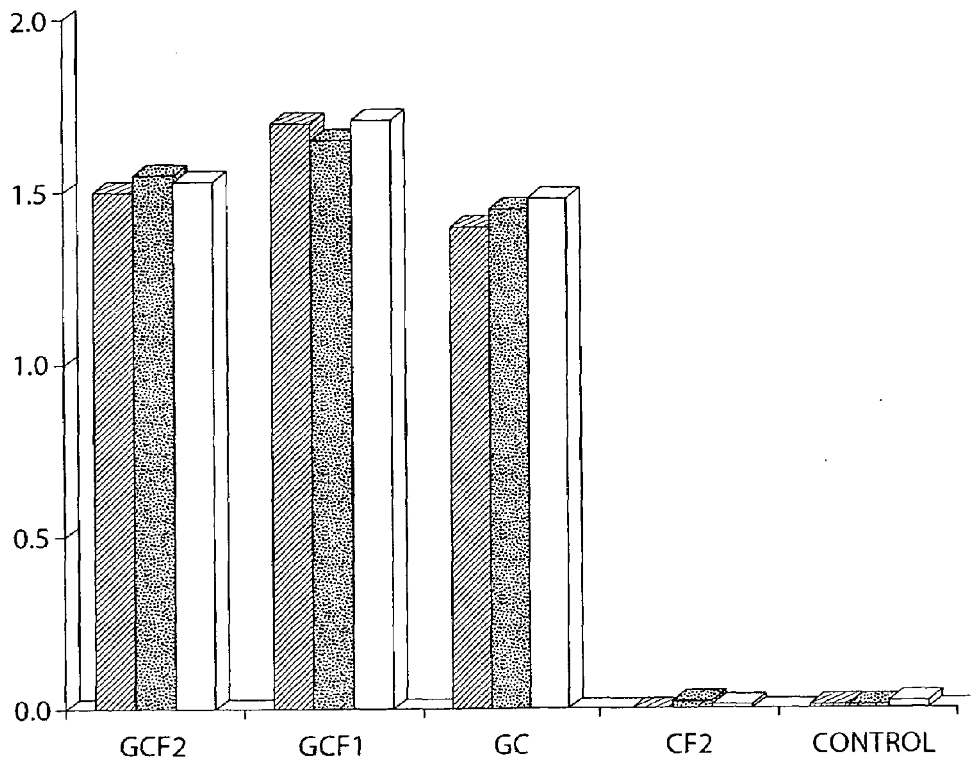

All four C-terminally 6×His tagged recombinant proteins were preparatively expressed in transiently transfected cultured mammalian cells and affinity purified to homogeneity from the conditioned growth media using chromatography on $Ni^{2+}$-chelate resin (FIG. 17). Apparently due to their glycosylation, the proteins migrate on SDS-PAAG somewhat higher than suggested by their predicted molecular weights of 34.7 kDa (GC), 41.5 (CF2), 45.6 kDa (GCF1) and 57.8 kDa (GCF2). Sequence of the extracellular domain of human EphB4 contains three predicted N-glycosylation sites (NXS/T) which are located in the Cys-rich domain, within the first fibronectin type III repeat and between the first and the second fibronectin repeats.

To confirm ability of the purified recombinant proteins to bind Ephrin B2, they were tested in an in vitro binding assay. As expected, GC, GCF1 and GCF2, but not CF2 are binding the cognate ligand Ephrin B2 as confirmed by interaction between Ephrin B2—alkaline phosphatase (Ephrin B2-AP) fusion protein with the B4 proteins immobilized on $Ni^{2+}$-resin or on nitrocellulose membrane (FIG. 17).

All four proteins were also tested for their ability to block ligand-dependent dimerization and activation of Eph B4 receptor kinase in PC3 cells. The PC3 human prostate cancer cell line is known to express elevated levels of human Eph B4. Stimulation of PC3 cells with Ephrin B2 IgG Fc fusion protein leads to a rapid induction of tyrosine phosphorylation of the receptor. However, preincubation of the ligand with GCF2, GCF1 or GC, but not CF2 proteins suppresses subsequent EphB4 autophosphorylation. Addition of the proteins alone to the PC3 cells or preincubation of the cells with the proteins followed by changing media and adding the ligand does not affect EphB4 phosphorylation status.

Further, we found that globular domain of EphB4 is required for the activity of EphB4-derived soluble proteins in endothelial tube formation assay.

B. Effects of Soluble EphB4 on HUV/AEC In Vitro.

Figure 18:
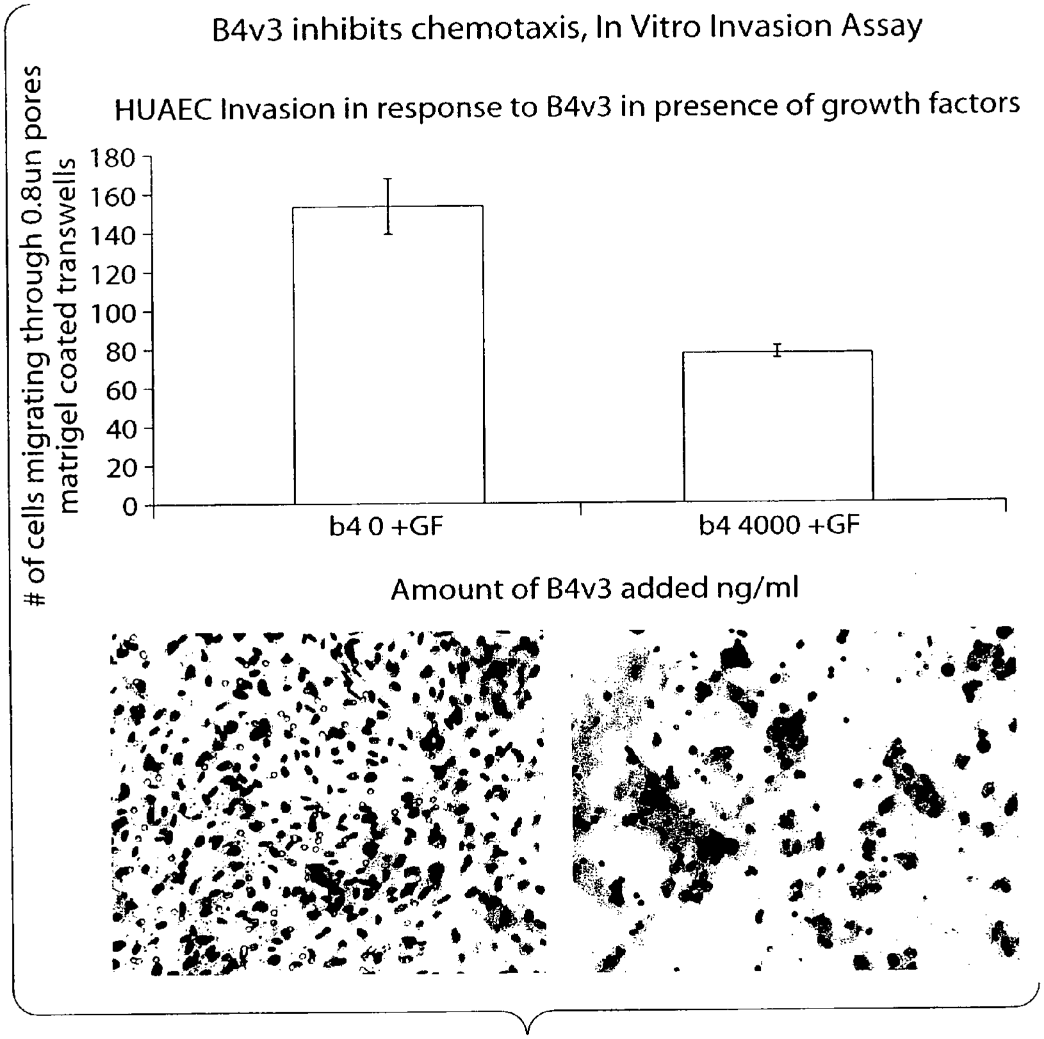
FIG. 18 shows that EphB4v3 inhibits chemotaxis.
Figure 19A:
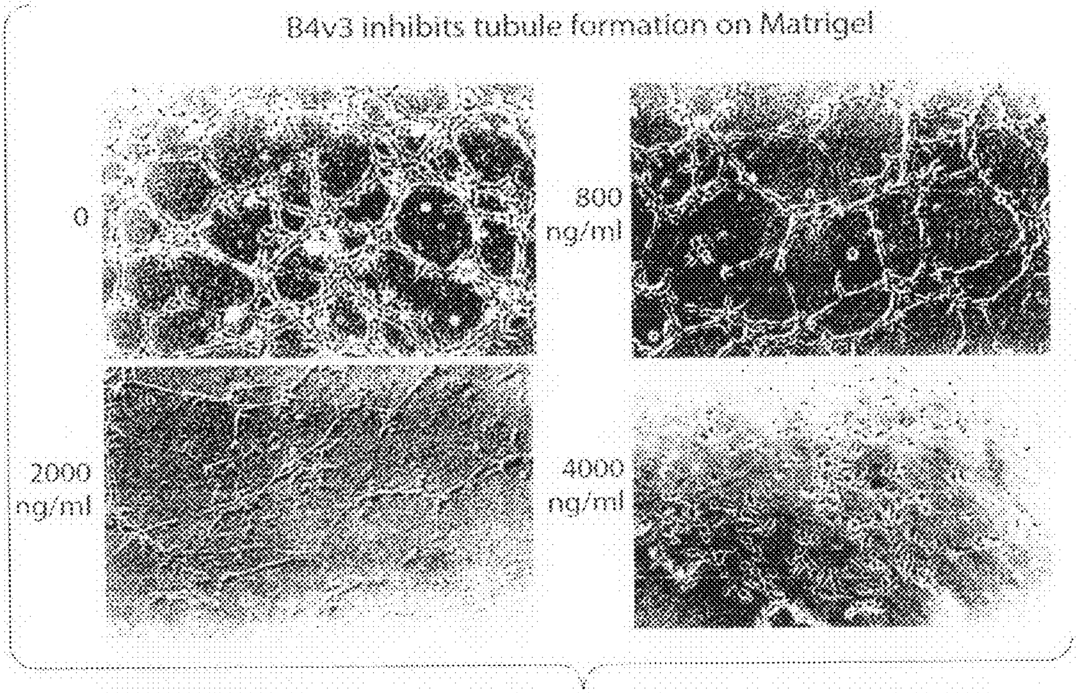
FIG. 19 shows that EphB4v3 inhibits tubule formation on Matrigel. A displays the strong inhibition of tubule formation by B4v3 in a representative experiment. B shows a quantitation of the reduction of tube-length obtained with B4v3 at increasing concentrations as well as a reduction in the number of junctions, in comparison to cells with no protein. Results are displayed as mean values ±S.D. obtained from three independent experiments performed with duplicate wells.
Figure 19B:
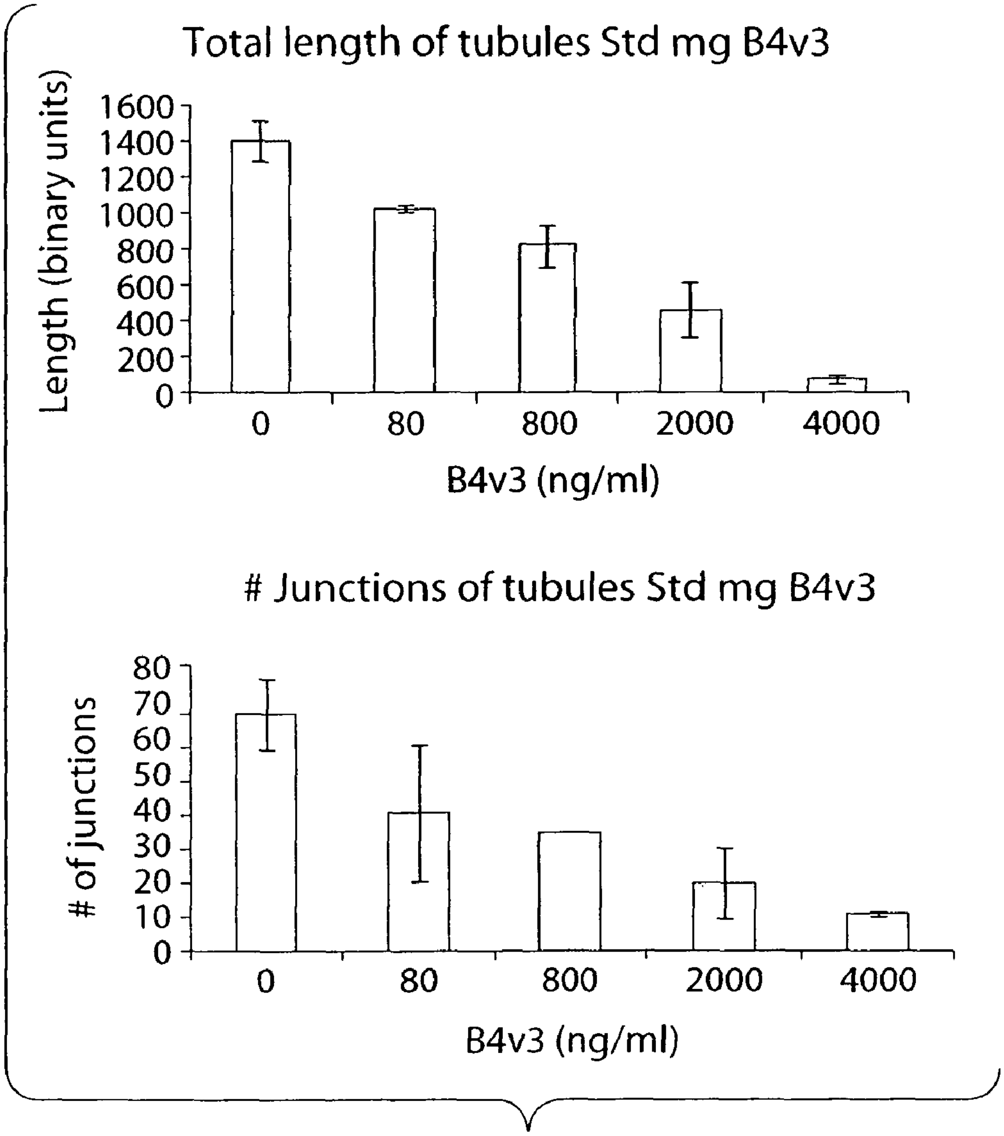
Figure 20:
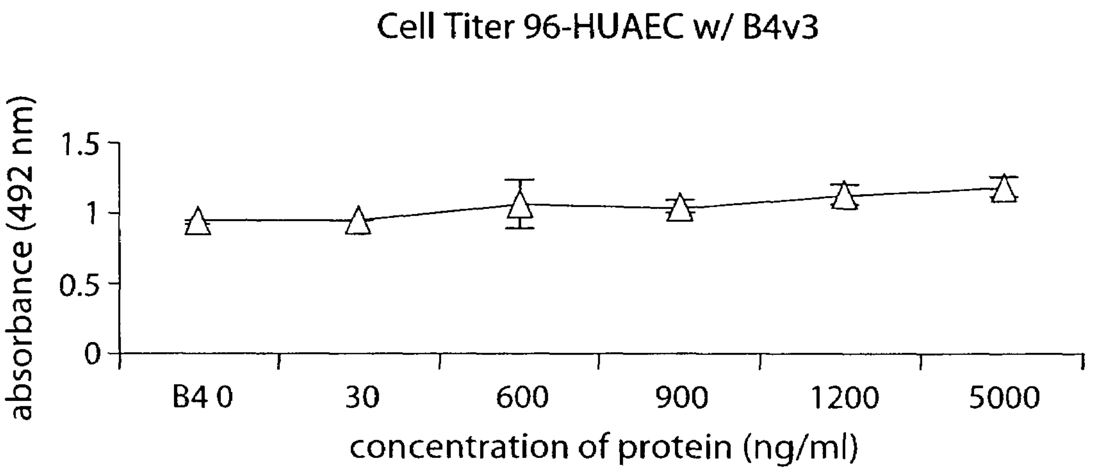
FIG. 20 shows that soluble EphB4 has no detectable cytotoxic effect as assessed by MTS assay.

Initial experiments were performed to determine whether soluble EphB4 affected the three main stages in the angiogenesis pathway. These were carried out by establishing the effects of soluble EphB4 on migration/invasion, proliferation and tubule formation by HUV/AEC in vitro. Exposure to soluble EphB4 significantly inhibited both bFGF and VEGF-induced migration in the Boyden chamber assay in a dose-dependent manner, achieving significance at nM (FIG. 18). Tubule formation by HUV/AECS on wells coated with Matrigel was significantly inhibited by soluble EphB4 in a dose-dependent manner in both the absence and presence of bFGF and VEGF (FIG. 19). We also assessed in vitro, whether nM of soluble EphB4 was cytotoxic for HUVECS. Soluble EphB4 was found to have no detectable cytotoxic effect at these doses, as assessed by MTS assay (FIG. 20).

C. Soluble EphB4 Receptor Inhibits Vascularization of Matrigel Plugs, In Vivo

Figure 21:
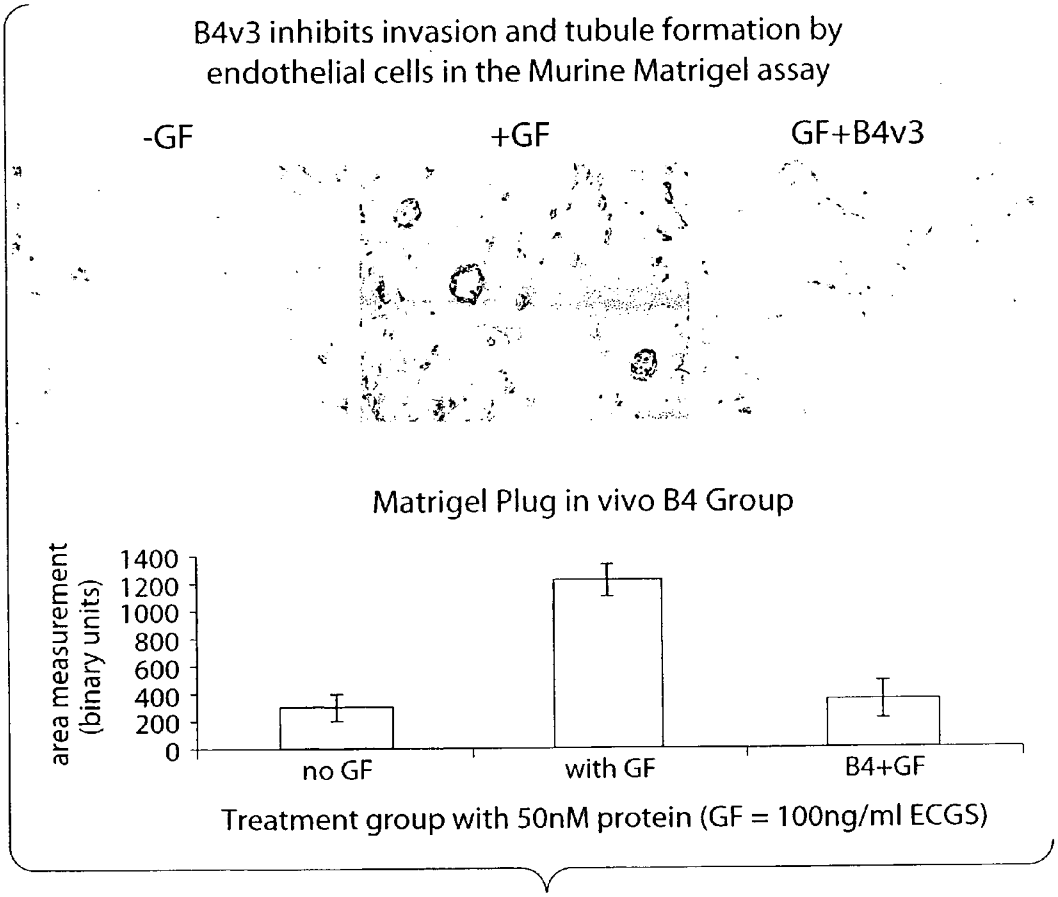
FIG. 21 shows that B4v3 inhibits invasion and tubule formation by endothelial cells in the Matrigel assay. (A) to detect total invading cells, photographed at 20× magnification or with Masson's Trichrome Top left of A B displays section of a Matrigel plug with no GF, top right of A displays section with B4IgG containing GF and lower left section contains GF, and lower right shows GF in the presence of B4v3. Significant invasion of endothelial cells is only seen in GF containing Matrigel. Top right displays an area with a high number of invaded cells induced by B4IgG, which signifies the dimeric form of B4v3. The left upper parts of the pictures correspond to the cell layers formed around the Matrigel plug from which cells invade toward the center of the plug located in the direction of the right lower corner. Total cells in sections of the Matrigel plugs were quantitated with Scion Image software. Results obtained from two experiments with duplicate plugs are displayed as mean values ±S.D.

To demonstrate that soluble EphB4 can directly inhibit angiogenesis in vivo, we performed a murine matrigel plug experiment. Matrigel supplemented with bFGF and VEGF with and without soluble EphB4 was injected s.c. into Balb/C nu/nu mice, forming semi-solid plugs, for six days. Plugs without growth factors had virtually no vascularization or vessel structures after 6 days (FIG. 21). In contrast, plugs supplemented with bFGF and VEGF had extensive vascularization and vessels throughout the plug. Plugs taken from mice treated with μg of soluble EphB4 had markedly reduced vascularization of plugs, comparable to plugs without growth factor (FIG. 21). Furthermore, histological examination of plugs showed decreased vessel staining (FIG. 21). Treatment at 0 μg/dose significantly inhibited the amount of infiltration in Matrigel plugs compared to control (FIG. 21).

Figure 22:
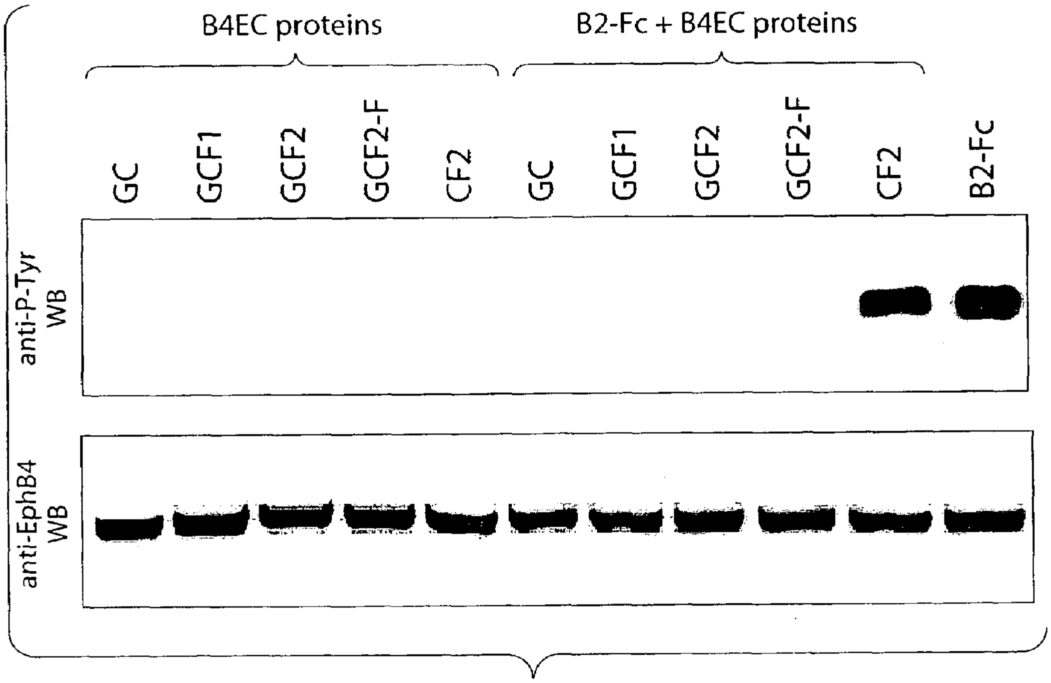
FIG. 22 shows tyrosine phosphorylation of EphB4 receptor in PC3 cells in response to stimulation with EphrinB2-Fc fusion in presence or absence of EphB4-derived recombinant soluble proteins.

We examined EphB4 receptor phosphorylation in HUVECs by performing Western blot analyses with lysates from soluble EphB4-treated cells and antibodies against phosphor-tyrosine. We found that soluble EphB4 treatment of serum-starved HUVECs stimulated a rapid and transient decrease in the level of phosphorylated EphB4, in the presence of EphrinB2Fc, EphB4 ligand dimer. Ephrin B2Fc without the soluble EphB4 protein induced phosphorylation of EphB4 receptor (FIG. 22).

D. Effects of Soluble EphB4 on Tumor Growth, In Vitro.

Figure 23A:
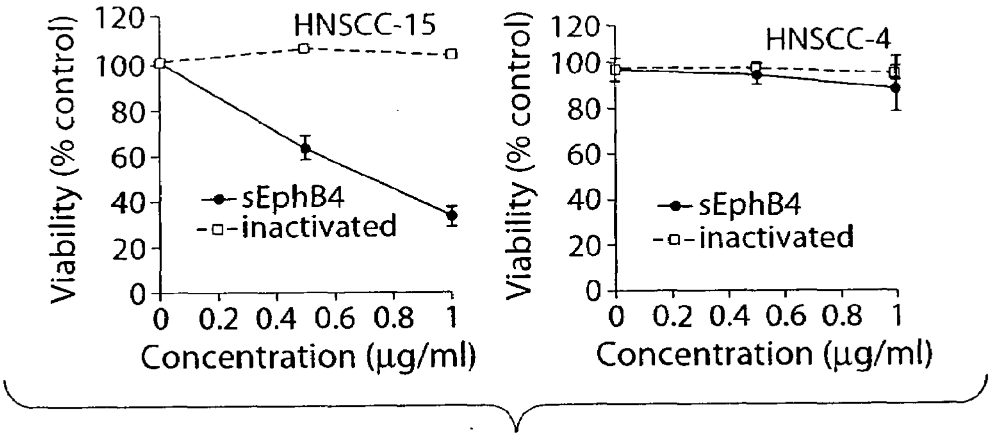
FIG. 23 shows effects of soluble EphB4ECD on viability and cell cycle. A) 3-day cell viability assay of two HNSCC cell lines. B) FACS analysis of cell cycle in HNSCC-15 cells treated as in A. Treatment of these cells resulted in accumulation in subG0/G1 and S/G2 phases as indicated by the arrows.
Figure 23B:
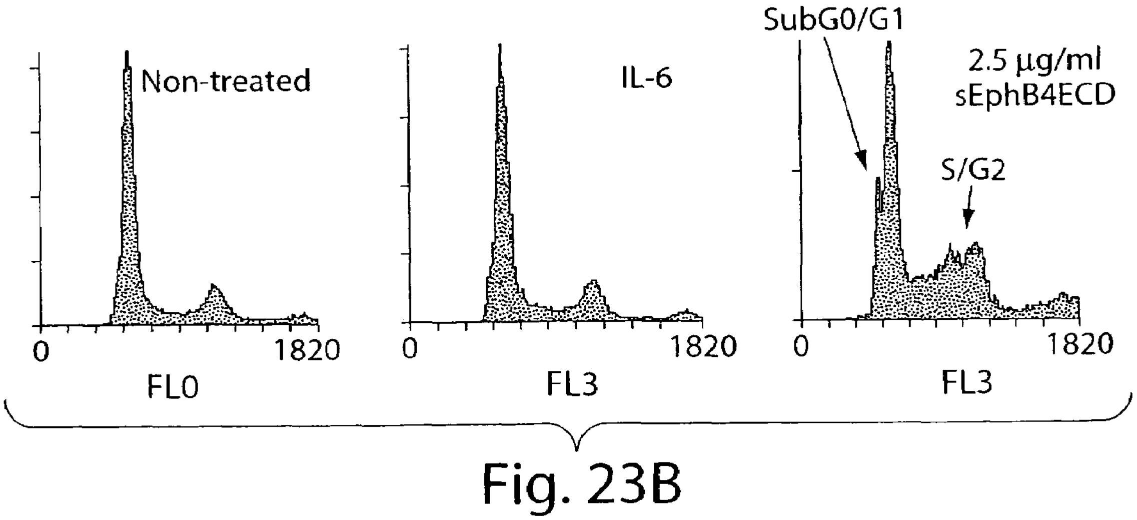

We found that soluble EphB4 inhibits the growth of SCC15 tumors grown in Balb/C Nu/Nu mice (FIG. 23).

E. Soluble EphB4 Inhibited Corneal Neovascularization

Figure 24:
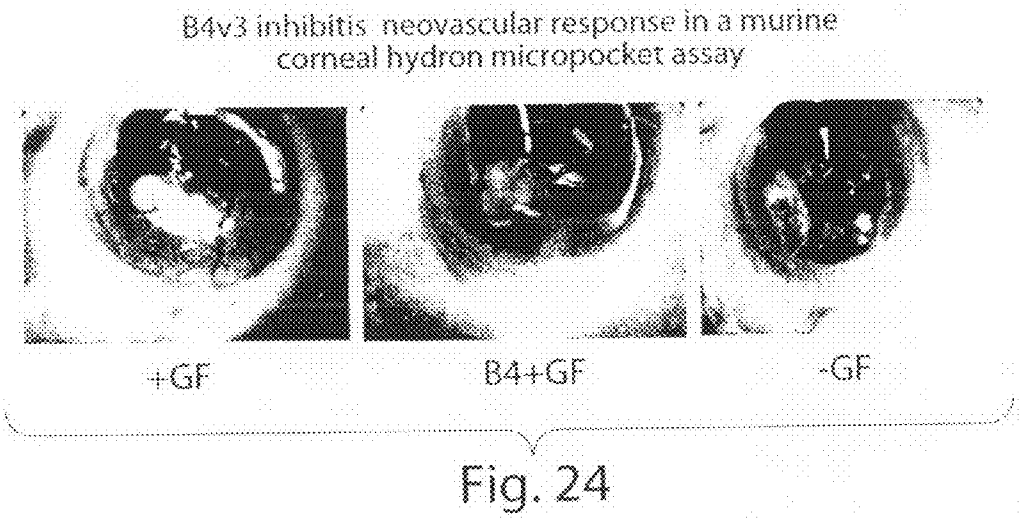
FIG. 24 shows that B4v3 inhibits neovascular response in a murine corneal hydron micropocket assay.

To further investigate the antiangiogenic activity of soluble EphB4 in vivo, we studied the inhibitory effect of administration of soluble EphB4 on neovascularization in the mouse cornea induced by bFGF. Hydron Pellets implanted into corneal micropocket could induce angiogenesis, in the presence of growth factors, in a typically avascular area. The angiogenesis response in mice cornea was moderate, the appearance of vascular buds was delayed and the new capillaries were sparse and grew slowly. Compared with the control group, on day 7 of implantation, the neovascularization induced by bFGF in mice cornea was markedly inhibited in soluble EphB4-treated group (FIG. 24).

F. Effects of Soluble EphB4 on Tumor Growth, In Vivo.

The same model was used to determine the effects of soluble EphB4 in vivo. SCC15 tumors implanted subcutaneously, pre-incubated with matrigel and with or w/o growth factors, as well as implanted sc alone, and mice treated sc or ip daily with 1-5 ug of soluble EphB4 were carried out.

Figure 25:
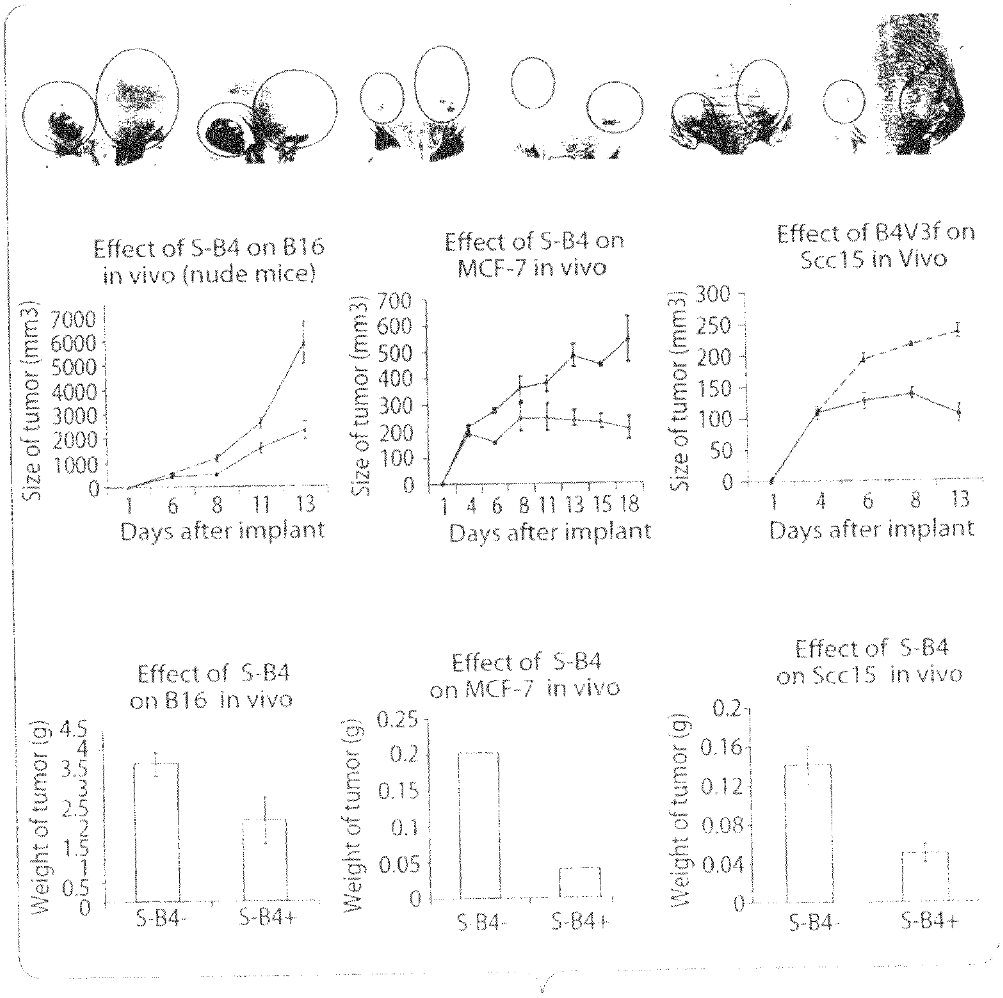
FIG. 25 shows that that SCC15, B16, and MCF-7 co-injected with sB4v3 in the presence of matrigel and growth factors, inhibits the in vivo tumor growth of these cells.

Tumors in the control group continued to grow steadily over the treatment period, reaching a final tumor volume of mm3. However, animals injected with soluble EphB4 exhibited a significantly (p<0.0/) reduced growth rate, reaching a final tumor volume of only mm3 (FIG. 25). Similar results were obtained in two further cohorts of such tumor-bearing mice. Soluble EphB4 administration appeared to be well tolerated in vivo, with no significant effect on body weight or the general well-being of the animals (as determined by the absence of lethargy, intermittent hunching, tremors or disturbed breathing patterns).

G. Effects of Soluble EphB4 on Tumor Histology.

Figure 26:
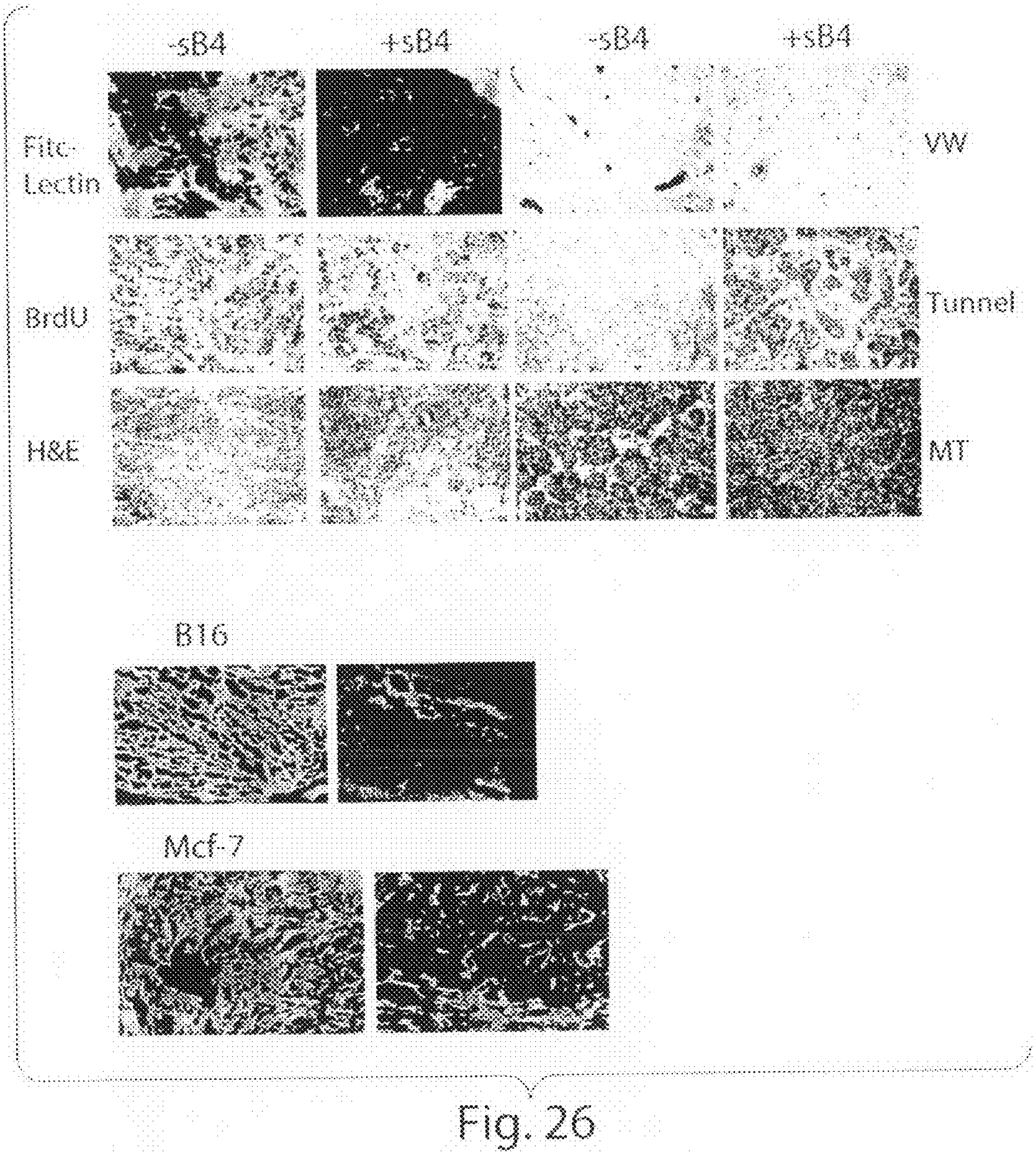
FIG. 26 shows that soluble EphB4 causes apoptosis, necrosis and decreased angiogenesis in three tumor types, B16 (melanoma), SCC 15 (head and neck carcinoma), and MCF-7 (breast carcinoma). Tumors were injected premixed with Matrigel plus growth factors and soluble EphB4 subcutaneously. After 10 to 14 days, the mice were injected intravenously with fitc-lectin (green) to assess blood vessel perfusion. Tumors treated with control PBS displayed abundant tumor density and a robust angiogenic response. Tumors treated with sEphB4 displayed a decrease in tumor cell density and a marked inhibition of tumor angiogenesis in regions with viable tumor cells, as well as tumor necrosis and apoptosis.

Histological analysis revealed the presence of a central area of necrosis in all SCC15 tumors, which was usually surrounded by a viable rim of tumor cells um in width. The central necrotic areas were frequently large and confluent and showed loss of cellular detail. Necrosis, assessed as a percentage of tumor section area, was significantly (p<0.02) more extensive in the soluble EphB4-treated group (% necrosis in treated vs. control). To determine whether the reduced volume of soluble EphB4 treated tumors was due to an effect of this protein on the tumor vascular supply, endothelial cells in blood vessels were identified in tumor sections using immunostaining with an anti-platelet cell adhesion molecule (PECAM-1; CD31) antibody (FIG. 26) and the density of microvessels was assessed. Microvessel density was similar in the outer viable rim of tumor cells (the uniform layer of cells adjacent to the tumor periphery with well defined nuclei) in control and soluble EphB4-treated tumors. Microvessel density was significantly in the inner, less viable region of tumor cells abutting the necrotic central areas in soluble EphB4-treated than control tumors. Fibrin deposition, as identified by Masson's Trichrome staining, was increased in and around blood vessels in the inner viable rim and the central necrotic core of soluble EphB4 treated than control tumors. In the outer viable rim of soluble EphB4 treated tumors, although the vessel lumen remained patent and contained red blood cells, fibrin deposition was evident around many vessels. Soluble EphB4 was found to have no such effects on the endothelium in the normal tissues examined (lungs, liver and kidneys).

H. Materials and Methods

1) Expression Constructs

As described above, to construct expression vectors for producing soluble, 6×His-tagged EphB4-ECD variants, cloned full-length human EphB4 cDNA was amplified by PCR using the following oligo primers: TACTAGTCCGCCATGGAGCTCCGGGTGCTGCT (SEQ ID NO: 9) (common EphB4 N-terminal primer) and GCGGCCGCTTAATGGTGATGGTGA TGATGAGCCGA AGGAGGGGTGGTGCA (SEQ ID NO: 10) (B4-GC), AGCGGCCGCTTAATGGTGATGGTGAT GATGGACATTGACAGGCTCAAATGGGA (SEQ ID NO: 11) (B4-GCF1) or TGCGGCCGCTTAATG GTGATGGTGATGAT GCTGCTCCCGCCAGCCCTCGCTCTCAT (SEQ ID NO: 12) (B4-GCF2). The resulting PCR fragments were TA-cloned into mammalian expression vector pEF6/V5-His-TOPO (Invitrogen) under EF-1α promoter control. The expressed recombinant proteins encode the following fragments of the mature extracellular part of human EphB4: amino acid positions 1-522 (GCF2), 1-412 (GCF1) and 1-312 (GC). To generate the B4-CF2 deletion (δ amino acids 13-183) PCR fragment for pEF6 cloning, EphB4 cDNA was amplified by two-step overlap PCR using oligo primers TACTAGTCCGCCATGGAGCTCCGGGTGCTGCT (SEQ ID NO: 13), CAGCTGAGTTTCCAATTTTGTGTTC, (SEQ ID NO: 14), GAACACAAAATTGGAAACTC AGCTGACTGTGAACCTGAC (SEQ ID NO: 15)and GCGGCCGCCCTG CTCCCGCCAGCCCTCGCT (SEQ ID NO: 16).

Vector for producing secreted human EphrinB2-alkaline phosphatase (B2-AP) reagent was constructed by PCR amplification of human Ephrin B2 cDNA using primers TAAAGCTTCCGCCATGGCTGTGAGAAGGGAC (SEQ ID NO: 17), and TAGGATCCTTCGGAACCGAGGATGTTGTTCCC (SEQ ID NO: 18), and cloning the resulting fragment, digested with Hind III and Bam HI, into Hind III-Bgl II digested pAPTag2 vector (GenHunter, Inc.). In each case, inserts in expression vectors were verified by complete sequencing.

2) Antibodies and Other Reagents

Anti-Eph B4 monoclonal antibodies mAB79 and mAB23 were raised in mice against the GCF2 protein containing amino acids 1-522 of mature human EphB4 and purified from hybridoma supernatants by Protein A chromatography. The anti-phosphotyrosine antibody 4G10 was from UBI (Lake Placid, N.Y.). Protein G-HRP conjugate was purchased from Bio-Rad.

3) Expression and Purification of EphB4-Derived Recombinant Proteins

To produce the EphB4-ECD soluble proteins, cultured human embryonic kidney cells HEK293T were transfected with the corresponding plasmid constructs using standard calcium phosphate or Lipofectamin 2000 reagent (Invitrogen) protocols. Twelve to sixteen hours post-transfection, the growth medium (DMEM+10% fetal bovine serum) was aspirated, cells washed once with serum free DMEM and replaced with serum free DMEM. Conditioned media containing the secreted proteins were harvested 72-96 hours later, clarified by centrifugation and used for purification of His-tagged proteins using Ni-NTA Agarose (Qiagen). The purity and quantity of the recombinant proteins was tested by SDS-PAAG electrophoresis with Coomassie Blue or silver staining, Western blotting and UV spectroscopy. Purified proteins were dialyzed against 20 mM Tris-HCl, 0.15 M NaCl, pH 8 and stored at −70° C.

To test ligand binding properties of the proteins, 10 μl of Ni-NTA-Agarose (Qiagen) were incubated in microcentrifuge tubes with 10-500 ng sample of a B4-ECD protein diluted in 0.5 ml of binding buffer BB (20 mM Tris-HCl, 0.15 M NaCl, 0.1% bovine serum albumin, pH 8). After incubation for 30 min on shaking platform, Ni-NTA beads were washed twice with 1.4 ml of BB, followed by addition of B2-AP fusion protein at concentration of 50 nM. Binding was performed for 30 min on a shaking platform. Tubes were centrifuged and washed once with 1.4 ml of BB. Amount of precipitated AP was measured colorimetrically at 420 nm after application of p-nitrophenyl phosphate (PNPP) and incubation for 5-30 min.

4) Immunoprecipitation

All lysates were processed at 4° C. Cells were lysed in 1 ml of buffer containing 20 mM Hepes at pH 7.4, 100 mM sodium chloride, 50 mM sodium fluoride, 2 mM EDTA, 2 mM EGTA, 1 mM sodium orthovanadate, 1% (v/v) NP-40, 0.5% (w/v) sodium deoxycholate, 1 mM phenyl methylsulphonyl fluoride (added freshly) and 100U Trasylol. Lysates were scraped into Eppendorf tubes and 50 μl of boiled, formalin-fixed *Staphylococcus aureus* was added (Calbiochem, San Diego). After 30 min of mixing, the lysates were centrifuged for 5 min at 25,000 g in a minifuge and the supernatants transferred to new tubes containing the appropriate antibody. Lysates were mixed with antibodies for 1 h, after which time 50 μl of protein A-Sepharose beads were added and the contents of the tubes mixed for 1 h to collect the immunoprecipitates. Protein A beads were collected by centrifugation at 25,000 g for 30 s. The supernatants were discarded and the beads washed three times with 1 ml lysis buffer minus deoxycholate.

5) Cell-Based EphB4 Tyrosine Kinase Assay

The human prostate carcinoma cell line PC3 cells were maintained in RPMI medium with 10% dialyzed fetal calf serum and 1% penicillin/streptomycin/neomycin antibiotics mix. Cells were maintained at 37° C. in a humidified atmosphere of 5% $CO_2$/95% air. Typically, cells were grown in 60 mm dishes until confluency and were either treated with mouse Ephrin B2-Fc fusion at 1 μg/ml in RPMI for 10 min to activate EphB4 receptor or plain medium as a control. To study the effect of different derivatives of soluble EphB4 ECD proteins on EphB4 receptor activation, three sets of cells were used. In the first set, cells were treated with various proteins (5 proteins; GC, GCF1, GCF2, GCF2-F, CF2) at 5 μg/ml for 20 min. In the second set of cells, prior to application, proteins were premixed with ephrinB2-Fc at 1:5 (EphB4 protein: B2-Fc) molar ratio, incubated for 20 min and applied on cells for 10 min. In the third set of cells, cells were first treated with the proteins for 20 min at 5 μg/ml, media was replaced with fresh media containing 1 μg/ml of EphrinB2-Fc and incubated for another 10 min.

After the stimulation, cells were immediately harvested with protein extraction buffer containing 20 mM Tris-HCl, pH 7.4, 150 mM NaCl, 1% (v/v) Triton X100, 1 mM EDTA, 1 mM PMSF, 1 mM Sodium vanadate. Protein extracts were clarified by centrifugation at 14,000 rpm for 20 min at 4° C. Clarified protein samples were incubated overnight with protein A/G coupled agarose beads pre-coated with anti-EphB4 monoclonal antibodies. The IP complexes were washed twice with the same extraction buffer containing 0.1% Triton X100. The immunoprecipitated proteins were solubilized in 1×SDS-PAGE sample loading buffer and separated on 10% SDS-PAGE. For EphB4 receptor activation studies, electroblotted membrane was probed with anti-pTyr specific antibody 4G10 at 1:1000 dilution followed by Protein G-HRP conjugate at 1:5000 dilutions.

6) Cell Culture

Normal HUVECs were obtained from Cambrex (BioWhittaker) and maintained in EBM2 medium supplemented with 0.1 mg/ml endothelial growth supplement (crude extract from bovine brain), penicillin (50 U/ml), streptomycin (50 U/ml), 2 mmol/l glutamine and 0.1 mg/ml sodium heparin. Aliquots of cells were preserved frozen between passages 1 and 3. For all experiments, HUVECs were used at passages 4 or below and collected from a confluent dish.

7) Endothelial Cell Tube Formation Assay

Matrigel (60 μl of 10 mg/ml; Collaborative Lab, Cat. No. 35423) was placed in each well of an ice-cold 96-well plate. The plate was allowed to sit at room temperature for 15 minutes then incubated at 37° C. for 30 minutes to permit Matrigel to polymerize. In the mean time, human umbilical vein endothelial cells were prepared in EGM-2 (Clonetic, Cat. No. CC3162) at a concentration of $2\times10^5$ cells/ml. The test protein was prepared at 2× the desired concentration (5 concentration levels) in the same medium. Cells (500 μl) and 2× protein (500 μl) were mixed and 200 μl of this suspension were placed in duplicate on the polymerized Matrigel. After 24 h incubation, triplicate pictures were taken for each concentration using a Bioquant Image Analysis system. Protein addition effect ($IC_{50}$) was assessed compared to untreated controls by measuring the length of cords formed and number of junctions.

8) Cell Migration Assay

Chemotaxis of HUVECs to VEGF was assessed using a modified Boyden chamber, transwell membrane filter inserts in 24 well plates, 6.5 mm diam, 8 μm pore size, 10 μm thick matrigel coated, polycarbonate membranes (BD Biosciences). The cell suspensions of HUVECs ($2\times10^5$ cells/ml) in 200 μl of EBM were seeded in the upper chamber and the soluble EphB4 protein were added simultaneously with stimulant (VEGF or bFGF) to the lower compartment of the chamber and their migration across a polycarbonate filter in response to 10-20 ng/ml of VEGF with or without 100 nM-1 M test compound was investigated. After incubation for 4-24 h at 37° C., the upper surface of the filter was scraped with swab and filters were fixed and stained with Diff Quick. Ten random fields at 200× mag were counted and the results expressed as mean # per field. Negative unstimulated control values were subtracted from stimulated control and protein treated sample values and the data was plotted as mean migrated cell ±S.D. $IC_{50}$ was calculated from the plotted data.

9) Growth Inhibition Assay

HUVEC ($1.5\times10^3$ cells) were plated in a 96-well plate in 100 μl of EBM-2 (Clonetic, Cat. No. CC3162). After 24 hours (day 0), the test recombinant protein (100 μl) is added to each well at 2× the desired concentration (5-7 concentration levels) in EBM-2 medium. On day 0, one plate was stained with 0.5% crystal violet in 20% methanol for 10 minutes, rinsed with water, and air-dried. The remaining plates were incubated for 72 h at 37° C. After 72 h, plates were stained with 0.5% crystal violet in 20% methanol, rinsed with water and air-dried. The stain was eluted with 1:1 solution of ethanol: 0.1 M sodium citrate (including day 0 plate), and absorbance measured at 540 nm with an ELISA reader (Dynatech Laboratories). Day 0 absorbance was subtracted from the 72 h plates and data is plotted as percentage of control proliferation (vehicle treated cells). $IC_{50}$ value was calculated from the plotted data.

10) Murine Matrigel Plug Angiogenesis Assay

In vivo angiogenesis was assayed in mice as growth of blood vessels from subcutaneous tissue into a Matrigel plug containing the test sample. Matrigel rapidly forms a solid gel at body temperature, trapping the factors to allow slow release and prolonged exposure to surrounding tissues. Matrigel (8.13 mg/ml, 0.5 ml) in liquid form at 4° C. was mixed with Endothelial Cell Growth Supplement (ECGS), test proteins plus ECGS or Matrigel plus vehicle alone (PBS containing 0.25% BSA). Matrigel (0.5 ml) was injected into the abdominal subcutaneous tissue of female nu/nu mice (6 wks old) along the peritoneal mid line. There were 3 mice in each group. The animals were cared for in accordance with institutional and NIH guidelines. At day 6, mice were sacrificed and plugs were recovered and processed for histology. Typically the overlying skin was removed, and gels were cut out by retaining the peritoneal lining for support, fixed in 10% buffered formalin in PBS and embedded in paraffin. Sections of 3 μm were cut and stained with H&E or Masson's trichrome stain and examined under light microscope 11) Mouse Corneal Micropocket Assay Mouse corneal micropocket assay was performed according to that detailed by Kenyon et al., 1996. Briefly, hydron pellets (polyhydroxyethylmethacrylate [polyHEMA], Interferon Sciences, New Brunswick, N.J., U.S.A.) containing either 90 ng of bFGF (R&D) or 180 ng of VEGF (R&D Systems, Minneapolis, Minn., U.S.A.) and 40 μg of sucrose aluminium sulfate (Sigma) were prepared. Using an operating microscope, a stromal linear keratotomy was made with a surgical blade (Bard-Parker no. 15) parallel to the insertion of the lateral rectus muscle in an anesthetized animal. An intrastromal micropocket was dissected using a modified von Graefe knife (2"30 mm). A single pellet was implanted and advanced toward the temporal corneal limbus (within 0±7±1±0 mm for bFGF pellets and 0±5 mm for VEGF pellets). The difference in pellet location for each growth factor was determined to be necessary given the relatively weaker angiogenic stimulation of VEGF in this model. Antibiotic ointment (erythromycin.) was then applied to the operated eye to prevent infection and to decrease surface irregularities. The subsequent vascular response was measured extending from the limbal vasculature toward the pellet and the contiguous circumferential zone of neovascularization Data and clinical photos presented here were obtained on day 6 after pellet implantation, which was found to be the day of maximal angiogenic response.

12) In Vitro Invasion Assay

"Matrigel" matrix-coated 9-mm cell culture inserts (pore size, 8 μm; Becton Dickinson, Franklin Lakes, N.J.) were set in a 24-well plate. The HUVEC cells were seeded at a density of $5\times10^3$ cells per well into the upper layer of the culture insert and cultured with serum-free EBM in the presence of EphB4 ECD for 24 h. The control group was cultured in the same media without EphB4. Then 0.5 ml of the human SCC15 cell line, conditioned medium was filled into the lower layer of the culture insert as a chemo-attractant. The cells were incubated for 24 h, then the remaining cells in the upper layer were swabbed with cotton and penetrating cells in the lower layer were fixed with 5% glutaraldehyde and stained with Diff Quick. The total number of cells passing through the Matrigel matrix and each 8 μm pore of the culture insert was counted using optical microscopy and designated as an invasion index (cell number/area).

13) SCC5 Tumor Growth in Mice

Subcutaneously inject logarithmically growing SCC15, head and neck squamous cell carcinoma cell line, at $5\times10^6$ cell density; with or without EphB4 ECD in the presence or absence of human bFGF, into athymic Balb/c nude mice, along with Matrigel (BD Bioscience) synthetic basement membrane (1:1 v/v), and examine tumors within 2 weeks. Tumor volumes in the EphB4 ECD group, in the presence and absence of growth factor after implantation were three-fold smaller than those in the vehicle groups. There was no difference in body weight between the groups. Immunohistochemical examination of cross-sections of resected tumors and TUNEL-positive apoptosis or necrosis, CD34 immunostaining, and BrdU proliferation rate will be performed, after deparaffinized, rehydrated, and quenched for endogenous peroxidase activity, and after 10 mm permeabilization with proteinase K. Quantitative assessment of vascular densities will also be performed. Local intratumoral delivery or IV delivery of EphB4 ECD will also be performed twice a week.

30 athymic nude mice, BALB/c (nu/nu), were each injected with $1\times10^6$ B16 melanoma cells with 0.1 ml PBS mixed with 0.1 ml matrigel or $1.5\times10^6$SCC15 cells resuspended in 200 μl of DMEM serum-free medium and injected subcutaneously on day 0 on the right shoulder region of mice. Proteins were injected intravenously or subcutaneously, around the tumor beginning on day 1 at a loading dose of 4 μg/mg, with weekly injections of 2 ug/mg. (10 μg/g, 50 μg/kg/day), and at 2 weeks post-inoculation. Mice are sacrificed on Day 14. Control mice received PBS 50 μl each day.

14) Tumor Formation in Nude Mice

All animals were treated under protocols approved by the institutional animal care committees. Cancer cells ($5\times10^6$) were subcutaneously inoculated into the dorsal skin of nude mice. When the tumor had grown to a size of about 100 $mm^3$ (usually it took 12 days), sEphB4 was either intraperitoneally or subcutaneously injected once/day, and tumorigenesis was monitored for 2 weeks. Tumor volume was calculated according to the formula $a^2\times b$, where a and b are the smallest and largest diameters, respectively. A Student's t test was used to compare tumor volumes, with $P<0.05$ being considered significant.

15) Quantification of Microvessel Density

Tumors were fixed in 4% formaldehyde, embedded in paraffin, sectioned by 5 μm, and stained with hematoxylineosin. Vessel density was semi-quantitated using a computer-based image analyzer (five fields per section from three mice in each group).

Example 3

EphB4 is Upregulated and Imparts Growth Advantage in Prostate Cancer

A. Expression of EphB4 in Prostate Cancer Cell Lines

Figure 27A:
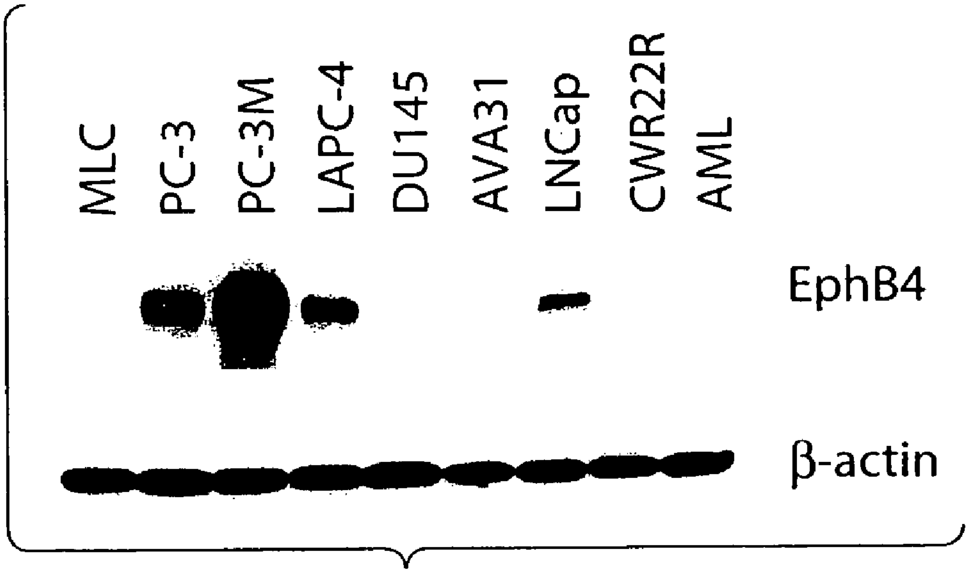
FIG. 27 shows expression of EphB4 in prostate cell lines. A) Western blot of total cell lysates of various prostate cancer cell lines, normal prostate gland derived cell line (MLC) and acute myeloblastic lymphoma cells (AML) probed with EphB4 monoclonal antibody. B) Phosphorylation of EphB4 in PC-3 cells determined by Western blot.
Figure 27B:
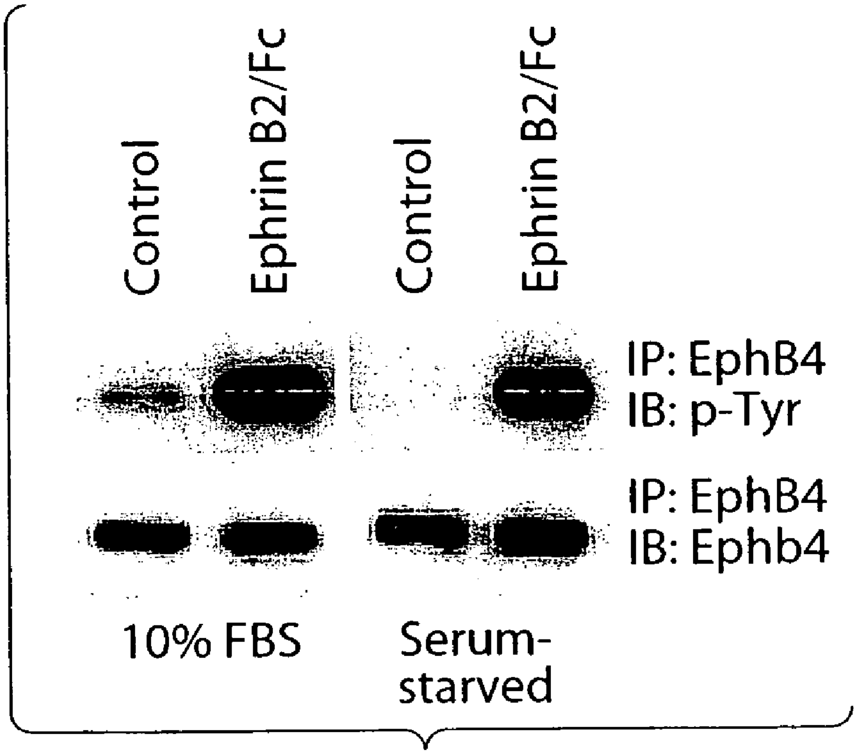

We first examined the expression of EphB4 protein in a variety of prostate cancer cell lines by Western blot. We found that prostate cancer cell lines show marked variation in the abundance of the 120 kD EphB4. The levels were relatively high in PC3 and even higher in PC3M, a metastatic clone of PC3, while normal prostate gland derived cell lines (MLC) showed low or no expression of EphB4 (FIG. 27A). We next checked the activation status of EphB4 in PC3 cells by phosphorylation study. We found that even under normal culture conditions, EphB4 is phosphorylated though it can be further induced by its ligand, ephrin B2 (FIG. 27B).

B. Expression of EphB4 in Clinical Prostate Cancer Samples

Figure 28:
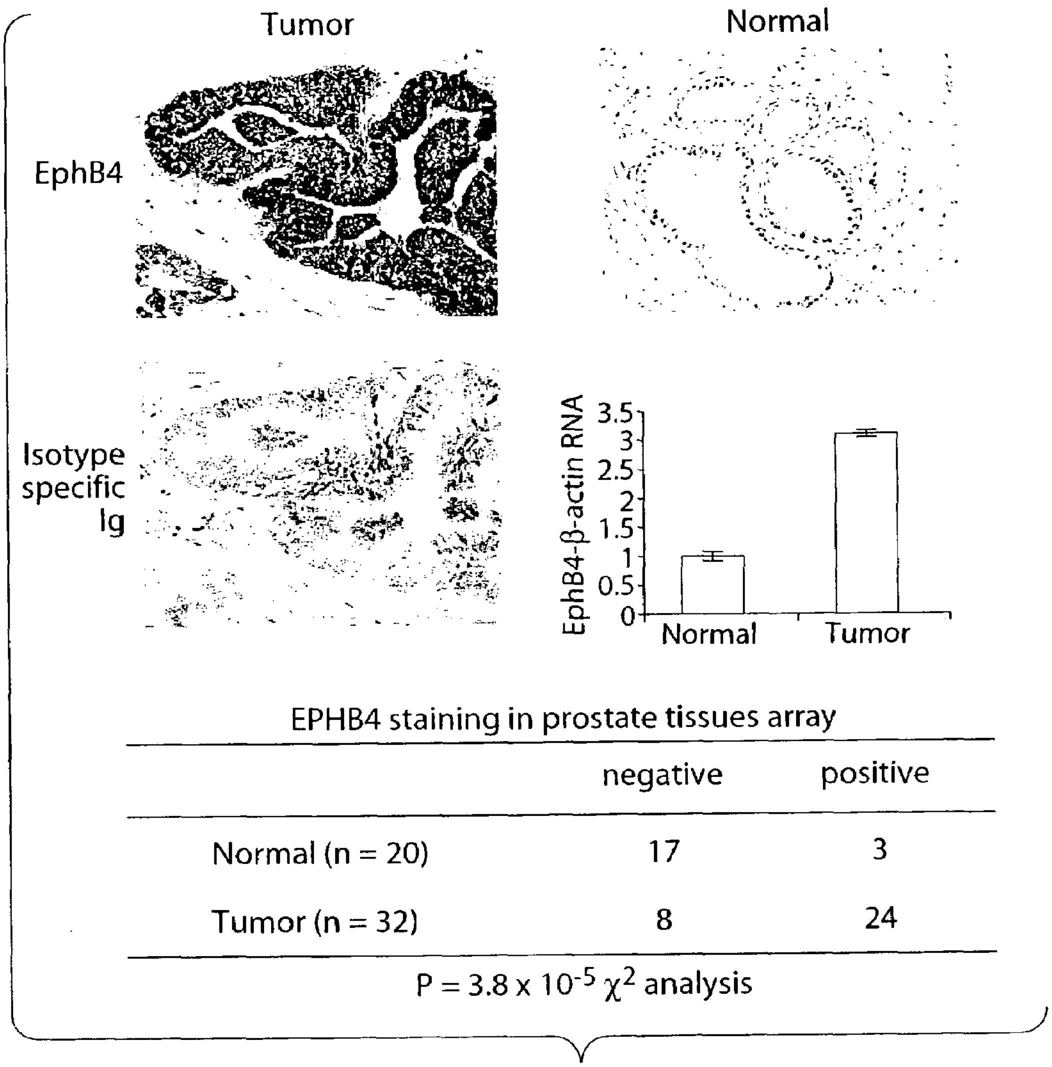
FIG. 28 shows expression of EphB4 in prostate cancer tissue. Representative prostate cancer frozen section stained with EphB4 monoclonal antibody (top left) or isotype specific control (bottom left). Adjacent BPH tissue stained with EphB4 monoclonal antibody (top right). Positive signal is brown color in the tumor cells. Stroma and the normal epithelia are negative. Note membrane localization of stain in the tumor tissue, consistent with trans-membrane localization of EphB4. Representative QRT-PCR of RNA extracted from cancer specimens and adjacent BPH tissues (lower right).

To determine whether EphB4 is expressed in clinical prostate samples, tumor tissues and adjacent normal tissue from prostate cancer surgical specimens were examined. The histological distribution of EphB4 in the prostate specimens was determined by immunohistochemistry. Clearly, EphB4 expression is confined to the neoplastic epithelium (FIG. 28, top left), and is absent in stromal and normal prostate epithelium (FIG. 28, top right). In prostate tissue array, 24 of the 32 prostate cancers examined were positive. We found EphB4 mRNA is expressed both in the normal and tumor tissues of clinical samples by quantitative RT-PCR. However, tumor EphB4 mRNA levels were at least 3 times higher than in the normal in this case (FIG. 28, lower right).

C. p53 and PTEN Inhibited the Expression of EphB4 in PC3 Cells

Figure 29A:
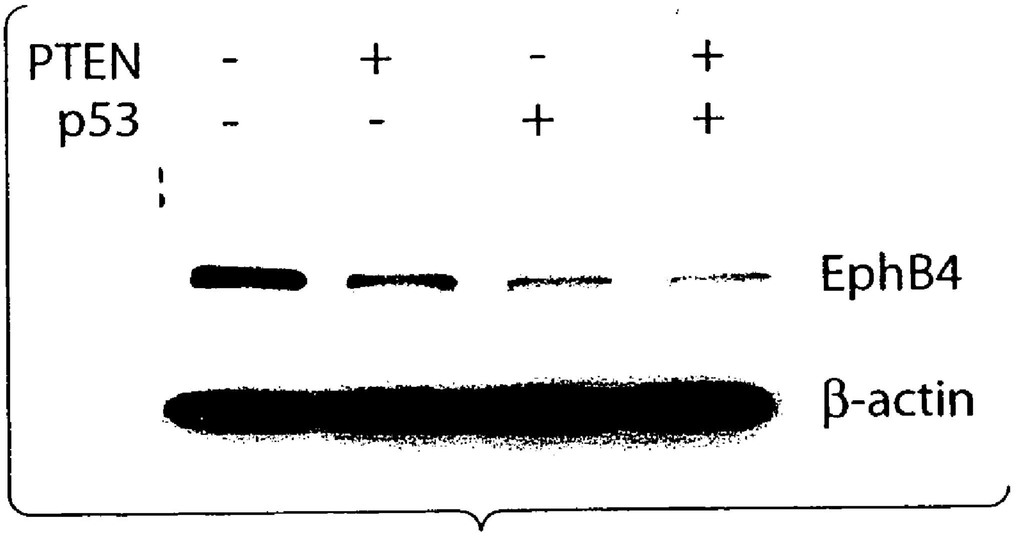
FIG. 29 shows downregulation of EphB4 in prostate cancer cells by tumor suppressors and RXR expression. A) PC3 cells were co-transfected with truncated CD4 and p53 or PTEN or vector only. 24 h later CD4-sorted cells were collected, lysed and analyzed sequentially by Western blot for the expression of EphB4 and β-actin, as a normalizer protein. B) Western blot as in (A) of various stable cell lines. LNCaP-FGF is a stable transfection clone of FGF-8, while CWR22R-RXR stably expresses the RXR receptor. BPH-1 was established from benign hypertrophic prostatic epithelium.

PC3 cells are known to lack PTEN expression (Davis, et al., 1994, Science. 266:816-819) and wild-type p53 function (Gale, et al., 1997, Cell Tissue Res. 290:227-241). We investigated whether the relatively high expression of EphB4 is related to p53 and/or PTEN by re-introducing wild-type p53 and/or PTEN into PC3 cells. To compensate for the transfection efficiency and the dilution effect, transfected cells were sorted for the cotransfected truncated CD4 marker. We found that the expression of EphB4 in PC3 cells was reduced by the re-introduction of either wild-type p53 or PTEN. The cotransfection of p53 and PTEN did not further inhibit the expression of EphB4 (FIG. 29A).

D. Retinoid X Receptor (RXRα) Regulates the Expression of EphB4

Figure 29B:
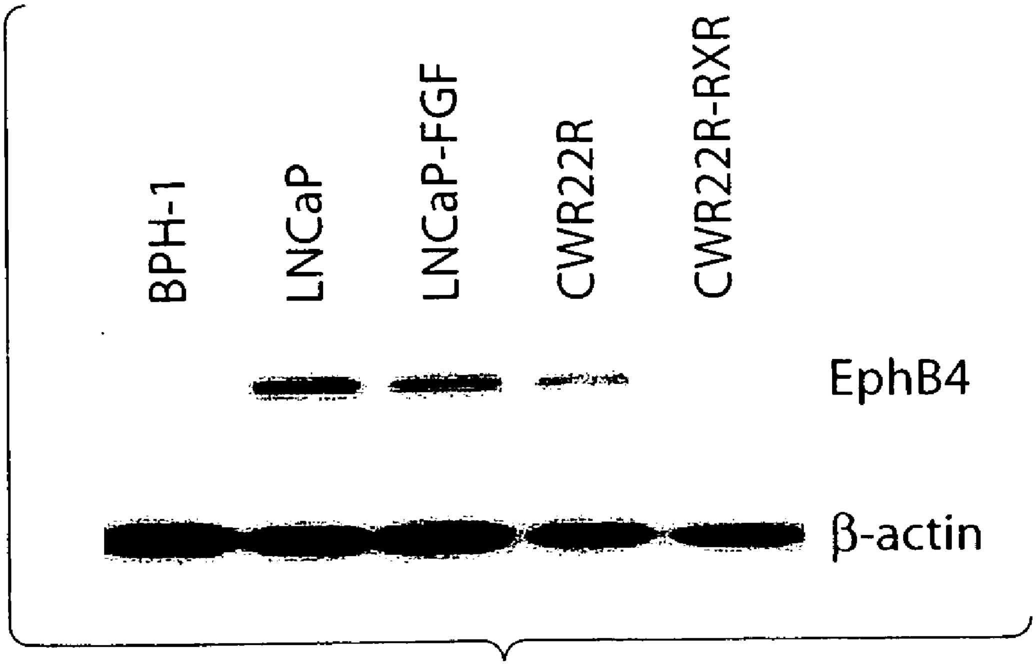

We previously found that RXRα was down-regulated in prostate cancer cell lines (Zhong, et al., 2003, Cancer Biol Ther. 2:179-184) and here we found EphB4 expression has the reverse expression pattern when we looked at "normal" prostate (MLC), prostate cancer (PC3), and metastatic prostate cancer (PC3M) (FIG. 27A), we considered whether RXRα regulates the expression of EphB4. To confirm the relationship, the expression of EphB4 was compared between CWR22R and CWR22R-RXRα, which constitutively expresses RXRα. We found a modest decrease in EphB4 expression in the RXRα overexpressing cell line, while FGF8 has no effect on EphB4 expression. Consistent with initial results, EphB4 was not found in "normal" benign prostate hypertrophic cell line BPH-1 (FIG. 29B).

Figure 30A:
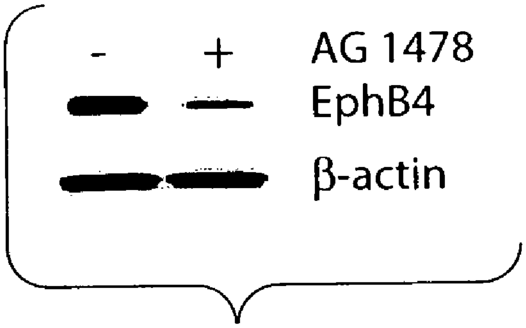
FIG. 30 shows regulation of EphB4 in prostate cancer cells by EGFR and IGFR-1. A) Western blot of PC3 cells treated with or without EGFR specific inhibitor AG1478 (1 nM) for 36 hours. Decreased EphB4 signal is observed after AG 1478 treatment. The membrane was stripped and reprobed with β-actin, which was unaffected. B) Western Blot of triplicate samples of PC3 cells treated with or without IGFR-1 specific neutralizing antibody MAB391 (2 μg/ml; overnight). The membrane was sequentially probed with EphB4, IGFR-1 and β-actin antibodies. IGFR-1 signal shows the expected repression of signal with MAB391 treatment.
Figure 30B:
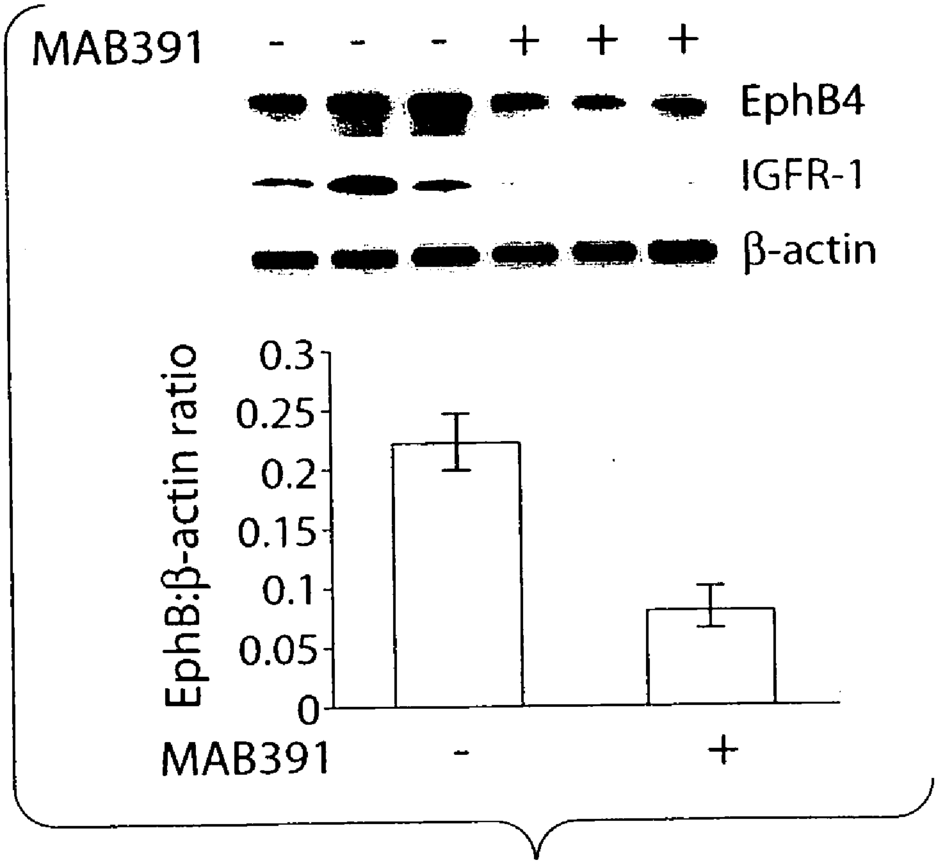

E. Growth Factor Signaling Pathway of EGFR and IGF-1R Regulates EphB4 Expression EGFR and IGF-1R have both been shown to have autocrine and paracrine action on PC3 cell growth. Because we found that EphB4 expression is higher in the more aggressive cell lines, we postulated that EphB4 expression might correlate with these pro-survival growth factors. We tested the relationship by independently blocking EGFR and IGF-1R signaling. EphB4 was down-regulated after blocking the EGFR signaling using EGFR kinase inhibitor AG 1478 (FIG. 30A) or upon blockade of the IGF-1R signaling pathway using IGF-1R neutralizing antibody (FIG. 30B).

F. EphB4 siRNA and Antisense ODNs Inhibit PC3 Cell Viability

Figure 31A:
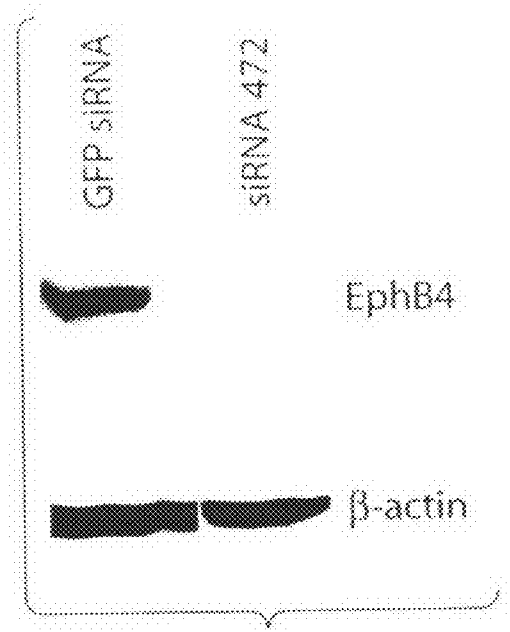
FIG. 31 shows effect of specific EphB4 AS-ODNs and siRNA on expression and prostate cell functions. A) 293 cells stably expressing full-length construct of EphB4 was used to evaluate the ability of siRNA 472 to inhibit EphB4 expression. Cells were transfected with 50 nM RNAi using Lipofectamine 2000. Western blot of cell lysates 40 h post transfection with control siRNA (green fluorescence protein; GFP siRNA) or EphB4 siRNA 472, probed with EphB4 monoclonal antibody, stripped and reprobed with β-actin monoclonal antibody. B) Effect of EphB4 AS-10 on expression in 293 transiently expressing full-length EphB4. Cells were exposed to AS-10 or sense ODN for 6 hours and analyzed by Western blot as in (A). C) 48 h viability assay of PC3 cells treated with siRNA as described in the Methods section. Shown is mean±s.e.m. of triplicate samples. D) 5-day viability assay of PC3 cells treated with ODNs as described in the Methods. Shown is mean±s.e.m. of triplicate samples. E) Scrape assay of migration of PC3 cells in the presence of 50 nM siRNAs transfected as in (A). Shown are photomicrographs of representative 20× fields taken immediately after the scrape was made in the monolayer (0 h) and after 20 h continued culture. A large number of cells have filled in the scrape after 20 h with control siRNA, but not with EphB4 siRNA 472. F) Shown is a similar assay for cells treated with AS-10 or sense ODN (both 10 μM). G) Matrigel invasion assay of PC3 cells transfected with siRNA or control siRNA as described in the methods. Cells migrating to the underside of the Matrigel coated insert in response to 5 mg/ml fibronectin in the lower chamber were fixed and stained with Giemsa. Shown are representative photomicrographs of control siRNA and siRNA 472 treated cells. Cell numbers were counted in 5 individual high-powered fields and the average ±s.e.m. is shown in the graph (bottom right).
Figure 31B:
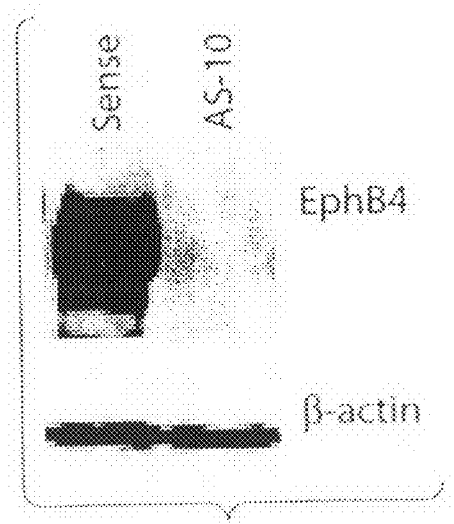
Figure 31C:
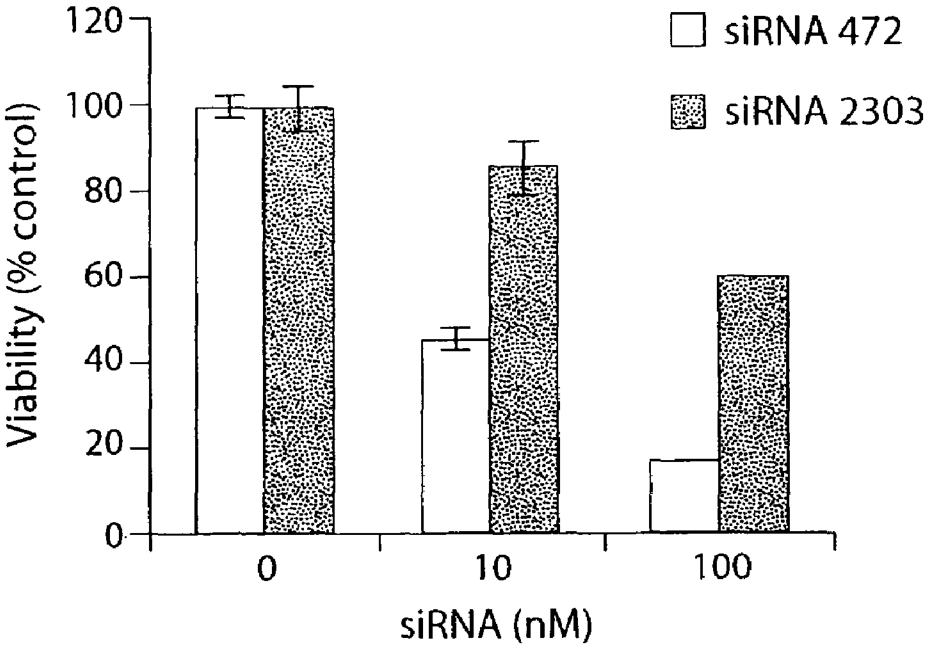
Figure 31D:
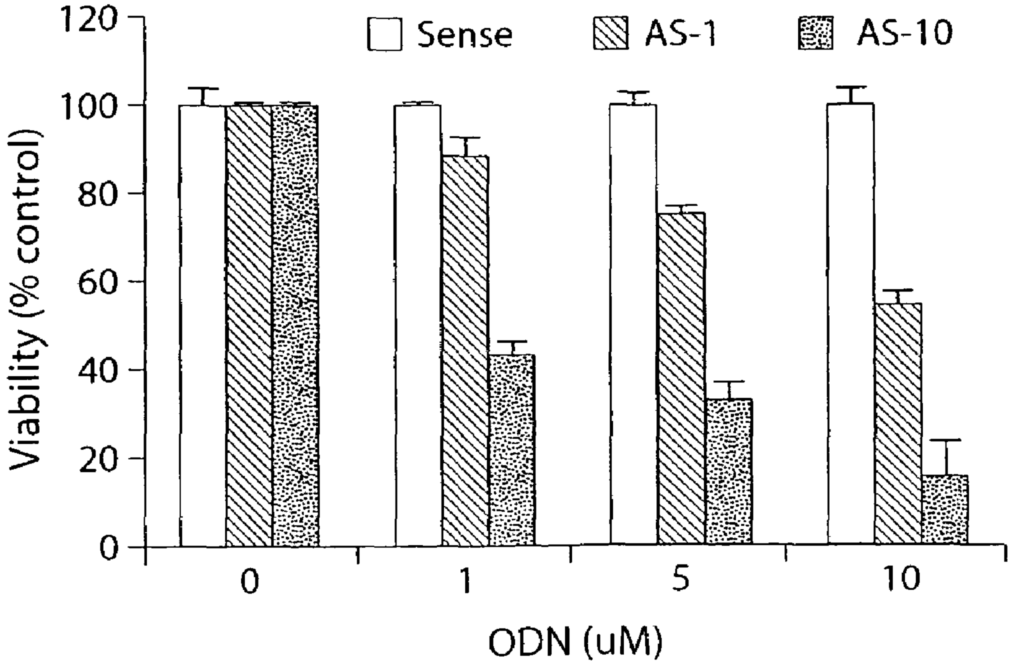

To define the significance of this EphB4 overexpression in our prostate cancer model, we concentrated our study on PC3 cells, which have a relatively high expression of EphB4. The two approaches to decreasing EphB4 expression were siRNA and AS-ODNs. A number of different phosphorothioate-modified AS-ODNs complementary to different segments of the EphB4 coding region were tested for specificity and efficacy of EphB4 inhibition. Using 293 cells transiently transfected with full-length EphB4 expression vector AS-10 was found to be the most effective (FIG. 31B). A Similar approach was applied to the selection of specific siRNA. EphB4 siRNA 472 effectively knocks down EphB4 protein expression (FIG. 31A). Both siRNA 472 and antisense AS-10 ODN reduced the viability of PC3 cells in a dose dependent manner (FIGS. 31C, D). Unrelated siRNA or sense oligonucleotide had no effect on viability.

G. EphB4 siRNA and Antisense ODNs Inhibit the Mobility of PC3 Cells

Figure 31E:
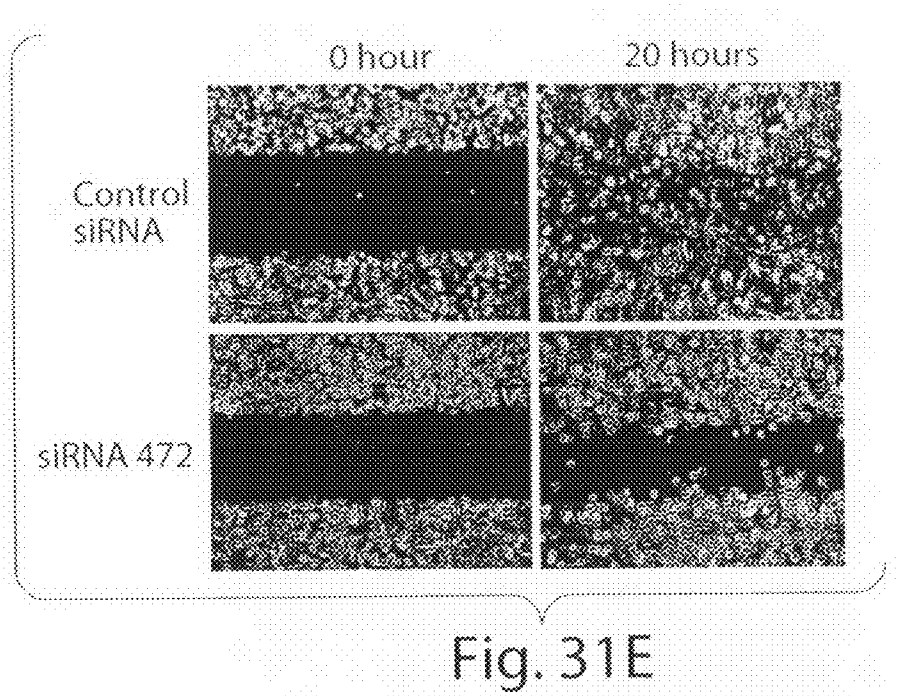
Figure 31F:
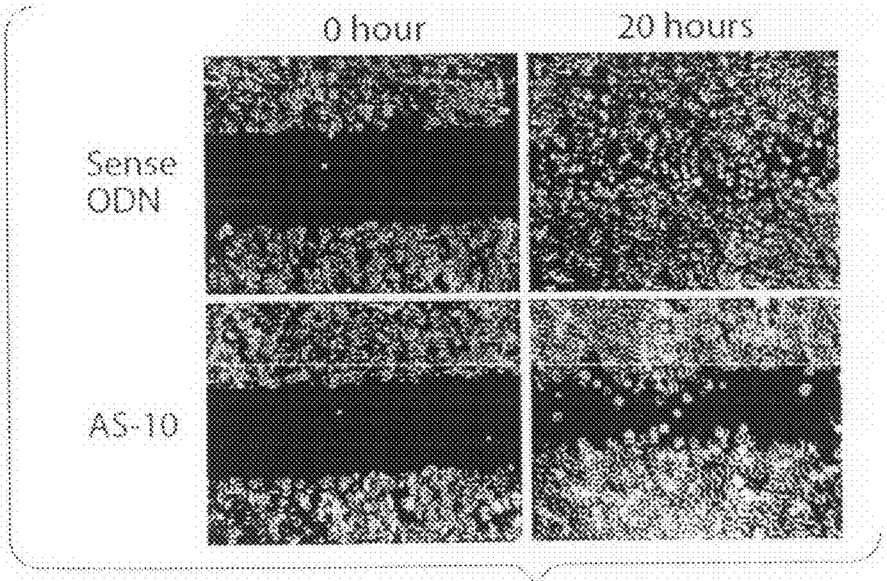
Figure 31G:
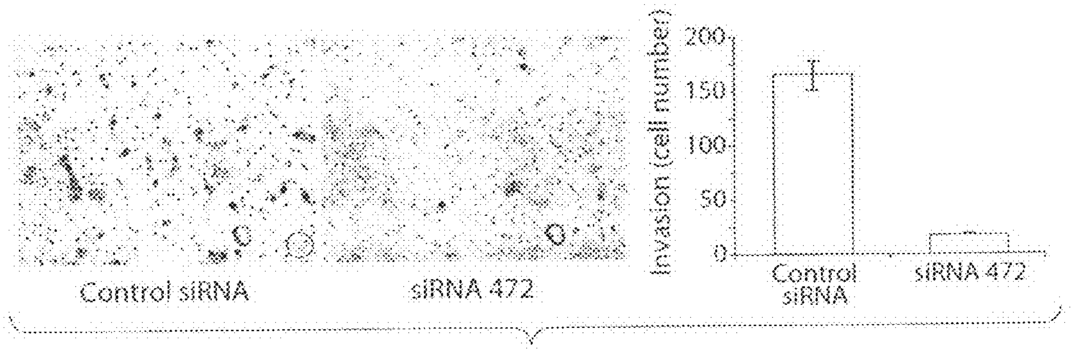

PC3 cells can grow aggressively locally and can form lymph node metastases when injected orthotopically into mice. In an effort to study the role of EphB4 on migration of PC3 cells in vitro, we performed a wound-healing assay. When a wound was introduced into a monolayer of PC3 cells, over the course of the next 20 hours cells progressively migrated into the cleared area. However, when cells were transfected with siRNA 472 and the wound was introduced, this migration was significantly inhibited (FIG. 31E). Pretreatment of PC3 cells with 10 µM EphB4 AS-10 for 12 hours generated the same effect (FIG. 31F). In addition, knock-down of EphB4 expression in PC3 cells with siRNA 472 severely reduced the ability of these cells to invade Matrigel as assessed by a double-chamber invasion assay (FIG. 31 G), compared to the control siRNA.

H. EphB4 siRNA Induces Cell Cycle Arrest and Apoptosis in PC3 Cells

Figure 32A:
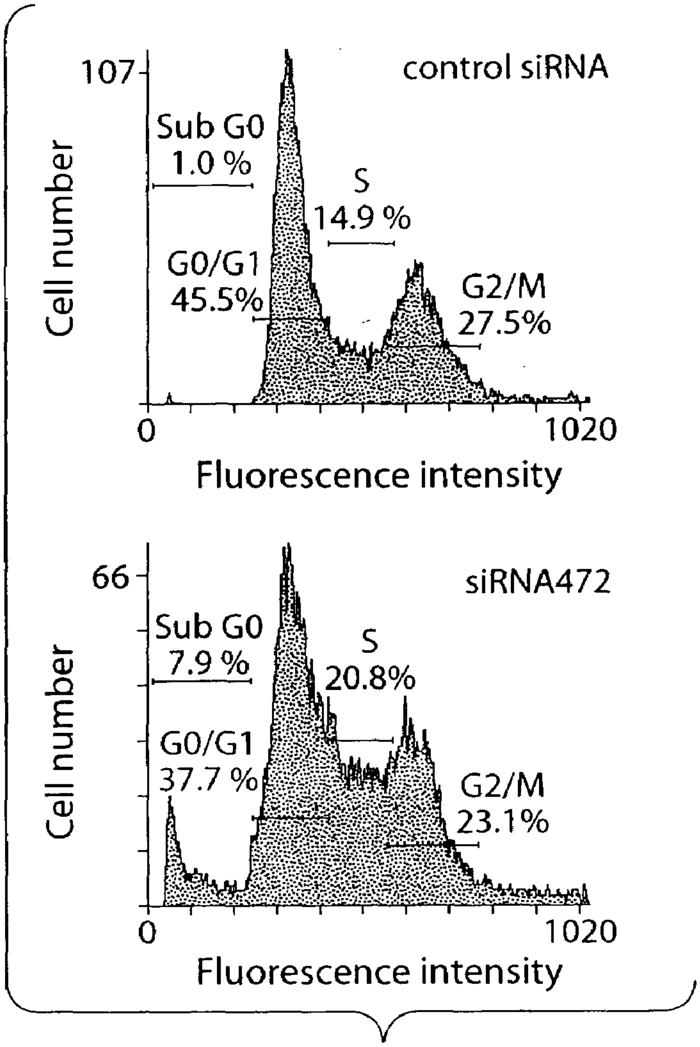
FIG. 32 shows effect of EphB4 siRNA 472 on cell cycle and apoptosis. A) PC3 cells transfected with siRNAs as indicated were analyzed 24 h post transfection for cell cycle status by flow cytometry as described in the Methods. Shown are the plots of cell number vs. propidium iodide fluorescence intensity. 7.9% of the cell population is apoptotic (in the Sub G0 peak) when treated with siRNA 472 compared to 1% with control siRNA. B) Apoptosis of PC3 cells detected by Cell Death Detection ELISA$^{plus}$ kit as described in the Methods. Absorbance at 405 nm increases in proportion to the amount of histone and DNA-POD in the nuclei-free cell fraction. Shown is the mean±s.e.m. of triplicate samples at the indicated concentrations of siRNA 472 and GFP siRNA (control).
Figure 32B:
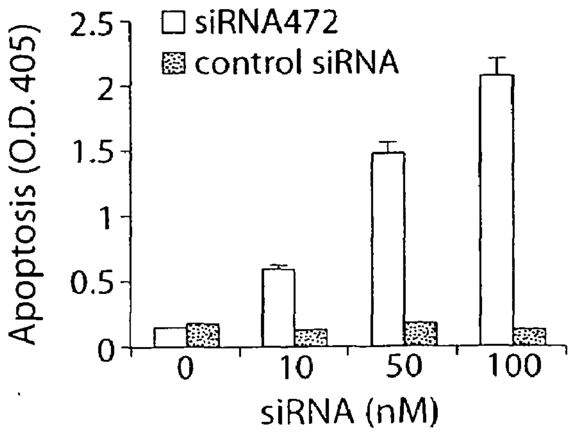

Since knock-down of EphB4 resulted in decreased cell viability (FIG. 31C) we sought to determine whether this was due to effects on the cell cycle. In comparison to control siRNA transfected cells, siRNA 472 resulted in an accumulation of cells in the sub G0 and S phase fractions compared to cells treated with control siRNA. The sub G0 fraction increased from 1% to 7.9%, and the S phase fraction from 14.9% to 20.8% in siRNA 472 treated cells compared to control siRNA treated cells (FIG. 32A). Cell cycle arrest at sub G0 and G2 is indicative of apoptosis. Apoptosis as a result of EphB4 knock-down was confirmed by ELISA assay. A dose-dependent increase in apoptosis was observed when PC3 cells were transfected with siRNA 472, but not with control siRNA (FIG. 32B). At 100 nM there was 15 times more apoptosis in siRNA 472 transfected than control siRNA transfected PC3 cells.

I. Materials and Methods

1) Reagents

Neutralizing IGF-1R antibody was from R&D Systems (Minneapolis Minn.). Anti-IGF-1R(β), -EGFR, -EphB4(C-16) were from Santa Cruz Biotech (Santa Cruz, Calif.). β-actin monoclonal antibody was purchased from Sigma Chemical Co. (St Louis, Mo.). Media and fetal bovine serum (FBS) were from Invitrogen (Carlsbad, Calif.). AG 1478(4-(3'-Chloroanilino)-6,7-dimethoxy-quinazoline) was from Calbiochem (San Diego, Calif.).

2) Antisense Oligodeoxynucleotides and EphB4 siRNAs

EphB4 specific antisense phosphorothioate-modified oligodeoxynucleotide (ODN) and sense ODN were synthesized and purified by Qiagen (Alameda Calif.). The sequences are: Sense, 5'-TCC-TGC-AAG-GAG-ACC-TTC-AC-3' (SEQ ID NO: 19); AS1: 5'-GTG-CAG-GGA-TAG-CAG-GGC-CAT-3' (SEQ ID NO: 20); AS10: 5'-ATG-GAG-GCC-TCG-CTC-AGA-AA-3' (SEQ ID NO: 21). siRNAs were synthesized at the USC/Norris Comprehensive Cancer Center Microchemical Core laboratory. Sequences of EphB4 siRNAs are siRNA 472 5'-GGU-GAA-UGU-CAA-GAC-GCU-GUU-3' (SEQ ID NO: 22) and siRNA 2303 5'-cuc-uuc-cga-ucc-cac-cua-cuu-3' (SEQ ID NO: 23). Negative control siRNA to scrambled GAPDH was from Ambion (Austin, Tex.).

3) Cell Lines and Culture

The prostate cancer cell lines, PC3, PC3M, DU145, ALVA31, LAPC-4, LNCaP, CWR22R and adult human normal prostate epithelial cell line MLC SV40, and BPH-1 were obtained and cultured as described previously (7). Stable cell line CWR22R-RXR, LNCaP-FGF8 were established and cultured as described before (7, 33).

4) Generation of EphB4 Monoclonal Antibody

The extracellular domain (ECD) of EphB4 was cloned into pGEX-4T-1 to generate GST-fused ECD (GST-ECD). EphB4ECD expressed as a GST fusion protein in BL21 *E. coli* was purified by affinity chromatography and the GST domain was cleaved by thrombin. Monoclonal antibody was generated and the sensitivity and specificity of the antibody was reconfirmed by Western blot with whole cell lysate of 293 cells stably transfected with EphB4.

5) One-Step RT-PCR and Quantitative RT-PCR

Total RNA was extracted using RNA STAT-60 (Tel-Test, Inc. Friendswood Tex.) from prostate cancer specimens and adjacent normal specimens. For quantitative RT-PCR first strand cDNA was synthesized from 5 μg of total RNA using SuperScript III (Invitrogen, Carlsbad Calif.). Quantitative RT-PCR was performed on the Stratagene MX3000P system (Stratagene, La Jolla Calif.) using SYBR Green I Brilliant Mastermix (Stragene) according to the manufacture's instructions. Optimized reactions for EphB4 and β-actin (used as the normalizer gene) were 150 nM each of the forward primer (β-actin, 5'-GGA-CCT-GAC-TGA-CTA-CCT-A-3' (SEQ ID NO: 24); EphB4,5'-AAG-GAG-ACC-TTC-ACC-GTC-TT-3' (SEQ ID NO: 25)) and reverse primer (β-actin 5'-TTG-AAG-GTA-GTT-TCG-TGG-AT-3' (SEQ ID NO: 26); EphB4,5'-TCG-AGT-CAG-GTT-CAC-AGT-CA-3' (SEQ ID NO: 27)) with DNA denaturation/activation of polymerase at 95° C. for 10 min followed by 40 cycles of 95° C. for 30 s, 60° C. for 1 min, 72° C. for 1 min. The specificity of the gene-specific amplification was confirmed by the presence of a single dissociation peak. All reactions were performed in triplicate with RT and no template negative controls.

6) Immunohistochemistry

OCT-embedded tissues were sectioned at 5 μm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody. Immunohistochemical staining on prostate array (BioMeda, Foster City, Calif.) was done using goat ABC Staining System (Santa Cruz Biotech.) according to the manufacturer's instructions.

7) Western Blot

Whole cell lysates were prepared using Cell Lysis Buffer (GeneHunter, Basgvukke TN) supplemented with protease inhibitor cocktail (Pierce, Rockford Ill.), unless otherwise noted. Total protein was determined using the DC reagent system (Bio-Rad, Hercules Calif.). Typically, 20 μg whole cell lysate was run on 4-20% Tris-Glycine gradient gel. The samples were electro-transferred to PVDF membrane and the non-specific binding was blocked in TBST buffer (0.5 mM Tris-HCl, 45 mM NaCl, 0.05% Tween-20, pH 7.4) containing 5% non-fat milk. Membranes were first probed with primary antibody overnight, stripped with Restore Western Blot stripping buffer (Pierce, Rockford Ill.) and reprobed with β-actin to confirm equivalent loading and transfer of protein. Signal was detected using SuperSignal West Femto Maximum Sensitivity Substrate (Pierce).

8) Phosphorylation Analysis

Cells growing in 60 mm dishes were either serum starved (1% FBS supplemented RPMI 1640, 24 hours) or cultured in normal conditions (10% FBS) and then treated with or without 1 μg/ml mouse ephrin B2/Fc for 10 min to activate EphB4 receptor Cleared cell lysates were incubated with EphB4 monoclonal antibody overnight at 4° C. Antigen-antibody complex was immunoprecipitated by the addition of 100 μl of Protein G-Sepharose in 20 mM sodium phosphate, pH 7.0 with incubation overnight at 4° C. Immunoprecipitates were analyzed by Western blot with pTyr specific antibody (Upstate, clone 4G10) at 1:1000 dilution followed by incubation with protein G-HRP (Bio-Rad) at 1:5000 dilution. To monitor immunoprecipitation efficiency, a duplicate membrane was probed with EphB4 specific monoclonal antibody.

9) Transient Transfection and Sorting of Transfected Cells

PC3 cells were cotransfected with pMACS 4.1 coding for CD4 and wild type p53 (pC53-SN3) or PTEN vector or both using Lipofectamine 2000 (Invitrogen) according to the manufacturer's instructions. The molar ratio of CD4 to p53 or PTEN or vector was 1:3 and total plasmid was 24 μg for a 10 $cm^2$ dish of 90% confluent cells using 60 μl of Lipofectamine 2000. 24 hours after transfection, a single cell suspension was made and sorted using truncated CD4 as a surface marker according to the manufacturer's protocol (Miltenyi Biotec, Germany). Sorted cells were lysed in 1×SDS sampling buffer and analyzed by Western blot.

10) Study of IGF and EGF Signaling Pathway on the Expression of EphB4

PC3 cells were seeded into 6-well plates and cultured until 80% confluent and treated with 2 μg/ml neutralizing IGF-1R monoclonal antibody, MAB391 (Hailey, et al., 2002, Mol Cancer Ther. 1:1349-1353), or with 1 nM AG 1478, a strong EGFR inhibitor (Liu, et al., 1999, J Cell Sci. 112 (Pt 14): 2409-2417) for 24 h. Crude cell lysates were analyzed by Western blot. Band density was quantified with the Bio-Rad QuantityOne System software.

11) Cell Viability Assay

PC3 cells were seeded on 48-well plates at a density of approximately $1\times10^4$ cells/well in a total volume of 200 ml. Media was changed after the cells were attached and the cells were treated with various concentrations (1-10 μM) of EphB4 antisense ODN or sense ODN as control. After three days media was changed and fresh ODNs added. Following a further 48 h incubation, cell viability was assessed by MTT as described previously (36). EphB4 siRNAs (10-100 nM) were introduced into $2\times10^4$ PC3 cells/well of a 48-well plate using 2 μl of Lipofectamine™ 2000 according to the manufacturer's instructions. 4 h post-transfection the cells were returned to growth media (RPMI 1640 supplemented with 10% FBS). Viability was assayed by MTT 48 h following transfection.

12) Wound Healing Migration Assay

PC3 cells were seeded into 6-well plates and cultured until confluent. 10 mM AS-10 or sense ODN as control were introduced to the wells as described for the viability assay 12 hours before wounding the monolayer by scraping it with a sterile pipette tip. Medium was changed to RPMI 1640 supplemented with 5% FBS and fresh ODNs. Confluent cultures transfected with 50 nM siRNA 472 or GAPDH negative control siRNA 12 hours prior to wounding were also examined. The healing process was examined dynamically and recorded with a Nikon Coolpix 5000 digital camera with microscope adapter.

13) Invasion Assay

PC3 cells were transfected with siRNA 472 or control siRNA using Lipofectamine™ 2000 and 6 hours later $0.5\times10^5$ cells were transferred into 8 μm Matrigel-precoated inserts (BD Bioscience, Palo Alto, Calif.). The inserts were placed in companion wells containing RPMI supplemented with 5% FBS and 5 μg/ml fibronectin as a chemoattractant. Following 22 h incubation the inserts were removed and the noninvading cells on the upper surface were removed by with a cotton swab. The cells on the lower surface of the membrane were fixed in 100% methanol for 15 min, air dried and stained with Giemsa stain for 2 min. The cells were counted in five individual high-powered fields for each membrane under a light microscope. Assays were performed in triplicate for each treatment group.

14) Cell Cycle Analysis

80% confluent cultures of PC3 cells in 6-well plates were transfected with siRNA472 (100 nM) using Lipofectamine™ 2000. 24 hours after transfection, cells were trypsinized, washed in PBS and incubated for 1 h at 4° C. in 1 ml of hypotonic solution containing 50 μg/ml propidium iodide, 0.1% sodium citrate, 0.1 Triton X-100 and 20 μg/ml Dnase-free RnaseA. Cells were analyzed in linear mode at the USC Flow cytometry facility. Results were expressed as percentages of elements detected in the different phases of the cell cycle, namely Sub G0 peak (apoptosis), G0/GC (no DNA synthesis), S (active DNA systhesis), G2 (premitosis) and M (mitosis).

15) Apoptosis ELISA

Apoptosis was studied using the Cell Death Detection ELISAplus Kit (Roche, Piscataway, N.J.) according to the manufacturer's instructions. Briefly, PC3 80% confluent cultures in 24-well plates were transfected using Lipofectamine 2000 with various concentrations (0-100 nM) of siRNA 472 or 100 nM control siRNA. 16 hours later, cells were detached and $1\times10^4$ cells were incubated in 200 μl lysis buffer. Nuclei were pelleted by centrifugation and 20 μl of supernatant containing the mono- or oligonucleosomes was taken for ELISA analysis. Briefly, the supernatant was incubated with anti-histone-biotin and anti-DNA-POD in streptavidin-coated 96-well plate for 2 hours at room temperature. The color was developed with ABST and absorbance at 405 nm was read in a microplate reader (Molecular Devices, Sunnyvale, Calif.).

Example 4

Expression of EPHB4 in Mesothelioma: a Candidate Target for Therapy

Malignant mesothelioma (MM) is a rare neoplasm that most often arises from the pleural and peritoneal cavity serous surface. The pleural cavity is by far the most frequent site affected (>90%), followed by the peritoneum (6-10%) (Carbone et al., 2002, Semin Oncol. 29:2-17). There is a strong association with asbestos exposure, about 80% of malignant mesothelioma cases occur in individuals who have ingested or inhaled asbestos. This tumor is particularly resistant to the current therapies and, up to now, the prognosis of these patients is dramatically poor (Lee et al., 2000, Curr Opin Pulm Med. 6:267-74).

Several clinical problems regarding the diagnosis and treatment of malignant mesothelioma remain unsolved. Making a diagnosis of mesothelioma from pleural or abdominal fluid is notoriously difficult and often requires a thoracoscopic or laproscopic or open biopsy and Immunohistochemical staining for certain markers such as meosthelin expressed preferentially in this tumor. Until now, no intervention has proven to be curative, despite aggressive chemotherapeutic regimens and prolonged radiotherapy. The median survival in most cases is only 12-18 months after diagnosis.

In order to identify new diagnostic markers and targets to be used for novel diagnostic and therapeutic approaches, we assessed the expression of EPHB4 and its ligand EphrinB2 in mesothelioma cell lines and clinical samples.

A. EPHB4 and EphrinB2 is Expressed in Mesothelioma Cell Lines

Figure 33A:
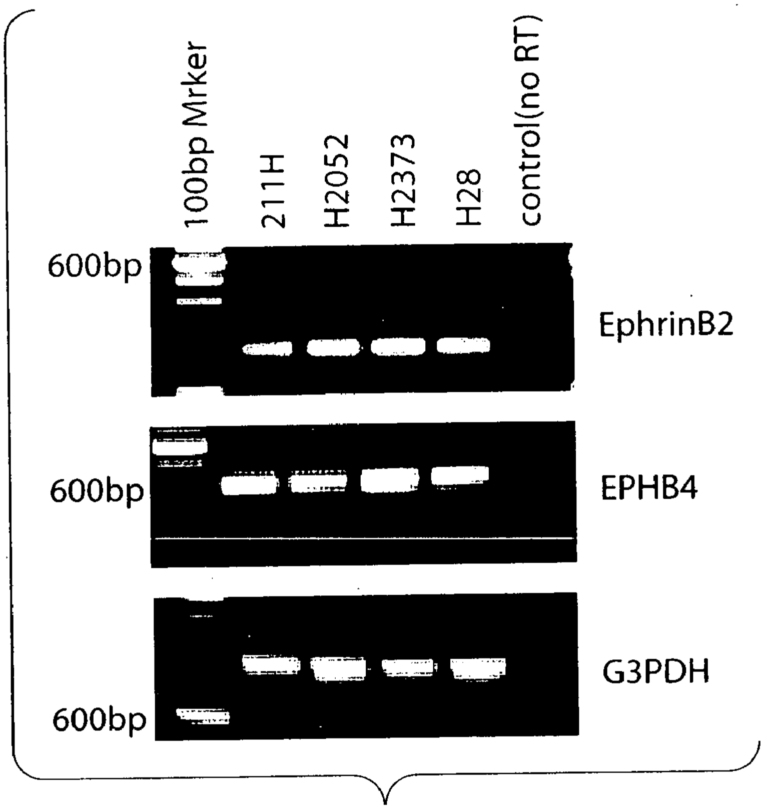
FIG. 33 shows that EphB4 and EphrinB2 are expressed in mesothelioma cell lines as shown by RT-PCR (A) and Western Blot (B).
Figure 33B:
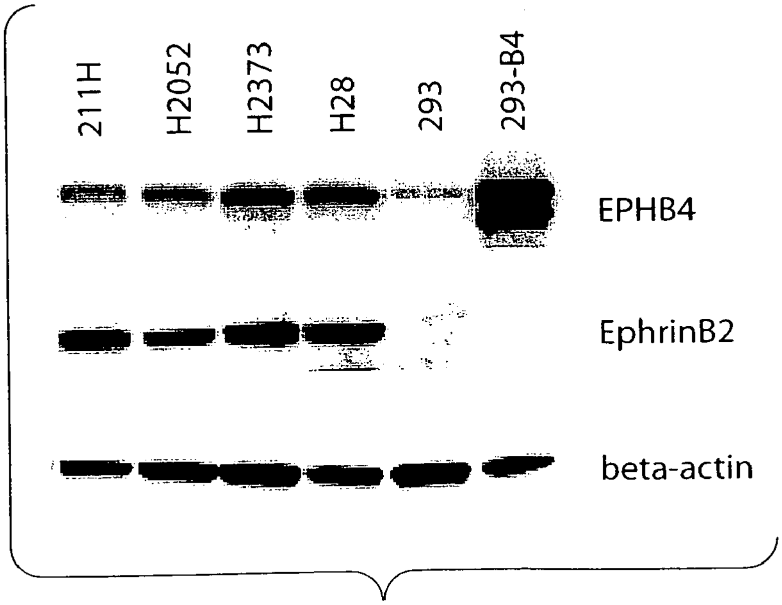

The expression of Ephrin B2 and EphB4 in malignant mesothelioma cell lines was determined at the RNA and protein level by a variety of methods. RT-PCR showed that all of the four cell lines express EphrinB2 and EPHB4 (FIG. 33A). Protein expression was determined by Western blot in these cell lines. Specific bands for EphB4 were seen at 120 kD. In addition, Ephrin B2 was detected in all cell lines tested as a 37 kD band on Western blot (FIG. 33B). No specific band for Ephrin B2 was observed in 293 human embryonic kidney cells, which were included as a negative control.

Figure 34:
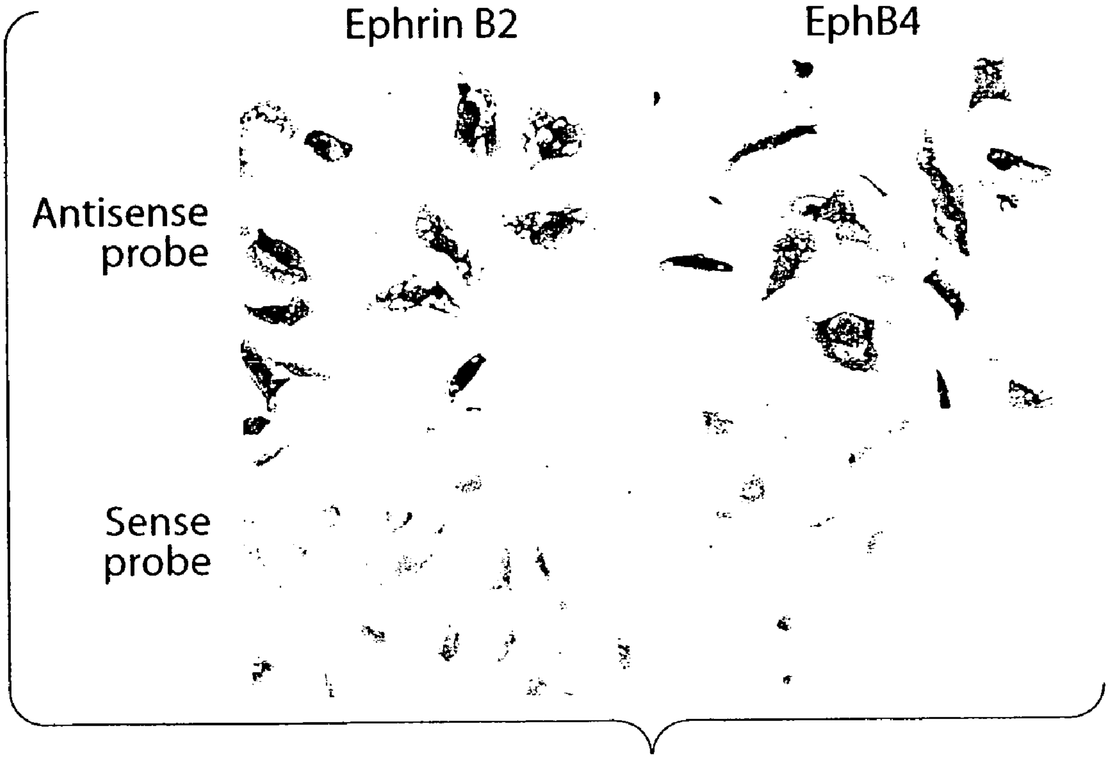
FIG. 34 shows expression of ephrin B2 and EphB4 by in situ hybridization in mesothelioma cells. NCI H28 mesothelioma cell lines cultured in chamber slides hybridized with antisense probe to ephrin B2 or EphB4 (top row). Control for each hybridization was sense (bottom row). Positive reaction is dark blue cytoplasmic stain.
Figure 35:
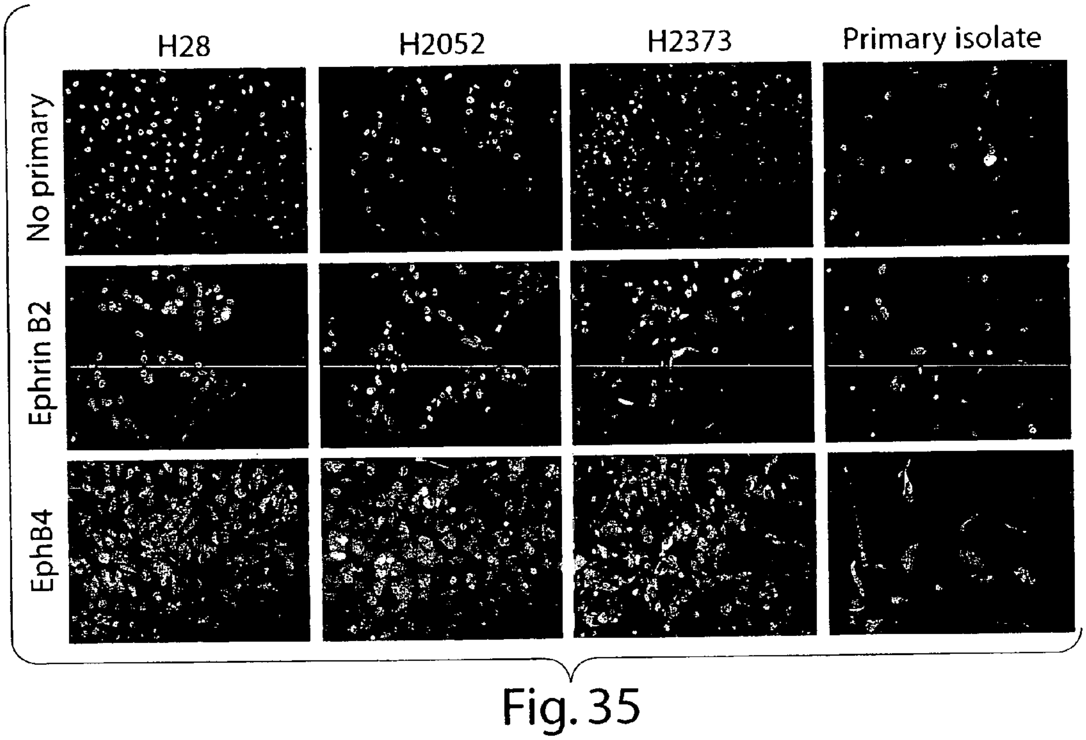
FIG. 35 shows cellular expression of EphB4 and ephrin B2 in mesothelioma cultures. Immunofluorescence staining of primary cell isolate derived from pleural effusion of a patient with malignant mesothelioma and cell lines NCI H28, NCI H2373, and NCI H2052 for ephrin B2 and EphB4. Green color is positive signal for FITC labeled secondary antibody. Specificity of immunofluorescence staining was demonstrated by lack of signal with no primary antibody (first row). Cell nuclei were counterstained with DAPI (blue color) to reveal location of all cells. Shown are merged images of DAPI and FITC fluorescence. Original magnification 200×.

To confirm the presence of EphB4 transcription in mesothelioma cells, in situ hybridization was carried out on NCI H28 cell lines cultured on chamber slides. Specific signal for EphB4 was detected using antisense probe Ephrin B2 transcripts were also detected in the same cell line. Sense probes for both EphB4 and Ephrin B2 served as negative controls and did not hybridize to the cells (FIG. 34). Expression of EphB4 and Ephrin B2 proteins was confirmed in the cell lines by immunofluorescence analysis (FIG. 35). Three cell lines showed strong expression of EphB4, whereas expression of Ephrin B2 was present in H28 and H2052, and weakly detectable in H2373.

B. Evidence of Expression of EPHB4 and EphrinB2 in Clinical Samples

Figure 36:
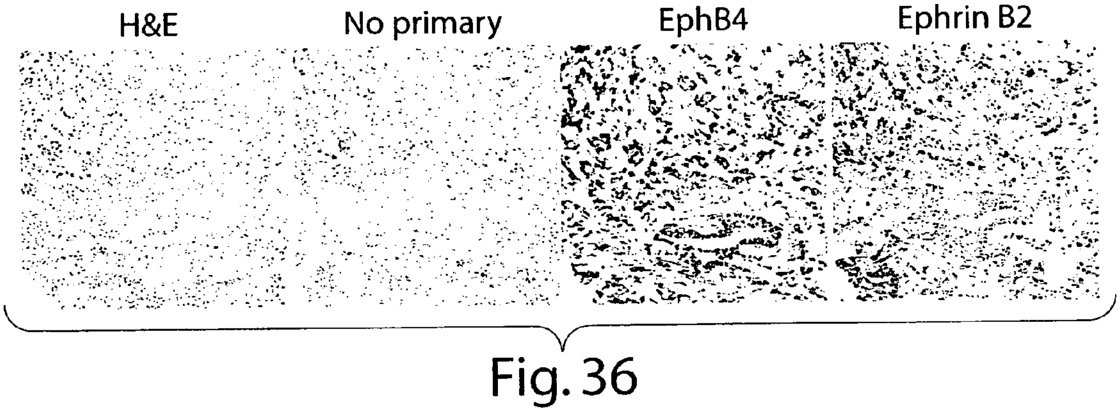
FIG. 36 shows expression of ephrin B2 and EphB4 in mesothelioma tumor. Immunohistochemistry of malignant mesothelioma biopsy. H&E stained section reveals tumor architecture; bottom left panel is background control with no primary antibody. EphB4 and ephrin B2 specific staining is brown color. Original magnification 200×.

Tumor cells cultured from the pleural effusion of a patient diagnosed with pleural malignant mesothelioma were isolated and showed positive staining for both EphB4 and Ephrin B2 at passage 1 (FIG. 35, bottom row). These results confirm co-expression of EphB4 and Ephrin B2 in mesothelioma cell lines. To determine whether these results seen in tumor cell lines were a real reflection of expression in the disease state, tumor biopsy samples were subjected to immunohistochemical staining for EphB4 and Ephrin B2. Antibodies to both proteins revealed positive stain in the tumor cells. Representative data is shown in FIG. 36.

C. EPHB4 is Involved in the Cell Growth and Migration of Mesothelioma

Figure 37A:
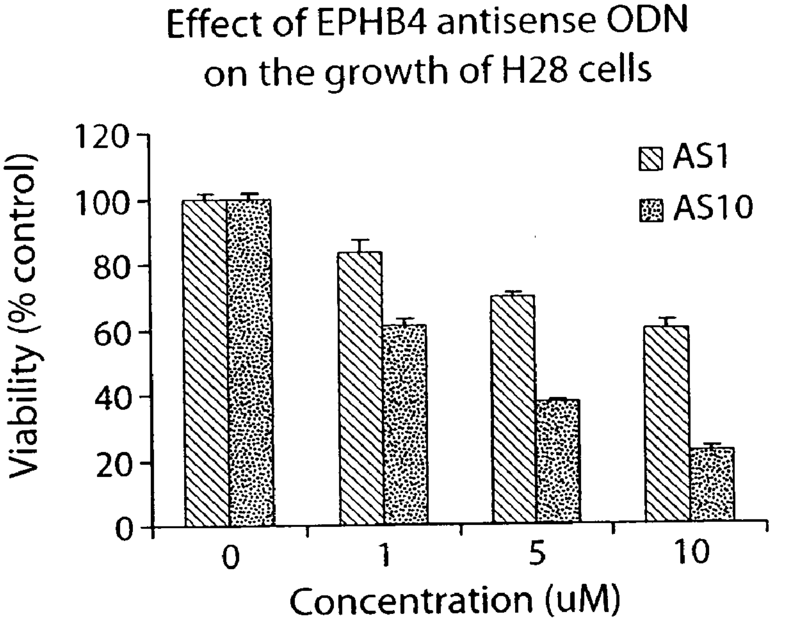
FIG. 37 shows effects of EPHB4 antisense probes (A) and EPHB4 siRNAs (B) on the growth of H28 cells.
Figure 37B:
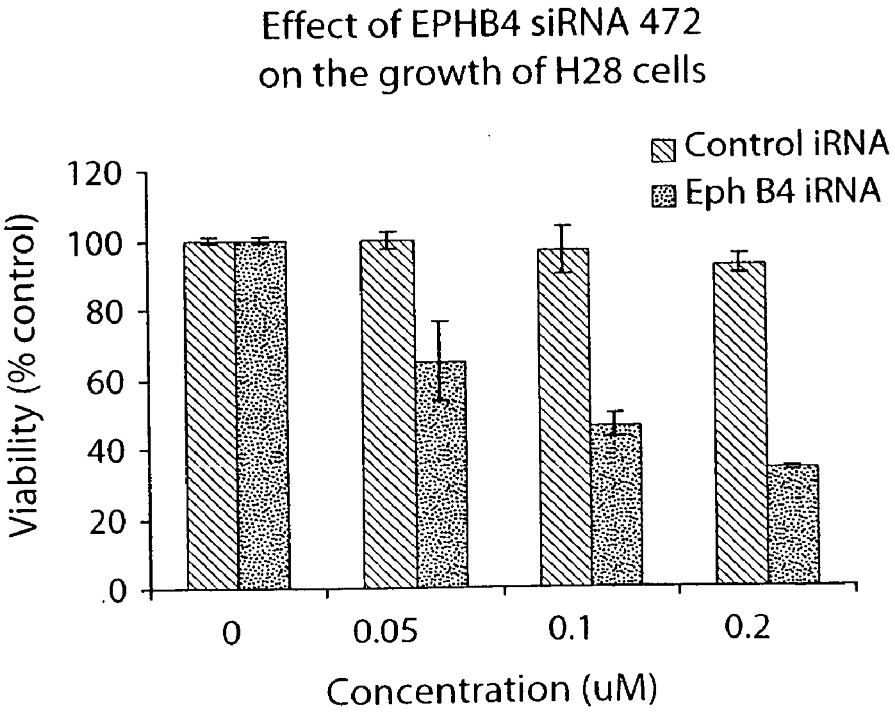

The role of EphB4 in cell proliferation was tested using EPHB4 specific antisepses oligonucleotides and siRNA. The treatment of cultured H28 with EPHB4 antisense reduced cell viability. One of the most active inhibitor of EphB4 expression is EPHB4AS-10 (FIG. 37A). Transfection of EPHB4 siRNA 472 generated the same effect (FIG. 37B).

Figure 38A:
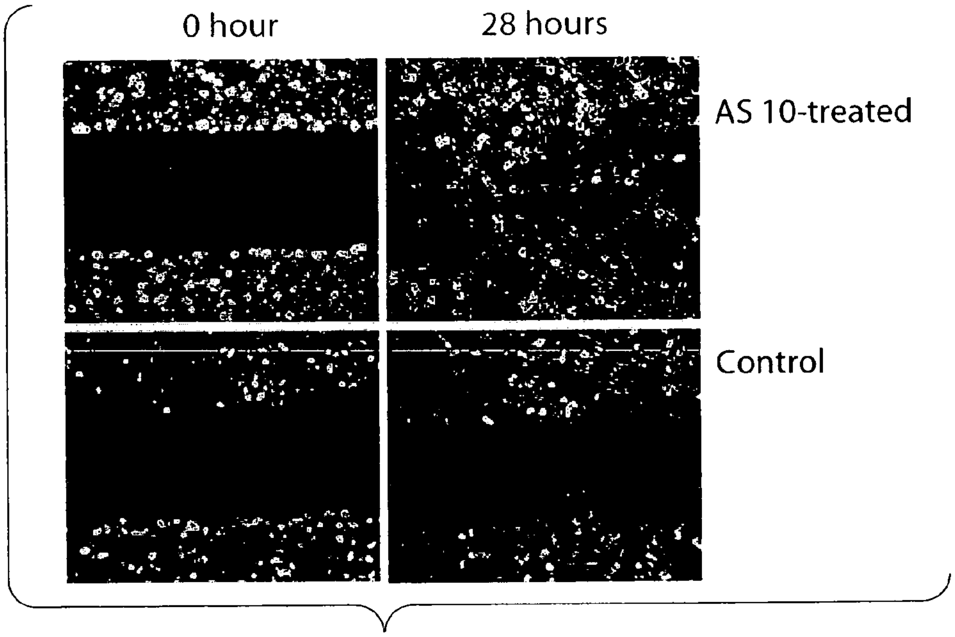
FIG. 38 shows effects of EPHB4 antisense probes (A) and EPHB4 siRNAs (B) on cell migration.
Figure 38B:
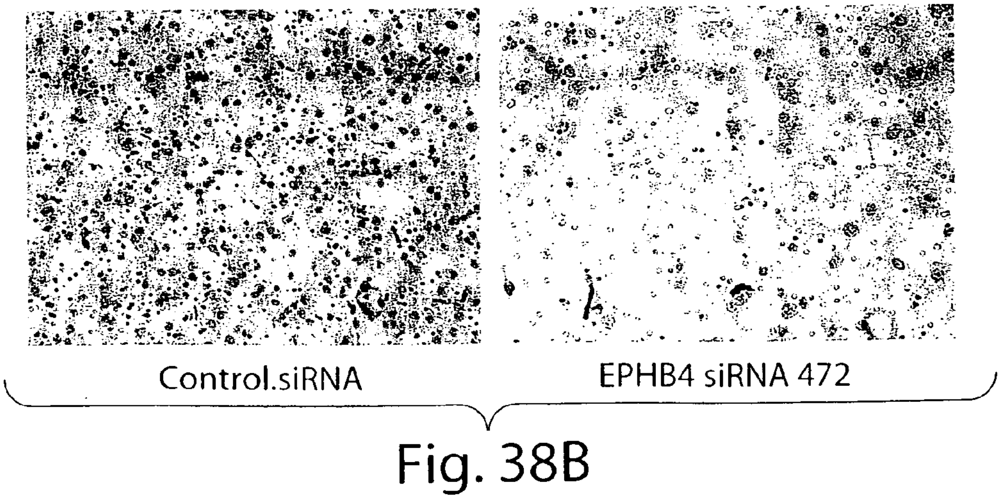

MM is a locally advancing disease with frequent extension and growth into adjacent vital structures such as the chest wall, heart, and esophagus. In an effort to study this process in vitro, we perform wound healing assay using previously described techniques (3:36). When a wound was introduced into sub confluent H28 cells, over the course of the next 28 hours cells would progressively migrate into the area of the wound. However, when cells were pretreated with EPHB4AS-10 for 24 hours, and the wound was introduced, this migration was virtually completely prevented (FIG. 38A). The migration study with Boyden Chamber assay with EPHB4 siRNA showed that cell migration was greatly inhibited with the inhibition of EPHB4 expression (FIG. 38B).

D. Materials and Methods

1) Cell Lines and Reagents

NCI H28, NCI H2052, NCI H2373, MSTO 211H mesothelioma cell lines and 293 human embryonic kidney cells were obtained from the ATCC (Manassas, Va.). Cells were maintained in RPMI 1640 media supplemented with 10% heat-inactivated fetal bovine serum (FBS; Life Technologies, Gaithersburg, Md.) and antibiotics. Primary cells were obtained from pleural effusion of patients with mesothelioma. A large number of EPHB4 phosphorothioate modified antisense oligonucleotides were synthesized. Similarly a number of EphB4 specific siRNAs were generated. Monoclonal antibody produced against EPHB4 was used for western blot. Polyclonal antibody against EphrinB2 and EPHB4 (C-16) (for immunohistochemical staining) was from Santa Cruz.

2) RT-PCR

Total RNA was reversed transcribed by use of random hexamers (Invitrogen). Primers for EphB4 and EphrinB2 were designed with Primer 3 software. The sequences for all primers are as follows: EPHB4 forward primer and EPHB4 reverse primer (see, e.g., in Example 2); EphrinB2 forward primer and EphrinB2 reverse primer (see, e.g., in Example 6); G3PDH forward primer, 5'-GGAGCCAAAAGGGTCATCAT-3' (SEQ ID NO: 28); G3PDH reverse primer, 5'-GGCATTGCTGCAAAGAAAGAG-3' (SEQ ID NO: 29); Clonetics kit was used for PCR. PCRs were performed with the ABI PCR System 2700 (Applied Biosystem). The PCR conditions were 95° C. for 5 min, followed by 35 cycles of 95° C. for 30 seconds, 60° C. for 30 seconds and 72° C. for 1 min.

3) Preparation of Digoxigenin-Labeled RNA Probes

Ephrin-B2 and EphB4 PCR products were cloned using the pGEM-T Easy System (Promega, Madison Wis.) according to the manufacturer's description. The primers and PCR products were 5'-tccgtgtggaagtactgctg-3' (SEQ ID NO: 30) (forward), 5'-tctggtttggcacagttgag-3' (SEQ ID NO: 31) (reverse), for ephrin-B2 that yielded a 296-bp product and 5'-ctttggaagagaccctgctg-3' (SEQ ID NO: 32) (forward), 5'-agacggtgaaggtctccttg-3' (SEQ ID NO: 33), for EphB4 that yielded a 297-bp product. The authenticity and insert orientation were confirmed by DNA sequencing.

The pGEM-T Easy plasmids containing the PCR product of the human ephrin-B2 or EphB4 gene were linearized with Spe I or Nco I. Antisense or sense digoxigenin (DIG)-labeled RNA probes were transcribed from T7 or SP6 promoters by run-off transcription using a DIG RNA labeling kit (Roche, Indianapolis Ind.). RNA probes were quantitated by spot assay as described in the DIG RNA labeling kit instructions.

4) In Situ Hybridization

Cells were cultured in Labtech II 4-well chamber slides (Nalge Nunc International, Naperville, Ill.). Cells were washed in PBS (37° C.), then fixed for 30 min at 25° C. in a solution of 4% (w/v) formaldehyde, 5% (v/v) acetic acid, and 0.9% (w/v) NaCl. After fixation, slides were rinsed with PBS and stored in 70% ethanol at 4° C. until further use. Before in situ hybridization, cells were dehydrated, washed in 100% xylene to remove residual lipid and then rehydrated, finally in PBS. Cells were permeabilized by incubating at 37° C. with 0.1% (w/v) pepsin in 0.1 N HCl for 20 min and post-fixed in 1% formaldehyde for 10 min. Prehybridization was performed for 30 min at 37° C. in a solution of 4×SSC containing 50% (v/v) deionized formamide. Slides were hybridized overnight at 42° C. with 25 ng antisense or sense RNA probes in 40% deionized formamide, 10% dextran sulfate, 1× enhardt's solution, 4×SSC, 10 mM DTT, 1 mg/ml yeast t-RNA and 1 mg/ml denatured and sheared salmon sperm DNA in a total volume of 40 μl. Slides were then washed at 37° C. as follows: 2×15 min with 2×SSC, 2×15 min with 1×SSC, 2×15 min with 0.5×SSC and 2×30 min with 0.2× SSC. Hybridization signal was detected using alkaline-phosphatase-conjugated anti-DIG antibodies (Roche) according to the manufacturer's instructions. Color development was stopped by two washes in 0.1 M Tris-HCl, 1 mM EDTA, pH 8.0 for 10 min. Cells were visualized by counterstaining of nucleic acids with Nuclear Fast Red (Vector Laboratories, Burlingame, Calif.) and the slides were mounted with IMMU-MOUNT (Shandon, Astmoor UK).

5) Western Blot

Crude cell lysates were prepared by incubation in cell lysis buffer (10 mM Tris, pH 7.5, 1 mM EDTA, 150 mM NaCl, 1% Triton X-100, 1 mM DTT, 10% glycerol). Lysates were cleared by centrifugation at 10,000×g for 10 min. Total protein was determined by Bradford assay (Bio-Rad). Samples (20 μg protein) were fractionated on a 4-20% Tris-glycine polyacrylamide gel and transferred to polyvinylidene difluoride (PVDT) membrane (Bio-Rad) by electroblotting. Membranes were blocked with 5% non-fat milk prior to incubation with antibody to EphB4 (1:5000 dilution) at 4° C., for 16 h. Secondary antibody (1:100,000 dilution) conjugated with horseradish peroxidase was applied for 1 h at 25° C. The membranes were developed using the SuperSignal West Femto Maximum sensitivity chemiluminescent substrate (Pierce, Rockford, Ill.) according to the manufacturer's instructions.

6) Immunohistochemistry

Formalin-fixed tissue sections were deparaffinized and incubated with 10% goat serum at −70° C. for 10 minutes and incubated with the primary rabbit antibodies against either Ephrin B2 or EphB4 (Santa Cruz Biotechnologies; 1:100) at 4° C. overnight. Isotype-specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with H&E.

7) Immunofluorescence Studies

Cells were cultured on Labtech II 4-well chamber slides and fixed in 4% parafomaldehyde in Dulbecco's phosphate buffered saline pH 7.4 (PBS) for 30 min. The slides were rinsed twice in PBS and preincubated with blocking buffer (0.2% Triton-X100, 1% BSA in PBS) for 20 min. The slides were then incubated with antibodies to EphB4 or ephrin B2 (1:100 dilution in PBS) in blocking buffer at 4° C. for 16 hr. After washing three times, the slides were incubated with the appropriate fluorescein-conjugated secondary antibodies (Sigma-Aldrich, St. Louis, Mo.). Nuclei were counterstained with 4',6-diamidino-2-phenylindole dihydrochloride hydrate (DAPI), washed extensively with PBS and mounted with Vectasheild antifade mounting solution (Vector Laboratories). Images were obtained using an Olympus AX70 fluorescence microscope and Spot v2.2.2 (Diagnostic Instruments Inc., Sterling Heights, Mich.) digital imaging system.

8) Cell Viability Assay

Cells were seeded at a density of $5\times10^3$ per well in 48-well plates on day 0 in appropriate growth media containing 2% fetal calf serum (FCS). On the following day, the media was changed and cells were treated with various concentrations (1-10 μM) of EphB4 Antisense. On day 4, viability was assessed using 3-(4,5-dimethylthiazol-2-yl)-2,5-diphenyltetrazolium bromide (MTT) at a final concentration of 0.5 mg/ml. Cells were incubated for 2 hr, medium was aspirated, and the cells were dissolved in acidic isopropanol (90% isopropanol, 0.5% SDS and 40 mM HCl). Optical density was read in an ELISA reader at 490 nm using isopropanol as blank (Molecular Devices, CA).

9) Cell Migration

In vitro wound healing assay was adopted. Briefly, cells were seeded onto 6-cm plates in full culture media for 24 hours, and then switched to medium containing 5% FBS. EPHB4 antisense 10 (10 μM) was also added to treated well. 24 hours later, wounds were made using the tip of a p-200 pipette man; a line was drawn through the middle of the plates. The plate was photographed at 0, 12, 24 hours. The experiment was repeated three times.

Example 5

EphB4 is Expressed in Squamous Cell Carcinoma of the Head and Neck: Regulation by Epidermal Growth Factor Signaling Pathway and Growth Advantage Squamous cell carcinoma of the head and neck (HNSCC) is the sixth most frequent cancer worldwide, with estimated 900,000 cases diagnosed each year. It comprises almost 50% of all malignancies in some developing nations. In the United States, 50,000 new cases and 8,000 deaths are reported each year. Tobacco carcinogens are believed to be the primary etiologic agents of the disease, with alcohol consumption, age, gender, and ethnic background as contributing factors.

The differences between normal epithelium of the upper aerodigestive tract and cancer cells arising from that tissue are the result of mutations in specific genes and alteration of their expression. These genes control DNA repair, proliferation, immortalization, apoptosis, invasion, and angiogenesis. For head and neck cancer, alterations of three signaling pathways occur with sufficient frequency and produce such dramatic phenotypic changes as to be considered the critical transforming events of the disease. These changes include mutation of the p53 tumor suppressor, overexpression of epidermal growth factor receptor (EGFR), and inactivation of the cyclin dependent kinase inhibitor p16. Other changes such as Rb mutation, ras activation, cyclin D amplification, and myc overexpression are less frequent in HNSCC.

Although high expression of EphB4 has been reported in hematologic malignancies, breast carcinoma, endometrial carcinoma, and colon carcinoma, there is limited data on the protein levels of EphB4, and complete lack of data on the biological significance of this protein in tumor biology such as HNSCC.

A. HNSCC Tumors Express EphB4

Figure 39A:
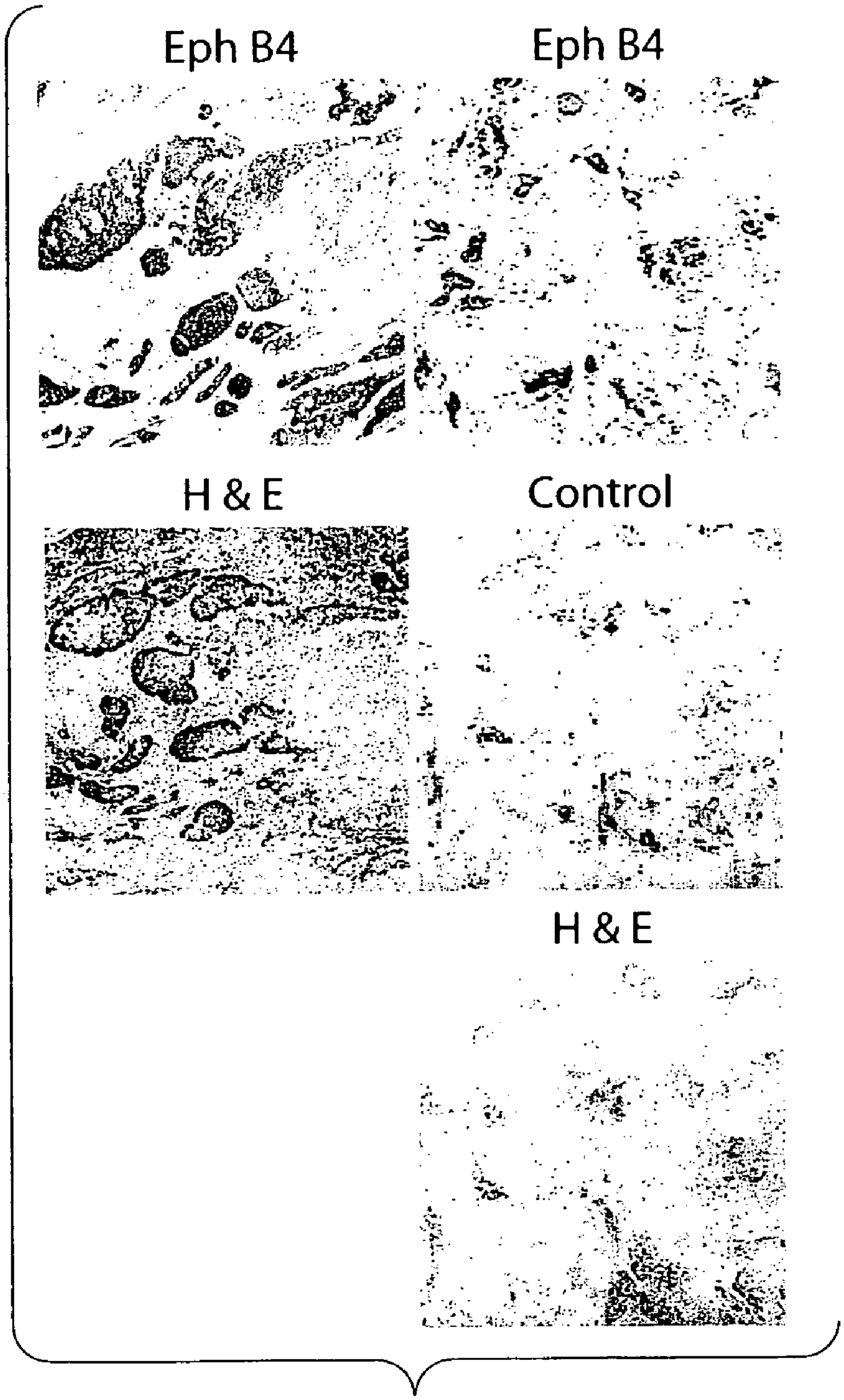
FIG. 39 shows that EphB4 is expressed in HNSCC primary tissues and metastases. A) Top: Immunohistochemistry of a representative archival section stained with EphB4 monoclonal antibody as described in the methods and visualized with DAB (brown color) localized to tumor cells. Bottom: Hematoxylin and Eosin (H&E) stain of an adjacent section. Dense purple staining indicates the presence of tumor cells. The right hand column are frozen sections of lymph node metastasis stained with EphB4 polyclonal antibody (top right) and visualized with DAB. Control (middle) was incubation with goat serum and H&E (bottom) reveals the location of the metastatic foci surrounded by stroma which does not stain. B) In situ hybridization of serial frozen sections of a HNSCC case probed with EphB4 (left column) and ephrin B2 (right column) DIG labeled antisense or sense probes generated by run-off transcription. Hybridization signal (dark blue) was detected using alkaline-phosphatase-conjugated anti-DIG antibodies and sections were counterstained with Nuclear Fast Red. A serial section stained with H&E is shown (bottom left) to illustrate tumor architecture. C) Western blot of protein extract of patient samples consisting of tumor (T), uninvolved normal tissue (N) and lymph node biopsies (LN). Samples were fractionated by polyacrylamide gel electrophoresis in 4-20% Tris-glycine gels and subsequently electroblotted onto nylon membranes. Membranes were sequentially probed with EphB4 monoclonal antibody and β-actin MoAb. Chemiluminescent signal was detected on autoradiography film. Shown is the EphB4 specific band which migrated at 120 kD and β-actin which migrated at 40 kD. The β-actin signal was used to control for loading and transfer of each sample.

We studied the expression of EphB4 in human tumor tissues by immunohistochemistry, in situ hybridization, and Western blot. Twenty prospectively collected tumor tissues following IRB approval have been evaluated with specific EphB4 monoclonal antibody that does not react with other members of the EphB and EphA family. EphB4 expression is observed in all cases, with varying intensity of staining. FIG. 39A (top left) illustrates a representative case, showing that EphB4 is expressed in the tumor regions only, as revealed by the H&E tumor architecture (FIG. 39A bottom left). Note the absence of staining for EphB4 in the stroma. Secondly, a metastatic tumor site in the lymph node shows positive staining while the remainder of the lymph node is negative (FIG. 39A, top right).

Figure 39B:
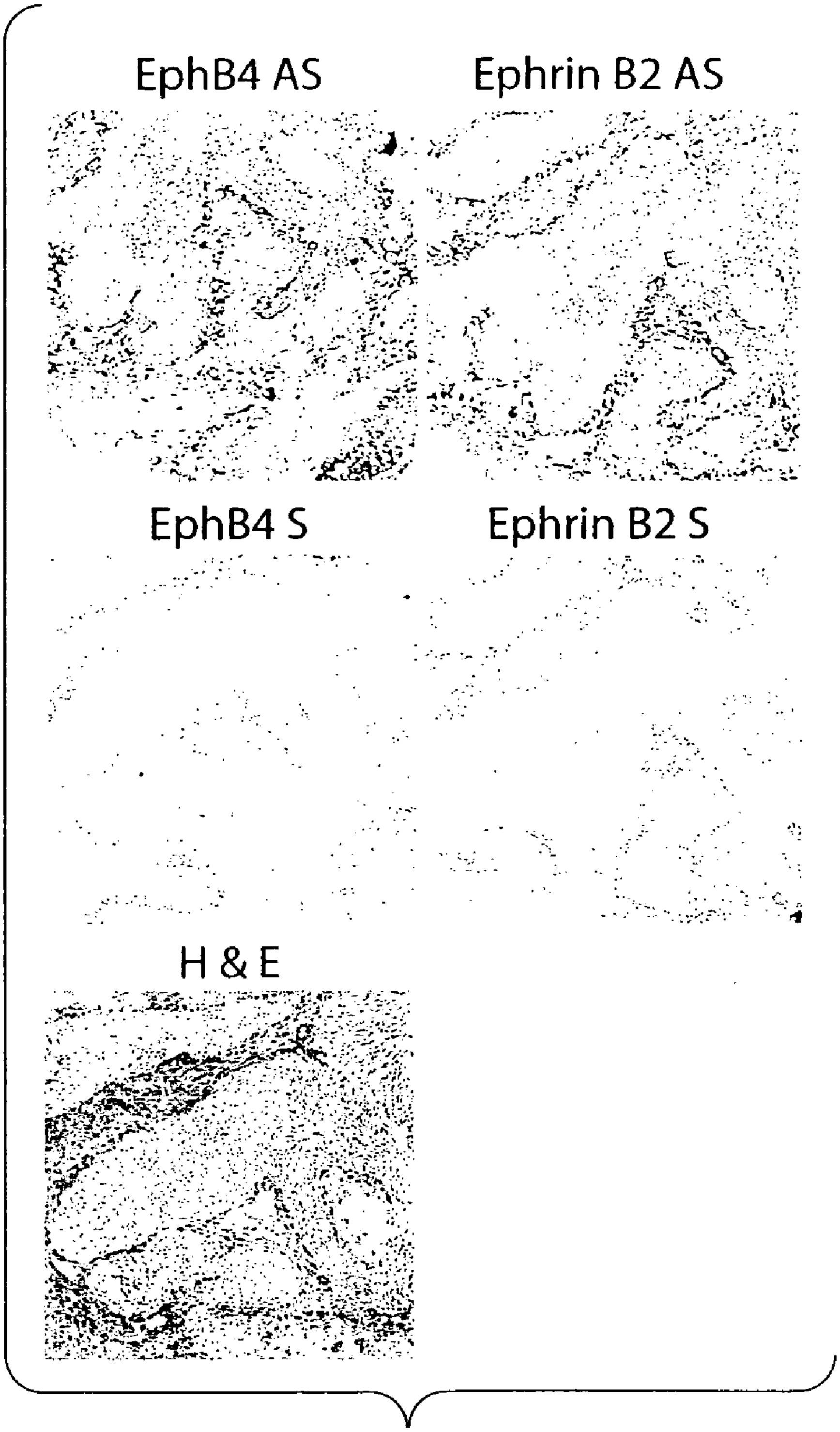

In situ hybridization was carried out to determine the presence and location of EphB4 transcripts in the tumor tissue. Strong signal for EphB4 specific antisense probe was detected indicating the presence of transcripts (FIG. 39 B, top left). Comparison with the H&E stain (FIG. 39B, bottom left) to illustrate tumor architecture reveals that the signal was localized to the tumor cells, and was absent from the stromal areas. Ephrin B2 transcripts were also detected in tumor sample, and as with EphB4, the signal was localized to the tumor cells (FIG. 39B, top right). Neither EphB4 nor ephrin B2 sense probes hybridized to the sections, proving specificity of the signals.

B. High Expression of EphB4 in Primary and Metastatic Sites of HNSCC

Figure 39C:
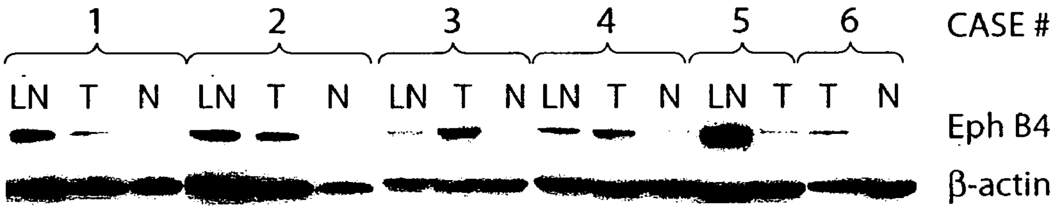

Western blots of tissue from primary tumor, lymph node metastases and uninvolved tissue were carried out to determine the relative levels of EphB4 expression in these sites. Tumor and normal adjacent tissues were collected on 20 cases, while lymph nodes positive for tumor were harvested in 9 of these 20 cases. Representative cases are shown in FIG. 39C. EphB4 expression is observed in each of the tumor samples. Similarly, all tumor positive lymph nodes show EphB4 expression that was equal to or greater than the primary tumor. No or minimal expression is observed in the normal adjacent tissue.

C. EphB4 Expression and Regulation by EGFR Activity in HNSCC Cell Lines

Figure 40A:
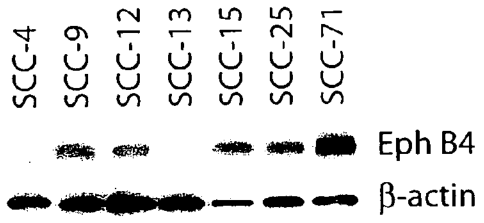
FIG. 40 shows that EphB4 is expressed in HNSCC cell lines and is regulated by EGF: A) Survey of EphB4 expression in SCC cell lines. Western blot of total cell lysates sequentially probed with EphB4 monoclonal antibody, stripped and reprobed with β-actin monoclonal antibody as described for FIG. 39C. B) Effect of the specific EGFR inhibitor AG1478 on EphB4 expression: Western blot of crude cell lysates of SCC15 treated with 0-1000 nM AG 1478 for 24 h in media supplemented with 10% FCS (left) or with 1 mM AG 1478 for 4, 8, 12 or 24 h (right). Shown are membranes sequentially probed for EphB4 and β-actin. C) Effect of inhibition of EGFR signaling on EphB4 expression in SCC cell lines: Cells maintained in growth media containing 10% FCS were treated for 24 hr with 1 μM AG 1478, after which crude cell lysates were analyzed by Western blots of cell lysates sequentially probed with for EGFR, EphB4, ephrin B2 and β-actin antibodies. Specific signal for EGFR was detected at 170 kD and ephrin B2 at 37 kD in addition to EphB4 and β-actin as described in FIG. 1C. β-actin serves as loading and transfer control.
Figure 40B:
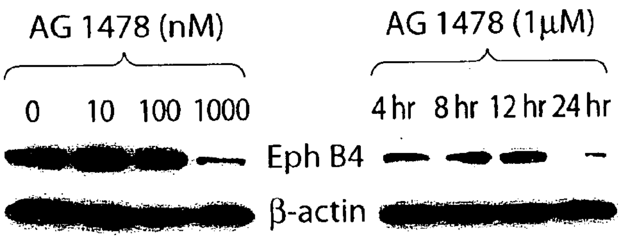
Figure 40C:
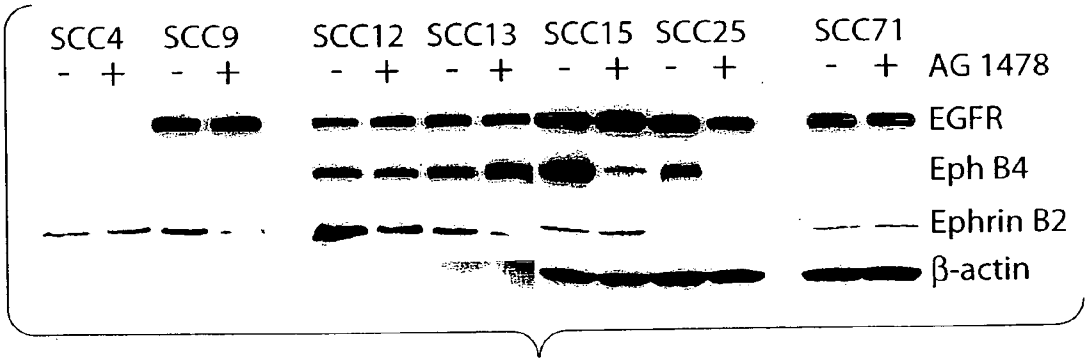

Having demonstrated the expression of EphB4 limited to tumor cells, we next sought to determine whether there was an in vitro model of EphB4 expression in HNSCC. Six HN SCC cell lines were surveyed for EphB4 protein expression by Western Blot (FIG. 40A). A majority of these showed strong EphB4 expression and thus established the basis for subsequent studies. Since EGFR is strongly implicated in HNSCC we asked whether EphB4 expression is associated with the activation of EGFR. Pilot experiments in SCC-15, which is an EGFR positive cell line, established an optimal time of 24 h and concentration of 1 mM of the specific EGFR kinase inhibitor AG 1478 (FIG. 40B) to inhibit expression of EphB4. When all the cell lines were studied, we noted robust EGFR expression in all but SCC-4, where it is detectable but not strong (FIG. 40C, top row). In response to EGFR inhibitor AG1478 marked loss in the total amount of EphB4 was observed in certain cell lines (SCC-15, and SCC-25) while no effect was observed in others (SCC-9, -12, -13 and -71). Thus SCC-15 and -25 serve as models for EphB4 being regulated by EGFR activity, while SCC-9, -12, -13 and -71 are models for regulation of EphB4 in HNSCC independent of EGFR activity, where there may be input from other factors such as p53, PTEN, IL-6 etc. We also noted expression of the ligand of EphB4, namely ephrin B2, in all of the cell lines tested. As with EphB4 in some lines ephrin B2 expression appears regulated by EGFR activity, while it is independent in other cell lines.

Figure 41A:
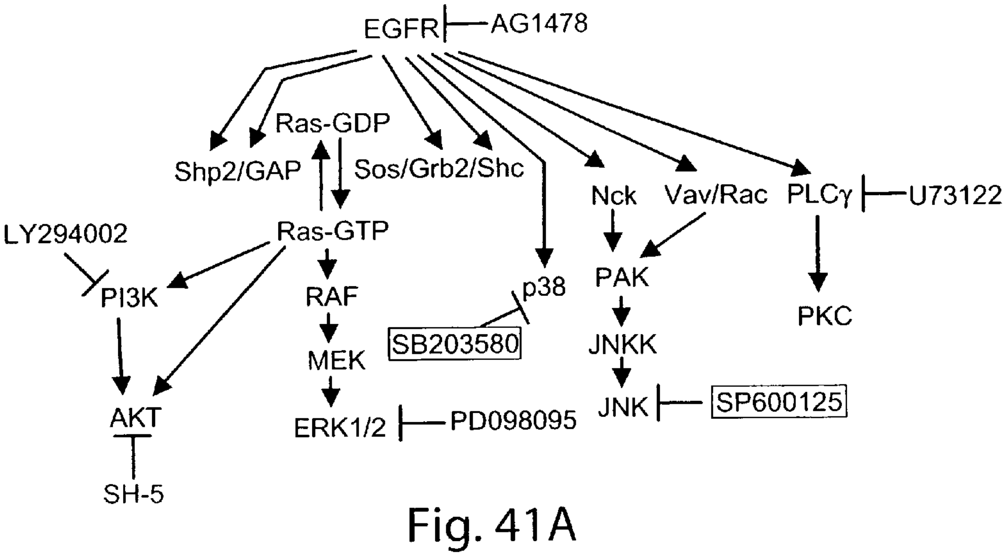
FIG. 41 shows mechanism of regulation of EphB4 by EGF: A) Schematic of the EGFR signaling pathways, showing in red the sites of action and names of specific kinase inhibitors used. B) SCC15 cells were serum-starved for 24 h prior to an additional 24 incubation as indicated with or without EGF (10 ng/ml), 3 μM U73122, or 5 μM SH-5, 5 μM SP600125, 25 nM LY294002, -- μM PD098095 or 5 μM SB203580. N/A indicates cultures that received equal volume of diluent (DMSO) only. Cell lysates were subjected to Western Blot with EphB4 monoclonal antibody. β-actin signal serves as control of protein loading and transfer.
Figure 41B:
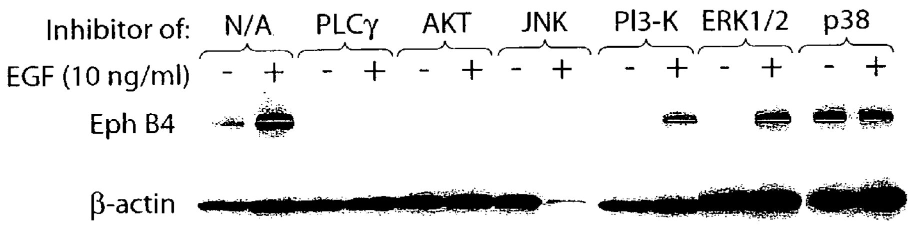

Clearly, inhibition of constitutive EGFR signaling repressed EphB4 levels in SCC15 cells. We next studied whether EGF could induce EphB4. We found that EphB4 levels were induced in SCC15 cells that had been serum starved for 24 h prior to 24 h treatment with 10 ng/ml EGF as shown in FIG. 41B (lanes 1 and 2). The downstream signaling pathways known for EGFR activation shown in FIG. 41A, (for review see Yarden & Slikowski 2001) were then investigated for their input into EGF mediated induction of EphB4. Blocking PLCg, AKT and JNK phosphorylation with the specific kinase inhibitors U73122, SH-5 and SP600125 respectively reduced basal levels and blocked EGF stimulated induction of EphB4 (FIG. 41B, lanes 3-8). In contrast, inhibition of ERK1/2 with PD098095 and PI3-K with LY294002 or Wortmannin had no discernible effect on EGF induction of EphB4 levels. However, basal levels of EphB4 were reduced when ERK1/2 phosphorylation was inhibited. Interestingly, inhibition of p38 MAPK activation with SB203580 increased basal, but not EGF induced EphB4 levels. Similar results were seen in the SCC25 cell line (data not shown).

Figure 42A:
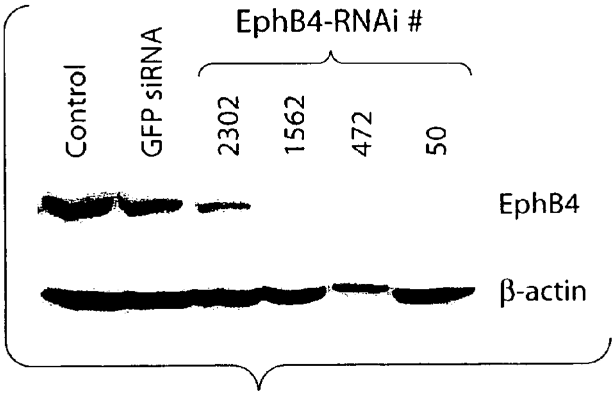
FIG. 42 shows that specific EphB4 siRNAs inhibit EphB4 expression, cell viability and cause cell cycle arrest. A) 293 cells stably expressing full length EphB4 were transfected with 50 nM RNAi using Lipofectamine™2000. 40 h post-transfection cells were harvested, lysed and processed for Western blot. Membranes were probed with EphB4 monoclonal antibody, stripped and reprobed with β-actin monoclonal antibody as control for protein loading and transfer. Negative reagent control was RNAi to scrambled green fluorescence protein (GFP) sequence and control is transfection with Lipofectamine™2000 alone. B) MTT cell viability assays of SCC cell lines treated with siRNAs for 48 h as described in the Methods section. Shown is mean±s.e.m. of triplicate samples. C) SCC15 cells transfected with siRNAs as indicated were analyzed 24 h post transfection for cell cycle status by flow cytometry as described in the Methods. Shown are the plots of cell number vs. propidium iodide fluorescence intensity. Top and middle row show plots for cells 16 h after siRNA transfection, bottom row shows plots for cells 36 h post transfection. Specific siRNA and concentration are indicated for each plot. Lipo=LIPOFECTAMINE™200 mock transfection.
Figure 42B:
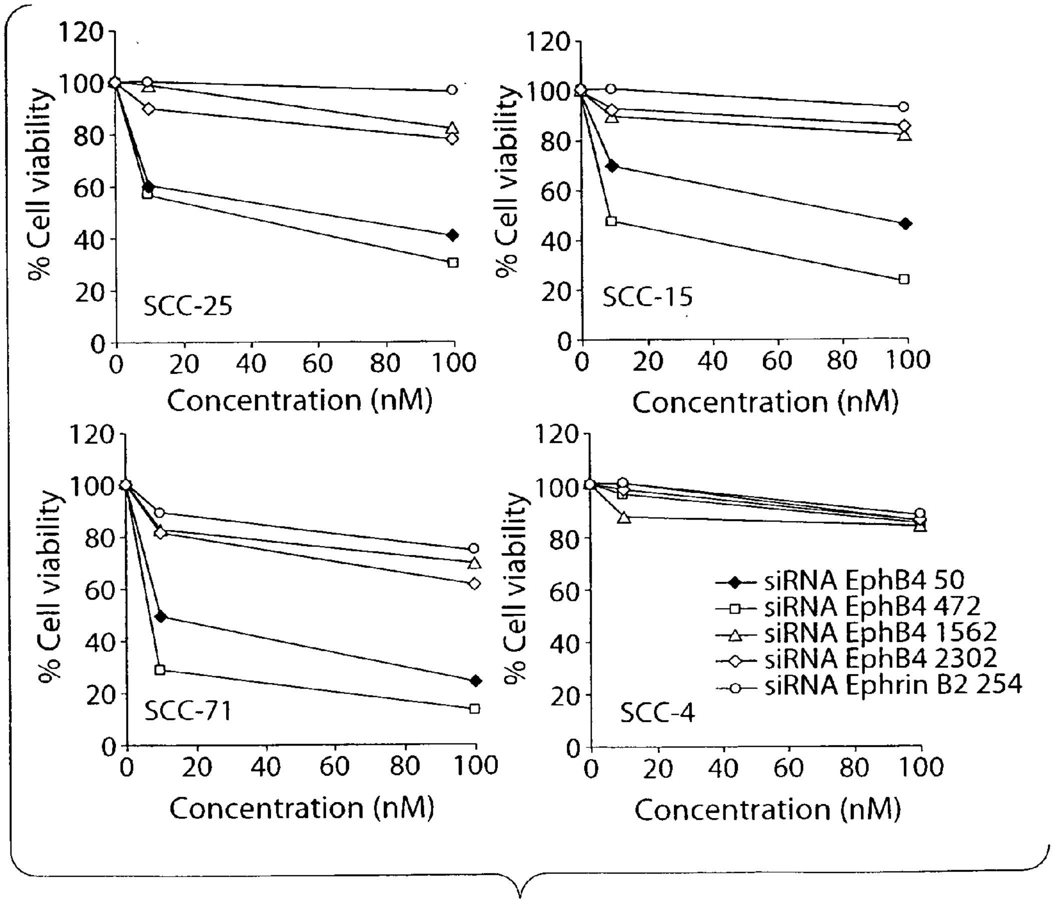
Figure 42C:
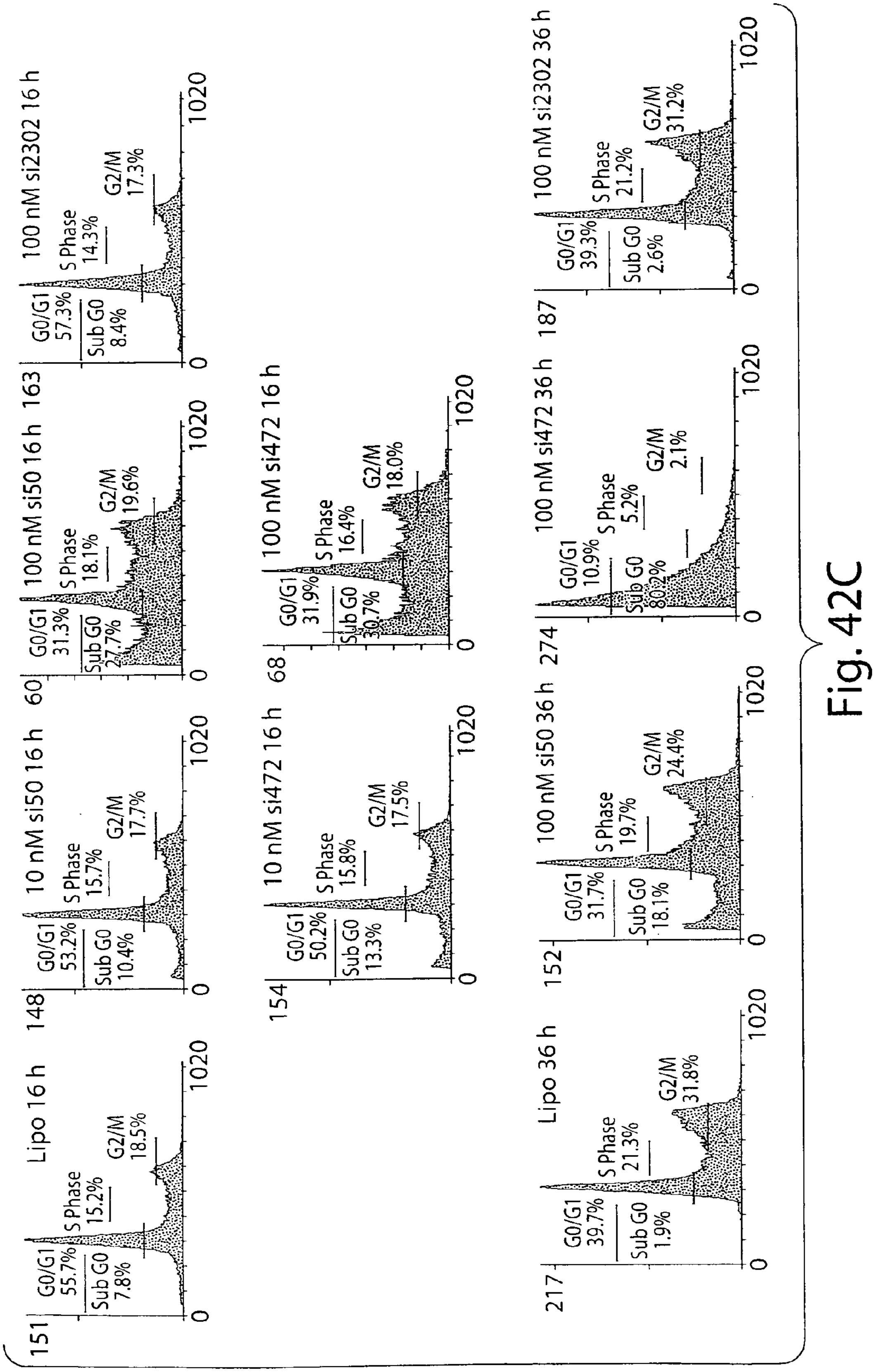

D. Inhibition of EphB4 in High Expressing Cell Lines Results in Reduced Viability and Causes Cell-Cycle Arrest We next turned to the role of EphB4 expression in HNSCC by investigating the effect of ablating expression using siRNA or AS-ODN methods. Several siRNAs to EphB4 sequence were developed (Table 1) which knocked-down EphB4 expression to varying degrees as seen in FIG. 42A. Viability was reduced in SCC-15, -25 and -71 cell lines transfected with siRNAs 50 and 472, which were most effective in blocking EphB4 expression (FIG. 42B). Little effect on viability was seen with EphB4 siRNA 1562 and 2302 or ephrin B2 siRNA 254. Note that in SCC-4, which does not express EphB4 (see FIG. 40A) there was no reduction in cell viability. The decreased cell viability seen with siRNA 50 and 472 treatment was attributable to accumulation of cells in sub G0, indicative of apoptosis. This effect was both time and dose-dependant (FIG. 42C and Table 2). In contrast, siRNA2302 that was not effective in reducing EphB4 levels and had only minor effects on viability did not produce any changes in the cell cycle when compared with the mock Lipofectamine™ 2000 transfection.

TABLE 1

| EphB4 siRNAs | | |
|---|---|---|
| Name | siRNA sequence | SEQ. ID NO: |
| Eph B4 50: | 5'-GAGACCCUGCUGAACACAAUU-3' | 34 |
| | 3'-UUCUCUGGGACGACUUGUGUU-5' | 35 |
| Eph B4 472: | 5'-GGUGAAUGUCAAGACGCUGUU-3' | 36 |
| | 3'-UUCCACUUACAGUUCUGCGAC-5' | 37 |
| Eph B4 1562: | 5'-CAUCACAGCCAGACCCAACUU-3' | 38 |
| | 3'-UUGUAGUGUCGGUCUGGGUUG-5' | 39 |
| Eph B4 2302 | 5'-CUCUUCCGAUCCCACCUACUU-3' | 40 |
| | 3'-UUGAGAAGGCUAGGGUGGAUG-5' | 41 |

TABLE 2

| Effect of different EphB4 siRNA on Cell Cycle | | | | |
|---|---|---|---|---|
| Treatment | Sub G0 | G1 | S | G2 |
| 36 hr | | | | |
| Lipo alone | 1.9 | 39.7 | 21.3 | 31.8 |
| 100 nM 2302 | 2.0 | 39.3 | 21.2 | 31.2 |
| 100 nM 50 | 18.1 | 31.7 | 19.7 | 24.4 |
| 100 nM 472 | 80.2 | 10.9 | 5.2 | 2.1 |
| 16 hr | | | | |
| Lipo alone | 7.8 | 55.7 | 15.2 | 18.5 |
| 100 nM 2302 | 8.4 | 57.3 | 14.3 | 17.3 |
| 10 nM 50 | 10.4 | 53.2 | 15.7 | 17.7 |
| 100 nM 50 | 27.7 | 31.3 | 18.1 | 19.6 |
| 10 nM 472 | 13.3 | 50.2 | 15.8 | 17.5 |
| 100 nM 472 | 30.7 | 31.9 | 16.4 | 18.0 |

Figure 43A:
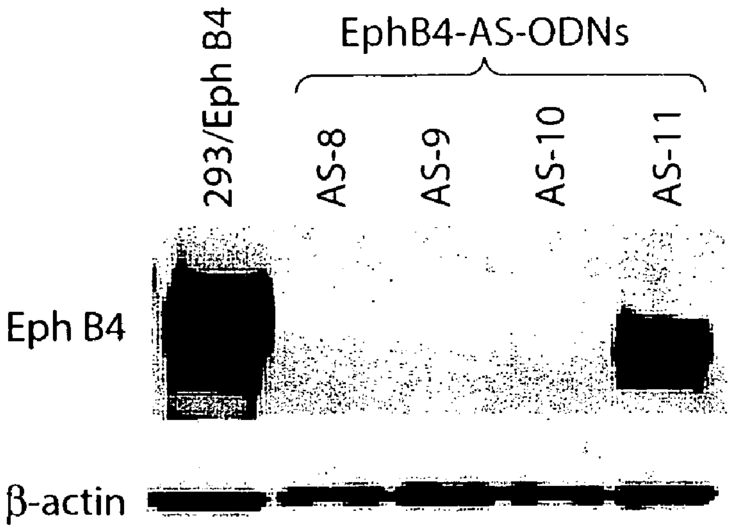
FIG. 43 shows in vitro effects of specific EphB4 AS-ODNs on SCC cells. A) 293 cells transiently transfected with EphB4 full-length expression plasmid were treated 6 h post transfection with antisense ODNs as indicated. Cell lysates were collected 24 h after AS-ODN treatment and subjected to Western Blot. B) SCC25 cells were seeded on 48 well plates at equal densities and treated with EphB4 AS-ODNs at 1, 5, and 10 μM on days 2 and 4. Cell viability was measured by MTT assay on day 5. Shown is the mean±s.e.m. of triplicate samples. Note that AS-ODNs that were active in inhibiting EphB4 protein levels were also effective inhibitors of SCC15 cell viability. C) Cell cycle analysis of SCC15 cells treated for 36 h with AS-10 (bottom) compared to cells that were not treated (top). D) Confluent cultures of SCC15 cells scraped with a plastic Pasteur pipette to produce 3 mm wide breaks in the monolayer. The ability of the cells to migrate and close the wound in the presence of inhibiting EphB4 AS-ODN (AS-10) and non-inhibiting AS-ODN (AS-1) was assessed after 48 h. Scrambled ODN is included as a negative control ODN. Culture labeled no treatment was not exposed to ODN. At initiation of the experiment, all cultures showed scrapes of equal width and similar to that seen in 1 μM EphB4 AS-10 after 48 h. The red brackets indicate the width of the original scrape. E) Migration of SCC15 cells in response to 20 mg/ml EGF in two-chamber assay as described in the Methods. Shown are representative photomicrographs of non-treated (NT), AS-6 and AS-10 treated cells and 10 ng/ml Taxol as positive control of migration inhibition. F) Cell numbers were counted in 5 individual high-powered fields and the average ±s.e.m. is shown in the graph.
Figure 43B:
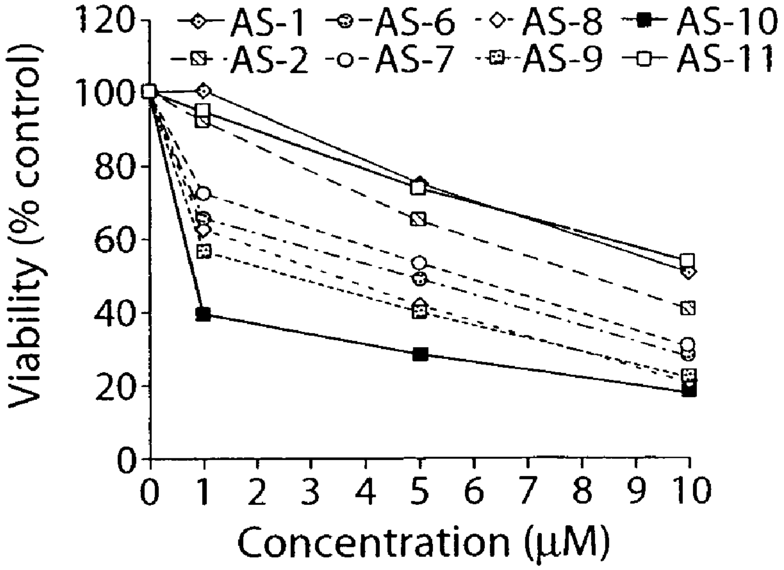
Figure 43C:
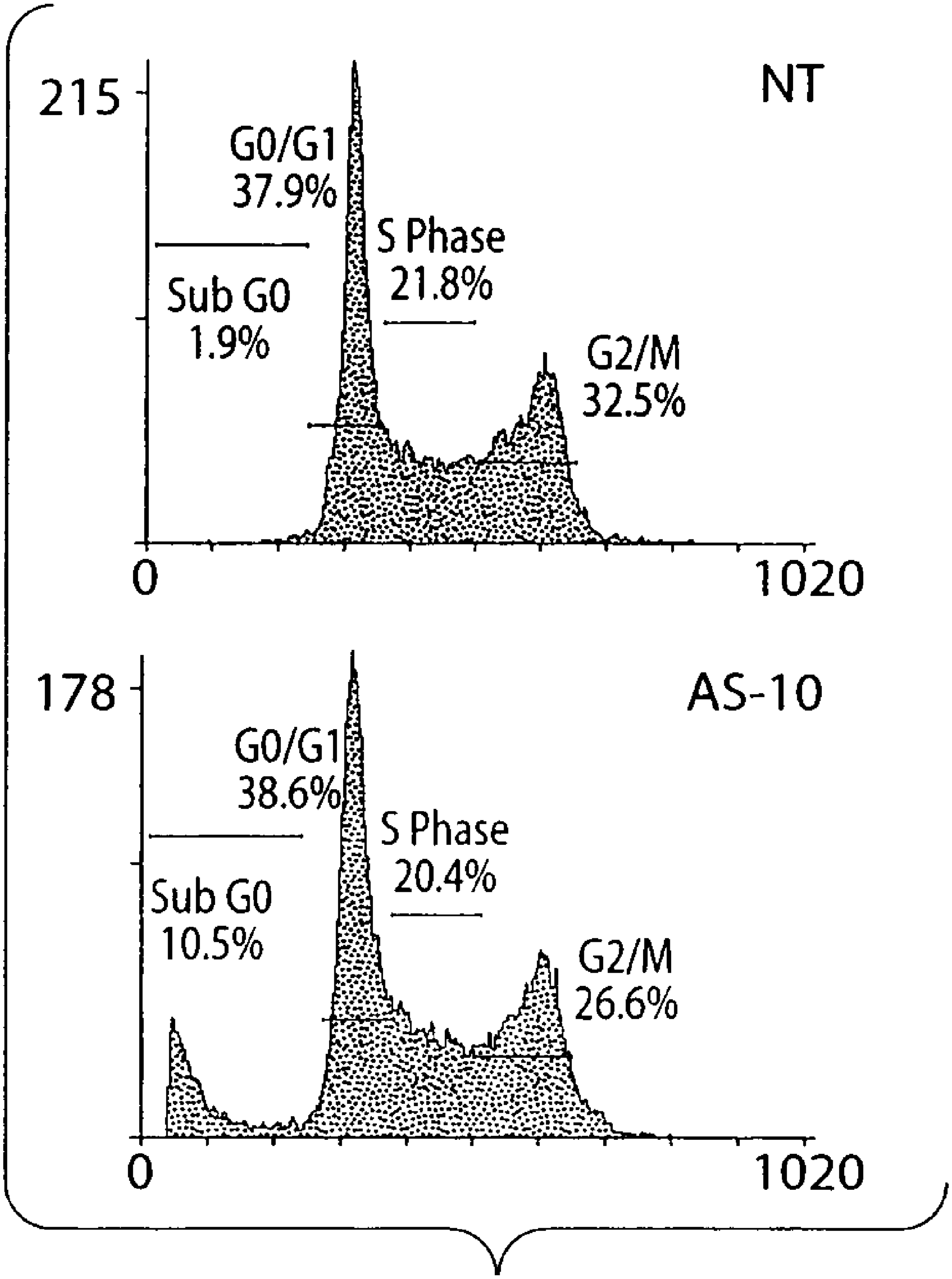

In addition, over 50 phosphorothioate AS-ODNs complementary to the human EphB4 coding sequences were synthesized and tested for their ability to inhibit EphB4 expression in 293 cells transiently transfected with full length EphB4 expression plasmid. FIG. 43A shows a representative sample of the effect of some of these AS-ODNs on EphB4 expression. Note that expression is totally abrogated with AS-10, while AS-11 has only a minor effect. The effect on cell viability in SCC15 cells was most marked with AS-ODNs that are most effective in inhibiting EphB4 expression as shown in FIG. 43B. The $IC_{50}$ for AS-10 was approximately 1 μM, while even 10 μM AS-11 was not sufficient to attain 50% reduction of viability. When the effect that AS-10 had on the cell cycle was investigated, it was found that the sub G0 fraction increased from 1.9% to 10.5% compared to non-treated cells, indicative of apoptosis (FIG. 43C).

E. EphB4 Regulates Cell Migration

Figure 43D:
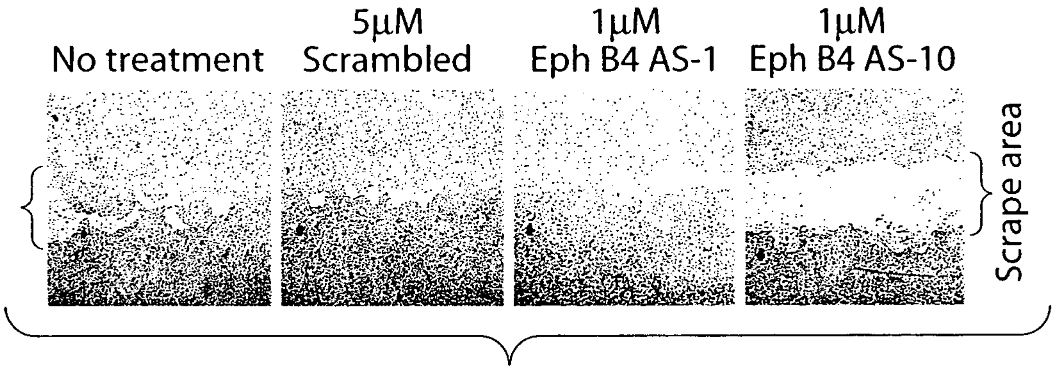
Figure 43E:
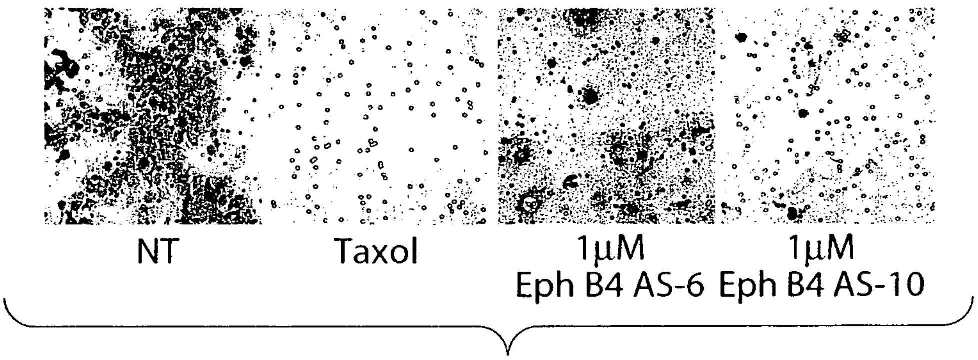
Figure 43F:
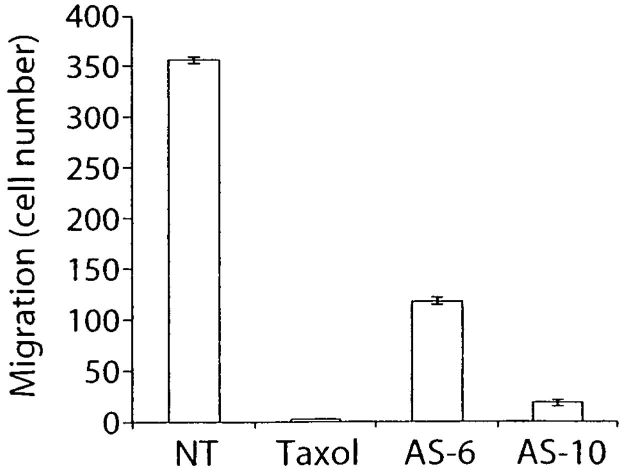

We next wished to determine if EphB4 participates in the migration of HNSCC. Involvement in migration may have implications for growth and metastasis. Migration was assessed using the wound-healing/scrape assay. Confluent SCC15 and SCC25 cultures were wounded by a single scrape with a sterile plastic Pasteur pipette, which left a 3 mm band with clearly defined borders. Migration of cells into the cleared area in the presence of test compounds was evaluated and quantitated after 24, 48 and 72 hr. Cell migration was markedly diminished in response to AS-10 that block EphB4 expression while the inactive compounds, AS-1 and scrambled ODN had little to no effect as shown in FIG. 43D. Inhibition of migration with AS-10 was also shown using the Boyden double chamber assay (FIG. 43E).

F. EphB4 AS-10 In Vivo Anti-Tumor Activity

Figure 44:
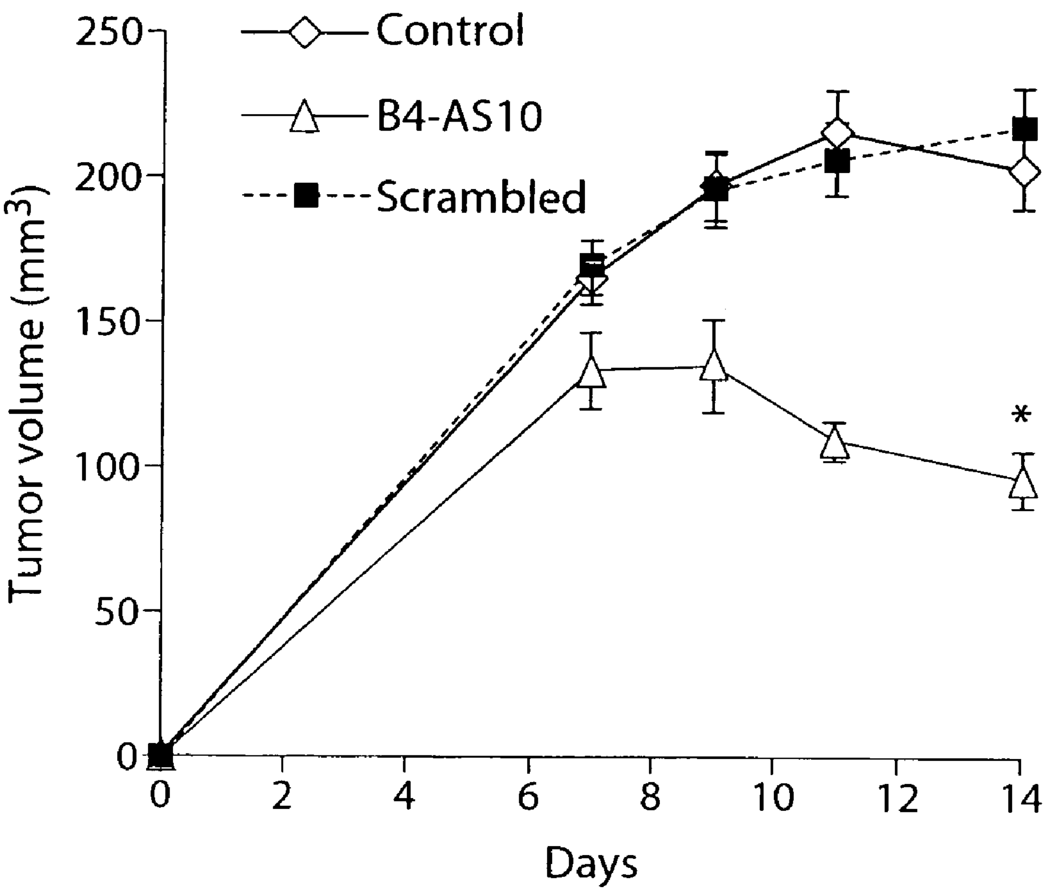
FIG. 44 shows that EphB4 AS-ODN inhibits tumor growth in vivo. Growth curves for SCC15 subcutaneous tumor xenografts in Balb/C nude mice treated with EphB4 AS-10 or scrambled ODN at 20 mg/kg/day starting the day following implantation of 5×106 cells. Control mice received and equal volume of diluent (PBS). Shown are the mean±s.e.m. of 6 mice/group. * P=0.0001 by Student's t-test compared to scrambled ODN treated group.

The effect of EphB4 AS-10, which reduces cell viability and motility, was determined in SCC15 tumor xenografts in Balb/C nude mice. Daily treatment of mice with 20 mg/kg AS-10, sense ODN or equal volume of PBS by I.P. injection was started the day following tumor cell implantation. Growth of tumors in mice receiving AS-10 was significantly retarded compared to mice receiving either sense ODN or PBS diluent alone (FIG. 44). Non-specific effects attributable to ODN were not observed, as there was no difference between the sense ODN treated and PBS treated groups.

G. Materials and Methods

1) Cell Lines and Reagents

HNSCC-4, -9, 12, -13, -15, -25, and -71 were obtained from and 293 human embryonic kidney cells were obtained from the ATCC (Manassas, Va.). Cells were maintained in RPMI 1640 media supplemented with 10% heat-inactivated fetal bovine serum (FBS; Invitrogen, Carlsbad, Calif.) and antibiotics. EGFR, EphB4(C-16) polyclonal antibodies were from Santa Cruz Biotech (Santa Cruz, Calif.). β-actin monoclonal antibody was purchased from Sigma Chemical Co. (St Louis, Mo.). Ephrin B2 and EphB4 polyclonal antibodies and their corresponding blocking peptides were obtained from Santa Cruz Biotechnology (Santa Cruz, Calif.). AG 1478 (4-(3'-Chloroanilino)-6,7-dimethoxy-quinazoline) was from Calbiochem (San Diego, Calif.). Kinase inhibitors SH-5 and SP 600125 were from A.G. Scientific (San Diego, Calif.), PD98095, U73122, SB203580, LY294002, and Wortmannin were obtained from Sigma.

2) Preparation of Digoxigenin-Labeled RNA Probes

See above, e.g., Example 3.

3) In Situ Hybridization

See above, e.g., Example 3.

4) Immunohistochemistry

Formalin-fixed tissue sections were deparaffinized and incubated with 10% goat serum at −70° C. for 10 minutes and incubated with the EphB4 monoclonal antibody 4° C. overnight. Isotype specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with 0.12% methylene blue or H&E. For frozen sections, OCT-embedded tissues were sectioned at 5 μm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody. Immunohistochemical staining on prostate array (BioMeda, Foster City, Calif.) was done using goat ABC Staining System (Santa Cruz Biotech.) according to the manufacturer's instructions.

5) Western Blot

See above, e.g., Example 3.

6) Synthesis of EphB4 siRNA by In Vitro Transcription

The Silencer™ siRNA construction kit (Ambion, Austin Tex.) was used to synthesize siRNA to EphB4. Briefly, 21 bp target sequences containing 19 bp downstream of 5'-AA dinucleotides were identified that showed no significant homology to other sequences in the GenBank database. Sense and antisense siRNA 29-mer DNA oligonucleotide templates were synthesized at the USC Norris Microchemical Core Facility. Antisense template corresponded to the target sequence followed by 8 bp addition (5'-CCTGTCTC-3') at the 3' end complementary to the T7 promoter primer provided by the Silencer™ siRNA construction kit. Sense template comprised 5'-AA followed by the complement of the target 19 bp, then the T7 8 bp sequence as above.

In separate reactions, the two siRNA oligonucleotide templates were hybridized to a T7 promoter primer. The 3' ends of the hybridized oligonucleotides were extended by the Klenow fragment of DNA polymerase to create double-stranded siRNA transcription templates. The sense and antisense siRNA templates were transcribed by T7 RNA polymerase and the resulting RNA transcripts were hybridized to create dsRNA. The leader sequences were removed by digesting the dsRNA with a single-stranded specific ribonuclease leaving the overhanging UU dinucleotides. The DNA template was removed at the same time by treatment with RNase free deoxyribonuclease. The resulting siRNA was purified by glass fiber filter binding to remove excess nucleotides, short oligomers, proteins, and salts in the reaction. The end products (shown in Table 3) were double-stranded 21-mer siRNAs with 3' terminal uridine that can effectively reduce the expression of target mRNA when transfected into cells.

A number of phosphorothioate AS-ODNs were also synthesized (Operon, Valencia Calif.) to test for inhibition of Eph1B4 expression (Table 3).

8) Cell Cycle Analysis

80% confluent cultures of SCC15 cells in 6-well plates were transfected with siRNA472 (100 nM) using Lipofectamine™ 2000. Either 16 or 36 hours after transfection, cells were trypsinized, washed in PBS and incubated for 1 h at 4° C. in 1 ml of hypotonic solution containing 50 μg/ml propidium iodide, 0.1% sodium citrate, 0.1 Triton X-100 and 20 μg/ml DNase-free RNaseA. Cells were analyzed in linear mode at the USC Flow cytometry facility. Results were expressed as percentages of elements detected in the different phases of the cell cycle, namely Sub G0 peak (apoptosis), G0/G1 (no DNA synthesis), S (active DNA systhesis), G2 (premitosis) and M (mitosis). For AS-ODN experiment the cells were exposed to 5 μM ODN for 36 h prior to processing.

9) Wound Healing Migration Assay

SCC15 cells were seeded into 6-well plates and cultured until confluent. 10 μM AS-1, AS-10, or sense ODN as control were introduced to the wells as described for the viability assay 12 hours before wounding the monolayer by scraping it with a sterile pipette tip. Medium was changed to RPMI 1640 supplemented with 5% FBS and fresh ODNs. The healing process was examined dynamically and recorded with a Nikon Coolpix 5000 digital camera with microscope adapter.

10) Boyden Chamber Assay of Migration

Cell migration assays were performed as previously described (Masood ANUP paper '99) except that 1 μM AS-10 or AS-6 were added to the upper chamber. EGF (20 ng/ml) was used as chemoattractant in the lower chamber. Taxol at 10 ng/ml was used as a negative control.

11) In Vivo Studies

SCC15 ($5\times10^6$ cells) were injected subcutaneously in the lower back of 5-week old male Balb/C $Nu^+/nu^+$ athymic mice. Treatment consisted of daily intraperitoneal injection of ODN (20 mg/kg in a total volume of 100 μl) or diluent (PBS) begun the day following tumor cell implantation and continued for two weeks. Tumor growth in mice was measured as previously described (Masood CCR '01). Mice were sacrificed at the conclusion of the study. All mice were maintained in accord with the University of Southern California Animal Care and Use Committee guidelines governing the care of laboratory mice.

TABLE 3

EphB4 Antisense ODNs

| Name | Position | Sequence (5' → 3') | SEQ. ID NO: |
|---|---|---|---|
| Eph B4 AS-1 | (552-572) | GTG CAG GGA TAG CAG GGC CAT | 42 |
| Eph B4 AS-2 | (952-972) | AAG GAG GGG TGG TGC ACG GTG | 43 |
| Eph B4 AS-3 | (1007-1027) | TTC CAG GTG CAG GGA GGA GCC | 44 |
| Eph B4 AS-4 | (1263-1285) | GTG GTG ACA TTG ACA GGC TCA | 45 |
| Eph B4 AS-5 | (1555-1575) | TCT GGC TGT GAT GTT CCT GGC | 46 |
| Eph B4 AS-6 | (123-140) | GCC GCT CAG TTC CTC CCA | 47 |
| Eph B4 AS-7 | (316-333) | TGA AGG TCT CCT TGC AGG | 48 |
| Eph B4 AS-8 | (408-428) | CGC GGC CAC CGT GTC CAC CTT | 49 |
| Eph B4 AS-9 | (1929-1949) | CTT CAG GGT CTT GAT TGC CAC | 50 |
| Eph B4 AS-10 | (1980-1999) | ATG GAG GCC TCG CTC AGA AA | 51 |
| Eph b4 AS-11 | (2138-2158) | CAT GCC CAC GAG CTG GAT GAC | 52 |

7) Cell Viability Assay

Cells were seeded at a density of $5\times10^3$ per well in 48-well plates on day 0 in appropriate growth media containing 2% fetal calf serum (FCS). Cells were treated with various concentrations (1-10 μg/ml) of ODNs on days 2 and 4. On day 5, viability was assessed using 3-(4,5-dimethylthiazol-2-yl)-2,5-diphenyltetrazolium bromide (MTT) as previously described (Masood et al '03). For viability with siRNA, $2\times10^4$ cells/well of SCC-4, -15, -25 or -71 in a 48-well plate were transfected with siRNAs (10-100 nM) using 2 μl of Lipofectamine™ 2000 according to the manufacturer's instructions. 4 h post-transfection the cells were returned to growth media (RPMI 1640 supplemented with 10% FBS). Viability was assayed by MTT 48 h following transfection.

Example 6

Ephrin B2 Expression in Kaposi's Sarcoma is Induced by Human Herpesvirus Type 8: Phenotype Switch from Venous to Arterial Endothelium Kaposi's Sarcoma (KS) manifests as a multifocal angioproliferative disease, most commonly of the skin and mucus membranes, with subsequent spread to visceral organs (1) Hallmarks of the disease are angiogenesis, edema, infiltration of lymphomononuclear cells and growth of spindle-shaped tumor cells. Pathologically, established lesions exhibit an extensive vascular network of slit-like spaces. The KS vascular network is distinct from normal vessels in the lack of basement membranes and the abnormal spindle shaped endothelial cell (tumor cell) lining these vessels. Defective vasculature results in an accumulation of the blood components including albumin, red and mononuclear cells in the lesions (1). The KS tumor is endothelial in origin; the tumor cells express many endothelial markers, including lectin binding sites for *Ulex europeaus* agglutinin-1 (UEA-1), CD34, EN-4, PAL-E (2) and the endothelial cell specific tyrosine kinase receptors, VEGFR-1 (Flt-1), VEGFR-2 (Flk-1/KDR), VEGFR-3 (Flt-4), Tie-1 and Tie-2 (3, RM & PSG unpublished data). KS cells co-express lymphatic endothelial cell related proteins including LYVE and podoplanin (4).

The herpesvirus HHV-8 is considered the etiologic agent for the disease. In 1994 sequences of this new herpes virus were identified in KS tumor tissue (5), and subsequent molecular-epidemiology studies have shown that nearly all KS tumors contain viral genome. Sero-epidemiology studies show that HIV infected patients with KS have the highest prevalence of HHV-8 and secondly that those with HIV infection but no KS have increased risk of development of KS over the ensuing years if they are also seropositive for HHV-8 (6). Direct evidence for the role of HHV-8 in KS is the transformation of bone marrow endothelial cells after infection with HHV-8 (7). A number of HHV-8 encoded genes could contribute to cellular transformation (reviewed in 8). However, the most evidence has accumulated for the G-protein coupled receptor (vGPCR) in this role (9).

We investigated whether KS tumor cells are derived from arterial or venous endothelium. In addition, we investigated whether HHV-8 has an effect on expression of arterial or venous markers in a model of KS. KS tumor cells were found to express the ephrin B2 arterial marker. Further, ephrin B2 expression was induced by HHV-8 vGPCR in KS and endothelial cell lines. Ephrin B2 is a potential target for treatment of KS because inhibition of ephrin B2 expression or signaling was detrimental to KS cell viability and function.

A. KS Tumors Express Ephrin B2, but not EphB4

Figure 45A:
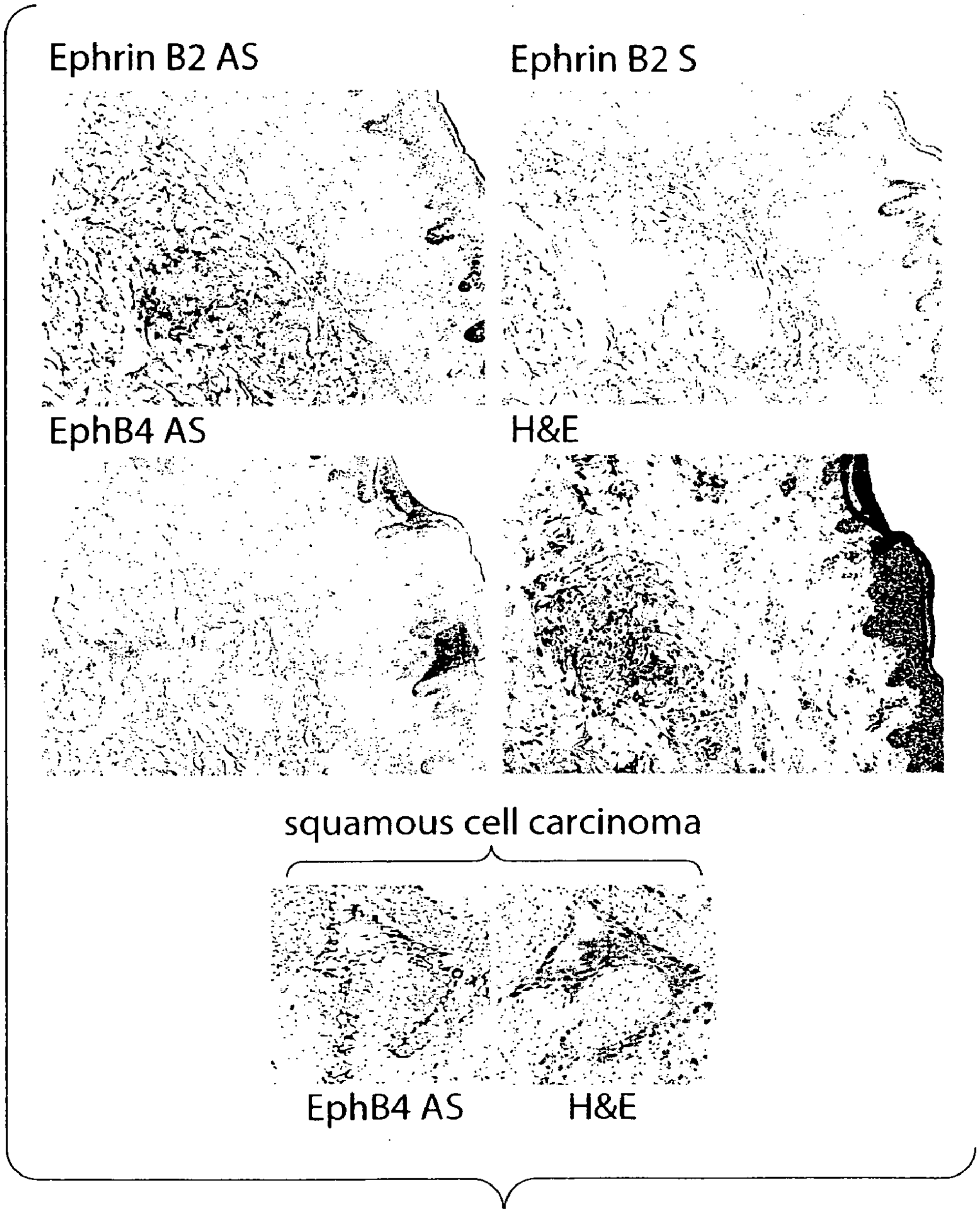
FIG. 45 shows that Ephrin B2, but not EphB4 is expressed in KS biopsy tissue. (A) In situ hybridization with antisense probes for ephrin B2 and EphB4 with corresponding H&E stained section to show tumor architecture. Dark blue color in the ISH indicates positive reaction for ephrin B2. No signal for EphB4 was detected in the Kaposi's sarcoma biopsy. For contrast, ISH signal for EphB4 is strong in squamous cell carcinoma tumor cells. Ephrin B2 was also detected in KS using EphB4-AP fusion protein (bottom left). (B) Detection of ephrin B2 with EphB4/Fc fusion protein. Adjacent sections were stained with H&E (left) to show tumor architecture, black rectangle indicates the area shown in the EphB4/Fc treated section (middle) detected with FITC-labeled anti-human Fc antibody as described in the methods section. As a control an adjacent section was treated with human Fc fragment (right). Specific signal arising from EphB4/Fc binding to the section is seen only in areas of tumor cells. (C) Co-expression of ephrin B2 and the HHV8 latency protein LANA1. Double-label confocal immunofluorescence microscopy with antibodies to ephrin B2 (red) LANA1 (green), or EphB4 (red) of frozen KS biopsy material directly demonstrates co-expression of LANA1 and ephrin B2 in KS biopsy. Coexpression is seen as yellow color. Double label confocal image of biopsy with antibodies to PECAM-1 (green) in cells with nuclear propidium iodide stain (red), demonstrating the vascular nature of the tumor.
Figure 45B:
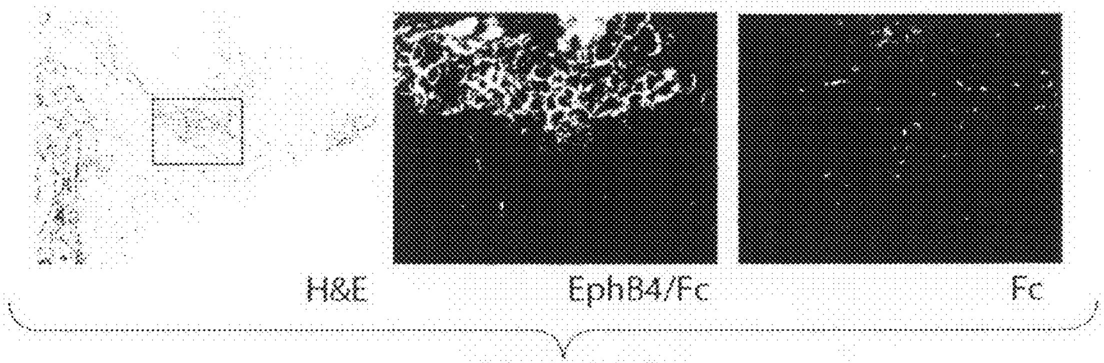
Figure 45C:
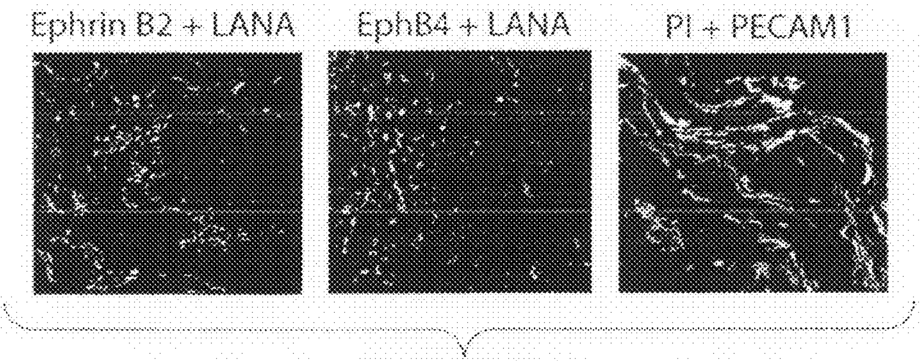

The highly vascular nature of KS lesions and the probable endothelial cell origin of the tumor cells prompted investigation of expression of EphB4 and ephrin B2 which are markers for venous and arterial endothelial cells, respectively. Ephrin B2, but not EphB4 transcripts were detected in tumor cells of KS biopsies by in situ hybridization (FIG. 45A). Comparison of the positive signal with ephrin B2 antisense probe and tumor cells as shown by H&E staining shows that ephrin B2 expression is limited to the areas of the biopsy that contain tumor cells. The lack of signal in KS with EphB4 antisense probe is not due to a defect in the probe, as it detected transcripts in squamous cell carcinoma, which we have shown expresses this protein (18). Additional evidence for the expression of ephrin B2 in KS tumor tissue is afforded by the localization of EphB4/Fc signal to tumor cells, detected by FITC conjugated anti human Fc antibody. Because ephrin B2 is the only ligand for EphB4 this reagent is specific for the expression of ephrin B2 (FIG. 45B, left). An adjacent section treated only with the secondary reagent shows no specific signal. Two-color confocal microscopy demonstrated the presence of the HHV-8 latency protein, LANA1 in the ephrin B2 positive cells (FIG. 45C, left), indicating that it is the tumor cells, not tumor vessels, which are expressing this arterial marker. Staining of tumor biopsy with PECAM-1 antibody revealed the highly vascular nature of this tumor (FIG. 45C, right). A pilot study of the prevalence of this pattern of ephrin B2 and EphB4 expression on KS biopsies was conducted by RT-PCR analysis. All six samples were positive for ephrin B2, while only 2 were weakly positive for EphB4 (data not shown).

Figure 46A:
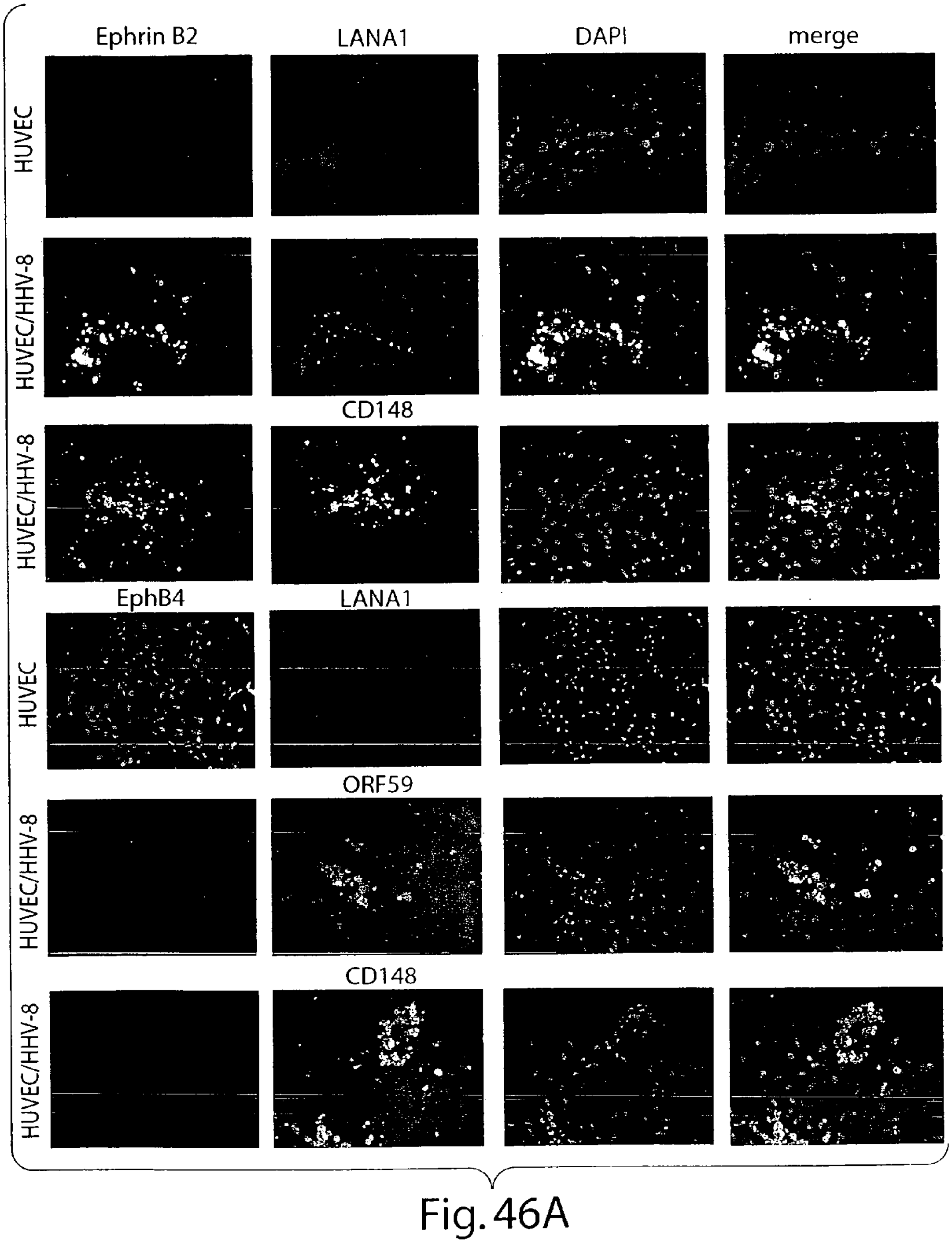
FIG. 46 shows that HHV-8 induces arterial marker expression in venous endothelial cells. (A) Immunofluorescence of cultures of HUVEC and HUVEC/BC-1 for artery/vein markers and viral proteins. Cultures were grown on chamber slides and processed for immunofluorescence detection of ephrin B2 (a, e, i), EphB4 (m, q, u), CD148 (j, v), and the HHV-8 proteins LANA1 (b, f, m) or ORF59 (r) as described in the Materials and Methods. Yellow color in the merged images of the same field demonstrate co-expression of ephrin B2 and LANA or ephrin B2 and CD148. The positions of viable cells were revealed by nuclear staining with DAPI (blue) in the third column (c, g, k, o, s, w). Photomicrographs are of representative fields. (B) RT-PCR of HUVEC and two HHV-8 infected cultures (HUVEC/BC-1 and HUVEC/BC-3) for ephrin B2 and EphB4. Ephrin B2 product (200 bp) is seen in HUVEC/BC-1, HUVEC/BC-3 and EphB4 product (400 bp) is seen in HUVEC. Shown also is β-actin RT-PCR as a control for amount and integrity of input RNA.
Figure 46B:
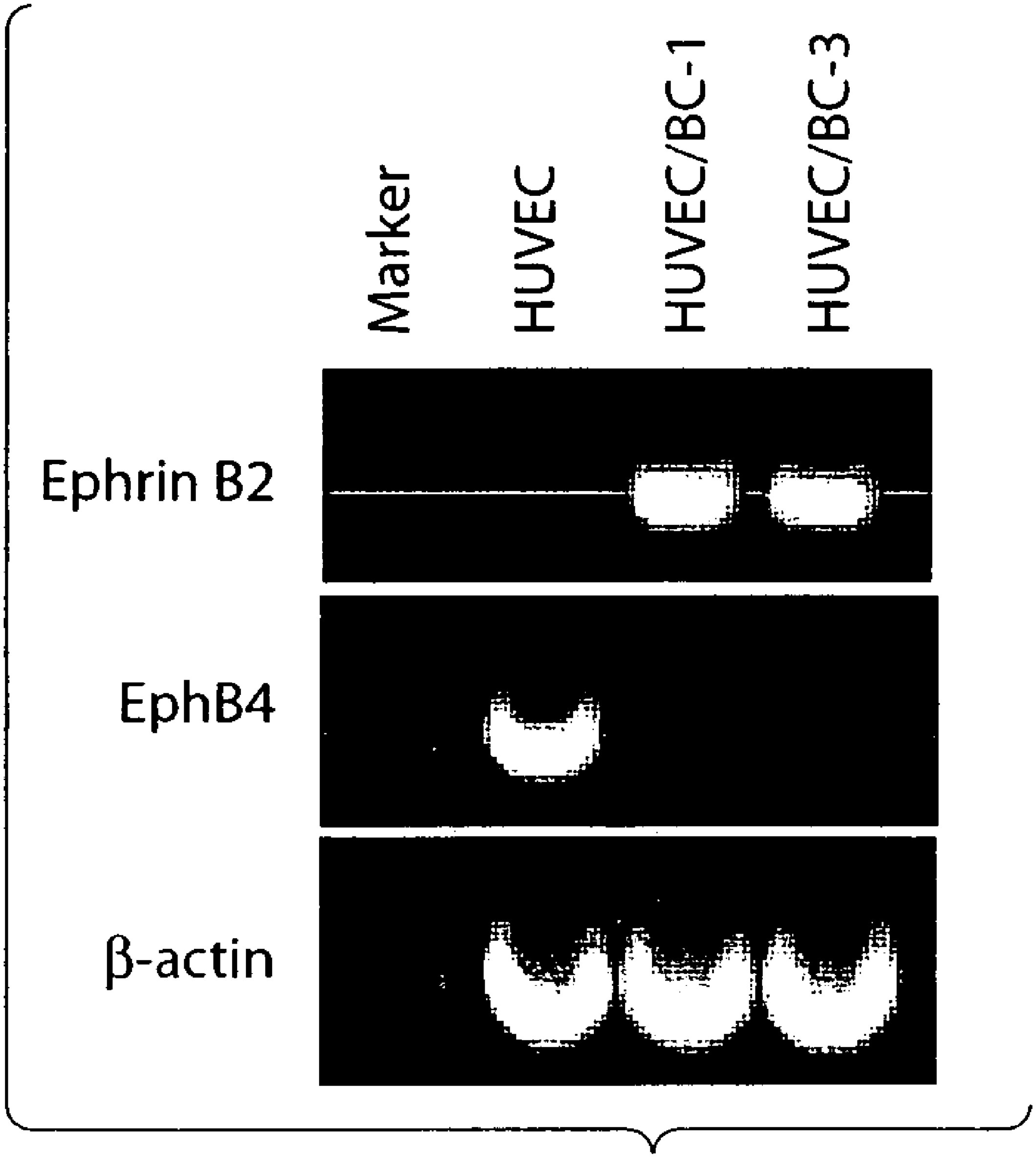

B. Infection of Venous Endothelial Cells with HHV-8 Causes a Phenotype Switch to Arterial Markers We next asked whether HHV-8, the presumed etiologic agent for KS, could itself induce expression of ephrin B2 and repress EphB4 expression in endothelial cells. Co-culture of HUVEC and BC-1 lymphoma cells, which are productively infected with HHV-8, results in effective infection of the endothelial cells (16). The attached monolayers of endothelial cells remaining after extensive washing were examined for ephrin B2 and EphB4 by RT-PCR and immunofluorescence. HUVEC express EphB4 venous marker strongly at the RNA level, but not ephrin B2 (FIG. 46B). In contrast, HHV-8 infected cultures (HUVEC/BC-1 and HUVEC/BC-3) express ephrin B2, while EphB4 transcripts are almost absent.

Immunofluorescence analysis of cultures of HUVEC and HUVEC/HHV-8 for artery/vein markers and viral proteins was undertaken to determine whether changes in protein expression mirrored that seen in the RNA. In addition, cellular localization of the proteins could be determined. Consistent with the RT-PCR data HUVEC are ephrin B2 negative and EphB4 positive (FIG. 46A(a & m)). As expected they do not express any HHV-8 latency associated nuclear antigen (LANA1) (FIG. 46A(b, n)). Co-culture of BC-1 cells, which are productively infected with HHV-8, resulted in infection of HUVEC as shown by presence of viral proteins LANA1 and ORF59 (FIG. 46A(f, r)). HHV-8 infected HUVEC now express ephrin B2 but not EphB4 (FIG. 46A(e, q, u), respectively). Expression of ephrin B2 and LANA1 co-cluster as shown by yellow signal in the merged image (FIG. 46A(h)). HHV-8 infected HUVEC positive for ephrin B2 and negative for Eph B4 also express the arterial marker CD148 (19) (FIG. 46A (j, v)). Expression of ephrin B2 and CD148 co-cluster as shown by yellow signal in the merged image (FIG. 46A(1)). Uninfected HUVEC expressing Eph B4 were negative for CD148 (not shown).

C. HHV-8 vGPCR Induces Ephrin B2 Expression

Figure 47A:
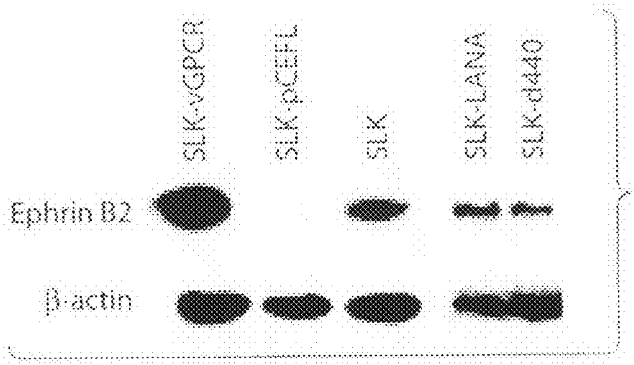
FIG. 47 shows that HHV-8 induces arterial marker expression in Kaposi's sarcoma cells. (A) Western blot for ephrin B2 on various cell lysates. SLK-vGPCR is a stable clone of SLK expressing the HHV-8 vGPCR, and SLK-pCEFL is control stable clone transfected with empty expression vector. SLK cells transfected with LANA or LANAΔ440 are SLK-LANA and SLK-Δ440 respectively. Quantity of protein loading and transfer was determined by reprobing the membranes with β-actin monoclonal antibody. (B) Transient transfection of KS-SLK cells with expression vector pvGPCR-CEFL resulted in the expression of ephrin B2 as shown by immunofluorescence staining with FITC (green), whereas the control vector pCEFL had no effect. KS-SLK cells (0.8×105/well) were transfected with 0.8 μg DNA using Lipofectamine 2000. 24 hr later cells were fixed and stained with ephrin B2 polyclonal antibody and FITC conjugated secondary antibody as described in the methods. (C) Transient transfection of HUVEC with vGPCR induces transcription from ephrin B2 luciferase constructs. 8×103 HUVEC in 24 well plates were transfected using Superfect with 0.8 μg/well ephrin B2 promoter constructs containing sequences from −2941 to −11 with respect to the translation start site, or two 5'-deletions as indicated, together with 80 ng/well pCEFL or pvGPCR-CEFL. Luciferase was determined 48 h post transfection and induction ratios are shown to the right of the graph. pGL3Basic is promoterless luciferase control vector. Luciferase was normalized to protein since GPCR induced expression of the cotransfected β-galactosidase. Graphed is mean±SEM of 6 replicates. Shown is one of three similar experiments.
Figure 47B:
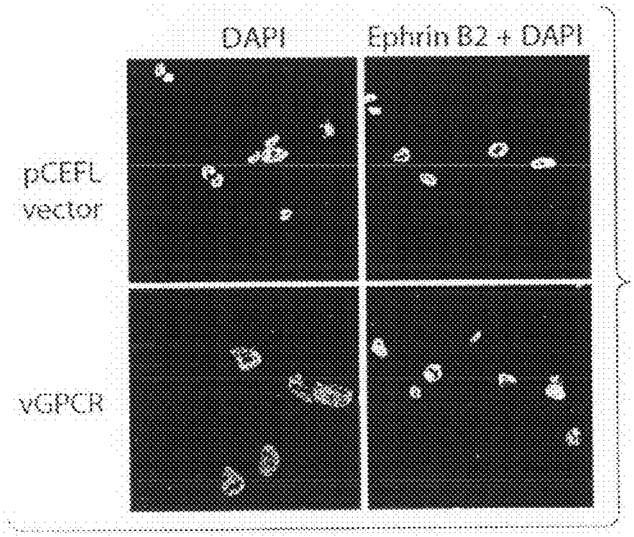
Figure 47C:
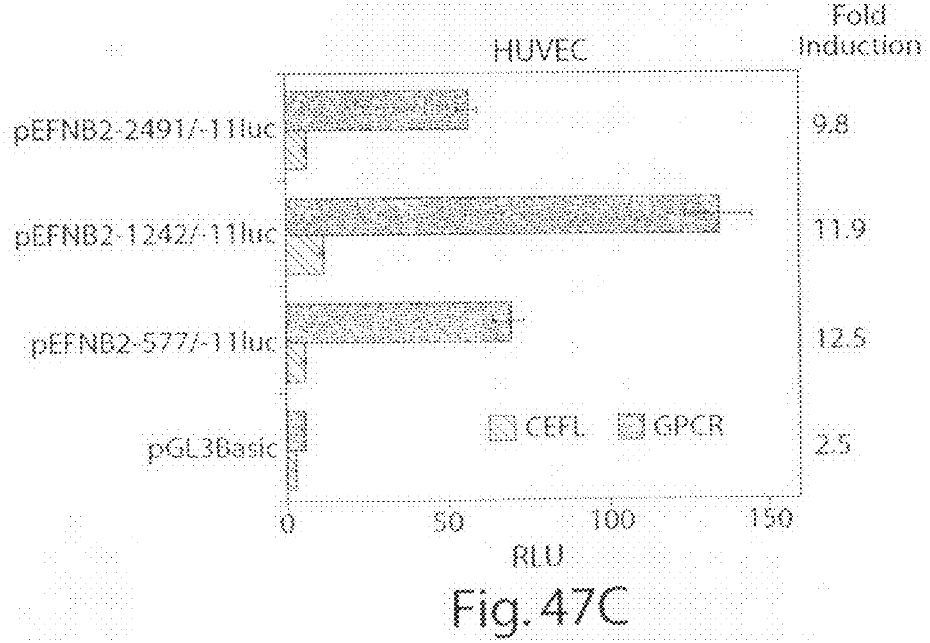

To test whether individual viral proteins could induce the expression of ephrin B2 seen with the whole virus KS-SLK cells were stably transfected with HHV-8 LANA, or LANAΔ440 or vGPCR. Western Blot of stable clones revealed a five-fold induction of ephrin B2 in KS-SLK transfected with vGPCR compared to SLK-LANA or SLK-LANAΔ440 (FIG. 47A). SLK transfected with vector alone (pCEFL) was used as a control. SLK-vGPCR and SLK-pCEFL cells were also examined for ephrin B2 and Eph B4 expression by immunofluorescence in transiently transfected KS-SLK cells. FIG. 47B shows higher expression of ephrin B2 in the SLK-vGPCR cells compared to SLK-pCEFL. No changes in Eph B4 were observed in SLK-vGPCR compared to SLK-pCEFL. This clearly demonstrates that SLK-vGPCR cells expressed high levels of ephrin B2 compared to SLK-pCEFL cells. This suggests that vGPCR of HHV-8 is directly involved in the induction of Ephrin B2 and the arterial phenotype switch in KS. Since we had shown that HHV-8 induced expression of ephrin B2 in HUVEC, we next asked if this could be mediated by a transcriptional effect. Ephrin B2 5'-flanking DNA-luciferase reporter plasmids were constructed as described in the Materials and Methods and transiently transfected into HUVECs. Ephrin B2 5'-flanking DNA sequences −2491/−11 have minimal activity in HUVEC cells (FIG. 47C). This is consistent with ephrin B2 being an arterial, not venous marker. However, we have noted that HUVEC in culture do express some ephrin B2 at the RNA level. Cotransfection of HHV-8 vGPCR induces ephrin B2 transcription approximately 10-fold compared to the control expression vector pCEFL. Roughly equal induction was seen with ephrin B2 sequences −2491/−11, −1242/−11, or −577/−11, which indicates that elements between −577 and −11 are sufficient to mediate the response to vGPCR, although maximal activity is seen with the −1242/−11 luciferase construct.

D. Expression of Ephrin B2 is Regulated by VEGF and VEGF-C

Figure 48A:
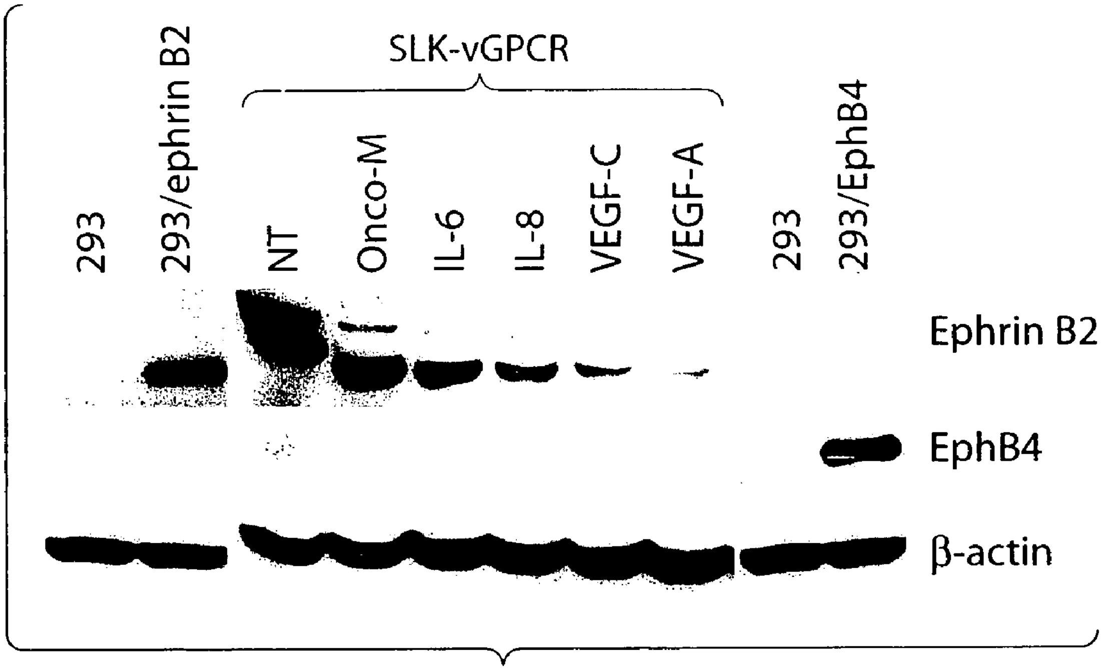
FIG. 48 shows that VEGF and VEGF-C regulate ephrin B2 expression. A) Inhibition of ephrin B2 by neutralizing antibodies. Cells were cultured in full growth medium and exposed to antibody (100 ng/ml) for 36 hr before collection and lysis for Western blot. B) For induction of ephrin B2 expression cells were cultured in EBM growth medium containing 5% serum lacking growth factors. Individual growth factors were added as indicated and the cells harvested after 36 h. Quantity of protein loading and transfer was determined by reprobing the membranes β-actin monoclonal antibody.
Figure 48B:
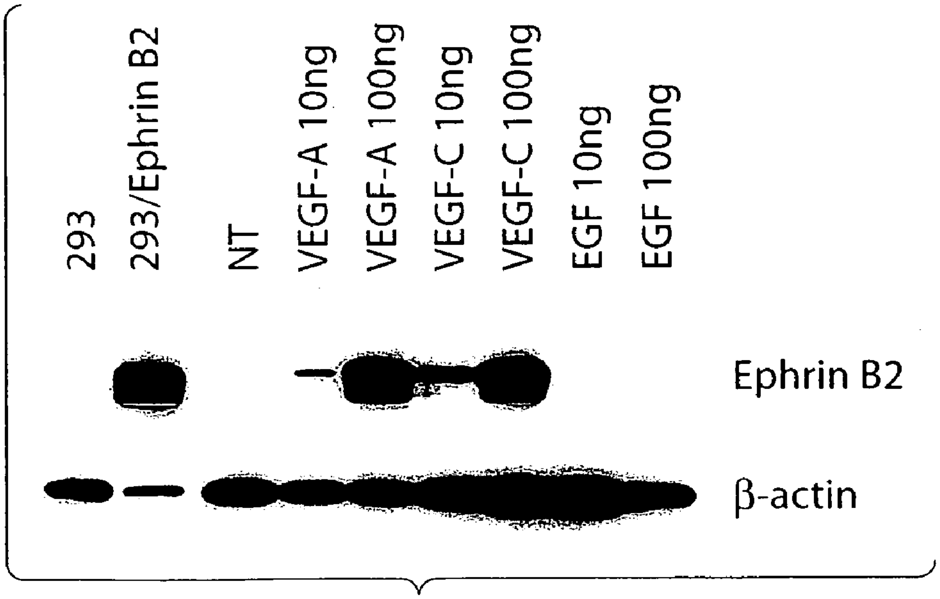

We next asked whether known KS growth factors could be involved in the vGPCR-mediated induction of ephrin B2 expression. SLK-vGPCR cells were treated with neutralizing antibodies to oncostatin-M, IL-6, IL-8, VEGF or VEGF-C for 36 hr. FIG. 48A shows that neutralization of VEGF completely blocked expression of ephrin B2 in SLK-vGPCR cells. A lesser, but significant decrease in ephrin B2 was seen neutralization of VEGF-C and IL-8. No appreciable effect was seen with neutralization of oncostatin-M or IL-6. To verify that VEGF and VEGF-C are integral to the induction of ephrin B2 expression we treated HUVEC with VEGF, VEGF-C or EGF. HUVECs were grown in EBM-2 media containing 5% FBS with two different concentration of individual growth factor (10 ng, 100 ng/ml) for 48 h. Only VEGF-A or VEGF-C induced ephrin B2 expression in a dose dependent manner (FIG. 48B). In contrast, EGF had no effect on expression of ephrin B2.

E. Ephrin B2 siRNA Inhibits the Expression of Ephrin B2 in KS

Figure 49A:
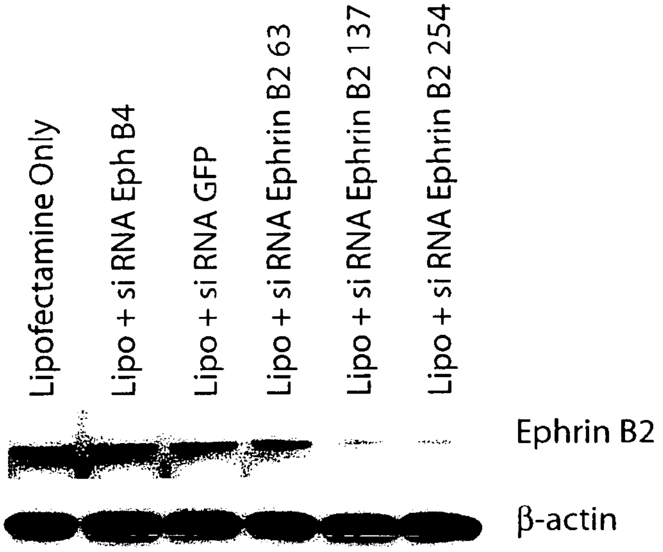
FIG. 49 shows that Ephrin B2 knock-down with specific siRNA inhibits viability in KS cells and HUVEC grown in the presence of VEGF but not IGF, EGF or bFGF. A) KS-SLK cells were transfected with various siRNA to ephrin B2 and controls. After 48 hr the cells were harvested and crude cell lysates fractionated on 4-20% SDS-PAGE. Western blot was performed with monoclonal antibody to ephrin B2 generated in-house. The membrane was stripped and reprobed with β-actin monoclonal antibody (Sigma) to illustrate equivalent loading and transfer. B) 3 day cell viability assay of KS-SLK cultures in the presence of ephrin B2 and EphB4 siRNAs. $1\times10^5$ cells/well in 24-well plates were treated with 0, 10 and 100 ng/ml siRNAs as indicated on the graph. Viability of cultures was determined by MTT assay as described in the methods section. Shown are the mean±standard deviation of duplicate samples. C) HUVE cells were seeded on eight wells chamber slides coated with fibronectin. The HUVE cells were grown overnight in EGM-2 media, which contains all growth supplements. On the following day, the media was replaced with media containing VEGF (10 ng/ml) or EGF, FGF and IGF as indicated. After 2 hrs of incubation at 37° C., the cells were transfected using Lipofectamine 2000 (Invitrogen) in Opti-MEM medium containing 10 nM of siRNA to ephrin B2, Eph B4 or green fluorescence protein (GFP) as control. The cells were incubated for 2 hr and then the fresh media containing growth factors or VEGF alone was added to their respective wells. After 48 hrs, the cells were stained with crystal violet and the pictures were taken immediately by digital camera at 10× magnification.

Three ephrin B2 siRNA were synthesized as described in the methods section. KS-SLK cells were transfected with siRNA and 48 h later ephrin B2 expression was determined by Western Blot. Ephrin B2 siRNAs 137 or 254 inhibited about 70% of ephrin B2 expression compared to control siRNA such as siRNA Eph B4 50 or siRNA GFP. Ephrin B2 63 siRNA was less effective than the above two siRNA Ephrin B2 (FIG. 49A).

Figure 49B:
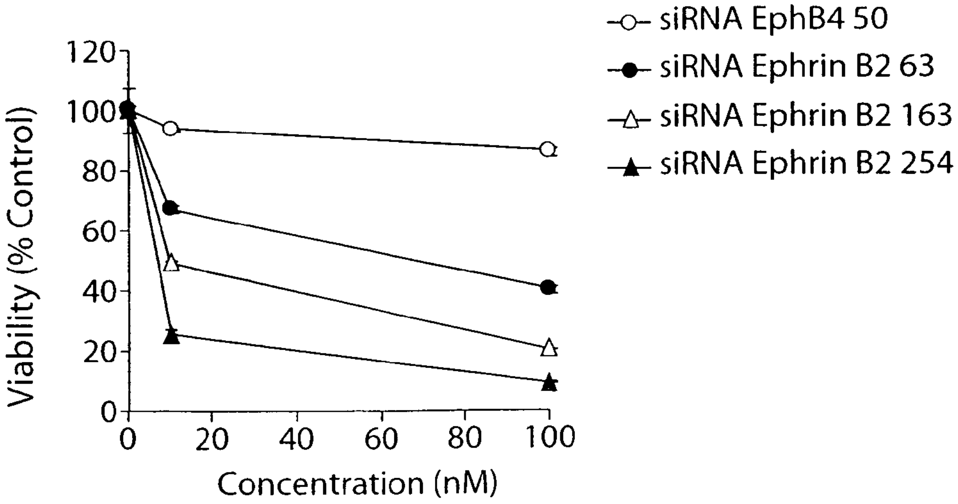
Figure 49C:
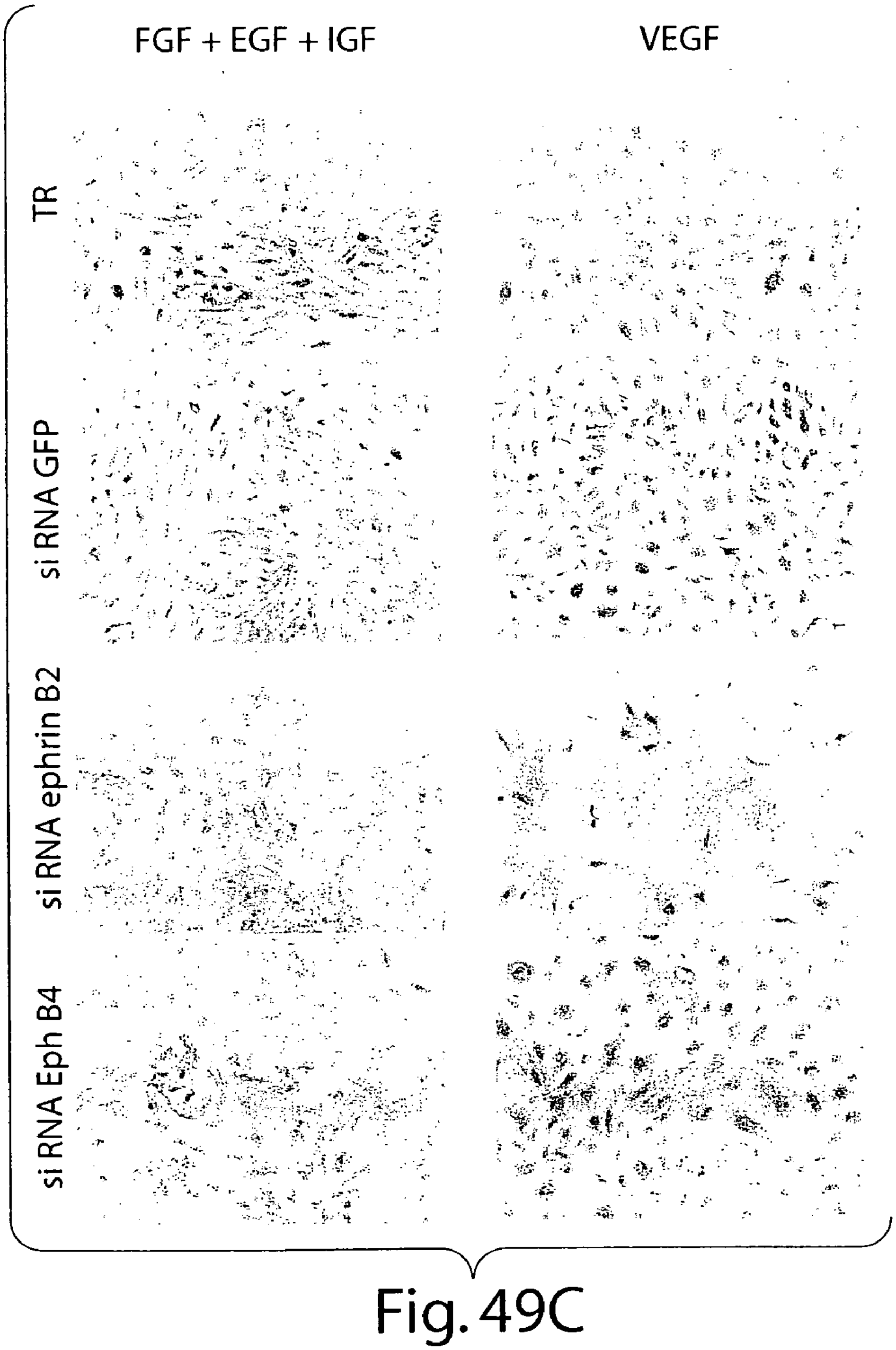
Figure 50:
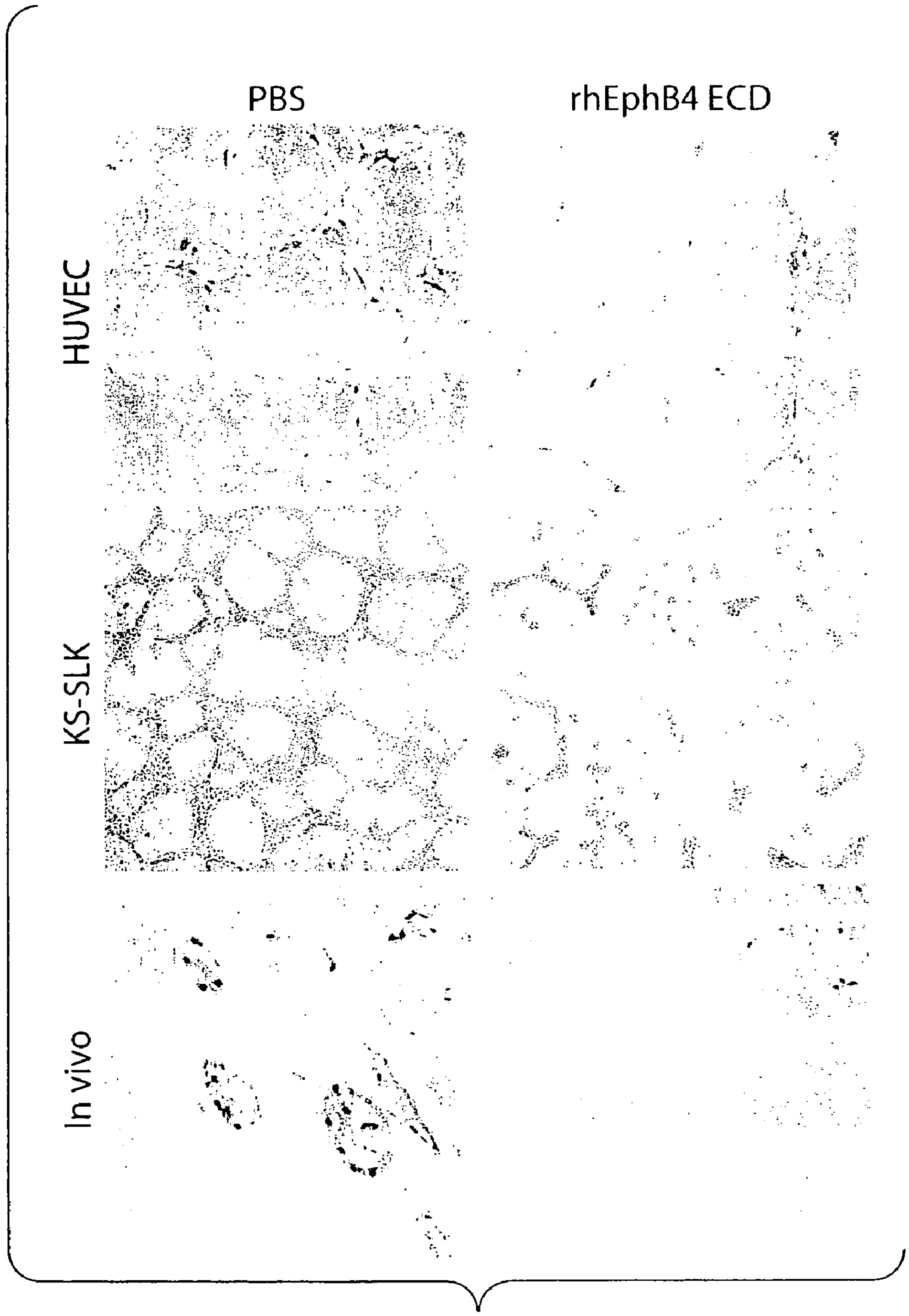
FIG. 50 shows that soluble EphB4 inhibits KS and EC cord formation and in vivo angiogenesis. Cord formation assay of HUVEC in MATRIGEL™ (upper row). Cells in exponential growth phase were treated overnight with the indicated concentrations of EphB4 extracellular domain (ECD) prior to plating on MATRIGEL™. Cells were trypsinized and plated ($1\times10^5$ cells/well) in a 24-well plate containing 0.5 ml MATRIGEL™. Shown are representative 20× phase contrast fields of cord formation after 8 hr plating on MATRIGEL™ in the continued presence of the test compounds as shown. Original magnification 200×. KS-SLK cells treated in a similar manner (middle row) in a cord formation assay on MATRIGEL™. Bottom row shows in vivo MATRIGEL™ assay: MATRIGEL™ plugs containing growth factors and EphB4 ECD or PBS were implanted subcutaneously in the mid-ventral region of mice. After 7 days the plugs were removed, sectioned and stained with H&E to visualize cells migrating into the matrix. Intact vessels with large lumens are observed in the control, whereas EphB4 ECD almost completely inhibited migration of cells into the Matrigel.

F. Ephrin B2 is Necessary for Full KS and EC Viability, Cord Formation and In Vivo Angiogenesis Activities The most effective ephrin B2 siRNA (254) was then used to determine whether inhibiting expression of ephrin B2 has any effect on the growth of KS-SLK or HUVEC cells. The viability of KS-SLK cells was decreased by the same siRNAs that inhibited ephrin B2 protein levels (FIG. 49B). KS-SLK express high levels of ephrin B2 and this result shows maintenance of ephrin B2 expression is integral to cell viability in this setting. HUVECs do not express ephrin B2, except when stimulated by VEGF as shown in FIG. 48B. Ephrin B2 siRNA 264 dramatically reduced growth of HUVECs cultured with VEGF as the sole growth factor. In contrast, no significant effect was seen when HUVECs were cultured with IGF, EGF and bFGF. As a control, EphB4 siRNA 50 had no detrimental effect on HUVECs in either culture condition (FIG. 49C). In addition to inhibition of viability of KS and primary endothelial cells, EphB4-ECD inhibits cord formation in HUVEC and KS-SLK and in vivo angiogenesis in the Matrigel™ plug assay (FIG. 50).

G. Methods and Materials

1) Cell Lines and Reagents

Human vascular endothelial cells (HUVEC) were from Clonetics (San Diego, Calif.) and were maintained in EGM-2 and EGM-2MV media respectively (Clonetics). T1 human fibroblast line was from Dr. Peter Jones, USC. BC-1 and BC-3 human pleural effusion lymphoma cell lines and monoclonal antibodies to LANA1 and ORF59 were the kind gift of Dr. Dharam Ablashi (Advanced Biotechnologies Inc., Columbia, Md.). KS-SLK was isolated from a Classic Kaposi's sarcoma patient (15). Polyclonal antibodies to EphB4, ephrin B2, CD148, PECAM-1 were obtained from Santa Cruz Biotechnology (Santa Cruz, Calif.). Mouse EphB4/$F_c$, and monoclonal antibodies to human vascular endothelial growth factor (VEGF), VEGF-C, interleukin-(IL)6, IL-8 and oncostatin-M were purchased from R & D Systems (Minneapolis, Minn.). Expression vectors pKSvGPCR-CEFL and pCEFL were the kind gift of Dr. Enrique Mesri (Cornell University, New York, N.Y.). Expression vectors for HHV-8 latency associated nuclear antigen (LANA) were kindly provided by Dr Matthew Rettig, Veteran's Administration Greater Los Angeles Healthcare System.

2) Collection and Preparation of Human Tissue

Human cutaneous Kaposi's sarcoma biopsy material was obtained under local anesthesia with informed consent from patients at the LAC/USC Medical Center, using an IRB approved consent form. Biopsies were processed for either total RNA, paraffin blocks or frozen tissue blocks in OCT. Total RNA was extracted by homogenization in guanidine isothiocyanate, (RNAzol: Tel-Test, Inc., Friendswoods, Tex.). cDNAs were synthesized by reverse transcriptase using a random hexamer primer (Superscript II; Invitrogen, Carlsbad, Calif.).

3) Preparation of Digoxigenin-Labeled RNA Probes

Ephrin B2 and EphB4 PCR products from the primers shown in Table 4 for in situ hybridization were cloned using the pGEM-T Easy system (Promega, Madison Wis.) according to the manufacturer's description using. The authenticity and insert orientation were confirmed by DNA sequencing. The pGEM-T Easy plasmids containing the PCR product of the human ephrin-B2 or EphB4 gene were linearized with Spe I or Nco I. Antisense or sense digoxigenin (DIG)-labeled RNA probes were transcribed from T7 or SP6 promoters by run-off transcription using a DIG RNA labeling kit (Roche, Indianapolis Ind.). RNA probes were quantitated by spot assay as described in the DIG RNA labeling kit instructions.

TABLE 4

Primers for Ephrin B2 and EphB4.

| Gene | Primer sequence | Product Size (bp) | SEQ. ID NO: |
|---|---|---|---|
| ISH Probe Primers | | | |
| ephrin B2 | 5'-TCC GTG TGG AGT ACT GCT G-3' | 296 | 53 |
| | 5'-TCT GGT TTG GCA GAG TTG AG-3' | | 54 |
| EphB4 | 5'-CTT TGG AAG AGA CCC TGC TG-3' | 297 | 55 |
| | 5'-AGA CGG TGA AGG TOT CCT TG-3' | | 56 |

TABLE 4-continued

| Primers for Ephrin B2 and EphB4. | | | |
|---|---|---|---|
| Gene | Primer sequence | Product Size (bp) | SEQ. ID NO: |
| RT-PCR Primers | | | |
| ephrin B2 | 5'-AGA CAA GAG CCA TGA AGA TC-3' | 200 | 57 |
| | 5'-GGA TCC CAC TTC GGA CCC GAG-3' | | 58 |
| EphB4 | 5'-TCA CGT CAC TGC ATT GAA CGG G-3' | 400 | 59 |
| | 5'-AAC TCG CTC TCA TCC AGT T-3' | | 60 |
| β-actin | 5'-GTG CCC CGC CCC AGG CAC CA-3' | 546 | 61 |
| | 5'-CTC CTT AAT GTC ACG CAC GAT TTC-3' | | 62 |

4) In Situ Hybridization

See above, e.g., Example 3.

5) Co-culture of HUVEC and BC-1

HUVEC cells were grown to 50-70% confluence in EGM-2 on gelatin-coated Labtech II 4-well chamber slides (Nalge Nunc International, Naperville, Ill.). Co-culture with BC-1 or BC-3 was essentially as described by Sakurada and coworkers (16). Briefly, BC-1 or BC-3 cells were pretreated with TPA (20 ng/ml) to induce virus for 48 hrs and then added to the HUVEC culture at a ratio of 10:1 for cocultivation for two days. The HUVECs were washed extensively with PBS to remove the attached BC-1 or BC-3 cells.

6) Preparation of cDNA and RT-PCR

The TITANIUM™ One-Step RT-PCR kit (Clontech, Palo Alto, Calif.) was used for RT-PCR from $1\times10^5$ cells. Primer pairs for amplification of EphB4, ephrin B2 and β-actin are shown in Table 4. Each PCR cycle consisted of denaturation at 94° C. for 30 s, primer annealing at 60° C. for 30 s and extension at 72° C. for 30 s. The samples were amplified for 30 cycles. PCR products were separated on 1.5% agarose gels and stained with ethidium bromide.

7) Cell Viability Assay

KS-SLK cells were seeded at a density of $1\times10^4$ per well in 48-well plates on day 0 in appropriate growth media containing 2% fetal calf serum (FCS). On the following day, the media was changed and cells were treated with 0, 10 or 100 nM siRNA. On day 3, viability was assessed using 3-(4,5-dimethylthiazol-2-yl)-2,5-diphenyltetrazolium bromide (MTT) as previously described (17).

8) Immunofluorescence Studies

Cells cultured on Labtech II 4-well chamber slides or frozen sections of KS biopsy material were fixed in 4% parafomaldehyde in Dulbecco's phosphate buffered saline pH 7.4 (PBS) for 30 min. The slides were rinsed twice in PBS and preincubated with blocking buffer (0.2% Triton-X100, 1% BSA in PBS) for 20 min, followed by incubation with antibodies to EphB4, ephrin B2, CD148, LANA1 or ORF59 (1:100 dilution in PBS) in blocking buffer at 4° C. for 16 hr. After washing three times, the slides were incubated with the appropriate fluorescein or rhodamine-conjugated secondary antibodies (Sigma-Aldrich, St. Louis, Mo.). Nuclei were counterstained with 4',6-diamidino-2-phenylindole dihydrochloride hydrate (DAPI), washed extensively with PBS and mounted with Vectasheild antifade mounting solution (Vector Laboratories, Burlingame, Calif.). Images were obtained using a Olympus AX70 fluorescence microscope and Spot v2.2.2 (Diagnostic Instruments Inc., Sterling Heights, Mich.) digital imaging system.

Immunofluorescence detection of EphrinB2 with EPHB4-Fc was done as follows. Frozen sections fixed in 4% paraformaldehyde and blocked with 20% FBS were incubated with 5 μg/ml EphB4/Fc (R&D Systems) for 1 h at RT. Sections were then incubated with 10 μg/ml rabbit anti-human IgG-FITC in PBS (Jackson ImmunoResearch Laboratories West Grove, Pa.) at RT for 1 hour. Nuclei were counterstained with DAPI and sections mounted as above. Human Fc (Jackson ImmunoResearch) was used as the negative control.

9) Western Blot

Crude cell lysates were prepared, quantitated, fractionated and transferred to membranes as described previously (17). Membranes were blocked with 5% non-fat milk prior to incubation with antibody to ephrin B2 (1:5000 dilution) at 4° C., for 16 h. Secondary antibody (1:100,000 dilution) conjugated with horseradish peroxidase was applied for 1 h at 25° C. The membranes were developed using the SuperSignal West Femto Maximum sensitivity chemiluminescent substrate (Pierce, Rockford, Ill.) according to the manufacturer's instructions. Membranes were stripped using Restore™ Western Blot Stripping Buffer (Pierce) and reprobed with EphB4 or actin.

10) Cord Formation Assay

Matrigel™ Basement Membrane Matrix (BD Biosciences Discovery Labware, Bedford, Mass.) was mixed with growth medium (3:1) on ice and 0.5 ml liquid placed in 24-well plates. Incubation of plates at 37° C. for 15 min caused Matrigel™ polymerization. HUVEC or KS-SLK in exponential phase growth were treated with 2 or 8 μg/ml EphB4-ECD or PBS as control for 16 h prior to trypsinizing and plating on the Matrigel™. Culture on Matrigel™ was continued in the presence of recombinant fusion proteins for 6 h. Cultures were fixed in 4% paraformaldehyde for 30 min and evaluated by inverted phase-contrast photomicroscopy.

11) Synthesis of Ephrin B2 and EphB4 siRNA by In Vitro Transcription

The Silencer™ siRNA construction kit (Ambion, Austin Tex.) was used to synthesize siRNA to ephrin B2 and EphB4. Briefly, three 21 bp target sequences comprising 19 bp downstream of a 5'-AA dinucleotide were identified in the ephrin B2 cDNA (Accession number NM_004093) that showed no significant homology to other sequences in the GenBank database. Sense and antisense siRNA 29-mer DNA oligonucleotide templates were synthesized at the USC Norris Microchemical Core Facility. Antisense template corresponded to the target sequence followed by 8 bp addition (5'-CCTGTCTC-3') at the 3' end complementary to the T7 promoter primer provided with the Silencer SiRNA Construction Kit. Sense template comprised 5'-AA followed by the complement of the target 19 bp, then the T7 8 bp sequence as above. In separate reactions, the two siRNA oligonucleotide templates were hybridized to a T7 promoter primer. The 3' ends of the hybridized oligonucleotides were extended by the Klenow fragment of DNA polymerase to create double-stranded siRNA transcription templates. The sense and antisense siRNA templates were transcribed by T7 RNA polymerase and the resulting RNA transcripts were hybridized to create dsRNA. The dsRNA consisted of 5' terminal single-stranded leader sequences, a 19 nt target specific dsRNA, and 3' terminal UUs. The leader sequences were removed by digesting the dsRNA with a single-stranded specific ribonuclease. The DNA template was removed at the same time by treatment with RNAse free deoxyribonuclease.

The resulting siRNAs were purified by glass fiber filter binding to remove excess nucleotides, short oligomers, proteins, and salts in the reaction. End product double-stranded 21mer siRNAs are shown in Table 5. Similarly, an EphB4 and green fluorescence protein (GFP) siRNAs were synthesized.

TABLE 5 siRNAs of ephrin B2 and EphB4.

| | | |
|---|---|---|
| ephrin B2 264 | 5'-GCAGACAGAUGCACUAUUAUU-3' | SEQ ID NO: 63 |
| | 3'-UUCGUCUGUCUACGUGAUAAU-5' | SEQ ID NO: 64 |
| ephrin B2 63: | 5'-CUGCGAUUUCCAAAUCGAUUU-3' | SEQ ID NO: 65 |
| | 3'-UUGACGCUAAAGGUUUAGCUA-5' | SEQ ID NO: 66 |
| ephrin B2 137: | 5'-GGACUGGUACUAUACCCACUU-3' | SEQ ID NO: 67 |
| | 3'-UUCCUGACCAUGAUAUGGGUG-5' | SEQ ID NO: 68 |
| Eph B4 50: | 5'-GAGACCCUGCUGAACACAAUU-3' | SEQ ID NO: 69 |
| | 3'-UUCUCUGGGACGACUUGUGUU-5' | SEQ ID NO: 70 |
| GFP | 5'-CGCUGACCCUGAAGUUCAUUU-3' | SEQ ID NO: 71 |
| | 3'-UUGCGACUGGGACUUCAAGUA-5' | SEQ ID NO: 72 |

12) Transfection of Ephrin B2 or EphB4 siRNA

HUVEC were seeded on eight-well chamber slides coated with fibronectin and grown overnight in EGM-2 (Cambrex, Walkersville, Md.). 16 h later media was replaced either with EBM-2 supplemented with 5% fetal calf serum (FCS) and EGM-2 BulletKit supplements bFGF, hEGF and $R^3$-IGF-I at the concentrations provided by the manufacturer, or EBM-2 supplemented with 5% FCS and 10 ng/ml rhVEGF (R&D Systems). After 2 h incubation at 37° C., the cells were transfected using Lipofectamine 2000 (1 μg/ml; Invitrogen) and 10 nM specific siRNAs in Opti-MEM-1 serum-free medium (Invitrogen). Following transfection for 2 hr in Opti-MEM-1, media supplemented as above was replaced in the appropriate wells. After 48 hrs, the cells were stained with crystal violet and immediately photographed at 10× magnification.

13) Construction of Ephrin B2 Reporter Plasmids

Human ephrin B2 5'-flanking DNA from −2491 to −11 with respect to the translation start site was amplified from BACPAC clone RP11-29716 (BacPac Resources, Children's Hospital, Oakland, Calif.) using the Advantage GC Genomic PCR kit (Clontech Palo Alto, Calif.) to overcome the large tracts of CG-rich sequence in the target area. Primers were designed to contain MluI sites for cloning. Amplified product was digested with MluI, gel purified and ligated into the MluI site in the multiple cloning site of pGL3Basic (Promega, Madison; WI). Orientation of the resulting clones was confirmed by restriction digest analysis. The correct clone was designated pEFNB2$_{-2491/-11}$luc. Digestion of this clone with either KpnI or SacI followed by recircularization yielded pEFNB2$_{-1242/-11}$luc and pEFNB2$_{-577/-11}$luc, respectively. Plasmid DNAs used for transient transfections were purified using a Mega Prep kit (QIAGEN, Valencia, Calif.).

14) Transient Transfection

HUVEC cells ($0.8\times10^4$ cells/well in 24 well plates) maintained in EGM-2 media were transiently co-transfected with 0.5 μg/well ephrin B2 promoter-luciferase constructs together with 50 ng/well either pCEFL or pKSvGPCR-CEFL, using Superfect reagent (QIAGEN) according to the manufacturer's instructions. Cells were harvested 48 h post-transfection and lysed with Luciferase cell lysis buffer (Promega). Luciferase activity was assayed using the Luciferase Assay System (Promega) according to the manufacturer's instructions. Luciferase was normalized to protein, because pCEFL-vGPCR induced the expression of β-galactosidase from pCMV-Sport-βgal (Invitrogen).

15) Construction and Purification of EphB4 Extra Cellular Domain (ECD) Protein

See above, e.g., Example 1.

Example 7

Expression of EphB4 in Bladder Cancer: a Candidate Target for Therapy

Figure 51:
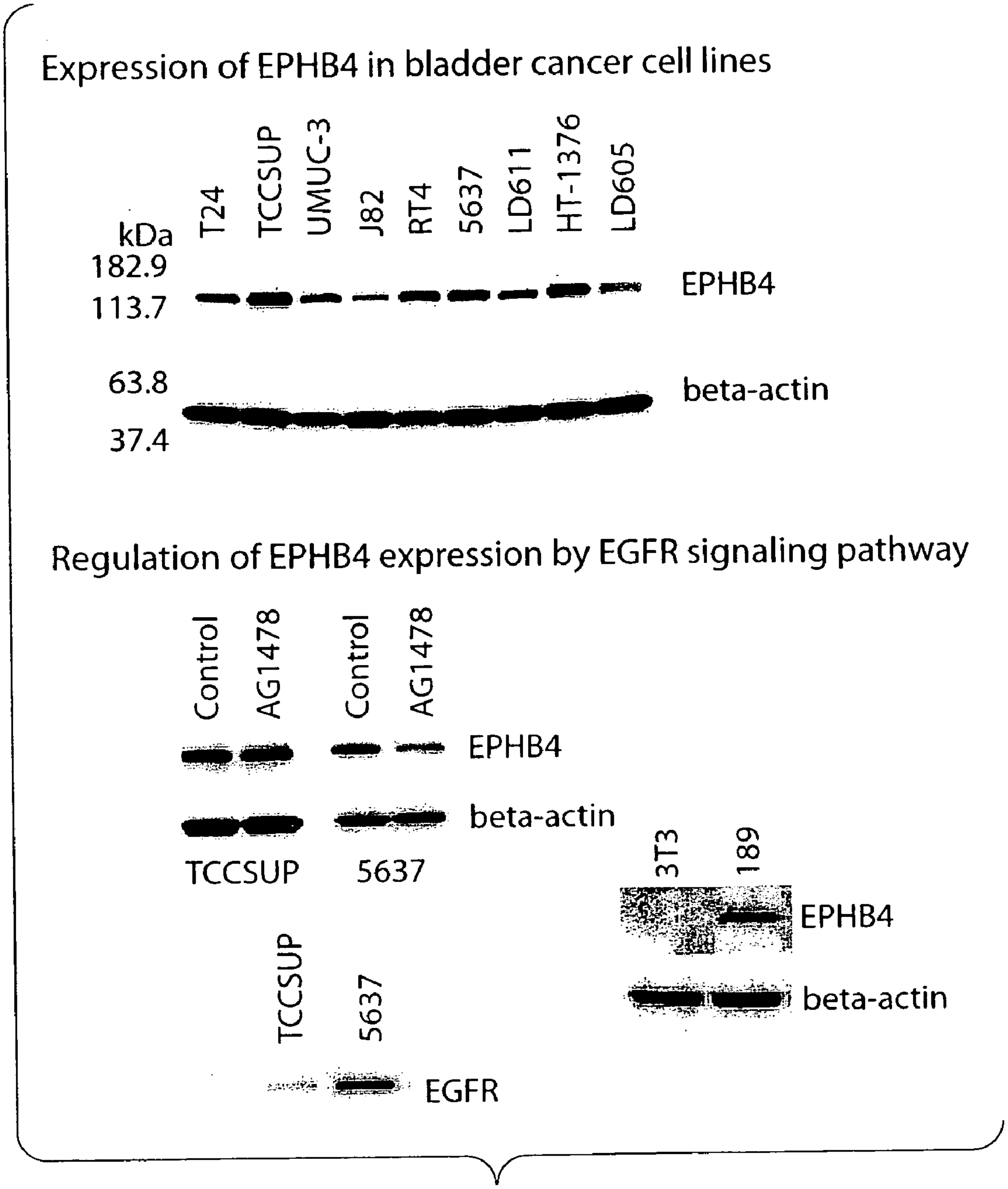
FIG. 51 shows expression of EPHB4 in bladder cancer cell lines (A), and regulation of EPHB4 expression by EGFR signaling pathway (B).

FIG. 51 shows expression of EPHB4 in bladder cancer cell lines (A), and regulation of EPHB4 expression by EGFR signaling pathway (B).

Figure 52:
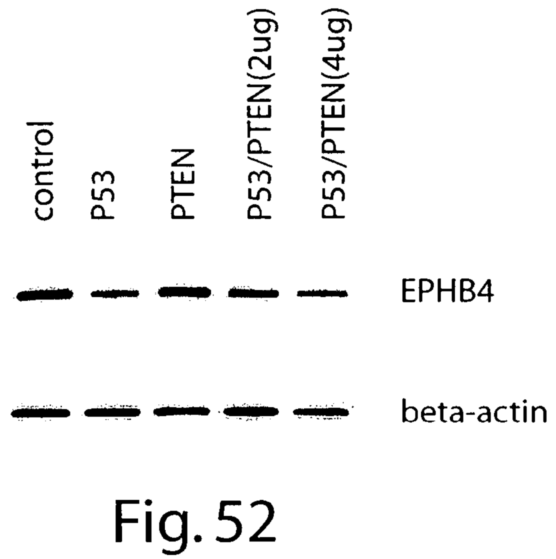
FIG. 52 shows that transfection of p53 inhibit the expression of EPHB4 in 5637 cell.

FIG. 52 shows that transfection of p53 inhibit the expression of EPHB4 in 5637 cell.

Figure 53:
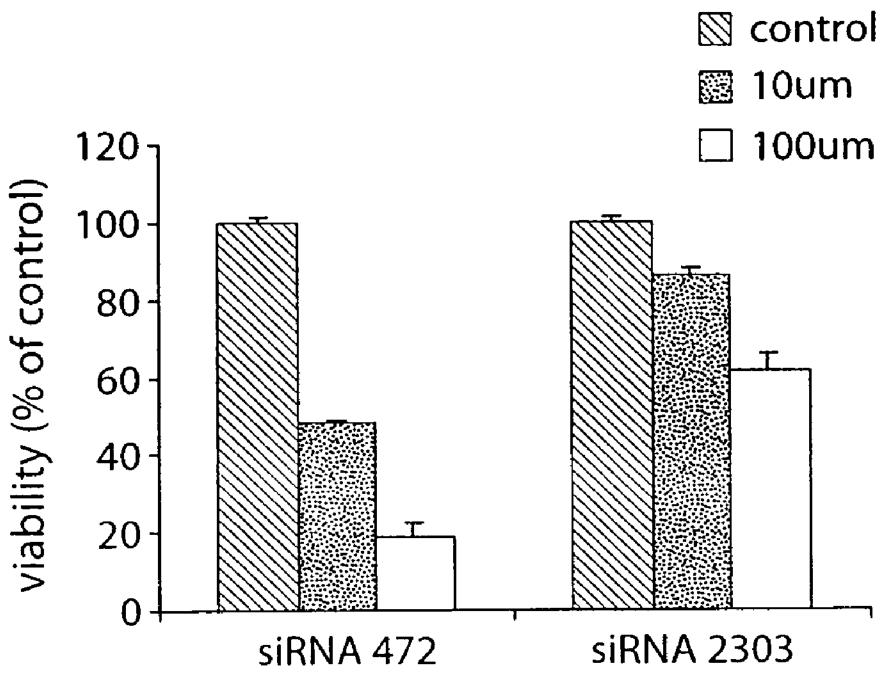
FIG. 53 shows growth inhibition of bladder cancer cell line (5637) upon treatment with EPHB4 siRNA 472.

FIG. 53 shows growth inhibition of bladder cancer cell line (5637) upon treatment with EPHB4 siRNA 472.

Figure 54:
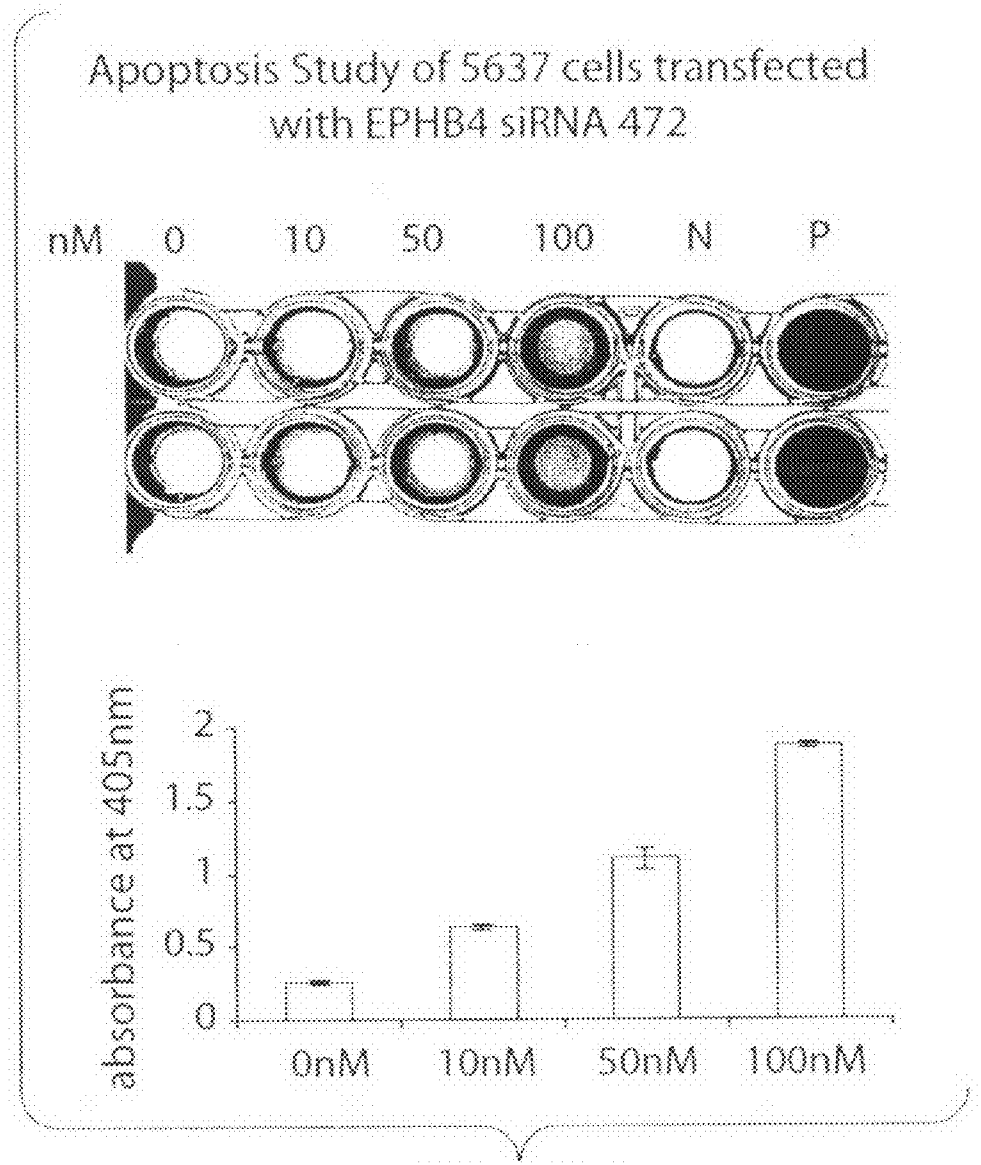
FIG. 54 shows results on apoptosis study of 5637 cells transfected with EPHB4 siRNA 472.

FIG. 54 shows results on apoptosis study of 5637 cells transfected with EPHB4 siRNA 472.

Figure 55:
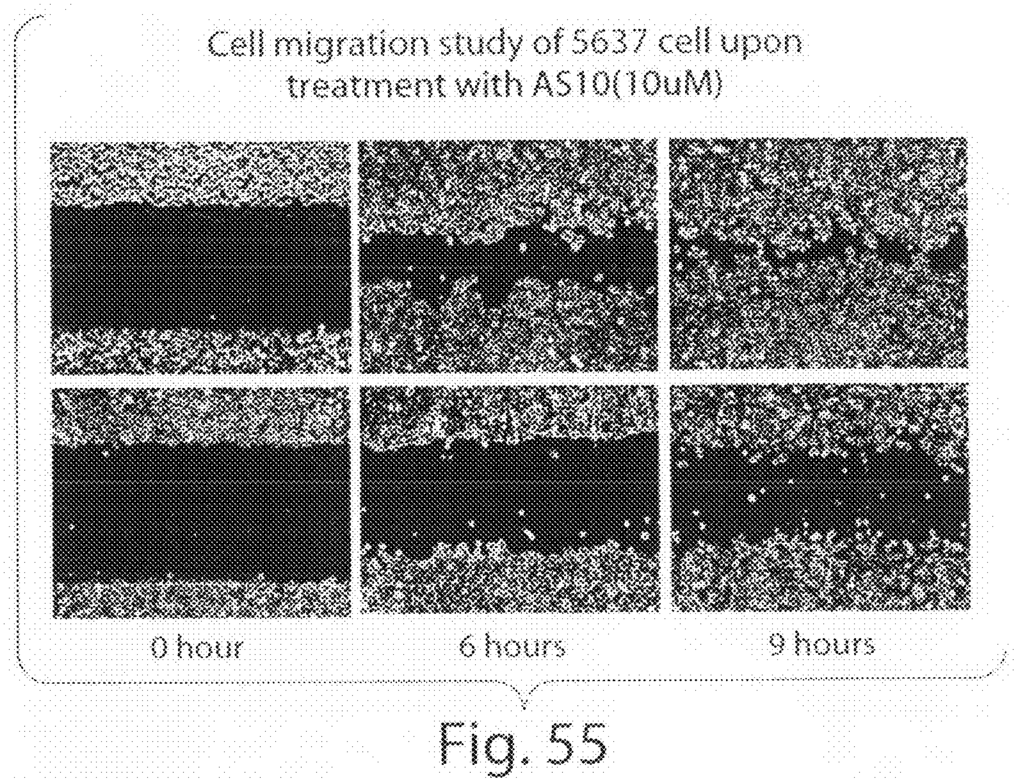
FIG. 55 shows effects of EPHB4 antisense probes on cell migration. 5637 cells were treated with EPHB4AS10 (10 μM) (bottom panels). Upper panels show control cells.

FIG. 55 shows effects of EPHB4 antisense probes on cell migration. 5637 cells were treated with EPHB4AS10 (10 μM).

Figure 56:
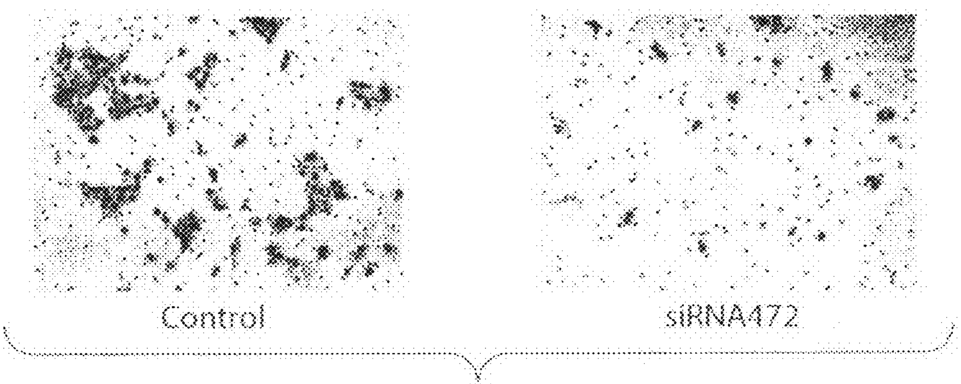
FIG. 56 shows effects of EPHB4 siRNA on cell invasion. 5637 cells were transfected with siRNA 472 or control siRNA.

FIG. 56 shows effects of EPHB4 siRNA on cell invasion. 5637 cells were transfected with siRNA 472 or control siRNA.

Example 8

Inhibition of EphB4 Gene Expression by EphB4 Antisense Probes and RNAi Probes

Cell lines expressing EphB4 were treated with the synthetic phosphorothioate modified oligonucleotides and harvested after 24 hr. Cell lysates were prepared and probed by western blot analysis for relative amounts of EphB4 compared to untreated control cells.

Studies on inhibition of cell proliferation were done in HNSCC cell lines characterized to express EphB4. Loss of cell viability was shown upon knock-down of EphB4 expression. Cells were treated in vitro and cultured in 48-well plates, seeded with 10 thousand cells per well. Test compounds were added and the cell viability was tested on day 3. The results on EphB4 antisense probes were summarized below in Table 6. The results on EphB4 RNAi probes were summarized below in Table 7.

TABLE 6

| Name | Sequence 5' → 3' | position | Inhibition of EphB4 Expression | Percent reduction in viability | SEQ ID NO: |
|---|---|---|---|---|---|
| Inhibition of EphB4 Gene Expression by EphB4 antisense probes | | | | | |
| Eph B4 169 | TCA GTA CTG CGG GGC CGG TCC | (2944-2963) | ++ | 36 | 73 |
| Eph B4 168 | TCC TGT CCC ACC CGG GGT TC | (2924-2943) | ++ | 51 | 74 |
| Eph B4 167 | CCG GCT TGG CCT GGG ACT TC | (2904-2923) | +++ | 66 | 75 |
| Eph B4 166 | ATG TGC TGG ACA CTG GCC PA | (2884-2903) | ++++ | 70 | 76 |
| Eph B4 165 | CAT TTT CTT CTG GTG TCC CG | (2864-2883) | ++++ | 75 | 77 |
| Eph B4 164 | CCA GAG TGA CTC CGA TTC GG | (2844-2863) | ++ | 40 | 78 |
| Eph B4 163 | AGC AGG TCC TCA GCA GAG AT | (2824-2843) | ++++ | 66 | 79 |
| Eph B4 162 | CTG GCT GAC CAG CTC GAA GG | (2804-2823) | | 25 | 80 |
| Eph B4 161 | AGC CAA AGC GAG CGG CTG CG | (2784-2803) | + | 33 | 81 |
| Eph B4 160 | AAA CTT TCT TCG TAT CTT CC | (2763-2783) | + | 25 | 82 |
| Eph B4 159 | CAT TTT GAT GGC CCG AAG CC | (2743-2762) | ++ | 40 | 83 |
| Eph B4 158 | ACT CGC CCA GAG AGC CAA AA | (2723-2742) | | 30 | 84 |
| Eph B4 157 | GCT GAG TAG TGA GGC TGC CG | (2703-2722) | + | 25 | 85 |
| Eph B4 156 | CTG GTC GAG GAG AGG GTG TG | (2683-2702) | ++ | 30 | 86 |
| Eph B4 155 | AGG CCC CGC CAT TCT CCC GG | (2663-2682) | | 25 | 87 |
| Eph B4 154 | GCC ACG ATT TTG AGG CTG GC | (2643-2662) | ++ | 40 | 88 |
| Eph B4 153 | GGG GTT CCG CAT CAT CTT GT | (2623-2642) | ++ | 35 | 89 |
| Eph B4 152 | CCA GGG CGC TGA CCA CCT GG | (2603-2622) | + | 30 | 90 |
| Eph B4 151 | GGG AAG CGG GGC CGG GCA TT | (2583-2602) | + | 25 | 91 |
| Eph B4 150 | CCC GTC TTT CTG CCA ACA GT | (2563-2582) | ++ | 25 | 92 |
| Eph B4 149 | CCA GCA TGA GCT GGT GGA GG | (2543-2562) | ++ | 20 | 93 |
| Eph B4 148 | GAG GTG GGA GAG TCT GGG GG | (2523-2542) | + | 30 | 94 |
| Eph B4 147 | CGG GGG GAG CCG GTA GTC CT | (2503-2522) | ++ | 40 | 95 |
| Eph B4 146 | GTT CAA TGG CAT TGA TCA CG | (2483-2502) | ++++ | 70 | 96 |
| Eph B4 145 | TCC TCA TTC CTC ATG TCC CA | (2463-2482) | ++++ | 80 | 97 |
| Eph B4 144 | CTA CCG CCT CTC CCC PAA TC | (2443-2462) | +++ | 60 | 98 |
| Eph B4 143 | ACA TCA CCT CCC ACA TCA CA | (2423-2442) | ++++ | 80 | 99 |
| Eph B4 142 | ATC CCC TPA CTC CAG GCA TC | (2403-2422) | ++ | 40 | 100 |
| Eph B4 141 | ACT GGC GGA AGT GAA CTT CC | (2383-2402) | +++ | 50 | 101 |
| Eph B4 140 | GGA AGG CPA TGG CCT CCC CG | (2363-2382) | ++ | 45 | 102 |
| Eph B4 139 | CCA GTC CAT CCC ATG GCA AT | (2343-2362) | ++++ | 70 | 103 |
| Eph B4 138 | CTT TCC TCC CAG GGA GCT CG | (2323-2342) | ++++ | 70 | 104 |
| Eph B4 137 | TGT AGG TGG CAT CGC AAG AG | (2303-2322) | ++ | 40 | 105 |

TABLE 6-continued

| Name | Sequence 5' → 3' | position | Inhibition of EphB4 Expression | Percent reduction in viability | SEQ ID NO: |
|---|---|---|---|---|---|
| Eph B4 136 | TTC TCC TCC AGG AAT CGG GA | (2283-2302) | ++ | 35 | 106 |
| Eph B4 135 | AAG GCC AAA CTC ACA CAC TT | (2263-2282) | ++++ | 60 | 107 |
| Eph B4 134 | GCA GAC GAG GTT CCT GTT GA | (2243-2262) | ++ | 50 | 108 |
| Eph B4 133 | CTA CCA TCT TCC GAG CAG CC | (2223-2242) | ++ | 40 | 109 |
| Eph B4 132 | ACC TCT CCC TCC ACC TAG CT | (2203-2222) | ++ | 40 | 110 |
| Eph B4 131 | CAT CTC CCC PAG CTA CCC CA | (2183-2202) | +++ | 50 | 111 |
| Eph B4 130 | TGC CCC ACC CCA TCC CCC CC | (2163-2182) | ++ | 50 | 112 |
| Eph B4 129 | AGC ATG CCC ACG AGC TGG AT | (2143-2162) | ++ | 50 | 113 |
| Eph B4 128 | GAC TGT CPA CTG TCC GTC CT | (2123-2142) | ++ | 50 | 114 |
| Eph B4 127 | TTA CCC CCA CCA ACC ACT CC | (2103-2122) | +++ | 60 | 115 |
| Eph B4 126 | ACC CCC CCC TTC TCC ATC PA | (2083-2102) | ++ | 50 | 116 |
| Eph B4 125 | CTC TGT GAG PAT CAT CAC CC | (2063-2082) | ++++ | 80 | 117 |
| Eph B4 124 | GCA TCC TCT TCC TCA CCA CC | (2043-2062) | ++++ | 70 | 118 |
| Eph B4 123 | CCC TCC AGG CCC ATG ATA TT | (2023-2042) | ++ | 50 | 119 |
| Eph B4 122 | CCC CTC CTC CPA CTC CCC CA | (2003-2022) | ++++ | 80 | 120 |
| Eph B4 121 | TCA TCC ACC CCT CCC TCA GA | (19S3-2002) | ++ | 50 | 121 |
| Eph B4 120 | PAC TCA CCC CCC TCC CCC TC | (1963-1982) | ++ | 40 | 122 |
| Eph B4 119 | CCT CTA CCC ACC CTT CAC CC | (1943-1962) | ++++ | 75 | 123 |
| Eph B4 118 | TCT TCA TTC CCA CAC ACC TC | (1923-1942) | ++++ | 80 | 124 |
| Eph B4 117 | TCC TTC TTC CCT CCC CCC TT | (1903-1922) | ++++ | 70 | 125 |
| Eph B4 116 | GAG CCC CCC CCC CCA CAC CT | (1883-1902) | ++ | 50 | 126 |
| Eph B4 115 | CCC CPA ACT CAC CTC CAC CA | (1863-1882) | ++++ | 60 | 127 |
| Eph B4 114 | ATC ACC TCT TCA ATC TTC AC | (1843-1862) | ++++ | 65 | 128 |
| Eph B4 113 | CTA CCA CAC ATC CAT CTC TT | (1823-1842) | ++++ | 90 | 129 |
| Eph B4 112 | TTC CPA ATT CCC TCA CAC CC | (1803-1822) | ++++ | 70 | 130 |
| Eph B4 111 | TCA TTA CCC TCT TCA TPA CT | (1783-1802) | ++++ | 70 | 131 |
| Eph B4 110 | CPA CCC CTC CAT CTA CAC CT | (1763-1782) | ++++ | 80 | 132 |
| Eph B4 109 | TAG TAC CAT CTC CCA TCA CA | (1743-1762) | ++ | 50 | 133 |
| Eph B4 108 | TAC TCT CCC TCT TTC TCC CA | (1723-1742) | ++ | 45 | 134 |
| Eph B4 107 | ATA TTC TCC TTC TCT CCC AT | (1703-1722) | ++++ | 70 | 135 |
| Eph B4 106 | TCC TCT CCT TCC TCA CCC AC | (1683-1702) | ++++ | 70 | 136 |
| Eph B4 105 | ACA ACT CCC ACC ACA ATC AC | (1663-1682) | ++ | 40 | 137 |
| Eph B4 104 | CAC CAC CAC CAC CAC CAC AC | (1643-1662) | ++++ | 70 | 138 |
| Eph B4 103 | CCA CCA CTC CCC TCC CCC CA | (1623-1642) | ++ | 40 | 139 |
| Eph B4 102 | ATC ACC CCC ACC TCC TCC CC | (1603-1622) | +++ | 50 | 140 |
| Eph B4 101 | CCA CCC CTC CCT CTC ATC CA | (1583-1602) | ++++ | 80 | 141 |
| Eph B4 100 | CTT CCC TCT CCC TCT CAT CT | (1563-1582) | ++++ | 80 | 142 |

TABLE 6-continued

| Name | Sequence 5' → 3' | position | Inhibition of EphB4 Expression | Percent reduction in viability | SEQ ID NO: |
|---|---|---|---|---|---|
| Eph B4 99 | TCC TCC CCC PAC CCC CCC TA | (1543-1562) | ++ | 35 | 143 |
| Eph B4 98 | CCC CCC CTC ACA CCC CCC CC | (1523-1542) | ++ | 50 | 144 |
| Eph B4 97 | CTA CCT CCA CCA CCT ACC TC | (1503-1522) | ++++ | 80 | 145 |
| Eph B4 96 | CCT CCC CCC TTC ACC CCC CC | (1483-1502) | ++ | 50 | 146 |
| Eph B4 95 | CAC CTC TCC CCC CTT TTC TC | (1463-1482) | ++ | 50 | 147 |
| Eph B4 94 | ACC TCT TCA CCA ACC CCA CC | (1443-1462) | ++++ | 80 | 148 |
| Eph B4 93 | CTC CTC CCA CCC TCC CCC CC | (1423-1442) | ++ | 40 | 149 |
| Eph B4 92 | CTT CTC ATG GTA TTT GAG CT | (1403-1422) | ++++ | 80 | 150 |
| Eph B4 91 | GCT ACT GGA CCA GAG CCC GA | (1383-1402) | ++++ | 85 | 151 |
| Eph B4 90 | GTG GGT GGG GGC GGA AGA GG | (1363-1382) | +++ | 50 | 152 |
| Eph B4 89 | GGA GGC GAG GGT GAA GGT GG | (1343-1462) | ++++ | 70 | 153 |
| Eph B4 88 | TGG GTG AGG AGG GGC TGA CC | (1323-1342) | ++ | 40 | 154 |
| Eph B4 87 | GGG ATG TGA GAG ACT GGA GG | (1303-1322) | ++++ | 60 | 155 |
| Eph B4 86 | AGG TAG GTG TGG GTG AGT GG | (1283-1302) | ++ | 50 | 156 |
| Eph B4 85 | TGA CAT TGA GAG GGT GAA AT | (1263-1282) | ++++ | 80 | 157 |
| Eph B4 84 | CCC AGG CCC CCC GTG GGT AA | (1243-1262) | ++ | 50 | 158 |
| Eph B4 83 | GGA GGA TAG CCC GTT CAA TG | (1223-1242) | +++ | 60 | 159 |
| Eph B4 82 | GAG TGA GGT CAA AGG TAT AG | (1203-1222) | ++++ | 70 | 160 |
| Eph B4 81 | GTG AAG TGA GGA GGT AGG CC | (1183-1202) | +++ | 60 | 161 |
| Eph B4 80 | TGG AAG GAG GAG GGA CCC CT | (1163-1182) | +++ | 50 | 162 |
| Eph B4 79 | GGA GGA GGT CCC CCC CCC CC | (1143-1162) | ++ | 40 | 163 |
| Eph B4 78 | CCC TGA AAA GTG AGG TGT CC | (1123-1142) | ++++ | 70 | 164 |
| Eph B4 77 | CCC CGA CCC CCC AGA GCA CC | (1103-1122) | +++ | 60 | 165 |
| Eph B4 76 | GTG CCC GTG CCC ACT CCC CC | (1083-1102) | +++ | 60 | 166 |
| Eph B4 75 | GAG CCC AGC CCC TAG CTC AG | (1063-1082) | ++ | 40 | 167 |
| Eph B4 74 | CTG GTG TGC CCC AGG ACA CT | (1043-1062) | ++ | 50 | 168 |
| Eph B4 73 | GGA CCC CCC GAG TGG ATT CC | (1023-1042) | ++ | 50 | 169 |
| Eph B4 72 | ACG TGG AGC GAG GAG CCC TT | (1003-1022) | ++++ | 70 | 170 |
| Eph B4 71 | GAG CCC GGA AAC GAG GGT CC | (983-1002) | ++ | 40 | 171 |
| Eph B4 70 | CCC GAG CCC AAC GAG CCC TC | (963-982) | +++ | 50 | 172 |
| Eph B4 69 | CTG GAG CGT GGA CCC CCC CC | (943-962) | +++ | 50 | 173 |
| Eph B4 68 | GTG TGT CCC TCG CCC GAA CT | (923-942) | ++ | 40 | 174 |
| Eph B4 67 | AGG GGA CCC CCC ACT CCC AC | (903-922) | ++ | 40 | 175 |
| Eph B4 66 | AGC GGT CAT GGA ATG GTG TT | (883-902) | ++ | 50 | 176 |
| Eph B4 65 | AGA GTG CGT ATT CCC TCC CC | (863-882( | ++++ | 60 | 177 |
| Eph B4 64 | ATC GGT CCC AGG AGG GTT CT | (843-862) | ++++ | 80 | 178 |
| Eph B4 63 | GGT GAG AGG CCC TTC AAG CT | (823-842) | ++++ | 80 | 179 |
| Eph B4 62 | CCC GTG CCC AGA CCC TGC CC | (803-822) | +++ | 70 | 180 |

TABLE 6-continued

| Name | Sequence 5' → 3' | position | Inhibition of EphB4 Expression | Percent reduction in viability | SEQ ID NO: |
|---|---|---|---|---|---|
| Eph B4 61 | ACT TCC TCT TGG GGT GAG CT | (783-802) | ++++ | 80 | 181 |
| Eph B4 60 | CCC TGC AAG CCC CCA GGA GA | (763-782) | +++ | 50 | 182 |
| Eph B4 59 | GGT GGA CCC GGT GAG CCC CT | (743-762) | ++++ | 50 | 183 |
| Eph B4 58 | CTT CCC CCC ACT CCC CAT CC | (723-742) | ++ | 45 | 184 |
| Eph B4 57 | TGA CCC GAG TAG AGG GTC CC | (703-722) | ++++ | 70 | 185 |
| Eph B4 56 | GGT CCC CCC AGG CCC CCC GA | (683-702) | ++ | 50 | 186 |
| Eph B4 55 | CCC CAT GGA GGA CCC AGG TA | (663-682) | ++ | 50 | 187 |
| Eph B4 54 | CCC CCC AGC CCC AGA AGG AC | (643-662) | ++ | 50 | 188 |
| Eph B4 53 | GTG CCC ACG GAG ACT GTG CC | (623-642) | +++ | 50 | 189 |
| Eph B4 52 | GCA ATG GAG TGA GGT TGA GA | (603-622) | ++++ | 90 | 190 |
| Eph B4 51 | GTG ACG TCC CCC GAG TTT TT | (583-602) | +++ | 70 | 191 |
| Eph B4 50 | CTA GAA GAG CTC GAG CCA TA | (563-582) | ++++ | 80 | 192 |
| Eph B4 49 | CGA CCC GGA TCG ACC GAG CC | (543-562) | ++++ | 80 | 193 |
| Eph B4 48 | TGG TGG TGG AAG CCC ACG TA | (523-542) | ++++ | 90 | 194 |
| Eph B4 47 | GAA CCC AGG GTT CGT GAG CC | (503-522) | ++++ | 80 | 195 |
| Eph B4 46 | GTG GGA GAG CGA CCC TGT TG | (483-502) | ++ | 40 | 196 |
| Eph B4 45 | AGA TTG AGG TTG CCC GTG CC | (463-482) | +++ | 50 | 197 |
| Eph B4 44 | GTG CCC CCC AGG CCC GTT CC | (443-462) | ++ | 50 | 198 |
| Eph B4 43 | CCC TCA CAT GGT CCC CCC CC | (423-442) | +++ | 60 | 199 |
| Eph B4 42 | AGG GTG TGG AGG TTG ATG TA | (403-422) | ++++ | 80 | 200 |
| Eph B4 41 | CCC GTT GTG CAT GGA CCC TC | (383-402) | ++++ | 80 | 201 |
| Eph B4 40 | CCC TCA CCC CCC TCC CCC TC | (363-382) | ++ | 50 | 202 |
| Eph B4 39 | TGG GCA TGC GTG TGA TAG TA | (343-362) | +++ | 60 | 203 |
| Eph B4 38 | GAA GAC GGT GAA GGT CTC CT | (323-342) | ++++ | 80 | 204 |
| Eph B4 37 | TGC AGG AGC GCC CAG CCC GA | (303-322) | +++ | 50 | 205 |
| Eph B4 36 | GGC AGG GAC AGG CAC TCG AG | (283-302) | +++ | 45 | 206 |
| Eph B4 35 | CAT GGT GAA GCG GAG CGT GG | (263-282) | ++ | 50 | 207 |
| Eph B4 34 | CGT ACA CGT GCA CGG CGC CC | (243-262) | ++ | 40 | 208 |
| Eph B4 33 | CGC CGT GGG AGC CAA CGT GT | (223-242) | +++ | 60 | 209 |
| Eph B4 32 | GGG AAG CGA GTG GGG GTC GG | (203-222) | ++++ | 70 | 210 |
| Eph B4 31 | GGG GGG CAC CGT GGA CGT GA | (183-202) | +++ | 60 | 211 |
| Eph B4 30 | GAC ACT TGG TAG GTG CGC AC | (163-182) | +++ | 70 | 212 |
| Eph B4 29 | GGT GTG CTG TTC GTC ATC GA | (143-162) | ++++ | 80 | 213 |
| Eph B4 28 | GGC CGC TGA CTT CGT CCC AC | (123-142) | ++ | 40 | 214 |
| Eph B4 27 | TGG GGG TGC ACC TGA GGG AA | (103-122) | ++ | 50 | 215 |
| Eph B4 26 | TGT GAC CGA CTT GAG ATC AG | (83-102) | ++++ | 70 | 216 |
| Eph B4 25 | GAG TTT GGA ATT TTG TGT TG | (63-82) | ++++ | 70 | 217 |

TABLE 6-continued

| Name | Sequence 5' → 3' | position | Inhibition of EphB4 Expression | Percent reduction in viability | SEQ ID NO: |
|---|---|---|---|---|---|
| Eph B4 24 | AGC AGG GTC TGT TCC AAA CC | (43-62) | ++++ | 80 | 218 |
| Eph B4 23 | TGC CGG CAA CGA AGG GGA GG | (23-42) | ++ | 50 | 219 |
| Eph B4 22 | AGA CGA GCA CCC GGA GCT CC | (3-22) | +++ | 50 | 220 |
| Eph B4 21 | AGG AGG ACC GGG AGC TGC AT | (1-20) | +++ | 50 | 221 |
| Additional antisense probes described in the specification | | | | | |
| Eph B4 AS-1 | GTG GAG GGA TAG GAG GGG CAT | (552-572) | | | 222 |
| Eph B4 AS-2 | AAC GAG GGG TGG TGC ACG GTG | (952-972) | | | 223 |
| Eph B4 AS-3 | TTG GAG GTG GAG GCA CCA GGG | (1007-1027) | | | 224 |
| Eph B4 AS-4 | CTC CTC ACA TTC AGA CCC TGA | (1263-1285) | | | 225 |
| Eph B4 AS-5 | TGT CCC TGT GAT GTT GGT CCC | (1555-1575) | | | 226 |
| Eph B4 AS-6 | GGG CCT GAG TTC CTC CGA | (123-140) | | | 227 |
| Eph B4 AS-7 | TGA ACG TGT GGT TGC AGC | (316-333) | | | 228 |
| Eph B4 AS-8 | CCC GCG GAG CGT GTC GAG CTT | (408-428) | | | 229 |
| Eph B4 AS-9 | GTT GAG GCT GTT GAT TGG GAG | (1929-1949) | | | 230 |
| Eph B4 AS-10 | ATG GAG CCC TCG CTC AGA AA | (1980-1999) | | | 231 |
| Eph B4 AS-11 | CAT CCC GAG GAG GTG CAT GAG | (2138-2158) | | | 232 |

TABLE 7

| RNAi | EphB4 RNAi sequence | | | Inhibition of EphB4 Expression | Percent reduction in viability | SEQ ID NO: |
|---|---|---|---|---|---|---|
| Inhibition of EphB4 Gene Expression by EphB4 RNAi probes | | | | | | |
| 1 | 446 | aaattggaaactgctgatctg | 466 | | | 233 |
| 2 | 447 | aattggaaactgctgatctga | 467 | +++ | 70 | 234 |
| 3 | 453 | aaactgctgatctgaagtggg | 473 | ++++ | 70 | 235 |
| 4 | 454 | aactgctgatctgaagtgggt | 474 | +++ | 80 | 236 |
| 5 | 854 | aatgtcaagacgctgcgtctg | 874 | +++ | 65 | 237 |
| 6 | 467 | aagtgggtgacattccctcag | 487 | + | 35 | 238 |
| 7 | 848 | aaggtgaatgtcaagacgctg | 868 | ++ | 50 | 239 |
| 8 | 698 | aaggagaccttcaccgtcttc | 718 | +++ | 75 | 240 |
| 9 | 959 | aaaaagtgcgcccagctgact | 979 | + | 40 | 241 |
| 10 | 1247 | aatagccactctaacaccatt | 1267 | ++ | 50 | 242 |
| 11 | 1259 | aacaccattggatcaqccgtc | 1279 | ++ | 50 | 243 |
| 12 | 1652 | aatgtcaccactgaccqagag | 1672 | + | 35 | 244 |
| 13 | 1784 | aaataccatqagaagggcgcc | 1804 | +++ | 65 | 245 |
| 14 | 1832 | aaqacgtcagaaaaccgggca | 1852 | + | 30 | 246 |
| 15 | 1938 | aacatcacagccagacccaac | 19 | ++ | 50 | 247 |
| 16 | 2069 | aagcagagcaatgggagagaa | 2089 | ++++ | 75 | 248 |

TABLE 7-continued

| RNAi | | EphB4 RNAi sequence | | Inhibition of EphB4 Expression | Percent reduction in viability | SEQ ID NO: |
|---|---|---|---|---|---|---|
| 17 | 2078 | aatgqgaqagaaqcagaatat | 2098 | +++ | 65 | 249 |
| 18 | 2088 | aagcagaatattcggacaaac | 2108 | +++ | 70 | 250 |
| 19 | 2094 | aatattcggacaaacacqqac | 2114 | ++ | 40 | 251 |
| 20 | 2105 | aaacacgqacagtatctcatc | 2125 | ++ | 50 | 252 |
| 21 | 2106 | aacacqgacagtatctcatcg | 2126 | + | 35 | 253 |
| 22 | 2197 | aaaagagatcqatgtctccta | 2217 | +++ | 65 | 254 |
| 23 | 2174 | aatgaggctgtgagggaattt | 2194 | ++ | 50 | 255 |
| 24 | 2166 | aagaccctaatqaggctqtga | 2186 | ++ | 50 | 256 |
| 25 | 2198 | aaagagatcgatgtctcctac | 2218 | +++ | 55 | 257 |
| 26 | 2199 | aaqagatcgatgtctcctacq | 2219 | +++ | 70 | 258 |
| 27 | 2229 | aagaggtgattggtqcaqgtg | 2249 | + | 33 | 259 |
| 28 | 2222 | aagattgaagaggtgattggt | 2242 | + | 30 | 260 |
| 29 | 2429 | aacagcatgcccgtcatgatt | 2449 | ++ | 40 | 261 |
| 30 | 2291 | aaqaaggagagctgtgtggca | 2311 | +++ | 50 | 262 |
| 31 | 2294 | aaqqagagctgtgtgqcaatc | 2314 | +++ | 60 | 263 |
| 32 | 2311 | aatcaagaccctgaaqgqtgg | 2331 | +++ | 70 | 264 |
| 33 | 2497 | aaacgacggacagttcacagt | 2517 | + | 35 | 265 |
| 34 | 2498 | aacgacggacagttcacagtc | 2518 | + | 40 | 266 |
| 35 | 2609 | aacatcctagtcaacagcaac | 2629 | ++ | 50 | 267 |
| 36 | 2621 | aacagcaacctcgtctqcaaa | 2641 | + | 35 | 268 |
| 37 | 2678 | aactcttccgatcccacctac | 2698 | ++ | 50 | 269 |
| 38 | 2640 | aagtgtctgactttggccttt | 2660 | +++ | 70 | 270 |
| 39 | 2627 | aacctcgtctgcaaagtqtct | 2647 | ++ | 50 | 271 |
| 40 | 2639 | aaagtgtctgactttggcctt | 2659 | + | 25 | 272 |
| 41 | 2852 | aatcagqacqtgatcaatgcc | 2872 | +++ | 75 | 273 |
| 42 | 2716 | aaagattcccatccgatggac | 2736 | ++ | 50 | 274 |
| 43 | 2717 | aagattcccatccgatggact | 2737 | ++ | 60 | 275 |
| 44 | 2762 | aaqttcacttccgccaqtgat | 2782 | +++ | 70 | 276 |
| 45 | 3142 | aagatacqaagaaagtttcqc | 3162 | ++ | 50 | 277 |
| 46 | 3136 | aatgqgaagatacgaagaaag | 3156 | +++ | 66 | 278 |
| 47 | 2867 | aatgccattqaacaggactac | 2887 | | | 279 |
| 48 | 3029 | aaaatcgtgqcccgggaqaat | 3049 | + | 33 | 280 |
| 49 | 3254 | aaaatcttggccagtqtccag | 3274 | ++ | 50 | 281 |
| 50 | 3255 | aaatcttggccaqtqtccagc | 3275 | +++ | 75 | 282 |
| 51 | 3150 | aagaaaqtttcgcagccqctg | 3170 | +++ | 80 | 283 |
| 52 | 3251 | aagaaaatcttggccagtgtc | 3271 | ++ | 50 | 284 |
| 53 | 3256 | aatctcqgccagtgtccagca | 3276 | ++ | 50 | 285 |

TABLE 7-continued

| RNAi | EphB4 RNAi sequence | Inhibition of EphB4 Expression | Percent reduction in viability | SEQ ID NO: |
|---|---|---|---|---|
| Additional RNAi probes described in the specification | | | | |
| Eph B4 50 | gagacccugcuqaacacaauu | | | 286 |
| Eph B4 472 | ggugaaugucaagacgcuquu | | | 287 |
| Eph B4 1562 | caucacagccagacccaacuu | | | 288 |
| siRNA 2303 | cucuuccgaucccaccuacuu | | | 289 |
| Eph B4 2302 | cucuuccgaucccaccuacuu | | | 290 |

Example 9

Inhibition of Ephrin B2 Gene Expression by Ephrin B2 Antisense Probes and RNAi Probes KS SLK, a cell line expressing endogenous high level of ephrin B2. Cell viability was tested using fixed dose of each oligonucleotide (5UM). Gene expression downregulation was done using cell line 293 engineered to stably express full-length ephrin B2. KS SLK expressing EphrinB2 were also used to test the viability in response to RNAi probes tested at the fixed dose of 50 nM. Protein expression levels were measured using 293 cells stably expressing full-length EphrinB2, in cell lysates after 24 hr treatment with fixed 50 nM of RNAi probes.

The results on Ephrin B2 antisense probes were summarized below in Table 8. The results on Ephrin B2 RNAi probes were summarized below in Table 9.

TABLE 8

Ephrin B2 antisense ODNs.

| | sequence | Coding region | Percent reduction in viability | Inhibition of Ephrin B2 Expression | SEQ ID NO: |
|---|---|---|---|---|---|
| Ephrin AS-51 | TCA GAC CTT GTA GTA AAT GT | (983-1002) | | ++ | 291 |
| Ephrin AS-50 | TCG CCG GGC TCT GCG GGG GC | (963-982) | 50 | +++ | 292 |
| Ephrin AS-49 | ATC TCC TGG ACG ATG TAC AC | (943-962) | 45 | ++ | 293 |
| Ephrin AS-48 | CGG GTG CCC GTA GTC CCC GC | (923-942) | 35 | ++ | 294 |
| Ephrin AS-47 | TGA CCT TCT CGT AGT GAG GG | (903-922) | 40 | +++ | 295 |
| Ephrin AS-46 | CAG AAG ACG CTG TCC GCA GT | (883-902) | 40 | ++ | 296 |
| Ephrin AS-45 | CCT TAG CGG GAT GAT AAT GT | (863-882) | 35 | ++ | 297 |
| Ephrin AS-44 | CAC TGG GCT CTG AGC CGT TG | (843-862) | 60 | +++ | 298 |
| Ephrin AS-43 | TTG TTG CCG CTG CGC TTG GG | (823-842) | 40 | ++ | 299 |
| Ephrin AS-42 | TGT GGC CAG TGT GCT GAG CG | (803-822) | 40 | ++ | 300 |
| Ephrin AS-41 | ACA GCG TGG TCG TGT GCT GC | (783-802) | 70 | +++ | 301 |
| Ephrin AS-40 | GGC GAG TGC TTC CTG TGT CT | (763-782) | 80 | ++++ | 302 |
| Ephrin AS-39 | CCT COG GTA CTT CAG CAA GA | (743-762) | 50 | +++ | 303 |
| Ephrin AS-38 | GGA CCA CCA GCG TGA TGA TG | (723-742) | 60 | +++ | 304 |
| Ephrin AS-37 | ATG ACG ATG AAG ATG ATG CA | (703-722) | 70 | +++ | 305 |
| Ephrin AS-36 | TCC TGA AGC AAT CCC TGC AA | (683-702) | 60 | +++ | 306 |
| Ephrin AS-35 | ATA AGG CCA CTT CGG AAC CG | (663-682) | 45 | ++ | 307 |
| Ephrin AS-34 | AGG ATG TTG TTC CCC GAA TG | (643-662) | 50 | +++ | 308 |
| Ephrin AS-33 | TCC GGC GCT GTT GCC GTC TG | (623-642) | 75 | +++ | 309 |
| Ephrin AS-32 | TGC TAG AAC CTG GAT TTG GT | (603-622) | 60 | +++ | 310 |
| Ephrin AS-31 | TTT ACA AAG GGA CTT GTT GT | (583-602) | 66 | +++ | 311 |

TABLE 8-continued

| Ephrin B2 antisense ODNs. | sequence | Coding region | Percent reduction in viability | Inhibition of Ephrin B2 Expression | SEQ ID NO: |
|---|---|---|---|---|---|
| Ephrin AS-30 | CGA ACT TCT TCC ATT TGT AC | (563-582) | 50 | ++ | 312 |
| Ephrin AS-29 | CAG CTT CTA GTT CTG GAC GT | (543-562) | 50 | +++ | 313 |
| Ephrin AS-28 | CTT GTT GGA TCT TTA TTC CT | (523-542) | 70 | +++ | 314 |
| Ephrin AS-27 | GGT TGA TCC AGC AGA ACT TG | (503-522) | 65 | +++ | 315 |
| Ephrin AS-26 | CAT CTT GTC CAA CTT TCA TG | (483-502) | 75 | +++ | 316 |
| Ephrin AS-25 | AGG ATC TTC ATG GCT CTT GT | (463-482) | 60 | +++ | 317 |
| Ephrin AS-24 | CTG GCA CAC CCC TCC CTC CT | (443-462) | 45 | ++ | 318 |
| Ephrin AS-23 | GGT TAT CCA GGC CCT CCA AA | (423-442) | 50 | +++ | 319 |
| Ephrin AS-22 | GAC CCA TTT GAT GTA GAT AT | (403-422) | 50 | +++ | 320 |
| Ephrin AS-21 | AAT GTA ATA ATC TTT GTT CT | (383-402) | 60 | +++ | 321 |
| Ephrin AS-20 | TCT GAA ATT CTA GAC CCC AG | (363-382) | 60 | +++ | 322 |
| Ephrin AS-19 | AGG TTA GGG CTG AAT TCT TG | (343-362) | 75 | +++ | 323 |
| Ephrin AS-18 | AAA CTT GAT GGT GAA TTT GA | (323-342) | 60 | +++ | 324 |
| Ephrin AS-17 | TAT CTT GGT CTG GTT TGG CA | (303-322) | 50 | ++ | 325 |
| Ephrin AS-16 | CAG TTG AGG AGA GGG GTA TT | (283-302) | 40 | ++ | 326 |
| Ephrin AS-15 | TTC CTT CTT AAT AGT GCA TC | (263-282) | 66 | +++ | 327 |
| Ephrin AS-14 | TGT CTG CTT GGT CTT TAT CA | (243-262) | 70 | ++++ | 328 |
| Ephrin AS-13 | ACC ATA TAA ACT TTA TAA TA | (223-242) | 50 | +++ | 329 |
| Ephrin AS-12 | TTC ATA CTG GCC AAC AGT TT | (203-222) | 50 | +++ | 330 |
| Ephrin AS-11 | TAG AGT CCA CTT TGG GGG AA | (183-202) | 70 | ++++ | 331 |
| Ephrin AS-10 | ATA ATA TCC AAT TTG TCT CC | (163-182) | 70 | ++++ | 332 |
| Ephrin AS-9 | TAT CTG TGG GTA TAG TAC CA | (143-162) | 80 | ++++ | 333 |
| Ephrin AS-8 | GTC CTT GTC CAG GTA GAA AT | (123-142) | 60 | +++ | 334 |
| Ephrin AS-7 | TTG GAG TTC GAG GAA TTC CA | (103-122) | 80 | ++++ | 335 |
| Ephrin AS-6 | ATA GAT AGG CTC TAA AAC TA | (83-102) | 70 | +++ | 336 |
| Ephrin AS-5 | TCG ATT TGG AAA TCG CAG TT | (63-82) | 50 | +++ | 337 |
| Ephrin AS-4 | CTG CAT AAA ACC ATC AAA AC | (43-62) | 80 | ++++ | 338 |
| Ephrin AS-3 | ACC CCA GCA GTA CTT CCA CA | (23-42) | 85 | ++++ | 339 |
| Ephrin AS-2 | COG AGT COO TTO TOA CAG CC | (3-22) | 70 | +++ | 340 |
| Ephrin AS-1 | GAG TCC CTT CTC ACA GCC AT | (1-20) | 80 | ++++ | 341 |

TABLE 9

| RNAi Sequence and homology with other human genes. | Percent reduction in viability | Inhibition of Ephrin B2 Expression | RNAi no. | SEQ ID NO: |
|---|---|---|---|---|
| Ephrin B2 RNAi probes. | | | | |
| 89 aactgcgatttccaaatcgat 109 | 80 | ++++ | 1 | 342 |
| 141 aactccaaatttctacctgga 161 | 70 | ++++ | 2 | 343 |
| 148 aatttctacctggacaaggac 168 | 75 | +++ | 3 | 344 |

TABLE 9-continued

| RNAi Sequence and homology with other human genes. | Percent reduction in viability | Inhibition of Ephrin B2 Expression | RNAi no. | SEQ ID NO: |
|---|---|---|---|---|
| 147 aaatttctacctggacaagga 167 | 60 | +++ | 4 | 345 |
| 163 aaggactggtactatacccac 183 | 40 | ++ | 5 | 346 |
| 217 aagtggactctaaaactgttg 237 | 80 | ++++ | 6 | 347 |
| 229 aaactgttggccagtatgaat 249 | 50 | +++ | 7 | 348 |
| 228 aaaactgttggccagtatgaa 248 | 80 | ++++ | 8 | 349 |
| 274 aagaccaagcagacagatgca 294 | 80 | ++++ | 11 | 350 |
| 273 aaaqaccaagcagacagatqc 293 | 60 | +++ | 12 | 351 |
| 363 aagtttcaagaattcagccct 383 | 66 | +++ | 13 | 352 |
| 370 aagaattcaqccctaacctct 390 | 50 | +++ | 14 | 353 |
| 373 aattcagccctaacctctggg 393 | 50 | +++ | 15 | 354 |
| 324 aactgtgccaaaccagaccaa 344 | 90 | ++++ | 16 | 355 |
| 440 aaatgggtccttggagggcct 460 | 80 | ++++ | 17 | 356 |
| 501 aagatcctcatgaaagttgqa 521 | 50 | +++ | 18 | 357 |
| 513 aaagttggacaagatgcaagt 533 | 50 | +++ | 19 | 358 |
| 491 aagagccatgaagatcctcat 511 | 50 | +++ | 20 | 359 |
| 514 aagttggacaagatgcaagtt 534 | 66 | +++ | 21 | 360 |
| 523 aagatgcaagttctgctggat 543 | 66 | +++ | 22 | 361 |
| 530 aagttctgccgqatcaaccag 550 | 50 | +++ | 23 | 362 |
| 545 aaccaqgaataaaqatccaac 565 | 35 | ++ | 24 | 363 |
| 555 aaagatccaacaagacqtcca 575 | 40 | ++ | 25 | 364 |
| 556 aagatccaacaagacqtccaq 576 | 60 | +++ | 26 | 365 |
| 563 aacaagacqtccagaactaga 583 | 60 | +++ | 27 | 366 |
| 566 aaqacgtccagaactagaagc 586 | 70 | +++ | 28 | 367 |
| 593 aaatggaagaagttcqacaac 613 | 75 | ++++ | 29 | 368 |
| 577 aactagaagctqgtacaaatq 597 | 66 | +++ | 30 | 369 |
| 594 aatggaagaagttcgacaaca 614 | 35 | ++ | 31 | 370 |
| 583 aagctggtacaaatggaagaa 603 | 50 | +++ | 32 | 371 |
| 611 aacaagtccctttqtaaaacc 631 | 70 | ++++ | 33 | 372 |
| 599 aagaagttcgacaacaagtcc 619 | 70 | ++++ | 34 | 373 |
| 602 aagttcgacaacaagtccctt 622 | 80 | ++++ | 35 | 374 |
| 626 aaaaccaaatccaggttctag 646 | 50 | +++ | 36 | 375 |
| 627 aaaccaaatccagqttctagc 647 | 25 | + | 37 | 376 |
| 628 aaccaaatccaggttctagca 648 | 30 | ++ | 38 | 377 |
| 632 aaatccagqttctagcacaga 652 | 60 | +++ | 39 | 378 |
| 633 aatccaggttctagcacagac 653 | 40 | ++ | 40 | 379 |
| 678 aacaacatcctcqgttccgaa 698 | 30 | ++ | 41 | 380 |
| 681 aacatcctcggttccgaagtg 701 | 20 | + | 42 | 381 |
| 697 aaqtggccttatttqcaggga 717 | 30 | ++ | 43 | 382 |

TABLE 9-continued

| RNAi Sequence and homology with other human genes. | Percent reduction in viability | Inhibition of Ephrin B2 Expression | RNAi no. | SEQ ID NO: |
|---|---|---|---|---|
| Additional Ephrin B2 RNAi probes described in the specification | | | | |
| GCAGACAGAUGCACUAUUAUU | | | ephrin B2 264 | 383 |
| CUGCGAUUUCCAAAUCGAUUU | | | ephrin B2 63 | 384 |
| GGACUGGUACUAUACCCACUU | | | ephrin B2 137 | 385 |

Example 10

Effect of Ephrin B2 and EphB4 Polyclonal Antibodies on Tumor Cell Growth

Two EphB4 polyclonal antibodies (H-200 and N-19) were purchased from Santa Cruz Biotech (Santa Cruz, Calif.). The H-200 antibody (also called sc-5536) has an epitope region corresponding to amino acids 201-400 within an extracellular domain of human EphB4, while the N-19 antibody (also called sc-7285) has an epitope region within an N-terminal extracellular domain of human EphB4. In addition, an Ephrin B2 polyclonal was purchased from R&D Systems (Minneapolis, Minn.).

Figure 67A:
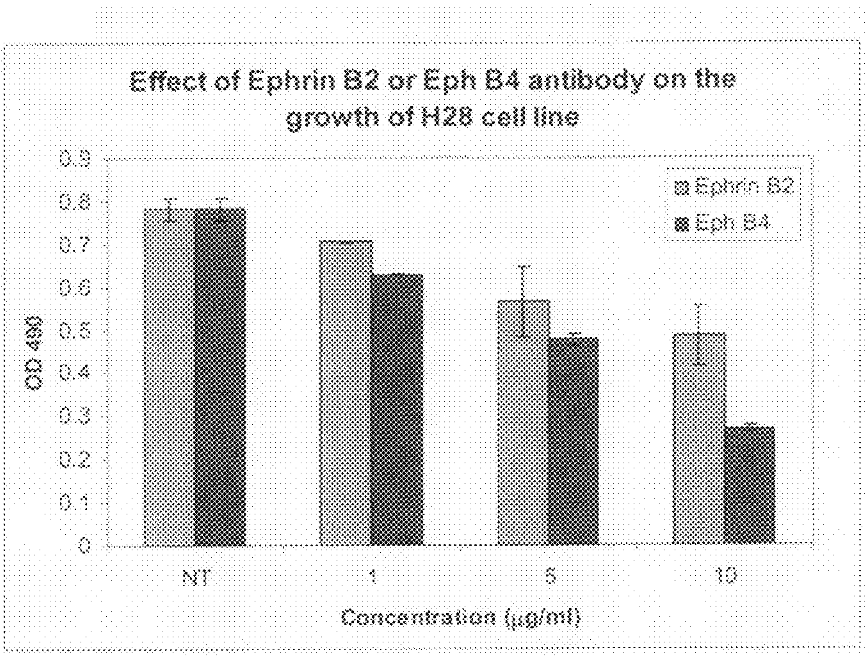
FIG. 67 shows effect of Ephrin B2 polyclonal antibodies and EphB4 polyclonal antibodies tumor cell growth. A) H28 cell line; B) H2373 cell line; and C) H2052 cell line.
Figure 67B:
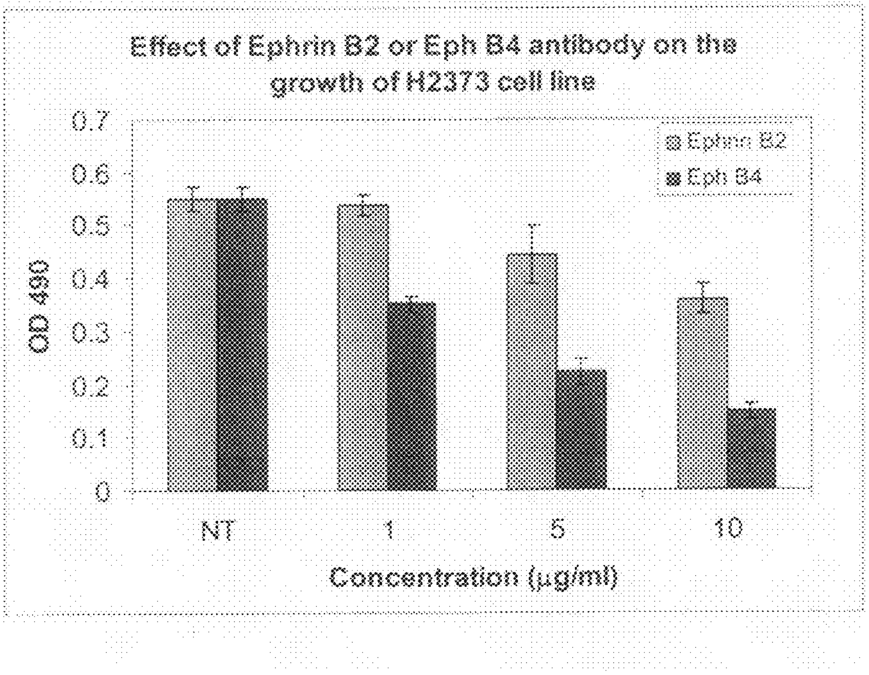

Three mesothelioma cell lines (H28, H2052, and H2373) were obtained from the ATCC (Manassas, Va.) and used to test the anti-tumor activities of these EphB4 and Ephrin B2 polyclonal antibodies. These cells (about 5,000 cells/well) were plated in 48 well plates, and were treated the following day with different concentrations of each antibody. The cell viability assay (MTT) was done on day 4. The effects of the Ephrin B2 and EphB4 polyclonal antibodies on tumor cell growth were shown in FIG. 67.

Example 11

Effect of EphB4 Monoclonal Antibodies on Angiogenesis and Tumor Growth

A. Generation and Functional Analysis of EphB4 Antibodies

Anti-EphB4 monoclonal antibodies were raised in mice against the extracellular domain (ECD) of EphB4. An EphB4ECD (FIG. 68) was cloned into expression vectors (e.g., pGEX) to generate EphB4ECD fusion proteins (e.g., GST-ECD). EphB4ECD fusion protein expressed in BL21 *E. coli* was purified by affinity chromatography. In the case of GST fusion proteins, the GST domain was cleaved by thrombin. Monoclonal antibody was purified from hybridoma supernatants by Protein A chromatography.

Figure 57:
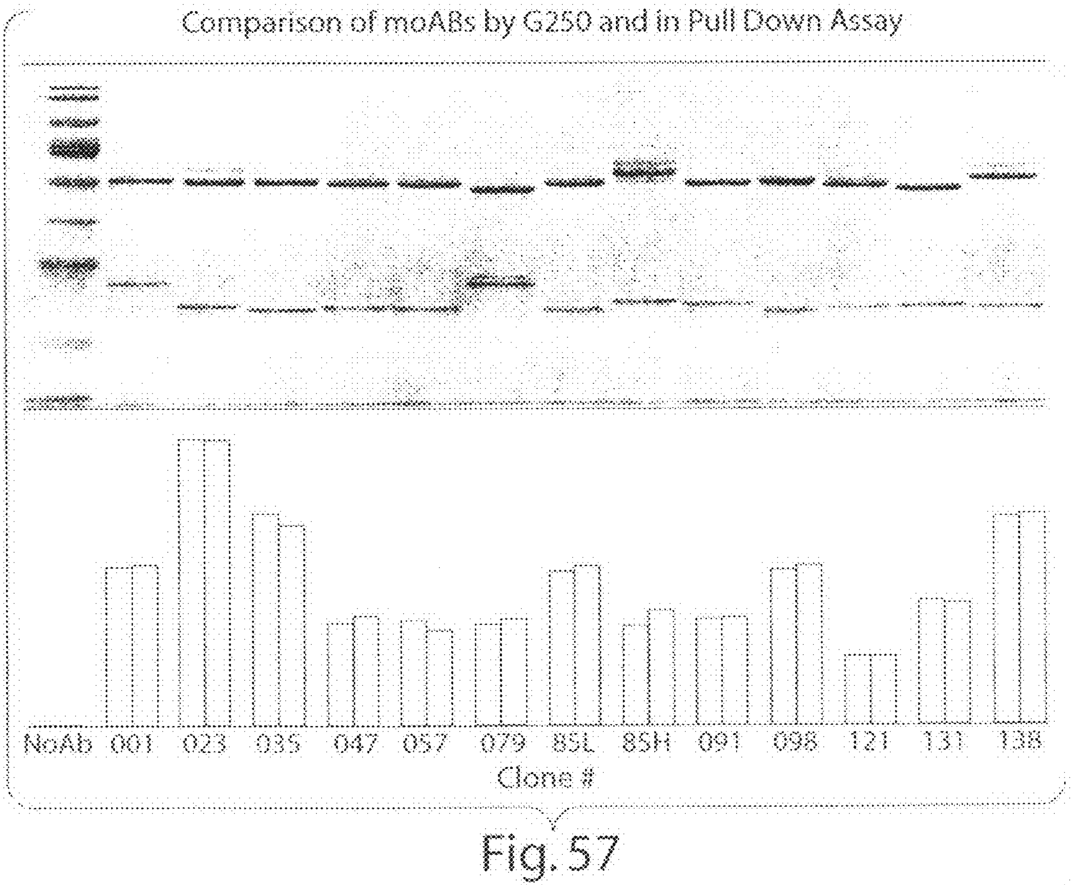
FIG. 57 shows comparison of EphB4 monoclonal antibodies by G250 and in pull-down assay.
Figure 68:
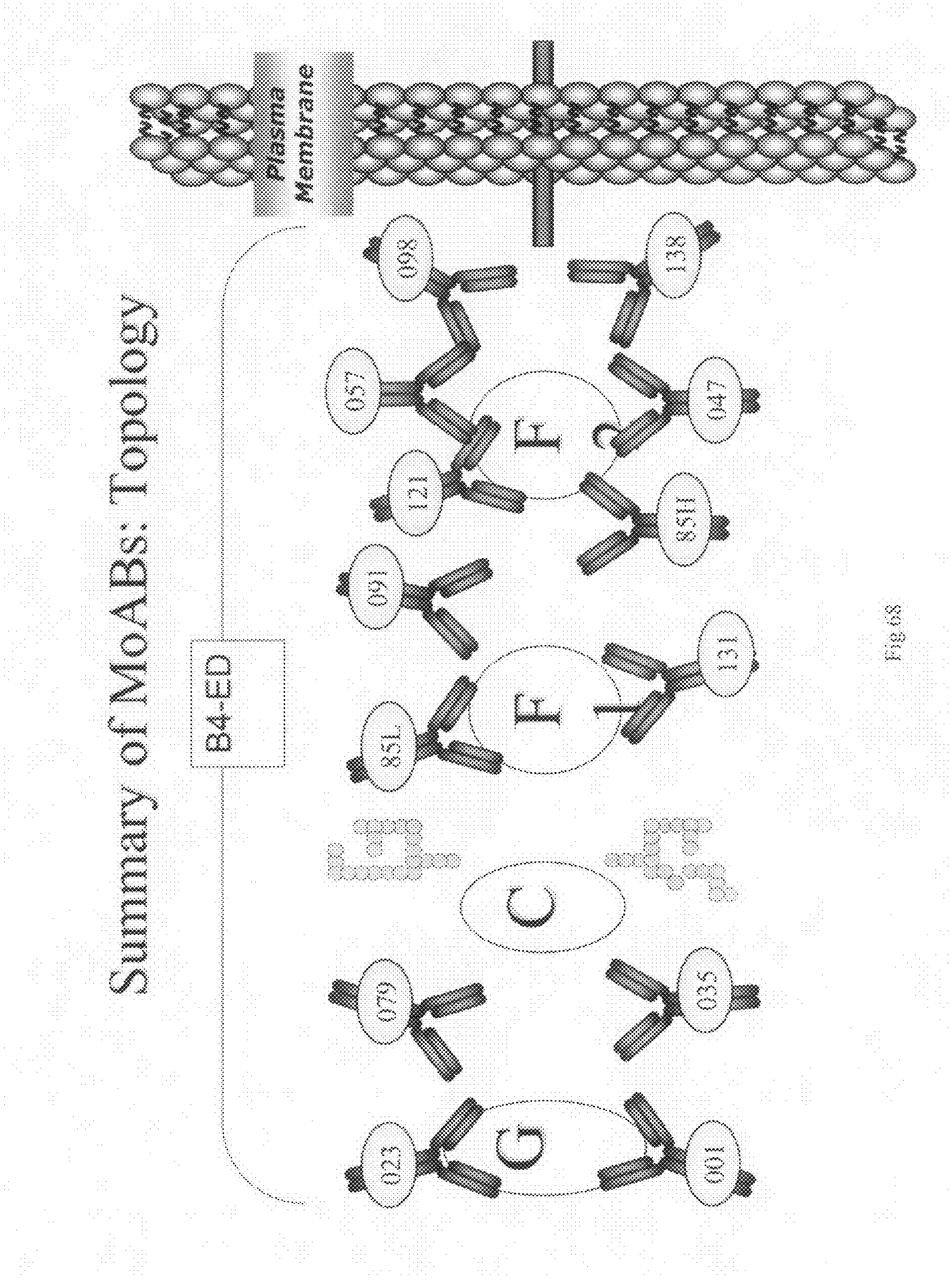
FIG. 68 shows the monoclonal antibodies generated against EphB4 and epitope mapping of these antibodies. The topology of the EphB4 extracellular domain is shown, including a globular domain (G), a cystein-rich domain (C), and two fibronectin type 3 domains (F1 and F2).
Figure 69:
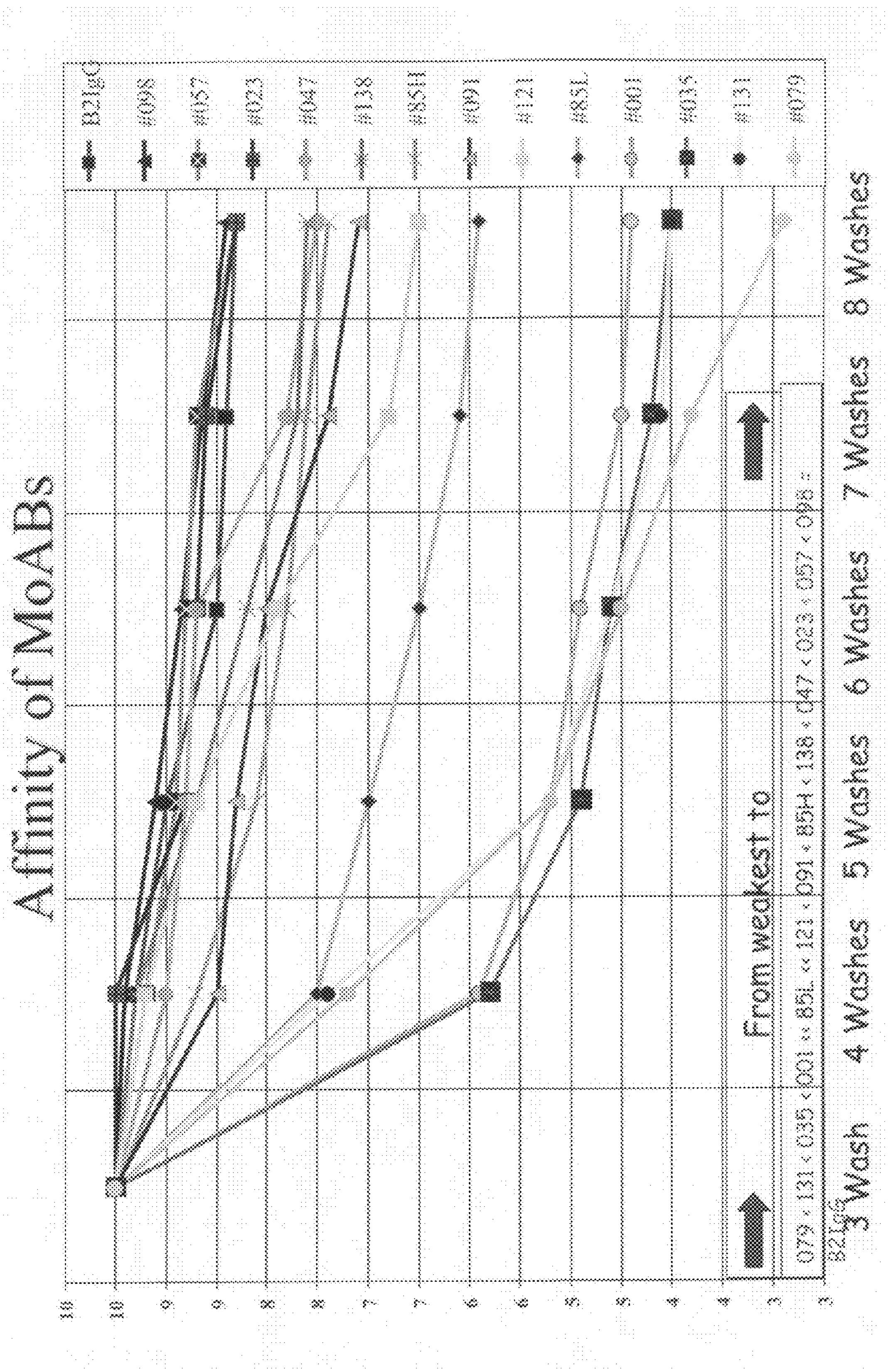
FIG. 69 shows results from affinity tests of EphB4 monoclonal antibodies. The order of the affinity (from weakest to strongest) is shown.

These monoclonal antibodies include EphB4 antibody Nos. 1, 23, 35, 47, 57, 79, 85L, 85H, 91, 98, 121, 131, and 138 (FIG. 57). Antibody mapping studies showed that the epitope domain for each of these antibodies (FIG. 68). Binding affinity of each EphB4 antibody was analyzed and shown in FIG. 69.

Further experiments were carried out to analyze the functional activities of these antibodies, including their abilities to compete with their binding partner such as Ephrin B2, to activate EphB4 tyrosine phosphorylation, to inhibit in vitro tube formation in HUAEC, to inhibit in vivo angiogenesis by matrigel plug assay, to stimulate apoptosis or necrosis in SCC15 tumor cell, and to inhibit SCC15 xenotransplant growth. The results are summarized in Table 1 below.

TABLE 1

A summary of activities of EphB4 antibodies.

| Antibody No. | Activation of EphB4 tyrosine phosphorylation | Inhibition of EphB4/Ephrin B2 interaction | Inhibition of HUAEC in vitro tube formation | Inhibition of in vivo angiogenesis (matrigel plug assay) | Stimulation of SCC15 tumor cell apoptosis or necrosis | Inhibition of SCC15 xenotransplant growth |
|---|---|---|---|---|---|---|
| 1 | -- | + | + | Nd | N | Nd |
| 23 | -- | + | + | + | A, N | -- |
| 35 | -- | + | + | Nd | A, N | -- |
| 47 | -- | -- | + | -- | Nd | + |
| 57 | -- | -- | -- | -- | Nd | + |
| 79 | -- | + | -- | Nd | A, N | -- |
| 85L | + | -- | -- | -- | Nd | -- |
| 85H | -- | -- | -- | Nd | Nd | Nd |
| 91 | + | -- | -- | Nd | -- | Nd |
| 98 | -- | -- | + | + | Nd | Nd |
| 121 | + | -- | -- | Nd | Nd | -- |

TABLE 1-continued

A summary of activities of EphB4 antibodies.

| Antibody No. | Activation of EphB4 tyrosine phosphorylation | Inhibition of EphB4/Ephrin B2 interaction | Inhibition of HUAEC in vitro tube formation | Inhibition of in vivo angiogenesis (matrigel plug assay) | Stimulation of SCC15 tumor cell apoptosis or necrosis | Inhibition of SCC15 xenotransplant growth |
|---|---|---|---|---|---|---|
| 131 | + | -- | + | Nd | Nd | + |
| 138 | -- | -- | + | + | A, N | + |

Figure 70:
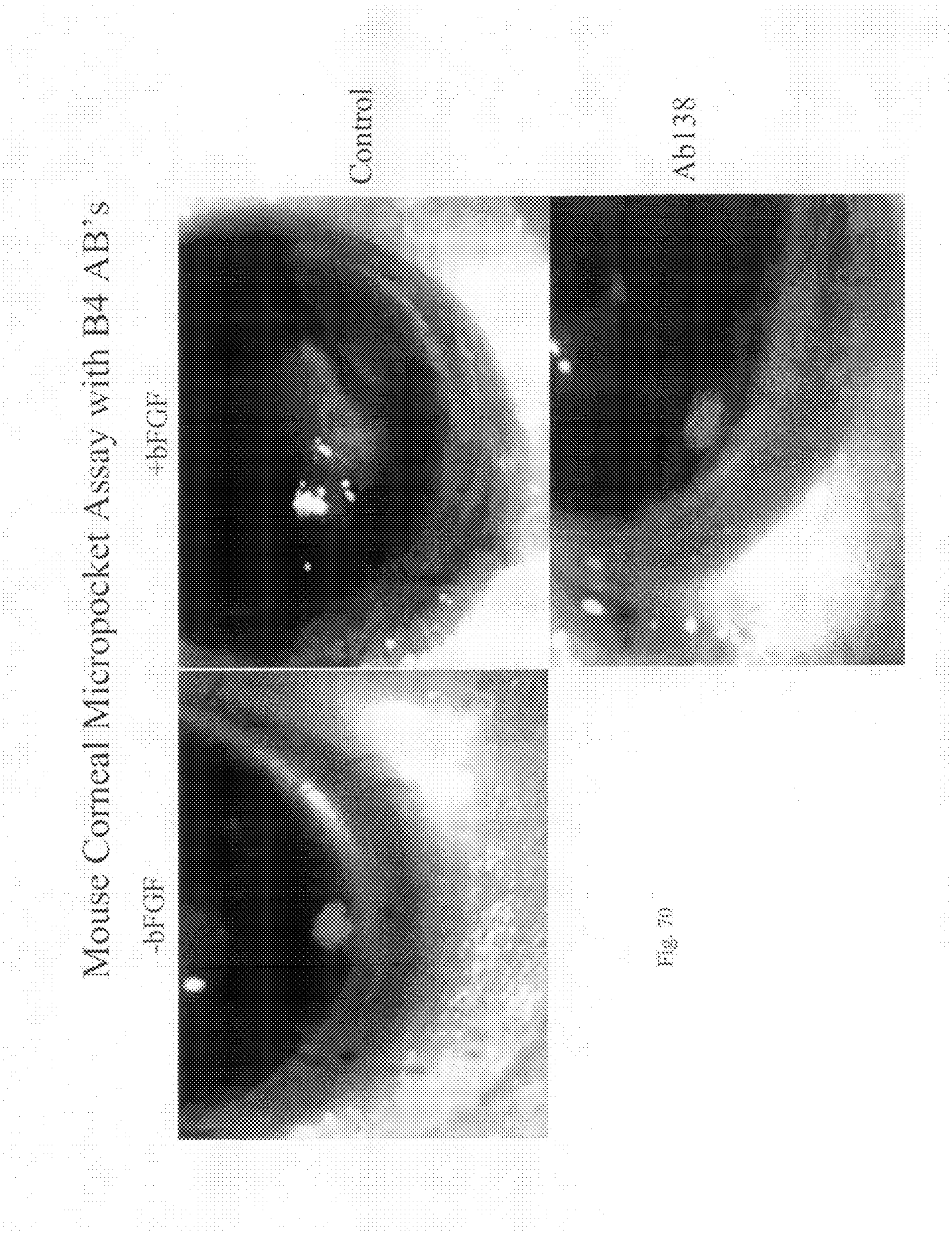
FIG. 70 shows mouse corneal micropocket assay with an exemplary EphB4 antibody (No. 138) in the presence or absence of bFGF.

Nd = not determined (no data provided)
-- = no clear effect
+ = clear effect
A = apoptosis
N = necrosis
A, N = both apoptosis and necrosis The effect of these antibodies on angiogenesis was further analyzed in mouse corneal micropocket assay. For example, EphB4 antibody No. 138 significantly inhibited angiogenesis as shown in FIG. 70.

Figure 58:
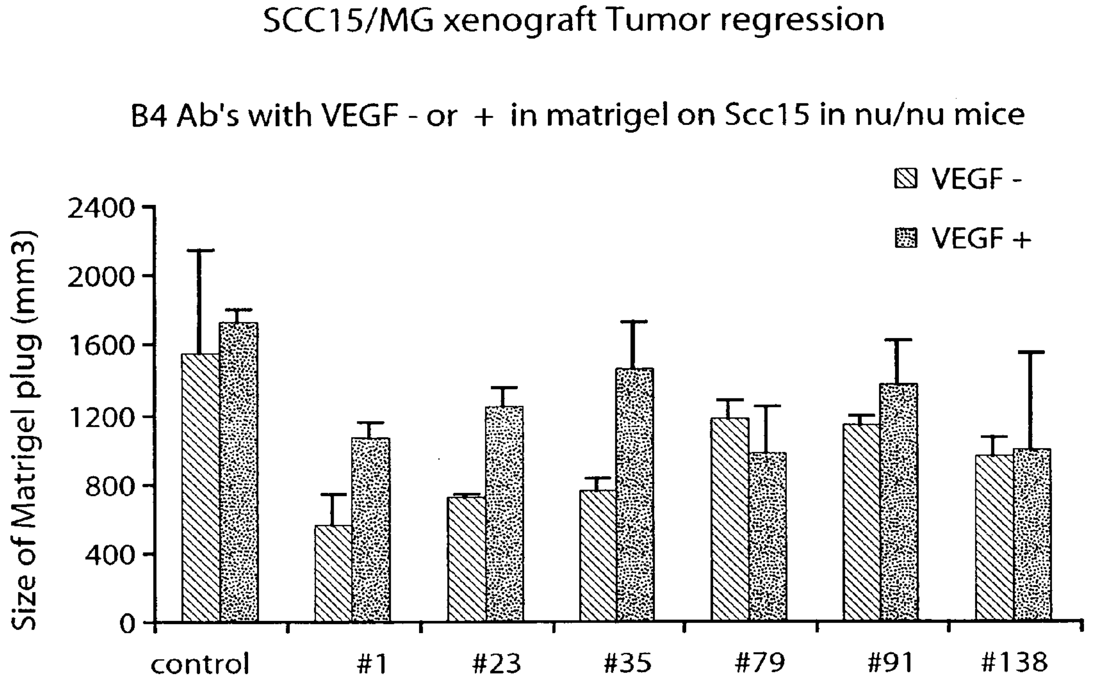
FIG. 58 shows that EphB4 antibodies inhibit the growth of SCC15 xenograft tumors.

A representative experiment is shown in FIG. 58 to illustrate the anti-tumor activities of EphB4 antibodies summarized in Table 1. BalbC nude mice were injected subcutaneously with $2.5\times10^6$ viable tumor cells (SCC15, a head and neck squamous cell carcinoma line). Tumors were initiated in nu/nu mice by injecting $2.5\text{-}5\times10^6$ cells premixed with matrigel and Growth factors, and Ab's subcutaneously to initiate tumor xenografts. Mice were opened 14 days after injections. SCC15 is a head and neck squamous cell carcinoma line, B16 is a melanoma cell line, and MCF-7 is a breast carcinoma line. The responses of tumors to these treatments were compared to control treated mice, which receive PBS injections. Animals were observed daily for tumor growth and subcutaneous tumors were measured using a caliper every 2 days. Antibodies #1 and #23 showed significant regression of SCC15 tumor size compared to control, especially with no additional growth factor added, indicating that EphB4 antibodies inhibited the in vivo tumor growth of SCC15 cells.

Figure 59:
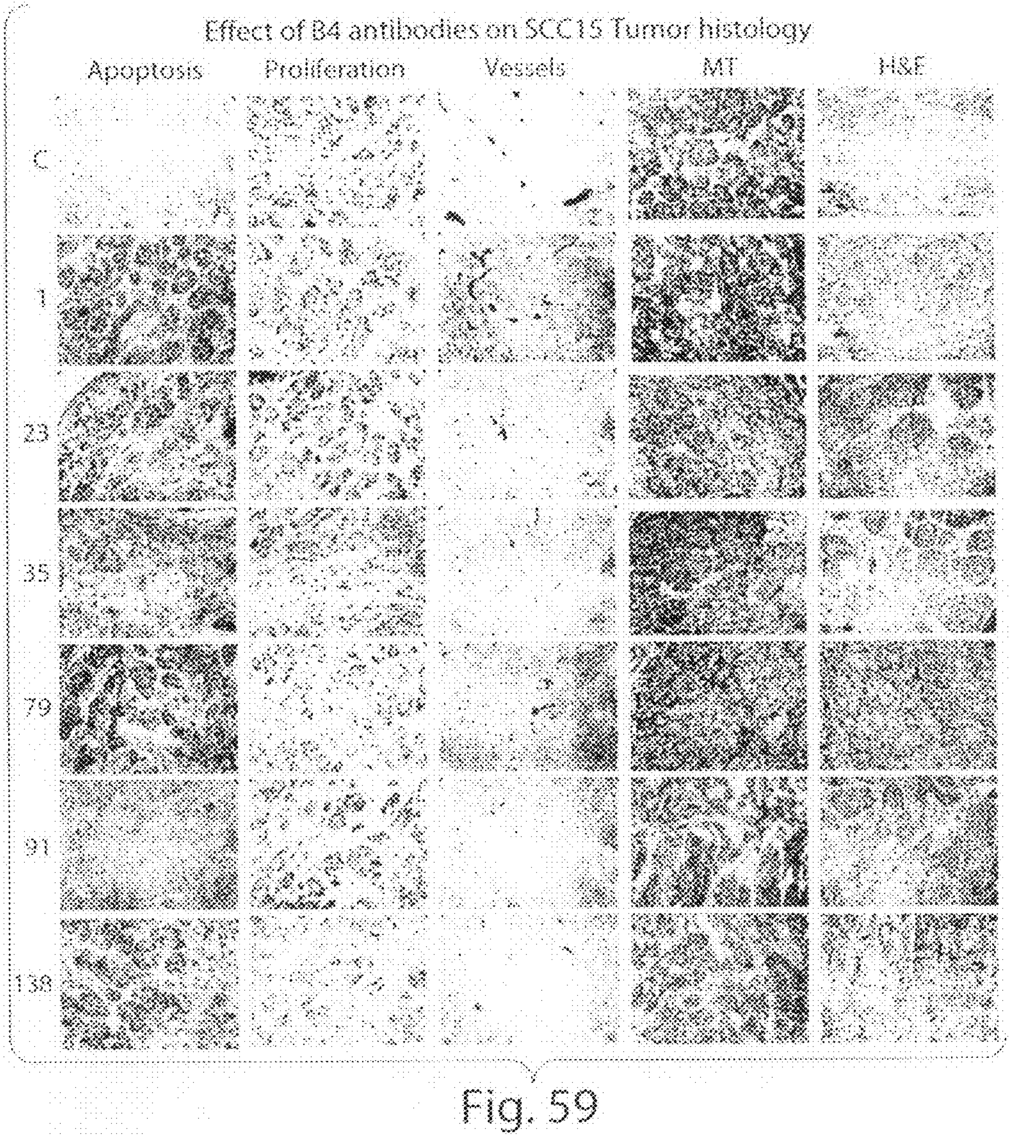
FIG. 59 shows that EphB4 antibodies cause apoptosis, necrosis and decreased angiogenesis in SCC15, head and neck carcinoma tumor type.

Another representative experiment is shown in FIG. 59 to illustrate the anti-tumor and anti-angiogenesis activities of EphB4 antibodies summarized in Table 1. Angiogenesis was assessed by CD-31 immunohistochemistry. Tumor tissue sections from treated and untreated mice were stained for CD31. Apoptosis was assessed by immunohistochemical TUNNEL, and proliferation by BrdU assay. Following surgical removal, tumors were immediately sliced into 2 mm serial sections and embedded in paraffin using standard procedures. Paraffin embedded tissue were sectioned at 5 μm, the wax removed and the tissue rehydrated. The rehydrated tissues were microwave irradiated in antigen retrieval solution. Slides were rinsed in PBS, and TUNNEL reaction mixture (Terminal deoxynucleotidyl transferase and flourescein labeled nucleotide solution), and BrdU were added in a humidity chamber completely shielded from light. The TUNNEL and BrdU reaction mixture were then removed, slides were rinsed and anti-flourescein antibody conjugated with horseradish peroxidase was added. After incubation and rinsing, 3,3'diaminobenzidine was added. Masson's Trichrome and Hematoxylin and Eosin were also used to stain the slides to visualize morphology. Masson's Trichrome allows to visualize necrosis and fibrosis. The tumor gets blood support from tumor/skin, muscle boundary. As tumor grows, inner regions get depleted of nutrients. This leads to necrosis (cell death), preferably at the tumor center. After cells die, (tumor) tissue gets replaced with fibroblastic tissue. Slides were visualized under 20-fold magnification with digital images acquired. A different morphology was obtained on SCC tumors with each antibody administered. Ab #1 showed an increase in necrosis and fibrosis but not apoptosis. Ab #23 showed an increase in apoptosis, necrosis and fibrosis and a decrease in vessel infiltration. Ab #35 showed an increase in necrosis and fibrosis, and a small increase in apoptosis and a decrease in vessel infiltration. Ab #79 showed a large increase in apoptosis, and necrossis and fibrosis. Ab #91 showed no change in apoptosis but an increase in proliferation. And Ab #138 showed an increase in apoptosis, necrosis, fibrosis and a decrease in proliferation and vessel infiltration. Tumors treated with control PBS displayed abundant tumor density and a robust angiogenic response. Tumors treated with EphB4 antibodies displayed a decrease in tumor cell density and a marked inhibition of tumor angiogenesis in regions with viable tumor cells, as well as tumor necrosis and apoptosis. These results shows that EphB4 antibodies caused apoptosis, necrosis and decreased angiogenesis in SCC15, head and neck carcinoma tumor type.

Figure 60:
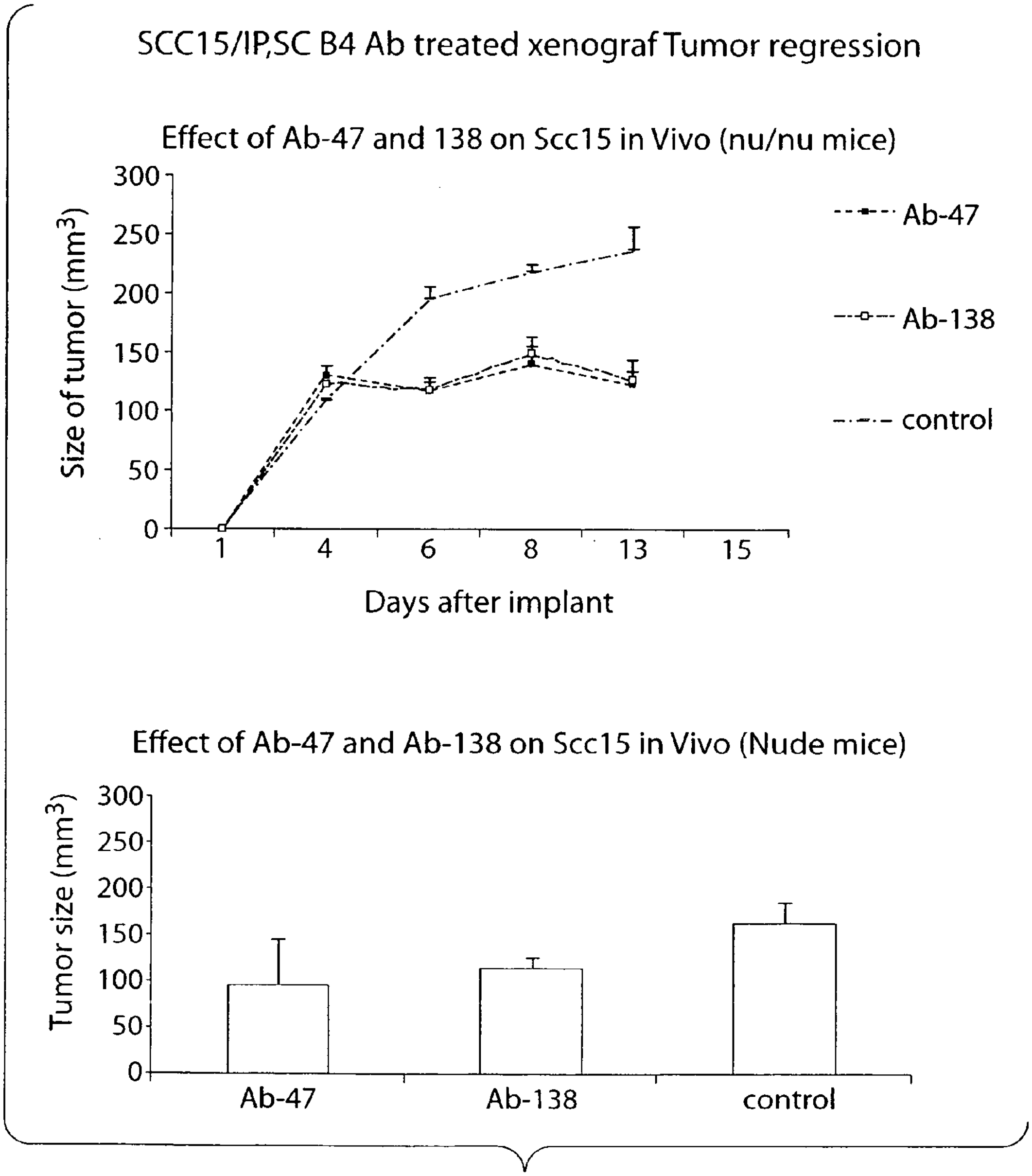
FIG. 60 shows that systemic administration of EphB4 antibodies leads to tumor regression.

A further representative experiment is shown in FIG. 60 to illustrate the anti-tumor activities of EphB4 antibodies summarized in Table 1. Alternate day treatment with EphB4 monoclonal antibody or an equal volume of PBS as control were initiated on day 4, after the tumors have established, and continued for 14 days. Systemic administration was administered either IP or SC with no significant difference. All the experiments were carried out in a double-blind manner to eliminate investigator bias. Mice were sacrificed at the conclusion of the two week treatment period. Tumors were harvested immediately postmortem and fixed and processed for immunohistochemistry. EphB4 antibodies 40 mg per kg body weight were administered. Treatment with EphB4 antibody significantly inhibited human SCC tumor growth compared with control-treated mice ($p<0.05$). Treatment with EphB4 antibody significantly inhibited tumor weight compared with control-treated mice ($p<0.05$). These results show that systemic administration of antibodies on xenografts led to tumor regression in SCC15 tumor xenografts.

B. Materials and Methods

1) Immunohistochemistry

Formalin-fixed tissue sections were deparaffinized and incubated with 10% goat serum at −70° C. for 10 minutes and incubated with the EphB4 monoclonal antibody 4° C. overnight. Isotype-specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with 0.12% methylene blue or H&E. For frozen sections, OCT-embedded tissues were sectioned at 5 μm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody.

2) Western Blot

Whole cell lysates were prepared using Cell Lysis Buffer (GeneHunter, Basgvukke TN) supplemented with protease inhibitor cocktail (Pierce, Rockford Ill.), unless otherwise noted. Total protein was determined using the DC reagent system (Bio-Rad, Hercules Calif.). Typically, 20 μg whole cell lysate was run on 4-20% Tris-Glycine gradient gel. The samples were electro-transferred to PVDF membrane and the nonspecific binding was blocked in TBST buffer (0.5 mM Tris-HCl, 45 mM NaCl, 0.05% Tween-20, pH 7.4) containing 5% non-fat milk. Membranes were first probed with primary antibody overnight, stripped with Restore Western Blot stripping buffer (Pierce, Rockford Ill.) and reprobed with β-actin to confirm equivalent loading and transfer of protein. Signal was detected using SuperSignal West Femto Maximum Sensitivity Substrate (Pierce).

3) Tyrosine Kinase Phosphorylation Analysis

Cells growing in 60 mm dishes were either serum starved (1% FBS supplemented RPMI 1640, 24 hours) or cultured in normal conditions (10% FBS) and then treated with or without 1 μg/ml mouse ephrin B2/$F_c$ for 10 min to activate EphB4 receptor. Cleared cell lysates were incubated with EphB4 monoclonal antibody overnight at 4° C. Antigen-antibody complex was immunoprecipitated by the addition of 100 μl of Protein G-Sepharose in 20 mM sodium phosphate, pH 7.0 with incubation overnight at 4° C. Immunoprecipitates were analyzed by Western blot with phosphotyrosine (pTyr) specific antibody (Upstate, clone 4G10) at 1:1000 dilution followed by incubation with protein G-HRP (Bio-Rad) at 1:5000 dilution. To monitor immunoprecipitation efficiency, a duplicate membrane was probed with EphB4 specific monoclonal antibody.

4) Cell Culture

Normal HUVECs were obtained from Cambrex (BioWhittaker) and maintained in EBM2 medium supplemented with 0.1 mg/ml endothelial growth supplement (crude extract from bovine brain), penicillin (50 U/ml), streptomycin (50 U/ml), 2 mmol/l glutamine and 0.1 mg/ml sodium heparin. Aliquots of cells were preserved frozen between passages 1 and 3. For all experiments, HUVECs were used at passages 4 or below and collected from a confluent dish.

NCI H28 and NCI H2373 mesothelioma cell lines were obtained from the ATCC (Manassas, Va.). Cells were maintained in RPMI 1640 media supplemented with 10% heat-inactivated fetal bovine serum (FBS; Life Technologies, Gaithersburg, Md.) and antibiotics. Primary cells were obtained from pleural effusion of patients with mesothelioma.

5) Endothelial Cell Tube Formation Assay

Matrigel (60 μl of 10 mg/ml; Collaborative Lab, Cat. No. 35423) was placed in each well of an ice-cold 96-well plate. The plate was allowed to sit at room temperature for 15 minutes then incubated at 37° C. for 30 minutes to permit Matrigel to polymerize. In the mean time, human umbilical vein endothelial cells were prepared in EGM-2 (Clonetic, Cat. No. CC3162) at a concentration of $2\times10^5$ cells/ml. Cells (500 μl) and the test EphB4 antibody were mixed and 200 μl of this suspension were placed in duplicate on the polymerized Matrigel. After 24 h incubation, triplicate pictures were taken for each concentration using a Bioquant Image Analysis system. Protein addition effect ($IC_{50}$) was assessed compared to untreated controls by measuring the length of cords formed and number of junctions.

6) Cell Migration Assay

Chemotaxis of HUVECs to VEGF was assessed using a modified Boyden chamber, transwell membrane filter inserts in 24 well plates, 6.5 mm diam, 8 μm pore size, 10 μm thick matrigel coated, polycarbonate membranes (BD Biosciences). The cell suspensions of HUVECs ($2\times10^5$ cells/ml) in 200 μl of EBM were seeded in the upper chamber and the test EphB4 antibodies were added simultaneously with stimulant (VEGF or bFGF) to the lower compartment of the chamber and their migration across a polycarbonate filter in response to 10-20 ng/ml of VEGF with or without 100 nM-1 μM test compound was investigated. After incubation for 4-24 h at 37° C., the upper surface of the filter was scraped with swab and filters were fixed and stained with Diff Quick. Ten random fields at 200× mag were counted and the results expressed as mean # per field. Negative unstimulated control values were subtracted from stimulated control and protein treated sample values and the data was plotted as mean migrated cell ±S.D. $IC_{50}$ was calculated from the plotted data.

7) Growth Inhibition Assay

HUVEC ($1.5\times10^3$ cells) were plated in a 96-well plate in 100 μl of EBM-2 (Clonetic, Cat. No. CC3162). After 24 hours (day 0), the test EphB4 antibody is added to each well at the desired concentration in EBM-2 medium. On day 0, one plate was stained with 0.5% crystal violet in 20% methanol for 10 minutes, rinsed with water, and air-dried. The remaining plates were incubated for 72 h at 37° C. After 72 h, plates were stained with 0.5% crystal violet in 20% methanol, rinsed with water and air-dried. The stain was eluted with 1:1 solution of ethanol: 0.1 M sodium citrate (including day 0 plate), and absorbance measured at 540 nm with an ELISA reader (Dynatech Laboratories). Day 0 absorbance was subtracted from the 72 h plates and data is plotted as percentage of control proliferation (vehicle treated cells). $IC_{50}$ value was calculated from the plotted data.

8) Murine Matrigel Plug Angiogenesis Assay

In vivo angiogenesis was assayed in mice as growth of blood vessels from subcutaneous tissue into a Matrigel plug containing the test sample. Matrigel rapidly forms a solid gel at body temperature, trapping the factors to allow slow release and prolonged exposure to surrounding tissues. Matrigel (8.13 mg/ml, 0.5 ml) in liquid form at 4° C. was mixed with Endothelial Cell Growth Supplement (ECGS), test EphB4 antibodies plus ECGS or Matrigel plus vehicle alone (PBS containing 0.25% BSA). Matrigel (0.5 ml) was injected into the abdominal subcutaneous tissue of female nu/nu mice (6 wks old) along the peritoneal mid line. There were 3 mice in each group. The animals were cared for in accordance with institutional and NIH guidelines. At day 6, mice were sacrificed and plugs were recovered and processed for histology. Typically, the overlying skin was removed, and gels were cut out by retaining the peritoneal lining for support, fixed in 10% buffered formalin in PBS and embedded in paraffin. Sections of 3 μm were cut and stained with H&E or Masson's trichrome stain and examined under light microscope.

9) Mouse Corneal Micropocket Assay

Mouse corneal micropocket assay was performed according to that detailed by Kenyon et al., 1996. Briefly, hydron pellets (polyhydroxyethylmethacrylate [polyHEMA], Interferon Sciences, New Brunswick, N.J., U.S.A.) containing either 90 ng of bFGF (R&D) or 180 ng of VEGF (R&D Systems, Minneapolis, Minn., U.S.A.) and 40 μg of sucrose aluminium sulfate (Sigma) were prepared. Using an operating microscope, a stromal linear keratotomy was made with a surgical blade (Bard-Parker no. 15) parallel to the insertion of the lateral rectus muscle in an anesthetized animal. An intrastromal micropocket was dissected using a modified von Graefe knife (2"30 mm). A single pellet was implanted and advanced toward the temporal corneal limbus (within 0±7±1±0 mm for bFGF pellets and 0±5 mm for VEGF pellets). The difference in pellet location for each growth factor was determined to be necessary given the relatively weaker angiogenic stimulation of VEGF in this model. Antibiotic ointment (erythromycin.) was then applied to the operated eye to prevent infection and to decrease surface irregularities. The subsequent vascular response was measured extending from the limbal vasculature toward the pellet and the contiguous circumferential zone of neovascularization. Data and clinical photos presented here were obtained on day 6 after pellet implantation, which was found to be the day of maximal angiogenic response.

10) In Vitro Invasion Assay

"Matrigel" matrix-coated 9-mm cell culture inserts (pore size, 8 μm; Becton Dickinson, Franklin Lakes, N.J.) were set in a 24-well plate. The HUVEC cells were seeded at a density of $5\times10^3$ cells per well into the upper layer of the culture insert and cultured with serum-free EBM in the presence of the test EphB4 antibodies for 24 h. The control group was cultured in the same media without EphB4 antibodies. Then 0.5 ml of the human SCC15 cell line, conditioned medium was filled into the lower layer of the culture insert as a chemo-attractant. The cells were incubated for 24 h, then the remaining cells in the upper layer were swabbed with cotton and penetrating cells in the lower layer were fixed with 5% glutaraldehyde and stained with Diff Quick. The total number of cells passing through the Matrigel matrix and each 8 μm pore of the culture insert was counted using optical microscopy and designated as an invasion index (cell number/area).

11) SCC15 Tumor Growth in Mice

Subcutaneously inject logarithmically growing SCC15, head and neck squamous cell carcinoma cell line, at $5\times10^6$ cell density; with or without the test EphB4 antibody in the presence or absence of human bFGF, into athymic Balb/c nude mice, along with Matrigel (BD Bioscience) synthetic basement membrane (1:1 v/v), and examine tumors within 2 weeks. Tumor volumes in the test EphB4 antibody group, in the presence and absence of growth factor after implantation were three-fold smaller than those in the vehicle groups. There was no difference in body weight between the groups. Immunohistochemical examination of cross-sections of resected tumors and TUNEL-positive apoptosis or necrosis, CD34 immunostaining, and BrdU proliferation rate will be performed, after deparaffinized, rehydrated, and quenched for endogenous peroxidase activity, and after 10 min permeabilization with proteinase K. Quantitative assessment of vascular densities will also be performed. Local intratumoral delivery or IV delivery of the test EphB4 antibody will also be performed twice a week.

30 athymic nude mice, BALB/c (nu/nu), were each injected with $1\times10^6$ B16 melanoma cells with 0.1 ml PBS mixed with 0.1 ml matrigel or $1.5\times10^6$ SCC15 cells resuspended in 200 μl of DMEM serum-free medium and injected subcutaneously on day 0 on the right shoulder region of mice. Test EphB4 antibodies were injected intravenously or subcutaneously, around the tumor beginning on day 1 at a loading dose of 4 μg/mg, with weekly injections of 2 μg/mg (10 μg/g, 50 μg/kg/day), and at 2 weeks post-inoculation. Mice are sacrificed on Day 14. Control mice received PBS 50 μl each day.

12) Tumor Formation in Nude Mice

All animals were treated under protocols approved by the institutional animal care committees. Cancer cells ($5\times10^6$) were subcutaneously inoculated into the dorsal skin of nude mice. When the tumor had grown to a size of about 100 $mm^3$ (usually it took 12 days), the test EphB4 antibody was either intraperitoneally or subcutaneously injected once/day, and tumorigenesis was monitored for 2 weeks. Tumor volume was calculated according to the formula a×b, where a and b are the smallest and largest diameters, respectively. A Student's t test was used to compare tumor volumes, with $P<0.05$ being considered significant.

13) Quantification of Microvessel Density

Tumors were fixed in 4% formaldehyde, embedded in paraffin, sectioned by 5 μm, and stained with hematoxylineosin. Vessel density was semi-quantitated using a computer-based image analyzer (five fields per section from three mice in each group).

Incorporation by Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. An isolated monoclonal antibody or antigen-binding portion thereof that binds to an epitope situated in the extracellular portion of EphB4, promotes apoptosis, and inhibits an EphB4 activity.

2. The isolated antibody or antigen-binding portion thereof of claim 1, wherein the antibody or antigen-binding portion thereof binds to an epitope situated within amino acids 16-198 of the EphB4 sequence of SEQ ID NO: 386.

3. The isolated antibody or antigen-binding portion thereof of claim 2, wherein the antibody or antigen-binding portion thereof inhibits the binding of EphB4 to the extracellular portion of EphrinB2.

4. The isolated antibody or antigen-binding portion thereof of claim 1, wherein the antibody or antigen-binding portion thereof binds to an epitope situated within amino acids 324-429 or 430-537 of the EphB4 sequence of SEQ ID NO: 386.

5. The isolated antibody or antigen-binding portion thereof of claim 4, wherein the antibody or antigen-binding portion thereof inhibits the formation of EphB4 dimers or multimers.

6. The isolated antibody or antigen-binding portion thereof of claim 4, wherein the antibody or antigen-binding portion thereof binds to the first fibronectin-like domain (FND1) of EphB4.

7. The isolated antibody or antigen-binding portion thereof of claim 4, wherein the antibody or antigen-binding portion thereof binds to the second fibronectin-like domain (FND2) of EphB4.

8. The isolated antibody or antigen-binding portion thereof of claim 1, wherein the antibody or antigen-binding portion thereof inhibits the EphrinB2-stimulated autophosphorylation of EphB4.

9. The isolated antibody or antigen-binding portion thereof of claim 1, wherein the antibody or antigen-binding portion thereof inhibits the formation of tubes by cultured endothelial cells.

10. The isolated antibody or antigen-binding portion thereof of claim 1, wherein the antibody or antigen-binding portion thereof inhibits the vascularization of a tissue in vivo.

11. The isolated antibody or antigen-binding portion thereof of claim 10, wherein the antibody or antigen-binding portion thereof inhibits the vascularization of tissue implanted in the cornea of an animal.

12. The isolated antibody or antigen-binding portion thereof of claim 10, wherein the antibody or antigen-binding portion thereof inhibits the vascularization of a Matrigel tissue plug implanted in an animal.

13. The isolated antibody or antigen-binding portion thereof of claim 1, wherein the antibody or antigen-binding portion thereof decreases the growth of a human tumor xenograft in a mouse.

14. The isolated antibody of claim 2, wherein the antibody is No. 023.

15. The isolated antibody of claim 2, wherein the antibody is a humanized version of antibody No. 023.

16. The isolated antibody or antigen-binding portion thereof of claim 2, wherein the antibody or antigen-binding portion thereof comprises at least one CDR portion derived from an antibody selected from antibodies denoted herein as No. 023, No. 035, and No. 079.

17. The isolated antibody of claim 4, wherein the antibody is No. 138.

18. The isolated antibody of claim 4, wherein the antibody is a humanized version of antibody No. 138.

19. The isolated antibody or antigen-binding portion thereof of claim 4, wherein the antibody or antigen-binding portion thereof comprises at least one CDR portion derived from antibody No. 138.

20. The antibody of claim 1, wherein the monoclonal antibody is clinically acceptable for administration to a human.

21. A hybridoma that produces an antibody of claim 1.

22. A pharmaceutical preparation comprising the isolated antibody or antigen-binding portion thereof of claim 1.

* * * * *